US012172986B2

(12) United States Patent
Pazolli et al.

(10) Patent No.: US 12,172,986 B2
(45) Date of Patent: Dec. 24, 2024

(54) SPLICING MODULATOR ANTIBODY-DRUG CONJUGATES AND METHODS OF USE

(71) Applicant: EISAI R&D MANAGEMENT CO., LTD., Tokyo (JP)

(72) Inventors: Ermira Pazolli, Wayland, MA (US); Silvia Buonamici, Boston, MA (US); Thiwanka Samarakoon, Westwood, MA (US); Sudeep Prajapati, Somerville, MA (US); Nathan Fishkin, Weymouth, MA (US); James Palacino, Wellesley, MA (US); Michael Seiler, Belmont, MA (US); Ping Zhu, Acton, MA (US); Andrew Cook, Stow, MA (US); Peter Smith, Arlington, MA (US); Xiang Liu, Winchester, MA (US); Shelby Ellery, Boston, MA (US); Dominic Reynolds, Stoneham, MA (US); Lihua Yu, Acton, MA (US); Zhenhua Wu, Belmont, MA (US); Shouyong Peng, Tbilisi (GE); Nicholas Calandra, Boston, MA (US); Megan Sheehan, Allston, MA (US); Yonghong Xiao, Belmont, MA (US)

(73) Assignee: EISAI R&D MANAGEMENT CO., LTD, Tokyo (JP)

( * ) Notice: Subject to any disclaimer, the term of this patent is extended or adjusted under 35 U.S.C. 154(b) by 937 days.

(21) Appl. No.: 17/059,635

(22) PCT Filed: May 31, 2019

(86) PCT No.: PCT/US2019/035015
§ 371 (c)(1),
(2) Date: Nov. 30, 2020

(87) PCT Pub. No.: WO2019/232449
PCT Pub. Date: Dec. 5, 2019

(65) Prior Publication Data
US 2021/0299269 A1    Sep. 30, 2021

Related U.S. Application Data

(60) Provisional application No. 62/679,631, filed on Jun. 1, 2018, provisional application No. 62/679,672, filed
(Continued)

(51) Int. Cl.
*C07D 405/12* (2006.01)
*A61K 9/127* (2006.01)
(Continued)

(52) U.S. Cl.
CPC .......... *C07D 405/12* (2013.01); *A61K 9/127* (2013.01); *A61K 9/51* (2013.01); *A61K 31/365* (2013.01);
(Continued)

(58) Field of Classification Search
CPC ............... C07D 405/12; C07D 313/00; C07D 405/06; C07D 405/14; C07D 407/06; C07D 407/12; A61K 9/127; A61K 9/51; A61K 31/365; A61K 31/496; A61K 39/0011; A61K 39/3955; A61K 39/39558; A61K 45/06; A61K 47/60; A61K 47/6845; A61K 47/6849; A61K 47/6851; A61K 47/6857; A61K 47/6869; A61K 47/6871; A61K 47/6889; A61K 2039/505; A61K 2039/53; A61K 2039/545; A61K 39/00; A61K 47/6855; A61K 47/6803; A61K 47/65; A61K 47/6867; A61P 35/00; C07K 16/24; C07K 16/28; C07K 16/2803; C07K 16/2818; C07K 16/2827; C07K 16/2896; C07K 16/3007; C07K 16/3092; C07K 16/32; C07K 16/40; C07K 2317/565; C07K 2317/76; C07K 16/00; C07K 16/243;
(Continued)

(56) References Cited

U.S. PATENT DOCUMENTS 7,256,178 B2    8/2007  Kotake et al.
7,555,503 B1    6/2009  Neal et al.
(Continued)

FOREIGN PATENT DOCUMENTS

EP    1508570 A1      2/2005
EP    2266978 B1 *   5/2015   ........... A61K 31/336
(Continued)

OTHER PUBLICATIONS

Charlton et al. Targeted Therapy in Cancer (Medicine, 44:1, 34-38) (Year: 2015).*
(Continued)

*Primary Examiner* — Matthew P Coughlin
*Assistant Examiner* — Meghan C Heasley
(74) *Attorney, Agent, or Firm* — Finnegan, Henderson, Farabow, Garrett & Dunner, LLP

(57) ABSTRACT

Linker-drug compounds and antibody-drug conjugates that bind to human oncology targets are disclosed. The linker-drug compounds and antibody-drug conjugates comprise a splicing modulator drug moiety. The disclosure further relates to methods and compositions for use in the treatment of neoplastic disorders by administering the antibody-drug conjugates provided herein. In an embodiment, the splicing modulator comprises a pladienolide or a pladienolide derivative.

46 Claims, 35 Drawing Sheets
Specification includes a Sequence Listing.

Related U.S. Application Data on Jun. 1, 2018, provisional application No. 62/779,324, filed on Dec. 13, 2018.

(51) Int. Cl.

| | | |
|---|---|---|
| *A61K 9/51* | (2006.01) | |
| *A61K 31/365* | (2006.01) | |
| *A61K 31/496* | (2006.01) | |
| *A61K 39/00* | (2006.01) | |
| *A61K 39/395* | (2006.01) | |
| *A61K 45/06* | (2006.01) | |
| *A61K 47/60* | (2017.01) | |
| *A61K 47/68* | (2017.01) | |
| *A61P 35/00* | (2006.01) | |
| *C07D 313/00* | (2006.01) | |
| *C07D 405/06* | (2006.01) | |
| *C07K 16/24* | (2006.01) | |
| *C07K 16/28* | (2006.01) | |
| *C07K 16/30* | (2006.01) | |
| *C07K 16/32* | (2006.01) | |
| *C07K 16/40* | (2006.01) | |
| *C12Q 1/6886* | (2018.01) | |
| *G01N 33/50* | (2006.01) | |
| *G01N 33/574* | (2006.01) | |

(52) U.S. Cl.
CPC ........ *A61K 31/496* (2013.01); *A61K 39/0011* (2013.01); *A61K 39/3955* (2013.01); *A61K 39/39558* (2013.01); *A61K 45/06* (2013.01); *A61K 47/60* (2017.08); *A61K 47/6845* (2017.08); *A61K 47/6849* (2017.08); *A61K 47/6851* (2017.08); *A61K 47/6857* (2017.08); *A61K 47/6869* (2017.08); *A61K 47/6871* (2017.08); *A61K 47/6889* (2017.08); *A61P 35/00* (2018.01); *C07D 313/00* (2013.01); *C07D 405/06* (2013.01); *C07K 16/24* (2013.01); *C07K 16/28* (2013.01); *C07K 16/2803* (2013.01); *C07K 16/2818* (2013.01); *C07K 16/2827* (2013.01); *C07K 16/2896* (2013.01); *C07K 16/3007* (2013.01); *C07K 16/3092* (2013.01); *C07K 16/32* (2013.01); *C07K 16/40* (2013.01); *C12Q 1/6886* (2013.01); *G01N 33/5011* (2013.01); *G01N 33/574* (2013.01); *A61K 2039/505* (2013.01); *A61K 2039/53* (2013.01); *A61K 2039/545* (2013.01); *C07K 2317/565* (2013.01); *C07K 2317/76* (2013.01); *C12Q 2600/106* (2013.01); *G01N 2500/10* (2013.01)

(58) Field of Classification Search
CPC .............. C07K 16/2866; C12Q 1/6886; C12Q 2600/106; C12Q 2600/158; G01N 33/5011; G01N 33/574; G01N 2500/10; G01N 33/56977; G01N 33/6893
See application file for complete search history.

(56) References Cited

U.S. PATENT DOCUMENTS

| | | |
|---|---|---|
| 8,337,856 B2 | 12/2012 | Blattler et al. |
| 10,322,192 B2 | 6/2019 | Albone et al. |
| 10,548,986 B2 | 2/2020 | Albone et al. |
| 2014/0275010 A1 | 9/2014 | Zheng et al. |
| 2020/0297860 A1 | 9/2020 | Albone et al. |
| 2021/0101888 A1 | 4/2021 | Pazolli et al. |
| 2021/0238304 A1 | 8/2021 | Albone et al. |
| 2022/0081486 A1 | 3/2022 | Henry et al. |

FOREIGN PATENT DOCUMENTS

| | | |
|---|---|---|
| EP | 3538080 A4 | 7/2020 |
| RU | 2683780 C2 | 4/2019 |
| WO | WO 2003/099813 A1 | 12/2003 |
| WO | WO 2004/011661 A1 | 2/2004 |
| WO | WO 2014/068443 A1 | 5/2014 |
| WO | WO 2014/202775 A1 | 12/2014 |
| WO | WO 2015/015448 A2 | 2/2015 |
| WO | WO 2017/151979 A1 | 9/2017 |
| WO | WO 2018/086139 A1 | 5/2018 |
| WO | WO 2019/232433 A2 | 12/2019 |
| WO | WO 2019/232449 A9 | 12/2019 |
| WO | WO 2020/123836 A2 | 6/2020 |
| WO | WO 2021/090062 A1 | 5/2021 |
| WO | WO 2021/148003 A1 | 7/2021 |

OTHER PUBLICATIONS

Puthenveetil et al. Natural Product Splicing Inhibitors: a New Class of Antibody-Drug Conjugate (ADC) Payloads (Bioconjugate Chem. 27, 1880-1888). (Year: 2016).*
Chilean Patent Application No. CL202102377, filed Sep. 10, 2021, by Eisai R&D Management, CO., LTD., Substantive Report, dated Nov. 22, 2023 (30 pages with English translation).
Japanese Patent Application No. 2020-567044, filed May 31, 2019, by Eisai R&D Management Co., Ltd., Office Action, dated Jun. 13, 2023 (4 pages with translation).
Manabe (2019) "Development and Current Status of Antibody-drug conjugate (ADC)", *Drug Delivery System*, 34(1):10-21.
International Patent Application No. PCT/US2019/035015, filed May 31, 2019, by Eisai R&D Management Co., Ltd., International Search Report and Written Opinion, mailed Sep. 11, 2019 (16 pages).
Li et al., (2017) "Preclinical and clinical development of neoantigen vaccines", Annals of Oncology, 28(Suppl_12):xii11-xii17.
Puthenveetil et al., (2017) "Multivalent peptidic linker enables identification of preferred sites of conjugation for a potent thialanstatin antibody drug conjugate", PLoS ONE, 12(5):e0178452.
GCC Patent Application No. 2019/37676, filed May 30, 2019, by Eisai R&D Management Co., Ltd., Examination Report, dated Feb. 9, 2021 (9 pages).
Beck et al., (2017) "Strategies and challenges for the next generation of antibody-drug conjugates" *Nat Rev Drug Discov.*, 16(5):315-337.
Mariuzza, (1987) "The structural basis of antigen-antibody recognition", *Ann. Rev. Biophys. Biophys. Chem.*, 16:139-159.
Russian Patent Application No. 2020143425, filed May 31, 2019, by Eisai R&D Management Co., Ltd., Office Action, dated Dec. 22, 2022 (7 pages).
Russian Patent Application No. 2020143425, filed May 31, 2019, by Eisai R&D Management Co., Ltd., Search Report, dated Dec. 22, 2022 (2 pages).

\* cited by examiner

SPLICING MODULATOR ANTIBODY-DRUG CONJUGATES AND METHODS OF USE

The present disclosure claims the benefit of priority to U.S. Provisional Patent Application No. 62/679,672, filed Jun. 1, 2018; U.S. Provisional Patent Application No. 62/679,631, filed Jun. 1, 2018; and U.S. Provisional Patent Application No. 62/779,324, filed Dec. 13, 2018. All of the aforementioned applications are incorporated herein by reference in their entirety.

The present disclosure relates to antibody-drug conjugates (ADCs) comprising a splicing modulator and an antibody or antigen binding fragment thereof that binds a human oncology antigen target. The disclosure further relates to methods and compositions useful in the treatment or diagnosis of cancers that express a target antigen and/or are amenable to treatment by disruption of RNA splicing, as well as methods of making those compositions.

The majority of protein-coding genes in the human genome are composed of multiple exons (coding regions) that are separated by introns (non-coding regions). Gene expression results in a single precursor messenger RNA (pre-mRNA). The intron sequences are subsequently removed from the pre-mRNA by a process called splicing, which results in the mature messenger RNA (mRNA). By including different combinations of exons, alternative splicing gives rise to mRNAs encoding distinct protein isoforms.

RNA splicing is catalyzed by the spliceosome, a dynamic multiprotein-RNA complex composed of five small nuclear RNAs (snRNAs U1, U2, U4, U5, and U6) and associated proteins. The spliceosome assembles on pre-mRNAs to establish a dynamic cascade of multiple RNA and protein interactions that catalyze excision of the introns and ligation of exons (Matera and Wang (2014) Nat Rev Mol Cell Biol. 15(2):108-21). Accumulating evidence has linked human diseases to dysregulation in RNA splicing that impact many genes (Scotti and Swanson (2016) Nat Rev Genet. 17(1): 19-32).

The spliceosome is an important target in cancer biology. Several studies have now documented significant alterations in the splicing profile of cancer cells, as well as in the splicing factors themselves (Agrawal et al. (2018) Curr Opin Genet Dev. 48:67-74). Alternative splicing can lead to differential exon inclusion/exclusion, intron retention, or usage of cryptic splice sites (Seiler et al. (2018) Cell Rep. 23(1):282-296). Altogether, these events account for functional changes that may contribute to tumorigenesis or resistance to therapy (Siegfried and Karni (2018) Curr Opin Genet Dev. 48:16-21).

Certain natural products can bind the SF3b spliceosome complex. These small molecules modulate splicing by promoting intron retention and/or exon skipping (Teng et al. (2017) Nat Commun. 8:15522). A significant portion of the resulting transcripts contain premature stop codons triggering nonsense mediated mRNA decay (NMD). Furthermore, because canonical splicing is impaired, canonical transcripts are considerably reduced, which can negatively impact cell function and viability. For this reason, splicing modulators have become a promising class of drugs for the treatment of cancer (Puthenveetil et al. (2016) Bioconjugate Chem. 27:1880-8).

The proto-oncogene human epidermal growth factor receptor 2 (HER2) encodes a transmembrane tyrosine kinase receptor that belongs to the human epidermal growth factor receptor (EGFR) family (King et al. (1985) Science 229: 974-6). Overexpression of HER2 enables constitutive activation of growth factor signaling pathways, such as the PI3K-AKT-mTOR pathway, and thereby serves as an oncogenic driver in several types of cancers, including approximately 20% of invasive breast carcinomas (Slamon et al. (1989) Science 244:707-12; Gajria and Chandarlapaty (2011) Expert Rev Anticancer Ther. 11:263-75). Given that HER2 amplification mediates the transformed phenotype, and because HER2 expression is largely restricted to malignant cells, HER2 is a promising antigen for targeting certain cancers and/or delivering novel cancer treatments (Parakh et al. (2017) Cancer Treat Rev. 59:1-21). Additional antigens for targeted delivery of cancer therapies include, but are not limited to, CD138 (also referred to as syndecan-1) and ephrin type-A receptor 2 (EPHA2).

CD138 is a cell surface heparan sulfate proteoglycan that is essential for maintaining cell morphology and interaction with the surrounding microenvironment (Akl et al. (2015) Oncotarget 6(30):28693-715; Szatmeri et al. (2015) Dis Markers 2015:796052). In general, the loss of CD138 expression in carcinoma cells reduces cell adhesion to the extracellular matrix and enhances cell motility and invasion (Teng et al. (2012) Matrix Biol. 31:3-16). Increased stromal CD138 expression also alters fibronectin production and extracellular matrix organization (Yang et al. (2011) Am J Pathol. 178:325-35). Additionally, increased expression of CD138 in stromal fibroblasts is associated with angiogenesis and cancer progression (Maeda et al. (2006) Oncogene 25:1408-12). CD138 expression increases during B cell development and its presence is a hallmark of plasma cells (Ribatti (2017) Immunol Lett. 188:64-7). CD138 expression is maintained in multiple myeloma, a malignancy of plasma cells. CD138 is therefore an attractive antigen for the targeted treatment of several cancers and other hematological malignancies (Sherbenou et al. (2015) Blood Rev. 29(2): 81-91; Wijdenes et al. (1996) Br J Haematol. 94(2):318-23).

EPHA2 is a transmembrane glycoprotein that is abundantly overexpressed in several malignant cancer-derived cell lines and in advanced forms of cancer (Wykosky and Debinski (2008) Mol Cancer Ref. 6(12):1795-1806). For instance, EPHA2 is strongly overexpressed in approximately 61% of GBM patient tumors (Wykosky et al. (2008) Clin Cancer Res. 14:199-208), 76% of ovarian cancers (Thaker et al. (2004) Clin Cancer Res. 10:5145-50), and 85% of prostate adenocarcinomas (Zeng et al. (2003) Am J Pathol. 163:2271-6). The EPHA2 protein is highly overexpressed with regard to percentage of patient tumors and percentage of cells within a tumor, and is a plasma membrane-localized receptor that can internalize on ligand binding (Walker-Daniels et al. (2002) Mol Cancer Res. 1:79-87). Moreover, expression of EPHA2 is associated with poor prognosis, increased metastasis, and decreased survival. Thus, due to its expression pattern, localization, and functional importance in the outcome of cancer patients, EPHA2 is another attractive antigen for the targeted delivery of novel anti-cancer therapies.

In various embodiments, the present disclosure provides, in part, novel compounds with biological activity against neoplastic cells. The compounds may slow, inhibit, and/or reverse tumor growth in mammals, and may be useful for treating human cancer patients. In various embodiments, the disclosure provides novel antibody-drug conjugates employing the novel compounds or other functional splice inhibitor molecules.

The present disclosure more specifically relates, in various embodiments, to antibody-drug conjugate (ADC) compounds that are capable of binding and killing neoplastic cells. In various embodiments, the ADC compounds disclosed herein comprise a linker that attaches a splicing modulator to a full-length antibody or an antigen binding fragment. In various embodiments, the ADC compounds are also capable of internalizing into a target cell after binding.

In various embodiments, ADC compounds may be represented by Formula (I):

Ab–(L–D)$_p$ (I)

wherein Ab is an antibody or an antigen binding fragment thereof which targets a
neoplastic cell or another oncology-related target;
D is a splicing modulator;
L is a linker which covalently attaches Ab to D; and
p is an integer from 1 to 15.

In various embodiments, ADC compounds may be represented by Formula (I):

Ab–(L–D)$_p$ (I)

wherein Ab is an antibody or an antigen binding fragment thereof which targets a neoplastic cell;
D is a splicing modulator of Formula (II):

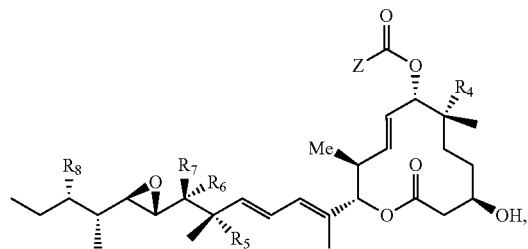

(II)

or a pharmaceutically acceptable salt thereof, wherein:
$R^1$ is chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(=O)—($C_1$-$C_6$ alkyl) groups, and —CD$_3$;
$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups; and
$R^4$, $R^5$, and $R^8$ are each independently chosen from hydrogen, hydroxyl groups, —O—($C_1$-$C_6$ alkyl) groups, —O—C(=O)—($C_1$-$C_6$ alkyl) groups, and $C_1$-$C_6$ alkyl groups;
$R^6$ and $R^7$ are each independently chosen from hydrogen, —O—$R^{17}$, —O—C(=O)—$R^{17}$, —O—C(=O)—NR$^{15}$R$^{16}$, $C_1$-$C_6$ alkyl groups, and —NR$^{15}$R$^{16}$;
$R^{15}$ and $R^{16}$ are each independently chosen from hydrogen, $R^{17}$, —C(=O)—$R^{17}$, and —C(=O)—O—$R^{17}$;
$R^{17}$ is chosen from hydrogen, $C_1$-$C_6$ alkyl groups, $C_3$-$C_8$ cycloalkyl groups, benzyl groups, and $C_3$-$C_8$ heterocyclyl groups; and
Z is chosen from

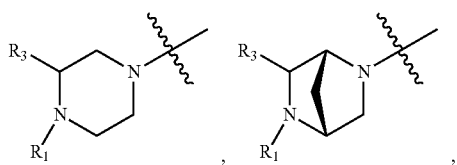

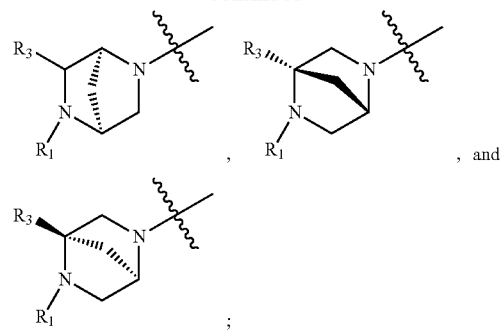

wherein $R^1$, $R^3$, $R^4$, $R^5$, $R^6$, $R^7$, $R^8$, $R^{15}$, $R^{16}$, and $R^{17}$ are each independently substituted with 0 to 3 groups independently chosen from halogens, hydroxyl groups, $C_1$-$C_6$ alkyl groups,
—O—($C_1$-$C_6$ alkyl) groups, —NR$^{15}$R$^{16}$, $C_3$-$C_8$ cycloalkyl groups, $C_1$-$C_6$ alkylhydroxy groups,
$C_1$-$C_6$ alkylalkoxy groups, benzyl groups, and $C_3$-$C_8$ heterocyclyl groups, wherein at least one of $R^6$ and $R^7$ is hydrogen;
and wherein L is a linker which covalently attaches Ab to D; and
p is an integer from 1 to 15.

In some embodiments, the antibody or antigen binding fragment is capable of internalization into a target cell. In some embodiments, the linker covalently attaches to the splicing modulator of Formula (II) ("L–D"), and L–D has a structure of Formula (II-A):

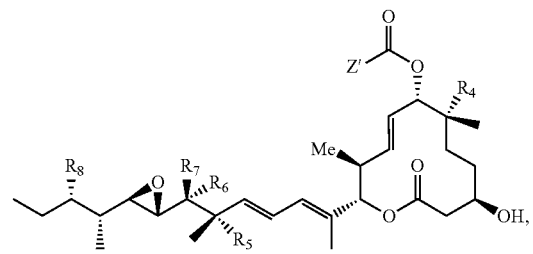

(II-A)

or a pharmaceutically acceptable salt thereof,
wherein Z' is chosen from

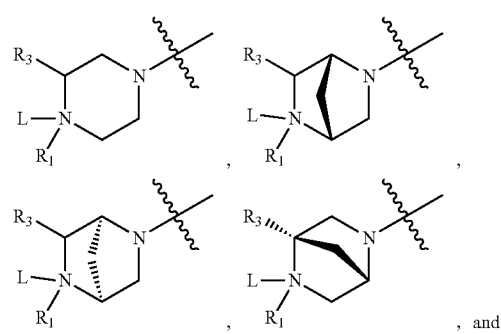

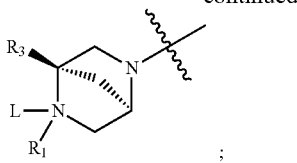

and
wherein all other variables are as defined for Formula (II).

In various other embodiments, ADC compounds may be represented by of Formula (I):

$$Ab-(L-D)_p \qquad (I)$$

wherein Ab is an antibody or an antigen binding fragment thereof which targets a neoplastic cell;
D is a splicing modulator of Formula (IV):

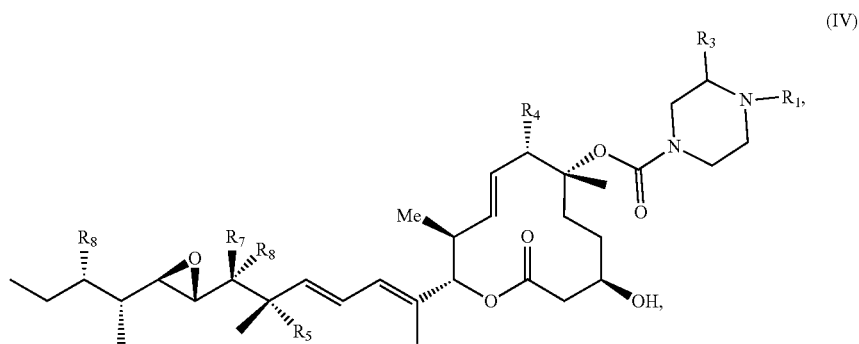

or a pharmaceutically acceptable salt thereof, wherein:

$R^1$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(=O)—($C_1$-$C_6$ alkyl) groups, and —$CD_3$;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups; and $R^4$, $R^5$, and $R^8$ are each independently chosen from hydrogen, hydroxyl groups, —O—($C_1$-$C_6$ alkyl) groups, —O—C(=O)—($C_1$-$C_6$ alkyl) groups, and $C_1$-$C_6$ alkyl groups;

$R^6$ and $R^7$ are each independently chosen from hydrogen, —O—$R^{17}$, —O—C(=O)—$R^{17}$, —O—C(=O)—$NR^{15}R^{16}$, $C_1$-$C$ alkyl groups, and —$NR^{15}R^{16}$;

$R^{15}$ and $R^{16}$ are each independently chosen from hydrogen, $R^{17}$, —C(=O)—$R^{17}$, and —C(=O)—O—$R^{17}$; and $R^{17}$ is chosen from hydrogen, $C_1$-$C_6$ alkyl groups, $C_3$-$C_8$ cycloalkyl groups, benzyl groups, and $C_3$-$C_8$ heterocyclyl groups;

wherein $R^1$, $R^3$, $R^4$, $R^5$, $R^6$, $R^7$, $R^8$, $R^{15}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —$NR^{15}R^{16}$, $C_3$-$C_8$ cycloalkyl groups, $C_1$-$C_6$ alkylhydroxy groups, $C_1$-$C_6$ alkylalkoxy groups, benzyl groups, and $C_3$-$C_8$ heterocyclyl groups, wherein at least one of $R^6$ and $R^7$ is hydrogen;

and wherein L is a linker which covalently attaches Ab to D; and p is an integer from 1 to 15.

In some embodiments, the antibody or antigen binding fragment is capable of internalization into a target cell. In some embodiments, the linker covalently attaches to the splicing modulator ("L-D"), and L-D has a structure of Formula (IV-A):

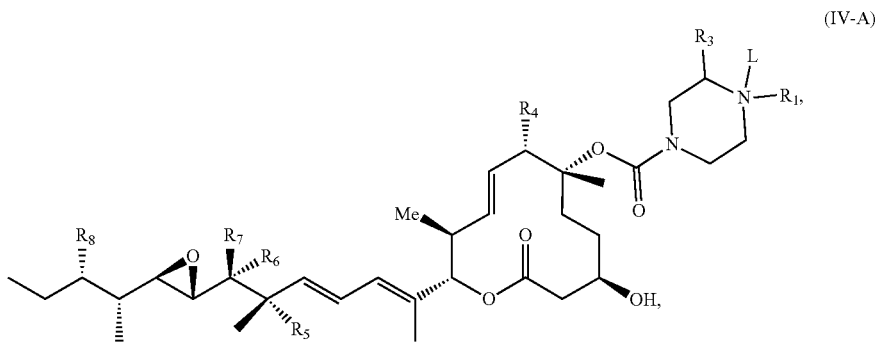

or a pharmaceutically acceptable salt thereof.

In various other embodiments, ADC compounds may be represented by Formula (I):

$$Ab-(L-D)_p \quad (I)$$

wherein Ab is an antibody or an antigen binding fragment thereof which targets a neoplastic cell;
D is a splicing modulator of Formula (VI):

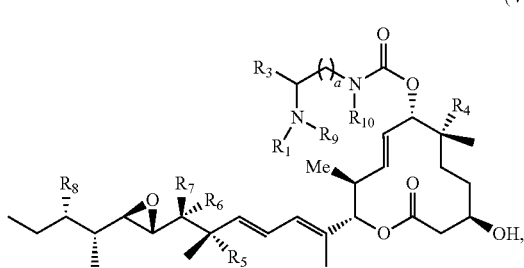

or a pharmaceutically acceptable salt thereof, wherein:
$R^1$ and $R^9$ are each independently chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(=O)—($C_1$-$C_6$ alkyl) groups, and —CD$_3$;
$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups;
$R^4$, $R^5$, and $R^8$ are each independently chosen from hydrogen, hydroxyl groups, —O—($C_1$-$C_6$ alkyl) groups, —O—C(=O)—($C_1$-$C_6$ alkyl) groups, and $C_1$-$C_6$ alkyl groups;
$R^6$ and $R^7$ are each independently chosen from hydrogen, —O—$R^{17}$, —O—C(=O)—$R^{17}$, —O—C(=O)—NR$^{15}$R$^{16}$, $C_1$-$C_6$alkyl groups, —NR$^{15}$R$^{16}$, and a linker;
$R^{10}$ is chosen from hydrogen, $C_1$-$C_6$ alkyl groups, —C(=O)—($C_1$-$C_6$ alkyl) groups, and —CD3;
$R^{15}$ and $R^{16}$ are each independently chosen from hydrogen, $R^{17}$, —C(=O)—$R^{17}$, and —C(=O)—O—$R^{17}$;

$R^{17}$ is chosen from hydrogen, $C_1$-$C_6$ alkyl groups, $C_3$-$C_8$ cycloalkyl groups, benzyl groups, and $C_3$-$C_8$ heterocyclyl groups; and a is 1, 2, 3, 4, 5, 6, 7, 8, 9, or 10;

wherein $R^1$, $R^3$, $R^4$, $R^5$, $R^6$, $R^7$, $R^8$, $R^9$, $R^{10}$, $R^{15}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —NR$^{15}$R$^{16}$, $C_3$-$C_a$ cycloalkyl groups, $C_1$-$C_6$ alkylhydroxy groups, $C_1$-$C_6$ alkylalkoxy groups, benzyl groups, and $C_3$-$C_8$ heterocyclyl groups;

wherein at least one of $R^6$ and $R^7$ is hydrogen; and wherein $R^1$ and $R^9$ cannot both be absent;

and wherein L is a linker which covalently attaches Ab to D; and p is an integer from 1 to 15.

In some embodiments, the antibody or antigen binding fragment is capable of internalization into a target cell. In some embodiments, the linker covalently attaches to the splicing modulator ("L-D"), and L-D has a structure of Formula (VI-A):

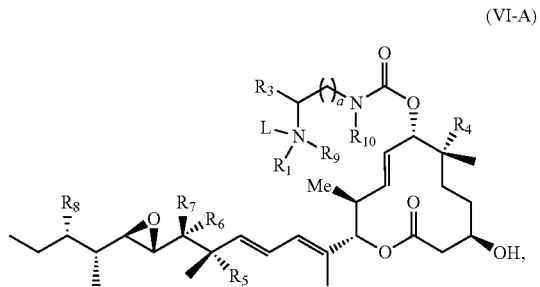

or a pharmaceutically acceptable salt thereof.

In various other embodiments, ADC compounds may be represented by Formula (I):

$$Ab-(L-D)_p \quad (I)$$

wherein Ab is an antibody or an antigen binding fragment thereof which targets a neoplastic cell;

D is a splicing modulator of Formula (VIII):

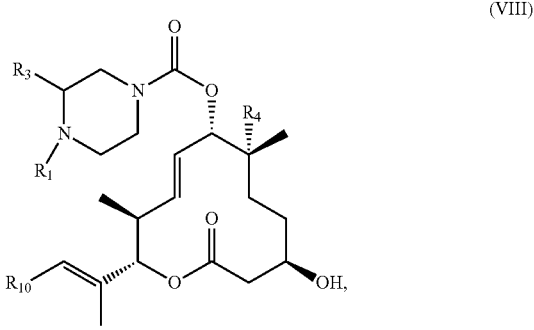

(VIII)

or a pharmaceutically acceptable salt thereof, wherein:
- $R^1$ is chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(=O)—($C_1$-$C_6$ alkyl) groups, and —$CD_3$;
- $R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups;
- $R^4$ is chosen from hydrogen, hydroxyl groups, —O—($C_1$-$C_6$ alkyl) groups, —O—C(=O)—($C_1$-$C_6$ alkyl) groups, and $C_1$-$C_6$ alkyl groups; and
- $R^{10}$ is chosen from 3 to 10 membered carbocycles and 3 to 10 membered heterocycles, each of which is substituted with 0 to 3 $R^a$, wherein each $R^a$ is independently chosen from halogens, $C_1$-$C_6$ alkyl groups, —O—($C_1$-$C_6$)alkyl groups, $C_1$-$C_6$ alkylalkoxy groups, $C_1$-$C_6$ alkylhydroxy groups, —S(=O)$_w$-(4 to 7 membered heterocycles), 4 to 7 membered carbocycles, and 4 to 7 membered heterocycles;
- $R^{15}$ and $R^{16}$ are each independently chosen from hydrogen, $R^{17}$, —C(=O)—$R^{17}$, and —C(=O)—O—$R^{17}$; and
- $R^{17}$ is chosen from hydrogen, $C_1$-$C_6$ alkyl groups, $C_3$-$C_8$ cycloalkyl groups, benzyl groups, and $C_3$-$C_8$ heterocyclyl groups;
- wherein $R^1$, $R^3$, $R^4$, $R^{10}$, $R^{15}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —$NR^{15}R^{16}$, $C_3$-$C_8$ cycloalkyl groups, $C_1$-$C_6$ alkylhydroxy groups, $C_1$-$C_6$ alkylalkoxy groups, benzyl groups, and $C_3$-$C_8$ heterocyclyl groups; and
- wherein each $R^a$ is independently substituted with 0 to 3 groups independently chosen from halogens, hydroxyl groups, —$NR^{15}R^{16}$, $C_1$-$C_6$ alkyl groups, —(C=O)—($C_1$-$C_6$ alkyl) groups, —(C=O)—($C_1$-$C_6$ alkyl)-($C_3$-$C_{10}$ heterocyclyl groups), —S(=O)$_w$—($C_3$-$C_3$ heterocyclyl) groups, and $C_1$-$C_6$ alkylcarboxylic acid groups, each of which is substituted with 0, 1, or 2 groups independently chosen from halogens, hydroxyl groups, —$NR^{15}R^{16}$, and $C_1$-$C_3$ alkyl groups; and
- w is 0, 1, or 2;

and wherein L is a linker which covalently attaches Ab to D; and
p is an integer from 1 to 15.

In some embodiments, the antibody or antigen binding fragment is capable of internalization into a target cell. In some embodiments, the linker covalently attaches to the splicing modulator ("L–D"), and L–D has a structure of Formula (VIII-A):

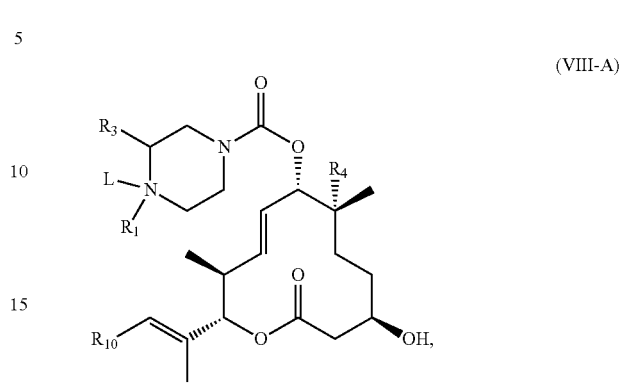

(VIII-A)

or a pharmaceutically acceptable salt thereof.

In some embodiments, the splicing modulator comprises a modulator of the SF3b complex.

In some embodiments, the splicing modulator comprises a pladienolide or a pladienolide derivative. In some embodiments, the splicing modulator comprises pladienolide D or a pladienolide D derivative. In some embodiments, the pladienolide D or derivative comprises D2, D1, D4, D8, D10, D11 (E7107), D20, D21, D22, D12, or D25. In some embodiments, the pladienolide D or derivative comprises D2. In some embodiments, the pladienolide D or derivative comprises D1. In some embodiments, the pladienolide D or derivative comprises D4. In some embodiments, the pladienolide D or derivative comprises D12.

In some embodiments, the pladienolide D or derivative is a zwitterionic pladienolide D or derivative. In some embodiments, the zwitterionic pladienolide D or derivative comprises D22 or D25.

In some other embodiments, the splicing modulator comprises pladienolide B or a pladienolide B derivative. In some embodiments, the pladienolide B or derivative comprises D9, D18, D19, or D13.

In some embodiments, the splicing modulator comprises an aryl pladienolide. In some embodiments, the aryl pladienolide comprises D15, D14, D16, D17, D26, or D33. In some embodiments, the aryl pladienolide comprises D15. In some embodiments, the aryl pladienolide is a zwitterionic aryl pladienolide. In some embodiments, the zwitterionic aryl pladienolide comprises D33.

In some embodiments, the splicing modulator comprises D1:

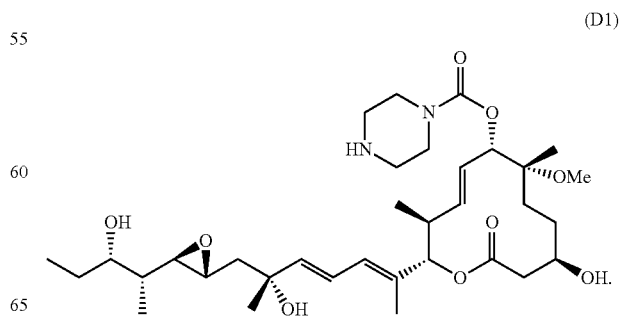

(D1)

In some embodiments, the splicing modulator comprises D2:
(D2)
In some embodiments, the splicing modulator comprises D3:
In some embodiments, the splicing modulator comprises D4:
(D4)
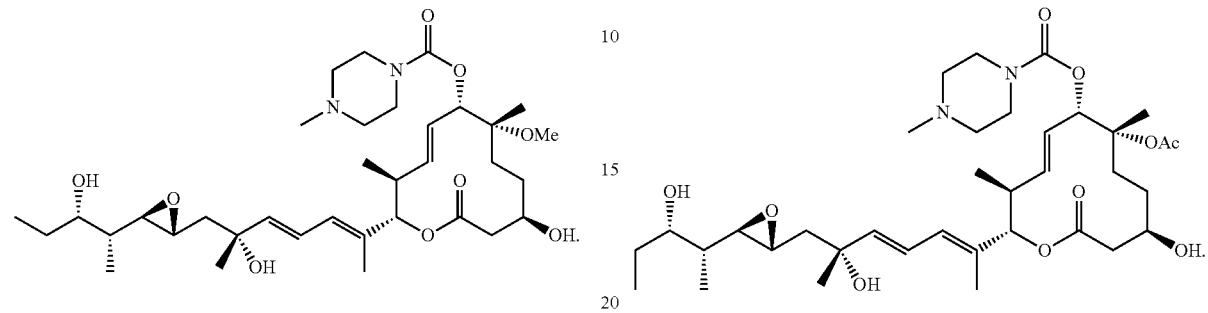
In some embodiments, the splicing modulator comprises D4':
(D4')
In some embodiments, the splicing modulator comprises D5:
(D5)
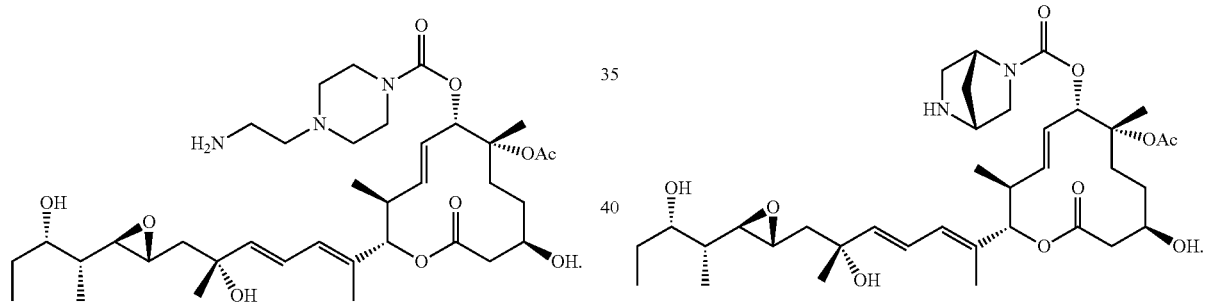
In some embodiments, the splicing modulator comprises D6:
(D6)
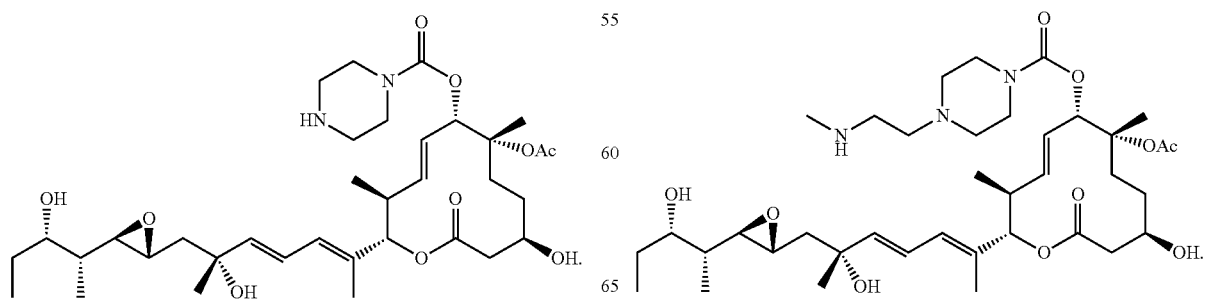

In some embodiments, the splicing modulator comprises D7:
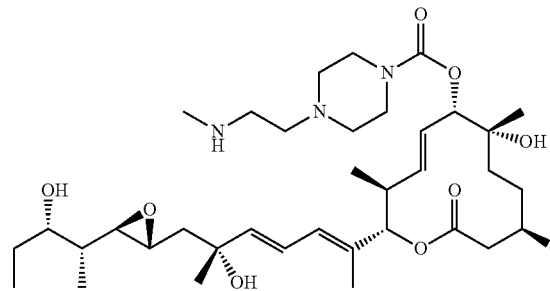
(D7)
In some embodiments, the splicing modulator comprises D8:
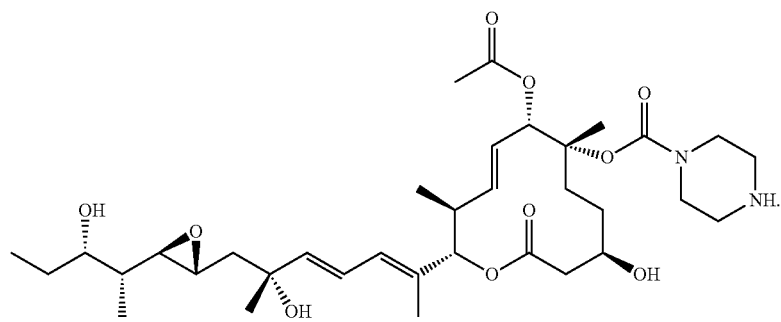
(D8)
In some embodiments, the splicing modulator comprises D9:
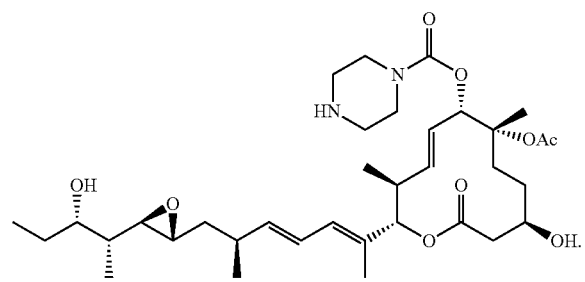
(D9)
In some embodiments, the splicing modulator comprises D10:
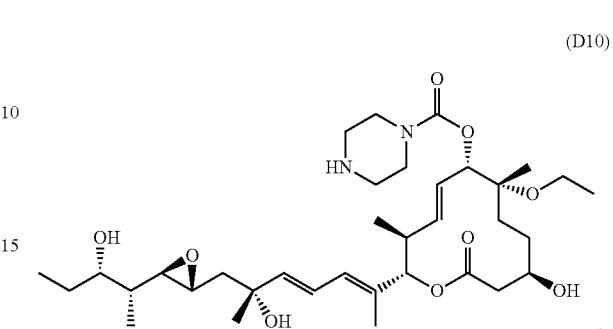
(D10)
In some embodiments, the splicing modulator comprises D11:
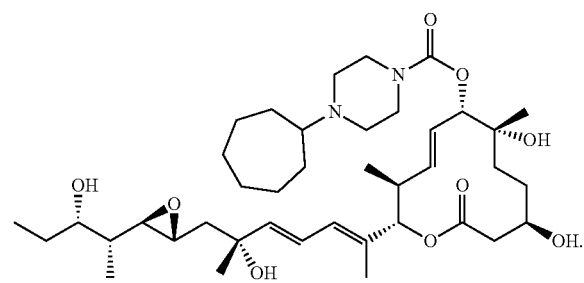
(D11)

In some embodiments, the splicing modulator comprises D12:
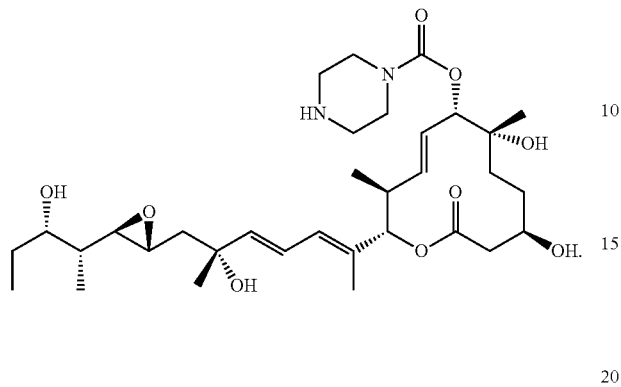
(D13)
In some embodiments, the splicing modulator comprises D13:
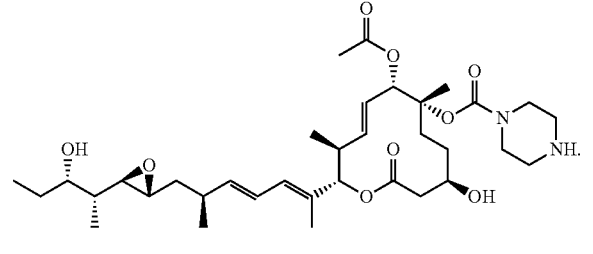
(D13)
In some embodiments, the splicing modulator comprises D14:
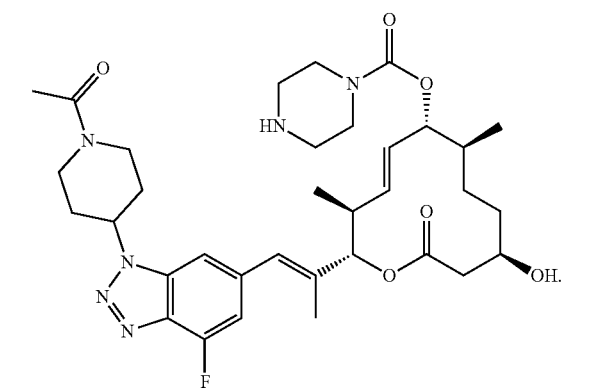
(D14)
In some embodiments, the splicing modulator comprises D15:
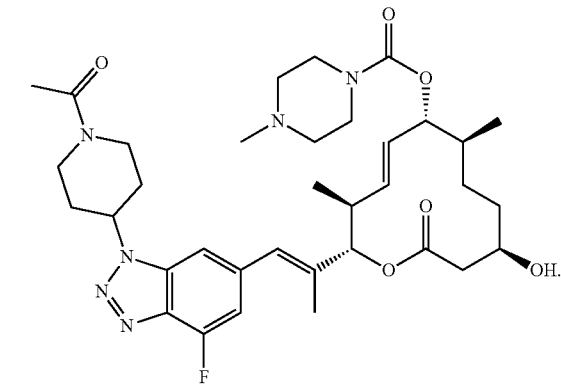
(D15)
In some embodiments, the splicing modulator comprises D16:
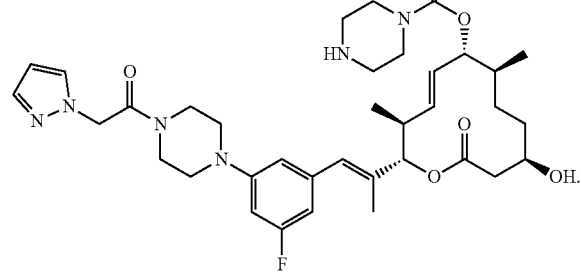
(D16)
In some embodiments, the splicing modulator comprises D17:
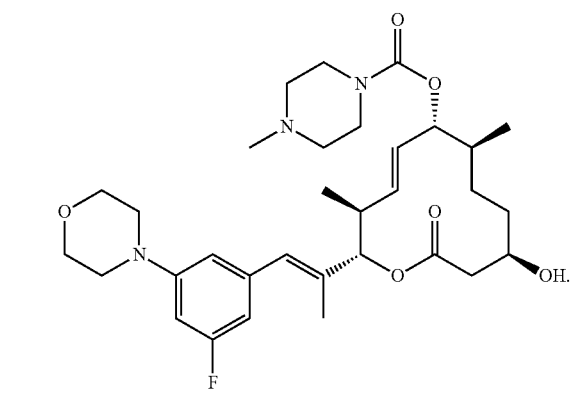
(D17)

In some embodiments, the splicing modulator comprises D18:
(D18)
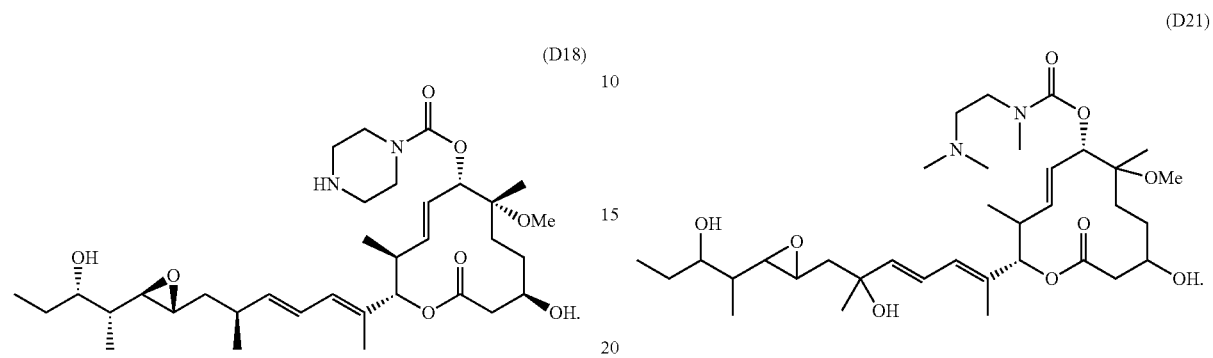
In some embodiments, the splicing modulator comprises D19:
(D19)
In some embodiments, the splicing modulator comprises 020:
(D20)
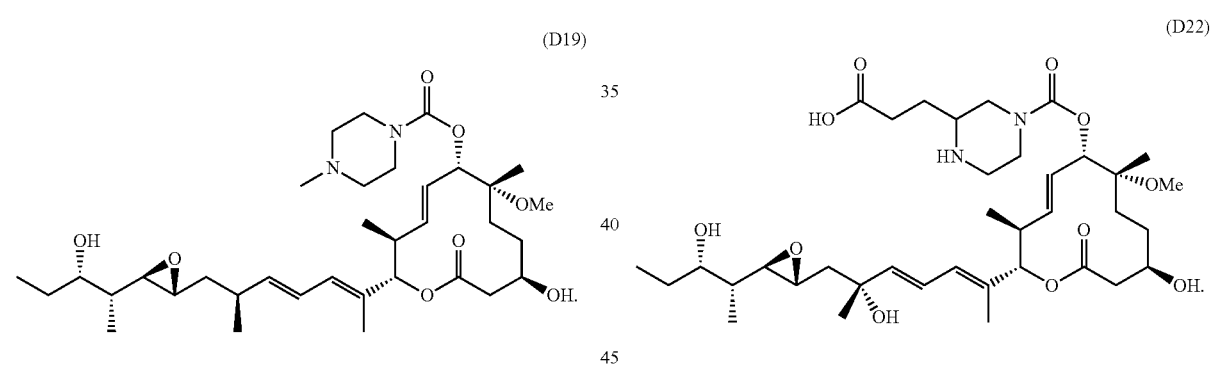
In some embodiments, the splicing modulator comprises D21:
(D21)
In some embodiments, the splicing modulator comprises D22:
(D22)
In some embodiments, the splicing modulator comprises D23:
(D23)
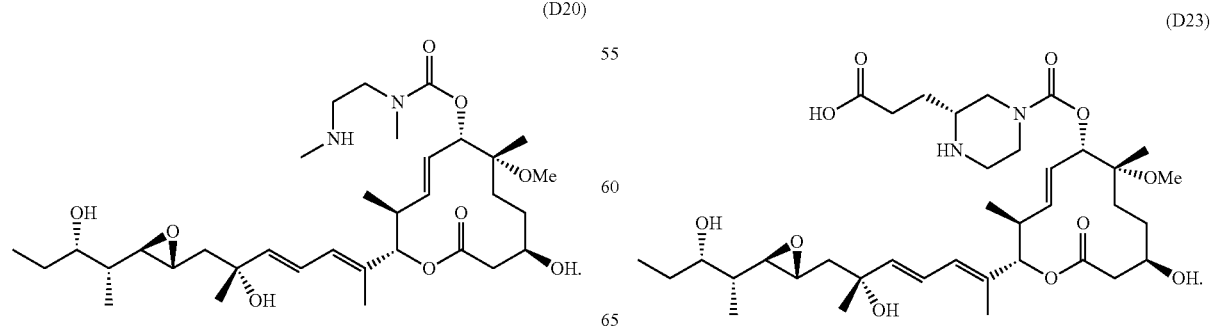

In some embodiments, the splicing modulator comprises D24:
(D24)
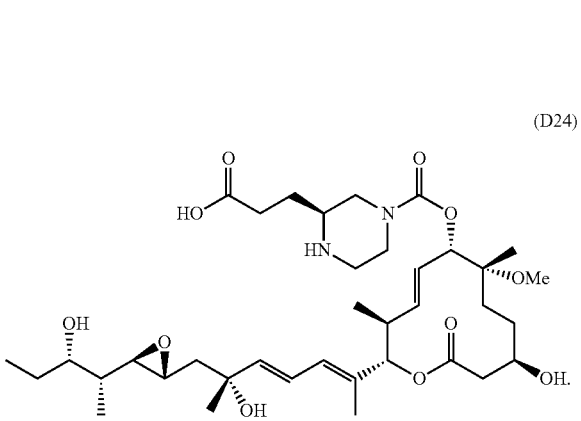 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN[C@@H](CCC(=O)O)C2)/C=C/[C@@H]1C]
In some embodiments, the splicing modulator comprises D25:
(D25)
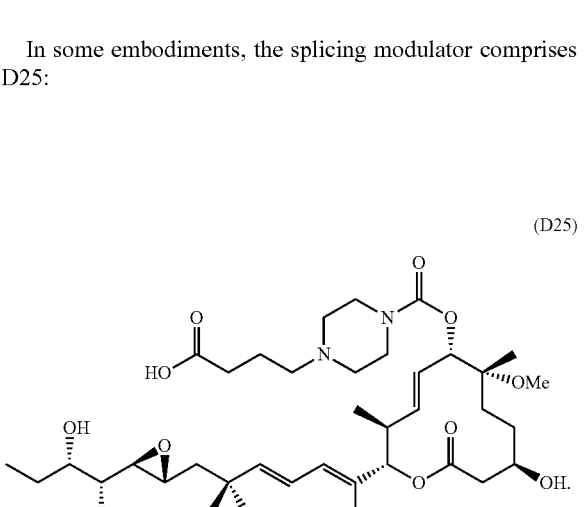
In some embodiments, the splicing modulator comprises D26:
(D26)
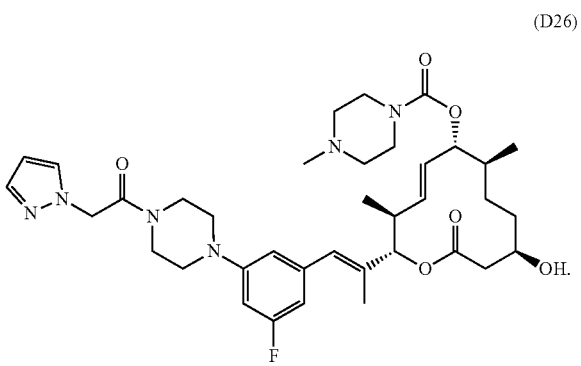 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CCN(C)CC2)/C=C/[C@@H]1C]
In some embodiments, the splicing modulator comprises D27:
(D27)
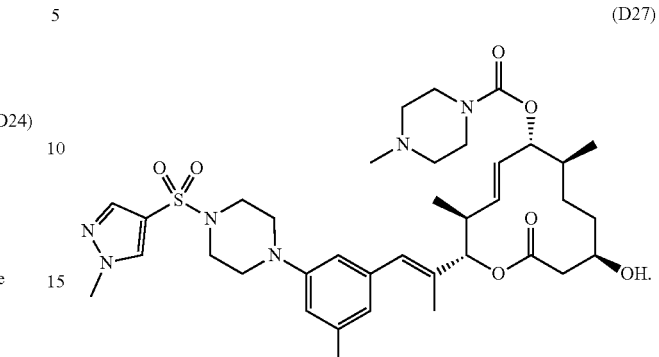
In some embodiments, the splicing modulator comprises D28:
(D28)
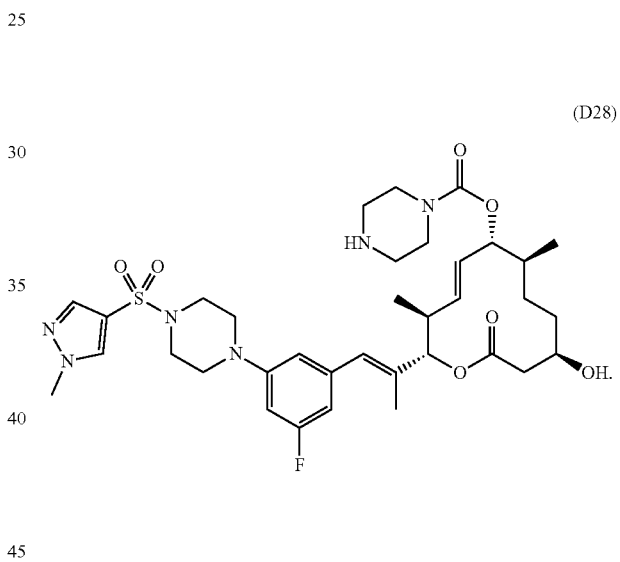
In some embodiments, the splicing modulator comprises D29:
(D29)
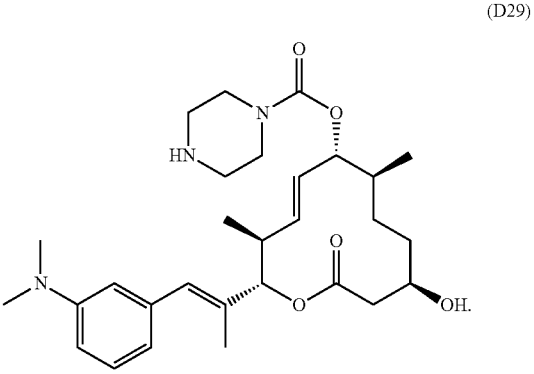 [SMILES: C/C(=C\c1cccc(N(C)C)c1)[C@H]1OC(=O)C[C@H](O)CC[C@H](C)[C@@H](OC(=O)N2CCNCC2)/C=C/[C@@H]1C]

In some embodiments, the splicing modulator comprises D30:

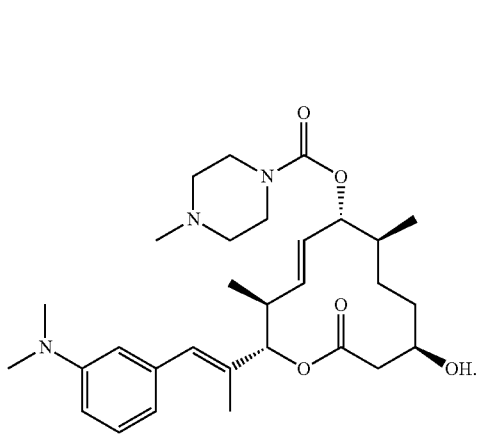
(D30)

In some embodiments, the splicing modulator comprises D31:

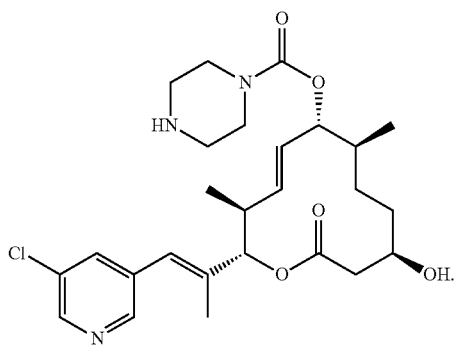
(D31)

In some embodiments, the splicing modulator comprises D32:

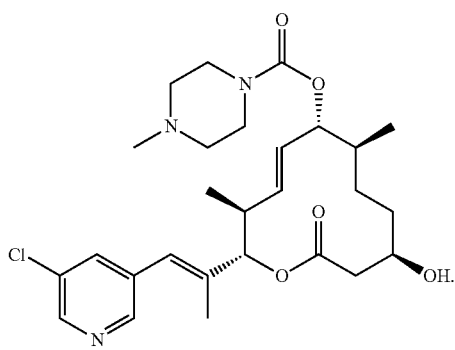
(D32)

In some embodiments, the splicing modulator comprises D33:

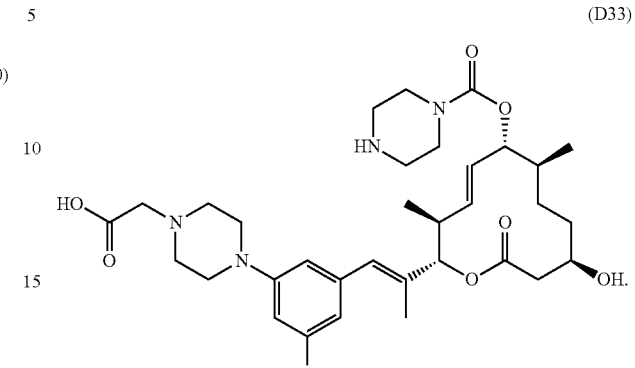
(D33)

In some embodiments, the splicing modulator comprises D34:

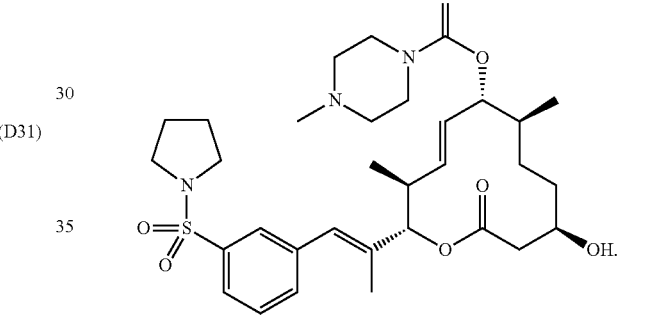
(D34)

In some embodiments, the splicing modulator comprises D35:

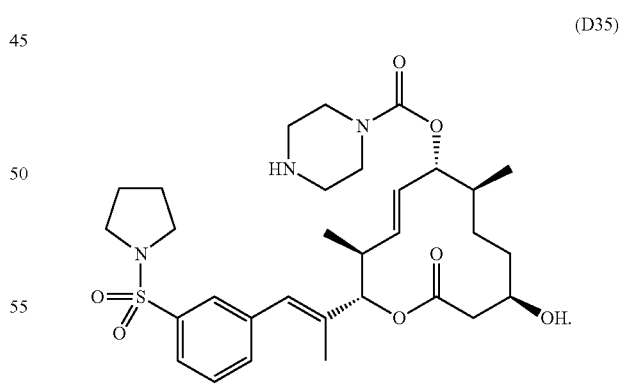
(D35)

In some embodiments, the splicing modulator comprises one of the drug moieties listed in Table 7. In some embodiments, the splicing modulator comprises D1, D2, D3, D4, D4', D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, and/or D35.

In some embodiments, a splicing modulator is disclosed, as well as its use as a therapeutic alone or as part of an ADC.

In some embodiments, the splicing modulator comprises D4, D4', D12, D15, D8, D9, D10, D13, D18, D19, D20, D21, D22, D25, or D33.

In some embodiments, the splicing modulator comprises D4 and the linker comprises MC-Val-Cit-pABC. In some embodiments, the splicing modulator comprises D4 and the linker comprises MC-β-glucuronide. In some embodiments, the splicing modulator comprises D12 and the linker comprises MC-Val-Cit-pABC. In some embodiments, the splicing modulator comprises D12 and the linker comprises MC-β-glucuronide. In some embodiments, the splicing modulator comprises D15 and the linker comprises MC-Val-Ala-pAB.

In various embodiments, the linker used in an ADC disclosed herein is stable outside a cell, such that the ADC remains intact when present in extracellular conditions, but is capable of being cleaved upon internalization into a cell, e.g., a tumor or cancer cell. In some embodiments, the splicing modulator is cleaved from the antibody or antigen binding fragment when the ADC enters a cell that expresses an antigen targeted by the antibody or antigen binding fragment of the ADC. In some embodiments, the linker is a cleavable linker.

In some embodiments, the linker comprises a cleavable peptide moiety. In some embodiments, the cleavable peptide moiety is cleavable by an enzyme. In some embodiments, the cleavable peptide moiety or linker comprises an amino acid unit. In some embodiments, the amino acid unit comprises valine-citrulline ("Val-Cit" or "VC").

In some other embodiments, the amino acid unit comprises valine-alanine ("Val-Ala" or "VA"). In some other embodiments, the amino acid unit comprises glutamic acid-valine-citrulline ("Glu-Val-Cit" or "EVC"). In some other embodiments, the amino acid unit comprises alanine-alanine-asparagine ("Ala-Ala-Asn" or "AAN").

In some embodiments, the linker comprises a cleavable glucuronide moiety. In some embodiments, the cleavable glucuronide moiety is cleavable by an enzyme. In some embodiments, the cleavable glucuronide moiety is cleavable by a glucuronidase.

In some embodiments, the cleavable glucuronide moiety is cleavable by β-glucuronidase.

In some embodiments, the linker comprises at least one spacer unit. In some embodiments, the spacer unit or linker comprises a polyethylene glycol (PEG) moiety.

In some embodiments, the PEG moiety comprises -(PEG)$_m$- and m is an integer from 1 to 10. In some embodiments, m is 2. In some other embodiments, the spacer unit or linker comprises an alkyl moiety. In some embodiments, the alkyl moiety comprises —(CH$_2$)$_n$- and n is an integer from 1 to 10. In some embodiments, n is 2. In some embodiments, n is 5. In some embodiments, n is 6.

In some embodiments, the spacer unit attaches to the antibody or antigen binding fragment via a maleimide (Mal) moiety ("Mal-spacer unit"). In some embodiments, the Mal-spacer unit is reactive with a cysteine residue on the antibody or antigen binding fragment. In some embodiments, the Mal-spacer unit is joined to the antibody or antigen binding fragment via a cysteine residue on the antibody or antigen binding fragment.

In some embodiments, the linker comprises the Mal-spacer unit and a cleavable peptide moiety. In some embodiments, the cleavable peptide moiety comprises an amino acid unit. In some embodiments, the cleavable peptide moiety or amino acid unit comprises Val-Cit. In some embodiments, the cleavable peptide moiety or amino acid unit comprises Val-Ala. In some embodiments, the cleavable peptide moiety or amino acid unit comprises Glu-Val-Cit. In some embodiments, the cleavable peptide moiety or amino acid unit comprises Ala-Ala-Asn. In some embodiments, the Mal-spacer unit comprises an alkyl moiety. In some embodiments, the Mal-spacer unit comprises a PEG moiety. In some embodiments, the Mal-spacer unit comprises a maleimidocaproyl (MC).

In some embodiments, the Mal-spacer unit attaches the antibody or antigen binding fragment to the cleavable moiety in the linker. In some embodiments, the cleavable moiety in the linker comprises a cleavable peptide moiety. In some embodiments, the cleavable peptide moiety comprises an amino acid unit. In some embodiments, the cleavable peptide moiety or amino acid unit comprises Val-Cit, Val-Ala, Glu-Val-Cit, or Ala-Ala-Asn. In some embodiments, the linker comprises MC-Val-Cit. In some embodiments, the linker comprises MC-Val-Ala. In some embodiments, the linker comprises MC-Glu-Val-Cit. In some embodiments, the linker comprises MC-Ala-Ala-Asn. In some embodiments, the Mal-spacer unit comprises an alkyl moiety. In some embodiments, the Mal-spacer unit comprises a PEG moiety. In some embodiments, the Mal-spacer unit comprises a maleimidocaproyl (MC).

In some embodiments, the cleavable moiety in the linker is directly joined to the splicing modulator, or a spacer unit attaches the cleavable moiety in the linker to the splicing modulator. In some embodiments, cleavage of the conjugate releases the splicing modulator from the antibody or antigen binding fragment and linker. In some embodiments, the spacer unit attaching the cleavable moiety in the linker to the splicing modulator is self-immolative.

In some embodiments, the spacer unit attaching the cleavable moiety in the linker to the splicing modulator comprises a β-aminobenzyloxycarbonyl (pABC). In some embodiments, the pABC attaches the cleavable moiety in the linker to the splicing modulator. In some embodiments, the cleavable moiety in the linker comprises a cleavable peptide moiety. In some embodiments, the cleavable peptide moiety comprises an amino acid unit. In some embodiments, the cleavable peptide moiety or amino acid unit comprises Val-Cit, Val-Ala, Glu-Val-Cit, or Ala-Ala-Asn. In some embodiments, the linker comprises Val-Cit-pABC. In some other embodiments, the linker comprises Val-Ala-pABC. In some embodiments, the linker comprises Glu-Val-Cit-pABC. In some embodiments, the linker comprises Ala-Ala-Asn-pABC.

In some embodiments, the spacer unit attaching the cleavable moiety in the linker to the splicing modulator comprises a β-aminobenzyl (pAB). In some embodiments, the pAB attaches the cleavable moiety in the linker to the splicing modulator. In some embodiments, the cleavable moiety in the linker comprises a cleavable peptide moiety. In some embodiments, the cleavable peptide moiety comprises an amino acid unit. In some embodiments, the cleavable peptide moiety or amino acid unit comprises Val-Cit, Val-Ala, Glu-Val-Cit, or Ala-Ala-Asn. In some embodiments, the linker comprises Val-Cit-pAB. In some other embodiments, the linker comprises Val-Ala-pAB. In some other embodiments, the linker comprises Glu-Val-Cit-pAB. In some other embodiments, the linker comprises Ala-Ala-Asn-pAB.

In various embodiments, the linker is a non-cleavable linker. In some embodiments, the splicing modulator of the ADC is released by degradation of the antibody or antigen binding fragment. In some embodiments, the linker remains covalently associated with at least one amino acid of the antibody and drug upon internalization by and degradation within the target cell.

In some embodiments, the linker is a non-cleavable linker comprising at least one spacer unit. In some embodiments, the spacer unit or linker comprises a polyethylene glycol (PEG) moiety. In some embodiments, the PEG moiety comprises -(PEG)$_m$- and m is an integer from 1 to 10. In some embodiments, m is 2. In some other embodiments, the spacer unit or linker comprises an alkyl moiety. In some embodiments, the alkyl moiety comprises —(CH$_2$)$_n$- or —(CH$_2$)$_n$-O—(CH$_2$)$_n$ and n is an integer from 1 to 10. In some embodiments, n is 2. In some embodiments, n is 5. In some embodiments, n is 6.

In some embodiments, the spacer unit in a non-cleavable linker attaches to the antibody or antigen binding fragment via a maleimide (Mal) moiety ("Mal-spacer unit").

In some embodiments, the Mal-spacer unit is reactive with a cysteine residue on the antibody or antigen binding fragment. In some embodiments, the Mal-spacer unit is joined to the antibody or antigen binding fragment via a cysteine residue on the antibody or antigen binding fragment. In some embodiments, the Mal-spacer unit comprises an alkyl moiety. In some embodiments, the Mal-spacer unit comprises a PEG moiety. In some embodiments, the linker or Mal-spacer unit comprises a maleimidocaproyl (MC).

In some embodiments, the linker or Mal-spacer unit comprises a maleimidocaproyl (MC) and at least one additional spacer unit. In some embodiments, the linker or Mal-spacer unit comprises MC-(PEG)$_2$. In some embodiments, the linker or Mal-spacer unit comprises MC-(PEG)$_2$ and at least one additional spacer unit. In some embodiments, the linker or Mal-spacer unit comprises Mal-Hex. In some embodiments, the linker or Mal-spacer unit comprises Mal-Hex and at least one additional spacer unit. In some embodiments, the linker or Mal-spacer unit comprises Mal-Et. In some embodiments, the linker or Mal-spacer unit comprises Mal-Et and at least one additional spacer unit.

In some embodiments, the linker or Mal-spacer unit comprises Mal-Et-O-Et. In some embodiments, the linker or Mal-spacer unit comprises Mal-Et-O-Et and at least one additional spacer unit. In some embodiments, the Mal-spacer unit attaches the antibody or antigen binding fragment to the splicing modulator.

In various embodiments, ADC compounds may be represented by Formula (I):

$$Ab-(L-D)_p \quad (I)$$

wherein Ab is an antibody or an antigen binding fragment thereof which targets a neoplastic cell or another oncology-related target such as a cancer antigen (e.g., any of the antibody or binding domain sequences disclosed herein); D is any small molecule suitable for treating a cancer (e.g., a splicing modulator, e.g., any of the splicing modulators disclosed herein); L is a linker which covalently attaches Ab to D (e.g., any of the linkers disclosed herein); and p is an integer from 1 to 15.

In some embodiments, Ab is selected from any of the antibody or binding domain sequences disclosed herein. In some embodiments, Ab is an antibody or binding domain sequence which targets HER2 and/or a HER2-expressing neoplastic cell. In some embodiments, Ab is an antibody or binding domain sequence which targets CD138 and/or a CD138-expressing neoplastic cell. In some embodiments, Ab is an antibody or binding domain sequence which targets EPHA2 and/or an EPHA2-expressing neoplastic cell. In some embodiments, Ab is an antibody or binding domain sequence which targets MSLN and/or a MSLN-expressing neoplastic cell. In some embodiments, Ab is an antibody or binding domain sequence which targets FOLH1 and/or a FOLH1-expressing neoplastic cell. In some embodiments, Ab is an antibody or binding domain sequence which targets CDH6 and/or a CDH6-expressing neoplastic cell. In some embodiments, Ab is an antibody or binding domain sequence which targets CEACAM5 and/or a CEACAM5-expressing neoplastic cell. In some embodiments, Ab is an antibody or binding domain sequence which targets CFC1B and/or a CFC1B-expressing neoplastic cell. In some embodiments, Ab is an antibody or binding domain sequence which targets ENPP3 and/or an ENPP3-expressing neoplastic cell. In some embodiments, Ab is an antibody or binding domain sequence which targets FOLR1 and/or a FOLR1-expressing neoplastic cell. In some embodiments, Ab is an antibody or binding domain sequence which targets HAVCR1 and/or a HAVCR1-expressing neoplastic cell. In some embodiments, Ab is an antibody or binding domain sequence which targets KIT and/or a KIT-expressing neoplastic cell.

In some embodiments, Ab is an antibody or binding domain sequence which targets MET and/or a MET-expressing neoplastic cell. In some embodiments, Ab is an antibody or binding domain sequence which targets MUC16 and/or a MUC16-expressing neoplastic cell. In some embodiments, Ab is an antibody or binding domain sequence which targets SLC39A6 and/or a SLC39A6-expressing neoplastic cell. In some embodiments, Ab is an antibody or binding domain sequence which targets SLC44A4 and/or a SLC44A4-expressing neoplastic cell. In some embodiments, Ab is an antibody or binding domain sequence which targets STEAP1 and/or a STEAP1-expressing neoplastic cell. In some embodiments, Ab is an antibody or binding domain sequence which targets another cancer antigen.

In some embodiments, D is a splicing modulator. In some embodiments, D is selected from any of the splicing modulators disclosed herein. In some embodiments, D is a splicing modulator selected from D2, D1, D4, D8, D10, D11 (E7107), D20, D21, D22, D12, D25, D9, D18, D19, D13, D15, D14, D16, D17, D26, and D33, or any derivative thereof. In some embodiments, D is a splicing modulator selected from D4, D12, D15, D8, D9, D10, D13, D18, D19, D20, D21, D22, D25, and D33, or any derivative thereof. In some embodiments, D is a splicing modulator comprising D2 or any derivative thereof. In some embodiments, D is a splicing modulator comprising D1 or any derivative thereof.

In some embodiments, L is selected from any of the linkers disclosed herein, or any combination of linker components disclosed herein. In some embodiments, L is a linker comprising MC-Val-Cit-pABC, Mal-(PEG)$_2$-CO, MC-Val-Ala-pAB, MC-Val-Ala-pABC, MC-Val-Cit-pAB, Mal-Hex, Mal-Et, or Mal-Et-O-Et. In some embodiments, the linker may also comprise one or more additional spacer units. In some embodiments, L is an ADL1, ADL2, ADL5, ADL6, ADL7, ADL10, ADL12, ADL13, ADL14, ADL15, ADL21, ADL22, or ADL23 linker. In some embodiments, L is an ADL1, ADL2, ADL5, ADL6, ADL7, ADL12, ADL13, ADL14, ADL21, ADL23, or ADL15 linker. In some embodiments, L is an ADL12, ADL14, or ADL15 linker. In some embodiments, the ADL1, ADL2, ADL5, ADL6, ADL7, ADL12, ADL13, ADL14, ADL21, ADL23, or ADL15 linker may also comprise one or more additional spacer units. In some embodiments, L is an ADL1 linker and may optionally comprise one or more additional spacer units. In some embodiments, L is an ADL2 linker and may optionally comprise one or more additional spacer units. In some embodiments, L is an ADL5 linker and may optionally comprise one or more additional spacer units. In some embodiments, L is an ADL6 linker and may optionally comprise one or more additional spacer units. In some embodiments, L is an ADL7 linker and may optionally comprise one or more additional spacer units. In some embodiments, L is an ADL12 linker and may optionally comprise one or more additional spacer units. In some embodiments, L is an ADL14 linker and may optionally comprise one or more additional spacer units. In some embodiments, L is an ADL15 linker and may optionally comprise one or more additional spacer units. In various embodiments of the ADCs described herein, p is from 1 to 10. In various embodiments, p is from 2 to 8. In various embodiments, p is from 4 to 8. In some embodiments, p is 4. In some embodiments, p is 8.

In some embodiments, L–D of Formula (I) is ADL1-D1. In some embodiments, L–D of Formula (I) is ADL6-D1. In some embodiments, L–D of Formula (I) is ADL5-D2. In some embodiments, L–D of Formula (I) is ADL1-D18. In some embodiments, L–D of Formula (I) is ADL5-D19. In some embodiments, L–D of Formula (I) is ADL14-D1. In some embodiments, L–D of Formula (I) is ADL12-D1. In some embodiments, L–D of Formula (I) is ADL15-D1. In some embodiments, L–D of Formula (I) is ADL12-D20. In some embodiments, L–D of Formula (I) is ADL10-D1. In some embodiments, L–D of Formula (I) is ADL12-D2. In some embodiments, L–D of Formula (I) is ADL15-D2. In some embodiments, L–D of Formula (I) is ADL12-D21. In some embodiments, L–D of Formula (I) is ADL6-D9. In some embodiments, L–D of Formula (I) is ADL1-D4. In some embodiments, L–D of Formula (I) is ADL1-D3. In some embodiments, L–D of Formula (I) is ADL1-D12. In some embodiments, L–D of Formula (I) is ADL1-D7. In some embodiments, L–D of Formula (I) is ADL1-D6. In some embodiments, L–D of Formula (I) is ADL1-D5. In some embodiments, L–D of Formula (I) is ADL22-D4. In some embodiments, L–D of Formula (I) is ADL5-D10. In some embodiments, L–D of Formula (I) is ADL5-D11. In some embodiments, L–D of Formula (I) is ADL1-D13. In some embodiments, L–D of Formula (I) is ADL1-D8. In some embodiments, L–D of Formula (I) is ADL1-D22. In some embodiments, L–D of Formula (I) is ADL5-D25. In some embodiments, L–D of Formula (I) is ADL12-D22. In some embodiments, L–D of Formula (I) is ADL5-D15. In some embodiments, L–D of Formula (I) is ADL1-D14. In some embodiments, L–D of Formula (I) is ADL5-D26. In some embodiments, L–D of Formula (I) is ADL1-D16. In some embodiments, L–D of Formula (I) is ADL5-D17. In some embodiments, L–D of Formula (I) is ADL1-D33. In some embodiments, L–D of Formula (I) is ADL1-D28. In some embodiments, L–D of Formula (I) is ADL1-D31. In some embodiments, L–D of Formula (I) is ADL1-D29. In some embodiments, L–D of Formula (I) is ADL1-D35. In some embodiments, L–D of Formula (I) is ADL5-D32. In some embodiments, L–D of Formula (I) is ADL5-D27. In some embodiments, L–D of Formula (I) is ADL12-D35. In some embodiments, L–D of Formula (I) is ADL12-D28. In some embodiments, L–D of Formula (I) is ADL1-D23. In some embodiments, L–D of Formula (I) is ADL1-D24.

In some embodiments, a pool of ADCs is provided whereby random conjugation occurs, and the average p in the pool is between about 2 and about 8. In some embodiments, a pool of ADCs is provided whereby random conjugation occurs, and the average p in the pool is between about 4 and about 8. In some embodiments, a pool of ADCs is provided whereby random conjugation occurs, and the average p in the pool is about 4. In some embodiments, a pool of ADCs is provided whereby random conjugation occurs, and the average p in the pool is about 8. Compositions (e.g., pharmaceutical compositions) comprising multiple copies of any of the described ADCs, wherein the average drug loading (average p) of the ADCs in the composition is from about 3.5 to about 5.5 (e.g., about 4), or from about 7 to about 9 (e.g., about 8) are provided herein.

In some embodiments, the antibody or antigen binding fragment (Ab) of the ADC targets a neoplastic cell derived from a hematological malignancy or a solid tumor. In some embodiments, the antibody or antigen binding fragment targets a neoplastic cell derived from a hematological malignancy. In some embodiments, the hematological malignancy is selected from a B-cell malignancy, a leukemia (e.g., acute myeloid leukemia), a lymphoma, and a myeloma (e.g., multiple myeloma). In some embodiments, the hematological malignancy is selected from acute myeloid leukemia and multiple myeloma. In some embodiments, the antibody or antigen binding fragment targets a neoplastic cell derived from a solid tumor. In some embodiments, the solid tumor is selected from breast cancer (e.g., HER2-positive breast cancer), gastric cancer (e.g., gastric adenocarcinoma), prostate cancer, ovarian cancer, lung cancer (e.g., lung adenocarcinoma), uterine cancer (e.g., uterine serous endometrial carcinoma), salivary duct carcinoma, melanoma, colon cancer, cervical cancer, pancreatic cancer, kidney cancer, colorectal cancer, and esophageal cancer. In some embodiments, the solid tumor is selected from HER2-positive breast cancer, gastric adenocarcinoma, prostate cancer, and osteosarcoma.

In various embodiments, the antibody or antigen binding fragment (Ab) of the ADC is an anti-HER2 antibody or an antigen binding fragment thereof. In some embodiments, the antibody or antigen binding fragment binds to HER2 and targets HER2-expressing neoplastic cells (i.e., the ADC targets HER2-expressing neoplastic cells). In some embodiments, the antibody or antigen binding fragment of the ADC is an internalizing anti-HER2 antibody or internalizing antigen binding fragment thereof.

In some embodiments, the anti-HER2 antibody or antigen binding fragment comprises three heavy chain complementarity determining regions (HCDR1, HCDR2, and HCDR3) comprising amino acid sequences of SEQ ID NO:1 (HCDR1), SEQ ID NO:2 (HCDR2), and SEQ ID NO:3 (HCDR3); and three light chain complementarity determining regions (LCDR1, LCDR2, and LCDR3) comprising amino acid sequences of SEQ ID NO:4 (LCDR1), SEQ ID NO:5 (LCDR2), and SEQ ID NO:6 (LCDR3). In some embodiments, the anti-HER2 antibody or antigen binding fragment is an internalizing antibody or internalizing antigen binding fragment. In some embodiments, the anti-HER2 antibody or antigen binding fragment comprises human framework sequences. In some embodiments, the anti-HER2 antibody or antigen binding fragment comprises a heavy chain variable region comprising an amino acid sequence of SEQ ID NO:19, and a light chain variable region comprising an amino acid sequence of SEQ ID NO:20. In some embodiments, the anti-HER2 antibody or antigen binding fragment comprises a human IgG heavy chain constant region. In some embodiments, the anti-HER2 antibody or antigen binding fragment comprises a human IgG1 heavy chain constant region. In some embodiments, the anti-HER2 antibody or antigen binding fragment comprises a human Ig kappa or lambda light chain constant region. In some embodiments, the anti-HER2 antibody or antigen binding competes for binding and/or binds the same epitope as an antibody comprising a heavy chain variable domain of SEQ ID NO:19 and a light chain variable domain of SEQ ID NO:20.

In various embodiments, the antibody or antigen binding fragment (Ab) of the ADC is an anti-CD138 antibody or an antigen binding fragment thereof. In some embodiments, the antibody or antigen binding fragment binds to CD138 and targets CD138-expressing neoplastic cells (i.e., the ADC targets CD138-expressing neoplastic cells). In some embodiments, the antibody or antigen binding fragment of the ADC is an internalizing anti-CD138 antibody or internalizing antigen binding fragment thereof.

In some embodiments, the anti-CD138 antibody or antigen binding fragment comprises three heavy chain complementarity determining regions (HCDR1, HCDR2, and HCDR3) comprising amino acid sequences of SEQ ID NO:7 (HCDR1), SEQ ID NO:8 (HCDR2), and SEQ ID NO:9 (HCDR3); and three light chain complementarity determining regions (LCDR1, LCDR2, and LCDR3) comprising amino acid sequences of SEQ ID NO:10 (LCDR1), SEQ ID NO:11 (LCDR2), and SEQ ID NO:12 (LCDR3). In some embodiments, the anti-CD138 antibody or antigen binding fragment is an internalizing antibody or internalizing antigen binding fragment. In some embodiments, the anti-CD138 antibody or antigen binding fragment comprises human framework sequences. In some embodiments, the anti-CD138 antibody or antigen binding fragment comprises a heavy chain variable region comprising an amino acid sequence of SEQ ID NO:21, and a light chain variable region comprising an amino acid sequence of SEQ ID NO:22. In some embodiments, the anti-CD138 antibody or antigen binding fragment comprises a murine IgG2a heavy chain constant region. In some embodiments, the anti-CD138 antibody or antigen binding fragment comprises a murine Ig kappa light chain constant region. In some embodiments, the anti-CD138 antibody or antigen binding fragment comprises a human IgG heavy chain constant region. In some embodiments, the anti-CD138 antibody or antigen binding fragment comprises a human IgG2a heavy chain constant region. In some embodiments, the anti-CD138 antibody or antigen binding fragment comprises a human Ig kappa or lambda light chain constant region. In some embodiments, the anti-CD138 antibody or antigen binding competes for binding and/or binds the same epitope as an antibody comprising a heavy chain variable domain of SEQ ID NO:21 and a light chain variable domain of SEQ ID NO:22.

In various embodiments, the antibody or antigen binding fragment (Ab) of the ADC is an anti-EPHA2 antibody or an antigen binding fragment thereof. In some embodiments, the antibody or antigen binding fragment binds to EPHA2 and targets EPHA2-expressing neoplastic cells (i.e., the ADC targets EPHA2-expressing neoplastic cells). In some embodiments, the antibody or antigen binding fragment of the ADC is an internalizing anti-EPHA2 antibody or internalizing antigen binding fragment thereof.

In some embodiments, the anti-EPHA2 antibody or antigen binding fragment comprises three heavy chain complementarity determining regions (HCDR1, HCDR2, and HCDR3) comprising amino acid sequences of SEQ ID NO:13 (HCDR1), SEQ ID NO:14 (HCDR2), and SEQ ID NO:15 (HCDR3); and three light chain complementarity determining regions (LCDR1, LCDR2, and LCDR3) comprising amino acid sequences of SEQ ID NO:16 (LCDR1), SEQ ID NO:17 (LCDR2), and SEQ ID NO:18 (LCDR3). In some embodiments, the anti-EPHA2 antibody or antigen binding fragment is an internalizing antibody or internalizing antigen binding fragment. In some embodiments, the anti-EPHA2 antibody or antigen binding fragment comprises human framework sequences. In some embodiments, the anti-EPHA2 antibody or antigen binding fragment comprises a heavy chain variable region comprising an amino acid sequence of SEQ ID NO:23, and a light chain variable region comprising an amino acid sequence of SEQ ID NO:24. In some embodiments, the anti-EPHA2 antibody or antigen binding fragment comprises a human IgG heavy chain constant region. In some embodiments, the anti-EPHA2 antibody or antigen binding fragment comprises a human IgG1 heavy chain constant region. In some embodiments, the anti-EPHA2 antibody or antigen binding fragment comprises a human Ig kappa or lambda light chain constant region. In some embodiments, the anti-EPHA2 antibody or antigen binding competes for binding and/or binds the same epitope as an antibody comprising a heavy chain variable domain of SEQ ID NO:23 and a light chain variable domain of SEQ ID NO:24.

Also provided herein, in various embodiments, are compounds comprising a linker-drug defined by the generic formula: L–D, wherein L=a linker moiety, and D=a drug moiety (e.g., a splicing modulator drug moiety). In various embodiments, the linker-drug (L–D) compounds disclosed herein may attach to an antibody or antigen binding fragment and/or are suitable for use in the ADCs disclosed herein, e.g., in ADCs of Formula (I).

In various embodiments, the linker-drug (L–D) compounds disclosed herein comprise a linker-drug structure according to Formula (III). In various embodiments, the present disclosure provides a linker-drug (L–D) compound of Formula (III):

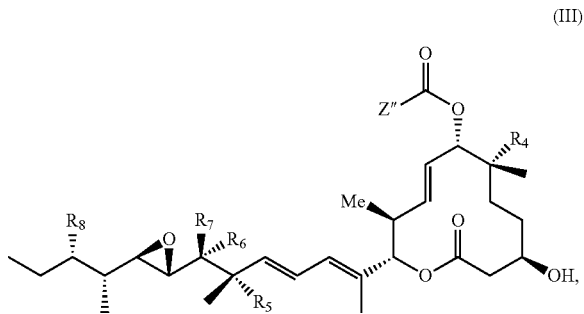

(III)

or a pharmaceutically acceptable salt thereof, wherein:

$R^1$ is chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(=O)—($C_1$-$C_6$ alkyl) groups, and —$CD_3$;

$R^2$ is absent or a linker;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups; and $R^4$, $R^5$, and $R^8$ are each independently chosen from hydrogen, hydroxyl groups, —O—($C_1$-$C_6$ alkyl) groups, —O—C(=O)—($C_1$-$C_6$alkyl) groups, and $C_1$-$C_6$alkyl groups;

$R^6$ and $R^7$ are each independently chosen from hydrogen, —O—$R^{17}$, —O—C(=O)—$R^{17}$, —O—C(=O)—$NR^{15}R^{16}$, $C_1$-$C_6$alkyl groups, —$NR^{15}R^{16}$, and a linker;

$R^{15}$ and $R^{16}$ are each independently chosen from hydrogen, $R^{17}$, —C(=O)—$R^{17}$, and —C(=O)—O—$R^{17}$;

$R^{17}$ is chosen from hydrogen, $C_1$-$C_6$ alkyl groups, $C_3$-$C_8$ cycloalkyl groups, benzyl groups, and $C_3$-$C_8$ heterocyclyl groups; and Z" is chosen from

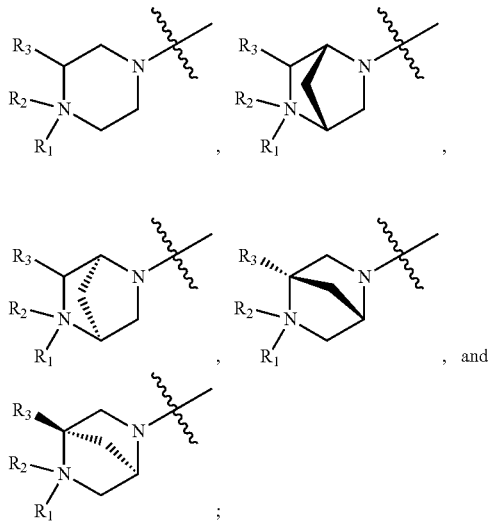

wherein $R^1$, $R^2$, $R^3$, $R^4$, $R^5$, $R^6$, $R^7$, $R^8$, $R^{15}$, $R^{16}$, and $R^{17}$ are each independently substituted with 0 to 3 groups independently chosen from halogens, hydroxyl groups, $C_1$—C alkyl groups, —O—($C_1$-$C_6$ alkyl) groups, —N$R^{15}R^{16}$, $C_3$-$C_8$ cycloalkyl groups, $C_1$-$C_6$ alkylhydroxy groups, $C_1$-$C_6$ alkylalkoxy groups, benzyl groups, and $C_3$-$C_8$ heterocyclyl groups;

wherein at least one of $R^6$ and $R^7$ is hydrogen; and wherein if $R^2$ is a linker, then neither $R^6$ or $R^7$ is a linker, and if $R^6$ or $R^7$ is a linker, then $R^2$ is absent.

In various other embodiments, the linker-drug (L–D) compounds disclosed herein comprise a linker-drug structure according to Formula (V). In various embodiments, the present disclosure provides a linker-drug (L–D) compound of Formula (V):

or a pharmaceutically acceptable salt thereof, wherein:

$R^1$ is chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(=O)—($C_1$-$C_6$ alkyl) groups, and —$CD_3$;

$R^2$ is absent or a linker;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups; and $R^4$, $R^5$, and $R^8$ are each independently chosen from hydrogen, hydroxyl groups, —O—($C_1$-$C_6$ alkyl) groups, —O—C(=O)—($C_1$-$C_6$alkyl) groups, and $C_1$-$C_6$alkyl groups;

$R^6$ and $R^7$ are each independently chosen from hydrogen, —O—$R^{17}$, —O—C(=O)—$R^{17}$, —O—C(=O)—N$R^{15}R^{16}$, $C_1$-$C_6$alkyl groups, —N$R^{15}R^{16}$, and a linker;

$R^{15}$ and $R^{16}$ are each independently chosen from hydrogen, $R^{17}$, —C(=O)—$R^{17}$, and —C(=O)—O—$R^{17}$; and $R^{17}$ is chosen from hydrogen, $C_1$-$C_6$ alkyl groups, $C_3$-$C_8$ cycloalkyl groups, benzyl groups, and $C_3$-$C_8$ heterocyclyl groups;

wherein $R^1$, $R^2$, $R^3$, $R^4$, $R^5$, $R^6$, $R^7$, $R^8$, $R^{15}$, $R^{16}$, and $R^{17}$ are each independently substituted with 0 to 3 groups independently chosen from halogens, hydroxyl groups, $C_1$—C alkyl groups, —O—($C_1$-$C_6$ alkyl) groups, —N$R^{15}R^{16}$, $C_3$-$C_8$ cycloalkyl groups, $C_1$-$C_6$ alkylhydroxy groups, $C_1$-$C_6$ alkylalkoxy groups, benzyl groups, and $C_3$-$C_8$ heterocyclyl groups;

wherein at least one of $R^6$ and $R^7$ is hydrogen; and wherein if $R^2$ is a linker, then neither $R^6$ or $R^7$ is a linker, and if $R^6$ or $R^7$ is a linker, then $R^2$ is absent.

In various other embodiments, the linker-drug (L–D) compounds disclosed herein comprise a linker-drug structure according to Formula (VII). In various embodiments, the present disclosure provides a linker-drug (L–D) compound of Formula (VII):

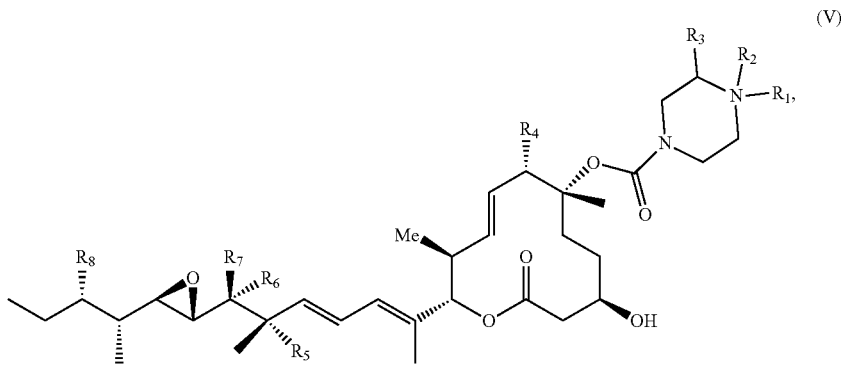

(V)

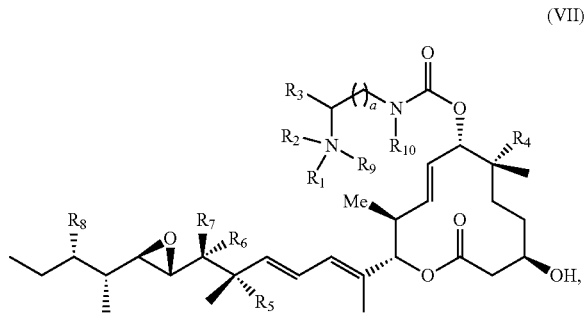

(VII)

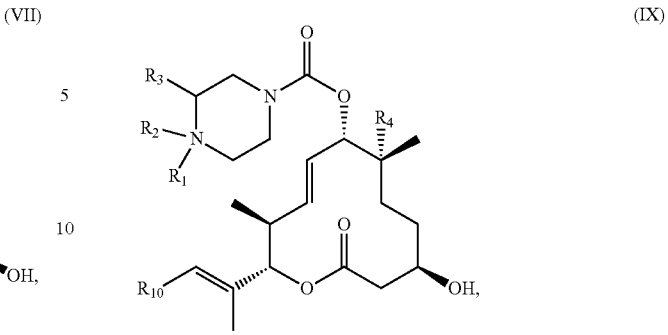

(IX)

or a pharmaceutically acceptable salt thereof, wherein:

$R^1$ and $R^9$ are each independently chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(=O)—($C_1$-$C_6$ alkyl) groups, and —$CD_3$;

$R^2$ is absent or a linker;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups;

$R^4$, $R^5$, and $R^3$ are each independently chosen from hydrogen, hydroxyl groups, —O—($C_1$-$C_6$ alkyl) groups, —O—C(=O)—($C_1$-$C_6$ alkyl) groups, and $C_1$-$C_6$ alkyl groups;

$R^6$ and $R^7$ are each independently chosen from hydrogen, —O—$R^{17}$, —O—C(=O)—$R^{17}$, —O—C(=O)—$NR^{15}R^{16}$, $C_1$-$C_6$ alkyl groups, —$NR^{15}R^{16}$, and a linker;

$R^{10}$ is chosen from hydrogen, $C_1$-$C_6$ alkyl groups, —C(=O)—($C_1$-$C_6$ alkyl) groups, and —CD3;

$R^{15}$ and $R^{16}$ are each independently chosen from hydrogen, $R^{17}$, —C(=O)—$R^{17}$, and —C(=O)—O—$R^{17}$;

$R^{17}$ is chosen from hydrogen, $C_1$-$C_6$ alkyl groups, $C_3$-$C_8$ cycloalkyl groups, benzyl groups, and $C_3$-$C_8$ heterocyclyl groups; and a is 1, 2, 3, 4, 5, 6, 7, 8, 9, or 10;

wherein $R^1$, $R^2$, $R^3$, $R^4$, $R^5$, $R^6$, $R^7$, $R^8$, $R^9$, $R^{10}$, $R^{15}$, $R^{16}$, and $R^{17}$ are each independently substituted with 0 to 3 groups independently chosen from halogens, hydroxyl groups, $C_1$-$C_6$alkyl groups, —O—($C_1$-$C_6$alkyl) groups, —$NR^{15}R^{16}$, $C_3$-$C_a$ cycloalkyl groups, $C_1$-$C_6$ alkylhydroxy groups, $C_1$-$C_6$ alkylalkoxy groups, benzyl groups, and $C_3$-$C_8$ heterocyclyl groups;

wherein at least one of $R^6$ and $R^7$ is hydrogen;

wherein if $R^2$ is a linker, then neither $R^6$ or $R^7$ is a linker, and if $R^6$ or $R^7$ is a linker, then $R^2$ is absent; and wherein $R^1$ and $R^9$ cannot both be absent.

In various other embodiments, the linker-drug (L-D) compounds disclosed herein comprise a linker-drug structure according to Formula (IX). In various embodiments, the present disclosure provides a linker-drug (L-D) compound of Formula (IX):

or a pharmaceutically acceptable salt thereof, wherein:

$R^1$ is chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(=O)—($C_1$-$C_6$ alkyl) groups, and —$CD_3$;

$R^2$ is a linker;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups;

$R^4$ is chosen from hydrogen, hydroxyl groups, —O—($C_1$-$C_6$ alkyl) groups, —O—C(=O)—($C_1$-$C_6$ alkyl) groups, and $C_1$-$C_6$ alkyl groups;

$R^{10}$ is chosen from 3 to 10 membered carbocycles and 3 to 10 membered heterocycles, each of which is substituted with 0 to 3 $R^a$, wherein each $R^a$ is independently chosen from halogens, $C_1$-$C_6$ alkyl groups, —O—($C_1$-$C_6$)alkyl groups, $C_1$-$C_6$ alkylalkoxy groups, $C_1$-$C_6$ alkylhydroxy groups, —S(=O)$_w$—(4 to 7 membered heterocycles), 4 to 7 membered carbocycles, and 4 to 7 membered heterocycles;

$R^{15}$ and $R^{16}$ are each independently chosen from hydrogen, $R^{17}$, —C(=O)—$R^{17}$, and —C(=O)—O—$R^{17}$; and $R^{17}$ is chosen from hydrogen, $C_1$-$C_6$ alkyl groups, $C_3$-$C_8$ cycloalkyl groups, benzyl groups, and $C_3$-$C_8$ heterocyclyl groups;

wherein $R^1$, $R^2$, $R^3$, $R^4$, $R^{10}$, $R^{15}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —$NR^{15}R^{16}$, $C_3$-$C_8$ cycloalkyl groups, $C_1$-$C_6$ alkylhydroxy groups, $C_1$-$C_6$ alkylalkoxy groups, benzyl groups, and $C_3$-$C_8$ heterocyclyl groups; and wherein each $R^a$ is independently substituted with 0 to 3 groups independently chosen from halogens, hydroxyl groups, —$NR^{15}R^{16}$, $C_1$-$C_6$ alkyl groups, —(C=O)—($C_1$-$C_6$ alkyl) groups, —(C=O)—($C_1$-$C_6$ alkyl)-($C_3$-$C_{10}$ heterocyclyl)groups, and $C_1$-$C_6$ alkylcarboxylic acid groups, each of which is substituted with 0, 1, or 2 groups independently chosen from halogens, hydroxyl groups, —$NR^{15}R^{16}$, and $C_1$-$C_3$alkyl groups; and w is 0, 1, or 2.

Also, in various embodiments, provided herein are therapeutic uses for the described ADC compounds and compositions, e.g., in treating a neoplastic disorder, e.g., a cancer. In certain aspects, the present disclosure provides methods of treating a neoplastic disorder, e.g., a cancer that expresses an antigen targeted by the antibody or antigen binding fragment of the ADC, such as HER2, CD138, EPHA2, MSLN, FOLH1, CDH6, CEACAM5, CFC1B, ENPP3, FOLR1, HAVCR1, KIT, MET, MUC16, SLC39A6, SLC44A4, or STEAP1.

In certain aspects, the present disclosure provides methods of treating a subject having or suspected of having a neoplastic disorder by administering to the subject a therapeutically effective amount and/or regimen of any one of the described ADCs or compositions. In some embodiments, the neoplastic disorder is a hematological malignancy or a solid tumor. In some embodiments, the neoplastic disorder is a hematological malignancy. In some embodiments, the hematological malignancy is selected from a B-cell malignancy, a leukemia, a lymphoma, and a myeloma. In some embodiments, the hematological malignancy is selected from acute myeloid leukemia and multiple myeloma. In some embodiments, the neoplastic disorder is a solid tumor.

In some embodiments, the solid tumor is selected from breast cancer (e.g., HER2-positive breast cancer), gastric cancer (e.g., gastric adenocarcinoma), prostate cancer, ovarian cancer, lung cancer (e.g., lung adenocarcinoma), uterine cancer (e.g., uterine serous endometrial carcinoma), salivary duct carcinoma, melanoma, colon cancer, cervical cancer, pancreatic cancer, kidney cancer, colorectal cancer, and esophageal cancer. In some embodiments, the solid tumor is selected from HER2-positive breast cancer, gastric adenocarcinoma, prostate cancer, and osteosarcoma.

In some embodiments, treatment with the antibody-drug conjugate or composition induces bystander killing of neoplastic cells which do not express a target antigen but are adjacent to neoplastic cells which express a target antigen. In some embodiments, the subject has one or more neoplastic cells which express a target antigen.

In some embodiments, the target antigen is HER2. In some embodiments, the one or more neoplastic cells are derived from a HER2-expressing breast cancer, ovarian cancer, gastric cancer, lung cancer (e.g., lung adenocarcinoma), uterine cancer (e.g., uterine serous endometrial carcinoma), osteosarcoma, or salivary duct carcinoma. In some embodiments, the subject is non-responsive or poorly responsive to treatment with (a) an anti-HER2 antibody when administered alone and/or (b) a splicing modulator when administered alone. In some embodiments, the subject is intolerant, non-responsive, or poorly responsive to treatment with a splicing modulator when administered alone.

In some embodiments, the target antigen is CD138. In some embodiments, the one or more neoplastic cells are derived from a CD138-expressing multiple myeloma. In some embodiments, the subject is non-responsive or poorly responsive to treatment with (a) an anti-CD138 antibody when administered alone and/or (b) a splicing modulator when administered alone. In some embodiments, the subject is intolerant, non-responsive, or poorly responsive to treatment with a splicing modulator when administered alone.

In some embodiments, the target antigen is EPHA2. In some embodiments, the one or more neoplastic cells are derived from an EPHA2-expressing breast cancer, prostate cancer, ovarian cancer, lung cancer, melanoma, colon cancer, or esophageal cancer. In some embodiments, the subject is non-responsive or poorly responsive to treatment with (a) an anti-EPHA2 antibody when administered alone and/or (b) a splicing modulator when administered alone. In some embodiments, the subject is intolerant, non-responsive, or poorly responsive to treatment with a splicing modulator when administered alone.

In some embodiments, the target antigen is MSLN. In some embodiments, the one or more neoplastic cells are derived from a MSLN-expressing ovarian cancer, cervical cancer, pancreatic cancer, or lung cancer (e.g., lung adenocarcinoma). In some embodiments, the subject is non-responsive or poorly responsive to treatment with (a) an anti-MSLN antibody when administered alone and/or (b) a splicing modulator when administered alone. In some embodiments, the subject is intolerant, non-responsive, or poorly responsive to treatment with a splicing modulator when administered alone.

In some embodiments, the target antigen is FOLH1. In some embodiments, the one or more neoplastic cells are derived from a FOLH1-expressing prostate cancer. In some embodiments, the subject is non-responsive or poorly responsive to treatment with (a) an anti-FOLH1 antibody when administered alone and/or (b) a splicing modulator when administered alone. In some embodiments, the subject is intolerant, non-responsive, or poorly responsive to treatment with a splicing modulator when administered alone.

In some embodiments, the target antigen is CDH6. In some embodiments, the one or more neoplastic cells are derived from a CDH6-expressing kidney cancer. In some embodiments, the subject is non-responsive or poorly responsive to treatment with (a) an anti-CDH6 antibody when administered alone and/or (b) a splicing modulator when administered alone. In some embodiments, the subject is intolerant, non-responsive, or poorly responsive to treatment with a splicing modulator when administered alone.

In some embodiments, the target antigen is CEACAM5. In some embodiments, the one or more neoplastic cells are derived from a CEACAM5-expressing colorectal cancer. In some embodiments, the subject is non-responsive or poorly responsive to treatment with (a) an anti-CEACAM5 antibody when administered alone and/or (b) a splicing modulator when administered alone. In some embodiments, the subject is intolerant, non-responsive, or poorly responsive to treatment with a splicing modulator when administered alone.

In some embodiments, the target antigen is CFC1B. In some embodiments, the one or more neoplastic cells are derived from a CFC1B-expressing pancreatic cancer. In some embodiments, the subject is non-responsive or poorly responsive to treatment with (a) an anti-CFC1B antibody when administered alone and/or (b) a splicing modulator when administered alone. In some embodiments, the subject is intolerant, non-responsive, or poorly responsive to treatment with a splicing modulator when administered alone.

In some embodiments, the target antigen is ENPP3. In some embodiments, the one or more neoplastic cells are derived from an ENPP3-expressing kidney cancer. In some embodiments, the subject is non-responsive or poorly responsive to treatment with (a) an anti-ENPP3 antibody when administered alone and/or (b) a splicing modulator when administered alone. In some embodiments, the subject is intolerant, non-responsive, or poorly responsive to treatment with a splicing modulator when administered alone.

In some embodiments, the target antigen is FOLR1. In some embodiments, the one or more neoplastic cells are derived from a FOLR1-expressing ovarian cancer. In some embodiments, the subject is non-responsive or poorly responsive to treatment with (a) an anti-FOLR1 antibody when administered alone and/or (b) a splicing modulator when administered alone. In some embodiments, the subject is intolerant, non-responsive, or poorly responsive to treatment with a splicing modulator when administered alone.

In some embodiments, the target antigen is HAVCR1. In some embodiments, the one or more neoplastic cells are derived from a HAVCR1-expressing kidney cancer or esophageal cancer. In some embodiments, the subject is non-responsive or poorly responsive to treatment with (a) an anti-HAVCR1 antibody when administered alone and/or (b) a splicing modulator when administered alone. In some embodiments, the subject is intolerant, non-responsive, or poorly responsive to treatment with a splicing modulator when administered alone.

In some embodiments, the target antigen is KIT. In some embodiments, the one or more neoplastic cells are derived from a KIT-expressing kidney cancer. In some embodiments, the subject is non-responsive or poorly responsive to treatment with (a) an anti-KIT antibody when administered alone and/or (b) a splicing modulator when administered alone. In some embodiments, the subject is intolerant, non-responsive, or poorly responsive to treatment with a splicing modulator when administered alone.

In some embodiments, the target antigen is MET. In some embodiments, the one or more neoplastic cells are derived from a MET-expressing kidney cancer or esophageal cancer. In some embodiments, the subject is non-responsive or poorly responsive to treatment with (a) an anti-MET antibody when administered alone and/or (b) a splicing modulator when administered alone. In some embodiments, the subject is intolerant, non-responsive, or poorly responsive to treatment with a splicing modulator when administered alone.

In some embodiments, the target antigen is MUC16. In some embodiments, the one or more neoplastic cells are derived from a MUC16-expressing ovarian cancer, cervical cancer, or breast cancer. In some embodiments, the subject is non-responsive or poorly responsive to treatment with (a) an anti-MUC16 antibody when administered alone and/or (b) a splicing modulator when administered alone. In some embodiments, the subject is intolerant, non-responsive, or poorly responsive to treatment with a splicing modulator when administered alone.

In some embodiments, the target antigen is SLC39A6. In some embodiments, the one or more neoplastic cells are derived from a SLC39A6-expressing breast cancer or prostate cancer. In some embodiments, the subject is non-responsive or poorly responsive to treatment with (a) an anti-SLC39A6 antibody when administered alone and/or (b) a splicing modulator when administered alone. In some embodiments, the subject is intolerant, non-responsive, or poorly responsive to treatment with a splicing modulator when administered alone.

In some embodiments, the target antigen is SLC44A4. In some embodiments, the one or more neoplastic cells are derived from a SLC44A4-expressing prostate cancer. In some embodiments, the subject is non-responsive or poorly responsive to treatment with (a) an anti-SLC44A4 antibody when administered alone and/or (b) a splicing modulator when administered alone. In some embodiments, the subject is intolerant, non-responsive, or poorly responsive to treatment with a splicing modulator when administered alone.

In some embodiments, the target antigen is STEAP1. In some embodiments, the one or more neoplastic cells are derived from a STEAP1-expressing prostate cancer. In some embodiments, the subject is non-responsive or poorly responsive to treatment with (a) an anti-STEAP1 antibody when administered alone and/or (b) a splicing modulator when administered alone. In some embodiments, the subject is intolerant, non-responsive, or poorly responsive to treatment with a splicing modulator when administered alone.

In certain other aspects, the present disclosure provides methods of reducing or inhibiting growth of a tumor in a subject having or suspected of having a neoplastic disorder by administering to the subject a therapeutically effective amount and/or regimen of any one of the described ADCs or compositions.

In some embodiments, treatment with the antibody-drug conjugate or composition induces bystander killing of neoplastic tumor cells which do not express a target antigen but are adjacent to neoplastic tumor cells which express a target antigen.

In some embodiments, the tumor comprises one or more neoplastic cells which express a target antigen.

In some embodiments, the target antigen is HER2. In some embodiments, the one or more neoplastic cells are derived from a HER2-expressing breast cancer, ovarian cancer, gastric cancer, lung cancer (e.g., lung adenocarcinoma), uterine cancer (e.g., uterine serous endometrial carcinoma), osteosarcoma, or salivary duct carcinoma.

In some embodiments, the tumor is resistant or refractory to treatment with (a) an anti-HER2 antibody when administered alone and/or (b) a splicing modulator when administered alone.

In some embodiments, the target antigen is CD138. In some embodiments, the one or more neoplastic cells are derived from a CD138-expressing multiple myeloma.

In some embodiments, the tumor is resistant or refractory to treatment with (a) an anti-CD138 antibody when administered alone and/or (b) a splicing modulator when administered alone.

In some embodiments, the target antigen is EPHA2. In some embodiments, the one or more neoplastic cells are derived from an EPHA2-expressing breast cancer, prostate cancer, ovarian cancer, lung cancer, melanoma, colon cancer, or esophageal cancer. In some embodiments, the tumor is resistant or refractory to treatment with (a) an anti-EPHA2 antibody when administered alone and/or (b) a splicing modulator when administered alone.

In some embodiments, the target antigen is MSLN. In some embodiments, the one or more neoplastic cells are derived from a MSLN-expressing ovarian cancer, cervical cancer, pancreatic cancer, or lung cancer (e.g., lung adenocarcinoma). In some embodiments, the tumor is resistant or refractory to treatment with (a) an anti-MSLN antibody when administered alone and/or (b) a splicing modulator when administered alone.

In some embodiments, the target antigen is FOLH1. In some embodiments, the one or more neoplastic cells are derived from a FOLH1-expressing prostate cancer. In some embodiments, the tumor is resistant or refractory to treatment with (a) an anti-FOLH1 antibody when administered alone and/or (b) a splicing modulator when administered alone.

In some embodiments, the target antigen is CDH6. In some embodiments, the one or more neoplastic cells are derived from a CDH6-expressing kidney cancer. In some embodiments, the tumor is resistant or refractory to treatment with (a) an anti-CDH6 antibody when administered alone and/or (b) a splicing modulator when administered alone.

In some embodiments, the target antigen is CEACAM5. In some embodiments, the one or more neoplastic cells are derived from a CEACAM5-expressing colorectal cancer. In some embodiments, the tumor is resistant or refractory to treatment with (a) an anti-CEACAM5 antibody when administered alone and/or (b) a splicing modulator when administered alone.

In some embodiments, the target antigen is CFC1B. In some embodiments, the one or more neoplastic cells are derived from a CFC1B-expressing pancreatic cancer.

In some embodiments, the tumor is resistant or refractory to treatment with (a) an anti-CFC1B antibody when administered alone and/or (b) a splicing modulator when administered alone.

In some embodiments, the target antigen is ENPP3. In some embodiments, the one or more neoplastic cells are derived from an ENPP3-expressing kidney cancer. In some embodiments, the tumor is resistant or refractory to treatment with (a) an anti-ENPP3 antibody when administered alone and/or (b) a splicing modulator when administered alone.

In some embodiments, the target antigen is FOLR1. In some embodiments, the one or more neoplastic cells are derived from a FOLR1-expressing ovarian cancer. In some embodiments, the tumor is resistant or refractory to treatment with (a) an anti-FOLR1 antibody when administered alone and/or (b) a splicing modulator when administered alone.

In some embodiments, the target antigen is HAVCR1. In some embodiments, the one or more neoplastic cells are derived from a HAVCR1-expressing kidney cancer or esophageal cancer. In some embodiments, the tumor is resistant or refractory to treatment with (a) an anti-HAVCR1 antibody when administered alone and/or (b) a splicing modulator when administered alone.

In some embodiments, the target antigen is KIT. In some embodiments, the one or more neoplastic cells are derived from a KIT-expressing kidney cancer. In some embodiments, the tumor is resistant or refractory to treatment with (a) an anti-KIT antibody when administered alone and/or (b) a splicing modulator when administered alone.

In some embodiments, the target antigen is MET. In some embodiments, the one or more neoplastic cells are derived from a MET-expressing kidney cancer or esophageal cancer. In some embodiments, the tumor is resistant or refractory to treatment with (a) an anti-MET antibody when administered alone and/or (b) a splicing modulator when administered alone.

In some embodiments, the target antigen is MUC16. In some embodiments, the one or more neoplastic cells are derived from a MUC16-expressing ovarian cancer, cervical cancer, or breast cancer. In some embodiments, the tumor is resistant or refractory to treatment with (a) an anti-MUC16 antibody when administered alone and/or (b) a splicing modulator when administered alone.

In some embodiments, the target antigen is SLC39A6. In some embodiments, the one or more neoplastic cells are derived from a SLC39A6-expressing breast cancer or prostate cancer. In some embodiments, the tumor is resistant or refractory to treatment with (a) an anti-SLC39A6 antibody when administered alone and/or (b) a splicing modulator when administered alone.

In some embodiments, the target antigen is SLC44A4. In some embodiments, the one or more neoplastic cells are derived from a SLC44A4-expressing prostate cancer. In some embodiments, the tumor is resistant or refractory to treatment with (a) an anti-SLC44A4 antibody when administered alone and/or (b) a splicing modulator when administered alone.

In some embodiments, the target antigen is STEAP1. In some embodiments, the one or more neoplastic cells are derived from a STEAP1-expressing prostate cancer. In some embodiments, the tumor is resistant or refractory to treatment with (a) an anti-STEAP1 antibody when administered alone and/or (b) a splicing modulator when administered alone.

In still other aspects, the present disclosure provides methods of determining whether a subject having or suspected of having a neoplastic disorder will be responsive to treatment with any one of the described ADCs or compositions by providing a biological sample from the subject and contacting the biological sample with the ADC or composition. In some embodiments, the biological sample is a tumor sample. In some embodiments, the tumor sample is a tumor biopsy or blood sample.

In some embodiments, the blood sample is selected from blood, a blood fraction, or a cell obtained from the blood or blood fraction. In some embodiments, the subject has one or more neoplastic cells which express a target antigen. In some embodiments, the target antigen is HER2. In some embodiments, the one or more neoplastic cells are derived from a HER2-expressing breast cancer, ovarian cancer, gastric cancer, lung cancer (e.g., lung adenocarcinoma), uterine cancer (e.g., uterine serous endometrial carcinoma), osteosarcoma, or salivary duct carcinoma. In some embodiments, the target antigen is CD138. In some embodiments, the one or more neoplastic cells are derived from a CD138-expressing multiple myeloma. In some embodiments, the target antigen is EPHA2. In some embodiments, the one or more neoplastic cells are derived from an EPHA2-expressing breast cancer, prostate cancer, ovarian cancer, lung cancer, melanoma, colon cancer, or esophageal cancer. In some embodiments, the target antigen is MSLN. In some embodiments, the one or more neoplastic cells are derived from a MSLN-expressing ovarian cancer, cervical cancer, pancreatic cancer, or lung cancer (e.g., lung adenocarcinoma). In some embodiments, the target antigen is FOLH1. In some embodiments, the one or more neoplastic cells are derived from a FOLH1-expressing prostate cancer. In some embodiments, the target antigen is CDH6.

In some embodiments, the one or more neoplastic cells are derived from a CDH6-expressing kidney cancer. In some embodiments, the target antigen is CEACAM5. In some embodiments, the one or more neoplastic cells are derived from a CEACAM5-expressing colorectal cancer. In some embodiments, the target antigen is CFC1B. In some embodiments, the one or more neoplastic cells are derived from a CFC1B-expressing pancreatic cancer. In some embodiments, the target antigen is ENPP3. In some embodiments, the one or more neoplastic cells are derived from an ENPP3-expressing kidney cancer. In some embodiments, the target antigen is FOLR1. In some embodiments, the one or more neoplastic cells are derived from a FOLR1-expressing ovarian cancer. In some embodiments, the target antigen is HAVCR1. In some embodiments, the one or more neoplastic cells are derived from a HAVCR1-expressing kidney cancer or esophageal cancer. In some embodiments, the target antigen is KIT. In some embodiments, the one or more neoplastic cells are derived from a KIT-expressing kidney cancer. In some embodiments, the target antigen is MET. In some embodiments, the one or more neoplastic cells are derived from a MET-expressing kidney cancer or esophageal cancer. In some embodiments, the target antigen is MUC16. In some embodiments, the one or more neoplastic cells are derived from a MUC16-expressing ovarian cancer, cervical cancer, or breast cancer. In some embodiments, the target antigen is SLC39A6. In some embodiments, the one or more neoplastic cells are derived from a SLC39A6-expressing breast cancer or prostate cancer. In some embodiments, the target antigen is SLC44A4. In some embodiments, the one or more neoplastic cells are derived from a SLC44A4-expressing prostate cancer. In some embodiments, the target antigen is STEAP1. In some embodiments, the one or more neoplastic cells are derived from a STEAP1-expressing prostate cancer.

Further provided herein, in various embodiments, are pharmaceutical compositions comprising an ADC and a pharmaceutically acceptable diluent, carrier, and/or excipient. Methods of producing the described ADC compounds and compositions are also disclosed.

BRIEF DESCRIPTION OF THE DRAWINGS

FIG. 17A shows ELISpot plates indicating Neoantigen 1 priming of CD8+ T-cell activation. Stimulation of CD8+ T-cells was monitored by secretion of IFNγ. FIG. 17B shows quantification of IFNγ spots (spot number) in Neoantigen 1 ELISpot plates (FIG. 17A). FIG. 17C shows ELISpot plates indicating Neoantigen 3 priming of CD8+ T-cell activation. Stimulation of CD8+ T-cells was monitored by secretion of IFNγ. FIG. 17D shows quantification of IFNγ spots (fold change) in Neoantigen 3 ELISpot plates (FIG. 17C).

DETAILED DESCRIPTION OF ILLUSTRATIVE EMBODIMENTS

Figure 1:
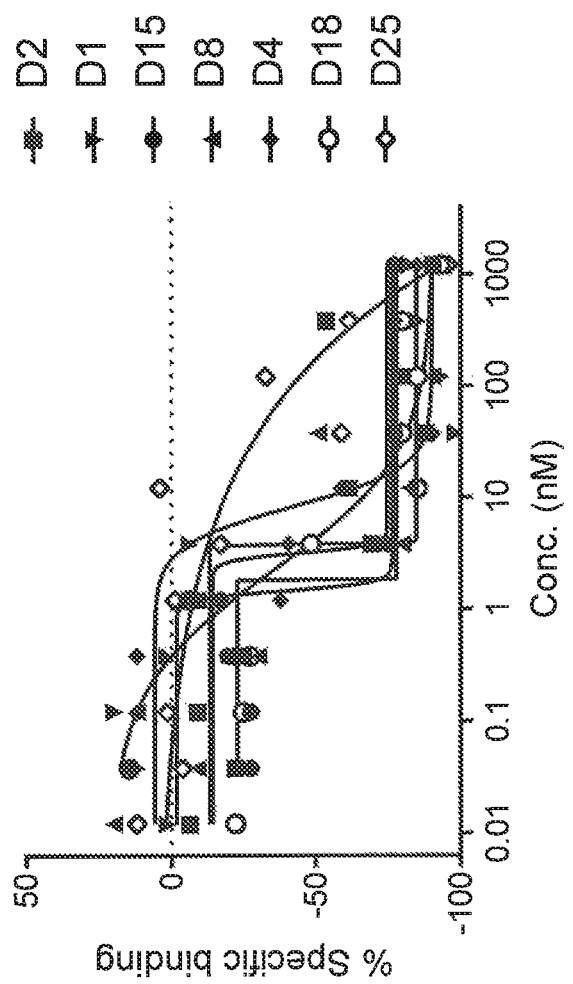
FIG. 1 shows dose response of exemplary payload compounds in a competitive binding assay. Nuclear extracts from 293F cells overexpressing wild type flag-tagged SF3B1 were immunoprecipitated with an anti-SF3B1 antibody and scintillation proximity assay (SPA) bead cocktail. Binding reactions contained the antibody-bead mixture and increasing concentrations of compound, followed by competition with an $^3$H-labelled pladienolide B (PB) probe. The y-axis represents the percent change (% response) of specific binding relative to the DMSO control (0%). Data are represented as mean±standard deviation (SD).

The disclosed compositions and methods may be understood more readily by reference to the following detailed description taken in connection with the accompanying figures, which form a part of this disclosure.

Throughout this text, the descriptions refer to compositions and methods of using the compositions. Where the disclosure describes or claims a feature or embodiment associated with a composition, such a feature or embodiment is equally applicable to the methods of using the composition. Likewise, where the disclosure describes or claims a feature or embodiment associated with a method of using a composition, such a feature or embodiment is equally applicable to the composition.

When a range of values is expressed, it includes embodiments using any particular value within the range. Further, reference to values stated in ranges includes each and every value within that range. All ranges are inclusive of their endpoints and combinable. When values are expressed as approximations, by use of the antecedent "about," it will be understood that the particular value forms another embodiment. Reference to a particular numerical value includes at least that particular value, unless the context clearly dictates otherwise. The use of "or" will mean "and/or" unless the specific context of its use dictates otherwise. All references cited herein are incorporated by reference for any purpose. Where a reference and the specification conflict, the specification will control.

It is to be appreciated that certain features of the disclosed compositions and methods, which are, for clarity, described herein in the context of separate embodiments, may also be provided in combination in a single embodiment. Conversely, various features of the disclosed compositions and methods that are, for brevity, described in the context of a single embodiment, may also be provided separately or in any subcombination.

Definitions

Various terms relating to aspects of the description are used throughout the specification and claims. Such terms are to be given their ordinary meaning in the art unless otherwise indicated. Other specifically defined terms are to be construed in a manner consistent with the definitions provided herein.

As used herein, the singular forms "a," "an," and "the" include plural forms unless the context clearly dictates otherwise.

The terms "about" or "approximately" in the context of numerical values and ranges refers to values or ranges that approximate or are close to the recited values or ranges such that the embodiment may perform as intended, such as having a desired amount of nucleic acids or polypeptides in a reaction mixture, as is apparent to the skilled person from the teachings contained herein. In some embodiments, about means plus or minus 10% of a numerical amount.

The terms "antibody-drug conjugate," "antibody conjugate," "conjugate," "immunoconjugate," and "ADC" are used interchangeably, and refer to one or more therapeutic compounds (e.g., a splicing modulator) that is linked to one or more antibodies or antigen binding fragments and is defined by the generic formula: Ab–(L–D)$_p$ (Formula I), wherein Ab=an antibody or antigen binding fragment, L=a linker moiety, D=a drug moiety (e.g., a splicing modulator drug moiety), and p=the number of drug moieties per antibody or antigen binding fragment. An ADC comprising a splicing modulator drug moiety may also be referred to herein more specifically as a "splicing modulator-loaded antibody" or a "SMLA." In ADCs comprising a splicing modulator drug moiety, "p" refers to the number of splicing modulator compounds linked to the antibody or antigen binding fragment. In some embodiments, the linker L can include a cleavable moiety between the antibody or antigen binding fragment and the therapeutic compound. In some embodiments, the linker L can include a cleavable moiety that can be attached to either or both the antibody or antigen binding fragment and therapeutic compound by spacer unit(s). In some embodiments, when a spacer unit attaches the cleavable moiety to the therapeutic compound, it is a self-immolative spacer unit. In other embodiments, the linker L does not include a cleavable moiety, and is a non-cleavable linker. In some embodiments, the linker L can include at least one spacer unit that can directly attach to the antibody or antigen binding fragment and to the therapeutic compound. Exemplary cleavable and non-cleavable linkers are described and exemplified herein.

The term "antibody" is used in the broadest sense to refer to an immunoglobulin molecule that recognizes and specifically binds to a target, such as a protein, polypeptide, carbohydrate, polynucleotide, lipid, or combinations of the foregoing through at least one antigen recognition site within the variable region of the immunoglobulin molecule. The heavy chain of an antibody is composed of a heavy chain variable domain (V$_H$) and a heavy chain constant region (C$_H$). The light chain is composed of a light chain variable domain (V$_L$) and a light chain constant domain (C$_L$). For the purposes of this application, the mature heavy chain and light chain variable domains each comprise three complementarity determining regions (CDR1, CDR2 and CDR3) within four framework regions (FR1, FR2, FR3, and FR4) arranged from N-terminus to C-terminus: FR1, CDR1, FR2, CDR2, FR3, CDR3, and FR4. An "antibody" can be naturally occurring or man-made, such as monoclonal antibodies produced by conventional hybridoma technology. The term "antibody" includes full-length monoclonal antibodies and full-length polyclonal antibodies, as well as antibody fragments such as Fab, Fab', F(ab')$_2$, Fv, and single chain antibodies. An antibody can be any one of the five major classes of immunoglobulins: IgA, IgD, IgE, IgG, and IgM, or subclasses thereof (e.g., isotypes IgG1, IgG2, IgG3, IgG4). The term further encompasses human antibodies, chimeric antibodies, humanized antibodies and any modified immunoglobulin molecule containing an antigen recognition site, so long as it demonstrates the desired biological activity (e.g., binds the target antigen, internalizes within a target-antigen expressing cell).

The term "monoclonal antibody," as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al. (1975) Nature 256:495, or may be made by recombinant DNA methods (see, e.g., U.S. Pat. No. 4,816,567). Monoclonal antibodies may also be isolated from phage antibody libraries using the techniques described in Clackson et al. (1991) Nature 352:624-8, and Marks et al. (1991) J Mol Biol. 222:581-97, for example.

The monoclonal antibodies described herein specifically include "chimeric" antibodies, in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity.

The term "human antibody," as used herein, refers an antibody produced by a human or an antibody having an amino acid sequence of an antibody produced by a human.

The term "chimeric antibody," as used herein, refers to antibodies wherein the amino acid sequence of the immunoglobulin molecule is derived from two or more species. In some instances, the variable regions of both heavy and light chains correspond to the variable regions of antibodies derived from one species with the desired specificity, affinity, and activity while the constant regions are homologous to antibodies derived from another species (e.g., human) to minimize an immune response in the latter species.

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the framework (FR) regions are those of a human immunoglobulin sequence. The humanized antibody optionally also will comprise at least a portion of an immunoglobulin constant region (Fc), typically that of a human immunoglobulin. The humanized antibody can be further modified by the substitution of residues, either in the Fv framework region and/or within the replaced non-human residues to refine and optimize antibody specificity, affinity, and/or activity.

The term "antigen binding fragment" or "antigen binding portion" of an antibody, as used herein, refers to one or more fragments of an antibody or protein that retain the ability to specifically bind to an antigen (e.g., HER2, CD138, EPHA2, MSLN, FOLH1, CDH6, CEACAM5, CFC1B, ENPP3, FOLR1, HAVCR1, KIT, MET, MUC16, SLC39A6, SLC44A4, STEAP1). Antigen binding fragments may also retain the ability to internalize into an antigen-expressing cell. In some embodiments, antigen binding fragments also retain immune effector activity. It has been shown that fragments of a full-length antibody can perform the antigen binding function of a full-length antibody. Examples of binding fragments encompassed within the term "antigen binding fragment" or "antigen binding portion" of an antibody include (i) a Fab fragment, a monovalent fragment consisting of the $V_L$, $V_H$, $C_L$, and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody; (v) a dAb fragment, which comprises a single variable domain, e.g., a $V_H$ domain (see, e.g., Ward et al. (1989) Nature 341:544-6; and Intl. Pub. No. WO 1990/005144); and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)). See, e.g., Bird et al. (1988) Science 242:423-6; and Huston et al. (1988) Proc Natl Acad Sci. USA 85:5879-83. Such single chain antibodies are also intended to be encompassed within the term "antigen binding fragment" or "antigen binding portion" of an antibody, and are known in the art as an exemplary type of binding fragment that can internalize into cells upon binding (see, e.g., Zhu et al. (2010) 9:2131-41; He et al. (2010) J Nucl Med. 51:427-32; and Fitting et al. (2015) MAbs 7:390-402). In certain embodiments, scFv molecules may be incorporated into a fusion protein. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) Proc Natl Acad Sci. USA 90:6444-8; and Poljak et al. (1994) Structure 2:1121-3). Antigen binding fragments are obtained using conventional techniques known to those of skill in the art, and the binding fragments are screened for utility (e.g., binding affinity, internalization) in the same manner as are intact antibodies.

Antigen binding fragments may be prepared by cleavage of the intact protein, e.g., by protease or chemical cleavage.

"Internalizing" as used herein in reference to an antibody or antigen binding fragment refers to an antibody or antigen binding fragment that is capable of being taken through the cell's lipid bilayer membrane to an internal compartment (i.e., "internalized") upon binding to the cell, preferably into a degradative compartment in the cell. For example, an internalizing anti-HER2 antibody is one that is capable of being taken into the cell after binding to HER2 on the cell membrane. In some embodiments, the antibody or antigen binding fragment used in the ADCs disclosed herein targets a cell surface antigen (e.g., HER2) and is an internalizing antibody or internalizing antigen binding fragment (i.e., the ADC transfers through the cellular membrane after antigen binding). In some embodiments, the internalizing antibody or antigen binding fragment binds a receptor on the cell surface. An internalizing antibody or internalizing antigen binding fragment that targets a receptor on the cell membrane may induce receptor-mediated endocytosis. In some embodiments, the internalizing antibody or internalizing antigen binding fragment is taken into the cell via receptor-mediated endocytosis.

"Non-internalizing" as used herein in reference to an antibody or antigen binding fragment refers to an antibody or antigen binding fragment that remains at the cell surface upon binding to the cell. In some embodiments, the antibody or antigen binding fragment used in the ADCs disclosed herein targets a cell surface antigen and is a non-internalizing antibody or non-internalizing antigen binding fragment (i.e., the ADC remains at the cell surface and does not transfer through the cellular membrane after antigen binding). In some embodiments, the non-internalizing antibody or antigen binding fragment binds a non-internalizing receptor or other cell surface antigen. Exemplary non-internalizing cell surface antigens include but are not limited to CA125 and CEA, and antibodies that bind to non-internalizing antigen targets are also known in the art (see, e.g., Bast et al. (1981) J Clin Invest. 68(5):1331-7; Scholler and Urban (2007) Biomark Med. 1(4):513-23; and Boudousq et al. (2013) PLoS One 8(7):e69613).

The term "human epidermal growth factor receptor 2," "HER2," or "HER2/NEU," as used herein, refers to any native form of human HER2. The term encompasses full-length HER2 (e.g., UniProt Reference Sequence: P04626; SEQ ID NO:31), as well as any form of human HER2 that may result from cellular processing. The term also encompasses functional variants or fragments of human HER2, including but not limited to splice variants, allelic variants, and isoforms that retain one or more biologic functions of human HER2 (i.e., variants and fragments are encompassed unless the context indicates that the term is used to refer to the wild-type protein only). HER2 can be isolated from human, or may be produced recombinantly or by synthetic methods.

The term "anti-HER2 antibody" or "antibody that binds to HER2" refers to any form of antibody or fragment thereof that binds, e.g., specifically binds, to HER2, and encompasses monoclonal antibodies (including full-length monoclonal antibodies), polyclonal antibodies, and biologically functional antibody fragments so long as they bind, e.g., specifically bind, to HER2. U.S. Pat. No. 5,821,337 provides and is incorporated herein by reference for exemplary HER2-binding sequences, including exemplary anti-HER2 antibody sequences. In some embodiments, the anti-HER2 antibody used in the ADCs disclosed herein is an internalizing antibody or internalizing antibody fragment. Trastuzumab (U.S. Pat. No. 5,821,337; Molina et al. (2001) Cancer Res. 61(12):4744-9) is an exemplary anti-human HER2 antibody.

The term "syndecan-1," "SDC1," or "CD138," as used herein, refers to any native form of human CD138. The term encompasses full-length CD138 (e.g., UniProt Reference Sequence: P18827; SEQ ID NO:32), as well as any form of human CD138 that may result from cellular processing. The term also encompasses functional variants or fragments of human CD138, including but not limited to splice variants, allelic variants, and isoforms that retain one or more biologic functions of human CD138 (i.e., variants and fragments are encompassed unless the context indicates that the term is used to refer to the wild-type protein only). CD138 can be isolated from a human, or may be produced recombinantly or by synthetic methods.

The term "anti-CD138 antibody" or "antibody that binds to CD138" refers to any form of antibody or fragment thereof that binds, e.g., specifically binds, to CD138, and encompasses monoclonal antibodies (including full-length monoclonal antibodies), polyclonal antibodies, and biologically functional antibody fragments so long as they bind, e.g., specifically bind, to CD138. In some embodiments, the anti-CD138 antibody used in the ADCs disclosed herein is an internalizing antibody or internalizing antibody fragment. B—B4 (Tassone et al. (2004) Blood 104:3688-96) is an exemplary anti-human CD138 antibody.

The term "ephrin type-A receptor 2" or "EPHA2," as used herein, refers to any native form of human EPHA2. The term encompasses full-length EPHA2 (e.g., UniProt Reference Sequence: P29317; SEQ ID NO:33), as well as any form of human EPHA2 that may result from cellular processing. The term also encompasses functional variants or fragments of human EPHA2, including but not limited to splice variants, allelic variants, and isoforms that retain one or more biologic functions of human EPHA2 (i.e., variants and fragments are encompassed unless the context indicates that the term is used to refer to the wild-type protein only). EPHA2 can be isolated from a human, or may be produced recombinantly or by synthetic methods.

The term "anti-EPHA2 antibody" or "antibody that binds to EPHA2" refers to any form of antibody or fragment thereof that binds, e.g., specifically binds, to EPHA2, and encompasses monoclonal antibodies (including full-length monoclonal antibodies), polyclonal antibodies, and biologically functional antibody fragments so long as they bind, e.g., specifically bind, to EPHA2. WO 2007/030642 provides and is incorporated herein by reference for exemplary EPHA2-binding sequences, including exemplary anti-EPHA2 antibody sequences. In some embodiments, the anti-EPHA2 antibody used in the ADCs disclosed herein is an internalizing antibody or internalizing antibody fragment. $1C_1$ (WO 2007/030642; Jackson et al. (2008) Cancer Res. 68(22): 9367-74) is an exemplary anti-human EPHA2 antibody.

The term "mesothelin" or "MSLN," as used herein, refers to any native form of human MSLN. The term encompasses full-length MSLN (e.g., UniProt Reference Sequence: Q13421; SEQ ID NO:43), as well as any form of human MSLN that may result from cellular processing. The term also encompasses functional variants or fragments of human MSLN, including but not limited to splice variants, allelic variants, and isoforms that retain one or more biologic functions of human MSLN (i.e., variants and fragments are encompassed unless the context indicates that the term is used to refer to the wild-type protein only). MSLN can be isolated from a human, or may be produced recombinantly or by synthetic methods.

The term "anti-MSLN antibody" or "antibody that binds to MSLN" refers to any form of antibody or fragment thereof that binds, e.g., specifically binds, to MSLN, and encompasses monoclonal antibodies (including full-length monoclonal antibodies), polyclonal antibodies, and biologically functional antibody fragments so long as they bind, e.g., specifically bind, to MSLN. WO 2011/074621 provides and is incorporated herein by reference for exemplary MSLN-binding sequences, including exemplary anti-MSLN antibody sequences. In some embodiments, the anti-MSLN antibody used in the ADCs disclosed herein is an internalizing antibody or internalizing antibody fragment. 11-25, IC14-30, IC7-4, IC17-35 and 2-9 are exemplary anti-human MSLN antibodies.

The term "glutamate carboxypeptidase 2" or "FOLH1," as used herein, refers to any native form of human FOLH1. The term encompasses full-length FOLH1 (e.g., UniProt Reference Sequence: Q04609; SEQ ID NO:44), as well as any form of human FOLH1 that may result from cellular processing. The term also encompasses functional variants or fragments of human FOLH1, including but not limited to splice variants, allelic variants, and isoforms that retain one or more biologic functions of human FOLH1 (i.e., variants and fragments are encompassed unless the context indicates that the term is used to refer to the wild-type protein only). FOLH1 can be isolated from a human, or may be produced recombinantly or by synthetic methods.

The term "anti-FOLH1 antibody" or "antibody that binds to FOLH1" refers to any form of antibody or fragment thereof that binds, e.g., specifically binds, to FOLH1, and encompasses monoclonal antibodies (including full-length monoclonal antibodies), polyclonal antibodies, and biologically functional antibody fragments so long as they bind, e.g., specifically bind, to FOLH1. WO 2019/012260 and WO 2017/212250 provide and are incorporated herein by reference for exemplary FOLH1-binding sequences, including exemplary anti-FOLH1 antibody sequences. In some embodiments, the anti-FOLH1 antibody used in the ADCs disclosed herein is an internalizing antibody or internalizing antibody fragment. J591 (deimmunized) is an exemplary anti-human FOLH1 antibody.

The term "cadherin-6" or "CDH6," as used herein, refers to any native form of human CDH6. The term encompasses full-length CDH6 (e.g., UniProt Reference Sequence: P55285; SEQ ID NO:45), as well as any form of human CDH6 that may result from cellular processing. The term also encompasses functional variants or fragments of human CDH6, including but not limited to splice variants, allelic variants, and isoforms that retain one or more biologic functions of human CDH6 (i.e., variants and fragments are encompassed unless the context indicates that the term is used to refer to the wild-type protein only). CDH6 can be isolated from a human, or may be produced recombinantly or by synthetic methods.

The term "anti-CDH6 antibody" or "antibody that binds to CDH6" refers to any form of antibody or fragment thereof that binds, e.g., specifically binds, to CDH6, and encompasses monoclonal antibodies (including full-length monoclonal antibodies), polyclonal antibodies, and biologically functional antibody fragments so long as they bind, e.g., specifically bind, to CDH6. WO 2018/185618 provides and is incorporated herein by reference for exemplary CDH6-binding sequences, including exemplary anti-CDH6 antibody sequences. In some embodiments, the anti-CDH6 antibody used in the ADCs disclosed herein is an internalizing antibody or internalizing antibody fragment.

The term "carcinoembryonic antigen-related cell adhesion molecule 5" or "CEACAM5," as used herein, refers to any native form of human CEACAM5. The term encompasses full-length CEACAM5 (e.g., UniProt Reference Sequence: P06731; SEQ ID NO:46), as well as any form of human CEACAM5 that may result from cellular processing. The term also encompasses functional variants or fragments of human CEACAM5, including but not limited to splice variants, allelic variants, and isoforms that retain one or more biologic functions of human CEACAM5 (i.e., variants and fragments are encompassed unless the context indicates that the term is used to refer to the wild-type protein only). CEACAM5 can be isolated from a human, or may be produced recombinantly or by synthetic methods.

The term "anti-CEACAM5 antibody" or "antibody that binds to CEACAM5" refers to any form of antibody or fragment thereof that binds, e.g., specifically binds, to CEACAM5, and encompasses monoclonal antibodies (including full-length monoclonal antibodies), polyclonal antibodies, and biologically functional antibody fragments so long as they bind, e.g., specifically bind, to CEACAM5. US 2015/0125386 provides and is incorporated herein by reference for exemplary CEACAM5-binding sequences, including exemplary anti-CEACAM5 antibody sequences. In some embodiments, the anti-CEACAM5 antibody used in the ADCs disclosed herein is an internalizing antibody or internalizing antibody fragment. hMN14 is an exemplary anti-human CEACAM5 antibody.

The term "cryptic family protein 1B" or "CFC1B," as used herein, refers to any native form of human CFC1B. The term encompasses full-length CFC1B (e.g., UniProt Reference Sequence: P0CG36; SEQ ID NO:47), as well as any form of human CFC1B that may result from cellular processing. The term also encompasses functional variants or fragments of human CFC1B, including but not limited to splice variants, allelic variants, and isoforms that retain one or more biologic functions of human CFC1B (i.e., variants and fragments are encompassed unless the context indicates that the term is used to refer to the wild-type protein only). CFC1B can be isolated from a human, or may be produced recombinantly or by synthetic methods.

The term "anti-CFC1B antibody" or "antibody that binds to CFC1B" refers to any form of antibody or fragment thereof that binds, e.g., specifically binds, to CFC1B, and encompasses monoclonal antibodies (including full-length monoclonal antibodies), polyclonal antibodies, and biologically functional antibody fragments so long as they bind, e.g., specifically bind, to CFC1B. WO 2002/088170 provides and is incorporated herein by reference for exemplary CFC1B-binding sequences, including exemplary anti-CFC1B antibody sequences. In some embodiments, the anti-CFC1B antibody used in the ADCs disclosed herein is an internalizing antibody or internalizing antibody fragment.

The term "ectonucleotide pyrophosphatase/phosphodiesterase family member 3" or "ENPP3," as used herein, refers to any native form of human ENPP3. The term encompasses full-length ENPP3 (e.g., UniProt Reference Sequence: O14638; SEQ ID NO:48), as well as any form of human ENPP3 that may result from cellular processing. The term also encompasses functional variants or fragments of human ENPP3, including but not limited to splice variants, allelic variants, and isoforms that retain one or more biologic functions of human ENPP3 (i.e., variants and fragments are encompassed unless the context indicates that the term is used to refer to the wild-type protein only). ENPP3 can be isolated from a human, or may be produced recombinantly or by synthetic methods.

The term "anti-ENPP3 antibody" or "antibody that binds to ENPP3" refers to any form of antibody or fragment thereof that binds, e.g., specifically binds, to ENPP3, and encompasses monoclonal antibodies (including full-length monoclonal antibodies), polyclonal antibodies, and biologically functional antibody fragments so long as they bind, e.g., specifically bind, to ENPP3. Donate et al. ((2016) Clin Cancer Res. 22(8):1989-99) provides and is incorporated herein by reference for exemplary ENPP3-binding sequences, including exemplary anti-ENPP3 antibody sequences. In some embodiments, the anti-ENPP3 antibody used in the ADCs disclosed herein is an internalizing antibody or internalizing antibody fragment.

The term "folate receptor alpha" or "FOLR1," as used herein, refers to any native form of human FOLR1. The term encompasses full-length FOLR1 (e.g., UniProt Reference Sequence: P15328; SEQ ID NO:49), as well as any form of human FOLR1 that may result from cellular processing. The term also encompasses functional variants or fragments of human FOLR1, including but not limited to splice variants, allelic variants, and isoforms that retain one or more biologic functions of human FOLR1 (i.e., variants and fragments are encompassed unless the context indicates that the term is used to refer to the wild-type protein only). FOLR1 can be isolated from a human, or may be produced recombinantly or by synthetic methods.

The term "anti-FOLR1 antibody" or "antibody that binds to FOLR1" refers to any form of antibody or fragment thereof that binds, e.g., specifically binds, to FOLR1, and encompasses monoclonal antibodies (including full-length monoclonal antibodies), polyclonal antibodies, and biologically functional antibody fragments so long as they bind, e.g., specifically bind, to FOLR1. WO 2005/080431 and Coney et al. ((1991) Cancer Res. 51(22):6125-32) provide and are incorporated herein by reference for exemplary FOLR1-binding sequences, including exemplary anti-FOLR1 antibody sequences. In some embodiments, the anti-FOLR1 antibody used in the ADCs disclosed herein is an internalizing antibody or internalizing antibody fragment. Farletuzumab and MOv19 are exemplary anti-human FOLR1 antibodies.

The term "hepatitis A virus cellular receptor 1" or "HAVCR1," as used herein, refers to any native form of human HAVCR1. The term encompasses full-length HAVCR1 (e.g., UniProt Reference Sequence: Q96D42; SEQ ID NO:50), as well as any form of human HAVCR1 that may result from cellular processing. The term also encompasses functional variants or fragments of human HAVCR1, including but not limited to splice variants, allelic variants, and isoforms that retain one or more biologic functions of human HAVCR1 (i.e., variants and fragments are encompassed unless the context indicates that the term is used to refer to the wild-type protein only). HAVCR1 can be isolated from a human, or may be produced recombinantly or by synthetic methods.

The term "anti-HAVCR1 antibody" or "antibody that binds to HAVCR1" refers to any form of antibody or fragment thereof that binds, e.g., specifically binds, to HAVCR1, and encompasses monoclonal antibodies (including full-length monoclonal antibodies), polyclonal antibodies, and biologically functional antibody fragments so long as they bind, e.g., specifically bind, to HAVCR1. Thomas et al. ((2016) Mol Cancer Ther. 15(12):2946-54) provides and is incorporated herein by reference for exemplary HAVCR1-binding sequences, including exemplary anti-HAVCR1 antibody sequences. In some embodiments, the anti-HAVCR1 antibody used in the ADCs disclosed herein is an internalizing antibody or internalizing antibody fragment.

The term "mast/stem cell growth factor receptor Kit" or "KIT," as used herein, refers to any native form of human KIT. The term encompasses full-length KIT (e.g., UniProt Reference Sequence: P10721; SEQ ID NO:51), as well as any form of human KIT that may result from cellular processing. The term also encompasses functional variants or fragments of human KIT, including but not limited to splice variants, allelic variants, and isoforms that retain one or more biologic functions of human KIT (i.e., variants and fragments are encompassed unless the context indicates that the term is used to refer to the wild-type protein only). KIT can be isolated from a human, or may be produced recombinantly or by synthetic methods.

The term "anti-KIT antibody" or "antibody that binds to KIT" refers to any form of antibody or fragment thereof that binds, e.g., specifically binds, to KIT, and encompasses monoclonal antibodies (including full-length monoclonal antibodies), polyclonal antibodies, and biologically functional antibody fragments so long as they bind, e.g., specifically bind, to KIT. Shi et al. ((2016) Proc Natl Acad Sci USA 113(33):E4784-93) and Abrams et al. ((2018) Clin Cancer Res. 24(17):4297-308) provide and are incorporated herein by reference for exemplary KIT-binding sequences, including exemplary anti-KIT antibody sequences. In some embodiments, the anti-KIT antibody used in the ADCs disclosed herein is an internalizing antibody or internalizing antibody fragment.

The term "hepatocyte growth factor receptor" or "MET," as used herein, refers to any native form of human MET. The term encompasses full-length MET (e.g., UniProt Reference Sequence: P08581; SEQ ID NO:52), as well as any form of human MET that may result from cellular processing. The term also encompasses functional variants or fragments of human MET, including but not limited to splice variants, allelic variants, and isoforms that retain one or more biologic functions of human MET (i.e., variants and fragments are encompassed unless the context indicates that the term is used to refer to the wild-type protein only). MET can be isolated from a human, or may be produced recombinantly or by synthetic methods.

The term "anti-MET antibody" or "antibody that binds to MET" refers to any form of antibody or fragment thereof that binds, e.g., specifically binds, to MET, and encompasses monoclonal antibodies (including full-length monoclonal antibodies), polyclonal antibodies, and biologically functional antibody fragments so long as they bind, e.g., specifically bind, to MET. Yang et al. ((2019) Acta Pharmacol Sin.) provides and is incorporated herein by reference for exemplary MET-binding sequences, including exemplary anti-MET antibody sequences. In some embodiments, the anti-MET antibody used in the ADCs disclosed herein is an internalizing antibody or internalizing antibody fragment.

The term "mucin-16" or "MUC16," as used herein, refers to any native form of human MUC16. The term encompasses full-length MUC16 (e.g., UniProt Reference Sequence: Q8WXI7; SEQ ID NO:53), as well as any form of human MUC16 that may result from cellular processing. The term also encompasses functional variants or fragments of human MUC16, including but not limited to splice variants, allelic variants, and isoforms that retain one or more biologic functions of human MUC16 (i.e., variants and fragments are encompassed unless the context indicates that the term is used to refer to the wild-type protein only).

MUC16 can be isolated from a human, or may be produced recombinantly or by synthetic methods.

The term "anti-MUC16 antibody" or "antibody that binds to MUC16" refers to any form of antibody or fragment thereof that binds, e.g., specifically binds, to MUC16, and encompasses monoclonal antibodies (including full-length monoclonal antibodies), polyclonal antibodies, and biologically functional antibody fragments so long as they bind, e.g., specifically bind, to MUC16. Liu et al. ((2016) Ann Oncol. 27(11):2124-30) provides and is incorporated herein by reference for exemplary MUC16-binding sequences, including exemplary anti-MUC16 antibody sequences. In some embodiments, the anti-MUC16 antibody used in the ADCs disclosed herein is an internalizing antibody or internalizing antibody fragment.

The term "zinc transporter ZIP6" or "SLC39A6," as used herein, refers to any native form of human SLC39A6. The term encompasses full-length SLC39A6 (e.g., UniProt Reference Sequence:Q13433; SEQ ID NO:54), as well as any form of human SLC39A6 that may result from cellular processing. The term also encompasses functional variants or fragments of human SLC39A6, including but not limited to splice variants, allelic variants, and isoforms that retain one or more biologic functions of human SLC39A6 (i.e., variants and fragments are encompassed unless the context indicates that the term is used to refer to the wild-type protein only). SLC39A6 can be isolated from a human, or may be produced recombinantly or by synthetic methods.

The term "anti-SLC39A6 antibody" or "antibody that binds to SLC39A6" refers to any form of antibody or fragment thereof that binds, e.g., specifically binds, to SLC39A6, and encompasses monoclonal antibodies (including full-length monoclonal antibodies), polyclonal antibodies, and biologically functional antibody fragments so long as they bind, e.g., specifically bind, to SLC39A6. Sussman et al. ((2014) Mol Cancer Ther. 13(12):2991-3000) provides and is incorporated herein by reference for exemplary SLC39A6-binding sequences, including exemplary anti-SLC39A6 antibody sequences. In some embodiments, the anti-SLC39A6 antibody used in the ADCs disclosed herein is an internalizing antibody or internalizing antibody fragment.

The term "choline transporter-like protein 4" or "SLC44A4," as used herein, refers to any native form of human SLC44A4. The term encompasses full-length SLC44A4 (e.g., UniProt Reference Sequence: Q53GD3; SEQ ID NO:55), as well as any form of human SLC44A4 that may result from cellular processing. The term also encompasses functional variants or fragments of human SLC44A4, including but not limited to splice variants, allelic variants, and isoforms that retain one or more biologic functions of human SLC44A4 (i.e., variants and fragments are encompassed unless the context indicates that the term is used to refer to the wild-type protein only). SLC44A4 can be isolated from a human, or may be produced recombinantly or by synthetic methods.

The term "anti-SLC44A4 antibody" or "antibody that binds to SLC44A4" refers to any form of antibody or fragment thereof that binds, e.g., specifically binds, to SLC44A4, and encompasses monoclonal antibodies (including full-length monoclonal antibodies), polyclonal antibodies, and biologically functional antibody fragments so long as they bind, e.g., specifically bind, to SLC44A4. Mattie et al. ((2016) Mol Cancer Ther. 15(11):2679-87) provides and is incorporated herein by reference for exemplary SLC44A4-binding sequences, including exemplary anti-SLC44A4 antibody sequences. In some embodiments, the anti-SLC44A4 antibody used in the ADCs disclosed herein is an internalizing antibody or internalizing antibody fragment.

The term "metalloreductase STEAP1" or "STEAP1," as used herein, refers to any native form of human STEAP1. The term encompasses full-length STEAP1 (e.g., UniProt Reference Sequence: Q9UHE8; SEQ ID NO:56), as well as any form of human STEAP1 that may result from cellular processing. The term also encompasses functional variants or fragments of human STEAP1, including but not limited to splice variants, allelic variants, and isoforms that retain one or more biologic functions of human STEAP1 (i.e., variants and fragments are encompassed unless the context indicates that the term is used to refer to the wild-type protein only). STEAP1 can be isolated from a human, or may be produced recombinantly or by synthetic methods.

The term "anti-STEAP1 antibody" or "antibody that binds to STEAP1" refers to any form of antibody or fragment thereof that binds, e.g., specifically binds, to STEAP1, and encompasses monoclonal antibodies (including full-length monoclonal antibodies), polyclonal antibodies, and biologically functional antibody fragments so long as they bind, e.g., specifically bind, to STEAP1. WO 2008/052187 provides and is incorporated herein by reference for exemplary STEAP1-binding sequences, including exemplary anti-STEAP1 antibody sequences. In some embodiments, the anti-STEAP1 antibody used in the ADCs disclosed herein is an internalizing antibody or internalizing antibody fragment.

As used herein, the term "specific," "specifically binds," and "binds specifically" refers to a binding reaction between an antibody or antigen binding fragment (e.g., an anti-HER2 antibody) and a target antigen (e.g., HER2) in a heterogeneous population of proteins and other biologics. Antibodies can be tested for specificity of binding by comparing binding to an appropriate antigen to binding to an irrelevant antigen or antigen mixture under a given set of conditions. If the antibody binds to the appropriate antigen with at least 2, 5, 7, and preferably 10 or more times more affinity than to the irrelevant antigen or antigen mixture, then it is considered to be specific. A "specific antibody" or a "target-specific antibody" is one that only binds the target antigen (e.g., HER2), but does not bind (or exhibits minimal binding) to other antigens. In certain embodiments, an antibody or antigen binding fragment that specifically binds a target antigen (e.g., HER2) has a $K_D$ of less than $1\times10^{-6}$ M, less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In certain embodiments, the $K_D$ is 1 µM to 500 µM. In some embodiments, the $K_D$ is between 500 µM to 1 µM, 1 µM to 100 nM, or 100 mM to 10 nM.

The term "epitope" refers to the portion of an antigen capable of being recognized and specifically bound by an antibody. When the antigen is a polypeptide, epitopes can be formed from contiguous amino acids or noncontiguous amino acids juxtaposed by tertiary folding of the polypeptide. The epitope bound by an antibody may be identified using any epitope mapping technique known in the art, including X-ray crystallography for epitope identification by direct visualization of the antigen-antibody complex, as well as monitoring the binding of the antibody to fragments or mutated variations of the antigen, or monitoring solvent accessibility of different parts of the antibody and the antigen. Exemplary strategies used to map antibody epitopes include, but are not limited to, array-based oligo-peptide scanning, limited proteolysis, site-directed mutagenesis, high-throughput mutagenesis mapping, hydrogen-deuterium exchange, and mass spectrometry (see, e.g., Gershoni et al.

(2007) 21:145-56; and Hager-Braun and Tomer (2005) Expert Rev Proteomics 2:745-56).

Competitive binding and epitope binning can also be used to determine antibodies sharing identical or overlapping epitopes. Competitive binding can be evaluated using a cross-blocking assay, such as the assay described in "Antibodies, A Laboratory Manual," Cold Spring Harbor Laboratory, Harlow and Lane ($1^{st}$ edition 1988, $2^{nd}$ edition 2014). In some embodiments, competitive binding is identified when a test antibody or binding protein reduces binding of a reference antibody or binding protein to a target antigen such as HER2 (e.g., a binding protein comprising CDRs and/or variable domains selected from those identified in Tables 2-4), by at least about 50% in the cross-blocking assay (e.g., 50%, 60%, 70%, 80%, 90%, 95%, 99%, 99.5%, or more, or any percentage in between), and/or vice versa. In some embodiments, competitive binding can be due to shared or similar (e.g., partially overlapping) epitopes, or due to steric hindrance where antibodies or binding proteins bind at nearby epitopes (see, e.g., Tzartos, Methods in Molecular Biology (Morris, ed. (1998) vol. 66, pp. 55-66)). In some embodiments, competitive binding can be used to sort groups of binding proteins that share similar epitopes. For example, binding proteins that compete for binding can be "binned" as a group of binding proteins that have overlapping or nearby epitopes, while those that do not compete are placed in a separate group of binding proteins that do not have overlapping or nearby epitopes.

The term "$k_{on}$" or "$k_a$" refers to the on-rate constant for association of an antibody to the antigen to form the antibody/antigen complex. The rate can be determined using standard assays, such as a surface plasmon resonance, biolayer inferometry, or ELISA assay.

The term "$k_{off}$" or "$k_d$" refers to the off-rate constant for dissociation of an antibody from the antibody/antigen complex. The rate can be determined using standard assays, such as a surface plasmon resonance, biolayer inferometry, or ELISA assay.

The term "$K_D$" refers to the equilibrium dissociation constant of a particular antibody-antigen interaction. $K_D$ is calculated by $k_a/k_d$. The rate can be determined using standard assays, such as a surface plasmon resonance, biolayer inferometry, or ELISA assay.

The term "p" or "drug loading" or "drug:antibody ratio" or "drug-to-antibody ratio" or "DAR" refers to the number of drug moieties per antibody or antigen binding fragment, i.e., drug loading, or the number of -L-D moieties per antibody or antigen binding fragment (Ab) in ADCs of Formula (I). In ADCs comprising a splicing modulator drug moiety, "p" refers to the number of splicing modulator compounds linked to the antibody or antigen binding fragment. For example, if two splicing modulator compounds (e.g., two compounds each having the structure of D1) are linked to an antibody or antigen binding fragment, p=2. In compositions comprising multiple copies of ADCs of Formula (I), "average p" refers to the average number of -L-D moieties per antibody or antigen binding fragment, also referred to as "average drug loading."

A "linker" or "linker moiety" is used herein to refer to any chemical moiety that is capable of covalently joining a compound, usually a drug moiety such as a splicing modulator drug moiety, to another moiety such as an antibody or antigen binding fragment. Linkers can be susceptible to or substantially resistant to acid-induced cleavage, peptidase-induced cleavage, light-based cleavage, esterase-induced cleavage, and/or disulfide bond cleavage, at conditions under which the compound or the antibody remains active.

The term "agent" is used herein to refer to a chemical compound, a mixture of chemical compounds, a biological macromolecule, or an extract made from biological materials. The term "therapeutic agent" or "drug" refers to an agent that is capable of modulating a biological process and/or has biological activity. The splicing modulator compounds described herein are exemplary therapeutic agents.

The term "chemotherapeutic agent" or "anti-cancer agent" is used herein to refer to all agents that are effective in treating cancer regardless of mechanism of action. Inhibition of metastasis or angiogenesis is frequently a property of a chemotherapeutic agent. Chemotherapeutic agents include antibodies, biological molecules, and small molecules, and encompass the splicing modulator compounds described herein. A chemotherapeutic agent may be a cytotoxic or cytostatic agent. The term "cytostatic agent" refers to an agent that inhibits or suppresses cell growth and/or multiplication of cells. The term "cytotoxic agent" refers to a substance that causes cell death primarily by interfering with a cell's expression activity and/or functioning.

As used herein, the terms "splicing modulator," "spliceosome modulator," or "splice modulator" refer to compounds that have anti-cancer activity by interacting with components of the spliceosome. In some embodiments, a splicing modulator alters the rate or form of splicing in a target cell. Splicing modulators that function as inhibitory agents, for example, are capable of decreasing uncontrolled cellular proliferation. In some embodiments, the splicing modulators may act by binding to the SF3b spliceosome complex. Such modulators may be natural compounds or synthetic compounds. Non-limiting examples of splicing modulators and categories of such modulators include pladienolide (e.g., pladienolide D or pladienolide B), pladienolide derivatives (e.g., pladienolide D or pladienolide B derivatives), herboxidiene, herboxidiene derivatives, spliceostatin, spliceostatin derivatives, sudemycin, or sudemycin derivatives. As used herein, the terms "derivative" and "analog" when referring to a splicing modulator, or the like, means any such compound that retains essentially the same, similar, or enhanced biological function or activity as the original compound but has an altered chemical or biological structure. In some embodiments, the splicing modulator is a pladienolide or pladienolide derivative.

As used herein, a "pladienolide derivative" refers to a compound which is structurally related to a member of the family of natural products known as the pladienolides and which retains one or more biological functions of the starting compound. Pladienolides were first identified in the bacteria *Streptomyces platensis* (Mizui et al. (2004) J Antibiot. 57:188-96) as being potently cytotoxic and resulting in cell cycle arrest in the G1 and G2/M phases of the cell cycle (e.g., Bonnal et al. (2012) Nat Rev Drug Dis 11:847-59). There are seven naturally occurring pladienolides, pladienolide A-G (Mizui et al. (2004) J Antibiot. 57:188-96; Sakai et al. (2004) J Antibiotics 57:180-7). U.S. Pat. Nos. 7,884,128 and 7,816,401 describe exemplary methods of synthesizing pladienolide B and D and are each incorporated herein by reference for such methods. Synthesis of pladienolide B and D may also be performed using the exemplary methods described in Kanada et al. ((2007) Angew Chem Int Ed. 46:4350-5). Kanada et al. and Intl. Pub. No. WO 2003/099813 describe exemplary methods for synthesizing E7107 (D11) (Compound 45 of WO 2003/099813) from Pladienolide D (11107D of WO 2003/099813). A corresponding U.S. Pat. No. is 7,550,503 to Kotake et al. Each of these references is incorporated herein for the described synthesis methods.

As used herein, a "splicing modulator drug moiety" refers to the component of an ADC or composition that provides the structure of a splicing modulator compound, e.g., the splicing modulator (D) component in an ADC of Formula (I), or in a composition comprising -L–D.

As used herein, a "spliceosome" refers to a ribonucleoprotein complex that removes introns from one or more RNA segments, such as pre-mRNA segments.

The term "homolog" refers to a molecule which exhibits homology to another molecule, by for example, having sequences of chemical residues that are the same or similar at corresponding positions.

The term "inhibit" or "inhibition of," as used herein, means to reduce by a measurable amount, and can include but does not require complete prevention or inhibition.

The term "target-negative," "target antigen-negative," or "antigen-negative" refers to the absence of target antigen expression by a cell or tissue. The term "target-positive," "target antigen-positive," or "antigen-positive" refers to the presence of target antigen expression. For example, a cell or a cell line that does not express a target antigen may be described as target-negative, whereas a cell or cell line that expresses a target antigen may be described as target-positive.

The term "bystander killing" or "bystander effect" refers to the killing of target-negative cells in the presence of target-positive cells, wherein killing of target-negative cells is not observed in the absence of target-positive cells. Cell-to-cell contact, or at least proximity between target-positive and target-negative cells, enables bystander killing. This type of killing is distinguishable from "off-target killing," which refers to the indiscriminate killing of target-negative cells. "Off-target killing" may be observed in the absence of target-positive cells.

The terms "neoplastic disorder" and "cancer" are used herein interchangeably to refer to the presence of cells possessing characteristics typical of cancer-causing cells, such as uncontrolled proliferation, immortality, metastatic potential, rapid growth and proliferation rate, and/or certain morphological features. Often, cancer cells can be in the form of a tumor or mass, but such cells may exist alone within a subject, or may circulate in the blood stream as independent cells, such as leukemic or lymphoma cells. The terms "neoplastic disorder" and "cancer" includes all types of cancers and cancer metastases, including hematological malignancy, solid tumors, sarcomas, carcinomas and other solid and non-solid tumor cancers. Hematological malignancies may include B-cell malignancies, cancers of the blood (leukemias), cancers of plasma cells (myelomas, e.g., multiple myeloma), or cancers of the lymph nodes (lymphomas). Exemplary B-cell malignancies include chronic lymphocytic leukemia (CLL), follicular lymphoma, mantle cell lymphoma, and diffuse large B-cell lymphoma. Leukemias may include acute lymphoblastic leukemia (ALL), acute myelogenous leukemia (AML), chronic lymphocytic leukemia (CLL), chronic myelogenous leukemia (CML), chronic myelomonocytic leukemia (CMML), acute monocytic leukemia (AMoL), etc. Lymphomas may include Hodgkin's lymphoma and non-Hodgkin's lymphoma. Other hematologic malignancies may include myelodysplasia syndrome (MDS). Solid tumors may include carcinomas such as adenocarcinoma, e.g., breast cancer, pancreatic cancer, prostate cancer, colon or colorectal cancer, lung cancer, gastric cancer, cervical cancer, endometrial cancer, ovarian cancer, cholangiocarcinoma, glioma, melanoma, etc.

The terms "tumor" and "neoplasm" refer to any mass of tissue that results from excessive cell growth or proliferation, either benign or malignant, including precancerous lesions.

The terms "tumor cell" and "neoplastic cell" are used interchangeably and refer to individual cells or the total population of cells derived from a tumor or neoplasm, including both non-tumorigenic cells and cancer stem cells. As used herein, the term "tumor cell" will be modified by the term "non-tumorigenic" when referring solely to those tumor cells lacking the capacity to renew and differentiate to distinguish those tumor cells from cancer stem cells.

The terms "subject" and "patient" are used interchangeably herein to refer to any animal, such as any mammal, including but not limited to, humans, non-human primates, rodents, and the like. In some embodiments, the mammal is a mouse. In some embodiments, the mammal is a human. In some embodiments, the subject is a mouse. In some embodiments, the subject is a human.

The term "co-administration" or administration "in combination with" one or more therapeutic agents includes concurrent administration and consecutive administration in any order.

A "pharmaceutical composition" refers to a preparation which is in such form as to permit administration and subsequently provide the intended biological activity of the active ingredient(s) and/or to achieve a therapeutic effect, and which contains no additional components which are unacceptably toxic to a subject to which the formulation would be administered. The pharmaceutical composition may be sterile.

A "pharmaceutical excipient" comprises a material such as an adjuvant, a carrier, pH-adjusting and buffering agents, tonicity adjusting agents, wetting agents, preservative, and the like.

"Pharmaceutically acceptable" means approved or approvable by a regulatory agency of the Federal or a state government, or listed in the U.S. Pharmacopeia or other generally recognized pharmacopeia, for use in animals, and more particularly in humans A "pharmaceutically acceptable salt" is a salt that retains the desired biological activity of the parent compound and does not impart undesired toxicological effects. Examples of such salts are: (a) acid addition salts formed with inorganic acids, for example, hydrochloric acid, hydrobromic acid, sulfuric acid, phosphoric acid, nitric acid and the like; and salts formed with organic acids, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, β-toluenesulfonic acid, naphthalenedisulfonic acid, polygalacturonic acid, and the like; and (b) salts formed from elemental anions such as chlorine, bromine, and iodine. See, e.g., Haynes et al. "Commentary: Occurrence of Pharmaceutically Acceptable Anions and Cations in the Cambridge Structural Database," J Pharmaceutical Sciences, vol. 94, no. 10 (2005), and Berge et al. "Pharmaceutical Salts," J Pharmaceutical Sciences, vol. 66, no. 1 (1977), which are incorporated by reference herein.

The term "effective amount," as used herein, refers to the amount of a compound, ADC, or composition described herein (e.g., a splicing modulator or an ADC) that is sufficient to perform a specifically stated purpose, for example to produce a therapeutic effect after administration, such as a reduction in tumor growth rate or tumor volume, a reduction in a symptom of cancer, or some other indicia of treatment efficacy. An effective amount can be determined in a routine manner in relation to the stated purpose. The term "therapeutically effective amount" refers to an amount of a compound, an ADC, or composition described herein effective for detectable killing, reduction, and/or inhibition of the growth or spread of tumor cells, the size or number of tumors, and/or other measure of the level, stage, progression and/or severity of the cancer. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., inhibition of cell growth. The specific dose may vary depending on, for example, the particular pharmaceutical composition, the subject and their age and existing health conditions or risk for health conditions, the dosing regimen to be followed, the severity of the disease, whether it is administered in combination with other agents, timing of administration, the tissue to which it is administered, and the physical delivery system in which it is carried. In the case of cancer, a therapeutically effective amount of ADC can reduce the number of cancer cells, reduce tumor size, inhibit (e.g., slow or stop) tumor metastasis, inhibit (e.g., slow or stop) tumor growth, and/or relieve one or more symptoms.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, "to treat" or "therapeutic" and grammatically related terms, refer to any improvement of any consequence of disease, such as prolonged survival, less morbidity, and/or a lessening of side effects which result from an alternative therapeutic modality. As is readily appreciated in the art, full eradication of disease is encompassed but not required for a treatment act. "Treatment" or "treat," as used herein, refers to the administration of a described ADC or composition to a subject, e.g., a patient. The treatment can be to cure, heal, alleviate, relieve, alter, remedy, ameliorate, palliate, improve or affect the disorder, the symptoms of the disorder or the predisposition toward the disorder, e.g., a cancer. In some embodiments, in addition to treating a subject with a condition, a composition disclosed herein can also be provided prophylactically to prevent or reduce the likelihood of developing that condition.

In some embodiments, a labeled ADC is used. Suitable "labels" include radionuclides, enzymes, substrates, cofactors, inhibitors, fluorescent moieties, chemiluminescent moieties, magnetic particles, and the like.

By "protein," as used herein, is meant at least two covalently attached amino acids. The term encompasses polypeptides, oligopeptides, and peptides. In some embodiments, the two or more covalently attached amino acids are attached by a peptide bond. The protein may be made up of naturally occurring amino acids and peptide bonds, for example when the protein is made recombinantly using expression systems and host cells. Alternatively, the protein may include synthetic amino acids (e.g., homophenylalanine, citrulline, ornithine, and norleucine), or peptidomimetic structures, i.e., "peptide or protein analogs," such as peptoids. Peptoids are an exemplary class of peptidomimetics whose side chains are appended to the nitrogen atom of the peptide backbone, rather than to the α-carbons (as they are in amino acids), and have different hydrogen bonding and conformational characteristics in comparison to peptides (see, e.g., Simon et al. (1992) Proc Natl Acad Sci. USA 89:9367). As such, peptoids can be resistant to proteolysis or other physiological or storage conditions, and effective at permeating cell membranes. Such synthetic amino acids may be incorporated in particular when the antibody is synthesized in vitro by conventional methods well known in the art. In addition, any combination of peptidomimetic, synthetic and naturally occurring residues/structures can be used. "Amino acid" also includes imino acid residues, such as proline and hydroxyproline. The amino acid "R group" or "side chain" may be in either the (L)- or the (S)-configuration. In a specific embodiment, the amino acids are in the (L)- or (S)-configuration.

A "recombinant protein" is a protein made using recombinant techniques using any techniques and methods known in the art, i.e., through the expression of a recombinant nucleic acid. Methods and techniques for the production of recombinant proteins are well known in the art.

An "isolated" protein is unaccompanied by at least some of the material with which it is normally associated in its natural state, for example constituting at least about 5%, or at least about 50% by weight of the total protein in a given sample. It is understood that the isolated protein may constitute from 5% to 99.9% by weight of the total protein content depending on the circumstances. For example, the protein may be made at a significantly higher concentration through the use of an inducible promoter or high expression promoter, such that the protein is made at increased concentration levels. The definition includes the production of an antibody in a wide variety of organisms and/or host cells that are known in the art.

For amino acid sequences, sequence identity and/or similarity may be determined using standard techniques known in the art, including, but not limited to, the local sequence identity algorithm of Smith and Waterman (1981) Adv Appl Math. 2:482, the sequence identity alignment algorithm of Needleman and Wunsch (1970) J Mol Biol. 48:443, the search for similarity method of Pearson and Lipman (1988) Proc Nat Acad Sci. USA 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al. (1984) Nucl Acid Res. 12:387-95, preferably using the default settings, or by inspection. Preferably, percent identity is calculated by FastDB based upon the following parameters: mismatch penalty of 1; gap penalty of 1; gap size penalty of 0.33; and joining penalty of 30 ("Current Methods in Sequence Comparison and Analysis," Macromolecule Sequencing and Synthesis, Selected Methods and Applications, pp. 127-149 (1988), Alan R. Liss, Inc).

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) J Mol Evol. 35:351-60; the method is similar to that described by Higgins and Sharp (1989) CABIOS 5:151-3. Useful PILEUP parameters including a default gap weight of 3.00, a default gap length weight of 0.10, and weighted end gaps.

Another example of a useful algorithm is the BLAST algorithm, described in: Altschul et al. (1990) J Mol Biol. 215:403-10; Altschul et al. (1997) Nucl Acid Res. 25:3389-402; and Karin et al. (1993) Proc Natl Acad Sci. USA 90:5873-87. A particularly useful BLAST program is the WU-BLAST-2 program which was obtained from Altschul et al. (1996) Methods in Enzymology 266:460-80. WU-BLAST-2 uses several search parameters, most of which are set to the default values. The adjustable parameters are set with the following values: overlap span=I, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. (1997) Nucl Acid Res. 25:3389-402. Gapped BLAST uses BLOSUM-62 substitution scores; threshold T parameter set to 9; the two-hit method to trigger ungapped extensions, charges gap lengths of k a cost of 10+k; Xu set to 16, and Xg set to 40 for database search stage and to 67 for the output stage of the algorithms. Gapped alignments are triggered by a score corresponding to about 22 bits.

Generally, the amino acid homology, similarity, or identity between proteins disclosed herein and variants thereof, including variants of target antigens (such as HER2, CD138, EPHA2, MSLN, FOLH1, CDH6, CEACAM5, CFC1B, ENPP3, FOLR1, HAVCR1, KIT, MET, MUC16, SLC39A6, SLC44A4, or STEAP1) and variants of antibody variable domains (including individual variant CDRs), are at least 80% to the sequences depicted herein, e.g., homologies or identities of at least 85%, 90%, 91%, 92%, 93%, 94%, 95%, 96%, 97%, 98%, 99%, almost 100%, or 100%.

In a similar manner, "percent (%) nucleic acid sequence identity" with respect to the nucleic acid sequence of the antibodies and other proteins identified herein is defined as the percentage of nucleotide residues in a candidate sequence that are identical with the nucleotide residues in the coding sequence of the antigen binding protein. A specific method utilizes the BLASTN module of WU-BLAST-2 set to the default parameters, with overlap span and overlap fraction set to 1 and 0.125, respectively.

While the site or region for introducing an amino acid sequence variation is predetermined, the mutation per se need not be predetermined. For example, in order to optimize the performance of a mutation at a given site, random mutagenesis may be conducted at the target codon or region and the expressed antigen binding protein CDR variants screened for the optimal combination of desired activity. Techniques for making substitution mutations at predetermined sites in DNA having a known sequence are well known, for example, MI3 primer mutagenesis and PCR mutagenesis "Alkyl" or "alkyl group," as used herein, means a straight-chain, branched, or cyclic hydrocarbon chain that is completely saturated. In certain embodiments, alkyl groups may contain 1-8 carbon atoms ("$C_1$-$C_8$alkyl"). In certain embodiments, alkyl groups may contain 1-6 carbon atoms ("$C_1$-$C_6$alkyl"). In certain embodiments, alkyl groups contain 1-3 carbon atoms. In still other embodiments, alkyl groups contain 2-3 carbon atoms, and in yet other embodiments alkyl groups contain 1-2 carbon atoms.

"Alkylalkoxy," as used herein, means an alkyl group substituted with an alkoxy group. "Alkoxy", as used herein, refers to an alkyl group, as previously defined, attached to the principal carbon chain through an oxygen ("alkoxy") atom.

"Alkylamino," as used herein, means an alkyl group substituted with an amino group. "Amino," as used herein, refers to —$NH_2$, —NH(alkyl), or —N(alkyl)(alkyl).

"Alkylhydroxy," as used herein, means an alkyl group substituted with an amino group. "Hydroxy" or "hydroxyl," as used herein, refers to —OH.

"Alkylene" refers to a divalent radical of an alkyl group. For example, —$CH_2$—, —$CH_2CH_2$—, —$CH_2CH_2CH_2$—, —$CH_2CH_2CH_2CH_2$—, —$CH_2CH_2CH_2CH_2CH_2$—, and —$CH_2CH_2CH_2CH_2CH_2CH_2$— refer to methylene, ethylene, n-propylene, n-butylene, n-pentylene, and n-hexylene, respectively.

"Carbocycle," as used herein, includes both aromatic (e.g., aryl) and non-aromatic (e.g., cycloalkyl) groups. In certain embodiments, carbocycle groups contain 3-10 carbon atoms ("3 to 10 membered carbocycle"). In certain embodiments, carbocycle groups contain 3-8 carbon atoms ("3 to 8 membered carbocycle"). In certain embodiments, carbocycle groups contain 3-6 carbon atoms ("3 to 6 membered carbocycle"). In certain embodiments, carbocycle groups contain 3-5 carbon atoms ("3 to 5 membered carbocycle").

"Halogen" refers to a radical of any halogen, e.g., —F, —Cl, —Br, or —I.

The terms "heterocycle", "heterocyclyl", and "heterocyclic" as used herein, mean a monocyclic heterocycle, a bicyclic heterocycle, or a tricyclic heterocycle containing at least one heteroatom in the ring.

The monocyclic heterocycle is a 3-, 4-, 5-, 6-, 7, or 8-membered ring containing at least one heteroatom independently chosen from O, N, and S. In some embodiments, the heterocycle is a 3- or 4-membered ring containing one heteroatom chosen from O, N and S. In some embodiments, the heterocycle is a 5-membered ring containing zero or one double bond and one, two or three heteroatoms chosen from O, N and S. In some embodiments, the heterocycle is a 6-, 7-, or 8-membered ring containing zero, one or two double bonds and one, two or three heteroatoms chosen from O, N and S. Representative examples of monocyclic heterocycle include, but are not limited to, azetidinyl, azepanyl, aziridinyl, diazepanyl, 1,3-dioxanyl, 1,3-dioxolanyl, dihydropyranyl (including 3,4-dihydro-2H-pyran-6-yl), 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl (including tetrahydro-2H-pyran-4-yl), tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The bicyclic heterocycles of the present disclosure may include a monocyclic heterocycle fused to an aryl group, or a monocyclic heterocycle fused to a monocyclic cycloalkyl, or a monocyclic heterocycle fused to a monocyclic cycloalkenyl, or a monocyclic heterocycle fused to a monocyclic heterocycle having a total of 5 to 12 ring atoms. Examples of bicyclic heterocycles include, but are not limited to, 3,4-dihydro-2H-pyranyl, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

The terms "heterocycle", "heterocyclyl", and "heterocyclic" encompass heteroaryls. "Heteroaryl" refers to a cyclic moiety having one or more closed rings, with one or more heteroatoms (oxygen, nitrogen or sulfur) in at least one of the rings, wherein at least one of the rings is aromatic, and wherein the ring or rings may independently be fused, and/or bridged. Examples include without limitation phenyl, thiophenyl, triazolyl, pyridinyl, pyrimidinyl, pyridazinyl, and pyrazinyl.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent chosen from a specified group, the substituent may be either the same or different at each position. Combinations of substituents envisioned under this disclosure are preferably those that result in the formation of stable or chemically feasible compounds.

One skilled in the art will be understand that "substitution" or "substituted with" or "absent" includes the implicit proviso that such substitution or absence is in accordance with permitted valence of the substituted atom and the substituent, and that the substitution or absence results in a stable compound, e.g., which does not spontaneously undergo transformation such as by rearrangement, cyclization, elimination, etc. For purposes of this disclosure, the heteroatoms such as nitrogen may have hydrogen substituents, and/or any permissible substituents of organic compounds described herein which satisfy the valences of the heteroatoms.

"Stable" refers to compounds that are not substantially altered chemically and/or physically when subjected to conditions to allow for their production, detection, and, in certain embodiments, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. In some embodiments, the compounds disclosed herein are stable.

Enantiomers taught herein may include "enantiomerically pure" isomers that comprise substantially a single enantiomer, for example, greater than or equal to 90%, 92%, 95%, 98%, or 99%, or equal to 100% of a single enantiomer, at a particular asymmetric center or centers. An "asymmetric center" or "chiral center" refers to a tetrahedral carbon atom that comprises four different substituents.

The compounds described herein may also contain unnatural proportions of atomic isotopes at one or more of the atoms that constitute such compounds. For example, the compounds may be radiolabeled with radioactive isotopes, such as, for example, deuterium ($^2$H), tritium ($^3$H), carbon-13 ($^{13}$C), or carbon-14 ($^{14}$C). All isotopic variations of the compounds disclosed herein, whether radioactive or not, are intended to be encompassed within the scope of the present disclosure. In addition, all tautomeric forms of the compounds described herein are intended to be within the scope of the claimed disclosure.

Antibody-Drug Conjugates

The antibody-drug conjugate (ADC) compounds of the present disclosure include those with anti-cancer activity. In particular, the ADC compounds include an antibody or antigen binding fragment (including an antigen binding fragment thereof) conjugated (i.e., covalently attached by a linker) to a drug moiety (e.g., a splicing modulator), wherein the drug moiety when not conjugated to an antibody or antigen binding fragment has a cytotoxic or cytostatic effect. In various embodiments, the drug moiety when not conjugated to an antibody or antigen binding fragment is capable of binding to and/or interacting with the SF3b spliceosome complex. In various embodiments, the drug moiety when not conjugated to an antibody or antigen binding fragment is capable of modulating in vitro and/or in vivo RNA splicing. By targeting RNA splicing, in various embodiments, the drug moieties and ADCs disclosed herein are potent antiproliferative agents. In various embodiments, the drug moieties and ADCs disclosed herein can target both actively dividing and quiescent cells.

In various embodiments, the present disclosure is based, at least in part, on the discovery that certain biologically active splicing modulators may provide improved properties when used in ADCs. While a splicing modulator may show desirably improved features (e.g., robust SF3b spliceosome complex binding, potent modulation of RNA splicing) when used on its own, in various embodiments, the splicing modulator may exhibit fewer of the same desirably improved features when conjugated to an antibody or antigen binding fragment. Thus, the development and production of an ADC for use as a human therapeutic agent, e.g., as an oncologic agent, may require more than the identification of an antibody capable of binding to a desired target or targets and attaching to a drug used on its own to treat cancer. Linking the antibody to the drug may have significant effects on the activity of one or both of the antibody and the drug, effects which will vary depending on the type of linker and/or drug chosen. In some embodiments, therefore, the components of the ADC are selected to (i) retain one or more therapeutic properties exhibited by the antibody and drug moieties in isolation, (ii) maintain the specific binding properties of the antibody or antigen binding fragment; (iii) optimize drug loading and drug-to-antibody ratios; (iv) allow delivery, e.g., intracellular delivery, of the drug moiety via stable attachment to the antibody or antigen binding fragment; (v) retain ADC stability as an intact conjugate until transport or delivery to a target site; (vi) minimize aggregation of the ADC prior to or after administration; (vii) allow for the therapeutic effect, e.g., cytotoxic effect, of the drug moiety after cleavage or other release mechanism in the cellular environment; (viii) exhibit in vivo anti-cancer treatment efficacy comparable to or superior to that of the antibody and drug moieties in isolation; (ix) minimize off-target killing by the drug moiety; and/or (x) exhibit desirable pharmacokinetic and pharmacodynamics properties, formulatability, and toxicologic/immunologic profiles. Each of these properties may be needed to identify an improved ADC for therapeutic use (Ab et al. (2015) Mol Cancer Ther. 14:1605-13).

In various embodiments, the ADCs disclosed herein exhibit unexpectedly favorable properties in some or each of the categories listed above. For instance, in some embodiments, the ADC constructs disclosed herein exhibit surprisingly favorable drug loading, aggregation, and/or stability profiles, and/or preserve antibody binding function, drug activity, and/or improved bystander killing, while reducing off-target killing, as compared to ADCs comprising an alternate linker and/or drug moiety (e.g., an alternate splicing modulator). In some embodiments, ADC constructs disclosed herein demonstrate superior stability, activity, potency, or other effect (measured in vivo or in vitro) as compared to ADCs using an alternate linker and/or drug moiety (e.g., an alternate splicing modulator). In some embodiments, the ADC constructs disclosed herein exhibit in vivo treatment efficacy when administered as a single dose. In some embodiments, the ADC constructs disclosed herein are surprisingly stable as compared to ADCs using an alternate linker and/or drug moiety (e.g., an alternate splicing modulator).

The ADC compounds of the present disclosure may selectively deliver an effective dose of a cytotoxic or cytostatic agent to cancer cells or to tumor tissue. It has been discovered that the disclosed ADCs have potent cytotoxic and/or cytostatic activity against cells expressing the respective target antigen (e.g., HER2, CD138, EPHA2, MSLN, FOLH1, CDH6, CEACAM5, CFC1B, ENPP3, FOLR1, HAVCR1, KIT, MET, MUC16, SLC39A6, SLC44A4, STEAP1). In some embodiments, the cytotoxic and/or cytostatic activity of the ADC is dependent on target antigen expression in a cell. In some embodiments, the disclosed ADCs are particularly effective at killing cancer cells expressing a target antigen while minimizing off-target killing. In some embodiments, the disclosed ADCs do not exhibit a cytotoxic and/or cytostatic effect on cancer cells that do not express a target antigen.

Exemplary HER2-expressing cancers include but are not limited to breast cancer, gastric cancer, bladder cancer, urothelial cell carcinoma, esophageal cancer, lung cancer (e.g., lung adenocarcinoma), uterine cancer (e.g., uterine serous endometrial carcinoma), salivary duct carcinoma, cervical cancer, endometrial cancer, and ovarian cancer (English et al. (2013) Mol Diagn Ther. 17:85-99).

Exemplary CD138-expressing cancers include but are not limited to intrathoracic cancer (e.g., lung cancer, mesothelioma), skin cancer (e.g., basal cell carcinoma, squamous cell carcinoma), head and neck cancer (e.g., laryngeal, hypopharynx, nasopharyngeal), breast cancer, urogenital cancer (e.g., cervical cancer, ovarian cancer, endometrial cancer, prostate cancer, bladder cancer, urothelial cancer), hematological malignancies (e.g., myeloma such as multiple myeloma, B-cell malignancies, Hodgkin's lymphoma), and thyroid cancer (Szatmeri et al. (2015) Dis Markers 2015: 796052).

Exemplary EPHA2-expressing cancers include breast cancer, brain cancer, ovarian cancer, bladder cancer, pancreatic cancer, esophageal cancer, lung cancer, prostate cancer, melanoma, esophageal cancer, and gastric cancer (Tandon et al. (2011) Expert Opin Ther Targets 15(1):31-51).

In some embodiments, cleavage of an ADC releases the splicing modulator from the antibody or antigen binding fragment and linker. In some embodiments, the linker and/or splicing modulator is designed to facilitate bystander killing (the killing of neighboring cells). In some embodiments, the linker and/or splicing modulator is designed to facilitate bystander killing through cleavage after cellular internalization and diffusion of the linker-drug moiety and/or the drug moiety alone to neighboring cells. In some embodiments, the linker promotes cellular internalization. In some embodiments, the linker is designed to minimize cleavage in the extracellular environment and thereby reduce toxicity to off-target tissue (e.g., non-cancerous tissue), while preserving ADC binding to target tissue and bystander killing of cancerous tissue that does not express an antigen targeted by the antibody or antigen binding fragment of an ADC, but surrounds target cancer tissue expressing that antigen. In some embodiments, the drug moiety, or the catabolite of the drug moiety produced by cleavage of an ADC, is designed to facilitate uptake by target cells or by neighboring cells (i.e., cell permeable). Such drug moieties and catabolites may be referred to herein as "bystander active," whereas drug moieties or catabolites with reduced cell permeability may be referred to as "bystander inactive."

In some embodiments, the disclosed ADCs also demonstrate bystander killing activity, but low off-target cytotoxicity. Without being bound by theory, the bystander killing activity of an ADC may be particularly beneficial where its penetration into a solid tumor is limited and/or target antigen expression among tumor cells is heterogeneous. In some embodiments, an ADC comprising a cleavable linker is particularly effective at bystander killing and/or demonstrates improved bystander killing activity, relative to comparable treatment with an ADC comprising a non-cleavable linker. In some embodiments, the ADCs disclosed herein exhibit improved solubility and target cell penetrance over the drug moieties on their own. In some embodiments, the ADCs disclosed herein exhibit improved cytotoxicity over that of the drug moiety on its own. In some embodiments, ADCs disclosed herein use drug moieties that exhibit lower cytotoxicity, when evaluated as a stand-alone drug, yet are surprisingly better than ADCs comprising other drug moieties which have higher cytotoxicity when evaluated as a stand-alone drug. In some embodiments, cleavage and release of the splicing modulator improves cytotoxicity of the ADC, relative to comparable treatment with an ADC comprising a non-cleavable linker. In other embodiments, cleavage and release of the splicing modulator is not required for an ADC to possess a desirable biological activity. In some embodiments, an ADC comprising a non-cleavable linker having increased spacer length (e.g., ADL12) provides the same or similar cytotoxicity relative to comparable treatment with an ADC comprising a cleavable linker (e.g., ADL1, ADL5) and surprisingly superior cytotoxicity relative to comparable treatment with an ADC comprising a shorter non-cleavable linker. In some embodiments, an ADC comprising a non-cleavable linker having increased spacer length without a carbonyl group (e.g., ADL12) provides the same or similar cytotoxicity relative to comparable treatment with an ADC comprising a cleavable linker (e.g., ADL1, ADL5) and surprisingly superior cytotoxicity relative to comparable treatment with an ADC comprising a non-cleavable linker having the same or similar spacer length with a carbonyl group (e.g., ADL10). In some embodiments, the removal of a carbonyl group from a non-cleavable MC linker (e.g., ADL12) can result in a greater than 50-fold, greater than 75-fold, greater than 100-fold, greater than 150-fold, or greater than 200-fold increase in cytotoxicity, relative to comparable treatment with an ADC comprising an unmodified non-cleavable MC linker (e.g., ADL10). In some embodiments, the removal of a carbonyl group from a non-cleavable MC linker (e.g., ADL12) and increased spacer length (e.g., the addition of at least one spacer unit) can result in a greater than 50-fold, greater than 75-fold, greater than 100-fold, greater than 150-fold, or greater than 200-fold increase in cytotoxicity, relative to comparable treatment with an ADC comprising an unmodified non-cleavable MC linker (e.g., ADL10).

Provided herein are ADC compounds comprising an antibody or antigen binding fragment thereof (Ab) which targets a tumor cell, a splicing modulator drug moiety (D), and a linker moiety (L) that covalently attaches Ab to D. In certain aspects, the antibody or antigen binding fragment is able to bind to a tumor-associated antigen (e.g., HER2, CD138, EPHA2, MSLN, FOLH1, CDH6, CEACAM5, CFC1B, ENPP3, FOLR1, HAVCR1, KIT, MET, MUC16, SLC39A6, SLC44A4, STEAP1) with high specificity and high affinity. In certain embodiments, the antibody or antigen binding fragment is internalized into a target cell upon binding, e.g., into a degradative compartment in the cell. In various embodiments, ADCs that internalize upon binding to a target cell, undergo degradation, and release the splicing modulator drug moiety to kill cancer cells may be used. The splicing modulator drug moiety may be released from the antibody and/or the linker moiety of the ADC by enzymatic action, hydrolysis, oxidation, or any other mechanism.

An exemplary ADC has Formula (I):

$$Ab-(L-D)_p \qquad (I)$$

wherein Ab=an antibody or antigen binding fragment, L=a linker moiety, D=a splicing modulator drug moiety, and p=the number of splicing modulator drug moieties per antibody or antigen binding fragment.

In certain preferred embodiments, the drug-targeting moiety for use in the described ADCs and compositions is an antibody or antigen binding fragment. Other exemplary drug-targeting moieties for use in the described ADCs and compositions are also provided and described herein. In some embodiments, a drug-targeting moiety can be any one of a variety of cell-binding agents and non-antibody scaffolds. In some embodiments, the drug-targeting moiety is a cell-binding agent. As used herein, the term "cell-binding agent" refers to any agent that is capable of binding to an animal (e.g., human) cell and delivering a drug moiety (e.g., a splicing modulator drug moiety as disclosed herein). The term encompasses the exemplary antibodies and antigen binding fragments disclosed herein (e.g., monoclonal antibodies and fragments thereof such as Fabs and scFVs). The term further encompasses exemplary cell-binding agents such as DARPins, duobodies, bicyclic peptides, nanobodies, centyrins, MSH (melanocyte-stimulating hormone), receptor-Fc fusion molecules, T-cell receptor structures, steroid hormones such as androgens and estrogens, growth factors, colony-stimulating factors such as EGF, and other non-antibody scaffolds. In various embodiments, non-antibody scaffolds can broadly fall into two structural classes, namely domain-sized compounds (approximately 6-20 kDa) and constrained peptides (approximately 2-4 kDa). Exemplary domain-sized scaffolds include but are not limited to affibodies, affilins, anticalins, atrimers, DARPins, FN3 scaffolds (e.g., adnectins and centyrins), fynomers, Kunitz domains, pronectins, O-bodies, and receptor-Fc fusion proteins, whereas exemplary constrained peptides include avimers, bicyclic peptides, and Cys-knots. In some embodiments, the drug-targeting moiety used in the described ADCs and compositions is selected from an affibody, an affilin, an anticalin, an atrimer, a DARPin, a FN3 scaffold such as an adnectin or a centyrin, a fynomer, a Kunitz domain, a pronectin, an O-body, an avimer, a bicyclic peptide, and a Cys-knot. In some embodiments, the drug-targeting moiety used in the described ADCs and compositions is a receptor-Fc fusion protein, e.g., a HER2-Fc chimeric fusion protein. Non-antibody scaffolds are reviewed, e.g., in Vazquez-Lombardi et al. (2015) Drug Dis Today 20(10):1271-83.

Antibodies

The antibody or antigen binding fragment (Ab) of Formula (I) includes within its scope any antibody or antigen binding fragment that specifically binds to a target antigen on a cancer cell. The antibody or antigen binding fragment may bind to a target antigen with a dissociation constant (Ko) of <1 mM, 5100 nM or <10 nM, or any amount in between, as measured by, e.g., BIAcore® analysis. In certain embodiments, the $K_D$ is 1 μM to 500 μM. In some embodiments, the $K_D$ is between 500 μM to 1 μM, 1 μM to 100 nM, or 100 mM to 10 nM.

In some embodiments, the antibody or antigen binding fragment is a four-chain antibody (also referred to as an immunoglobulin or a full-length or intact antibody), comprising two heavy chains and two light chains. In some embodiments, the antibody or antigen binding fragment is a two-chain half body (one light chain and one heavy chain), or an antigen binding fragment of an immunoglobulin. In some embodiments, the antibody or antigen binding fragment is an antigen binding fragment of an immunoglobulin that retains the ability to bind a target cancer antigen and/or provide a function of an immunoglobulin.

In some embodiments, the antibody or antigen binding fragment is an antibody or antigen binding fragment thereof. In some embodiments, the antibody or antigen binding fragment is an internalizing antibody or internalizing antigen binding fragment thereof. In some embodiments, the internalizing antibody or internalizing antigen binding fragment thereof binds to a target cancer antigen expressed on the surface of a cell and enters the cell upon binding. In some embodiments, the splicing modulator drug moiety of the ADO is released from the antibody or antigen binding fragment of the ADO after the ADO enters and is present in a cell expressing the target cancer antigen (i.e., after the ADO has been internalized), e.g., by cleavage, by degradation of the antibody or antigen binding fragment, or by any other suitable release mechanism.

Amino acid sequences of exemplary antibodies of the present disclosure are set forth in Tables 2-4.

TABLE 1

Antibodies

| mAb | Type | Target |
|---|---|---|
| trastuzumab (AB185) | humanized | HER2/NEU |
| B-B4 (AB205) | murine | CD138 (syndecan-1) |
| 1C1 (AB206) | humanized | EPHA2 |

TABLE 2

Amino acid sequences of mAb variable regions

| mAb | IgG chain | SEQ ID NO | Amino acid sequence |
|---|---|---|---|
| trastuzumab (AB185) | Heavy chain | 19 | EVQLVESGGGLVQPGGSLRLSCAASGF NIKDTYIHWVRQAPGKGLEWVARIYPT NGYTRYADSVKGRFTISADTSKNTAYL QMNSLRAEDTAVYYCSRWGGDGFYAMD YWGQGTLVTVSS |
| trastuzumab (AB185) | Light chain | 20 | DIQMTQSPSSLSASVGDRVTITCRASQ DVNTAVAWYQQKPGKAPKLLIYSASFL YSGVPSRFSGSRSGTDFTLTISSLQPE DFATYYCQQHYTTPPTFGQGTKVEIKR T |
| B-B4 (AB205) | Heavy chain | 21 | QVQLQQSGSELMMPGASVKISCKATGY TFSNYWIQRPGHGLEWIGEILPGTGRT IYNEKFKGKATFTADISSNTVQMQLSS LTSEDSAVYYCARRDYYGNFYYAMDYW GQGTSVTVSS |
| B-B4 (AB205) | Light chain | 22 | DIQMTQSTSSLSASLGDRVTISCSASQ GINNYLNWYQQKPDGTVELLIYTSTL QSGVPSRFSGSGSGTDYSLTISNLEPE DIGTYYCQQYSKLPRTFGGGTKLEIK |
| 1C1 (AB206) | Heavy chain | 23 | EVQLLESGGGLVQPGGSLRLSCAASGF TFSHYMMAWVRQAPGKGLEWVSRIGPS |

TABLE 2-continued

Amino acid sequences of mAb variable regions

| mAb | IgG chain | SEQ ID NO | Amino acid sequence |
|---|---|---|---|
| | | | GGPTHYADSVKGRFTISRDNSKNTLYL QMNSLRAEDTAVYYCAGYDSGYDYVAV AGPAE-YFQHWGQGTLVTVSS |
| 1C1 (AB206) | Light chain | 24 | DIQMTQSPSSLSASVGDRVTITCRASQ SISTWLAWYQQKPGKAPKLLIYKASNL HTGVPSRFSGSGSGTEFSLTISGLQPD DFATYYCQQYNSYS-RTFGQGTKVEIK |

TABLE 3

Amino acid sequences of mAb CDRs

| mAb | IgG chain | SEQ ID NO | Amino acid sequence |
|---|---|---|---|
| trastuzumab (AB185) | HCDR1 | 1 | GFNIKDTYIH |
| trastuzumab (AB185) | HCDR2 | 2 | RIYPTNGYTRYADSVKG |
| trastuzumab (AB185) | HCDR3 | 3 | WGGDGFYAMDV |
| trastuzumab (AB185) | LCDR1 | 4 | RASQDVNTAVAW |
| trastuzumab (AB185) | LCDR2 | 5 | SASFLES |
| trastuzumab (AB185) | LCDR3 | 6 | QQHYTTPPT |

TABLE 3-continued

Amino acid sequences of mAb CDRs

| mAb | IgG chain | SEQ ID NO | Amino acid sequence |
|---|---|---|---|
| B-B4 (AB205) | HCDR1 | 7 | NYWIE |
| B-B4 (AB205) | HCDR2 | 8 | ILPGTGRTIYNEKFKGKA |
| B-B4 (AB205) | HCDR3 | 9 | RDYYGNFYYAMDY |
| B-B4 (AB205) | LCDR1 | 10 | ASQGINNYLN |
| B-B4 (AB205) | LCDR2 | 11 | TSTLQS |
| B-B4 (AB205) | LCDR3 | 12 | QQYSKLPRT |
| 1C1 (AB206) | HCDR1 | 13 | HYMMA |
| 1C1 (AB206) | HCDR2 | 14 | RIGPSGGPTHYADSVKG |
| 1C1 (AB206) | HCDR3 | 15 | YDSGYDYVAVAGPAE-YFQH |
| 1C1 (AB206) | LCDR1 | 16 | RASWSISTWLA |
| 1C1 (AB206) | LCDR2 | 17 | KASNLHT |
| 1C1 (AB206) | LCDR3 | 18 | QQYNSYS-RT |

TABLE 4

Amino acid sequences of full-length mAb Ig chains

| mAb | IgG chain | Class | SEQ ID NO | Amino acid sequence |
|---|---|---|---|---|
| trastuzumab (AB185) | Heavy chain | IgG1 | 25 | EVQLVESGGGLVQPGGSLRLSCAA SGFNIKDTYIHWVRQAPGKGLEWV ARIYPTNGYTRYADSVKGRFTISA DTSKNTAYLQMNSLRAEDTAVYYC SRWGGDGFYAMDYWGQGTLVTVSS ASTKGPSVFPLAPSSKSTSGGTAA LGCLVKDYFPEPVTVSWNSGALTS GVHTFPAVLQSSGLYSLSSVVTVP SSSLGTQTYICNVNHKPSNTKVDK KVEPPKSCDKTHTCPPCPAPELLG GPSVFLFPPKPKDTLMISRTPEVT CVVVDVSHEDPEVKENWYVDGVEV HNAKTKPREEQYNSTYRVVSVLTV LHQDWLNGKEYKCKVSNKALPAPI EKTISKAKGQPREPQVYTLPPSRD ELTKNQVSLTCLVKGFYPSDIAVE WESNGQPENNYKTTPPVLDSDGSF FLYSKLTVDKSRWQQGNVFSCSVM HEALHNHYTQKSLSLSPGK |
| trastuzumab (AB185) | Light chain | kappa | 26 | DIQMTQSPSSLSASVGDRVTITCR ASQDVNTAVAWYQQKPGKAPKLLI YSASFLYSGVPSRESGSRSGTDFT LTISSLQPEDFATYYCQQHYTTPP TFGQGTKVEIKRTVAAPSVFIFPP SDEQLKSGTASVVCLLNNFYPREA KVQWKVDNALQSGNSQESVTEQDS KDSTYSLSSTLTLSKADYEKHKVY ACEVTHQGLSSPVTKSFNRGEC |

TABLE 4-continued

Amino acid sequences of full-length mAb Ig chains

| mAb | IgG chain | Class | SEQ ID NO | Amino acid sequence |
|---|---|---|---|---|
| B-B4 (AB205) | Heavy chain | IgG2a | 27 | QVQLQQSGSELMMPGASVKISCKATGYTFSNYWIQRPGHGLEWIGEILPGTGRTIYNEKFKGKATFTADISSNTVQMQLSSLTSEDSAVYYCARRDYYGNFYYAMDYWGQGTSVTVSSAKTTPPSVYPLAPGSAAQTNSMVTLGCLVKGYFPEPVTVTWNSGSLSSGVHTFPAVLQSDLYTLSSSVTVPSSTWPSETVTCNVAHPASSTKVDKKIVPRDCGCKPCICTVPEVSSVFIFPPKPKDVLTITLTPKVTCVVVDISKDDPEVQFSWFVDDVEVHTAQTQPREEQFNSTERSVSELPIMHQDWLNGKEFKCRVNSAAFPAPIEKTISKTKGRPKAPQVYTIPPPKEQMAKDKVSLTCMITDFFPEDITVEWQWNGQPAENYKNTQPIMDTDGSYFVYSKLNVQKSNWEAGNTFTCSVLHEGLHNHHTEKSLSHSPG |
| B-B4 (AB205) | Light chain | kappa | 28 | DIQMTQSTSSLSASLGDRVTISCSASQGINNYLNWYQQKPDGTVELLIYYTSTLQSGVPSRESGSGSGTDYSLTISNLEPEDIGTYYCQQYSKLPRTFGGGTKLEIKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSENRNEC |
| 1C1 (AB206) | Heavy chain | IgG1 | 29 | EVQLLESGGGLVQPGGSLRLSCAASGFTFSHYMMAWVRQAPGKGLEWVSRIGPSGGPTHYADSVKGRFTISRDNSKNTLYLQMNSLRAEDTAVYYCAGYDSGYDYVAVAGPAEYFQHWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG |
| 1C1 (AB206) | Light chain | kappa | 30 | DIQMTQSPSSLSASVGDRVTITCRASQSISTWLAWYQQKPGKAPKLLIYKASNLHTGVPSRFSGSGSGTEFSLTISGLQPDDFATYYCQQYNSYSRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSENRGEC |

TABLE 5

Exemplary target antigen amino acid sequences

| Antigen | SEQ ID NO | Amino acid sequence |
|---|---|---|
| HER2/NEU | 31 | MELAALCRWGLLLALLPPGAASTQVCTGTDMKLRLPASPETHLDMLRHLYQGCQVVQGNLELTYLPTNASLSFLQDIQEVQGYVLIAHNQVRQVPLQRLRIVRGTQLFEDNYALAVLDNGDPLNNTTPVTGASPGGLRELQLRSLTEILKGGVLIQRNPQLCYQDTILWKDIFHKNNQLALTLIDTNRSRACHPCSPMCKGSRCWGESSEDCQSLTRTVCAGGCA |

TABLE 5-continued

Exemplary target antigen amino acid sequences

| Antigen | SEQ ID NO | Amino acid sequence |
|---------|-----------|---------------------|
| | | RCKGPLPTDCCHEQCAAGCTGPKHSDCLACLHENHSGICELHCPA
LVTYNTDTFESMPNPEGRYTFGASCVTACPYNYLSTDVGSCTLVC
PLHNQEVTAEDGTQRCEKCSKPCARVCYGLGMEHLREVRAVTSAN
IQEFAGCKKIFGSLAFLPESFDGDPASNTAPLQPEQLQVFETLEE
ITGYLYISAWPDSLPDLSVFQNLQVIRGRILHNGAYSLTLQGLGI
SWLGLRSLRELGSGLALIHHNTHLCFVHTVPWDQLERNPHQALLH
TANRPEDECVGEGLACHQLCARGHCWGPGPTQCVNCSQFLRGQEC
VEECRVLQGLPREYVNARHCLPCHPECQPQNGSVTCFGPEADQCV
ACAHYKDPPFCVARCPSGVKPDLSYMPIWKFPDEEGACQPCPINC
THSCVDLDDKGCPAEQRASPLTSIISAVVGILLVVVLGVVEGILI
KRRQQKIRKYTMRRLLQETELVEPLTPSGAMPNQAQMRILKETEL
RKVKVLGSGAFGTVYKGIWIPDGENVKIPVAIKVLRENTSPKANK
EILDEAYVMAGVGSPYVSRLLGICLTSTVQLVTQLMPYGCLLDHV
RENRGRLGSQDLLNWCMQIAKGMSYLEDVRLVHRDLAARNVLVKS
PNHVKITDFGLARLLDIDETEYHADGGKVPIKWMALESILRRRFT
HQSDVWSYGVTVWELMTFGAKPYDGIPAREIPDLLEKGERLPQPP
ICTIDVYMIMVKCWMIDSECRPRFRELVSEFSRMARDPQREVVIQ
NEDLGPASPLDSTFYRSLLEDDDMGDLVDAEEYLVPQQGFFCPDP
APGAGGMVHHRHSSSTRSGGGDLTLGLEPSEEEAPRSPLAPSEG
AGSDVFDGDLGMGAAKGLQSLPTHDPSPLQRYSEDPTVPLPSETD
GYVAPLTCSPQPEYVNQPDVRPQPPSPREGPLPAARPAGATLERP
KTLSPGKNGVVKDVFAFGGAVENPEYLTPQGGAAPQPHPPPAFSP
AFDNLYYWDQDPPERGAPPSTFKGTPTAENPEYLGLDVPV |
| CD138 | 32 | MRRAALWLWLCALALSLQPALPQIVATNLPPEDQDGSGDDSDNFS
GSGAGALQDITLSQQTPSTWKDTQLLTAIPTSPEPTGLEATAAST
STLPAGEGPKEGEAVVLPEVEPGLTAREQEATPRPRETTQLPTTH
LASTTTATTAQEPATSHPHRDMQPGHHETSTPAGPSQADLHTPHT
EDGGPSATERAAEDGASSQLPAAEGSGEQDFTFETSGENTAVVAV
EPDRRNQSPVDQGATGASQGLLDRKEVLGGVIAGGLVGLIFAVCL
VGFMLYRMKKKDEGSYSLEEPKQANGGAYQKPTKQEEFYA |
| EPHA2 | 33 | MELQAARACFALLWGCALAAAAAAQGKEVVLLDFAAAGGELGWLT
HPYGKGWDLMQNIMNDMPIYMYSVCNVMSGDQDNWLRTNWVYRGE
AERIFIELKFTVRDCNSFPGGASSCKETENLYYAESDLDYGTNFQ
KRLFTKIDTIAPDEITVSSDFEARHVKLNVEERSVGPLTRKGFYL
AFQDIGACVALLSVRVYYKKCPELLQGLAHFPETIAGSDAPSLAT
VAGTCVDHAVVPPGGEEPRMHCAVDGEWLVPIGQCLCQAGYEKVE
DACQQACSPGFFKFEASESPCLECPEHTLPSPEGATSCECEEGFFR
APQDPASMPCTRPPSAPHYLTAVGMGAKVELRWTPPQDSGGREDI
VYSVTCEQCWPESGECGPCEASVRYSEPPHGLTRTSVTVSDLEPH
MNYTFTVEARNGVSGLVTSRSFRTASVSINQTEPPKVRLEGRSTT
SLSVSWSIPPPQQSRVWKYEVTYRKKGDSNSYNVRRTEGFSVTLD
DLAPDTTYLVQVQALTQEGQGAGSKVHEFQTLSPEGSGNLAVIGG
VAVGVVLLLVLAGVGFFIHRRRKNQRARQSPEDVYFSKSEQLKPL
KTYVDPHTYEDPNQAVLKFTTEIHPSCVTRQKVIGAGEFGEVYKG
MLKTSSGKKEVPVAIKTLKAGYTEKQRVDFLGEAGIMGQFSHHNI
IRLEGVISKYKPMMIITEYMENGALDKFLREKDGEFSVLQLVGML
RGIAAGMKYLANMNYVHRDLAARNILVNSNLVCKVSDFGLSRVLE
DDPEATYTTSGGKIPIRWTAPEAISYRKFTSASDVWSFGIVMWEV
MTYGERPYWELSNHEVMKAINDGFRLPTPMDCPSAIYQLMMQCWQ
QERARRPKFADIVSILDKLIRAPDSLKTLADFDPRVSIRLPSTSG
SEGVPFRTVSEWLESIKMQQYTEHFMAAGYTAIEKVVQMINDDIK
RIGVRLPGHQKRIAYSLLGLKDQVNTVGIPI |
| MSLN | 43 | MALPTARPLLGSCGTPALGSLLFLLFSLGWVQPSRTLAGETGQEA
APLDGVLANPPNISSLSPRQLLGFPCAEVSGLSTERVRELAVALA
QKNVKLSTEQLRCLAHRLSEPPEDLDALPLDLLLFLNPDAFSGPQ
ACTRFFSRITKANVDLLPRGAPERQRLLPAALACWGVRGSLLSEA
DVRALGGLACDLPGRFVAESAEVLLPRLVSCPGPLDQDQQEAARA
ALQGGGPPYGPPSTWSVSTMDALRGLLPVLGQPIIRSIPQGIVAA
WRQRSSRDPSWRQPERTILRPRFRREVEKTACPSGKKAREIDESL
IFYKKWELEACVDAALLATQMDRVNAIPFTYEQLDVLKHKLDELY
PQGYPESVIQHLGYLFLKMSPEDIRKWNVTSLETLKALLEVNKGH
EMSPQAPRRPLPQVATLIDRFVKGRGQLDKDTLDTLTAFYPGYLC
SLSPEELSSVPPSSIWAVRPQDLDTCDPRQLDVLYPKARLAFQNM
NGSEYFVKIQSFLGGAPTEDLKALSQQNVSMDLATFMKLRTDAVL
PLTVAEVQKLLGPHVEGLKAEERHRPVRDWILRQRQDDLDTLGLG
LQGGIPNGYLVLDLSMQEALSGTPCLLGPGPVLTVALLLASTLA |
| FOLH1 | 44 | MWNLLHETDSAVATARRPRWLCAGALVLAGGFFLLGFLFGWFIKS
SNEATNITPKHNMKAFLDELKAENIKKFLYNFTQIPHLAGTEQNF
QLAKQIQSQWKEFGLDSVELAHYDVLLSYPNKTHPNYISIINEDG
NEIFNTSLFEPPPPGYENVSDIVPPFSAFSPQGMPEGDLVYVNYA
RTEDFFKLERDMKINCSGKIVIARYGKVERGNKVKNAQLAGAKGV
ILYSDPADYFAPGVKSYPDGWNLPGGGVQRGNILNLNGAGDPLTP |

TABLE 5-continued

Exemplary target antigen amino acid sequences

| Antigen | SEQ ID NO | Amino acid sequence |
|---|---|---|
| | | GYPANEYAYRRGIAEAVGLPSIPVHPIGYYDAQKLLEKMGGSAPP
DSSWRGSLKVPYNVGPGFTGNFSTQKVKMHIHSTNEVTRIYNVIG
TLRGAVEPDRYVILGGHRDSWVFGGIDPQSGAAVVHEIVRSFGTL
KKEGWRPRRTILFASWDAEEFGLLGSTEWAEENSRLLQERGVAYI
NADSSIEGNYTLRVDCTPLMYSLVHNLTKELKSPDEGFEGKSLYE
SWTKKSPSPEFSGMPRISKLGSGNDFEVFFQRLGIASGRARYTKN
WETNKFSGYPLYHSVYETYELVEKFYDPMFKYHLTVAQVRGGMVF
ELANSIVLPFDCRDYAVVLRKYADKIYSISMKHPQEMKTYSVSFD
SLFSAVKNFTEIASKESERLQDEDKSNPIVLRMMNDQLMFLERAF
IDPLGLPDRPFYRHVIYAPSSHNKYAGESFPGIYDALFDIESKVD
PSKAWGEVKRQIYVAAFTVQAAAETLSEVA |
| CDH6 | 45 | MRTYRYFLLLFWVGQPYPTLSTPLSKRTSGFPAKKRALELSGNSK
NELNRSKRSWMWNQFFLLEEYTGSDYQYVGKLHSDQDRGDGSLKY
ILSGDGAGDLFIINENTGDIQATKRLDREEKPVYILRAQAINRRT
GRPVEPESEFIIKIHDINDNEPIFTKEVYTATVPEMSDVGTFVVQ
VTATDADDPTYGNSAKVVYSILQGQPYFSVESETGIIKTALLNMD
RENREQYQVVIQAKDMGGQMGGLSGTTTVNITLTDVNDNPPRFPQ
STYQFKTPESSPPGTPIGRIKASDADVGENAEIEYSITDGEGLDM
FDVITDQETQEGIITVKKLLDFEKKKVYTLKVEASNPYVEPRFLY
LGPFKDSATVRIVVEDVDEPPVFSKLAYILQIREDAQINTTIGSV
TAQDPDAARNPVKYSVDRHTDMDRIFNIDSGNGSIFTSKLLDRET
LLWHNITVIATEINNPKQSSRVPLYIKVLDVNDNAPEFAEFYETF
VCEKAKADQLIQTLHAVDKDDPYSGHQFSFSLAPEAASGSNFTIQ
DNKDNTAGILTRKNGYNRHEMSTYLLPVVISDNDYPVQSSTGTVT
VRVCACDHHGNMQSCHAEALIHPTGLSTGALVAILLCIVILLVTV
VLFAALRRQRKKEPLIISKEDIRDNIVSYNDEGGGEEDTQAFDIG
TLRNPEAIEDNKLRRDIVPEALFLPRRTPTARDNTDVRDFINQRL
KENDTDPTAPPYDSLATYAYEGTGSVADSLSSLESVTTDADQDYD
YLSDWGPRFKKLADMYGGVDSDKDS |
| CEACAM5 | 46 | MESPSAPPHRWCIPWQRLLLLTASLLTFWNPPTTAKLTIESTPFNV
AEGKEVLLLVHNLPQHLFGYSWYKGERVDGNRQIIGYVIGTQQAT
PGPAYSGREIIYPNASLLIQNIIQNDTGFYTLHVIKSDLVNEEAT
GQFRVYPELPKPSISSNNSKPVEDKDAVAFTCEPETQDATYLWWV
NNQSLPVSPRLQLSNGNRTLTLFNVTRNDTASYKCETQNPVSARR
SDSVILNVLYGPDAPTISPLNTSYRSGENLNLSCHAASNPPAQYS
WFVNGTFQQSTQELFIPNITVNNSGSYTCQAHNSDTGLNRTTVTT
ITVYAEPPKPFITSNNSNPVEDEDAVALTCEPEIQNTTYLWWVNN
QSLPVSPRLQLSNDNRTLTLLSVTRNDVGPYECGIQNKLSVDHSD
PVILNVLYGPDDPTISPSYTYYRPGVNLSLSCHAASNPPAQYSWL
IDGNIQQHTQELFISNITEKNSGLYTCQANNSASGHSRTTVKTIT
VSAELPKPSISSNNSKPVEDKDAVAFTCEPEAQNTTYLWWVNGQS
LPVSPRLQLSNGNRTLTLFNVTRNDARAYVCGIQNSVSANRSDPV
TLDVLYGPDTPIISPPDSSYLSGANLNLSCHSASNPSPQYSWRIN
GIPQQHTQVLFIAKITPNNNGTYACFVSNLATGRNNSIVKSITVS
ASGTSPGLSAGATVGIMIGVLVGVALI |
| CFC1B | 47 | MTWRHHVRLLFTVSLALQIINLGNSYQREKHNGGREEVTKVATQK
HRQSPLNWTSSHFGEVTGSAEGWGPEEPLPYSWAFGEGASARPRC
CRNGGTCVLGSFCVCPAHFTGRYCEHDQRRSECGALEHGAWTLRA
CHLCRCIFGALHCLPLQTPDRCDPKDFLASHAHGPSAGGAPSLLL
LLPCALLHRLLRPDAPAHPRSLVPSVLQRERRPCGRPGLGHRL |
| ENPP3 | 48 | MESTLTLATEQPVKKNTLKKYKIACIVLLALLVIMSLGLGLGLGL
RKLEKQGSCRKKCFDASFRGLENCRCDVACKDRGDCCWDFEDTCV
ESTRIWMCNKFRCGETRLEASLCSCSDDCLQRKDCCADYKSVCQG
ETSWLEENCDTAQQSQCPEGFDLPPVILFSMDGFRAEYLYTWDTL
MPNINKLKTCGIHSKYMRAMYPTKTFPNHYTIVTGLYPESHGIID
NNMYDVNLNKNFSLSSKEQNNPAWWHGQPMWLTAMYQGLKAATYF
WPGSEVAINGSFPSIYMPYNGSVPFEERISTLLKWLDLPKAERPR
FYTMYFEEPDSSGHAGGPVSARVIKALQVVDHAFGMLMEGLKQRN
LHNCVNIILLADHGMDQTYCNKMEYMTDYFPRINFFYMYEGPAPR
IRAHNIPHDFFSENSEEIVRNLSCRKPDQHFKPYLTPDLPKRLHY
AKNVRIDKVHLFVDQQWLAVRSKSNTNCGGGNHGYNNEFRSMEAI
FLAHGPSFKEKTEVEPFENIEVYNLMCDLLRIQPAPNNGTHGSLN
HLLKVPFYEPSHAEEVSKFSVCGFANPLPTESLDCFCPHLQNSTQ
LEQVNQMLNLTQEEITATVKVNLPFGRPRVLQKNVDHCLLYHREY
VSGFGKAMRPMPWSSYTVPQLGDTSPLPPTVPDCLRADVRVPPSE
SQKCSFYLADKNITHGFLYPPASNRTSDSQYDALITSNLVPMYEE
FRKMWDYFHSVLLIKHATERNGVNVVSGPIFDYNYDGHPFDAPDEI
TKHLANTDVPIPTHYFVVLTSCKNKSHTPENCPGWLDVLPFIIPH
RPTNVESCPEGKPEALWVEERFTAHIARVRDVELLTGLDFYQDKV
QPVSEILQLKTYLPTFETTI |

TABLE 5-continued

Exemplary target antigen amino acid sequences

| Antigen | SEQ ID NO | Amino acid sequence |
|---|---|---|
| FOLR1 | 49 | MAQRMTTQLLLLLVWVAVVGEAQTRIAWARTELLNVCMNAKHHKE<br>KPGPEDKLHEQCRPWRKNACCSTNTSQEAHKDVSYLYRFNWNHCG<br>EMAPACKRHFIQDTCLYECSPNLGPWIQQVDQSWRKERVLNVPLC<br>KEDCEQWWEDCRTSYTCKSNWHKGWNWTSGFNKCAVGAACQPFHF<br>YFPTPTVLCNEIWTHSYKVSNYSRGSGRCIQMWFDPAQGNPNEEV<br>ARFYAAAMSGAGPWAAWPFLLSLALMLLWLLS |
| HAVCR1 | 50 | MHPQVVILSLILHLADSVAGSVKVGGEAGPSVTLPCHYSGAVTSM<br>CWNRGSCSLFTCQNGIVWTNGTHVTYRKDTRYKLLGDLSRRDVSL<br>TIENTAVSDSGVYCCRVEHRGWFNDMKITVSLEIVPPKVTTTPIV<br>TTVPTVTTVRTSTTVPTTTTVPMTTVPTTTVPTTMSIPTTTTVLT<br>TMTVSTTTSVPTTTSIPTTTSVPVTTTVSTFVPPMPLPRQNHEPV<br>ATSPSSPQPAETHPTTLQGAIRREPTSSPLYSYTTDGNDTVTESS<br>DGLWNNNQTQLFLEHSLLTANTTKGIYAGVCISVLVLLALLGVII<br>AKKYFFKKEVQQLSVSFSSLQIKALQNAVEKEVQAEDNIYIENSL<br>YATD |
| KIT | 51 | MRGARGAWDFLCVLLLLLRVQTGSSQPSVSPGEPSPPSIHPGKSD<br>LIVRVGDEIRLLCTDPGFVKWTFEILDETNENKQNEWITEKAEAT<br>NTGKYTCTNKHGLSNSIYVFVRDPAKLFLVDRSLYGKEDNDTLVR<br>CPLTDPEVTNYSLKGCQGKPLPKDLRFIPDPKAGIMIKSVKRAYH<br>RLCLHCSVDQEGKSVLSEKFILKVRPAFKAVPVVSVSKASYLLRE<br>GEEFTVTCTIKDVSSSVYSTWKRENSQTKLQEKYNSWHHGDFNYE<br>RQATLTISSARVNDSGVFMCYANNTFGSANVTTTLEVVDKGFINI<br>FPMINTTVFVNDGENVDLIVEYEAFPKPEHQQWIYMNRTFTDKWE<br>DYPKSENESNIRYVSELHLTRLKGTEGGTYTFLVSNSDVNAAIAF<br>NVYVNTKPEILTYDRLVNGMLQCVAAGFPEPTIDWYFCPGTEQRC<br>SASVLPVDVQTLNSSGPPFGKLVVQSSIDSSAFKHNGTVECKAYN<br>DVGKTSAYFNFAFKGNNKEQIHPHTLFTPLLIGFVIVAGMMCIIV<br>MILTYKYLQKPMYEVQWKVVEEINGNNYVYIDPTQLPYDHKWEFP<br>RNRLSFGKTLGAGAFGKVVEATAYGLIKSDAAMTVAVKMLKPSAH<br>LTEREALMSELKVLSYLGNHMNIVNLLGACTIGGPTLVITEYCCY<br>GDLLNFLRRKRDSFICSKQEDHAEAALYKNLLHSKESSCSDSTNE<br>YMDMKPGVSYVVPTKADKRRSVRIGSYIERDVTPAIMEDDELALD<br>LEDLLSFSYQVAKGMAFLASKNCIHRDLAARNILLTHGRITKICD<br>FGLARDIKNDSNYVVKGNARLPVKWMAPESIFNCVYTFESDVWSY<br>GIFLWELFSLGSSPYPGMPVDSKFYKMIKEGERMLSPEHAPAEMY<br>DIMKTCWDADPLKRPTFKQIVQLIEKQISESTNHIYSNLANCSPN<br>RQKPVVDHSVRINSVGSTASSSQPLLVHDDV |
| MET | 52 | MKAPAVLAPGILVLLFTLVQRSNGECKEALAKSEMNVNMKYQLPN<br>FTAETPIQNVILHEHHIFLGATNYIYVLNEEDLQKVAEYKTGPVL<br>EHPDCFPCQDCSSKANLSGGVWKDNINMALVVDTYYDDQLISCGS<br>VNRGTCQRHVFPHNHTADIQSEVHCIFSPQIEEPSQCPDCVVSAL<br>GAKVLSSVKDRFINFFVGNTINSSYFPDHPLHSISVRRLKETKDG<br>FMFLTDQSYIDVLPEFRDSYPIKYVHAFESNNFIYFLTVQRETLD<br>AQTFHTRIIRFCSINSGLHSYMEMPLECILTEKRKKRSTKKEVFN<br>ILQAAYVSKPGAQLARQIGASLNDDILFGVFAQSKPDSAEPMDRS<br>AMCAFPIKYVNDFFNKIVNKNNVRCLQHFYGPNHEHCFNRTLLRN<br>SSGCEARRDEYRTEFTTALQRVDLFMGQFSEVLLTSISTFIKGDL<br>TIANLGTSEGREMQVVVSRSGPSTPHVNFLLDSHPVSPEVIVEHT<br>LNQNGYTLVITGKKITKIPLNGLGCRHFQSCSQCLSAPPFVQCGW<br>CHDKCVRSEECLSGTWTQQICLPAIYKVFPNSAPLEGGTRLTICG<br>WDFGFRRNNKFDLKKTRVLLGNESCTLTLSESTMNTLKCTVGPAM<br>NKHFNMSIIISNGHGTTQYSTFSYVDPVITSISPKYGPMAGGTLL<br>TLTGNYLNSGNSRHISIGGKTCTLKSVSNSILECYTPAQTISTEF<br>AVKLKIDLANRETSIFSYREDPIVYEIHPTKSFISGGSTITGVGK<br>NLNSVSVPRMVINVHEAGRNFTVACQHRSNSEIICCTTPSLQQLN<br>LQLPLKTKAFFMLDGILSKYFDLIYVHNPVFKPFEKPVMISMGNE<br>NVLEIKGNDIDPEAVKGEVLKVGNKSCENIHLHSEAVLCTVPNDL<br>LKLNSELNIEWKQAISSTVLGKVIVQPDQNFTGLIAGVVSISTAL<br>LLLLGFFLWLKKRKQIKDLGSELVRYDARVHTPHLDRLVSARSVS<br>PTTEMVSNESVDYRATFPEDQFPNSSQNGSCRQVQYPLTDMSPIL<br>TSGDSDISSPLLQNTVHIDLSALNPELVQAVQHVVIGPSSLIVHF<br>NEVIGRGHFGCVYHGTLLDNDGKKIHCAVKSLNRITDIGEVSQFL<br>TEGIIMKDFSHPNVLSLLGICLRSEGSPLVVLPYMKHGDLRNFIR<br>NETHNPTVKDLIGFGLQVAKGMKYLASKKFVHRDLAARNCMLDEK<br>FTVKVADFGLARDMYDKEYYSVHNKTGAKLPVKWMALESLQTQKF<br>TTKSDVWSFGVLLWELMTRGAPPYPDVNTFDITVYLLQGRRLLQP<br>EYCPDPLYEVMLKCWHPKAEMRPSFSELVSRISAIFSTFIGEHYV<br>HVNATYVNVKCVAPYPSLLSSEDNADDEVDTRPASFWETS |
| MUC16 | 53 | MLKPSGLPGSSSPTRSLMTGSRSTKATPEMDSGLTGATLSPKTST<br>GAIVVTEHTLPFTSPDKTLASPTSSVVGRTTQSLGVMSSALPEST<br>SRGMTHSEQRTSPSLSPQVNGTPSRNYPATSMVSGLSSPRTRTSS |

TABLE 5-continued

Exemplary target antigen amino acid sequences

| Antigen | SEQ ID NO | Amino acid sequence |
|---|---|---|
| | | TEGNFTKEASTYTLTVETTSGPVTEKYTVPTETSTTEGDSTETPW
DTRYIPVKITSPMKTFADSTASKENAPVSMTPAETTVTDSHTPGR
TNPSFGTLYSSFLDLSPKGTPNSRGETSLELILSTTGYPESSPEP
GSAGHSRISTSAPLSSSASVLDNKISETSIFSGQSLTSPLSPGVP
EARASTMPNSAIPESMTLSNAETSAERVRSTISSLGTPSISTKQT
AETILTFHAFAETMDIPSTHIAKTLASEWLGSPGTLGGTSTSALT
TTSPSTTLVSEETNTHHSTSGKETEGTLNTSMTPLETSAPGEESE
MTATLVPTLGFTTLDSKIRSPSQVSSSHPTRELRTTGSTSGRQSS
STAAHGSSDILRATTSSTSKASSWTSESTAQQFSEPQHTQWVETS
PSMKTERPPASTSVAAPITTSVPSVVSGFTTLKTSSTKGIWLEET
SADTLIGESTAGPTTHQFAVPTGISMTGGSSTRGSQGTTHLLTRA
TASSETSADLTLATNGVPVSVSPAVSKTAAGSSPPGGTKPSYTMV
SSVIPETSSLQSSAFREGTSLGLTPLNTRHPFSSPEPDSAGHTKI
STSIPLLSSASVLEDKVSATSTFSHHKATSSITTGTPEISTKTKP
SSAVLSSMTLSNAATSPERVRNATSPLTHPSPSGEETAGSVLTLS
TSAETTDSPNIHPTGTLTSESSESPSTLSLPSVSGVKTTFSSSTP
STHLFTSGEETEETSNPSVSQPETSVSRVRTTLASTSVPTPVFPT
MDTWPTRSAQFSSSHLVSELRATSSTSVINSTGSALPKISHLTGT
ATMSQTNRDTFNDSAAPQSTTWPETSPRFKTGLPSATTTVSTSAT
SLSATVMVSKFTSPATSSMEATSIREPSTTILTTETTNGPGSMAV
ASTNIPIGKGYITEGRLDTSHLPIGTTASSETSMDFTMAKESVSM
SVSPSQSMDAAGSSTPGRTSQFVDTFSDDVYHLTSREITIPRDGT
SSALTPQMTATHPPSPDPGSARSTWLGILSSSPSSPTPKVTMSST
FSTQRVTTSMIMDTVETSRWNMPNLPSTTSLTPSNIPTSGAIGKS
TLVPLDTPSPATSLEASEGGLPTLSTYPESTNTPSIHLGAHASSE
SPSTIKLTMASVVKPGSYTPLTFPSIETHIHVSTARMAYSSGSSP
EMTAPGETNTGSTWDPTTYITTTDPKDTSSAQVSTPHSVRTLRTT
ENHPKTESATPAAYSGSPKISSSPNLTSPATKAWTITDTTEHSTQ
LHYTKLAEKSSGFETQSAPGPVSVVIPTSPTIGSSTLELTSDVPG
EPLVLAPSEQTTITLPMATWLSTSLTEEMASTDLDISSPSSPMST
FAIFPPMSTPSHELSKSEADTSAIRNTDSTTLDQHLGIRSLGRTG
DLTTVPITPLTTWTSVIEHSTQAQDTLSATMSPTHVTQSLKDQT
SIPASASPSHLTEVYPELGTQGRSSSEATTFWKPSTDTLSREIET
GPTNIQSTPPMDNTTTGSSSSGVTLGIAHLPIGTSSPAETSTNMA
LERRSSTATVSMAGTMGLLVTSAPGRSISQSLGRVSSVLSESTTE
GVTDSSKGSSPRLNTQGNTALSSSLEPSYAEGSQMSTSIPLTSSP
TTPDVEFIGGSTFWTKEVTTVMTSDISKSSARTESSSATLMSTAL
GSTENTGKEKLRTASMDLPSPTPSMEVTPWISLTLSNAPNTTDSL
DLSHGVHTSSAGTLATDRSLNTGVTRASRLENGSDTSSKSLSMGN
STHTSMTYTEKSEVSSSIHPRPETSAPGAETTLTSTPGNRAISLT
LPFSSIPVEEVISTGITSGPDINSAPMTHSPITPPTIVWTSTGTI
EQSTQPLHAVSSEKVSVQTQSTPYVNSVAVSASPTHENSVSSGSS
TSSPYSSASLESLDSTISRRNAITSWLWDLTTSLPTTTWPSTSLS
EALSSGHSGVSNPSSTTTEFPLFSAASTSAAKQRNPETETHGPQN
TAASTLNTDASSVTGLSETPVGASISSEVPLPMAITSRSDVSGLT
SESTANPSLGTASSAGTKLTRTISLPTSESLVSFRMNKDPWTVSI
PLGSHPTTNTETSIPVNSAGPPGLSTVASDVIDTPSDGAESIPTV
SFSPSPDTEVTTISHFPEKTTHSFRTISSLTHELTSRVTPIPGDW
MSSAMSTKPTGASPSITLGERRTITSAAPTTSPIVLTASFTETST
VSLDNETTVKTSDILDARKTNELPSDSSSSSDLINTSIASSTMDV
TKTASISPTSISGMTASSSPSLFSSDRPQVPTSTTETNTATSPSV
SSNTYSLDGGSNVGGTPSTLPPFTITHPVETSSALLAWSRPVRTF
STMVSTDTASGENPTSSNSVVTSVPAPGTWTSVGSTTDLPAMGFL
KTSPAGEAHSLLASTIEPATAFTPHLSAAVVTGSSATSEASLLTT
SESKAIHSSPQTPTTPTSGANWETSATPESLLVVTETSDTTLTSK
ILVTDTILFSTVSTPPSKFPSTGTLSGASFPTLLPDTPAIPLTAT
EPTSSLATSFDSTPLVTIASDSLGTVPETTLTMSETSNGDALVLK
TVSNPDRSIPGITIQGVTESPLHPSSTSPSKIVAPRNTTYEGSIT
VALSTLPAGTTGSLVFSQSSENSETTALVDSSAGLERASVMPLTT
GSQGMASSGGIRSGSTHSTGTKTFSSLPLTMNPGEVTAMSEITTN
RLTATQSTAPKGIPVKPTSAESGLLTPVSASSSPSKAFASLTTAP
PTWGIPQSTLTFEFSEVPSLDTKSASLPTPGQSLNTIPDSDASTA
SSSLSKSPEKNPRARMMTSTKAISASSFQSTGFTETPEGSASPSM
AGHEPRVPTSGTGDPRYASESMSYPDPSKASSAMTSTSLASKLTT
LFSTGQAARSGSSSSPISLSTEKETSFLSPTASTSRKTSLFLGPS
MARQPNILVHLQTSALTLSPTSTLNMSQEEPPELTSSQTIAEEEG
TTAETQTLTFTPSETPTSLLPVSSPTEPTARRKSSPETWASSISV
PAKTSLVETTDGTLVTTIKMSSQAAQGNSTWPAPAEETGSSPAGT
SPGSPEMSTTLKIMSSKEPSISPEIRSTVRNSPWKTPETTVPMET
TVEPVTLQSTALGSGSTSISHLPTGTTSPTKSPTENMLATERVSL
SPSPPEAWTNLYSGTPGGTRQSLATMSSVSLESPTARSITGTGQQ
SSPELVSKTTGMEFSMWHGSTGGTTGDTHVSLSTSSNILEDPVTS
PNSVSSLTDKSKHKTETWVSTTAIPSTVLNNKIMAAEQQTSRSVD
EAYSSTSSWSDQTSGSDITLGASPDVTNTLYITSTAQTTSLVSLP
SGDQGITSLTNPSGGKTSSASSVTSPSIGLETLRANVSAVKSDIA
PTAGHLSQTSSPAEVSILDVTTAPTPGISTTITTMGTNSISTTTP |

TABLE 5-continued

Exemplary target antigen amino acid sequences

| Antigen | SEQ ID NO | Amino acid sequence |
|---|---|---|
| | | NPEVGMSTMDSTPATERRTTSTEHPSTWSSTAASDSWTVTDMTSN
LKVARSPGTISTMHTTSFLASSTELDSMSTPHGRITVIGTSLVTP
SSDASAVKTETSTSERTLSPSDTTASTPISTFSRVQRMSISVPDI
LSTSWTPSSTEAEDVPVSMVSTDHASTKTDPNTPLSTFLFDSLST
LDWDTGRSLSSATATTSAPQGATTPQELTLETMISPATSQLPFSI
GHITSAVTPAAMARSSGVTFSRPDPTSKKAEQTSTQLPTTTSAHP
GQVPRSAATTLDVIPHTAKTPDATFQRQGQTALTTEARATSDSWN
EKEKSTPSAPWITEMMNSVSEDTIKEVTSSSSVLRTLNTLDINLE
SGTTSSPSWKSSPYERIAPSESTTDKEAIHPSTNTVETTGWVTSS
EHASHSTIPAHSASSKLTSPVVTTSTREQAIVSMSTTTWPESTRA
RTEPNSFLTIELRDVSPYMDTSSTTQTSIISSPGSTAITKGPRTE
ITSSKRISSSFLAQSMRSSDSPSEAITRLSNFPAMTESGGMILAM
QTSPPGATSLSAPTLDTSATASWTGTPLATTQRFTYSEKTTLFSK
GPEDTSQPSPPSVEETSSSSSLVPIHATTSPSNILLTSQGHSPSS
TPPVTSVFLSETSGLGKTTDMSRISLEPGTSLPPNLSSTAGEALS
TYEASRDTKAIHHSADTAVTNMEATSSEYSPIPGHTKPSKATSPL
VTSHIMGDITSSTSVEGSSETTEIETVSSVNQGLQERSTSQVASS
ATETSTVITHVSSGDATTHVTKTQATFSSGTSISSPHQFITSTNT
FTDVSTNPSTSLIMTESSGVTITTQTGPTGAATQGPYLLDTSTMP
YLTETPLAVTPDFMQSEKTTLISKGPKDVSWTSPPSVAETSYPSS
LTPFLVTTIPPATSTLQGQHTSSPVSATSVLTSGLVKTTDMLNTS
MEPVTNSPQNLNNPSNEILATLAATTDIETIHPSINKAVTNMGTA
SSAHVLHSTLPVSSEPSTATSPMVPASSMGDALASISIPGSETTD
IEGEPTSSLTAGRKENSTLQEMNSTTESNIILSNVSVGAITEATK
MEVPSFDATFIPTPAQSTKFPDIFSVASSRLSNSPPMTISTHMTT
TQTGSSGATSKIPLALDTSTLETSAGTPSVVTEGFAHSKITTAMN
NDVKDVSQTNPPFQDEASSPSSQAPVLVTTLPSSVAFTPQWHSTS
SPVSMSSVLTSSLVKTAGKVDTSLETVTSSPQSMSNTLDDISVTS
AATTDIETTHPSINTVVTNVGTTGSAFESHSTVSAYPEPSKVTSP
NVTTSTMEDTTISRSIPKSSKTTRTETETTSSLTPKLRETSISQE
ITSSTETSTVPYKELTGATTEVSRTDVTSSSSTSFPGPDQSTVSL
DISTETNTRLSTSPIMTESAEITITTQTGPHGATSQDTFTMDPSN
TTPQAGIHSAMTHGFSQLDVTTLMSRIPQDVSWTSPPSVDKTSSP
SSFLSSPAMTTPSLISSTLPEDKLSSPMTSLLTSGLVKITDILRT
RLEPVTSSLPNESSTSDKILATSKDSKDTKEIFPSINTEETNVKA
NNSGHESHSPALADSETPKATTQMVITTTVGDPAPSTSMPVHGSS
ETTNIKREPTYFLTPRLRETSTSQESSFPTDTSFLLSKVPTGTIT
EVSSTGVNSSSKISTPDHDKSTVPPDTFTGEIPRVFTSSIKTKSA
EMTITTQASPPESASHSTLPLDTSTTLSQGGTHSTVTQGFPYSEV
TTLMGMGPGNVSWMTTPPVEETSSVSSLMSSPAMTSPSPVSSTSP
QSIPSSPLPVTALPTSVLVTTTDVLGTTSPESVTSSPPNLSSITH
ERPATYKDTAHTEAAMHHSTNTAVTNVGTSGSGHKSQSSVLADSE
TSKATPLMSTTSTLGDTSVSTSTPNISQTNQIQTEPTASLSPRLR
ESSTSEKTSSTTETNTAFSYVPTGAITQASRTEISSSRTSISDLD
RPTIAPDISTGMITRLFTSPIMTKSAEMTVTTQTTTPGATSQGIL
PWDTSTTLFQGGTHSTVSQGFPHSEITTLRSRTPGDVSWMTTPPV
EETSSGFSLMSPSMTSPSPVSSTSPESIPSSPLPVTALLTSVLVT
TTNVLGTTSPEPVTSSPPNLSSPTQERLTTYKDTAHTEAMHASMH
TNTAVANVGTSISGHESQSSVPADSHTSKATSPMGITFAMGDTSV
STSTPAFFETRIQTESTSSLIPGLRDTRTSEEINTVTETSTVLSE
VPTTTTTEVSRTEVITSSRTTISGPDHSKMSPYISTETITRLSTF
PFVTGSTEMAITNQTGPIGTISQATLTLDTSSTASWEGTHSPVTQ
RFPHSEETTTMSRSTKGVSWQSPPSVEETSSPSSPVPLPAITSHS
SLYSAVSGSSPTSALPVTSLLTSGRRKTIDMLDTHSELVTSSLPS
ASSFSGEILTSEASTNTETIHFSENTAETNMGTTNSMHKLHSSVS
IHSQPSGHTPPKVTGSMMEDAIVSTSTPGSPETKNVDRDSTSPLT
PELKEDSTALVMNSTTESNTVFSSVSLDAATEVSRAEVTYYDPTF
MPASAQSTKSPDISPEASSSHSNSPPLTISTHKTIATQTGPSGVT
SLGQLTLDTSTIATSAGTPSARTQDFVDSETTSVMNNDLNDVLKT
SPFSAEEANSLSSQAPLLVTTSPSPVTSTLQEHSTSSLVSVTSVP
TPTLAKITDMDTNLEPVTRSPQNLRNTLATSEATTDTHTMHPSIN
TAVANVGTTSSPNEFYFTVSPDSDPYKATSAVVITSTSGDSIVST
SMPRSSAMKKIESETTFSLIFRLRETSTSQKIGSSSDTSTVFDKA
FTAATTEVSRTELTSSSRTSIQGTEKPTMSPDTSTRSVTMLSTFA
GLTKSEERTIATQTGPHRATSQGTLTWDTSITTSQAGTHSAMTHG
FSQLDLSTLTSRVPEYISGTSPPSVEKTSSSSSLLLSLPAITSPSP
VPTTLPESRPSSPVHLTSLPTSGLVKTTDMLASVASLPPNLGSTS
HKIPTTSEDIKDTEKMYPSTNIAVTNVGTTTSEKESYSSVPAYSE
PPKVTSPMVTSFNIRDTIVSTSMPGSSEITRIEMESTFSLAHGLK
GTSTSQDPIVSTEKSAVLHKLTTGATETSRTEVASSRRTSIPGPD
HSTESPDISTEVIPSLPISLGITESSNMTIITRTGPPLGSTSQGT
FTLDTPTTSSRAGTHSMATQEFPHSEMTTVMNKDPEILSWTIPPS
IEKTSFSSSLMPSPAMTSPPVSSTLPKTIHTTSPSMTSLLTPSLV
MTTDTLGTSPEPTTSSPPNLSSTSHEILTTDEDTTAIEAMHPSTS
TAATNVETTSSGHGSQSSVLADSEKTKATAPMDTTSTMGHTTVST
SMSVSSETTKIKRESTYSLTPGLRETSISQNASFSTDTSIVLSEV |

TABLE 5-continued

Exemplary target antigen amino acid sequences

| Antigen | SEQ ID NO | Amino acid sequence |
|---|---|---|
| | | PTGTTAEVSRTEVTSSGRTSIPGPSQSTVLPEISTRTMTRLFASP
TMTESAEMTIPTQTGPSGSTSQDTLTLDTSTTKSQAKTHSTLTQR
FPHSEMTTLMSRGPGDMSWQSSPSLENPSSLPSLLSLPATTSPPP
ISSTLPVTISSSPLPVTSLLTSSPVTTTDMLHTSPELVTSSPPKL
SHTSDERLTTGKDTTNTEAVHPSTNTAASNVEIPSSGHESPSSAL
ADSETSKATSPMFITSTQEDTTVAISTPHFLETSRIQKESISSLS
PKLRETGSSVETSSAIETSAVLSEVSIGATTEISRTEVTSSSRTS
ISGSAESTMLPEISTTRKIIKFPTSPILAESSEMTIKTQTSPPGS
TSESTFTLDTSTTPSLVITHSTMTQRLPHSEITTLVSRGAGDVPR
PSSLPVEETSPPSSQLSLSAMISPSPVSSTLPASSHSSSASVTSL
LTPGQVKTTEVLDASAEPETSSPPSLSSTSVEILATSEVTTDTEK
IHPFSNTAVTKVGTSSSGHESPSSVLPDSETTKATSAMGTISIMG
DTSVSTLTPALSNTRKIQSEPASSLTTRLRETSTSEETSLATEAN
TVLSKVSTGATTEVSRTEAISESRTSMSGPEQSTMSQDISIGTIP
RISASSVLTESAKMTITTQTGPSESTLESTLNLNTATTPSWVETH
SIVIQGFPHPEMTTSMGRGPGGVSWPSPPFVKETSPPSSPLSLPA
VTSPHPVSTTFLAHIPPSPLPVTSLLTSGPATTTDILGTSTEPGT
SSSSSLSTTSHERLTTYKDTAHTEAVHPSTNTGGTNVATTSSGYK
SQSSVLADSSPMCTTSTMGDTSVLTSTPAFLETRRIQTELASSLT
PGLRESSGSEGTSSGTKMSTVLSKVPTGATTEISKEDVTSIPGPA
QSTISPDISTRTVSWFSTSPVMTESAEITMNTHTSPLGATTQGTS
TLDTSSTTSLTMTHSTISQGFSHSQMSTLMRRGPEDVSWMSPPLL
EKTRPSFSLMSSPATTSPSPVSSTLPESISSSPLPVTSLLTSGLA
KTTDMLHKSSEPVTNSPANLSSTSVEILATSEVTTDTEKTHPSSN
RTVTDVGTSSSGHESTSFVLADSQTSKVTSPMVITSTMEDTSVST
STPGFFETSRIQTEPTSSLTLGLRKTSSSEGTSLATEMSTVLSGV
PTGATAEVSRTEVTSSSRTSISGFAQLTVSPETSTETITRLPTSS
IMTESAEMMIKTQTDPPGSTPESTHTVDISTTPNWVETHSTVTQR
FSHSEMTTLVSRSPGDMLWPSQSSVEETSSASSLLSLPATTSPSP
VSSTLVEDFPSASLPVTSLLNPGLVITTDRMGISREPGTSSTSNL
SSTSHERLTTLEDTVDTEDMQPSTHTAVTNVRTSISGHESQSSVL
SDSETPKATSPMGTTYTMGETSVSISTSDFFETSRIQIEPTSSLT
SGLRETSSSERISSATEGSTVLSEVPSGATTEVSRTEVISSRGTS
MSGPDQFTISPDISTEAITRLSTSPIMTESAESAITIETGSPGAT
SEGTLTLDTSTTTFWSGTHSTASPGFSHSEMTTLMSRTPGDVPWP
SLPSVEEASSVSSSLSSPAMTSTSFFSTLPESISSSPHPVTALLT
LGPVKTTDMLRTSSEPETSSPPNLSSTSAEILATSEVTKDREKIH
PSSNTPVVNVGTVIYKHLSPSSVLADLVTTKPTSPMATTSTLGNT
SVSTSTPAFPETMMTQPTSSLTSGLREISTSQETSSATERSASLS
GMPTGATTKVSRTEALSLGRTSTPGPAQSTISPEISTETITRIST
PLTTTGSAEMTITPKTGHSGASSQGTFTLDTSSRASWPGTHSAAT
HRSPHSGMTTPMSRGPEDVSWPSRPSVEKTSPPSSLVSLSAVTSP
SPLYSTPSESSHSSPLRVTSLFTPVMMKTTDMLDTSLEPVTTSPP
SMNITSDESLATSKATMETEAIQLSENTAVTQMGTISARQEFYSS
YPGLPEPSKVTSPVVTSSTIKDIVSTTIPASSEITRIEMESTSTL
TPTPRETSTSQEIHSATKPSTVPYKALTSATIEDSMTQVMSSSRG
PSPDQSTMSQDISTEVITRLSTSPIKTESTEMTITTQTGSPGATS
RGTLTLDTSTTFMSGTHSTASQGFSHSQMTALMSRTPGDVPWLSH
PSVEEASSASFSLSSPVMTSSSPVSSTLPDSIHSSSLPVTSLLTS
GLVKTTELLGTSSEPETSSPPNLSSTSAEILAITEVTTDTEKLEM
TNVVTSGYTHESPSSVLADSVTTKATSSMGITYPTGDTNVLTSTP
AFSDTSRIQTKSKLSLTPGLMETSISEETSSATEKSTVLSSVPTG
ATTEVSRTEAISSSRTSIPGPAQSTMSSDTSMETITRISTPLTRK
ESTDMAITPKTGPSGATSQGTFTLDSSSTASWPGTHSATTQRFPQ
SVVTTPMSRGPEDVSWPSPLSVEKNSPPSSLVSSSSVTSPSPLYS
TPSGSSHSSPVPVTSLFTSIMMKATDMLDASLEPETTSAPNMNIT
SDESLAASKATTETEAIHVFENTAASHVETTSATEELYSSSPGFS
EPTKVISPVVTSSSIRDNMVSTTMPGSSGITRIEIESMSSLTPGL
RETRTSQDITSSTETSTVLYKMPSGATPEVSRTEVMPSSRTSIPG
PAQSTMSLDISDEVVTRLSTSPIMTESAEITITTQTGYSLATSQV
TLPLGTSMTFLSGTHSTMSQGLSHSEMTNLMSRGPESLSWTSPRF
VETTRSSSSLTSLPLTTSLSPVSSTLLDSSPSSPLPVTSLILPGL
VKTTEVLDTSSEPKTSSSPNLSSTSVEIPATSEIMTDTEKIHPSS
NTAVAKVRTSSSVHESHSSVLADSETTITIPSMGITSAVDDTTVF
TSNPAFSETRRIPTEPTESLTPGFRETSTSEETTSITETSAVLYG
VPTSATTEVSMTEIMSSNRIHIPDSDQSTMSPDIITEVITRLSSS
SMMSESTQMTITTQKSSPGATAQSTLTLATTTAPLARTHSTVPPR
FLHSEMTTLMSRSPENPSWKSSLFVEKTSSSSSLLSLPVTTSPSV
SSTLPQSIPSSSFSVTSLLTPGMVKTTDTSTEPGTSLSPNLSGTS
VEILAASEVTTDTEKIHPSSSMAVTNVGTTSSGHELYSSVSIHSE
PSKATYPVGTPSSMAETSISTSMPANFETTGFEAEPFSHLTSGFR
KTNMSLDTSSVTPTNTPSSPGSTHLLQSSKTDFTSSAKTSSPDWP
PASQYTEIPVDIITPFNASPSITESTGITSFPESRFTMSVTESTH
HLSTDLLPSAETISTGTVMPSLSEAMTSFATTGVPRAISGSGSPF
SRTESGPGDATLSTIAESLPSSTPVPFSSSTFTTTDSSTIPALHE
ITSSSATPYRVDTSLGTESSTTEGRLVMVSTLDTSSQPGRTSSSP |

TABLE 5-continued

Exemplary target antigen amino acid sequences

| Antigen | SEQ ID NO | Amino acid sequence |
|---|---|---|
| | | ILDTRMTESVELGTVTSAYQVPSLSTRLTRTDGIMEHITKIPNEA
AHRGTIRPVKGPQTSTSPASPKGLHTGGTKRMETTTTALKTTTTA
LKTTSRATLTTSVYTPTLGTLTPLNASMQMASTIPTEMMITTPYV
FPDVPETTSSLATSLGAETSTALPRTTPSVFNRESETTASLVSRS
GAERSPVIQTLDVSSSEPDTTASWVIHPAETIPTVSKTTPNFFHS
ELDTVSSTATSHGADVSSAIPTNISPSELDALTPLVTISGTDTST
TFPPTLTKSPHETETRTTWLTHPAETSSTIPRTIPNESHHESDATP
SIATSPGAETSSAIPIMTVSPGAEDLVTSQVTSSGTDRNMTIPTL
TLSPGEPKTIASLVTHPEAQTSSAIPTSTISPAVSRLVTSMVTSL
AAKTSTTNRALTNSPGEPATTVSLVTHPAQTSPTVPWTTSIFFHS
KSDTTPSMTTSHGAESSSAVPTPTVSTEVPGVVTPLVTSSRAVIS
TTIPILTLSPGEPETTPSMATSHGEEASSAIPTPTVSPGVPGVVT
SLVTSSRAVTSTTIPILTESLGEPETTPSMATSHGTEAGSAVPTV
LPEVPGMVTSLVASSRAVTSTTLPTLTLSPGEPETTPSMATSHGA
EASSTVPTVSPEVPGVVTSLVTSSSGVNSTSIPTLILSPGELETT
PSMATSHGAEASSAVPTPTVSPGVSGVVTPLVTSSRAVTSTTIPI
LTLSSSEPETTPSMATSHGVEASSAVLTVSPEVPGMVTSLVTSSR
AVTSTTIPTLTISSDEPETTTSLVTHSEAKMISAIPTLAVSPTVQ
GLVTSLVTSSGSETSAFSNITVASSQPETIDSWVAHPGTEASSVV
PTLTVSTGEPFTNISLVTHPAESSSTLPRTTSRESHSELDTMPST
VTSPEAESSSAISTTISPGIPGVLTSLVTSSGRDISATFPTVPES
PHESEATASWVTHPAVTSTTVPRTTPNYSHSEPDTTPSIATSPGA
EATSDFPTITVSPDVPDMVTSQVTSSGTDTSITIPTLTLSSGEPE
TTTSFITYSETHTSSAIPTLPVSPGASKMLTSLVISSGTDSTTTF
PTLTETPYEPETTAIQLIHPAETNTMVPRTTPKFSHSKSDTTLPV
AITSPGPEASSAVSTTTISPDMSDLVTSLVPSSGTDTSTTFPTLS
ETPYEPETTATWLTHPAETSTTVSGTIPNFSHRGSDTAPSMVTSP
GVDTRSGVPTTTIPPSIPGVVTSQVTSSATDTSTAIPTLTPSPGE
PETTASSATHPGTQTGFTVPIRTVPSSEPDTMASWVTHPPQTSTP
VSRTTSSFSHSSPDATPVMATSPRTEASSAVLTTISPGAPEMVTS
QITSSGAATSTTVPTLTHSPGMPETTALLSTHPRTETSKTFPAST
VFPQVSETTASLTIRPGAETSTALPTQTTSSLFTLLVTGTSRVDL
SPTASPGVSAKTAPLSTHPGTETSTMIPTSTLSLGLLETTGLLAT
SSSAETSTSTLTLTVSPAVSGLSSSASITTDKPQTVTSWNTETSPS
VTSVGPPEFSRTVTGTTMTLIPSEMPTPPKTSHGEGVSPTTILRT
TMVEATNLATTGSSPTVAKTTTTFNTLAGSLFTPLTTPGMSTLAS
ESVTSRTSYNHRSWISTTSSYNRRYWTPATSTPVTSTFSPGISTS
SIPSSTAATVPFMVPFTLNFTITNLQYEEDMRHPGSRKENATERE
LQGLLKPLFRNSSLEYLYSGCRLASLRPEKDSSATAVDAICTHRP
DPEDLGLDRERLYWELSNLINGIQELGPYTLDRNSLYVNGFTHRS
SMPTTSTPGTSTVDVGTSGTPSSSPSPTTAGPLLMPFTLNFTITN
LQYEEDMRRTGSRKENTMESVLQGLLKPLFKNTSVGPLYSGCRLT
LLRPEKDGAATGVDAICTHRLDPKSPGLNREQLYWELSKLTNDIE
ELGPYTLDRNSLYVNGFTHQSSVSTTSTPGTSTVDLRTSGTPSSL
SSPTIMAAGPLLVPFTLNFTITNLQYGEDMGHPGSRKFNTTERVL
QGLLGPIFKNTSVGPLYSGCRLTSLRSEKDGAATGVDAICIHHLD
PKSPGLNRERLYWELSQLTNGIKELGPYTLDRNSLYVNGFTHRTS
VPTSSTPGTSTVDLGTSGTPFSLPSPATAGPLLVLFTLNFTITNL
KYEEDMHRPGSRKFNTTERVLQTLLGPMFKNTSVGLLYSGCRLTL
LRSEKDGAATGVDAICTHRLDPKSPGVDREQLYWELSQLINGIKE
LGPYTLDRNSLYVNGFTHWIPVPTSSTPGTSTVDLGSGTPSSLPS
PTTAGPLLVPFTLNFTITNLKYEEDMHCPGSRKFNTTERVLQSLL
GPMFKNTSVGPLYSGCRLTLLRSEKDGAATGVDAICTHRLDPKSP
GVDREQLYWELSQLTNGIKELGPYTLDRNSLYVNGFTHQTSAPNT
STPGTSTVDLGTSGTPSSLPSPTSAGPLLVPFTLNFTITNLQYEE
DMHHPGSRKFNTTERVLQGLLGPMFKNTSVGLLYSGCRLTLLRPE
KNGAATGMDAICSHRLDPKSPGLNREQLYWELSQLTHGIKELGPY
TLDRNSLYVNGFTHRSSVAPTSTPGTSTVDLGTSGTPSSLPSPTT
AVPLLVPFTLNFTITNLQYGEDMRHPGSRKFNTTERVLQGLLGPL
FKNSSVGPLYSGCRLISLRSEKDGAATGVDAICTHHLNPQSPGLD
REQLYWQLSQMTNGIKELGPYTLDRNSLYVNGFTHRSSGLTTSTP
WTSTVDLGTSGTPSPVPSPTTTGPLLVPFTLNFTITNLQYEENMG
HPGSRKFNITESVLQGLLKPLFKSTSVGPLYSGCRLTLLRPEKDG
VATRVDAICTHRPDPKIPGLDRQQLYWELSQLTHSITELGPYTLD
RDSLYVNGFTQRSSVPTTSTPGTFTVQPETSETPSSLPGPTATGP
VLLPFTLNFTITNLQYEEDMRRPGSRKFNTTERVLQGLLMPLEKN
TSVSSLYSGCRLTLLRPEKDGAATRVDAVCTHRPDPKSPGLDRER
LYWKLSQLTHGITELGPYTLDRHSLYVNGFTHQSSMTTTRTPDTS
TMHLATSRTPASLSGPMTASPLLVLFTINFTITNLRYEENMHHPG
SRKFNTTERVLQGLLRPVFKNTSVGPLYSGCRLTLLRPKKDGAAT
KVDAICTYRPDPKSPGLDREQLYWELSQLTHSITELGPYTLDRDS
LYVNGFTQRSSVPTTSIPGTPTVDLGTSGTPVSKPGPSAASPLLV
LFTLNFTITNLRYEENMQHPGSRKFNTTERVLQGLLRSLFKSTSV
GPLYSGCRLTLLRPEKDGTATGVDAICTHHPDPKSPRLDREQLYW
ELSQLTHNITELGPYALDNDSLFVNGFTHRSSVSTTSTPGTPTVY
LGASKTPASIFGPSAASHLLILFTLNFTITNLRYEENMWPGSRKF |

TABLE 5-continued

Exemplary target antigen amino acid sequences

| Antigen | SEQ ID NO | Amino acid sequence |
|---|---|---|
| | | NTTERVLQGLLRPLFKNTSVGPLYSGCRLTLLRPEKDGEATGVDA<br>ICTHRPDPTGPGLDREQLYLELSQLTHSITELGPYTLDRDSLYVN<br>GFTHRSSVPTTSTGVVSEEPFTLNFTINNLRYMADMGQPGSLKFN<br>ITDNVMQHLLSPLFQRSSLGARYTGCRVIALRSVKNGAETRVDLL<br>CTYLQPLSGPGLPIKQVFHELSQQTHGITRLGPYSLDKDSLYLNG<br>YNEPGPDEPPTTPKPATTFLPPLSEATTAMGYHLKTLTLNFTISN<br>LQYSPDMGKGSATFNSTEGVLQHLLRPLFQKSSMGPFYLGCQLIS<br>LRPEKDGAATGVDTTCTYHPDPVGPGLDIQQLYWELSQLTHGVTQ<br>LGFYVLDRDSLFINGYAPQNLSIRGEYQINFHIVNWNLSNPDPTS<br>SEYITLLRDIQDKVTTLYKGSQLHDTFRFCLVTNLTMDSVLVTVK<br>ALFSSNLDPSLVEQVELDKTLNASFHWLGSTYQLVDIHVTEMESS<br>VYQPTSSSSTQHFYLNFTITNLPYSQDKAQPGTTNYQRNKRNIED<br>ALNQLFRNSSIKSYFSDCQVSTFRSVPNRHHTGVDSLCNFSPLAR<br>RVDRVAIYEEFLRMTRNGTQLQNFTLDRSSVLVDGYSPNRNEPLT<br>GNSDLPFWAVILIGLAGLIGVITCLICGVLVTTRRRKKEGEYNVQ<br>QQCPGYYQSHLDLEDLQ |
| SLC39A6 | 54 | MARKLSVILILTFALSVINPLHELKAAAFPQTTEKISPNWESGIN<br>VDLAISTRQYHLQQLFYRYGENNSLSVEGFRKLLQNIGIDKIKRI<br>HIHHDHDHHSDHEHHSDHERHSDHEHHSEHEHHSDHDHHSHHNHA<br>ASGKNKRKALCPDHDSDSSGKDPRNSQGKGAHRPEHASGRRNVKD<br>SVSASEVTSTVYNTVSEGTHFLETIETPRPGKLFPKDVSSSTPPS<br>VTSKSRVSRLAGRKTNESVSEPRKGFMYSRNTNENPQECFNASKL<br>LTSHGMGIQVPLNATEFNYLCPAIINQIDARSCLIHTSEKKAEIP<br>PKTYSLQIAWVGGFIAISIISFLSLLGVILVPLMNRVFFKFLLSF<br>LVALAVGTLSGDAFLHLLPHSHASHHHSHSHEEPAMEMKRGPLFS<br>HLSSQNIEESAYFDSTWKGLTALGGLYFMFLVEHVLTLIKQFKDK<br>KKKNQKKPENDDDVEIKKQLSKYESQLSTNEEKVDTDDRTEGYLR<br>ADSQEPSHFDSQQPAVLEEEEVMIAHAHPQEVYNEYVPRGCKNKC<br>HSHFHDTLGQSDDLIHHHHDYHHILHHHHHQNHHPHSHSQRYSRE<br>ELKDAGVATLAWMVIMGDGLHNESDGLAIGAAFTEGLSSGLSTSV<br>AVFCHELPHELGDFAVLLKAGMTVKQAVLYNALSAMLAYLGMATG<br>IFIGHYAENVSMWIFALTAGLFMYVALVDMVPEMLHNDASDHGCS<br>RWGYFFLQNAGMLLGFGIMLLISIFEHKIVFRINF |
| SLC44A4 | 55 | MGGKQRDEDDEAYGKPVKYDPSFRGPIKNRSCTDVICCVLFLLFI<br>LGYIVVGIVAWLYGDPRQVLYPRNSTGAYCGMGENKDKPYLLYFN<br>IFSCILSSNIISVAENGLQCPTPQVCVSSCPEDPWTVGKNEFSQT<br>VGEVFYTKNRNFCLPGVPWNMTVITSLQQELCPSFLLPSAPALGR<br>CFPWTNVTPPALPGITNDTTIQQGISGLIDSLNARDISVKIFEDF<br>AQSWYWILVALGVALVLSLLFILLLRLVAGPLVLVLILGVLGVLA<br>YGIYYCWEEYRVLRDKGASISQLGFTTNLSAYQSVQETWLAALIV<br>LAVLEAILLLMLIFLRQRIRIAIALLKEASKAVGQMMSTMFYPLV<br>TFVLLLICIAYWAMTALYLATSGQPQYVLWASNISSPGCEKVPIN<br>TSCNPTAHLVNSSCPGLMCVFQGYSSKGLIQRSVFNLQIYGVLGL<br>FWTLNWVLALGQCVLAGAFASFYWAFHKPQDIPTFPLISAFIRTL<br>RYHTGSLAFGALILTLVQIARVILEYIDHKLRGVQNPVARCIMCC<br>FKCCLWCLEKFIKELNRNAYIMIAIYGKNFCVSAKNAFMLLMRNI<br>VRVVVLDKVTDLLLFFGKLLVVGGVGVLSFFFFSGRIPGLGKDFK<br>SPHLNYYWLPIMTSILGAYVIASGFFSVFGMCVDTLFLCFLEDLE<br>RNNGSLDRPYYMSKSLLKILGKKNEAPPDNKKRKK |
| STEAP1 | 56 | MESRKDITNQEELWKMKPRRNLEEDDYLHKDTGETSMLKRPVLLH<br>LHQTAHADEFDCPSELQHTQELFPQWHLPIKIAAIIASLTFLYTL<br>LREVIHPLATSHQQYFYKIPILVINKVLPMVSITLLALVYLPGVI<br>AAIVQLHNGTKYKKFPHWLDKWMLTRKQFGLLSFFFAVLHAIYSL<br>SYPMRRSYRYKLLNWAYQQVQQNKEDAWIEHDVWRMEIYVSLGIV<br>GLAILALLAVTSIPSVSDSLTWREFHYIQSKLGIVSLLLGTIHAL<br>IFAWNKWIDIKQFVWYTPPTFMIAVFLPIVVLIFKSILFLPCLRK<br>KILKIRHGWEDVTKINKTEICSQL |

In various embodiments, an ADC disclosed herein may comprise any set of heavy and light chain variable domains listed in the tables above, or the set of six CDR sequences from the heavy and light chain set, e.g., by transplanting the six CDRs into a chosen human donor antibody framework. In various embodiments, an ADC disclosed herein may comprise amino acid sequences that are homologous to the sequences listed in the tables above, so long as the ADC retains the ability to bind to its target cancer antigen (e.g., with a $K_D$ of less than $1 \times 10^{-8}$ M) and retains one or more functional properties of the ADCs disclosed herein (e.g., ability to internalize, modulate RNA splicing, inhibit cell growth, etc.).

In some embodiments, the ADC further comprises human heavy and light chain constant domains or fragments thereof. For instance, the ADC may comprise a human IgG heavy chain constant domain (such as an IgG1) and a human kappa or lambda light chain constant domain. In various embodiments, the antibody or antigen binding fragment of the described ADCs comprises a human immunoglobulin G subtype 1 (IgG1) heavy chain constant domain with a human Ig kappa light chain constant domain.

In various other embodiments, the target cancer antigen for an ADC is human epidermal growth factor receptor 2 (HER2).

In various embodiments, the anti-HER2 antibody or antigen binding fragment thereof comprises three heavy chain CDRs and three light chain CDRs as follows: heavy chain CDR1 (HCDR1) consisting of SEQ ID NO:1, heavy chain CDR2 (HCDR2) consisting of SEQ ID NO:2, heavy chain CDR3 (HCDR3) consisting of SEQ ID NO:3; light chain CDR1 (LCDR1) consisting of SEQ ID NO:4, light chain CDR2 (LCDR2) consisting of SEQ ID NO:5, and light chain CDR3 (LCDR3) consisting of SEQ ID NO:6, as defined by the Kabat numbering system.

In various embodiments, the anti-HER2 antibody or antigen binding fragment thereof comprises a heavy chain variable region comprising the amino acid sequence of SEQ ID NO:19, and a light chain variable region comprising the amino acid sequence of SEQ ID NO:20. In some embodiments, the anti-HER2 antibody or antigen binding fragment thereof comprises the heavy chain variable region amino acid sequence of SEQ ID NO:19 and the light chain variable region amino acid sequence of SEQ ID NO:20, or sequences that are at least 95% identical to the disclosed sequences. In some embodiments, the anti-HER2 antibody or antigen binding fragment thereof has a heavy chain variable region amino acid sequence that is at least 96%, at least 97%, at least 98%, or at least 99% identical to SEQ ID NO:19 and/or a light chain variable region amino acid sequence that is at least 96%, at least 97%, at least 98%, or at least 99% identical to SEQ ID NO:20.

In various embodiments, the anti-HER2 antibody or antigen binding fragment thereof is an internalizing antibody or internalizing antigen binding fragment. In various embodiments, the anti-HER2 antibody comprises a human IgG1 heavy chain constant domain and a human Ig kappa light chain constant domain.

In various embodiments, the anti-HER2 antibody comprises the heavy chain amino acid sequence of SEQ ID NO:19 or a sequence that is at least 95% identical to SEQ ID NO:19, and the light chain amino acid sequence of SEQ ID NO:20 or a sequence that is at least 95% identical to SEQ ID NO:20. In particular embodiments, the anti-HER2 antibody comprises the heavy chain amino acid sequence of SEQ ID NO:19 and the light chain amino acid sequence of SEQ ID NO:20, or sequences that are at least 95% identical to the disclosed sequences. In some embodiments, the anti-HER2 antibody has a heavy chain amino acid sequence that is at least 96%, at least 97%, at least 98%, or at least 99% identical to SEQ ID NO:19 and a light chain amino acid sequence that is at least 96%, at least 97%, at least 98%, or at least 99% identical to SEQ ID NO:20. In various embodiments, the anti-HER2 antibody is trastuzumab, or an antigen binding fragment thereof.

In various embodiments, the anti-HER2 antibody or antigen binding fragment thereof comprises the three heavy chain CDRs and three light chain CDRs of trastuzumab or wherein the CDRs include no more than one, two, three, four, five, or six amino acid additions, deletions or substitutions of HCDR1 (SEQ ID NO:1), HCDR2 (SEQ ID NO:2), HCDR3 (SEQ ID NO:3); LCDR1 (SEQ ID NO:4), LCDR2 (SEQ ID NO:5), and LCDR3 (SEQ ID NO:6).

In various other embodiments, the target cancer antigen for an ADC is human syndecan-1 (CD138).

In various embodiments, the anti-CD138 antibody or antigen binding fragment thereof comprises three heavy chain CDRs and three light chain CDRs as follows: heavy chain CDR1 (HCDR1) consisting of SEQ ID NO:7, heavy chain CDR2 (HCDR2) consisting of SEQ ID NO:8, heavy chain CDR3 (HCDR3) consisting of SEQ ID NO:9; light chain CDR1 (LCDR1) consisting of SEQ ID NO:10, light chain CDR2 (LCDR2) consisting of SEQ ID NO:11, and light chain CDR3 (LCDR3) consisting of SEQ ID NO:12, as defined by the Kabat numbering system.

In various embodiments, the anti-CD138 antibody or antigen binding fragment thereof comprises a heavy chain variable region comprising the amino acid sequence of SEQ ID NO:21, and a light chain variable region comprising the amino acid sequence of SEQ ID NO:22. In some embodiments, the anti-CD138 antibody or antigen binding fragment thereof comprises the heavy chain variable region amino acid sequence of SEQ ID NO:21 and the light chain variable region amino acid sequence of SEQ ID NO:22, or sequences that are at least 95% identical to the disclosed sequences. In some embodiments, the anti-CD138 antibody or antigen binding fragment thereof has a heavy chain variable region amino acid sequence that is at least 96%, at least 97%, at least 98%, or at least 99% identical to SEQ ID NO:21 and/or a light chain variable region amino acid sequence that is at least 96%, at least 97%, at least 98%, or at least 99% identical to SEQ ID NO:22.

In various embodiments, the anti-CD138 antibody or antigen binding fragment thereof is an internalizing antibody or internalizing antigen binding fragment. In various embodiments, the anti-CD138 antibody comprises a murine IgG2a heavy chain constant domain and a murine Ig kappa light chain constant domain. In various embodiments, the anti-CD138 antibody comprises a human IgG2a heavy chain constant domain and a human Ig kappa light chain constant domain.

In various embodiments, the anti-CD138 antibody comprises the heavy chain amino acid sequence of SEQ ID NO:21 or a sequence that is at least 95% identical to SEQ ID NO:21, and the light chain amino acid sequence of SEQ ID NO:22 or a sequence that is at least 95% identical to SEQ ID NO:22. In particular embodiments, the anti-CD138 antibody comprises the heavy chain amino acid sequence of SEQ ID NO:21 and the light chain amino acid sequence of SEQ ID NO:22, or sequences that are at least 95% identical to the disclosed sequences. In some embodiments, the anti-CD138 antibody has a heavy chain amino acid sequence that is at least 96%, at least 97%, at least 98%, or at least 99% identical to SEQ ID NO:21 and a light chain amino acid sequence that is at least 96%, at least 97%, at least 98%, or at least 99% identical to SEQ ID NO:22. In various embodiments, the anti-CD138 antibody is B—B4, or an antigen binding fragment thereof.

In various embodiments, the anti-CD138 antibody or antigen binding fragment thereof comprises the three heavy chain CDRs and three light chain CDRs of B—B4 or wherein the CDRs include no more than one, two, three, four, five, or six amino acid additions, deletions or substitutions of HCDR1 (SEQ ID NO:7), HCDR2 (SEQ ID NO:8), HCDR3 (SEQ ID NO:9); LCDR1 (SEQ ID NO:10), LCDR2 (SEQ ID NO:11), and LCDR3 (SEQ ID NO:12).

In various other embodiments, the target cancer antigen for an ADC is human ephrin type-A receptor 2 (EPHA2).

In various embodiments, the anti-EPHA2 antibody or antigen binding fragment thereof comprises three heavy chain CDRs and three light chain CDRs as follows: heavy chain CDR1 (HCDR1) consisting of SEQ ID NO:13, heavy chain CDR2 (HCDR2) consisting of SEQ ID NO:14, heavy chain CDR3 (HCDR3) consisting of SEQ ID NO:15; light chain CDR1 (LCDR1) consisting of SEQ ID NO:16, light chain CDR2 (LCDR2) consisting of SEQ ID NO:17, and light chain CDR3 (LCDR3) consisting of SEQ ID NO:18, as defined by the Kabat numbering system.

In various embodiments, the anti-EPHA2 antibody or antigen binding fragment thereof comprises a heavy chain variable region comprising the amino acid sequence of SEQ ID NO:23, and a light chain variable region comprising the amino acid sequence of SEQ ID NO:24. In some embodiments, the anti-EPHA2 antibody or antigen binding fragment thereof comprises the heavy chain variable region amino acid sequence of SEQ ID NO:23 and the light chain variable region amino acid sequence of SEQ ID NO:24, or sequences that are at least 95% identical to the disclosed sequences. In some embodiments, the anti-EPHA2 antibody or antigen binding fragment thereof has a heavy chain variable region amino acid sequence that is at least 96%, at least 97%, at least 98%, or at least 99% identical to SEQ ID NO:23 and/or a light chain variable region amino acid sequence that is at least 96%, at least 97%, at least 98%, or at least 99% identical to SEQ ID NO:24.

In various embodiments, the anti-EPHA2 antibody or antigen binding fragment thereof is an internalizing antibody or internalizing antigen binding fragment. In various embodiments, the anti-EPHA2 antibody comprises a human IgG1 heavy chain constant domain and a human Ig kappa light chain constant domain.

In various embodiments, the anti-EPHA2 antibody comprises the heavy chain amino acid sequence of SEQ ID NO:23 or a sequence that is at least 95% identical to SEQ ID NO:23, and the light chain amino acid sequence of SEQ ID NO:24 or a sequence that is at least 95% identical to SEQ ID NO:24. In particular embodiments, the anti-EPHA2 antibody comprises the heavy chain amino acid sequence of SEQ ID NO:23 and the light chain amino acid sequence of SEQ ID NO:24, or sequences that are at least 95% identical to the disclosed sequences. In some embodiments, the anti-EPHA2 antibody has a heavy chain amino acid sequence that is at least 96%, at least 97%, at least 98%, or at least 99% identical to SEQ ID NO:23 and a light chain amino acid sequence that is at least 96%, at least 97%, at least 98%, or at least 99% identical to SEQ ID NO:24. In some embodiments, the anti-EPHA2 antibody comprises a heavy chain encoded by the nucleotide sequence of SEQ ID NO:23; and a light chain encoded by the nucleotide sequence of SEQ ID NO:24. In various embodiments, the anti-EPHA2 antibody is $1C_1$, or an antigen binding fragment thereof.

In various embodiments, the anti-EPHA2 antibody or antigen binding fragment thereof comprises the three heavy chain CDRs and three light chain CDRs of $1C_1$ or wherein the CDRs include no more than one, two, three, four, five, or six amino acid additions, deletions or substitutions of HCDR1 (SEQ ID NO:13), HCDR2 (SEQ ID NO:14), HCDR3 (SEQ ID NO:15); LCDR1 (SEQ ID NO:16), LCDR2 (SEQ ID NO:17), and LCDR3 (SEQ ID NO:18).

In various embodiments, amino acid substitutions are of single residues. Insertions usually will be on the order of from about 1 to about 20 amino acid residues, although considerably larger insertions may be tolerated as long as biological function is retained (e.g., binding to a target antigen). Deletions usually range from about 1 to about 20 amino acid residues, although in some cases deletions may be much larger. Substitutions, deletions, insertions, or any combination thereof may be used to arrive at a final derivative or variant. Generally, these changes are done on a few amino acids to minimize the alteration of the molecule, particularly the immunogenicity and specificity of the antigen binding protein. However, larger changes may be tolerated in certain circumstances. Conservative substitutions are generally made in accordance with the following chart depicted as Table 6.

TABLE 6

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Table 6. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general may produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

In various embodiments where variant antibody sequences are used in an ADC, the variants typically exhibit the same qualitative biological activity and will elicit the same immune response, although variants may also be selected to modify the characteristics of the antigen binding proteins as needed. Alternatively, the variant may be designed such that the biological activity of the antigen binding protein is altered. For example, glycosylation sites may be altered or removed.

Various antibodies may be used with the ADCs used herein to target cancer cells. As shown below, the linker-payloads in the ADCs disclosed herein are surprisingly effective with different tumor antigen-targeting antibodies. Suitable antigens expressed on tumor cells but not healthy cells, or expressed on tumor cells at a higher level than on healthy cells, are known in the art, as are antibodies directed against them. These antibodies may be used with the linkers and splicing modulator payloads disclosed herein. In some embodiments, the antibody or antigen binding fragment targets HER2, and the HER2-targeting antibody or antigen binding fragment is trastuzumab. In some embodiments, the antibody or antigen binding fragment targets CD138, and the CD138-targeting antibody or antigen binding fragment is B—B4. In some embodiments, the antibody or antigen binding fragment targets EPHA2, and the EPHA2-targeting antibody or antigen binding fragment is $1C_1$. In some embodiments, while the disclosed linkers and splicing modulator payloads are surprisingly effective with several different tumor-targeting antibodies, HER2-targeting antibodies such as trastuzumab, CD138-targeting antibodies such as B—B4, and EPHA2-targeting antibodies such as $1C_1$ provided particularly improved drug:antibody ratio, aggregation level, stability (i.e., in vitro and in vivo stability), tumor targeting (i.e., cytotoxicity, potency), and/or treatment efficacy. Improved treatment efficacy can be measured in vitro or in vivo, and may include reduced tumor growth rate and/or reduced tumor volume.

In certain embodiments, alternate antibodies to the same targets or antibodies to different antigen targets are used and provide at least some of the favorable functional properties described above (e.g., improved stability, improved tumor targeting, improved treatment efficacy, etc.). In some embodiments, some or all of these favorable functional properties are observed when the disclosed linkers and splicing modulator payloads are conjugated to an alternate HER2-, CD138-, or EPHA2-targeting antibody or antigen binding fragment. In some other embodiments, some or all of these favorable functional properties are observed when the disclosed linkers and splicing modulator payloads are conjugated to a HER2-targeting antibody or antigen binding fragment. In some embodiments, the antibody or antigen binding fragment targets HER2. In some embodiments, the HER2-targeting antibody or antigen binding fragment is trastuzumab. In some other embodiments, some or all of these favorable functional properties are observed when the disclosed linkers and splicing modulator payloads are conjugated to a CD138-targeting antibody or antigen binding fragment. In some embodiments, the antibody or antigen binding fragment targets CD138. In some embodiments, the CD138-targeting antibody or antigen binding fragment is B—B4. In some other embodiments, some or all of these favorable functional properties are observed when the disclosed linkers and splicing modulator payloads are conjugated to an EPHA2-targeting antibody or antigen binding fragment. In some embodiments, the antibody or antigen binding fragment targets EPHA2. In some embodiments, the EPHA2-targeting antibody or antigen binding fragment is $1C_1$.

Linkers

In various embodiments, the linker in an ADC is stable extracellularly in a sufficient manner to be therapeutically effective. In some embodiments, the linker is stable outside a cell, such that the ADC remains intact when present in extracellular conditions (e.g., prior to transport or delivery into a cell). The term "intact," used in the context of an ADC, means that the antibody or antigen binding fragment remains attached to the drug moiety (e.g., the splicing modulator). As used herein, "stable," in the context of a linker or ADC comprising a linker, means that no more than 20%, no more than about 15%, no more than about 10%, no more than about 5%, no more than about 3%, or no more than about 1% of the linkers (or any percentage in between) in a sample of ADC are cleaved (or in the case of an overall ADC are otherwise not intact) when the ADC is present in extracellular conditions. In some embodiments, the linkers and/or ADCs disclosed herein are surprisingly stable compared to alternate linkers and/or ADCs with alternate linkers and/or splicing modulator payloads. In some embodiments, the ADCs disclosed herein can remain intact for more than about 48 hours, more than 60 hours, more than about 72 hours, more than about 84 hours, or more than about 96 hours.

Whether a linker is stable extracellularly can be determined, for example, by including an ADC in plasma for a predetermined time period (e.g., 2, 4, 6, 8, 16, 24, 48, or 72 hours) and then quantifying the amount of free drug moiety present in the plasma. Stability may allow the ADC time to localize to target tumor cells and prevent the premature release of the drug moiety, which could lower the therapeutic index of the ADC by indiscriminately damaging both normal and tumor tissues. In some embodiments, the linker is stable outside of a target cell and releases the drug moiety from the ADC once inside of the cell, such that the drug can bind to its target (e.g., to the SF3b spliceosome complex). Thus, an effective linker will: (i) maintain the specific binding properties of the antibody or antigen binding fragment; (ii) allow delivery, e.g., intracellular delivery, of the drug moiety via stable attachment to the antibody or antigen binding fragment; (iii) remain stable and intact until the ADC has been transported or delivered to its target site; and (iv) allow for the therapeutic effect, e.g., cytotoxic effect, of the drug moiety after cleavage or alternate release mechanism.

Linkers may impact the physico-chemical properties of an ADC. As many cytotoxic agents are hydrophobic in nature, linking them to the antibody with an additional hydrophobic moiety may lead to aggregation. ADC aggregates are insoluble and often limit achievable drug loading onto the antibody, which can negatively affect the potency of the ADC. Protein aggregates of biologics, in general, have also been linked to increased immunogenicity. As shown below, linkers disclosed herein result in ADCs with low aggregation levels and desirable levels of drug loading.

A linker may be "cleavable" or "non-cleavable" (Ducry and Stump (2010) Bioconjugate Chem. 21:5-13). Cleavable linkers are designed to release the drug moiety (e.g., the splicing modulator) when subjected to certain environment factors, e.g., when internalized into the target cell, whereas non-cleavable linkers generally rely on the degradation of the antibody or antigen binding fragment itself.

In some embodiments, the linker is a non-cleavable linker. In some embodiments, the splicing modulator drug moiety of the ADC is released by degradation of the antibody or antigen binding fragment. Non-cleavable linkers tend to remain covalently associated with at least one amino acid of the antibody and the drug upon internalization by and degradation within the target cell. Numerous exemplary non-cleavable linkers are described herein, and others are known in the art. Exemplary non-cleavable linkers may comprise thioether, cyclohexyl, N-succinimidyl 4-(N-maleimidomethyl) cyclohexane-1 carboxylate (SMCC), or N-hydroxysuccinimide (NHS), one or more polyethylene glycol (PEG) moieties, e.g., 1, 2, 3, 4, 5, or 6 PEG moieties, or one or more alkyl moieties.

In some embodiments, the linker is a cleavable linker. A cleavable linker refers to any linker that comprises a cleavable moiety. As used herein, the term "cleavable moiety" refers to any chemical bond that can be cleaved. Suitable cleavable chemical bonds are well known in the art and include, but are not limited to, acid labile bonds, protease/peptidase labile bonds, photolabile bonds, disulfide bonds, and esterase labile bonds. Linkers comprising a cleavable moiety can allow for the release of the splicing modulator drug moiety from the ADC via cleavage at a particular site in the linker.

In some embodiments, the linker is cleavable under intracellular conditions, such that cleavage of the linker sufficiently releases the splicing modulator drug moiety from the antibody or antigen binding fragment in the intracellular environment to activate the drug and/or render the drug therapeutically effective. In some embodiments, the splicing modulator drug moiety is not cleaved from the antibody or antigen binding fragment until the ADC enters a cell that expresses an antigen specific for the antibody or antigen binding fragment of the ADC, and the splicing modulator drug moiety is cleaved from the antibody or antigen binding fragment upon entering the cell. In some embodiments, the linker comprises a cleavable moiety that is positioned such that no part of the linker or the antibody or antigen binding fragment remains bound to the splicing modulator drug moiety upon cleavage. Exemplary cleavable linkers include acid labile linkers, protease/peptidase-sensitive linkers, photolabile linkers, dimethyl-, disulfide-, or sulfonamide-containing linkers.

In some embodiments, the linker is a pH-sensitive linker, and is sensitive to hydrolysis at certain pH values. Typically, the pH-sensitive linker is cleavable under acidic conditions. This cleavage strategy generally takes advantage of the lower pH in the endosomal (pH~ 5-6) and lysosomal (pH~4.8) intracellular compartments, as compared to the cytosol (pH~ 7.4), to trigger hydrolysis of an acid labile group in the linker, such as a hydrazone (Jain et al. (2015) Pharm Res 32:3526-40). In some embodiments, the linker is an acid labile and/or hydrolyzable linker. For example, an acid labile linker that is hydrolyzable in the lysosome, and contains an acid labile group (e.g., a hydrazone, a semicarbazone, a thiosemicarbazone, a cis-aconitic amide, an orthoester, an acetal, a ketal, or the like) can be used. See, e.g., U.S. Pat. Nos. 5,122,368; 5,824,805; 5,622,929; Dubowchik and Walker (1999) Pharm Therapeutics 83:67-123; Neville et al. (1989) Biol Chem. 264:14653-61. Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond) (see, e.g., U.S. Pat. No. 5,622,929).

In some embodiments, the linker is cleavable under reducing conditions. In some embodiments, the linker is cleavable in the presence of a reducing agent, such as glutathione or dithiothreitol. In some embodiments, the linker is a cleavable disulfide linker or a cleavable sulfonamide linker.

In some embodiments, the linker is a cleavable disulfide linker. A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyloxycarbonyl-alpha-methyl-alpha-(2-pyridyl-dithio) toluene), SPDB and SMPT. See, e.g., Thorpe et al. (1987) Cancer Res. 47:5924-31; Wawrzynczak et al., In Immunoconjugates: Antibody Conjugates in Radioimagery and Therapy of Cancer (C. W. Vogel ed., Oxford U. Press, 1987). See also U.S. Pat. No. 4,880,935. Disulfide linkers are typically used to exploit the abundance of intracellular thiols, which can facilitate the cleavage of their disulfide bonds. The intracellular concentrations of the most abundance intracellular thiol, reduced glutathione, are generally in the range of 1-10 nM, which is about 1,000-fold higher than that of the most abundant low-molecular thiol in the blood (i.e., cysteine) at about 5 µM (Goldmacher et al., In Cancer Drug Discovery and Development: Antibody-Drug Conjugates and Immunotoxins (G. L. Phillips ed., Springer, 2013)). The intracellular enzymes of the protein disulfide isomerase family may also contribute to the intracellular cleavage of a disulfide linker. As used herein, a cleavable disulfide linker refers to any linker that comprises a cleavable disulfide moiety. The term "cleavable disulfide moiety" refers to a disulfide bond that can be cleaved and/or reduced, e.g., by a thiol or enzyme.

In some embodiments, the linker is a cleavable sulfonamide linker. As used herein, a cleavable sulfonamide linker refers to any linker that comprises a cleavable sulfonamide moiety. The term "cleavable sulfonamide moiety" refers to a sulfonamide group, i.e., sulfonyl group connected to an amine group, wherein the sulfur-nitrogen bond can be cleaved.

In some embodiments, the linker may be a dendritic type linker for covalent attachment of more than one drug moiety to an antibody or antigen binding fragment through a branching, multifunctional linker moiety. See, e.g., Sun et al. (2002) Bioorg Med Chem Lett. 12:2213-5; Sun et al. (2003) Bioorg Med Chem. 11:1761-8. Dendritic linkers can increase the molar ratio of drug to antibody, i.e., drug loading, which is related to the potency of the ADC. Thus, where an antibody or antigen binding fragment bears only one reactive cysteine thiol group, for example, a multitude of splicing modulator drug moieties may be attached through a dendritic linker. In some embodiments, the linker moiety or linker-drug moiety may be attached to the antibody or antigen binding fragment via reduced disulfide bridging chemistry or limited lysine utilization technology. See, e.g., Intl. Publ. Nos. WO 2013/173391 and WO 2013/173393.

In some embodiments, the linker is cleavable by a cleaving agent, e.g., an enzyme, that is present in the intracellular environment (e.g., within a lysosome or endosome or caveola). The linker can be, e.g., a peptide linker that is cleaved by an intracellular peptidase or protease enzyme, including, but not limited to, a lysosomal or endosomal protease.

In some embodiments, the linker is a cleavable peptide linker. As used herein, a cleavable peptide linker refers to any linker that comprises a cleavable peptide moiety. The term "cleavable peptide moiety" refers to any chemical bond linking amino acids (natural or synthetic amino acid derivatives) that can be cleaved by an agent that is present in the intracellular environment. For instance, a linker may comprise a valine-alanine (Val-Ala) sequence, or a valine-citrulline (Val-Cit) sequence that is cleavable by a peptidase such as cathepsin, e.g., cathepsin B. In some embodiments, a linker may comprise a glutamic acid-valine-citrulline (Glu-Val-Cit) sequence. In some embodiments, the linker is an enzyme-cleavable linker and a cleavable peptide moiety in the linker is cleavable by the enzyme. In some embodiments, the cleavable peptide moiety is cleavable by a lysosomal enzyme, e.g., cathepsin. In some embodiments, the linker is a cathepsin-cleavable linker. In some embodiments, the cleavable peptide moiety in the linker is cleavable by a lysosomal cysteine cathepsin, such as cathepsin B, C, F, H, K, L, O, S, V, X, or W. In some embodiments, the cleavable peptide moiety is cleavable by cathepsin B. An exemplary dipeptide that may be cleaved by cathepsin B is valine-citrulline (Val-Cit) (Dubowchik et al. (2002) Bioconjugate Chem. 13:855-69).

In some embodiments, the linker or the cleavable peptide moiety in the linker comprises an amino acid unit. In some embodiments, the amino acid unit allows for cleavage of the linker by a protease, thereby facilitating release of the splicing modulator drug moiety from the ADC upon exposure to one or more intracellular proteases, such as one or more lysosomal enzymes (Doronina et al. (2003) Nat Biotechnol. 21:778-84; Dubowchik and Walker (1999) Pharm Therapeutics 83:67-123). Exemplary amino acid units include, but are not limited to, dipeptides, tripeptides, tetrapeptides, and pentapeptides. Exemplary dipeptides include, but are not limited to, valine-alanine (Val-Ala), valine-citrulline (Val-Cit), alanine-asparagine (Ala-Asn), alanine-phenylalanine (Ala-Phe), phenylalanine-lysine (Phe-Lys), alanine-lysine (Ala-Lys), alanine-valine (Ala-Val), valine-lysine (Val-Lys), lysine-lysine (Lys-Lys), phenylalanine-citrulline (Phe-Cit), leucine-citrulline (Leu-Cit), isoleucine-citrulline (Ile-Cit), tryptophan-citrulline (Trp-Cit), and phenylalanine-alanine (Phe-Ala). Exemplary tripeptides include, but are not limited to, alanine-alanine-asparagine (Ala-Ala-Asn), glycine-valine-citrulline (Gly-Val-Cit), glycine-glycine-glycine (Gly-Gly-Gly), phenylalanine-phenylalanine-lysine (Phe-Phe-Lys), glutamic acid-valine-citrulline (Glu-Val-Cit) (see, e.g., Anami et al. (2018) Nat Comm. 9:2512, which is incorporated herein by reference for exemplary linkers comprising Glu-Val-Cit), and glycine-phenylalanine-lysine (Gly-Phe-Lys). Other exemplary amino acid units include, but are not limited to, Gly-Phe-Gly-Gly (SEQ ID NO:34), Gly-Phe-Leu-Gly (SEQ ID NO:35), Ala-Leu-Ala-Leu (SEQ ID NO:36), Phe-$N^9$-tosyl-Arg, and Phe-$N^9$-Nitro-Arg, as described in, e.g., U.S. Pat. No. 6,214,345. In some embodiments, the amino acid unit in the linker comprises Val-Ala. In some embodiments, the amino acid unit in the linker comprises Val-Cit. In some embodiments, the amino acid unit in the linker comprises Glu-Val-Cit. An amino acid unit may comprise amino acid residues that occur naturally and/or minor amino acids and/or non-naturally occurring amino acid analogs, such as citrulline. Amino acid units can be designed and optimized for enzymatic cleavage by a particular enzyme, for example, a tumor-associated protease, a lysosomal protease such as cathepsin B, C, D, or S, or a plasmin protease.

In some embodiments, the linker is a cleavable β-glucuronide linker. As used herein, a cleavable β-glucuronide linker refers to any linker that comprises a cleavable β-glucuronide moiety. An exemplary cleavable β-glucuronide linker comprises the structure:

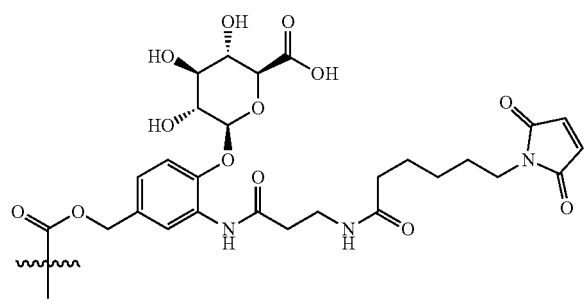 [SMILES: *C(=O)OCc1ccc(O[C@@H]2O[C@H](C(=O)O)[C@@H](O)[C@H](O)[C@H]2O)c(NC(=O)CCNC(=O)CCCCCN2C(=O)C=CC2=O)c1]

The term "cleavable β-glucuronide moiety" refers to a glycosidic bond that can be cleaved by an agent having β-glucuronidase activity. In some embodiments, the linker comprises a glycosidic bond that can be cleaved by a β-glucuronidase. A β-glucuronidase is a UDP-glucuronosyl transferase that catalyzes the hydrolysis of the glycosidic bond of glucuronides with β-configuration.

In some embodiments, an ADC disclosed herein comprises a cleavable β-glucuronide moiety in the linker that is cleavable by the enzyme. In some embodiments, the cleavable β-glucuronide moiety in the linker is cleavable by a lysosomal enzyme, e.g., a β-glucuronidase. In some embodiments, the linker is a β-glucuronidase-cleavable linker. In some embodiments, the cleavable β-glucuronide moiety in the linker allows for cleavage of the linker by a β-glucuronidase after internalization of the ADC, thereby facilitating release of the drug moiety from the ADC in the cellular environment.

In some embodiments, the linker in any of the ADCs disclosed herein may comprise at least one spacer unit joining the antibody or antigen binding fragment to the drug moiety (e.g., the splicing modulator drug moiety). In some embodiments, a spacer unit between the antibody or antigen binding fragment and cleavable moiety, when present, joins a cleavage site (e.g., a cleavable peptide moiety) in the linker to the antibody or antigen binding fragment. In some embodiments, a spacer unit between the drug moiety and cleavable moiety, when present, joins a cleavage site (e.g., a cleavable peptide moiety) in the linker to the drug moiety. In some embodiments, no cleavage site is present, and the spacer unit is used to link the antibody or antigen binding fragment to the drug moiety.

In some embodiments, the linker, and/or spacer unit in the linker, is substantially hydrophilic. A hydrophilic linker may be used to reduce the extent to which the drug may be pumped out of resistant cancer cells through multiple drug resistance (MDR) or functionally similar transporters. In some embodiments, a hydrophilic linker may include one or more polyethylene glycol (PEG) moieties, e.g., 1, 2, 3, 4, 5, or 6 PEG moieties. In some embodiments, the linker comprises 2 PEG moieties.

In some embodiments, the spacer unit in the linker comprises one or more PEG moieties. In some embodiments, the spacer unit comprises one or more -(PEG)$_m$-, and m is an integer from 1 to 10 (i.e., m may be 1, 2, 3, 4, 5, 6, 7, 8, 9, or 10). In some embodiments, m ranges from 1 to 10; from 2 to 8; from 2 to 6; from 2 to 5; from 2 to 4; or from 2 to 3. In some embodiments, m is 2. In some embodiments, the spacer unit comprises (PEG)$_2$, (PEG)$_3$, (PEG)$_4$, (PEG)$_5$, (PEG)$_6$, (PEG)$_7$, (PEG)$_8$, (PEG)$_9$, or (PEG)$_{10}$. In some embodiments, the spacer unit comprises (PEG)$_2$.

In some embodiments, the spacer unit in the linker comprises an alkyl moiety. In some embodiments, the spacer unit comprises one or more —(CH$_2$)$_n$-, and n is an integer from 1 to 10 (i.e., n may be 1, 2, 3, 4, 5, 6, 7, 8, 9, or 10). In some embodiments, n ranges from 1 to 10; from 2 to 8; from 2 to 6; from 2 to 5; from 2 to 4; or from 2 to 3. In some embodiments, n is 2. In some embodiments, n is 5. In some embodiments, n is 6. In some embodiments, the spacer unit comprises (CH$_2$)$_2$, (CH$_2$)$_3$, (CH$_2$)$_4$, (CH$_2$)$_5$, (CH$_2$)$_6$, (CH$_2$)$_7$, (CH$_2$)$_8$, (CH$_2$)$_9$, or (CH$_2$)$_{10}$. In some embodiments, the spacer unit comprises (CH$_2$)$_2$("Et"). In some embodiments, the spacer unit comprises (CH$_2$)$_6$ ("Hex"). In some embodiments, the spacer unit comprises (CH$_2$)$_2$-O—(CH$_2$)$_2$("Et-O-Et").

A spacer unit may be used, for example, to link the antibody or antigen binding fragment to the drug moiety, either directly or indirectly. In some embodiments, the spacer unit links the antibody or antigen binding fragment to the splicing modulator drug moiety directly. In some embodiments, the antibody or antigen binding fragment and the splicing modulator drug moiety are attached via a spacer unit comprising one or more PEG moieties (e.g., (PEG)$_2$), or one or more alkyl moieties (e.g., (CH$_2$)$_2$, (CH$_2$)$_6$, or (CH$_2$)$_2$-O—(CH$_2$)$_2$). In some embodiments, the spacer unit links the antibody or antigen binding fragment to the splicing modulator drug moiety indirectly. In some embodiments, the spacer unit links the antibody or antigen binding fragment to the splicing modulator drug moiety indirectly through a cleavable moiety (e.g., a cleavable peptide or a cleavable β-glucuronide) and/or an attachment moiety to join the spacer unit to the antibody or antigen binding fragment, e.g., a maleimide moiety.

The spacer unit, in various embodiments, attaches to the antibody or antigen binding fragment (i.e., the antibody or antigen binding fragment) via a maleimide (Mal) moiety.

A spacer unit that attaches to the antibody or antigen binding fragment via a Mal is referred to herein as a "Mal-spacer unit." The term "Mal" or "maleimide moiety," as used herein, means a compound that contains a maleimide group and that is reactive with a sulfhydryl group, e.g., a sulfhydryl group of a cysteine residue on the antibody or antigen binding fragment. Other functional groups that are reactive with sulfhydryl groups (thiols) include, but are not limited to, iodoacetamide, bromoacetamide, vinyl pyridine, disulfide, pyridyl disulfide, isocyanate, and isothiocyanate. In some embodiments, the Mal-spacer unit is reactive with a cysteine residue on the antibody or antigen binding fragment. In some embodiments, the Mal-spacer unit is joined to the antibody or antigen binding fragment via the cysteine residue. In some embodiments, the Mal-spacer unit comprises a PEG moiety. In some embodiments, the Mal-spacer unit comprises an alkyl moiety.

In certain embodiments, the linker comprises the Mal-spacer unit and a cleavable peptide moiety. In some embodiments, the cleavable peptide moiety comprises an amino acid unit. In some embodiments, the amino acid unit comprises Val-Cit. In some embodiments, the amino acid unit comprises Val-Ala. In some embodiments, the amino acid unit comprises Glu-Val-Cit. In some embodiments, the linker comprises the Mal-spacer unit and Val-Cit. In some embodiments, the linker comprises the Mal-spacer unit and Val-Ala. In some embodiments, the linker comprises the Mal-spacer unit and Val-Cit, wherein the Mal-spacer unit comprises a maleimidocaproyl (MC). In some embodiments, the linker comprises the Mal-spacer unit and Val-Ala, wherein the Mal-spacer unit comprises a maleimidocaproyl (MC). In some embodiments, the linker comprises the Mal-spacer unit and a cleavable β-glucuronide moiety.

In some embodiments, the linker comprises the structure: Mal-spacer unit. In some embodiments, the Mal-spacer unit comprises a maleimidocaproyl (MC). In some embodiments, the linker comprises the structure: MC. In some embodiments, the linker comprises the structure: Mal-(CH$_2$)$_2$ ("Mal-Et"). In some embodiments, the linker comprises the structure: Mal-(CH$_2$)$_6$ ("Mal-Hex"). In some embodiments, the linker comprises the structure: Mal-(CH$_2$)$_2$-O—(CH$_2$)$_2$ ("Mal-Et-O-Et"). In some embodiments, the linker comprises the structure: Mal-(PEG)$_2$. In some embodiments, the linker comprises the structure: Mal-(PEG)$_2$-CO.

In various embodiments, the Mal-spacer unit attaches the antibody or antigen binding fragment to a cleavable peptide moiety. In some embodiments, the linker comprises Mal-spacer unit-peptide. In some embodiments, the linker comprises the structure: Mal-spacer unit-Val-Cit. In some embodiments, the Mal-spacer unit comprises a maleimidocaproyl (MC). In some embodiments, the linker comprises the structure: MC-Val-Cit.

In some embodiments, the linker comprises the structure: Mal-spacer unit-Val-Ala. In some embodiments, the Mal-spacer unit comprises a maleimidocaproyl (MC). In some embodiments, the linker comprises the structure: MC-Val-Ala.

In various embodiments, the Mal-spacer unit attaches the antibody or antigen binding fragment to a cleavable β-glucuronide moiety. In some embodiments, the linker comprises Mal-spacer unit-β-glucuronide. In some embodiments, the linker comprises MC-β-glucuronide.

In various embodiments, the cleavable moiety in the linker is joined directly to the splicing modulator drug moiety. In other embodiments, a spacer unit is used to attach the cleavable moiety in the linker to the splicing modulator drug moiety. In various embodiments, the splicing modulator is attached to the cleavable moiety in the linker by a spacer unit.

A spacer unit may be "self-immolative" or "non-self-immolative." A "non-self-immolative" spacer unit is one in which part or all of the spacer unit remains bound to the splicing modulator drug moiety upon cleavage of the linker. Examples of non-self-immolative spacer units include, but are not limited to, a glycine spacer unit and a glycine-glycine spacer unit. Non-self-immolative spacer units may eventually degrade over time but do not readily release a linked native drug moiety entirely under cellular conditions. A "self-immolative" spacer unit allows for release of the native drug moiety under intracellular conditions. A "native drug" or "native drug moiety" is one where no part of the spacer unit or other chemical modification remains after cleavage/degradation of the spacer unit.

Self-immolation chemistry is known in the art and could be readily selected for the disclosed ADCs. In various embodiments, the spacer unit attaching the cleavable moiety in the linker to the splicing modulator drug moiety is self-immolative, and undergoes self-immolation concurrently with or shortly before/after cleavage of the cleavable moiety under intracellular conditions. In some embodiments, the splicing modulator is attached to the cleavable moiety in the linker by a self-immolative spacer unit. In certain embodiments, the splicing modulator is attached to the cleavable moiety in the linker by a self-immolative spacer unit, the cleavable moiety comprises Val-Cit, and a maleimidocaproyl (MC) joins the cleavable moiety to the antibody or antigen binding fragment. In certain embodiments, the splicing modulator is attached to the cleavable moiety in the linker by a self-immolative spacer unit, the cleavable moiety comprises Val-Ala, and a maleimidocaproyl (MC) joins the cleavable moiety to the antibody or antigen binding fragment. In certain embodiments, the splicing modulator is attached to the cleavable moiety in the linker by a self-immolative spacer unit, the cleavable moiety comprises Glu-Val-Cit, and a maleimidocaproyl (MC) joins the cleavable moiety to the antibody or antigen binding fragment. In certain embodiments, the splicing modulator is joined to the antibody or antigen binding fragment via a Mal-spacer unit (e.g., MC) in the linker joined to a Val-Cit cleavable moiety and a pABC or pAB self-immolative spacer unit. In certain other embodiments, the splicing modulator is joined to the antibody or antigen binding fragment via a Mal-spacer unit (e.g., MC) in the linker joined to a Val-Ala cleavable moiety and a pABC or pAB self-immolative spacer unit. In certain other embodiments, the splicing modulator is joined to the antibody or antigen binding fragment via a Mal-spacer unit (e.g., MC) in the linker joined to a Glu-Val-Cit cleavable moiety and a pABC or pAB self-immolative spacer unit.

In certain embodiments, the self-immolative spacer unit in the linker comprises a p-aminobenzyl unit. In some embodiments, a β-aminobenzyl alcohol (pABOH) is attached to an amino acid unit or other cleavable moiety in the linker via an amide bond, and a carbamate, methylcarbamate, or carbonate is made between the pABOH and the drug moiety (Hamann et al. (2005) Expert Opin Ther Patents 15:1087-103). In some embodiments, the self-immolative spacer unit is or comprises β-aminobenzyloxycarbonyl (pABC). Without being bound by theory, it is thought that the self-immolation of pABC involves a spontaneous 1,6-elimination reaction (Jain et al. (2015) Pharm Res. 32:3526-40).

In various embodiments, the structure of the β-aminobenzyloxycarbonyl (pABC) used in the disclosed ADCs is shown below:

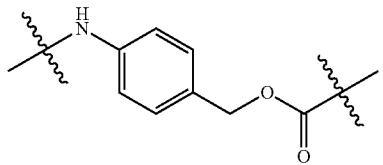 [SMILES: *Nc1ccc(COC(*)=O)cc1]

In various embodiments, the self-immolative spacer unit attaches the cleavable moiety in the linker to the splicing modulator. In some embodiments, the self-immolative spacer unit is pABC. In some embodiments, the pABC attaches the cleavable moiety in the linker to the splicing modulator. In some embodiments, the pABC undergoes self-immolation upon cleavage of the cleavable moiety, and the splicing modulator is released from the ADC in its native, active form.

In some embodiments, an anti-HER2 antibody or antigen binding fragment is joined to the splicing modulator by a linker comprising MC-Val-Cit-pABC. In other embodiments, an anti-HER2 antibody or antigen binding fragment is joined to the splicing modulator by a linker comprising MC-Val-Ala-pABC.

In some embodiments, an anti-CD138 antibody or antigen binding fragment is joined to the splicing modulator by a linker comprising MC-Val-Cit-pABC. In other embodiments, an anti-CD138 antibody or antigen binding fragment is joined to the splicing modulator by a linker comprising MC-Val-Ala-pABC.

In some embodiments, an anti-EPHA2 antibody or antigen binding fragment is joined to the splicing modulator by a linker comprising MC-Val-Cit-pABC. In other embodiments, an anti-EPHA2 antibody or antigen binding fragment is joined to the splicing modulator by a linker comprising MC-Val-Ala-pABC.

In some embodiments, the pABC undergoes self-immolation upon cleavage of a cleavable peptide moiety in the linker. In some embodiments, the cleavable peptide moiety comprises an amino acid unit. In some embodiments, the linker comprises amino acid unit-pABC. In some embodiments, the amino acid unit is Val-Cit. In some embodiments, the linker comprises Val-Cit-pABC. In some embodiments, the amino acid unit is Val-Ala. In some embodiments, the linker comprises Val-Ala-pABC. In some embodiments, the amino acid unit is Glu-Val-Cit. In some embodiments, the linker comprises Glu-Val-Cit-pABC. In some embodiments, the amino acid unit is Ala-Ala-Asn. In some embodiments, the linker comprises Ala-Ala-Asn-pABC.

In some embodiments, the pABC undergoes self-immolation upon cleavage of a cleavable β-glucuronide moiety in the linker. In some embodiments, the linker comprises β-glucuronide-pABC.

In certain embodiments, the self-immolative spacer unit in the linker comprises a p-aminobenzyl unit. In some embodiments, the self-immolative spacer unit in the linker comprises a β-aminobenzyl (pAB). In some embodiments, the self-immolation of pAB involves a spontaneous 1,6-elimination reaction.

In various embodiments, the structure of the β-aminobenzyl (pAB) used in the disclosed ADCs is shown below:

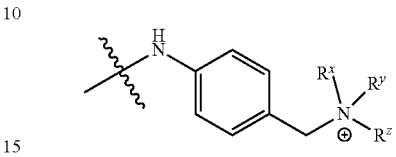

In various embodiments, the self-immolative spacer unit attaches the cleavable moiety in the linker to the splicing modulator. In some embodiments, the self-immolative spacer unit is pAB. In some embodiments, the pAB attaches the cleavable moiety in the linker to the splicing modulator. In some embodiments, the pAB undergoes self-immolation upon cleavage of the cleavable moiety, and the splicing modulator is released from the ADC in its native, active form.

In some embodiments, an anti-HER2 antibody or antigen binding fragment is joined to the splicing modulator by a linker comprising MC-Val-Cit-pAB. In other embodiments, an anti-HER2 antibody or antigen binding fragment is joined to the splicing modulator by a linker comprising MC-Val-Ala-pAB.

In some embodiments, an anti-CD138 antibody or antigen binding fragment is joined to the splicing modulator by a linker comprising MC-Val-Cit-pAB. In other embodiments, an anti-CD138 antibody or antigen binding fragment is joined to the splicing modulator by a linker comprising MC-Val-Ala-pAB.

In some embodiments, an anti-EPHA2 antibody or antigen binding fragment is joined to the splicing modulator by a linker comprising MC-Val-Cit-pAB. In other embodiments, an anti-EPHA2 antibody or antigen binding fragment is joined to the splicing modulator by a linker comprising MC-Val-Ala-pAB.

In some embodiments, the pAB undergoes self-immolation upon cleavage of a cleavable peptide moiety in the linker. In some embodiments, the cleavable peptide moiety comprises an amino acid unit. In some embodiments, the linker comprises amino acid unit-pAB. In some embodiments, the amino acid unit is Val-Cit. In some embodiments, the linker comprises Val-Cit-pAB. In some embodiments, the amino acid unit is Val-Ala. In some embodiments, the linker comprises Val-Ala-pAB. In some embodiments, the amino acid unit is Glu-Val-Cit. In some embodiments, the linker comprises Glu-Val-Cit-pAB. In some embodiments, the amino acid unit is Ala-Ala-Asn. In some embodiments, the linker comprises Ala-Ala-Asn-pAB.

In some embodiments, the pAB undergoes self-immolation upon cleavage of a cleavable β-glucuronide moiety in the linker. In some embodiments, the linker comprises β-glucuronide-pAB.

In some other embodiments, the splicing modulator is attached to the cleavable moiety in the linker by a non-self-immolative spacer unit. In certain embodiments, the splicing modulator is attached to the cleavable moiety in the linker by a non-self-immolative spacer unit, the cleavable moiety comprises Val-Cit, and a maleimidocaproyl (MC) joins the cleavable moiety to the antibody or antigen binding fragment. In certain embodiments, the splicing modulator is attached to the cleavable moiety in the linker by a non-self-immolative spacer unit, the cleavable moiety comprises Val-Ala, and a maleimidocaproyl (MC) joins the cleavable moiety to the antibody or antigen binding fragment.

In various aspects, the antibody or antigen binding fragment of the ADC is conjugated to the splicing modulator drug moiety via a linker, wherein the linker comprises a Mal-spacer unit (e.g., MC), a cleavable amino acid unit, and a pABC. In some embodiments, the spacer unit comprises an alkyl moiety. In some embodiments, the Mal-spacer unit comprises a maleimidocaproyl (MC). In some embodiments, the linker comprises Mal-spacer unit-amino acid unit-pABC. In some embodiments, the linker comprises MC-amino acid unit-pABC. In some embodiments, the linker comprises MC-Val-Cit-pABC. In some embodiments, the linker comprises MC-Val-Ala-pABC. In some embodiments, the linker comprises MC-Glu-Val-Cit-pABC. In some embodiments, the linker comprises MC-Ala-Ala-Asn-pABC.

In various other aspects, the antibody or antigen binding fragment of the ADC is conjugated to the splicing modulator drug moiety via a linker, wherein the linker comprises a Mal-spacer unit (e.g., MC), a cleavable amino acid unit, and a pAB. In some embodiments, the spacer unit comprises an alkyl moiety. In some embodiments, the Mal-spacer unit comprises a maleimidocaproyl (MC). In some embodiments, the linker comprises Mal-spacer unit-amino acid unit-pAB. In some embodiments, the linker comprises MC-amino acid unit-pAB. In some embodiments, the linker comprises MC-Val-Cit-pAB. In some embodiments, the linker comprises MC-Val-Ala-pAB. In some embodiments, the linker comprises MC-Glu-Val-Cit-pAB. In some embodiments, the linker comprises MC-Ala-Ala-Asn-pAB.

In various other aspects, the antibody or antigen binding fragment of the ADC is conjugated to the splicing modulator drug moiety via a linker, wherein the linker comprises a Mal-spacer unit (e.g., MC), a cleavable β-glucuronide, and a pABC. In some embodiments, the linker comprises Mal-spacer unit-β-glucuronide-pABC. In some embodiments, the linker comprises MC-β-glucuronide-pABC.

In still other aspects, the antibody or antigen binding fragment of the ADC is conjugated to the splicing modulator drug moiety via a linker, wherein the linker comprises a Mal-spacer unit (e.g., MC), a cleavable β-glucuronide, and a pAB. In some embodiments, the linker comprises Mal-spacer unit-β-glucuronide-pAB. In some embodiments, the linker comprises MC-β-glucuronide-pAB.

In various embodiments, the ADC compound has Formula (I):

$$Ab-(L-D)_p \quad (I)$$

wherein Ab is an antibody or antigen binding fragment which targets a neoplastic cell;
D is a splicing modulator;
L is a linker that covalently attaches Ab to D; and
p is an integer from 1 to 15.

In some embodiments, the antibody or antigen binding fragment (Ab) of the ADC is conjugated to the splicing modulator drug moiety via a linker, wherein the linker is any of the linkers disclosed or incorporated by reference herein, or comprises one or more components of any of the linkers disclosed or incorporated by reference herein.

In some embodiments, the linker comprises a cleavable moiety that is positioned such that no part of the linker or the antibody or antigen binding fragment remains bound to the splicing modulator after cleavage. In some embodiments, the cleavable moiety is a cleavable peptide moiety, e.g., an amino acid unit such as Val-Cit or Val-Ala. In some embodiments, the amino acid unit or linker comprises Val-Cit. In some embodiments, the amino acid unit or linker comprises Val-Ala. In some embodiments, the amino acid unit or linker comprises Glu-Val-Cit.

In some embodiments, the linker comprises at least one spacer unit joining the antibody or antigen binding fragment to the cleavable moiety. In some embodiments, the linker comprises at least one spacer unit joining the antibody or antigen binding fragment to the drug moiety. In some embodiments, the spacer unit or linker comprises at least one alkyl moiety.

In some embodiments, a spacer unit in the linker attaches to the antibody or antigen binding fragment via a Mal moiety ("Mal-spacer unit"). In some embodiments, the Mal-spacer unit comprises at least one alkyl moiety. In some embodiments, the linker comprises a maleimidocaproyl (MC). In some embodiments, the linker comprises Mal-$(CH_2)_2$ ("Mal-Et"). In some embodiments, the linker comprises Mal-$(CH_2)_6$ ("Mal-Hex"). In some embodiments, the linker comprises Mal-$(CH_2)_2$-O—$(CH_2)_2$ ("Mal-Et-O-Et"). In some embodiments, the linker comprises Mal-$(PEG)_2$-CO. In some embodiments, the Mal-spacer unit attaches the antibody or antigen binding fragment to the drug moiety.

In some embodiments, the Mal-spacer unit or linker comprises Mal-$(PEG)_2$, Mal-$(PEG)_3$, Mal-$(PEG)_4$, Mal-$(PEG)_5$, Mal-$(PEG)_6$, Mal-$(PEG)_7$, or Mal-$(PEG)_8$. In some embodiments, the Mal-spacer unit or linker comprises Mal-$(PEG)_2$. In some embodiments, the Mal-spacer unit or linker comprises Mal-$(PEG)_2$-CO, Mal-$(PEG)_3$-CO, Mal-$(PEG)_4$-CO, Mal-$(PEG)_5$-CO, Mal-$(PEG)_6$-CO, Mal-$(PEG)_7$-CO, or Mal-$(PEG)_3$-CO. In some embodiments, the Mal-spacer unit or linker comprises Mal-$(PEG)_2$-CO. In some embodiments, the Mal-spacer unit or linker comprises Mal-$(PEG)_2$-CO and at least one additional spacer unit. In some embodiments, the Mal-$(PEG)_2$-CO attaches the antibody or antigen binding fragment to the drug moiety. In some embodiments, linker comprises or consists of Mal-$(PEG)_2$-CO. An example of a "Mal-$(PEG)_2$-CO" linker is also referred to herein as "ADL2" or an "ADL2" linker.

In some embodiments, the Mal-spacer unit or linker comprises MC. In some embodiments, the Mal-spacer unit or linker comprises MC and at least one additional spacer unit. In some embodiments, the MC attaches the antibody or antigen binding fragment to the drug moiety. In some embodiments, the linker comprises or consists of MC. An example of an "MC" linker is also referred to herein as "ADL10" or an "ADL10" linker.

In some embodiments, the Mal-spacer unit or linker comprises Mal-$(CH_2)_6$ ("Mal-Hex"). In some embodiments, the Mal-spacer unit or linker comprises Mal-Hex and at least one additional spacer unit. In some embodiments, the Mal-Hex attaches the antibody or antigen binding fragment to the drug moiety. In some embodiments, the linker comprises Mal-Hex. An example of a "Mal-Hex" linker is also referred to herein as "ADL12" or an "ADL12" linker.

In some embodiments, the Mal-spacer unit or linker comprises Mal-$(CH_2)_2$ ("Mal-Et"). In some embodiments, the Mal-spacer unit or linker comprises Mal-Et and at least one additional spacer unit. In some embodiments, the Mal-Et attaches the antibody or antigen binding fragment to the drug moiety. In some embodiments, the linker comprises Mal-Et. An example of a "Mal-Et" linker is also referred to herein as "ADL14" or an "ADL14" linker.

In some embodiments, the Mal-spacer unit or linker comprises Mal-$(CH_2)_2$-O—$(CH_2)_2$ ("Mal-Et-O-Et"). In some embodiments, the Mal-spacer unit or linker comprises Mal-Et-O-Et and at least one additional spacer unit. In some embodiments, the Mal-Et-O-Et attaches the antibody or antigen binding fragment to the drug moiety. In some embodiments, the linker comprises Mal-Et-O-Et. An example of a "Mal-Et-O-Et" linker is also referred to herein as "ADL15" or an "ADL15" linker.

In some other embodiments, the Mal-spacer unit attaches the antibody or antigen binding fragment to the cleavable moiety in the linker. In some embodiments, the cleavable moiety in the linker is a cleavable peptide moiety, e.g., an amino acid unit. In some embodiments, the cleavable peptide moiety is Val-Cit or Val-Ala. In some embodiments, the Mal-spacer unit or linker comprises MC. In some embodiments, the linker comprises MC-Val-Cit. In some embodiments, the linker comprises MC-Val-Ala. In some embodiments, the linker comprises MC-Glu-Val-Cit. In some embodiments, the linker comprises MC-Ala-Ala-Asn.

In some embodiments, a spacer unit attaches the cleavable moiety in the linker to the splicing modulator. In some embodiments, the spacer unit that attaches the cleavable moiety to the splicing modulator is self-immolative.

In some embodiments, the spacer unit comprises pABC. In some embodiments, the pABC attaches the cleavable moiety to the splicing modulator. In some embodiments, the cleavable moiety is a cleavable peptide moiety, e.g., an amino acid unit. In some embodiments, the linker comprises amino acid unit-pABC.

In some embodiments, the linker comprises Val-Cit-pABC. In some embodiments, the linker comprises Val-Cit-pABC and a MC Mal-spacer unit joining the linker to the antibody or antigen binding fragment. In some embodiments, the linker comprises MC-Val-Cit-pABC. In some embodiments, the linker comprises MC-Val-Cit-pABC and at least one additional spacer unit. An example of an MC-Val-Cit-pABC linker is also referred to herein as "ADL1" or an "ADL1" linker.

In some embodiments, the linker comprises Val-Ala-pABC. In some embodiments, the linker comprises Val-Ala-pABC and a MC Mal-spacer unit joining the linker to the antibody or antigen binding fragment. In some embodiments, the linker comprises MC-Val-Ala-pABC. In some embodiments, the linker comprises MC-Val-Ala-pABC and at least one additional spacer unit. An example of an MC-Val-Ala-pABC linker is also referred to herein as "ADL6" or an "ADL6" linker.

In some embodiments, the linker comprises Glu-Val-Cit-pABC. In some embodiments, the linker comprises Glu-Val-Cit-pABC and a MC Mal-spacer unit joining the linker to the antibody or antigen binding fragment. In some embodiments, the linker comprises MC-Glu-Val-Cit-pABC. In some embodiments, the linker comprises MC-Glu-Val-Cit-pABC and at least one additional spacer unit. An example of an MC-Glu-Val-Cit-pABC linker is also referred to herein as "ADL23" or an "ADL23" linker.

In some embodiments, the linker comprises Ala-Ala-Asn-pABC. In some embodiments, the linker comprises Ala-Ala-Asn-pABC and a MC Mal-spacer unit joining the linker to the antibody or antigen binding fragment. In some embodiments, the linker comprises MC-Ala-Ala-Asn-pABC. In some embodiments, the linker comprises MC-Ala-Ala-Asn-pABC and at least one additional spacer unit. An example of an MC-Ala-Ala-Asn-pABC linker is also referred to herein as "ADL21" or an "ADL21" linker.

In some other embodiments, the spacer unit comprises pAB. In some embodiments, the pAB attaches the cleavable moiety to the splicing modulator. In some embodiments, the cleavable moiety is a cleavable peptide moiety, e.g., an amino acid unit. In some embodiments, the linker comprises amino acid unit-pAB.

In some embodiments, the linker comprises Val-Ala-pAB. In some embodiments, the linker comprises Val-Ala-pAB and an MC Mal-spacer unit joining the linker to the antibody or antigen binding fragment. In some embodiments, the linker comprises MC-Val-Ala-pAB. In some embodiments, the linker comprises MC-Val-Ala-pAB and at least one additional spacer unit. An example of an MC-Val-Ala-pAB linker is also referred to herein as "ADL5" or an "ADL5" linker.

In some embodiments, the linker comprises Val-Cit-pAB. In some embodiments, the linker comprises Val-Cit-pAB and an MC Mal-spacer unit joining the linker to the antibody or antigen binding fragment. In some embodiments, the linker comprises MC-Val-Cit-pAB. In some embodiments, the linker comprises MC-Val-Cit-pAB and at least one additional spacer unit. An example of an MC-Val-Cit-pAB linker is also referred to herein as "ADL7" or an "ADL7" linker.

In some embodiments, the linker comprises β-glucuronide-pABC. In some embodiments, the linker comprises β-glucuronide-pABC and an MC Mal-spacer unit joining the linker to the antibody or antigen binding fragment. In some embodiments, the linker comprises MC-β-glucuronide-pABC. In some embodiments, the linker comprises MC-β-glucuronide-pABC and at least one additional spacer unit. An example of an MC-β-glucuronide-pABC is also referred to herein as "ADL13" or an "ADL13" linker.

In some embodiments, the linker comprises β-glucuronide-pAB. In some embodiments, the linker comprises β-glucuronide-pAB and an MC Mal-spacer unit joining the linker to the antibody or antigen binding fragment. In some embodiments, the linker comprises MC-β-glucuronide-pAB.

In some embodiments, the antibody or antigen binding fragment is conjugated to the splicing modulator drug moiety via an ADL1, ADL2, ADL5, ADL6, ADL7, ADL12, ADL13, ADL14, ADL21, ADL23, or ADL15 linker. It has been discovered, in various embodiments, that ADCs comprising an ADL1, ADL2, ADL5, ADL6, ADL7, ADL12, ADL13, ADL14, ADL21, ADL23, or ADL15 linker and a splicing modulator drug moiety disclosed herein demonstrate desirable properties for a therapeutic ADC. In various embodiments, these properties include, but are not limited to, effective levels of drug loading, low aggregation levels, stability under storage conditions or when in circulation in the body (e.g., serum stability), retained affinity for target-expressing cells comparable to unconjugated antibody, potent cytotoxicity against target-expressing cells, low levels of off-target cell killing, high levels of bystander killing, and/or effective in vivo anti-cancer activity, all as compared to ADCs using other linker-payloads. For instance, in various embodiments, ADCs comprising an ADL1, ADL2, ADL5, ADL6, ADL7, ADL12, ADL13, ADL14, ADL21, ADL23, or ADL15 linker and a splicing modulator drug moiety disclosed herein exhibit an increased ability to inhibit growth and/or proliferation in target-expressing cells, as compared to ADCs using other linker-payloads (e.g., an ADL10 linker and a splicing modulator drug moiety). In various embodiments, ADCs comprising an ADL1, ADL2, ADL5, ADL6, ADL7, ADL12, ADL13, ADL14, ADL21, ADL23, or ADL15 linker and a splicing modulator drug moiety disclosed herein exhibit surprisingly increased in vivo stability (e.g., plasma stability), as compared to other splicing modulator-based ADCs (e.g., a thailanstatin A-based ADC, for example, as reported in Puthenveetil et al. Bioconjugate Chem. (2016) 27:1880-8).

In some embodiments, the good or superior functional properties provided by the particular combination of an ADL1, ADL2, ADL5, ADL6, ADL7, ADL12, ADL13, ADL14, ADL21, ADL23, or ADL15 linker and a splicing modulator drug moiety disclosed herein may be observed with the linker-payload conjugated to, e.g., an anti-HER2 antibody such as trastuzumab; an anti-CD138 antibody such as B—B4; or an anti-EPHA2 antibody such as $1C_1$.

In some embodiments, the ADC comprises ADL1-splicing modulator and an antibody or antigen binding fragment comprising an antibody or an antigen binding fragment thereof that retains the ability to target and internalize in a neoplastic cell. In some embodiments, the ADC comprises ADL2-splicing modulator and an antibody or antigen binding fragment comprising an antibody or an antigen binding fragment thereof that retains the ability to target and internalize in a neoplastic cell. In some embodiments, the ADC comprises ADL5-splicing modulator and an antibody or antigen binding fragment comprising an antibody or an antigen binding fragment thereof that retains the ability to target and internalize in a neoplastic cell. In some embodiments, the ADC comprises ADL6-splicing modulator and an antibody or antigen binding fragment comprising an antibody or an antigen binding fragment thereof that retains the ability to target and internalize in a neoplastic cell. In some embodiments, the ADC comprises ADL7-splicing modulator and an antibody or antigen binding fragment comprising an antibody or an antigen binding fragment thereof that retains the ability to target and internalize in a neoplastic cell. In some embodiments, the ADC comprises ADL12-splicing modulator and an antibody or antigen binding fragment comprising an antibody or an antigen binding fragment thereof that retains the ability to target and internalize in a neoplastic cell. In some embodiments, the ADC comprises ADL13-splicing modulator and an antibody or antigen binding fragment comprising an antibody or an antigen binding fragment thereof that retains the ability to target and internalize in a neoplastic cell. In some embodiments, the ADC comprises ADL14-splicing modulator and an antibody or antigen binding fragment comprising an antibody or an antigen binding fragment thereof that retains the ability to target and internalize in a neoplastic cell. In some embodiments, the ADC comprises ADL15-splicing modulator and an antibody or an antigen binding fragment comprising an antibody or an antigen binding fragment thereof that retains the ability to target and internalize in a neoplastic cell.

In some embodiments, the ADC comprises ADL1-splicing modulator and an antibody or antigen binding fragment thereof that targets a HER2-expressing neoplastic cell. In some embodiments, the ADC comprises ADL2-splicing modulator and an antibody or antigen binding fragment thereof that targets a HER2-expressing neoplastic cell. In some embodiments, the ADC comprises ADL5-splicing modulator and an antibody or antigen binding fragment thereof that targets a HER2-expressing neoplastic cell. In some embodiments, the ADC comprises ADL6-splicing modulator and an antibody or antigen binding fragment thereof that targets a HER2-expressing neoplastic cell. In some embodiments, the ADC comprises ADL7-splicing modulator and an antibody or antigen binding fragment thereof that targets a HER2-expressing neoplastic cell. In some embodiments, the ADC comprises ADL12-splicing modulator and an antibody or antigen binding fragment thereof that targets a HER2-expressing neoplastic cell. In some embodiments, the ADC comprises ADL13-splicing modulator and an antibody or antigen binding fragment thereof that targets a HER2-expressing neoplastic cell. In some embodiments, the ADC comprises ADL14-splicing modulator and an antibody or antigen binding fragment thereof that targets a HER2-expressing neoplastic cell. In some embodiments, the ADC comprises ADL15-splicing modulator and an antibody or antigen binding fragment thereof that targets a HER2-expressing neoplastic cell.

In some embodiments, the antibody or antigen binding fragment thereof that targets a HER2-expressing neoplastic cell is an internalizing antibody or internalizing antigen binding fragment. In some embodiments, the antibody or antigen binding fragment thereof that targets a HER2-expressing neoplastic cell comprises three heavy chain complementarity determining regions (HCDRs) comprising amino acid sequences of SEQ ID NO:1 (HCDR1), SEQ ID NO:2 (HCDR2), and SEQ ID NO:3 (HCDR3); and three light chain complementarity determining regions (LCDRs) comprising amino acid sequences of SEQ ID NO:4 (LCDR1), SEQ ID NO:5 (LCDR2), and SEQ ID NO:6 (LCDR3).

In some embodiments, the ADC has Formula (I):

$$Ab-(L-D)_p \qquad (I)$$

wherein:
- (i) Ab is an anti-HER2 antibody or antigen binding fragment thereof comprising three heavy chain complementarity determining regions (HCDRs) comprising amino acid sequences of SEQ ID NO:1 (HCDR1), SEQ ID NO:2 (HCDR2), and SEQ ID NO:3 (HCDR3); and three light chain complementarity determining regions (LCDRs) comprising amino acid sequences of SEQ ID NO:4 (LCDR1), SEQ ID NO:5 (LCDR2), and SEQ ID NO:6 (LCDR3);
- (ii) D is a splicing modulator;
- (iii) L is a linker comprising ADL1, ADL2, ADL5, ADL6, ADL7, ADL12, ADL13, ADL14, ADL21, ADL23, or ADL15; and
- (iv) p is an integer from 1 to 15.

In some embodiments, the antibody or antigen binding fragment thereof that targets a HER2-expressing neoplastic cell comprises a heavy chain variable region comprising an amino acid sequence of SEQ ID NO:19, and a light chain variable region comprising an amino acid sequence of SEQ ID NO:20. In some embodiments, the antibody or antigen binding fragment thereof that targets a HER2-expressing neoplastic cell comprises a human IgG1 heavy chain constant domain and a human Ig kappa light chain constant domain. In some embodiments, the antibody is trastuzumab. In some embodiments, p is an integer from 1 to 10, from 2 to 8, or from 4 to 8. In some embodiments, p is 4. In some embodiments, p is 8.

In some embodiments, the ADC comprises ADL1-splicing modulator and an antibody or antigen binding fragment thereof that targets a CD138-expressing neoplastic cell. In some embodiments, the ADC comprises ADL2-splicing modulator and an antibody or antigen binding fragment thereof that targets a CD138-expressing neoplastic cell. In some embodiments, the ADC comprises ADL5-splicing modulator and an antibody or antigen binding fragment thereof that targets a CD138-expressing neoplastic cell. In some embodiments, the ADC comprises ADL6-splicing modulator and an antibody or antigen binding fragment thereof that targets a CD138-expressing neoplastic cell. In some embodiments, the ADC comprises ADL7-splicing modulator and an antibody or antigen binding fragment thereof that targets a CD138-expressing neoplastic cell. In some embodiments, the ADC comprises ADL12-splicing modulator and an antibody or antigen binding fragment thereof that targets a CD138-expressing neoplastic cell. In some embodiments, the ADC comprises ADL13-splicing modulator and an antibody or antigen binding fragment thereof that targets a CD138-expressing neoplastic cell. In some embodiments, the ADC comprises ADL14-splicing modulator and an antibody or antigen binding fragment thereof that targets a CD138-expressing neoplastic cell. In some embodiments, the ADC comprises ADL15-splicing modulator and an antibody or antigen binding fragment thereof that targets a CD138-expressing neoplastic cell.

In some embodiments, the antibody or antigen binding fragment thereof that targets a CD138-expressing neoplastic cell is an internalizing antibody or internalizing antigen binding fragment. In some embodiments, the antibody or antigen binding fragment thereof that targets a CD138-expressing neoplastic cell comprises three heavy chain complementarity determining regions (HCDRs) comprising amino acid sequences of SEQ ID NO:7 (HCDR1), SEQ ID NO:8 (HCDR2), and SEQ ID NO:9 (HCDR3); and three light chain complementarity determining regions (LCDRs) comprising amino acid sequences of SEQ ID NO:10 (LCDR1), SEQ ID NO:11 (LCDR2), and SEQ ID NO:12 (LCDR3).

In some embodiments, the ADC has Formula (I):

$$Ab-(L-D)_p \quad (I)$$

wherein:
  (i) Ab is an anti-CD138 antibody or antigen binding fragment thereof comprising three heavy chain complementarity determining regions (HCDRs) comprising amino acid sequences of SEQ ID NO:7 (HCDR1), SEQ ID NO:8 (HCDR2), and SEQ ID NO:9 (HCDR3); and three light chain complementarity determining regions (LCDRs) comprising amino acid sequences of SEQ ID NO:10 (LCDR1), SEQ ID NO:11 (LCDR2), and SEQ ID NO:12 (LCDR3);
  (ii) D is a splicing modulator;
  (iii) L is a linker comprising ADL1, ADL2, ADL5, ADL6, ADL7, ADL12, ADL13, ADL14, ADL21, ADL23, or ADL15; and
  (iv) p is an integer from 1 to 15.

In some embodiments, the antibody or antigen binding fragment thereof that targets a CD138-expressing neoplastic cell comprises a heavy chain variable region comprising an amino acid sequence of SEQ ID NO:21, and a light chain variable region comprising an amino acid sequence of SEQ ID NO:22. In some embodiments, the antibody or antigen binding fragment thereof that targets a CD138-expressing neoplastic cell comprises a murine IgG2a heavy chain constant domain and a murine Ig kappa light chain constant domain. In some embodiments, the antibody or antigen binding fragment thereof that targets a CD138-expressing neoplastic cell comprises a human IgG2a heavy chain constant domain and a human Ig kappa light chain constant domain. In some embodiments, the antibody is B—B4. In some embodiments, p is an integer from 1 to 10, from 2 to 8, or from 4 to 8. In some embodiments, p is 4. In some embodiments, p is 8.

In some embodiments, the ADC comprises ADL1-splicing modulator and an antibody or antigen binding fragment thereof that targets an EPHA2-expressing neoplastic cell. In some embodiments, the ADC comprises ADL2-splicing modulator and an antibody or antigen binding fragment thereof that targets an EPHA2-expressing neoplastic cell. In some embodiments, the ADC comprises ADL5-splicing modulator and an antibody or antigen binding fragment thereof that targets an EPHA2-expressing neoplastic cell. In some embodiments, the ADC comprises ADL6-splicing modulator and an antibody or antigen binding fragment thereof that targets an EPHA2-expressing neoplastic cell. In some embodiments, the ADC comprises ADL7-splicing modulator and an antibody or antigen binding fragment thereof that targets an EPHA2-expressing neoplastic cell. In some embodiments, the ADC comprises ADL12-splicing modulator and an antibody or antigen binding fragment thereof that targets an EPHA2-expressing neoplastic cell. In some embodiments, the ADC comprises ADL13-splicing modulator and an antibody or antigen binding fragment thereof that targets an EPHA2-expressing neoplastic cell. In some embodiments, the ADC comprises ADL14-splicing modulator and an antibody or antigen binding fragment thereof that targets an EPHA2-expressing neoplastic cell. In some embodiments, the ADC comprises ADL15-splicing modulator and an antibody or antigen binding fragment thereof that targets an EPHA2-expressing neoplastic cell.

In some embodiments, the antibody or antigen binding fragment thereof that targets an EPHA2-expressing neoplastic cell is an internalizing antibody or internalizing antigen binding fragment. In some embodiments, the antibody or antigen binding fragment thereof that targets an EPHA2-expressing neoplastic cell comprises three heavy chain complementarity determining regions (HCDRs) comprising amino acid sequences of SEQ ID NO:13 (HCDR1), SEQ ID NO:14 (HCDR2), and SEQ ID NO:15 (HCDR3); and three light chain complementarity determining regions (LCDRs) comprising amino acid sequences of SEQ ID NO:16 (LCDR1), SEQ ID NO:17 (LCDR2), and SEQ ID NO:18 (LCDR3).

In some embodiments, the ADC has Formula (I):

$$Ab-(L-D)_p \quad (I)$$

wherein:
  (i) Ab is an anti-EPHA2 antibody or antigen binding fragment thereof comprising three heavy chain complementarity determining regions (HCDRs) comprising amino acid sequences of SEQ ID NO:13 (HCDR1), SEQ ID NO:14 (HCDR2), and SEQ ID NO:15 (HCDR3); and three light chain complementarity determining regions (LCDRs) comprising amino acid sequences of SEQ ID NO:16 (LCDR1), SEQ ID NO:17 (LCDR2), and SEQ ID NO:18 (LCDR3);
  (ii) D is a splicing modulator;
  (iii) L is a linker comprising ADL1, ADL2, ADL5, ADL6, ADL7, ADL12, ADL13, ADL14, ADL21, ADL23, or ADL15; and
  (iv) p is an integer from 1 to 15.

In some embodiments, the antibody or antigen binding fragment thereof that targets an EPHA2-expressing neoplastic cell comprises a heavy chain variable region comprising an amino acid sequence of SEQ ID NO:23, and a light chain variable region comprising an amino acid sequence of SEQ ID NO:24. In some embodiments, the antibody or antigen binding fragment thereof that targets an EPHA2-expressing neoplastic cell comprises a human IgG1 heavy chain constant domain and a human Ig kappa light chain constant domain. In some embodiments, the antibody is $1C_1$. In some embodiments, p is an integer from 1 to 10, from 2 to 8, or from 4 to 8. In some embodiments, p is 4. In some embodiments, p is 8.

Drug Moieties

The drug moiety (D) of the ADCs described herein can be any chemotherapeutic agent. Useful classes of chemotherapeutic agents include, for example, modulators of RNA splicing. In certain preferred embodiments, the drug moiety is a splicing modulator. Exemplary splicing modulator compounds are described and exemplified herein.

In various embodiments, the drug moiety is a splicing modulator compound of Formula (II):

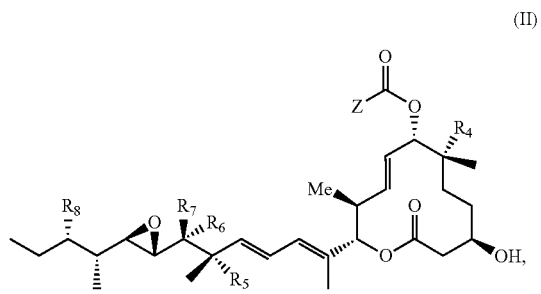

(II)

or a pharmaceutically acceptable salt thereof, wherein:

$R^1$ is chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(=O)—($C_1$-$C_e$ alkyl) groups, and —CD$_3$;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups; and $R^4$, $R^5$, and $R^8$ are each independently chosen from hydrogen, hydroxyl groups, —O—($C_1$-$C_6$ alkyl) groups, —O—C(=O)—($C_1$-$C_6$alkyl) groups, and $C_1$-$C_6$alkyl groups;

$R^6$ and $R^7$ are each independently chosen from hydrogen, —O—$R^{17}$, —O—C(=O)—$R^{17}$, —O—C(=O)—$NR^{15}R^{16}$, $C_1$-$C_6$ alkyl groups, and —$NR^{15}R^{16}$;

$R^{15}$ and $R^{16}$ are each independently chosen from hydrogen, $R^{17}$, —C(=O)—$R^{17}$, and —C(=O)—O—$R^{17}$;

$R^{17}$ is chosen from hydrogen, $C_1$-$C_6$ alkyl groups, $C_3$-$C_8$ cycloalkyl groups, benzyl groups, and $C_3$-$C_8$ heterocyclyl groups; and Z is chosen from

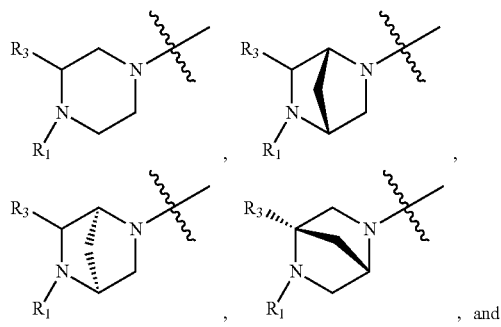

,

-continued

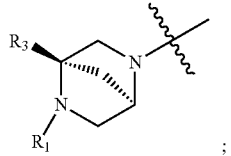

;

wherein $R^1$, $R^3$, $R^4$, $R^5$, $R^6$, $R^7$, $R^8$, $R^{15}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —$NR^{15}R^{16}$, $C_3$-$C_8$ cycloalkyl groups, $C_1$-$C_6$ alkylhydroxy groups, $C_1$-$C_6$ alkylalkoxy groups, benzyl groups, and $C_3$-$C_8$ heterocyclyl groups, wherein at least one of $R^6$ and $R^7$ is hydrogen.

In some embodiments, $R^1$ is chosen from hydrogen, $C_1$-$C_4$ alkyl groups, $C_1$-$C_4$ alkylcarboxylic acid groups, and $C_3$-$C_8$ cycloalkyl groups. In some embodiments, $R^1$ is hydrogen. In some embodiments, $R^1$ is a $C_1$-$C_4$ alkyl group. In some embodiments, $R^1$ is methyl. In some embodiments, $R^1$ is ethyl. In some embodiments, $R^1$ is a $C_1$-$C_4$ alkylcarboxylic acid group. In some embodiments, $R^1$ is —CH$_2$CH$_2$CH$_2$CO$_2$H. In some embodiments, $R^1$ is a $C_3$-$C_8$ cycloalkyl group. In some embodiments, $R^1$ is cycloheptyl.

In some embodiments, $R^3$ is chosen from hydrogen, $C_1$-$C_4$ alkyl groups, $C_1$-$C_4$ alkylalkoxy groups, $C_1$-$C_4$ alkylcarboxylic acid groups, and $C_1$-$C_4$ alkylhydroxy groups. In some embodiments, $R^3$ is chosen from hydrogen and $C_1$-$C_4$ alkylcarboxylic acid groups. In some embodiments, $R^3$ is hydrogen. In some embodiments, $R^3$ is a $C_1$-$C_4$ alkylcarboxylic acid group. In some embodiments, $R^3$ is —CH$_2$CH$_2$CO$_2$H.

In some embodiments, $R^4$ is chosen from hydrogen, hydroxyl groups, —O—($C_1$-$C_4$ alkyl) groups, —O—C(=O)—($C_1$-$C_4$ alkyl) groups, and $C_1$-$C_4$ alkyl groups. In some embodiments, $R^4$ is hydrogen. In some embodiments, $R^4$ is hydroxyl. In some embodiments, $R^4$ is a —O—($C_1$-$C_4$ alkyl) group. In some embodiments, $R^4$ is —OCH$_3$. In some embodiments, $R^4$ is —OCH$_2$CH$_3$. In some embodiments, $R^4$ is a —O—C(=O)—($C_1$-$C_4$ alkyl) group. In some embodiments, $R^4$ is —O—C(=O)—CH$_3$. In some embodiments, $R^4$ is —O—C(=O)—CH$_2$CH$_3$. In some embodiments, $R^4$ is a $C_1$-$C_4$ alkyl group. In some embodiments, $R^4$ is methyl. In some embodiments, $R^4$ is ethyl.

In some embodiments, $R^5$ is chosen from hydrogen, hydroxyl groups, —O—($C_1$-$C_4$ alkyl) groups, and $C_1$-$C_4$ alkyl groups. In some embodiments, $R^5$ is hydrogen. In some embodiments, $R^5$ is hydroxyl. In some embodiments, $R^5$ is a —O—($C_1$-$C_4$ alkyl) group. In some embodiments, $R^5$ is a $C_1$-$C_4$ alkyl group. In some embodiments, $R^6$ is hydrogen. In some embodiments, $R^7$ is hydrogen. In some embodiments, $R^6$ is hydrogen and $R^7$ is —O—$R^{17}$. In some embodiments, $R^6$ is hydrogen and $R^7$ is —OR$^{17}$, wherein $R^{17}$ is chosen from hydrogen and $C^1$-$C^4$ alkyl groups.

In some embodiments, $R^6$ is hydrogen and $R^7$ is —O—$R^{17}$, wherein $R^{17}$ is hydrogen. In some embodiments, $R^6$ is —O—$R^{17}$ and $R^7$ is hydrogen. In some embodiments, $R^6$ is —O—$R^{17}$ and $R^7$ is hydrogen, wherein $R^{17}$ is chosen from hydrogen and $C^1$-$C^4$ alkyl groups. In some embodiments, $R^6$ is —O—$R^{17}$ and $R^7$ is hydrogen, wherein $R^{17}$ is hydrogen. In some embodiments, $R^6$ is hydrogen and $R^7$ is —$NR^{15}R^{16}$. In some embodiments, $R^6$ is hydrogen and $R^7$ is —$NR^{15}R^{16}$, wherein $R^{15}$ is H and $R^{16}$ is chosen from hydrogen, $R^{17}$, —C(=O)—$R^{17}$, and —C(=O)—O—$R^{17}$. In some embodiments, $R^6$ is hydrogen and $R^7$ is —$NR^{15}R^{16}$, wherein $R^{15}$ is H and $R^{16}$ is chosen from hydrogen, $R^{17}$, —C(=O)—$R^{17}$, and —C(=O)—O—$R^{17}$, and wherein $R^{17}$ is chosen from hydrogen, $C_1$-$C_6$ alkyl groups, $C_3$-$C_8$ cycloalkyl groups, and $C_3$-$C_8$ heterocyclyl groups. In some embodiments, $R^6$ is —O—$R^{17}$. In some embodiments, $R^6$ is —O—C(=O)—$R^{17}$. In some embodiments, $R^6$ is $C_1$-$C_6$ alkyl. In some embodiments, $R^6$ is $C_1$-$C_4$ alkyl. In some embodiments, $R^6$ is $C_1$ alkyl. In some embodiments, $R^6$ is —$NR^{15}R^{16}$. In some embodiments, $R^7$ is —O—$R^{17}$. In some embodiments, $R^7$ is —O—C(=O)—$R^{17}$. In some embodiments, $R^7$ is $C_1$-$C_6$ alkyl. In some embodiments, $R^7$ is $C_1$-$C_4$ alkyl. In some embodiments, $R^7$ is $C_1$ alkyl. In some embodiments, $R^7$ is —$NR^{15}R^{16}$.

In some embodiments, $R^3$ is chosen from hydrogen, hydroxyl groups, —O—($C_1$-$C_4$ alkyl) groups, and ($C_1$-$C_4$ alkyl). In some embodiments, $R^3$ is hydrogen. In some embodiments, $R^3$ is a hydroxyl group. In some embodiments, $R^3$ is an —O—($C_1$-$C_4$ alkyl) group. In some embodiments, $R^8$ is an —O—($C_1$ alkyl) group.

In some embodiments, $R^{15}$ is hydrogen. In some embodiments, $R^{15}$ is $R^{17}$. In some embodiments, $R^{15}$ is —C(=O)—$R^{17}$. In some embodiments, $R^{15}$ is —C(=O)—O—$R^{17}$.

In some embodiments, $R^{16}$ is hydrogen. In some embodiments, $R^{16}$ is $R^{17}$. In some embodiments, $R^{16}$ is —C(=O)—$R^{17}$. In some embodiments, $R^{16}$ is —C(=O)—O—$R^{17}$.

In some embodiments, $R^{17}$ is chosen from hydrogen, $C_1$-$C_4$ alkyl groups, $C_3$-$C_6$ cycloalkyl groups, and $C_3$-$C_8$ heterocyclyl groups. In some embodiments, $R^{17}$ is hydrogen. In some embodiments, $R^{17}$ is a $C_1$-$C_4$ alkyl group. In some embodiments, $R^{17}$ is a $C_1$ alkyl group. In some embodiments, $R^{17}$ is a $C_3$-$C_6$ cycloalkyl group. In some embodiments, $R^{17}$ is a $C_3$ cycloalkyl group. In some embodiments, $R^{17}$ is a $C_4$ cycloalkyl group. In some embodiments, $R^{17}$ is a $C_5$ cycloalkyl group. In some embodiments, $R^{17}$ is a $C_6$ cycloalkyl group. In some embodiments, $R^{17}$ is a $C_3$-$C_8$ heterocyclyl group. In some embodiments, $R^{17}$ is a $C_3$ heterocyclyl group. In some embodiments, $R^{17}$ is a $C_4$ heterocyclyl group. In some embodiments, $R^{17}$ is a $C_5$ heterocyclyl group. In some embodiments, $R^{17}$ is a $C_6$ heterocyclyl group. In some embodiments, $R^{17}$ is a $C_7$ heterocyclyl group. In some embodiments, $R^{17}$ is a $C_8$ heterocyclyl group.

In some embodiments, Z is

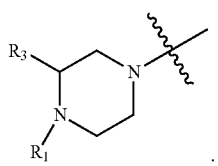

In some embodiments, Z is

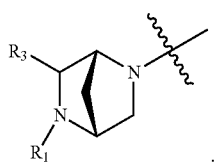

In some embodiments, Z is

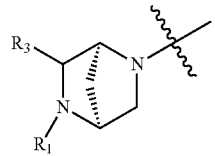

In some embodiments, Z is

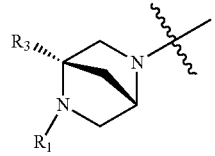

In some embodiments, Z is

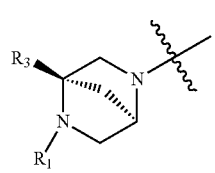

In some embodiments, the splicing modulator compound of Formula (II) attaches to the linker L, e.g., in an ADC of Formula (I), as shown in Formula (II-A):

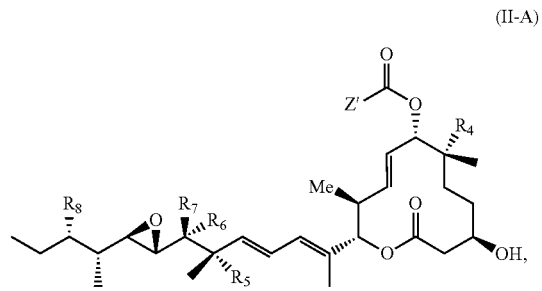

(II-A)

wherein Z' is chosen from

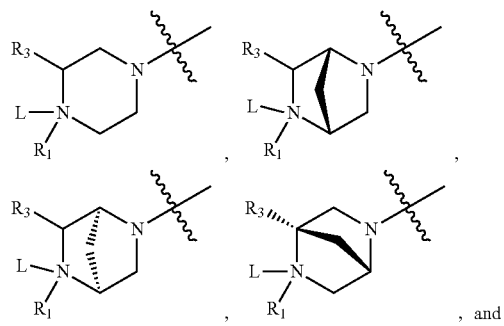

, and

-continued

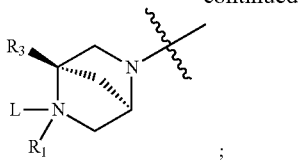

and wherein all other variables are as defined for Formula (II).

In various other embodiments, the drug moiety is a splicing modulator compound of Formula (IV):

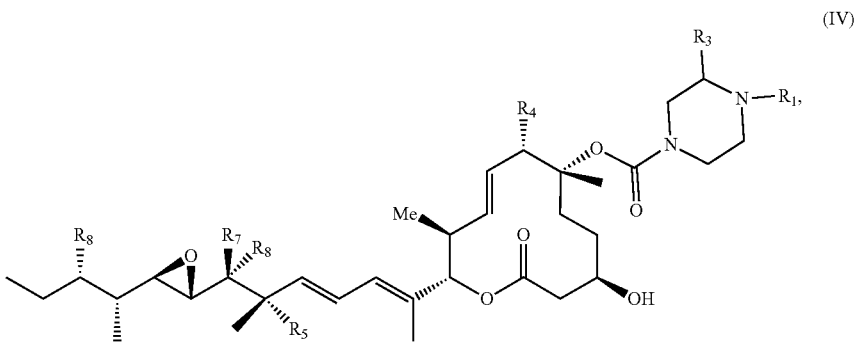

or a pharmaceutically acceptable salt thereof, wherein:
$R^1$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(=O)—($C_1$-$C_6$ alkyl) groups, and —$CD_3$;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups; and $R^4$, $R^5$, and $R^8$ are each independently chosen from hydrogen, hydroxyl groups, —O—($C_1$-$C_6$ alkyl) groups, —O—C(=O)—($C_1$-$C_6$ alkyl) groups, and $C_1$-$C_6$ alkyl groups;

$R^6$ and $R^7$ are each independently chosen from hydrogen, —O—$R^{17}$, —O—C(=O)—$R^{17}$, —O—C(=O)—$NR^{15}R^{16}$, $C_1$-$C_6$ alkyl groups, and —$NR^{15}R^{16}$;

$R^{15}$ and $R^{16}$ are each independently chosen from hydrogen, $R^{17}$, —C(=O)—$R^{17}$, and —C(=O)—O—$R^{17}$; and $R^{17}$ is chosen from hydrogen, $C_1$-$C_6$ alkyl groups, $C_3$-$C_8$ cycloalkyl groups, benzyl groups, and $C_3$-$C_8$ heterocyclyl groups;

wherein $R^1$, $R^3$, $R^4$, $R^5$, $R^6$, $R^7$, $R^8$, $R^{15}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —$NR^{15}R^{16}$, $C_3$-$C_8$ cycloalkyl groups, $C_1$-$C_6$ alkylhydroxy groups, $C_1$-$C_6$ alkylalkoxy groups, benzyl groups, and $C_3$-$C_8$ heterocyclyl groups, wherein at least one of $R^6$ and $R^7$ is hydrogen.

In some embodiments, $R^1$ is chosen from hydrogen, $C_1$-$C_4$ alkyl groups, $C_1$-$C_4$ alkylcarboxylic acid groups, and $C_3$-$C_8$ cycloalkyl groups. In some embodiments, $R^1$ is hydrogen. In some embodiments, $R^1$ is a $C_1$-$C_4$ alkyl group. In some embodiments, $R^1$ is methyl. In some embodiments, $R^1$ is ethyl. In some embodiments, $R^1$ is a $C_1$-$C_4$ alkylcarboxylic acid group. In some embodiments, $R^1$ is —$CH_2CH_2CH_2CO_2H$. In some embodiments, $R^1$ is a $C_3$-$C_8$ cycloalkyl group. In some embodiments, $R^1$ is cycloheptyl.

In some embodiments, $R^3$ is chosen from hydrogen, $C_1$-$C_4$alkyl groups, $C_1$-$C_4$ alkylalkoxy groups, $C_1$-$C_4$ alkylcarboxylic acid groups, and $C_1$-$C_4$ alkylhydroxy groups. In some embodiments, $R^3$ is chosen from hydrogen and $C_1$-$C_4$ alkylcarboxylic acid groups.

In some embodiments, $R^3$ is hydrogen. In some embodiments, $R^3$ is a $C_1$-$C_4$ alkylcarboxylic acid group. In some embodiments, $R^3$ is —$CH_2CH_2CO_2H$.

In some embodiments, $R^4$ is chosen from hydrogen, hydroxyl groups, —O—($C_1$-$C_4$ alkyl) groups, —O—C(=O)—($C_1$-$C_4$ alkyl) groups, and $C_1$-$C_4$ alkyl groups. In some embodiments, $R^4$ is hydrogen. In some embodiments, $R^4$ is hydroxyl. In some embodiments, $R^4$ is a —O—($C_1$-$C_4$ alkyl) group. In some embodiments, $R^4$ is —$OCH_3$. In some embodiments, $R^4$ is —$OCH_2CH_3$. In some embodiments, $R^4$ is a —O—C(=O)—($C_1$-$C_4$ alkyl) group. In some embodiments, $R^4$ is —O—C(=O)—$CH_3$. In some embodiments, $R^4$ is —O—C(=O)—$CH_2CH_3$. In some embodiments, $R^4$ is a $C_1$-$C_4$ alkyl group. In some embodiments, $R^4$ is methyl. In some embodiments, $R^4$ is ethyl.

In some embodiments, $R^5$ is chosen from hydrogen, hydroxyl groups, —O—($C_1$-$C_4$ alkyl) groups, and $C_1$-$C_4$ alkyl groups. In some embodiments, $R^5$ is hydrogen. In some embodiments, $R^5$ is hydroxyl. In some embodiments, $R^5$ is a —O—($C_1$-$C_4$ alkyl) group. In some embodiments, $R^5$ is a $C_1$-$C_4$ alkyl group.

In some embodiments, $R^6$ is hydrogen. In some embodiments, $R^7$ is hydrogen. In some embodiments, $R^6$ is hydrogen and $R^7$ is —O—$R^{17}$. In some embodiments, $R^6$ is hydrogen and $R^7$ is —$OR^{17}$, wherein $R^{17}$ is chosen from hydrogen and $C_1$-$C^4$ alkyl groups. In some embodiments, $R^6$ is hydrogen and $R^7$ is —O—$R^{17}$, wherein $R^{17}$ is hydrogen. In some embodiments, $R^6$ is —O—$R^{17}$ and $R^7$ is hydrogen. In some embodiments, $R^6$ is —O—$R^{17}$ and $R^7$ is hydrogen, wherein $R^{17}$ is chosen from hydrogen and $C_1$-$C^4$ alkyl groups. In some embodiments, $R^6$ is —O—$R^{17}$ and $R^7$ is hydrogen, wherein $R^{17}$ is hydrogen. In some embodiments, $R^6$ is hydrogen and $R^7$ is —$NR^{15}R^{16}$. In some embodiments, $R^6$ is hydrogen and $R^7$ is —$NR^{15}R^{16}$, wherein $R^{15}$ is H and $R^{16}$ is chosen from hydrogen, $R^{17}$, —C(=O)—$R^{17}$, and —C(=O)—O—$R^{17}$. In some embodiments, $R^6$ is hydrogen and $R^7$ is —$NR^{15}R^{16}$, wherein $R^{15}$ is H and $R^{16}$ is chosen from hydrogen, $R^{17}$, —C(=O)—$R^{17}$, and —C(=O)—O—$R^{17}$, and wherein $R^{17}$ is chosen from hydrogen, $C_1$-$C_6$ alkyl groups, $C_3$-$C_8$ cycloalkyl groups, and $C_3$-$C_8$ heterocyclyl groups. In some embodiments, $R^6$ is —O—$R^{17}$.

In some embodiments, $R^6$ is —O—C(=O)—$R^{17}$. In some embodiments, $R^6$ is $C_1$-$C_6$ alkyl. In some embodiments, $R^6$ is $C_1$-$C_4$ alkyl. In some embodiments, $R^6$ is $C_1$ alkyl. In some embodiments, $R^6$ is —$NR^{15}R^{16}$.

In some embodiments, $R^7$ is —O—$R^{17}$. In some embodiments, $R^7$ is —O—C(=O)—$R^{17}$.

In some embodiments, $R^7$ is $C_1$-$C_6$ alkyl. In some embodiments, $R^7$ is $C_1$-$C_4$ alkyl. In some embodiments, $R^7$ is $C_1$ alkyl. In some embodiments, $R^7$ is —$NR^{15}R^{16}$.

In some embodiments, $R^3$ is chosen from hydrogen, hydroxyl groups, —O—($C_1$-$C_4$ alkyl) groups, and ($C_1$-$C_4$ alkyl). In some embodiments, $R^3$ is hydrogen. In some embodiments, $R^3$ is a hydroxyl group. In some embodiments, $R^8$ is an —O—($C_1$-$C_4$ alkyl) group. In some embodiments, $R^3$ is an —O—($C_1$ alkyl) group.

In some embodiments, $R^{15}$ is hydrogen. In some embodiments, $R^{15}$ is $R^{17}$. In some embodiments, $R^{15}$ is —C(=O)—$R^{17}$. In some embodiments, $R^{15}$ is —C(=O)—O—$R^{17}$.

In some embodiments, $R^{16}$ is hydrogen. In some embodiments, $R^{16}$ is $R^{17}$. In some embodiments, $R^{16}$ is —C(=O)—$R^{17}$. In some embodiments, $R^{16}$ is —C(=O)—O—$R^{17}$.

In some embodiments, $R^{17}$ is chosen from hydrogen, $C_1$-$C_4$ alkyl groups, $C_3$-$C_6$ cycloalkyl groups, and $C_3$-$C_8$ heterocyclyl groups. In some embodiments, $R^{17}$ is hydrogen. In some embodiments, $R^{17}$ is a $C_1$-$C_4$ alkyl group. In some embodiments, $R^{17}$ is a $C_1$ alkyl group. In some embodiments, $R^{17}$ is a $C_3$-$C_6$ cycloalkyl group. In some embodiments, $R^{17}$ is a $C_3$ cycloalkyl group. In some embodiments, $R^{17}$ is a $C_4$ cycloalkyl group. In some embodiments, $R^{17}$ is a $C_5$ cycloalkyl group. In some embodiments, $R^{17}$ is a C cycloalkyl group. In some embodiments, $R^{17}$ is a $C_3$-$C_8$ heterocyclyl group. In some embodiments, $R^{17}$ is a $C_3$ heterocyclyl group. In some embodiments, $R^{17}$ is a $C_4$ heterocyclyl group. In some embodiments, $R^{17}$ is a $C_5$ heterocyclyl group. In some embodiments, $R^{17}$ is a C heterocyclyl group. In some embodiments, $R^{17}$ is a $C_7$ heterocyclyl group. In some embodiments, $R^{17}$ is a $C_8$ heterocyclyl group.

In some embodiments, the splicing modulator compound of Formula (IV) attaches to the linker L, e.g., in an ADC of Formula (I), as shown in Formula (IV-A):

In various other embodiments, the drug moiety is a splicing modulator compound of Formula (VI):

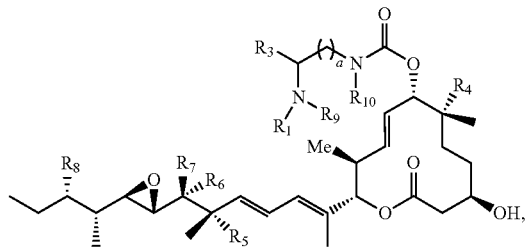

(VI)

or a pharmaceutically acceptable salt thereof, wherein:

$R^1$ and $R^9$ are each independently chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(=O)—($C_1$-$C_6$ alkyl) groups, and —$CD_3$;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups;

$R^4$, $R^5$, and $R^3$ are each independently chosen from hydrogen, hydroxyl groups, —O—($C_1$-$C_6$ alkyl) groups, —O—C(=O)—($C_1$-$C_6$ alkyl) groups, and $C_1$-$C_6$ alkyl groups;

$R^6$ and $R^7$ are each independently chosen from hydrogen, —O—$R^{17}$, —O—C(=O)—$R^{17}$, —O—C(=O)—$NR^{15}R^{16}$, $C_1$-$C_6$alkyl groups, —$NR^{15}R^{16}$, and a linker;

$R^{10}$ is chosen from hydrogen, $C_1$-$C_6$ alkyl groups, —C(=O)—($C_1$-$C_6$ alkyl) groups, and —CD3;

$R^{15}$ and $R^{16}$ are each independently chosen from hydrogen, $R^{17}$, —C(=O)—$R^{17}$, and —C(=O)—O—$R^{17}$;

$R^{17}$ is chosen from hydrogen, $C_1$-$C_6$ alkyl groups, $C_3$-$C_8$ cycloalkyl groups, benzyl groups, and $C_3$-$C_8$ heterocyclyl groups; and a is 1, 2, 3, 4, 5, 6, 7, 8, 9, or 10;

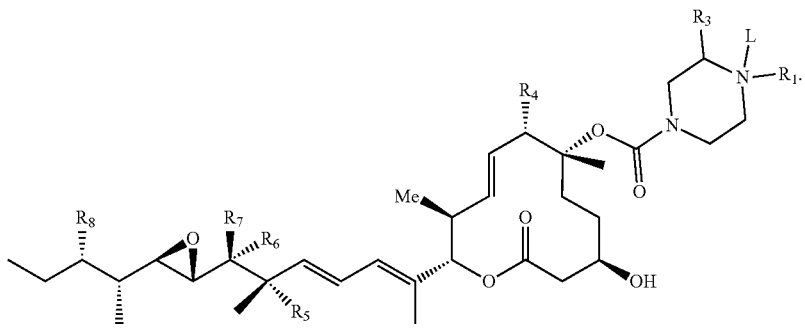

(IV-A)

wherein $R^1$, $R^3$, $R^4$, $R^5$, $R^6$, $R^7$, $R^8$, $R^9$, $R^{10}$, $R^{15}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —$NR^{15}R^{16}$, $C_3$-$C_a$ cycloalkyl groups, $C_1$-$C_6$ alkylhydroxy groups, $C_1$-$C_6$ alkylalkoxy groups, benzyl groups, and $C_3$-$C_8$ heterocyclyl groups;

wherein at least one of $R^6$ and $R^7$ is hydrogen; and wherein $R^1$ and $R^9$ cannot both be absent.

In some embodiments, $R^1$ is chosen from hydrogen, $C_1$-$C_4$ alkyl groups, $C_1$-$C_4$ alkylcarboxylic acid groups, and $C_3$-$C_8$ cycloalkyl groups. In some embodiments, $R^1$ is hydrogen. In some embodiments, $R^1$ is a $C_1$-$C_4$ alkyl group. In some embodiments, $R^1$ is methyl. In some embodiments, $R^1$ is ethyl. In some embodiments, $R^1$ is a $C_1$-$C_4$ alkylcarboxylic acid group. In some embodiments, $R^1$ is —$CH_2CH_2CH_2CO_2H$. In some embodiments, $R^1$ is a $C_3$-$C_8$ cycloalkyl group. In some embodiments, $R^1$ is cycloheptyl.

In some embodiments, $R^3$ is chosen from hydrogen, $C_1$-$C_4$ alkyl groups, $C_1$-$C_4$ alkylalkoxy groups, $C_1$-$C_4$ alkylcarboxylic acid groups, and $C_1$-$C_4$ alkylhydroxy groups. In some embodiments, $R^3$ is chosen from hydrogen and $C_1$-$C_4$ alkylcarboxylic acid groups.

In some embodiments, $R^3$ is hydrogen. In some embodiments, $R^3$ is a $C_1$-$C_4$ alkylcarboxylic acid group. In some embodiments, $R^3$ is —$CH_2CH_2CO_2H$.

In some embodiments, $R^4$ is chosen from hydrogen, hydroxyl groups, —O—($C_1$-$C_4$ alkyl) groups, —O—C(=O)—($C_1$-$C_4$ alkyl) groups, and $C_1$-$C_4$ alkyl groups. In some embodiments, $R^4$ is hydrogen. In some embodiments, $R^4$ is hydroxyl. In some embodiments, $R^4$ is a —O—($C_1$-$C_4$ alkyl) group. In some embodiments, $R^4$ is —$OCH_3$. In some embodiments, $R^4$ is —$OCH_2CH_3$. In some embodiments, $R^4$ is a —O—C(=O)—($C_1$-$C_4$ alkyl) group. In some embodiments, $R^4$ is —O—C(=O)—$CH_3$. In some embodiments, $R^4$ is —O—C(=O)—$CH_2CH_3$. In some embodiments, $R^4$ is a $C_1$-$C_4$ alkyl group. In some embodiments, $R^4$ is methyl. In some embodiments, $R^4$ is ethyl.

In some embodiments, $R^5$ is chosen from hydrogen, hydroxyl groups, —O—($C_1$-$C_4$ alkyl) groups, and $C_1$-$C_4$ alkyl groups. In some embodiments, $R^5$ is hydrogen. In some embodiments, $R^5$ is hydroxyl. In some embodiments, $R^5$ is a —O—($C_1$-$C_4$ alkyl) group. In some embodiments, $R^5$ is a $C_1$-$C_4$ alkyl group.

In some embodiments, $R^9$ is chosen from absent, hydrogen, $C_1$-$C_4$ alkyl groups, —(C=O)—($C_1$-$C_4$ alkyl) groups, and —$CD_3$. In some embodiments, $R^9$ is absent. In some embodiments, $R^9$ is hydrogen. In some embodiments, $R^9$ is a $C_1$-$C_4$ alkyl group. In some embodiments, the $C_1$-$C_4$ alkyl group is methyl. In some embodiments, the $C_1$-$C_4$ alkyl group is ethyl. In some embodiments, $R^9$ is a —(C=O)—($C_1$-$C_4$ alkyl) group. In some embodiments, the —(C=O)—($C_1$-$C_4$ alkyl) group is —(C=O)-methyl. In some embodiments, $R^9$ is —CD3.

In some embodiments, $R^{10}$ is chosen from hydrogen, $C_1$-$C_4$ alkyl groups, —(C=O)—($C_1$-$C_4$ alkyl) groups, and —$CD_3$. In some embodiments, $R^{10}$ is hydrogen. In some embodiments, $R^{10}$ is a $C_1$-$C_4$ alkyl group. In some embodiments, the $C_1$-$C_4$ alkyl group is methyl. In some embodiments, the $C_1$-$C_4$ alkyl group is ethyl. In some embodiments, $R^{10}$ is a —(C=O)—($C_1$-$C_4$ alkyl) group. In some embodiments, the —(C=O)—($C_1$-$C_4$ alkyl) group is —(C=O)-methyl. In some embodiments, $R^{10}$ is —$CD_3$.

In some embodiments, $R^6$ is hydrogen. In some embodiments, $R^7$ is hydrogen. In some embodiments, $R^6$ is hydrogen and $R^7$ is —O—$R^{17}$. In some embodiments, $R^6$ is hydrogen and $R^7$ is —$OR^{17}$, wherein $R^{17}$ is chosen from hydrogen and $C^1$-$C^4$ alkyl groups. In some embodiments, $R^6$ is hydrogen and $R^7$ is —O—$R^{17}$, wherein $R^{17}$ is hydrogen. In some embodiments, $R^6$ is —O—$R^{17}$ and $R^7$ is hydrogen. In some embodiments, $R^6$ is —O—$R^{17}$ and $R^7$ is hydrogen, wherein $R^{17}$ is chosen from hydrogen and $C^1$-$C^4$ alkyl groups. In some embodiments, $R^6$ is —O—$R^{17}$ and $R^7$ is hydrogen, wherein $R^{17}$ is hydrogen. In some embodiments, $R^6$ is hydrogen and $R^7$ is —$NR^{15}R^{16}$. In some embodiments, $R^6$ is hydrogen and $R^7$ is —$NR^{15}R^{16}$, wherein $R^{15}$ is H and $R^{16}$ is chosen from hydrogen, $R^{17}$, —C(=O)—$R^{17}$, and —C(=O)—O—$R^{17}$. In some embodiments, $R^6$ is hydrogen and $R^7$ is —$NR^{15}R^{16}$, wherein $R^{15}$ is H and $R^{16}$ is chosen from hydrogen, $R^{17}$, —C(=O)—$R^{17}$, and —C(=O)—O—$R^{17}$, and wherein $R^{17}$ is chosen from hydrogen, $C_1$-$C_6$ alkyl groups, $C_3$-$C_8$ cycloalkyl groups, and $C_3$-$C_8$ heterocyclyl groups. In some embodiments, $R^6$ is —O—$R^{17}$.

In some embodiments, $R^6$ is —O—C(=O)—$R^{17}$. In some embodiments, $R^6$ is $C_1$-$C_6$ alkyl. In some embodiments, $R^6$ is $C_1$-$C_4$ alkyl. In some embodiments, $R^6$ is $C_1$ alkyl. In some embodiments, $R^6$ is —$NR^{15}R^{16}$.

In some embodiments, $R^7$ is —O—$R^{17}$. In some embodiments, $R^7$ is —O—C(=O)—$R^{17}$. In some embodiments, $R^7$ is $C_1$-$C_6$ alkyl. In some embodiments, $R^7$ is $C_1$-$C_4$ alkyl. In some embodiments, $R^7$ is $C_1$ alkyl. In some embodiments, $R^7$ is —$NR^{15}R^{16}$.

In some embodiments, $R^8$ is chosen from hydrogen, hydroxyl groups, —O—($C_1$-$C_4$ alkyl) groups, and ($C_1$-$C_4$ alkyl). In some embodiments, $R^3$ is hydrogen. In some embodiments, $R^3$ is a hydroxyl group. In some embodiments, $R^3$ is an —O—($C_1$-$C_4$ alkyl) group. In some embodiments, $R^3$ is an —O—($C_1$ alkyl) group.

In some embodiments, $R^{15}$ is hydrogen. In some embodiments, $R^{15}$ is $R^{17}$. In some embodiments, $R^{15}$ is —C(=O)—$R^{17}$. In some embodiments, $R^{15}$ is —C(=O)—O—$R^{17}$.

In some embodiments, $R^{16}$ is hydrogen. In some embodiments, $R^{16}$ is $R^{17}$. In some embodiments, $R^{16}$ is —C(=O)—$R^{17}$. In some embodiments, $R^{16}$ is —C(=O)—O—$R^{17}$.

In some embodiments, $R^{17}$ is chosen from hydrogen, $C_1$-$C_4$ alkyl groups, $C_3$-$C_5$ cycloalkyl groups, and $C_3$-$C_8$ heterocyclyl groups. In some embodiments, $R^{17}$ is hydrogen. In some embodiments, $R^{17}$ is a $C_1$-$C_4$ alkyl group. In some embodiments, $R^{17}$ is a $C_1$ alkyl group. In some embodiments, $R^{17}$ is a $C_3$-$C_6$ cycloalkyl group. In some embodiments, $R^{17}$ is a $C_3$ cycloalkyl group. In some embodiments, $R^{17}$ is a $C_4$ cycloalkyl group. In some embodiments, $R^{17}$ is a $C_5$ cycloalkyl group. In some embodiments, $R^{17}$ is a C cycloalkyl group. In some embodiments, $R^{17}$ is a $C_3$-$C_8$ heterocyclyl group. In some embodiments, $R^{17}$ is a $C_3$ heterocyclyl group. In some embodiments, $R^{17}$ is a $C_4$ heterocyclyl group. In some embodiments, $R^{17}$ is a $C_5$ heterocyclyl group. In some embodiments, $R^{17}$ is a C heterocyclyl group. In some embodiments, $R^{17}$ is a $C_7$ heterocyclyl group. In some embodiments, $R^{17}$ is a $C_8$ heterocyclyl group.

In some embodiments, a is 1, 2, 3, 4, 5, 6, 7, 8, 9, or 10. In some embodiments, a is 1, 2, 3, 4, 5, or 6. In some embodiments, a is 1, 2, 3, 4, or 5. In some embodiments, a is 1, 2, 3, or 4. In some embodiments, a is 1, 2, or 3. In some embodiments, a is 1 or 2. In some embodiments, a is 1. In some embodiments, a is 2. In some embodiments, a is 3. In some embodiments, a is 4. In some embodiments, a is 5. In some embodiments, a is 6. In some embodiments, a is 7. In some embodiments, a is 8. In some embodiments, a is 9. In some embodiments, a is 10.

In some embodiments, the splicing modulator compound of Formula (VI) attaches to the linker L, e.g., in an ADC of Formula (I), as shown in Formula (VI-A):

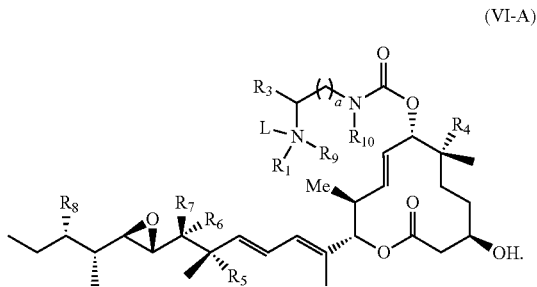

(VI-A)

In various other embodiments, the drug moiety is a splicing modulator compound of Formula (VIII):

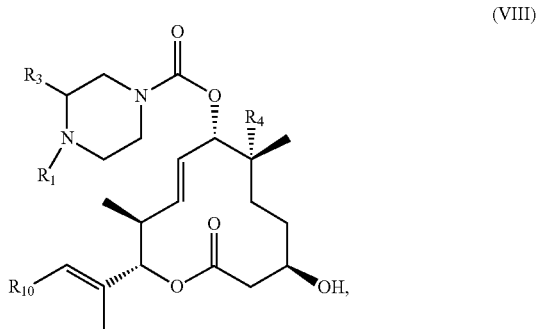

(VIII)

or a pharmaceutically acceptable salt thereof, wherein:

$R^1$ is chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(=O)—($C_1$-$C_6$ alkyl) groups, and —$CD_3$;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups;

$R^4$ is chosen from hydrogen, hydroxyl groups, —O—($C_1$-$C_6$ alkyl) groups, —O—C(=O)—($C_1$-$C_6$ alkyl) groups, and $C_1$-$C_6$ alkyl groups; and $R^{10}$ is chosen from 3 to 10 membered carbocycles and 3 to 10 membered heterocycles, each of which is substituted with 0 to 3 $R^a$, wherein each $R^a$ is independently chosen from halogens, $C_1$-$C_6$ alkyl groups, —O—($C_1$-$C_6$)alkyl groups, $C_1$-$C_6$ alkylalkoxy groups, $C_1$-$C_6$ alkylhydroxy groups, —S(=O)$_w$-(4 to 7 membered heterocycles), 4 to 7 membered carbocycles, and 4 to 7 membered heterocycles;

$R^{15}$ and $R^{16}$ are each independently chosen from hydrogen, $R^{17}$, —C(=O)—$R^{17}$, and —C(=O)—O—$R^{17}$; and $R^{17}$ is chosen from hydrogen, $C_1$-$C_6$ alkyl groups, $C_3$-$C_8$ cycloalkyl groups, benzyl groups, and $C_3$-$C_8$ heterocyclyl groups;

wherein $R^1$, $R^3$, $R^4$, $R^{10}$, $R^{15}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —$NR^{15}R^{16}$, $C_3$-$C_8$ cycloalkyl groups, $C_1$-$C_6$ alkylhydroxy groups, $C_1$-$C_6$ alkylalkoxy groups, benzyl groups, and $C_3$-$C_8$ heterocyclyl groups; and wherein each $R^a$ is independently substituted with 0 to 3 groups independently chosen from halogens, hydroxyl groups, —$NR^{15}R^{16}$, $C_1$-$C_6$ alkyl groups, —(C=O)—($C_1$-$C_6$ alkyl) groups, —(C=O)—($C_1$-$C_6$ alkyl)-($C_3$-$C_{10}$ heterocyclyl groups), and $C_1$-$C_6$ alkylcarboxylic acid groups, each of which is substituted with 0, 1, or 2 groups independently chosen from halogens, hydroxyl groups, —$NR^{15}R^{16}$, and $C_1$-$C_3$ alkyl groups; and w is 0, 1, or 2.

In some embodiments, $R^1$ is chosen from absent, hydrogen, $C_1$-$C_4$ alkyl groups, $C_1$-$C_4$ alkylcarboxylic acid groups, and $C_3$-$C_8$ cycloalkyl groups. In some embodiments, $R^1$ is hydrogen. In some embodiments, $R^1$ is a $C_1$-$C_4$ alkyl group. In some embodiments, $R^1$ is methyl. In some embodiments, $R^1$ is ethyl. In some embodiments, $R^1$ is a $C_1$-$C_4$ alkylcarboxylic acid group. In some embodiments, $R^1$ is —$CH_2CH_2CH_2CO_2H$. In some embodiments, $R^1$ is a $C_3$-$C_8$ cycloalkyl group. In some embodiments, $R^1$ is cycloheptyl.

In some embodiments, $R^3$ is chosen from hydrogen, $C_1$-$C_4$alkyl groups, $C_1$-$C_4$ alkylalkoxy groups, $C_1$-$C_4$ alkylcarboxylic acid groups, and $C_1$-$C_4$ alkylhydroxy groups. In some embodiments, $R^3$ is chosen from hydrogen and $C_1$-$C_4$ alkylcarboxylic acid groups. In some embodiments, $R^3$ is hydrogen. In some embodiments, $R^3$ is a $C_1$-$C_4$ alkylcarboxylic acid group. In some embodiments, $R^3$ is —$CH_2CH_2CO_2H$.

In some embodiments, $R^4$ is chosen from hydrogen, hydroxyl groups, —O—($C_1$-$C_4$ alkyl) groups, —O—C(=O)—($C_1$-$C_4$ alkyl) groups, and $C_1$-$C_4$ alkyl groups. In some embodiments, $R^4$ is hydrogen. In some embodiments, $R^4$ is hydroxyl. In some embodiments, $R^4$ is a —O—($C_1$-$C_4$ alkyl) group. In some embodiments, $R^4$ is —$OCH_3$. In some embodiments, $R^4$ is —$OCH_2CH_3$. In some embodiments, $R^4$ is a —O—C(=O)—($C_1$-$C_4$ alkyl) group. In some embodiments, $R^4$ is —O—C(=O)—$CH_3$. In some embodiments, $R^4$ is —O—C(=O)—$CH_2CH_3$. In some embodiments, $R^4$ is a $C_1$-$C_4$ alkyl group. In some embodiments, $R^4$ is methyl. In some embodiments, $R^4$ is ethyl.

In some embodiments, $R^{10}$ is chosen from 6 to 9 membered carbocycles and 6 to 9 membered heterocycles, each of which is substituted with 0 to 2 $R^a$, wherein each $R^a$ is independently substituted with 0 to 3 groups independently chosen from halogens, hydroxyl groups, $C_1$-$C_6$ alkyl groups, —(C=O)—($C_1$-$C_6$ alkyl) groups, —(C=O)—($C_1$-$C_6$ alkyl)-(3 to 10 membered heterocycle) groups, and $C_1$-$C_5$ alkylcarboxylic acid groups.

In some embodiments, the carbocycle is a phenyl substituted with 0 to 2 $R^a$, wherein each $R^a$ is independently substituted with 0 to 3 groups independently chosen from halogens, hydroxyl groups, $C_1$-$C_6$ alkyl groups, —(C=O)—($C_1$-$C_6$ alkyl) groups, —(C=O)—($C_1$-$C_6$ alkyl)-(3 to 10 membered heterocycle) groups, and $C_1$—C alkylcarboxylic acid groups. In some embodiments, the phenyl is substituted with 2 $R^a$, wherein each $R^a$ is independently substituted with 0 to 3 groups independently chosen from halogens, hydroxyl groups, $C_1$-$C_6$ alkyl groups, —(C=O)—($C_1$-$C_6$ alkyl) groups, —(C=O)—($C_1$-$C_6$ alkyl)-(3 to 10 membered heterocycle) groups, and $C_1$-$C_6$alkylcarboxylic acid groups. In some embodiments, the phenyl is

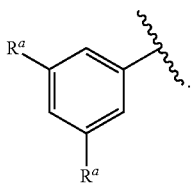

In some embodiments, the heterocycle is a 9 membered heterocycle substituted with 0 to 2 $R^a$, wherein each $R^a$ is independently substituted with 0 to 3 groups independently chosen from halogens, hydroxyl groups, $C_1$-$C_6$ alkyl groups, —(C=O)—($C_1$-$C_6$ alkyl) groups, —(C=O)—($C_1$-$C_6$ alkyl)-(3 to 10 membered heterocycle) groups, and $C_1$-$C_6$alkylcarboxylic acid groups. In some embodiments, the 9 membered heterocycle is

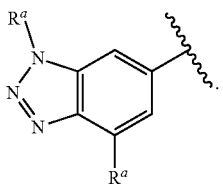

In some embodiments, $R^a$ is chosen from halogens, 3 to 10 membered carbocycles, and 3 to 10 membered heterocycles, wherein each $R^a$ is independently substituted with 0 to 3 groups independently chosen from halogens, hydroxyl groups, $C_1$-$C_6$ alkyl groups, —(C=O)—($C_1$-$C_6$ alkyl) groups, —(C=O)—($C_1$-$C_6$ alkyl)-(3 to 10 membered heterocycle) groups, and $C_1$-$C_6$ alkylcarboxylic acid groups. In some embodiments, $R^a$ is chosen from halogens,

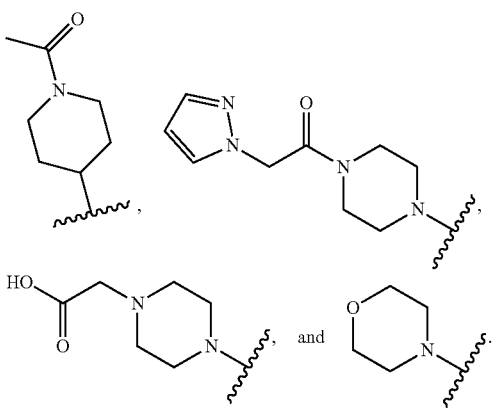

In some embodiments, $R^{15}$ is hydrogen. In some embodiments, $R^{15}$ is $R^{17}$. In some embodiments, $R^{15}$ is —C(=O)—$R^{17}$. In some embodiments, $R^{15}$ is —C(=O)—O—$R^{17}$.

In some embodiments, $R^{16}$ is hydrogen. In some embodiments, $R^{16}$ is $R^{17}$. In some embodiments, $R^{16}$ is —C(=O)—$R^{17}$. In some embodiments, $R^{16}$ is —C(=O)—O—$R^{17}$.

In some embodiments, $R^{17}$ is chosen from hydrogen, $C_1$-$C_4$ alkyl groups, $C_3$-$C_6$ cycloalkyl groups, and $C_3$-$C_8$ heterocyclyl groups. In some embodiments, $R^{17}$ is hydrogen. In some embodiments, $R^{17}$ is a $C_1$-$C_4$ alkyl group. In some embodiments, $R^{17}$ is a $C_1$ alkyl group. In some embodiments, $R^{17}$ is a $C_3$-$C_6$ cycloalkyl group. In some embodiments, $R^{17}$ is a $C_3$ cycloalkyl group. In some embodiments, $R^{17}$ is a $C_4$ cycloalkyl group. In some embodiments, $R^{17}$ is a $C_5$ cycloalkyl group. In some embodiments, $R^{17}$ is a C cycloalkyl group. In some embodiments, $R^{17}$ is a $C_3$-$C_8$ heterocyclyl group. In some embodiments, $R^{17}$ is a $C_3$ heterocyclyl group. In some embodiments, $R^{17}$ is a $C_4$ heterocyclyl group. In some embodiments, $R^{17}$ is a $C_5$ heterocyclyl group. In some embodiments, $R^{17}$ is a C heterocyclyl group. In some embodiments, $R^{17}$ is a $C_7$ heterocyclyl group. In some embodiments, $R^{17}$ is a C heterocyclyl group.

In some embodiments, the splicing modulator compound of Formula (VIII) attaches to the linker L, e.g., in an ADC of Formula (I), as shown in Formula (VIII-A):

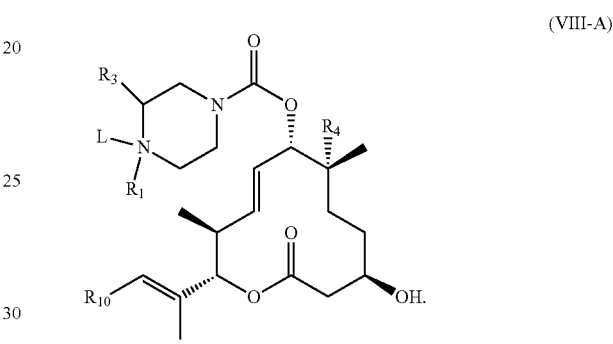

(VIII-A)

In various embodiments, the drug moiety is a splicing modulator selected from D2 and D1.

In various embodiments, the drug moiety is D2. In various embodiments, the structure of the D2 drug moiety used in the disclosed ADCs is shown below:

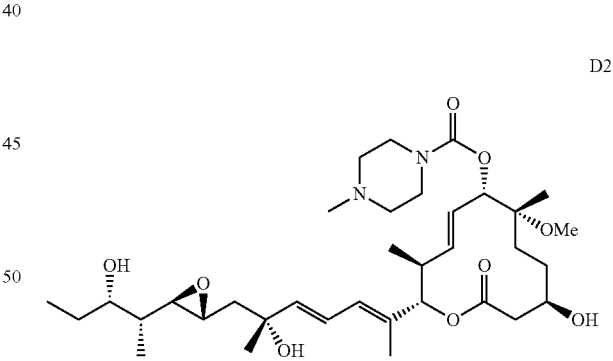

D2

In various embodiments, the linker in the ADCs (e.g., ADCs of Formula (I)) described herein covalently attaches to the D2 drug moiety via an amine on the piperazine group. In various embodiments, the drug moiety is a derivative of D2. In various embodiments, the D2 derivative retains at least one biological function or activity as D2 (e.g., SF3b complex binding, in vitro splicing activity, cytotoxicity) but has an altered chemical structure.

In various embodiments, the drug moiety is D1 or a pharmaceutically acceptable salt thereof. In various embodiments, the structure of the D1 drug moiety used in the disclosed ADCs is shown below:

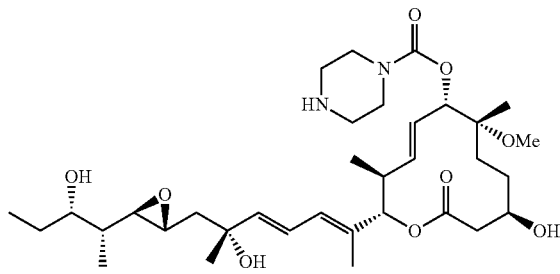

D1

In various embodiments, the linker in the ADCs (e.g., ADCs of Formula (I)) described herein covalently attaches to the D1 drug moiety via an amine on the piperazine group. In various embodiments, the drug moiety is a derivative of D1. In various embodiments, the D1 derivative retains at least one biological function or activity as D1 (e.g., SF3b complex binding, in vitro splicing activity, cytotoxicity) but has an altered chemical structure.

In some embodiments, the splicing modulator comprises D1:

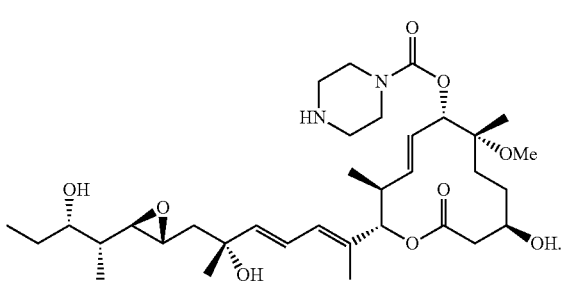

(D1)

In some embodiments, the splicing modulator comprises D2:

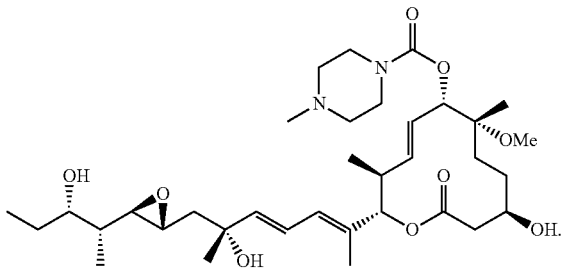

(D2)

In some embodiments, the splicing modulator comprises D3:

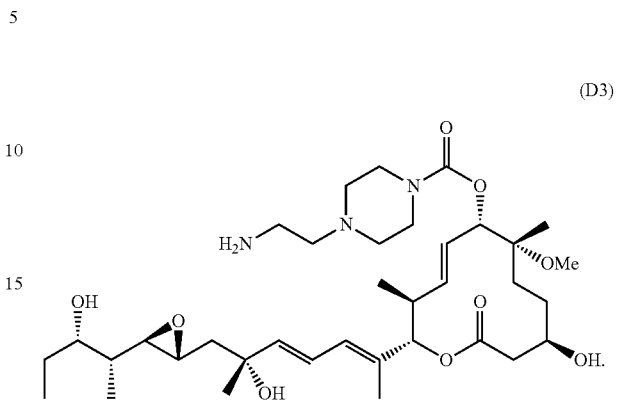

(D3)

In some embodiments, the splicing modulator comprises D4:

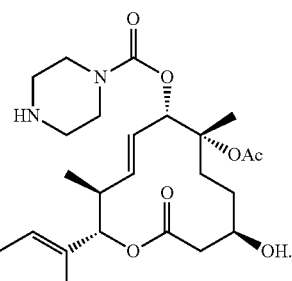

(D4)

In some embodiments, the splicing modulator comprises D4':

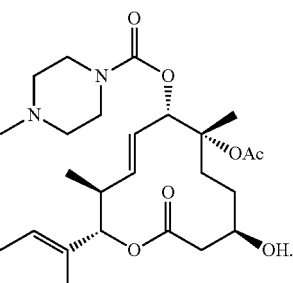

(D4')

In some embodiments, the splicing modulator comprises D5:

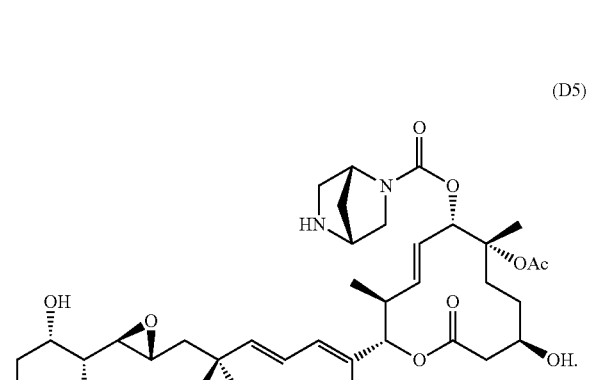
(D5)

In some embodiments, the splicing modulator comprises D6:

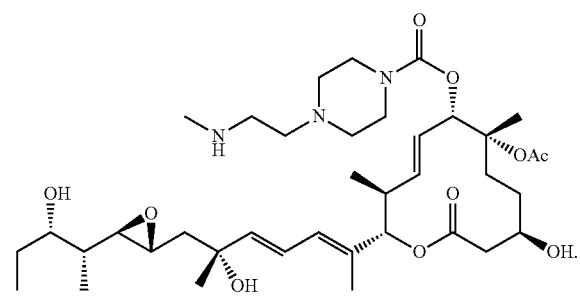
(D6)

In some embodiments, the splicing modulator comprises D7:

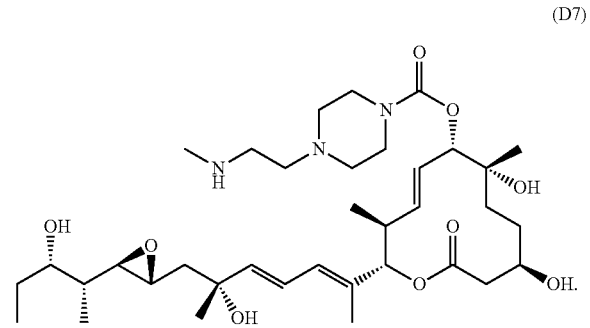 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(O)[C@@H](OC(=O)N2CCN(CCNC)CC2)/C=C/[C@@H]1C]
(D7)

In some embodiments the splicing modulator comprises D8:

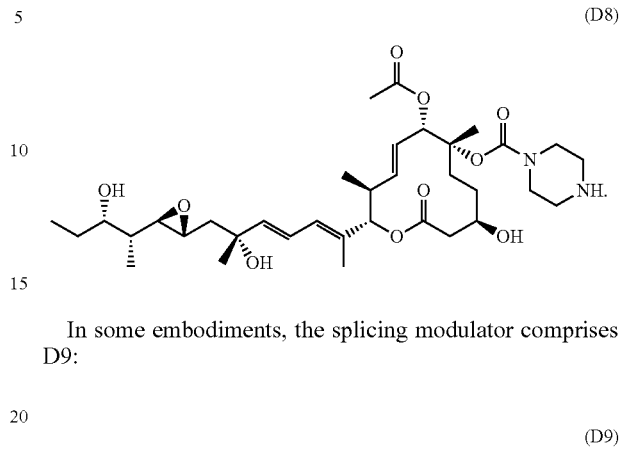
(D8)

In some embodiments, the splicing modulator comprises D9:

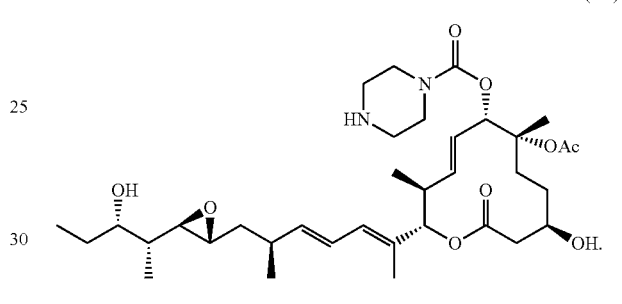
(D9)

In some embodiments, the splicing modulator comprises D10:

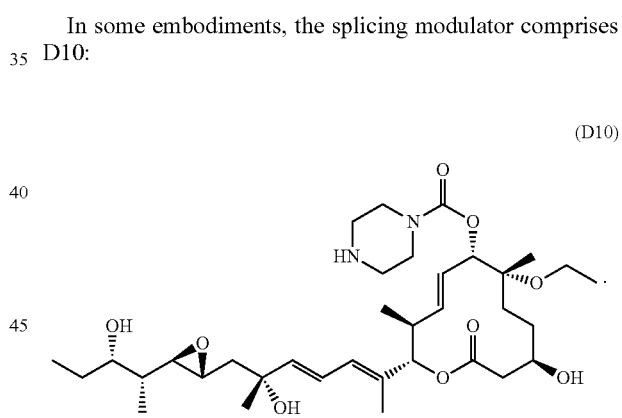
(D10)

In some embodiments, the splicing modulator comprises D11:

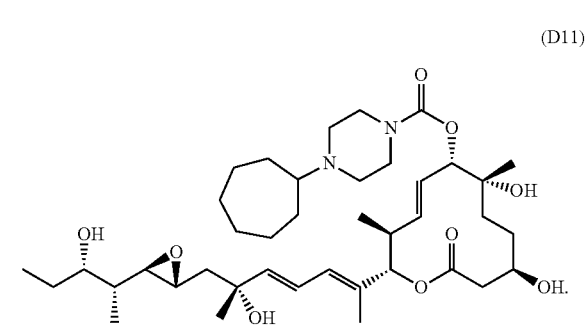 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(O)[C@@H](OC(=O)N2CCN(C3CCCCCC3)CC2)/C=C/[C@@H]1C]
(D11)

In some embodiments, the splicing modulator comprises D12:
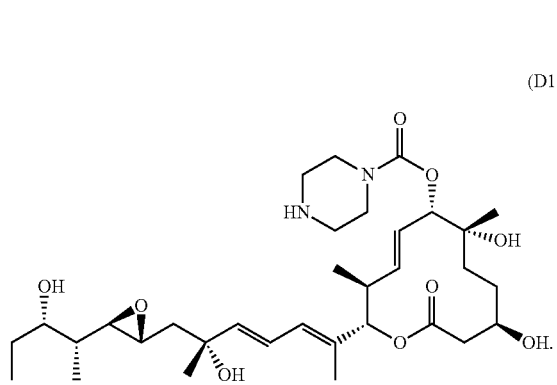
(D12)
In some embodiments, the splicing modulator comprises D13:
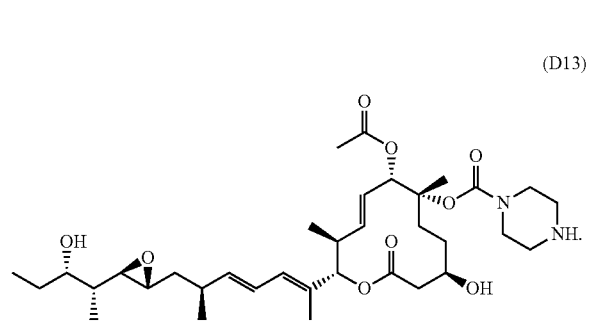 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC(=O)N2CCNCC2)[C@@H](OC(C)=O)/C=C/[C@@H]1C]
(D13)
In some embodiments, the splicing modulator comprises D14:
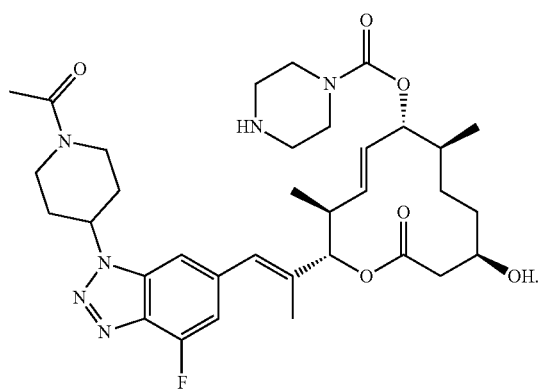
(D14)
In some embodiments, the splicing modulator comprises D15:
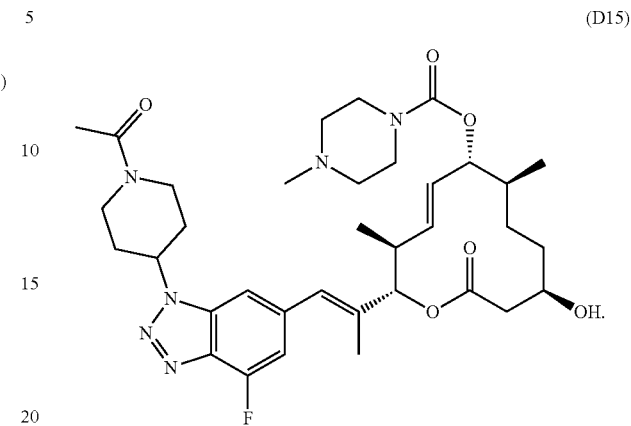
(D15)
In some embodiments, the splicing modulator comprises D16:
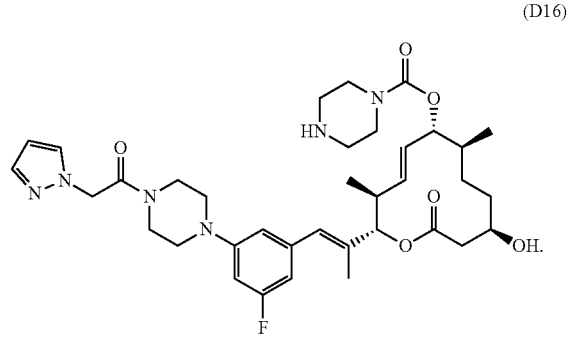 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CCNCC2)/C=C/[C@@H]1C]
(D16)
In some embodiments, the splicing modulator comprises D17:
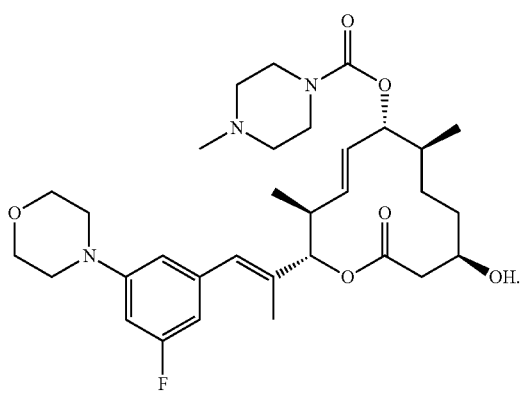
(D17)

In some embodiments, the splicing modulator comprises D18:

(D18)

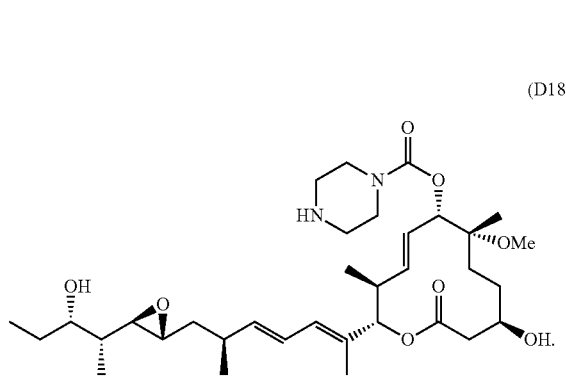

In some embodiments, the splicing modulator comprises D19:

(D19)

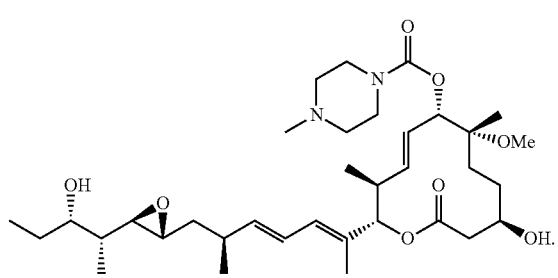

In some embodiments, the splicing modulator comprises D20:

(D20)

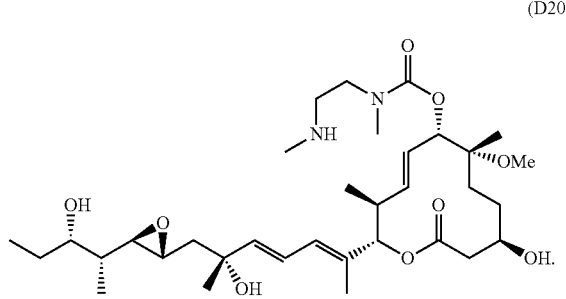

In some embodiments, the splicing modulator comprises D21:

(D21)

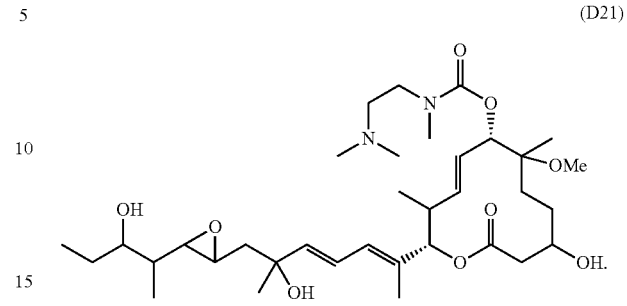

In some embodiments, the splicing modulator comprises D22:

(D22)

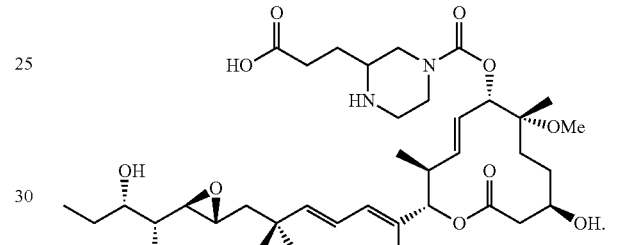

In some embodiments, the splicing modulator comprises D23:

(D23)

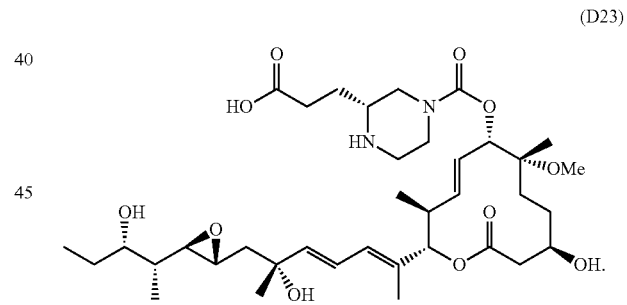

In some embodiments, the splicing modulator comprises D24:

(D24)

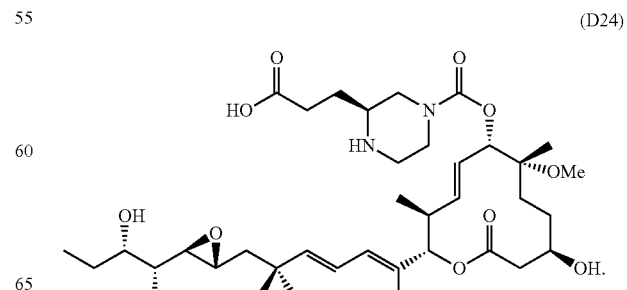

In some embodiments, the splicing modulator comprises D25:
(D25)
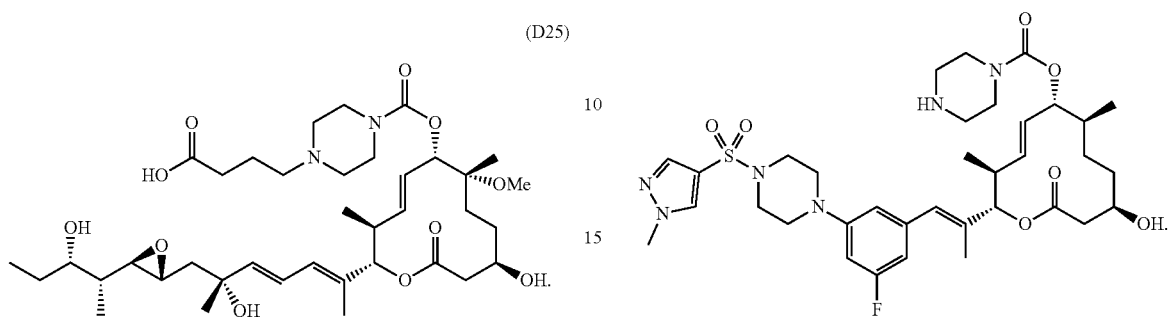
In some embodiments, the splicing modulator comprises D26:
(D26)
In some embodiments, the splicing modulator comprises D27:
(D27)
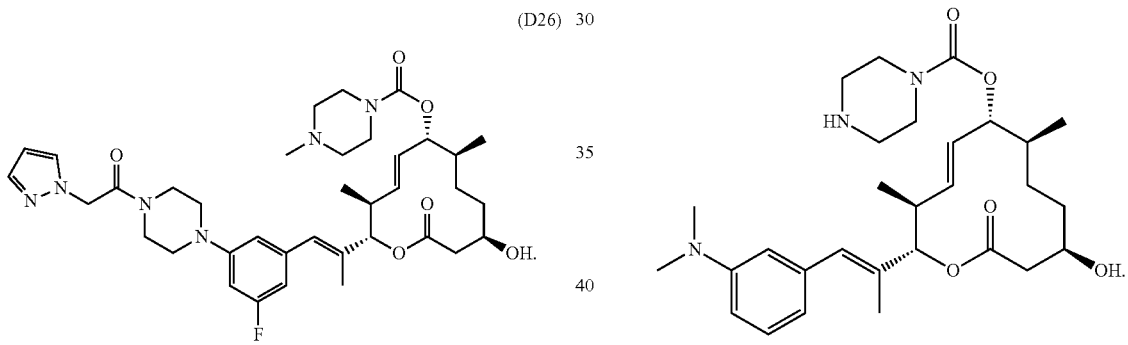
In some embodiments, the splicing modulator comprises D28:
(D28)
In some embodiments, the splicing modulator comprises D29:
(D29)
In some embodiments, the splicing modulator comprises D30:
(D30)
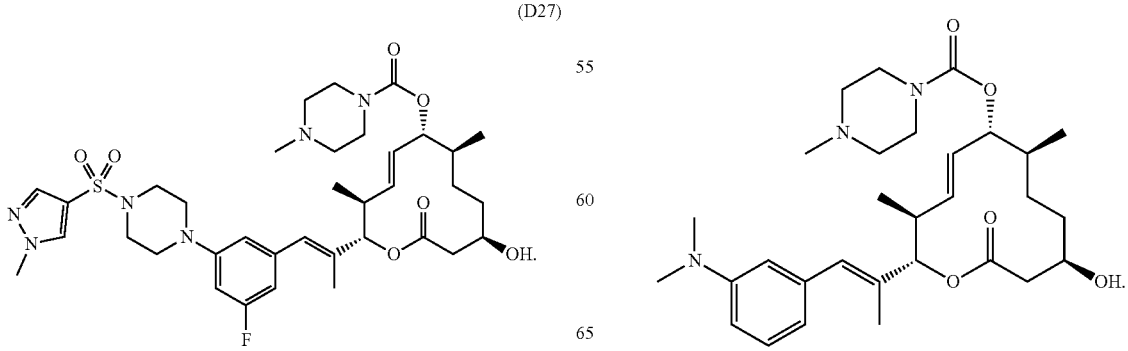

In some embodiments, the splicing modulator comprises D31:

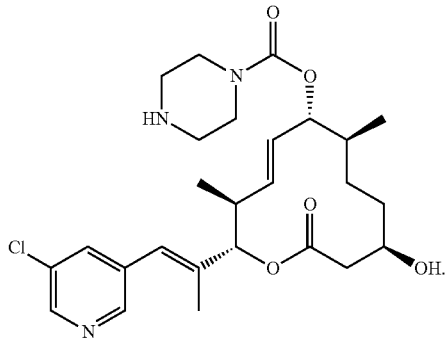

(D31)

In some embodiments, the splicing modulator comprises D32:

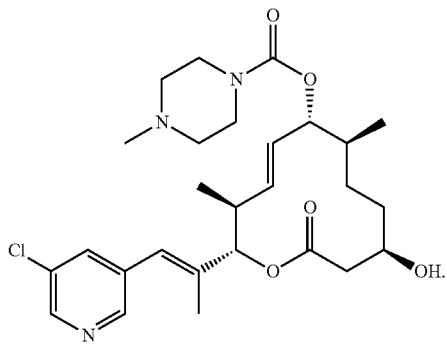

(D32)

In some embodiments, the splicing modulator comprises D33:

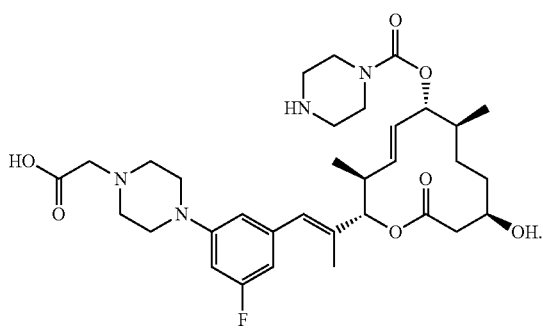

(D33)

In some embodiments, the splicing modulator comprises D34:

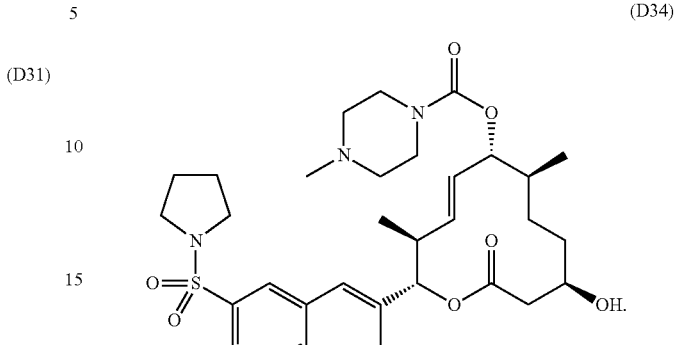

(D34)

In some embodiments, the splicing modulator comprises D35:

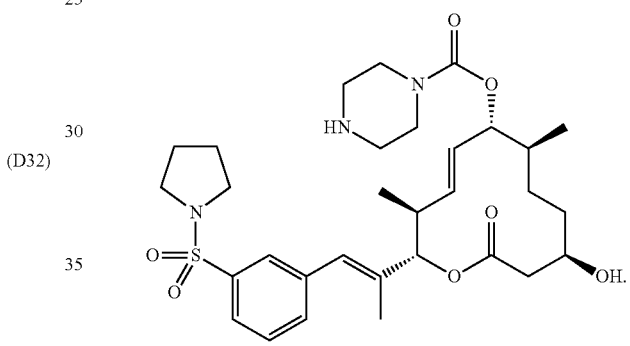

(D35)

An exemplary ADC has Formula (I):

$$Ab-(L-D)_p \qquad (I)$$

wherein
Ab is an antibody or antigen binding fragment which targets a neoplastic cell;
D is D2;
L is a linker that covalently attaches Ab to D; and
p is an integer from 1 to 15.

In some embodiments, the antibody or antigen binding fragment targets a cell expressing HER2, CD138, EPHA2, MSLN, FOLH1, CDH6, CEACAM5, CFC1B, ENPP3, FOLR1, HAVCR1, KIT, MET, MUC16, SLC39A6, SLC44A4, and/or STEAP1.

In some embodiments, the antibody or antigen binding fragment targets a HER2-expressing cell. In some embodiments, the antibody or antigen binding fragment is an anti-HER2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:1 (HCDR1), SEQ ID NO:2 (HCDR2), and SEQ ID NO:3 (HCDR3); and three light chain complementarity determining regions (LCDR1, LCDR2, and LCDR3) comprising amino acid sequences of SEQ ID NO:4 (LCDR1), SEQ ID NO:5 (LCDR2), and SEQ ID NO:6 (LCDR3). In some embodiments, the antibody or antigen binding fragment comprises a heavy chain variable region comprising an amino acid sequence of SEQ ID NO:19, and a light chain variable region comprising an amino acid sequence of SEQ ID NO:20. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a CD138-expressing cell. In some embodiments, the antibody or antigen binding fragment is an anti-CD138 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:7 (HCDR1), SEQ ID NO:8 (HCDR2), and SEQ ID NO:9 (HCDR3); and three light chain complementarity determining regions (LCDR1, LCDR2, and LCDR3) comprising amino acid sequences of SEQ ID NO:10 (LCDR1), SEQ ID NO:11 (LCDR2), and SEQ ID NO:12 (LCDR3). In some embodiments, the antibody or antigen binding fragment comprises a heavy chain variable region comprising an amino acid sequence of SEQ ID NO:21, and a light chain variable region comprising an amino acid sequence of SEQ ID NO:22. In some embodiments, the antibody or antigen binding fragment comprises a murine IgG2a heavy chain constant region. In some embodiments, the antibody or antigen binding fragment comprises a murine Ig kappa light chain constant region. In some embodiments, the antibody or antigen binding fragment comprises a human IgG2a heavy chain constant region. In some embodiments, the antibody or antigen binding fragment comprises a human Ig kappa light chain constant region.

In some other embodiments, the antibody or antigen binding fragment targets an EPHA2-expressing cell. In some embodiments, the antibody or antigen binding fragment is an anti-EPHA2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:13 (HCDR1), SEQ ID NO:14 (HCDR2), and SEQ ID NO:15 (HCDR3); and three light chain complementarity determining regions (LCDR1, LCDR2, and LCDR3) comprising amino acid sequences of SEQ ID NO:16 (LCDR1), SEQ ID NO:17 (LCDR2), and SEQ ID NO:18 (LCDR3). In some embodiments, the antibody or antigen binding fragment comprises a heavy chain variable region comprising an amino acid sequence of SEQ ID NO:23, and a light chain variable region comprising an amino acid sequence of SEQ ID NO:24. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a MSLN-expressing cell. In some embodiments, the antibody or antigen binding fragment is an anti-MSLN antibody or antigen binding fragment.

In some other embodiments, the antibody or antigen binding fragment targets a FOLH1-expressing cell. In some embodiments, the antibody or antigen binding fragment is an anti-FOLH1 antibody or antigen binding fragment.

In some other embodiments, the antibody or antigen binding fragment targets a CDH6-expressing cell. In some embodiments, the antibody or antigen binding fragment is an anti-CDH6 antibody or antigen binding fragment.

In some other embodiments, the antibody or antigen binding fragment targets a CEACAM5-expressing cell. In some embodiments, the antibody or antigen binding fragment is an anti-CEACAM5 antibody or antigen binding fragment.

In some other embodiments, the antibody or antigen binding fragment targets a CFC1B-expressing cell. In some embodiments, the antibody or antigen binding fragment is an anti-CFC1B antibody or antigen binding fragment.

In some other embodiments, the antibody or antigen binding fragment targets an ENPP3-expressing cell. In some embodiments, the antibody or antigen binding fragment is an anti-ENPP3 antibody or antigen binding fragment.

In some other embodiments, the antibody or antigen binding fragment targets a FOLR1-expressing cell. In some embodiments, the antibody or antigen binding fragment is an anti-FOLR1 antibody or antigen binding fragment.

In some other embodiments, the antibody or antigen binding fragment targets a HAVCR1-expressing cell. In some embodiments, the antibody or antigen binding fragment is an anti-HAVCR1 antibody or antigen binding fragment.

In some other embodiments, the antibody or antigen binding fragment targets a KIT-expressing cell. In some embodiments, the antibody or antigen binding fragment is an anti-KIT antibody or antigen binding fragment.

In some other embodiments, the antibody or antigen binding fragment targets a MET-expressing cell. In some embodiments, the antibody or antigen binding fragment is an anti-MET antibody or antigen binding fragment.

In some other embodiments, the antibody or antigen binding fragment targets a MUC16-expressing cell. In some embodiments, the antibody or antigen binding fragment is an anti-MUC16 antibody or antigen binding fragment.

In some other embodiments, the antibody or antigen binding fragment targets a SLC39A6-expressing cell. In some embodiments, the antibody or antigen binding fragment is an anti-SLC39A6 antibody or antigen binding fragment.

In some other embodiments, the antibody or antigen binding fragment targets a SLC44A4-expressing cell. In some embodiments, the antibody or antigen binding fragment is an anti-SLC44A4 antibody or antigen binding fragment.

In some other embodiments, the antibody or antigen binding fragment targets a STEAP1-expressing cell. In some embodiments, the antibody or antigen binding fragment is an anti-STEAP1 antibody or antigen binding fragment.

In some embodiments, L is selected from any of the linkers disclosed herein, or any combination of linker components disclosed herein. In some embodiments, L is a linker comprising MC-Val-Cit-pABC, Mal-(PEG)$_2$-CO, MC-Val-Ala-pAB, MC-Val-Ala-pABC, MC-Val-Cit-pAB, Mal-Hex, Mal-Et, or Mal-Et-O-Et. In some embodiments, the linker may also comprise one or more additional spacer units. In some embodiments, L is an ADL1, ADL2, ADL5, ADL6, ADL7, ADL12, ADL13, ADL14, ADL21, ADL23, or ADL15 linker. In some embodiments, L is an ADL12, ADL14, or ADL15 linker. In some embodiments, the ADL1, ADL2, ADL5, ADL6, ADL7, ADL12, ADL13, ADL14, ADL21, ADL23, or ADL15 linker may also comprise one or more additional spacer units.

Another exemplary ADC has Formula (I):

$$Ab-(L-D)_p \qquad (I)$$

wherein
  Ab is an antibody or antigen binding fragment which targets a neoplastic cell;
  D is D1;
  L is a linker that covalently attaches Ab to D; and
  p is an integer from 1 to 15.

In some embodiments, the antibody or antigen binding fragment targets a cell expressing HER2, CD138, EPHA2, MSLN, FOLH1, CDH6, CEACAM5, CFC1B, ENPP3, FOLR1, HAVCR1, KIT, MET, MUC16, SLC39A6, SLC44A4, and/or STEAP1.

In some embodiments, the antibody or antigen binding fragment targets a HER2-expressing cell. In some embodiments, the antibody or antigen binding fragment is an anti-HER2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:1 (HCDR1), SEQ ID NO:2 (HCDR2), and SEQ ID NO:3 (HCDR3); and three light chain complementarity determining regions (LCDR1, LCDR2, and LCDR3) comprising amino acid sequences of SEQ ID NO:4 (LCDR1), SEQ ID NO:5 (LCDR2), and SEQ ID NO:6 (LCDR3). In some embodiments, the antibody or antigen binding fragment comprises a heavy chain variable region comprising an amino acid sequence of SEQ ID NO:19, and a light chain variable region comprising an amino acid sequence of SEQ ID NO:20. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a CD138-expressing cell. In some embodiments, the antibody or antigen binding fragment is an anti-CD138 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:7 (HCDR1), SEQ ID NO:8 (HCDR2), and SEQ ID NO:9 (HCDR3); and three light chain complementarity determining regions (LCDR1, LCDR2, and LCDR3) comprising amino acid sequences of SEQ ID NO:10 (LCDR1), SEQ ID NO:11 (LCDR2), and SEQ ID NO:12 (LCDR3). In some embodiments, the antibody or antigen binding fragment comprises a heavy chain variable region comprising an amino acid sequence of SEQ ID NO:21, and a light chain variable region comprising an amino acid sequence of SEQ ID NO:22. In some embodiments, the antibody or antigen binding fragment comprises a murine IgG2a heavy chain constant region. In some embodiments, the antibody or antigen binding fragment comprises a murine Ig kappa light chain constant region. In some embodiments, the antibody or antigen binding fragment comprises a human IgG2a heavy chain constant region. In some embodiments, the antibody or antigen binding fragment comprises a human Ig kappa light chain constant region.

In some other embodiments, the antibody or antigen binding fragment targets an EPHA2-expressing cell. In some embodiments, the antibody or antigen binding fragment is an anti-EPHA2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:13 (HCDR1), SEQ ID NO:14 (HCDR2), and SEQ ID NO:15 (HCDR3); and three light chain complementarity determining regions (LCDR1, LCDR2, and LCDR3) comprising amino acid sequences of SEQ ID NO:16 (LCDR1), SEQ ID NO:17 (LCDR2), and SEQ ID NO:18 (LCDR3). In some embodiments, the antibody or antigen binding fragment comprises a heavy chain variable region comprising an amino acid sequence of SEQ ID NO:23, and a light chain variable region comprising an amino acid sequence of SEQ ID NO:24. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a MSLN-expressing cell. In some embodiments, the antibody or antigen binding fragment is an anti-MSLN antibody or antigen binding fragment.

In some other embodiments, the antibody or antigen binding fragment targets a FOLH1-expressing cell. In some embodiments, the antibody or antigen binding fragment is an anti-FOLH1 antibody or antigen binding fragment.

In some other embodiments, the antibody or antigen binding fragment targets a CDH6-expressing cell. In some embodiments, the antibody or antigen binding fragment is an anti-CDH6 antibody or antigen binding fragment.

In some other embodiments, the antibody or antigen binding fragment targets a CEACAM5-expressing cell. In some embodiments, the antibody or antigen binding fragment is an anti-CEACAM5 antibody or antigen binding fragment.

In some other embodiments, the antibody or antigen binding fragment targets a CFC1B-expressing cell. In some embodiments, the antibody or antigen binding fragment is an anti-CFC1B antibody or antigen binding fragment.

In some other embodiments, the antibody or antigen binding fragment targets an ENPP3-expressing cell. In some embodiments, the antibody or antigen binding fragment is an anti-ENPP3 antibody or antigen binding fragment.

In some other embodiments, the antibody or antigen binding fragment targets a FOLR1-expressing cell. In some embodiments, the antibody or antigen binding fragment is an anti-FOLR1 antibody or antigen binding fragment.

In some other embodiments, the antibody or antigen binding fragment targets a HAVCR1-expressing cell. In some embodiments, the antibody or antigen binding fragment is an anti-HAVCR1 antibody or antigen binding fragment.

In some other embodiments, the antibody or antigen binding fragment targets a KIT-expressing cell. In some embodiments, the antibody or antigen binding fragment is an anti-KIT antibody or antigen binding fragment.

In some other embodiments, the antibody or antigen binding fragment targets a MET-expressing cell. In some embodiments, the antibody or antigen binding fragment is an anti-MET antibody or antigen binding fragment.

In some other embodiments, the antibody or antigen binding fragment targets a MUC16-expressing cell. In some embodiments, the antibody or antigen binding fragment is an anti-MUC16 antibody or antigen binding fragment.

In some other embodiments, the antibody or antigen binding fragment targets a SLC39A6-expressing cell. In some embodiments, the antibody or antigen binding fragment is an anti-SLC39A6 antibody or antigen binding fragment.

In some other embodiments, the antibody or antigen binding fragment targets a SLC44A4-expressing cell. In some embodiments, the antibody or antigen binding fragment is an anti-SLC44A4 antibody or antigen binding fragment.

In some other embodiments, the antibody or antigen binding fragment targets a STEAP1-expressing cell. In some embodiments, the antibody or antigen binding fragment is an anti-STEAP1 antibody or antigen binding fragment.

Another exemplary ADC has Formula (I):

$$Ab-(L-D)_p \quad (I)$$

wherein

Ab is an antibody or antigen binding fragment which targets a neoplastic cell;

D is D4;

L is a linker that covalently attaches Ab to D; and p is an integer from 1 to 15.

In some embodiments, the antibody or antigen binding fragment targets a cell expressing HER2, CD138, EPHA2, MSLN, FOLH1, CDH6, CEACAM5, CFC1B, ENPP3, FOLR1, HAVCR1, KIT, MET, MUC16, SLC39A6, SLC44A4, and/or STEAP1.

In some embodiments, the antibody or antigen binding fragment targets a HER2-expressing cell. In some embodiments, the antibody or antigen binding fragment is an anti-HER2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:1 (HCDR1), SEQ ID NO:2 (HCDR2), and SEQ ID NO:3 (HCDR3); and three light chain complementarity determining regions (LCDR1, LCDR2, and LCDR3) comprising amino acid sequences of SEQ ID NO:4 (LCDR1), SEQ ID NO:5 (LCDR2), and SEQ ID NO:6 (LCDR3). In some embodiments, the antibody or antigen binding fragment comprises a heavy chain variable region comprising an amino acid sequence of SEQ ID NO:19, and a light chain variable region comprising an amino acid sequence of SEQ ID NO:20. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a CD138-expressing cell. In some embodiments, the antibody or antigen binding fragment is an anti-CD138 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:7 (HCDR1), SEQ ID NO:8 (HCDR2), and SEQ ID NO:9 (HCDR3); and three light chain complementarity determining regions (LCDR1, LCDR2, and LCDR3) comprising amino acid sequences of SEQ ID NO:10 (LCDR1), SEQ ID NO:11 (LCDR2), and SEQ ID NO:12 (LCDR3). In some embodiments, the antibody or antigen binding fragment comprises a heavy chain variable region comprising an amino acid sequence of SEQ ID NO:21, and a light chain variable region comprising an amino acid sequence of SEQ ID NO:22. In some embodiments, the antibody or antigen binding fragment comprises a murine IgG2a heavy chain constant region. In some embodiments, the antibody or antigen binding fragment comprises a murine Ig kappa light chain constant region. In some embodiments, the antibody or antigen binding fragment comprises a human IgG2a heavy chain constant region. In some embodiments, the antibody or antigen binding fragment comprises a human Ig kappa light chain constant region.

In some other embodiments, the antibody or antigen binding fragment targets an EPHA2-expressing cell. In some embodiments, the antibody or antigen binding fragment is an anti-EPHA2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:13 (HCDR1), SEQ ID NO:14 (HCDR2), and SEQ ID NO:15 (HCDR3); and three light chain complementarity determining regions (LCDR1, LCDR2, and LCDR3) comprising amino acid sequences of SEQ ID NO:16 (LCDR1), SEQ ID NO:17 (LCDR2), and SEQ ID NO:18 (LCDR3). In some embodiments, the antibody or antigen binding fragment comprises a heavy chain variable region comprising an amino acid sequence of SEQ ID NO:23, and a light chain variable region comprising an amino acid sequence of SEQ ID NO:24. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a MSLN-expressing cell. In some embodiments, the antibody or antigen binding fragment is an anti-MSLN antibody or antigen binding fragment.

In some other embodiments, the antibody or antigen binding fragment targets a FOLH1-expressing cell. In some embodiments, the antibody or antigen binding fragment is an anti-FOLH1 antibody or antigen binding fragment.

In some other embodiments, the antibody or antigen binding fragment targets a CDH6-expressing cell. In some embodiments, the antibody or antigen binding fragment is an anti-CDH6 antibody or antigen binding fragment.

In some other embodiments, the antibody or antigen binding fragment targets a CEACAM5-expressing cell. In some embodiments, the antibody or antigen binding fragment is an anti-CEACAM5 antibody or antigen binding fragment.

In some other embodiments, the antibody or antigen binding fragment targets a CFC1B-expressing cell. In some embodiments, the antibody or antigen binding fragment is an anti-CFC1B antibody or antigen binding fragment.

In some other embodiments, the antibody or antigen binding fragment targets a ENPP3-expressing cell. In some embodiments, the antibody or antigen binding fragment is an anti-ENPP3 antibody or antigen binding fragment.

In some other embodiments, the antibody or antigen binding fragment targets a FOLR1-expressing cell. In some embodiments, the antibody or antigen binding fragment is an anti-FOLR1 antibody or antigen binding fragment.

In some other embodiments, the antibody or antigen binding fragment targets a HAVCR1-expressing cell. In some embodiments, the antibody or antigen binding fragment is an anti-HAVCR1 antibody or antigen binding fragment.

In some other embodiments, the antibody or antigen binding fragment targets a KIT-expressing cell. In some embodiments, the antibody or antigen binding fragment is an anti-KIT antibody or antigen binding fragment.

In some other embodiments, the antibody or antigen binding fragment targets a MET-expressing cell. In some embodiments, the antibody or antigen binding fragment is an anti-MET antibody or antigen binding fragment.

In some other embodiments, the antibody or antigen binding fragment targets a MUC16-expressing cell. In some embodiments, the antibody or antigen binding fragment is an anti-MUC16 antibody or antigen binding fragment.

In some other embodiments, the antibody or antigen binding fragment targets a SLC39A6-expressing cell. In some embodiments, the antibody or antigen binding fragment is an anti-SLC39A6 antibody or antigen binding fragment.

In some other embodiments, the antibody or antigen binding fragment targets a SLC44A4-expressing cell. In some embodiments, the antibody or antigen binding fragment is an anti-SLC44A4 antibody or antigen binding fragment.

In some other embodiments, the antibody or antigen binding fragment targets a STEAP1-expressing cell. In some embodiments, the antibody or antigen binding fragment is an anti-STEAP1 antibody or antigen binding fragment.

Another exemplary ADC has Formula (I):

$$Ab-(L-D)_p \quad (I)$$

wherein
Ab is an antibody or antigen binding fragment which targets a neoplastic cell;
D is D12;
L is a linker that covalently attaches Ab to D; and
p is an integer from 1 to 15.

In some embodiments, the antibody or antigen binding fragment targets a cell expressing HER2, CD138, EPHA2, MSLN, FOLH1, CDH6, CEACAM5, CFC1B, ENPP3, FOLR1, HAVCR1, KIT, MET, MUC16, SLC39A6, SLC44A4, and/or STEAP1.

In some embodiments, the antibody or antigen binding fragment targets a HER2-expressing cell. In some embodiments, the antibody or antigen binding fragment is an anti-HER2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:1 (HCDR1), SEQ ID NO:2 (HCDR2), and SEQ ID NO:3 (HCDR3); and three light chain complementarity determining regions (LCDR1, LCDR2, and LCDR3) comprising amino acid sequences of SEQ ID NO:4 (LCDR1), SEQ ID NO:5 (LCDR2), and SEQ ID NO:6 (LCDR3). In some embodiments, the antibody or antigen binding fragment comprises a heavy chain variable region comprising an amino acid sequence of SEQ ID NO:19, and a light chain variable region comprising an amino acid sequence of SEQ ID NO:20. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a CD138-expressing cell. In some embodiments, the antibody or antigen binding fragment is an anti-CD138 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:7 (HCDR1), SEQ ID NO:8 (HCDR2), and SEQ ID NO:9 (HCDR3); and three light chain complementarity determining regions (LCDR1, LCDR2, and LCDR3) comprising amino acid sequences of SEQ ID NO:10 (LCDR1), SEQ ID NO:11 (LCDR2), and SEQ ID NO:12 (LCDR3). In some embodiments, the antibody or antigen binding fragment comprises a heavy chain variable region comprising an amino acid sequence of SEQ ID NO:21, and a light chain variable region comprising an amino acid sequence of SEQ ID NO:22. In some embodiments, the antibody or antigen binding fragment comprises a murine IgG2a heavy chain constant region. In some embodiments, the antibody or antigen binding fragment comprises a murine Ig kappa light chain constant region. In some embodiments, the antibody or antigen binding fragment comprises a human IgG2a heavy chain constant region. In some embodiments, the antibody or antigen binding fragment comprises a human Ig kappa light chain constant region.

In some other embodiments, the antibody or antigen binding fragment targets an EPHA2-expressing cell. In some embodiments, the antibody or antigen binding fragment is an anti-EPHA2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:13 (HCDR1), SEQ ID NO:14 (HCDR2), and SEQ ID NO:15 (HCDR3); and three light chain complementarity determining regions (LCDR1, LCDR2, and LCDR3) comprising amino acid sequences of SEQ ID NO:16 (LCDR1), SEQ ID NO:17 (LCDR2), and SEQ ID NO:18 (LCDR3). In some embodiments, the antibody or antigen binding fragment comprises a heavy chain variable region comprising an amino acid sequence of SEQ ID NO:23, and a light chain variable region comprising an amino acid sequence of SEQ ID NO:24. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a MSLN-expressing cell. In some embodiments, the antibody or antigen binding fragment is an anti-MSLN antibody or antigen binding fragment.

In some other embodiments, the antibody or antigen binding fragment targets a FOLH1-expressing cell. In some embodiments, the antibody or antigen binding fragment is an anti-FOLH1 antibody or antigen binding fragment.

In some other embodiments, the antibody or antigen binding fragment targets a CDH6-expressing cell. In some embodiments, the antibody or antigen binding fragment is an anti-CDH6 antibody or antigen binding fragment.

In some other embodiments, the antibody or antigen binding fragment targets a CEACAM5-expressing cell. In some embodiments, the antibody or antigen binding fragment is an anti-CEACAM5 antibody or antigen binding fragment.

In some other embodiments, the antibody or antigen binding fragment targets a CFC1B-expressing cell. In some embodiments, the antibody or antigen binding fragment is an anti-CFC1B antibody or antigen binding fragment.

In some other embodiments, the antibody or antigen binding fragment targets a ENPP3-expressing cell. In some embodiments, the antibody or antigen binding fragment is an anti-ENPP3 antibody or antigen binding fragment.

In some other embodiments, the antibody or antigen binding fragment targets a FOLR1-expressing cell. In some embodiments, the antibody or antigen binding fragment is an anti-FOLR1 antibody or antigen binding fragment.

In some other embodiments, the antibody or antigen binding fragment targets a HAVCR1-expressing cell. In some embodiments, the antibody or antigen binding fragment is an anti-HAVCR1 antibody or antigen binding fragment.

In some other embodiments, the antibody or antigen binding fragment targets a KIT-expressing cell. In some embodiments, the antibody or antigen binding fragment is an anti-KIT antibody or antigen binding fragment.

In some other embodiments, the antibody or antigen binding fragment targets a MET-expressing cell. In some embodiments, the antibody or antigen binding fragment is an anti-MET antibody or antigen binding fragment.

In some other embodiments, the antibody or antigen binding fragment targets a MUC16-expressing cell. In some embodiments, the antibody or antigen binding fragment is an anti-MUC16 antibody or antigen binding fragment.

In some other embodiments, the antibody or antigen binding fragment targets a SLC39A6-expressing cell. In some embodiments, the antibody or antigen binding fragment is an anti-SLC39A6 antibody or antigen binding fragment.

In some other embodiments, the antibody or antigen binding fragment targets a SLC44A4-expressing cell. In some embodiments, the antibody or antigen binding fragment is an anti-SLC44A4 antibody or antigen binding fragment.

In some other embodiments, the antibody or antigen binding fragment targets a STEAP1-expressing cell. In some embodiments, the antibody or antigen binding fragment is an anti-STEAP1 antibody or antigen binding fragment.

Another exemplary ADC has Formula (I):

$$Ab-(L-D)_p \quad (I)$$

wherein
Ab is an antibody or antigen binding fragment which targets a neoplastic cell;
D is D15;
L is a linker that covalently attaches Ab to D; and
p is an integer from 1 to 15.

In some embodiments, the antibody or antigen binding fragment targets a cell expressing HER2, CD138, EPHA2, MSLN, FOLH1, CDH6, CEACAM5, CFC1B, ENPP3, FOLR1, HAVCR1, KIT, MET, MUC16, SLC39A6, SLC44A4, and/or STEAP1.

In some embodiments, the antibody or antigen binding fragment targets a HER2-expressing cell. In some embodiments, the antibody or antigen binding fragment is an anti-HER2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:1 (HCDR1), SEQ ID NO:2 (HCDR2), and SEQ ID NO:3 (HCDR3); and three light chain complementarity determining regions (LCDR1, LCDR2, and LCDR3) comprising amino acid sequences of SEQ ID NO:4 (LCDR1), SEQ ID NO:5 (LCDR2), and SEQ ID NO:6 (LCDR3). In some embodiments, the antibody or antigen binding fragment comprises a heavy chain variable region comprising an amino acid sequence of SEQ ID NO:19, and a light chain variable region comprising an amino acid sequence of SEQ ID NO:20. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a CD138-expressing cell. In some embodiments, the antibody or antigen binding fragment is an anti-CD138 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:7 (HCDR1), SEQ ID NO:8 (HCDR2), and SEQ ID NO:9 (HCDR3); and three light chain complementarity determining regions (LCDR1, LCDR2, and LCDR3) comprising amino acid sequences of SEQ ID NO:10 (LCDR1), SEQ ID NO:11 (LCDR2), and SEQ ID NO:12 (LCDR3). In some embodiments, the antibody or antigen binding fragment comprises a heavy chain variable region comprising an amino acid sequence of SEQ ID NO:21, and a light chain variable region comprising an amino acid sequence of SEQ ID NO:22. In some embodiments, the antibody or antigen binding fragment comprises a murine IgG2a heavy chain constant region. In some embodiments, the antibody or antigen binding fragment comprises a murine Ig kappa light chain constant region. In some embodiments, the antibody or antigen binding fragment comprises a human IgG2a heavy chain constant region. In some embodiments, the antibody or antigen binding fragment comprises a human Ig kappa light chain constant region.

In some other embodiments, the antibody or antigen binding fragment targets an EPHA2-expressing cell. In some embodiments, the antibody or antigen binding fragment is an anti-EPHA2 antibody or antigen binding fragment. In some embodiments, the antibody or antigen binding fragment comprises three heavy chain complementarity determining regions (HCDR1, HCDR2, and HCDR3) comprising amino acid sequences of SEQ ID NO:13 (HCDR1), SEQ ID NO:14 (HCDR2), and SEQ ID NO:15 (HCDR3); and three light chain complementarity determining regions (LCDR1, LCDR2, and LCDR3) comprising amino acid sequences of SEQ ID NO:16 (LCDR1), SEQ ID NO:17 (LCDR2), and SEQ ID NO:18 (LCDR3). In some embodiments, the antibody or antigen binding fragment comprises a heavy chain variable region comprising an amino acid sequence of SEQ ID NO:23, and a light chain variable region comprising an amino acid sequence of SEQ ID NO:24. In some embodiments, the antibody or antigen binding fragment comprises a human IgG1 heavy chain constant region. In some embodiments, the antibody or antigen binding fragment comprises a human Ig kappa light chain constant region.

In some other embodiments, the antibody or antigen binding fragment targets a MSLN-expressing cell. In some embodiments, the antibody or antigen binding fragment is an anti-MSLN antibody or antigen binding fragment.

In some other embodiments, the antibody or antigen binding fragment targets a FOLH1-expressing cell. In some embodiments, the antibody or antigen binding fragment is an anti-FOLH1 antibody or antigen binding fragment.

In some other embodiments, the antibody or antigen binding fragment targets a CDH6-expressing cell. In some embodiments, the antibody or antigen binding fragment is an anti-CDH6 antibody or antigen binding fragment.

In some other embodiments, the antibody or antigen binding fragment targets a CEACAM5-expressing cell. In some embodiments, the antibody or antigen binding fragment is an anti-CEACAM5 antibody or antigen binding fragment.

In some other embodiments, the antibody or antigen binding fragment targets a CFC1B-expressing cell. In some embodiments, the antibody or antigen binding fragment is an anti-CFC1B antibody or antigen binding fragment.

In some other embodiments, the antibody or antigen binding fragment targets a ENPP3-expressing cell. In some embodiments, the antibody or antigen binding fragment is an anti-ENPP3 antibody or antigen binding fragment.

In some other embodiments, the antibody or antigen binding fragment targets a FOLR1-expressing cell. In some embodiments, the antibody or antigen binding fragment is an anti-FOLR1 antibody or antigen binding fragment.

In some other embodiments, the antibody or antigen binding fragment targets a HAVCR1-expressing cell. In some embodiments, the antibody or antigen binding fragment is an anti-HAVCR1 antibody or antigen binding fragment.

In some other embodiments, the antibody or antigen binding fragment targets a KIT-expressing cell. In some embodiments, the antibody or antigen binding fragment is an anti-KIT antibody or antigen binding fragment.

In some other embodiments, the antibody or antigen binding fragment targets a MET-expressing cell. In some embodiments, the antibody or antigen binding fragment is an anti-MET antibody or antigen binding fragment.

In some other embodiments, the antibody or antigen binding fragment targets a MUC16-expressing cell. In some embodiments, the antibody or antigen binding fragment is an anti-MUC16 antibody or antigen binding fragment.

In some other embodiments, the antibody or antigen binding fragment targets a SLC39A6-expressing cell. In some embodiments, the antibody or antigen binding fragment is an anti-SLC39A6 antibody or antigen binding fragment.

In some other embodiments, the antibody or antigen binding fragment targets a SLC44A4-expressing cell. In some embodiments, the antibody or antigen binding fragment is an anti-SLC44A4 antibody or antigen binding fragment.

In some other embodiments, the antibody or antigen binding fragment targets a STEAP1-expressing cell. In some embodiments, the antibody or antigen binding fragment is an anti-STEAP1 antibody or antigen binding fragment.

In some embodiments, L is selected from any of the linkers disclosed herein, or any combination of linker components disclosed herein. In some embodiments, L is a cleavable linker. In some embodiments, L is a non-cleavable linker. In some embodiments, L is a linker comprising MC-Val-Cit-pABC, MC-Val-Ala-pABC, MC-Val-Ala-pAB, MC-Glu-Val-Cit-pABC, Ala-Ala-Asn-pABC, or β-glucuronide. In some embodiments, L is a linker comprising Mal-Hex, Mal-Et, or Mal-Et-O-Et. In some embodiments, L is a linker comprising MC-Val-Cit-pABC, Mal-(PEG)$_2$-CO, MC-Val-Ala-pAB, MC-Val-Ala-pABC, MC-Val-Cit-pAB, Mal-Hex, Mal-Et, or Mal-Et-O-Et. In some embodiments, the linker may also comprise one or more additional spacer units. In some embodiments, L is an ADL1, ADL2, ADL5, ADL6, ADL7, ADL12, ADL13, ADL14, ADL21, ADL23, or ADL15 linker. In some embodiments, L is an ADL12, ADL14, or ADL15 linker. In some embodiments, the ADL1, ADL2, ADL5, ADL6, ADL7, ADL12, ADL13, ADL14, ADL21, ADL23, or ADL15 linker may also comprise one or more additional spacer units.

In some embodiments, p is from 1 to 10. In some embodiments, p is from 2 to 8.

In some embodiments, p is from 4 to 8. In some embodiments, p is 4. In some embodiments, p is 8.

Another exemplary ADC has Formula (I):

$$Ab-(L-D)_p \qquad (I)$$

wherein Ab is an anti-HER2 antibody or antigen binding fragment comprising three heavy chain complementarity determining regions (HCDR1, HCDR2, and HCDR3) comprising amino acid sequences of SEQ ID NO:1 (HCDR1), SEQ ID NO:2 (HCDR2), and SEQ ID NO:3 (HCDR3); and three light chain complementarity determining regions (LCDR1, LCDR2, and LCDR3) comprising amino acid sequences of SEQ ID NO:4 (LCDR1), SEQ ID NO:5 (LCDR2), and SEQ ID NO:6 (LCDR3);

D is D2, D1, D4, D12, or D15;

L is a linker that covalently attaches Ab to D; and p is an integer from 1 to 15.

In some embodiments, the antibody or antigen binding fragment comprises a heavy chain variable region comprising an amino acid sequence of SEQ ID NO:19, and a light chain variable region comprising an amino acid sequence of SEQ ID NO:20.

In some embodiments, L is selected from any of the linkers disclosed herein, or any combination of linker components disclosed herein. In some embodiments, L is a linker comprising MC-Val-Cit-pABC, Mal-(PEG)$_2$-CO, MC-Val-Ala-pAB, MC-Val-Ala-pABC, MC-Val-Cit-pAB, Mal-Hex, Mal-Et, or Mal-Et-O-Et. In some embodiments, the linker may also comprise one or more additional spacer units. In some embodiments, L is an ADL1, ADL2, ADL5, ADL6, ADL7, ADL12, ADL13, ADL14, ADL21, ADL23, or ADL15 linker. In some embodiments, L is an ADL12, ADL14, or ADL15 linker. In some embodiments, the ADL1, ADL2, ADL5, ADL6, ADL7, ADL12, ADL13, ADL14, ADL21, ADL23, or ADL15 linker may also comprise one or more additional spacer units.

Another exemplary ADC has Formula (I):

$$Ab-(L-D)_p \qquad (I)$$

wherein Ab is an anti-CD138 antibody or antigen binding fragment comprising three heavy chain complementarity determining regions (HCDR1, HCDR2, and HCDR3) comprising amino acid sequences of SEQ ID NO:7 (HCDR1), SEQ ID NO:8 (HCDR2), and SEQ ID NO:9 (HCDR3); and three light chain complementarity determining regions (LCDR1, LCDR2, and LCDR3) comprising amino acid sequences of SEQ ID NO:10 (LCDR1), SEQ ID NO:11 (LCDR2), and SEQ ID NO:12 (LCDR3);

D is D2, D1, D4, D12, or D15;

L is a linker that covalently attaches Ab to D; and p is an integer from 1 to 15.

In some embodiments, the antibody or antigen binding fragment comprises a heavy chain variable region comprising an amino acid sequence of SEQ ID NO:21, and a light chain variable region comprising an amino acid sequence of SEQ ID NO:22.

In some embodiments, L is selected from any of the linkers disclosed herein, or any combination of linker components disclosed herein. In some embodiments, L is a linker comprising MC-Val-Cit-pABC, Mal-(PEG)$_2$-CO, MC-Val-Ala-pAB, MC-Val-Ala-pABC, MC-Val-Cit-pAB, Mal-Hex, Mal-Et, or Mal-Et-O-Et. In some embodiments, the linker may also comprise one or more additional spacer units. In some embodiments, L is an ADL1, ADL2, ADL5, ADL6, ADL7, ADL12, ADL13, ADL14, ADL21, ADL23, or ADL15 linker. In some embodiments, L is an ADL12, ADL14, or ADL15 linker. In some embodiments, the ADL1, ADL2, ADL5, ADL6, ADL7, ADL12, ADL13, ADL14, ADL21, ADL23, or ADL15 linker may also comprise one or more additional spacer units.

Another exemplary ADC has Formula (I):

$$Ab-(L-D)_p \qquad (I)$$

wherein Ab is an anti-EPHA2 antibody or antigen binding fragment comprising three heavy chain complementarity determining regions (HCDR1, HCDR2, and HCDR3) comprising amino acid sequences of SEQ ID NO:13 (HCDR1), SEQ ID NO:14 (HCDR2), and SEQ ID NO:15 (HCDR3); and three light chain complementarity determining regions (LCDR1, LCDR2, and LCDR3) comprising amino acid sequences of SEQ ID NO:16 (LCDR1), SEQ ID NO:17 (LCDR2), and SEQ ID NO:18 (LCDR3);

D is D2, D1, D4, D12, or D15;

L is a linker that covalently attaches Ab to D; and p is an integer from 1 to 15.

In some embodiments, the antibody or antigen binding fragment comprises a heavy chain variable region comprising an amino acid sequence of SEQ ID NO:23, and a light chain variable region comprising an amino acid sequence of SEQ ID NO:24.

In some embodiments, L is selected from any of the linkers disclosed herein, or any combination of linker components disclosed herein. In some embodiments, L is a linker comprising MC-Val-Cit-pABC, Mal-(PEG)$_2$-CO, MC-Val-Ala-pAB, MC-Val-Ala-pABC, MC-Val-Cit-pAB, Mal-Hex, Mal-Et, or Mal-Et-O-Et. In some embodiments, the linker may also comprise one or more additional spacer units. In some embodiments, L is an ADL1, ADL2, ADL5, ADL6, ADL7, ADL12, ADL13, ADL14, ADL21, ADL23, or ADL15 linker. In some embodiments, L is an ADL12, ADL14, or ADL15 linker. In some embodiments, the ADL1, ADL2, ADL5, ADL6, ADL7, ADL12, ADL13, ADL14, ADL21, ADL23, or ADL15 linker may also comprise one or more additional spacer units.

In various embodiments, ADCs comprising a D2 or D1 drug moiety can include a cleavable or non-cleavable linker.

In various embodiments, the linker is a cleavable linker. In various embodiments, the cleavable linker comprises MC-Val-Cit-pABC. In various embodiments, the cleavable linker comprises MC-Val-Ala-pABC. In various embodiments, the cleavable linker comprises MC-Val-Ala-pAB. In various embodiments, the cleavable linker comprises MC-Glu-Val-Cit-pABC. In various embodiments, the cleavable linker comprises MC-Ala-Ala-Asn-pABC.

In various other embodiments, the linker is a non-cleavable linker. In various embodiments, the non-cleavable linker comprises MC, alone or in combination with at least one additional spacer unit. In various embodiments, the non-cleavable linker comprises Mal-Hex, alone or in combination with at least one additional spacer unit. In various embodiments, the non-cleavable linker comprises Mal-Et, alone or in combination with at least one additional spacer unit. In various embodiments, the non-cleavable linker comprises Mal-Et-O-Et, alone or in combination with at least one additional spacer unit.

In various embodiments, in ADCs comprising a D2 or D1 drug moiety, p is from 1 to 10. In various embodiments, p is from 2 to 8. In various embodiments, p is from 4 to 8. In various embodiments, p is 4. In various embodiments, p is 8.

In various embodiments, an ADC comprising a D2 or D1 drug moiety as disclosed herein demonstrates improved drug:antibody ratio, lower aggregation levels, increased stability, increased on-target killing of cancer cells, decreased off-target killing of non-cancer cells, and/or increased cytotoxicity and/or potency relative to an ADC comprising an alternate drug moiety (e.g., an alternate splicing modulator drug moiety). In some embodiments, an ADC comprising a D2 or D1 drug moiety as disclosed herein provides good or superior properties in one or more of the categories listed above, or across a spectrum of functional properties for a therapeutic ADC. In some embodiments, an ADC comprising a D2 or D1 drug moiety exhibits surprisingly effective potency and increased inhibition of cell growth and/or proliferation in cells that express the antigen targeted by the ADC, as compared to an ADC comprising an alternate drug moiety (e.g., an alternate splicing modulator drug moiety). In some embodiments, potency can be measured in terms of the concentration of compound to cause 50% reduction in cell proliferation (GI$_{50}$). In various embodiments, ADCs comprising a D2 or D1 drug moiety exhibit surprisingly increased in vivo stability (e.g., plasma stability), as compared to an ADC with an alternate drug moiety (e.g., an alternate splicing modulator drug moiety, e.g., thailanstatin A). See, e.g., the ADC described in Puthenveetil et al. (Bioconjugate Chem. (2016) 27:1880-8), which shows complete bioconversion of payload by 72 hours (i.e., acetate is completely hydrolyzed).

In certain embodiments, an intermediate, which is the precursor of the linker moiety, is reacted with the drug moiety (e.g., the splicing modulator) under appropriate conditions. In certain embodiments, reactive groups are used on the drug and/or the intermediate or linker. The product of the reaction between the drug and the intermediate, or the derivatized drug (drug plus linker), is subsequently reacted with the antibody or antigen binding fragment under appropriate conditions. Alternatively, the intermediate or linker may first be reacted with the antibody or antigen binding fragment, or a derivatized antibody or antigen binding fragment, and then reacted with the drug or derivatized drug.

A number of different reactions are available for covalent attachment of the drug moiety and/or linker moiety to the antibody or antigen binding fragment. This is often accomplished by reaction of one or more amino acid residues of the antibody or antigen binding fragment, including the amine groups of lysine, the free carboxylic acid groups of glutamic acid and aspartic acid, the sulfhydryl groups of cysteine, and the various moieties of the aromatic amino acids. For instance, non-specific covalent attachment may be undertaken using a carbodiimide reaction to link a carboxy (or amino) group on a drug moiety to an amino (or carboxy) group on an antibody or antigen binding fragment. Additionally, bifunctional agents such as dialdehydes or imidoesters may also be used to link the amino group on a drug moiety to an amino group on an antibody or antigen binding fragment. Also available for attachment of drugs (e.g., a splicing modulator) to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates may also be used as coupling agents for covalently attaching drugs to binding agents. Other techniques are known to the skilled artisan and within the scope of the present disclosure. Examples of drug moieties that can be generated and linked to an antibody or antigen binding fragment using various chemistries known to in the art include splicing modulators, e.g., the splicing modulators described and exemplified herein.

Linker-Drug/Drug Compounds

Further disclosed herein are exemplary linker-drug (L–D) compounds, as well as compositions comprising multiple copies of such compounds. In various embodiments, the linker-drug compounds disclosed herein can be defined by the generic formula: L–D, wherein L=a linker moiety, and D=a drug moiety (e.g., a splicing modulator drug moiety). In certain embodiments, the disclosed L–D compounds are suitable for use in the ADCs described herein, e.g., in ADCs of Formula (I).

In various embodiments, the linker-drug (L–D) compounds disclosed herein comprise a linker-drug structure according to Formula (III). In various embodiments, the present disclosure provides a linker-drug (L–D) compound of Formula (III):

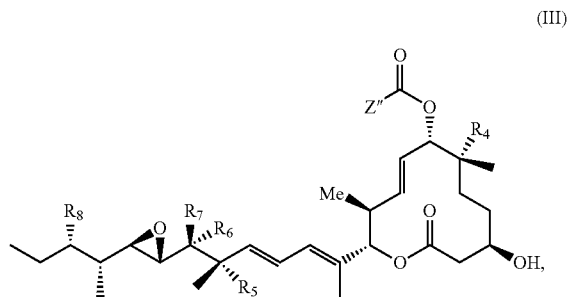

(III)

or a pharmaceutically acceptable salt thereof, wherein:
$R^1$ is chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(=O)—($C_1$-$C_6$ alkyl) groups, and —$CD_3$;
$R^2$ is absent or a linker;
$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups; and
$R^4$, $R^5$, and $R^3$ are each independently chosen from hydrogen, hydroxyl groups, —O—($C_1$-$C_6$ alkyl) groups, —O—C(=O)—($C_1$-$C_6$ alkyl) groups, and $C_1$-$C_6$ alkyl groups;
$R^6$ and $R^7$ are each independently chosen from hydrogen, —O—$R^{17}$, —O—C(=O)—$R^{17}$, —O—C(=O)—$NR^{15}R^{16}$, $C_1$-$C_6$alkyl groups, —$NR^{15}R^{16}$, and a linker;
$R^{15}$ and $R^{16}$ are each independently chosen from hydrogen, $R^{17}$, —C(=O)—$R^{17}$, and —C(=O)—O—$R^{17}$;
$R^{17}$ is chosen from hydrogen, $C_1$-$C_6$ alkyl groups, $C_3$-$C_8$ cycloalkyl groups, benzyl groups, and $C_3$-$C_8$ heterocyclyl groups; and
Z" is chosen from

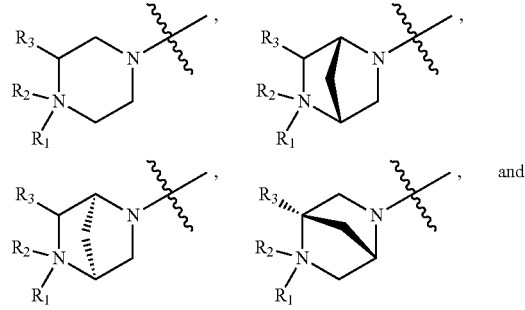

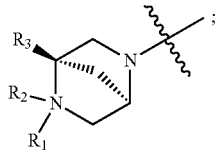

wherein $R^1$, $R^2$, $R^3$, $R^4$, $R^5$, $R^6$, $R^1$, $R^8$, $R^{15}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —$NR^{15}R^{16}$, $C_3$-$C_8$ cycloalkyl groups, $C_1$-$C_6$ alkylhydroxy groups, $C_1$-$C_6$ alkylalkoxy groups, benzyl groups, and $C_3$-$C_8$ heterocyclyl groups;
wherein at least one of $R^6$ and $R^7$ is hydrogen; and
wherein if $R^2$ is a linker, then neither $R^6$ or $R^7$ is a linker, and if $R^6$ or $R^7$ is a linker, then $R^2$ is absent.

In some embodiments, $R^1$ is chosen from absent, hydrogen, $C_1$-$C_4$ alkyl groups, $C_1$-$C_4$ alkylcarboxylic acid groups, and $C_3$-$C_8$ cycloalkyl groups. In some embodiments, $R^1$ is absent. In some embodiments, $R^1$ is hydrogen. In some embodiments, $R^1$ is a $C_1$-$C_4$ alkyl group. In some embodiments, $R^1$ is methyl. In some embodiments, $R^1$ is ethyl.

In some embodiments, $R^1$ is a $C_1$-$C_4$ alkylcarboxylic acid group. In some embodiments, $R^1$ is —$CH_2CH_2CH_2CO_2H$. In some embodiments, $R^1$ is a $C_3$-$C_8$ cycloalkyl group. In some embodiments, $R^1$ is cycloheptyl.

In some embodiments, $R^3$ is chosen from hydrogen, $C_1$-$C_4$alkyl groups, $C_1$-$C_4$ alkylalkoxy groups, $C_1$-$C_4$ alkylcarboxylic acid groups, and $C_1$-$C_4$ alkylhydroxy groups. In some embodiments, $R^3$ is chosen from hydrogen and $C_1$-$C_4$ alkylcarboxylic acid groups. In some embodiments, $R^3$ is hydrogen. In some embodiments, $R^3$ is a $C_1$-$C_4$ alkylcarboxylic acid group. In some embodiments, $R^3$ is —$CH_2CH_2CO_2H$.

In some embodiments, $R^4$ is chosen from hydrogen, hydroxyl groups, —O—($C_1$-$C_4$ alkyl) groups, —O—C(=O)—($C_1$-$C_4$ alkyl) groups, and $C_1$-$C_4$ alkyl groups. In some embodiments, $R^4$ is hydrogen. In some embodiments, $R^4$ is hydroxyl. In some embodiments, $R^4$ is a —O—($C_1$-$C_4$ alkyl) group. In some embodiments, $R^4$ is —$OCH_3$. In some embodiments, $R^4$ is —$OCH_2CH_3$. In some embodiments, $R^4$ is a —O—C(=O)—($C_1$-$C_4$ alkyl) group. In some embodiments, $R^4$ is —O—C(=O)—$CH_3$. In some embodiments, $R^4$ is —O—C(=O)—$CH_2CH_3$. In some embodiments, $R^4$ is a $C_1$-$C_4$ alkyl group. In some embodiments, $R^4$ is methyl. In some embodiments, $R^4$ is ethyl.

In some embodiments, $R^5$ is chosen from hydrogen, hydroxyl groups, —O—($C_1$-$C_4$ alkyl) groups, and $C_1$-$C_4$ alkyl groups. In some embodiments, $R^5$ is hydrogen. In some embodiments, $R^5$ is hydroxyl. In some embodiments, $R^5$ is a —O—($C_1$-$C_4$ alkyl) group. In some embodiments, $R^5$ is a $C_1$-$C_4$ alkyl group.

In some embodiments, $R^2$ is absent and $R^6$ is a linker. In some embodiments, $R^2$ is absent and $R^7$ is a linker. In some embodiments, $R^2$ is a linker. In some embodiments, $R^6$ is hydrogen. In some embodiments, $R^7$ is hydrogen.

In some embodiments, $R^6$ is hydrogen and $R^7$ is —O—$R^{17}$. In some embodiments, $R^6$ is hydrogen and $R^7$ is —$OR^{17}$, wherein $R^{17}$ is chosen from hydrogen and $C^1$-$C^4$ alkyl groups. In some embodiments, $R^6$ is hydrogen and $R^7$ is —O—$R^{17}$, wherein $R^{17}$ is hydrogen. In some embodiments, $R^6$ is —O—$R^{17}$ and $R^7$ is hydrogen. In some embodiments, $R^6$ is —O—$R^{17}$ and $R^7$ is hydrogen, wherein $R^{17}$ is chosen from hydrogen and $C^1$-$C^4$ alkyl groups. In some embodiments, $R^6$ is —O—$R^{17}$ and $R^7$ is hydrogen, wherein $R^{17}$ is hydrogen. In some embodiments, $R^6$ is hydrogen and $R^7$ is —$NR^{15}R^{16}$. In some embodiments, $R^6$ is hydrogen and $R^7$ is —$NR^{15}R^{16}$, wherein $R^{15}$ is H and $R^{16}$ is chosen from hydrogen, $R^{17}$, —C(=O)—$R^{17}$, and —C(=O)—O—$R^{17}$. In some embodiments, $R^6$ is hydrogen and $R^7$ is —$NR^{15}R^{16}$, wherein $R^{15}$ is H and $R^{16}$ is chosen from hydrogen, $R^{17}$, —C(=O)—$R^{17}$, and —C(=O)—O—$R^{17}$, and wherein $R^{17}$ is chosen from hydrogen, $C_1$-$C_6$ alkyl groups, $C_3$-$C_3$ cycloalkyl groups, and $C_3$-$C_3$ heterocyclyl groups. In some embodiments, $R^6$ is —O—$R^{17}$. In some embodiments, $R^6$ is —O—C(=O)—$R^{17}$. In some embodiments, $R^6$ is $C_1$-$C_6$ alkyl. In some embodiments, $R^6$ is $C_1$-$C_4$ alkyl. In some embodiments, $R^6$ is $C_1$ alkyl. In some embodiments, $R^6$ is —$NR^{15}R^{16}$.

In some embodiments, $R^7$ is —O—$R^{17}$. In some embodiments, $R^7$ is —O—C(=O)—$R^{17}$. In some embodiments, $R^7$ is $C_1$-$C_6$ alkyl. In some embodiments, $R^7$ is $C_1$-$C_4$ alkyl. In some embodiments, $R^7$ is $C_1$ alkyl. In some embodiments, $R^7$ is —$NR^{15}R^{16}$.

In some embodiments, $R^3$ is chosen from hydrogen, hydroxyl groups, —O—($C_1$-$C_4$ alkyl) groups, and ($C_1$-$C_4$ alkyl). In some embodiments, $R^3$ is hydrogen. In some embodiments, $R^3$ is a hydroxyl group. In some embodiments, $R^3$ is an —O—($C_1$-$C_4$ alkyl) group. In some embodiments, $R^3$ is an —O—($C_1$ alkyl) group.

In some embodiments, $R^{15}$ is hydrogen. In some embodiments, $R^{15}$ is $R^{17}$. In some embodiments, $R^{15}$ is —C(=O)—$R^{17}$. In some embodiments, $R^{15}$ is —C(=O)—O—$R^{17}$.

In some embodiments, $R^{16}$ is hydrogen. In some embodiments, $R^{16}$ is $R^{17}$. In some embodiments, $R^{16}$ is —C(=O)—$R^{17}$. In some embodiments, $R^{16}$ is —C(=O)—O—$R^{17}$.

In some embodiments, $R^{17}$ is chosen from hydrogen, $C_1$-$C_4$ alkyl groups, $C_3$-$C_6$ cycloalkyl groups, and $C_3$-$C_8$ heterocyclyl groups. In some embodiments, $R^{17}$ is hydrogen. In some embodiments, $R^{17}$ is a $C_1$-$C_4$ alkyl group. In some embodiments, $R^{17}$ is a $C_1$ alkyl group. In some embodiments, $R^{17}$ is a $C_3$-$C_8$ cycloalkyl group. In some embodiments, $R^{17}$ is a $C_3$ cycloalkyl group. In some embodiments, $R^{17}$ is a $C_4$ cycloalkyl group. In some embodiments, $R^{17}$ is a $C_5$ cycloalkyl group. In some embodiments, $R^{17}$ is a C cycloalkyl group. In some embodiments, $R^{17}$ is a $C_3$-$C_8$ heterocyclyl group. In some embodiments, $R^{17}$ is a $C_3$ heterocyclyl group. In some embodiments, $R^{17}$ is a $C_4$ heterocyclyl group. In some embodiments, $R^{17}$ is a $C_5$ heterocyclyl group. In some embodiments, $R^{17}$ is a C heterocyclyl group. In some embodiments, $R^{17}$ is a $C_7$ heterocyclyl group. In some embodiments, $R^{17}$ is a C heterocyclyl group.

In some embodiments, Z' is

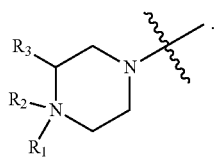

In some embodiments, Z' is

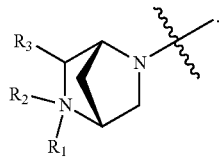

In some embodiments, Z' is

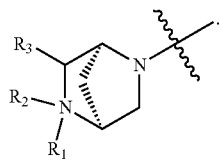

In some embodiments, Z' is

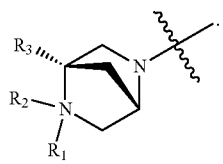

In some embodiments, Z' is

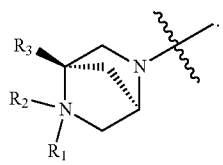

In some embodiments, $R^2$ is a linker. In some embodiments, the linker comprises at least one cleavable peptide moiety. In some embodiments, the at least one cleavable peptide moiety is cleavable by an enzyme. In some embodiments, the linker or cleavable peptide moiety comprises at least one amino acid unit. In some embodiments, the at least one amino acid unit is chosen from arginine, histidine, lysine, aspartic acid, glutamic acid, serine, threonine, asparagine, glutamine, cysteine, selenocysteine, glycine, proline, alanine, valine, isoleucine, methionine, phenylalanine, tyrosine, tryptophan, and citrulline. In some embodiments, the at least one amino acid unit is chosen from alanine, citrulline, and valine. In some embodiments, the linker comprises citrulline and valine. In some embodiments, the linker comprises alanine and valine.

In some embodiments, the linker comprises a moiety chosen from a sulfonamide, a β-glucuronide, a disulfide, and a carbonyl. In some embodiments, the linker comprises a sulfonamide. In some embodiments, the linker comprises a β-glucuronide. In some embodiments, the linker comprises a disulfide. In some embodiments, the linker comprises a carbonyl.

In some embodiments, the linker comprises a spacer unit. In some embodiments, the spacer unit is chosen from alkyl groups and polyethylene glycol (PEG) moieties. In some embodiments, the alkyl group is a $C_1$-$C_{12}$ alkyl group. In some embodiments, the alkyl group is a $C_1$-$C_6$ alkyl group.

In some embodiments, the alkyl group is methylene. In some embodiments, the alkyl group is ethylene. In some embodiments, the alkyl group is n-propylene. In some embodiments, the alkyl group is n-butylene. In some embodiments, the alkyl group is n-pentylene. In some embodiments, the alkyl group is n-hexylene. In some embodiments, the PEG moiety comprises -(PEG)$_m$-, wherein m is an integer from 1 to 10. In some embodiments, m is 1. In some embodiments, m is 2. In some embodiments, m is 3. In some embodiments, m is 4. In some embodiments, m is 5. In some embodiments, m is 6.

In some embodiments, the linker comprises a maleimide (Mal) moiety ("Mal-spacer unit"). In some embodiments, the linker comprises a self-immolative spacer unit. In some embodiments, the self-immolative spacer unit is chosen from β-aminobenzyloxycarbonyl (pABC) and β-aminobenzyl (pAB).

In some embodiments, the linker comprises a Mal-spacer unit, an alkyl group, at least one amino acid unit, and a self-immolative spacer. In some embodiments, at least one amino acid unit is chosen from alanine, citrulline, and valine. In some embodiments, the at least one amino acid unit comprises alanine and valine. In some embodiments, the at least one amino acid unit comprises citrulline and valine. In some embodiments, the self-immolative spacer is chosen from pAB and pABC. In some embodiments, the self-immolative spacer comprises pAB. In some embodiments, the self-immolative spacer comprises pABC. In some embodiments, the alkyl group comprises a $C_1$-$C_6$ alkyl group.

In some embodiments, the linker comprises a Mal-spacer unit, PEG moiety, at least one amino acid unit, and a self-immolative spacer. In some embodiments, at least one amino acid unit is chosen from alanine, citrulline, and valine. In some embodiments, the at least one amino acid unit comprises alanine and valine. In some embodiments, the at least one amino acid unit comprises citrulline and valine. In some embodiments, the self-immolative spacer is chosen from pAB and pABC. In some embodiments, the self-immolative spacer comprises pAB. In some embodiments, the self-immolative spacer comprises pABC. In some embodiments, the PEG moiety comprises -(PEG)$_m$-, wherein m is an integer from 1 to 6.

In various other embodiments, the linker-drug (L–D) compounds disclosed herein comprise a linker-drug structure according to Formula (V). In various embodiments, the present disclosure provides a linker-drug (L–D) compound of Formula (V):

or a pharmaceutically acceptable salt thereof, wherein:

$R^1$ is chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(=O)—($C_1$-$C_6$ alkyl) groups, and —CD$_3$;

$R^2$ is absent or a linker;

$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups; and $R^4$, $R^5$, and $R^8$ are each independently chosen from hydrogen, hydroxyl groups, —O—($C_1$-$C_6$ alkyl) groups, —O—C(=O)—($C_1$-$C_6$alkyl) groups, and $C_1$-$C_6$alkyl groups;

$R^6$ and $R^7$ are each independently chosen from hydrogen, —O—$R^{17}$, —O—C(=O)—$R^{17}$, —O—C(=O)—NR$^{15}$R$^{16}$, $C_1$-$C_6$alkyl groups, —NR$^{15}$R$^{16}$, and a linker;

$R^{15}$ and $R^{16}$ are each independently chosen from hydrogen, $R^{17}$, —C(=O)—$R^{17}$, and —C(=O)—O—$R^{17}$; and $R^{17}$ is chosen from hydrogen, $C_1$-$C_6$ alkyl groups, $C_3$-$C_8$ cycloalkyl groups, benzyl groups, and $C_3$-$C_8$ heterocyclyl groups;

wherein $R^1$, $R^2$, $R^3$, $R^4$, $R^5$, $R^6$, $R^7$, $R^8$, $R^{15}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —NR$^{15}$R$^{16}$, $C_3$-$C_8$ cycloalkyl groups, $C_1$-$C_6$ alkylhydroxy groups, $C_1$-$C_6$ alkylalkoxy groups, benzyl groups, and $C_3$-$C_8$ heterocyclyl groups;

wherein at least one of $R^6$ and $R^7$ is hydrogen; and wherein if $R^2$ is a linker, then neither $R^6$ or $R^7$ is a linker, and if $R^6$ or $R^7$ is a linker, then $R^2$ is absent.

In some embodiments, $R^1$ is chosen from absent, hydrogen, $C_1$-$C_4$ alkyl groups, $C_1$-$C_4$ alkylcarboxylic acid groups, and $C_3$-$C_8$ cycloalkyl groups. In some embodiments, $R^1$ is absent. In some embodiments, $R^1$ is hydrogen. In some embodiments, $R^1$ is a $C_1$—$C_4$ alkyl group. In some embodiments, $R^1$ is methyl. In some embodiments, $R^1$ is ethyl. In some embodiments, $R^1$ is a $C_1$-$C_4$ alkylcarboxylic acid group. In some embodiments, $R^1$ is —CH$_2$CH$_2$CH$_2$CO$_2$H. In some embodiments, $R^1$ is a $C_3$-$C_8$ cycloalkyl group. In some embodiments, $R^1$ is cycloheptyl.

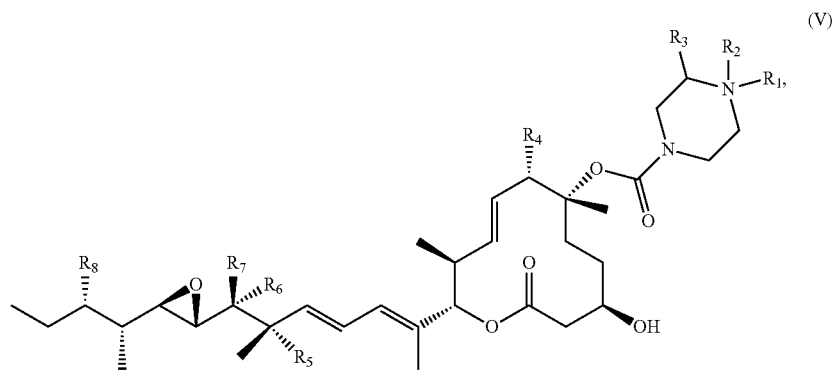

(V)

In some embodiments, $R^3$ is chosen from hydrogen, $C_1$-$C_4$ alkyl groups, $C_1$-$C_4$ alkylalkoxy groups, $C_1$-$C_4$ alkylcarboxylic acid groups, and $C_1$-$C_4$ alkylhydroxy groups. In some embodiments, $R^3$ is chosen from hydrogen and $C_1$-$C_4$ alkylcarboxylic acid groups.

In some embodiments, $R^3$ is hydrogen. In some embodiments, $R^3$ is a $C_1$-$C_4$ alkylcarboxylic acid group. In some embodiments, $R^3$ is —$CH_2CH_2CO_2H$.

In some embodiments, $R^4$ is chosen from hydrogen, hydroxyl groups, —O—($C_1$-$C_4$ alkyl) groups, —O—C(=O)—($C_1$-$C_4$ alkyl) groups, and $C_1$-$C_4$ alkyl groups. In some embodiments, $R^4$ is hydrogen. In some embodiments, $R^4$ is hydroxyl. In some embodiments, $R^4$ is a —O—($C_1$-$C_4$ alkyl) group. In some embodiments, $R^4$ is —$OCH_3$. In some embodiments, $R^4$ is —$OCH_2CH_3$. In some embodiments, $R^4$ is a —O—C(=O)—($C_1$-$C_4$ alkyl) group. In some embodiments, $R^4$ is —O—C(=O)—$CH_3$. In some embodiments, $R^4$ is —O—C(=O)—$CH_2CH_3$. In some embodiments, $R^4$ is a $C_1$-$C_4$ alkyl group. In some embodiments, $R^4$ is methyl. In some embodiments, $R^4$ is ethyl.

In some embodiments, $R^5$ is chosen from hydrogen, hydroxyl groups, —O—($C_1$-$C_4$ alkyl) groups, and $C_1$-$C_4$ alkyl groups. In some embodiments, $R^5$ is hydrogen. In some embodiments, $R^5$ is hydroxyl. In some embodiments, $R^5$ is a —O—($C_1$-$C_4$ alkyl) group. In some embodiments, $R^5$ is a $C_1$-$C_4$ alkyl group.

In some embodiments, $R^2$ is absent and $R^6$ is a linker. In some embodiments, $R^2$ is absent and $R^7$ is a linker. In some embodiments, $R^2$ is a linker. In some embodiments, $R^6$ is hydrogen. In some embodiments, $R^7$ is hydrogen.

In some embodiments, $R^6$ is hydrogen and $R^7$ is —O—$R^{17}$. In some embodiments, $R^6$ is hydrogen and $R^7$ is —$OR^{17}$, wherein $R^{17}$ is chosen from hydrogen and $C^1$-$C^4$ alkyl groups. In some embodiments, $R^6$ is hydrogen and $R^7$ is —O—$R^{17}$, wherein $R^{17}$ is hydrogen. In some embodiments, $R^6$ is —O—$R^{17}$ and $R^7$ is hydrogen. In some embodiments, $R^6$ is —O—$R^{17}$ and $R^7$ is hydrogen, wherein $R^{17}$ is chosen from hydrogen and $C^1$-$C^4$ alkyl groups. In some embodiments, $R^6$ is —O—$R^{17}$ and $R^7$ is hydrogen, wherein $R^{17}$ is hydrogen. In some embodiments, $R^6$ is hydrogen and $R^7$ is —$NR^{15}R^{16}$. In some embodiments, $R^6$ is hydrogen and $R^7$ is —$NR^{15}R^{16}$, wherein $R^{15}$ is H and $R^{16}$ is chosen from hydrogen, $R^{17}$, —C(=O)—$R^{17}$, and —C(=O)—O—$R^{17}$. In some embodiments, $R^6$ is hydrogen and $R^7$ is —$NR^{15}R^{16}$, wherein $R^{15}$ is H and $R^{16}$ is chosen from hydrogen, $R^{17}$, —C(=O)—$R^{17}$, and —C(=O)—O—$R^{17}$, and wherein $R^{17}$ is chosen from hydrogen, $C_1$-$C_6$ alkyl groups, $C_3$-$C_3$ cycloalkyl groups, and $C_3$-$C_3$ heterocyclyl groups. In some embodiments, $R^6$ is —O—$R^{17}$. In some embodiments, $R^6$ is —O—C(=O)—$R^{17}$. In some embodiments, $R^6$ is $C_1$-$C_6$ alkyl. In some embodiments, $R^6$ is $C_1$-$C_4$ alkyl. In some embodiments, $R^6$ is $C_1$ alkyl. In some embodiments, $R^6$ is —$NR^{15}R^{16}$.

In some embodiments, $R^7$ is —O—$R^{17}$. In some embodiments, $R^7$ is —O—C(=O)—$R^{17}$.

In some embodiments, $R^7$ is $C_1$-$C_6$ alkyl. In some embodiments, $R^7$ is $C_1$-$C_4$ alkyl. In some embodiments, $R^7$ is $C_1$ alkyl. In some embodiments, $R^7$ is —$NR^{15}R^{16}$.

In some embodiments, $R^8$ is chosen from hydrogen, hydroxyl groups, —O—($C_1$-$C_4$ alkyl) groups, and ($C_1$-$C_4$ alkyl). In some embodiments, $R^3$ is hydrogen. In some embodiments, $R^3$ is a hydroxyl group. In some embodiments, $R^3$ is an —O—($C_1$-$C_4$ alkyl) group. In some embodiments, $R^3$ is an —O—($C_1$ alkyl) group.

In some embodiments, $R^{15}$ is hydrogen. In some embodiments, $R^{15}$ is $R^{17}$. In some embodiments, $R^{15}$ is —C(=O)—$R^{17}$. In some embodiments, $R^{15}$ is —C(=O)—O—$R^{17}$.

In some embodiments, $R^{16}$ is hydrogen. In some embodiments, $R^{16}$ is $R^{17}$. In some embodiments, $R^{16}$ is —C(=O)—$R^{17}$. In some embodiments, $R^{16}$ is —C(=O)—O—$R^{17}$.

In some embodiments, $R^{17}$ is chosen from hydrogen, $C_1$-$C_4$ alkyl groups, $C_3$-$C_6$ cycloalkyl groups, and $C_3$-$C_8$ heterocyclyl groups. In some embodiments, $R^{17}$ is hydrogen. In some embodiments, $R^{17}$ is a $C_1$-$C_4$ alkyl group. In some embodiments, $R^{17}$ is a $C_1$ alkyl group. In some embodiments, $R^{17}$ is a $C_3$-$C_6$ cycloalkyl group. In some embodiments, $R^{17}$ is a $C_3$ cycloalkyl group. In some embodiments, $R^{17}$ is a $C_4$ cycloalkyl group. In some embodiments, $R^{17}$ is a $C_5$ cycloalkyl group. In some embodiments, $R^{17}$ is a C cycloalkyl group. In some embodiments, $R^{17}$ is a $C_3$-$C_8$ heterocyclyl group. In some embodiments, $R^{17}$ is a $C_3$ heterocyclyl group. In some embodiments, $R^{17}$ is a $C_4$ heterocyclyl group. In some embodiments, $R^{17}$ is a $C_5$ heterocyclyl group. In some embodiments, $R^{17}$ is a C heterocyclyl group. In some embodiments, $R^{17}$ is a $C_7$ heterocyclyl group. In some embodiments, $R^{17}$ is a $C_8$ heterocyclyl group.

In some embodiments, $R^2$ is a linker. In some embodiments, the linker comprises at least one cleavable peptide moiety. In some embodiments, the at least one cleavable peptide moiety is cleavable by an enzyme. In some embodiments, the linker or cleavable peptide moiety comprises at least one amino acid unit. In some embodiments, the at least one amino acid unit is chosen from arginine, histidine, lysine, aspartic acid, glutamic acid, serine, threonine, asparagine, glutamine, cysteine, selenocysteine, glycine, proline, alanine, valine, isoleucine, methionine, phenylalanine, tyrosine, tryptophan, and citrulline. In some embodiments, the at least one amino acid unit is chosen from alanine, citrulline, and valine. In some embodiments, the linker comprises citrulline and valine. In some embodiments, the linker comprises alanine and valine.

In some embodiments, the linker comprises a moiety chosen from a sulfonamide, a β-glucuronide, a disulfide, and a carbonyl. In some embodiments, the linker comprises a sulfonamide. In some embodiments, the linker comprises a β-glucuronide. In some embodiments, the linker comprises a disulfide. In some embodiments, the linker comprises a carbonyl.

In some embodiments, the linker comprises a spacer unit. In some embodiments, the spacer unit is chosen from alkyl groups and polyethylene glycol (PEG) moieties. In some embodiments, the alkyl group is a $C_1$-$C_{12}$ alkyl group. In some embodiments, the alkyl group is a $C_1$-$C_6$ alkyl group. In some embodiments, the alkyl group is methylene. In some embodiments, the alkyl group is ethylene. In some embodiments, the alkyl group is n-propylene. In some embodiments, the alkyl group is n-butylene. In some embodiments, the alkyl group is n-pentylene. In some embodiments, the alkyl group is n-hexylene. In some embodiments, the PEG moiety comprises -(PEG)$_m$-, wherein m is an integer from 1 to 10. In some embodiments, m is 1. In some embodiments, m is 2. In some embodiments, m is 3. In some embodiments, m is 4. In some embodiments, m is 5. In some embodiments, m is 6.

In some embodiments, the linker comprises a maleimide (Mal) moiety ("Mal-spacer unit"). In some embodiments, the linker comprises a self-immolative spacer unit. In some embodiments, the self-immolative spacer unit is chosen from β-aminobenzyloxycarbonyl (pABC) and β-aminobenzyl (pAB).

In some embodiments, the linker comprises a Mal-spacer unit, an alkyl group, at least one amino acid unit, and a self-immolative spacer. In some embodiments, at least one amino acid unit is chosen from alanine, citrulline, and valine. In some embodiments, the at least one amino acid unit comprises alanine and valine. In some embodiments, the at least one amino acid unit comprises citrulline and valine. In some embodiments, the self-immolative spacer is chosen from pAB and pABC. In some embodiments, the self-immolative spacer comprises pAB. In some embodiments, the self-immolative spacer comprises pABC. In some embodiments, the alkyl group comprises a $C_1$-$C_6$ alkyl group.

In some embodiments, the linker comprises a Mal-spacer unit, PEG moiety, at least one amino acid unit, and a self-immolative spacer. In some embodiments, at least one amino acid unit is chosen from alanine, citrulline, and valine. In some embodiments, the at least one amino acid unit comprises alanine and valine. In some embodiments, the at least one amino acid unit comprises citrulline and valine. In some embodiments, the self-immolative spacer is chosen from pAB and pABC. In some embodiments, the self-immolative spacer comprises pAB. In some embodiments, the self-immolative spacer comprises pABC. In some embodiments, the PEG moiety comprises -(PEG)$_m$-, wherein m is an integer from 1 to 6.

In various other embodiments, the linker-drug (L–D) compounds disclosed herein comprise a linker-drug structure according to Formula (VII). In various embodiments, the present disclosure provides a linker-drug (L–D) compound of Formula (VII):

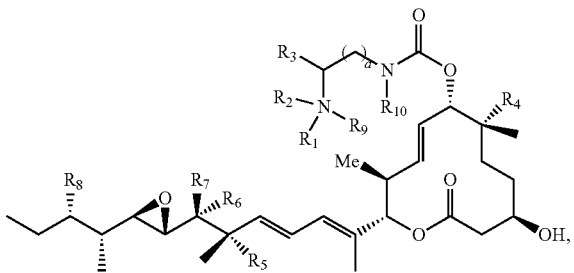

(VII)

or a pharmaceutically acceptable salt thereof, wherein:
$R^1$ and $R^9$ are each independently chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(=O)—($C_1$-$C_6$ alkyl) groups, and —CD$_3$;
$R^2$ is absent or a linker;
$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups;
$R^4$, $R^5$, and $R^8$ are each independently chosen from hydrogen, hydroxyl groups, —O—($C_1$-$C_6$ alkyl) groups, —O—C(=O)—($C_1$-$C_6$alkyl) groups, and $C_1$-$C_6$alkyl groups;
$R^6$ and $R^7$ are each independently chosen from hydrogen, —O—$R^{17}$, —O—C(=O)—$R^{17}$, —O—C(=O)—NR$^{15}$R$^{16}$, $C_1$-$C_6$alkyl groups, —NR$^{15}$R$^{16}$, and a linker;

$R^{10}$ is chosen from hydrogen, $C_1$-$C_6$ alkyl groups, —C(=O)—($C_1$-$C_6$ alkyl) groups, and —CD3;
$R^{15}$ and $R^{16}$ are each independently chosen from hydrogen, $R^{17}$, —C(=O)—$R^{17}$, and —C(=O)—O—$R^{17}$;
$R^{17}$ is chosen from hydrogen, $C_1$-$C_6$ alkyl groups, $C_3$-$C_8$ cycloalkyl groups, benzyl groups, and $C_3$-$C_8$ heterocyclyl groups; and
a is 1, 2, 3, 4, 5, 6, 7, 8, 9, or 10;
wherein $R^1$, $R^2$, $R^3$, $R^4$, $R^5$, $R^6$, $R^7$, $R^8$, $R^9$, $R^{10}$, $R^{15}$, $R^{16}$, and $R^{17}$ are each independently substituted with 0 to 3 groups independently chosen from halogens, hydroxyl groups, $C_1$-$C_6$alkyl groups, —O—($C_1$-$C_6$alkyl) groups, —NR$^{15}$R$^{16}$, $C_3$-$C_a$ cycloalkyl groups, $C_1$-$C_6$ alkylhydroxy groups, $C_1$-$C_6$ alkylalkoxy groups, benzyl groups, and $C_3$-$C_8$ heterocyclyl groups;
wherein at least one of $R^6$ and $R^7$ is hydrogen;
wherein if $R^2$ is a linker, then neither $R^6$ or $R^7$ is a linker, and if $R^6$ or $R^7$ is a linker, then $R^2$ is absent; and
wherein $R^1$ and $R^9$ cannot both be absent.

In some embodiments, $R^1$ is chosen from absent, hydrogen, $C_1$-$C_4$ alkyl groups, $C_1$-$C_4$ alkylcarboxylic acid groups, and $C_3$-$C_8$ cycloalkyl groups. In some embodiments, $R^1$ is absent. In some embodiments, $R^1$ is hydrogen. In some embodiments, $R^1$ is a $C_1$-$C_4$ alkyl group. In some embodiments, $R^1$ is methyl. In some embodiments, $R^1$ is ethyl. In some embodiments, $R^1$ is a $C_1$-$C_4$ alkylcarboxylic acid group. In some embodiments, $R^1$ is —CH$_2$CH$_2$CH$_2$CO$_2$H. In some embodiments, $R^1$ is a $C_3$-$C_8$ cycloalkyl group. In some embodiments, $R^1$ is cycloheptyl.

In some embodiments, $R^3$ is chosen from hydrogen, $C_1$-$C_4$alkyl groups, $C_1$-$C_4$ alkylalkoxy groups, $C_1$-$C_4$ alkylcarboxylic acid groups, and $C_1$-$C_4$ alkylhydroxy groups. In some embodiments, $R^3$ is chosen from hydrogen and $C_1$-$C_4$ alkylcarboxylic acid groups. In some embodiments, $R^3$ is hydrogen. In some embodiments, $R^3$ is a $C_1$-$C_4$ alkylcarboxylic acid group. In some embodiments, $R^3$ is —CH$_2$CH$_2$CO$_2$H.

In some embodiments, $R^4$ is chosen from hydrogen, hydroxyl groups, —O—($C_1$-$C_4$ alkyl) groups, —O—C(=O)—($C_1$-$C_4$ alkyl) groups, and $C_1$-$C_4$ alkyl groups. In some embodiments, $R^4$ is hydrogen. In some embodiments, $R^4$ is hydroxyl. In some embodiments, $R^4$ is a —O—($C_1$-$C_4$ alkyl) group. In some embodiments, $R^4$ is —OCH$_3$. In some embodiments, $R^4$ is —OCH$_2$CH$_3$. In some embodiments, $R^4$ is a —O—C(=O)—($C_1$-$C_4$ alkyl) group. In some embodiments, $R^4$ is —O—C(=O)—CH$_3$. In some embodiments, $R^4$ is —O—C(=O)—CH$_2$CH$_3$. In some embodiments, $R^4$ is a $C_1$-$C_4$ alkyl group. In some embodiments, $R^4$ is methyl. In some embodiments, $R^4$ is ethyl.

In some embodiments, $R^5$ is chosen from hydrogen, hydroxyl groups, —O—($C_1$-$C_4$ alkyl) groups, and $C_1$-$C_4$ alkyl groups. In some embodiments, $R^5$ is hydrogen. In some embodiments, $R^5$ is hydroxyl. In some embodiments, $R^5$ is a —O—($C_1$-$C_4$ alkyl) group. In some embodiments, $R^5$ is a $C_1$-$C_4$ alkyl group.

In some embodiments, $R^9$ is chosen from absent, hydrogen, $C_1$-$C_4$alkyl groups, —(C=O)—($C_1$-$C_4$ alkyl) groups, and —CD$_3$. In some embodiments, $R^9$ is absent. In some embodiments, $R^9$ is hydrogen. In some embodiments, $R^9$ is a $C_1$-$C_4$ alkyl group. In some embodiments, the $C_1$-$C_4$alkyl group is methyl. In some embodiments, the $C_1$-$C_4$ alkyl group is ethyl. In some embodiments, $R^9$ is a —(C=O)—($C_1$-$C_4$ alkyl) group. In some embodiments, the —(C=O)—($C_1$-$C_4$ alkyl) group is —(C=O)-methyl. In some embodiments, $R^9$ is —CD3.

In some embodiments, $R^{10}$ is chosen from hydrogen, $C_1$-$C_4$alkyl groups, —(C=O)—($C_1$-$C_4$alkyl) groups, and —CD$_3$. In some embodiments, R$^{10}$ is hydrogen. In some embodiments, R$^{10}$ is a C$_1$-C$_4$ alkyl group. In some embodiments, the C$_1$-C$_4$ alkyl group is methyl. In some embodiments, the C$_1$-C$_4$alkyl group is ethyl. In some embodiments, R$^{10}$ is a —(C═O)—(C$_1$-C$_4$alkyl) group. In some embodiments, the —(C═O)—(C$_1$-C$_4$alkyl) group is —(C═O)-methyl. In some embodiments, R$^{10}$ is —CD$_3$.

In some embodiments, R$^2$ is absent and R$^6$ is a linker. In some embodiments, R$^2$ is absent and R$^7$ is a linker. In some embodiments, R$^2$ is a linker. In some embodiments, R$^6$ is hydrogen. In some embodiments, R$^7$ is hydrogen. In some embodiments, R$^6$ is hydrogen and R$^7$ is —O—R$^{17}$. In some embodiments, R$^6$ is hydrogen and R$^7$ is —OR$^{17}$, wherein R$^{17}$ is chosen from hydrogen and C$^1$-C$^4$ alkyl groups. In some embodiments, R$^6$ is hydrogen and R$^7$ is —O—R$^{17}$, wherein R$^{17}$ is hydrogen. In some embodiments, R$^6$ is —O—R$^{17}$ and R$^7$ is hydrogen. In some embodiments, R$^6$ is —O—R$^{17}$ and R$^7$ is hydrogen, wherein R$^{17}$ is chosen from hydrogen and C$^1$-C$^4$ alkyl groups. In some embodiments, R$^6$ is —O—R$^{17}$ and R$^7$ is hydrogen, wherein R$^{17}$ is hydrogen. In some embodiments, R$^6$ is hydrogen and R$^7$ is —NR$^{15}$R$^{16}$. In some embodiments, R$^6$ is hydrogen and R$^7$ is —NR$^{15}$R$^{16}$, wherein R$^{15}$ is H and R$^{16}$ is chosen from hydrogen, R$^{17}$, —C(═O)—R$^{17}$, and —C(═O)—O—R$^{17}$. In some embodiments, R$^6$ is hydrogen and R$^7$ is —NR$^{15}$R$^{16}$, wherein R$^{15}$ is H and R$^{16}$ is chosen from hydrogen, R$^{17}$, —C(═O)—R$^{17}$, and —C(═O)—O—R$^{17}$, and wherein R$^{17}$ is chosen from hydrogen, C$_1$-C$_6$ alkyl groups, C$_3$-C$_8$ cycloalkyl groups, and C$_3$-C$_8$ heterocyclyl groups. In some embodiments, R$^6$ is —O—R$^{17}$. In some embodiments, R$^6$ is —O—C(═O)—R$^{17}$. In some embodiments, R$^6$ is C$_1$-C$_6$ alkyl. In some embodiments, R$^6$ is C$_1$-C$_4$ alkyl. In some embodiments, R$^6$ is C$_1$ alkyl. In some embodiments, R$^6$ is —NR$^{15}$R$^{16}$.

In some embodiments, R$^7$ is —O—R$^{17}$. In some embodiments, R$^7$ is —O—C(═O)—R$^{17}$. In some embodiments, R$^7$ is C$_1$-C$_6$ alkyl. In some embodiments, R$^7$ is C$_1$-C$_4$ alkyl. In some embodiments, R$^7$ is C$_1$ alkyl. In some embodiments, R$^7$ is —NR$^{15}$R$^{16}$.

In some embodiments, R$^8$ is chosen from hydrogen, hydroxyl groups, —O—(C$_1$-C$_4$ alkyl) groups, and (C$_1$-C$_4$ alkyl). In some embodiments, R$^3$ is hydrogen. In some embodiments, R$^3$ is a hydroxyl group. In some embodiments, R$^3$ is an —O—(C$_1$-C$_4$ alkyl) group. In some embodiments, R$^3$ is an —O—(C$_1$ alkyl) group.

In some embodiments, R$^{15}$ is hydrogen. In some embodiments, R$^{15}$ is R$^{17}$. In some embodiments, R$^{15}$ is —C(═O)—R$^{17}$. In some embodiments, R$^{15}$ is —C(═O)—O—R$^{17}$.

In some embodiments, R$^{16}$ is hydrogen. In some embodiments, R$^{16}$ is R$^{17}$. In some embodiments, R$^{16}$ is —C(═O)—R$^{17}$. In some embodiments, R$^{16}$ is —C(═O)—O—R$^{17}$.

In some embodiments, R$^{17}$ is chosen from hydrogen, C$_1$-C$_4$ alkyl groups, C$_3$-C$_6$ cycloalkyl groups, and C$_3$-C$_8$ heterocyclyl groups. In some embodiments, R$^{17}$ is hydrogen. In some embodiments, R$^{17}$ is a C$_1$-C$_4$ alkyl group. In some embodiments, R$^{17}$ is a C$_1$ alkyl group. In some embodiments, R$^{17}$ is a C$_3$-C$_6$ cycloalkyl group. In some embodiments, R$^{17}$ is a C$_3$ cycloalkyl group. In some embodiments, R$^{17}$ is a C$_4$ cycloalkyl group. In some embodiments, R$^{17}$ is a C$_5$ cycloalkyl group. In some embodiments, R$^{17}$ is a C$_6$ cycloalkyl group. In some embodiments, R$^{17}$ is a C$_3$-C$_8$ heterocyclyl group. In some embodiments, R$^{17}$ is a C$_3$ heterocyclyl group. In some embodiments, R$^{17}$ is a C$_4$ heterocyclyl group. In some embodiments, R$^{17}$ is a C$_5$ heterocyclyl group. In some embodiments, R$^{17}$ is a C$_6$ heterocyclyl group. In some embodiments, R$^{17}$ is a C$_7$ heterocyclyl group. In some embodiments, R$^{17}$ is a C$_8$ heterocyclyl group.

In some embodiments, a is 1, 2, 3, 4, 5, 6, 7, 8, 9, or 10. In some embodiments, a is 1, 2, 3, 4, 5, or 6. In some embodiments, a is 1, 2, 3, 4, or 5. In some embodiments, a is 1, 2, 3, or 4. In some embodiments, a is 1, 2, or 3. In some embodiments, a is 1 or 2. In some embodiments, a is 1. In some embodiments, a is 2. In some embodiments, a is 3. In some embodiments, a is 4. In some embodiments, a is 5. In some embodiments, a is 6. In some embodiments, a is 7. In some embodiments, a is 8. In some embodiments, a is 9. In some embodiments, a is 10.

In some embodiments, R$^2$ is a linker. In some embodiments, the linker comprises at least one cleavable peptide moiety. In some embodiments, the at least one cleavable peptide moiety is cleavable by an enzyme. In some embodiments, the linker or cleavable peptide moiety comprises at least one amino acid unit. In some embodiments, the at least one amino acid unit is chosen from arginine, histidine, lysine, aspartic acid, glutamic acid, serine, threonine, asparagine, glutamine, cysteine, selenocysteine, glycine, proline, alanine, valine, isoleucine, methionine, phenylalanine, tyrosine, tryptophan, and citrulline. In some embodiments, the at least one amino acid unit is chosen from alanine, citrulline, and valine. In some embodiments, the linker comprises citrulline and valine. In some embodiments, the linker comprises alanine and valine.

In some embodiments, the linker comprises a moiety chosen from a sulfonamide, a β-glucuronide, a disulfide, and a carbonyl. In some embodiments, the linker comprises a sulfonamide. In some embodiments, the linker comprises a β-glucuronide. In some embodiments, the linker comprises a disulfide. In some embodiments, the linker comprises a carbonyl.

In some embodiments, the linker comprises a spacer unit. In some embodiments, the spacer unit is chosen from alkyl groups and polyethylene glycol (PEG) moieties. In some embodiments, the alkyl group is a C$_1$-C$_{12}$ alkyl group. In some embodiments, the alkyl group is a C$_1$-C$_6$ alkyl group. In some embodiments, the alkyl group is methylene. In some embodiments, the alkyl group is ethylene. In some embodiments, the alkyl group is n-propylene. In some embodiments, the alkyl group is n-butylene. In some embodiments, the alkyl group is n-pentylene. In some embodiments, the alkyl group is n-hexylene. In some embodiments, the PEG moiety comprises -(PEG)$_m$-, wherein m is an integer from 1 to 10. In some embodiments, m is 1. In some embodiments, m is 2. In some embodiments, m is 3. In some embodiments, m is 4. In some embodiments, m is 5. In some embodiments, m is 6.

In some embodiments, the linker comprises a maleimide (Mal) moiety ("Mal-spacer unit"). In some embodiments, the linker comprises a self-immolative spacer unit. In some embodiments, the self-immolative spacer unit is chosen from β-aminobenzyloxycarbonyl (pABC) and β-aminobenzyl (pAB).

In some embodiments, the linker comprises a Mal-spacer unit, an alkyl group, at least one amino acid unit, and a self-immolative spacer. In some embodiments, at least one amino acid unit is chosen from alanine, citrulline, and valine. In some embodiments, the at least one amino acid unit comprises alanine and valine. In some embodiments, the at least one amino acid unit comprises citrulline and valine. In some embodiments, the self-immolative spacer is chosen from pAB and pABC. In some embodiments, the self-immolative spacer comprises pAB. In some embodiments, the self-immolative spacer comprises pABC. In some embodiments, the alkyl group comprises a C$_1$-C$_6$ alkyl group.

In some embodiments, the linker comprises a Mal-spacer unit, PEG moiety, at least one amino acid unit, and a self-immolative spacer. In some embodiments, at least one amino acid unit is chosen from alanine, citrulline, and valine. In some embodiments, the at least one amino acid unit comprises alanine and valine. In some embodiments, the at least one amino acid unit comprises citrulline and valine. In some embodiments, the self-immolative spacer is chosen from pAB and pABC. In some embodiments, the self-immolative spacer comprises pAB. In some embodiments, the self-immolative spacer comprises pABC. In some embodiments, the PEG moiety comprises -(PEG)$_m$-, wherein m is an integer from 1 to 6.

In various other embodiments, the linker-drug (L-D) compounds disclosed herein comprise a linker-drug structure according to Formula (IX). In various embodiments, the present disclosure provides a linker-drug (L-D) compound of Formula (IX):

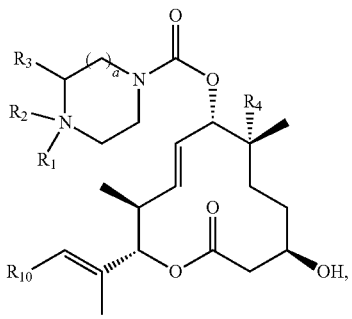

(IX)

or a pharmaceutically acceptable salt thereof, wherein:
$R^1$ is chosen from absent, hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, —O—C(=O)—($C_1$-$C_6$ alkyl) groups, and —CD$_3$;
$R^2$ is a linker;
$R^3$ is chosen from hydrogen, $C_1$-$C_6$ alkyl groups, $C_1$-$C_6$ alkylalkoxy groups, $C_1$-$C_6$ alkylamino groups, $C_1$-$C_6$ alkylcarboxylic acid groups, $C_1$-$C_6$ alkylhydroxy groups, $C_3$-$C_8$ cycloalkyl groups, benzyl groups, $C_3$-$C_8$ heterocyclyl groups, and —O—C(=O)—($C_1$-$C_6$ alkyl) groups;
$R^4$ is chosen from hydrogen, hydroxyl groups, —O—($C_1$-$C_6$ alkyl) groups, —O—C(=O)—($C_1$-$C_6$ alkyl) groups, and $C_1$-$C_6$ alkyl groups;
$R^{10}$ is chosen from 3 to 10 membered carbocycles and 3 to 10 membered heterocycles, each of which is substituted with 0 to 3 $R^a$, wherein each $R^a$ is independently chosen from halogens, $C_1$-$C_6$ alkyl groups, —O—($C_1$-$C_6$)alkyl groups, $C_1$-$C_6$ alkylalkoxy groups, $C_1$-$C_6$ alkylhydroxy groups, —S(=O)$_w$-(4 to 7 membered heterocycles), 4 to 7 membered carbocycles, and 4 to 7 membered heterocycles;
$R^{15}$ and $R^{16}$ are each independently chosen from hydrogen, $R^{17}$, —C(=O)—$R^{17}$, and —C(=O)—O—$R^{17}$; and
$R^{17}$ is chosen from hydrogen, $C_1$-$C_6$ alkyl groups, $C_3$-$C_8$ cycloalkyl groups, benzyl groups, and $C_3$-$C_8$ heterocyclyl groups;
wherein $R^1$, $R^2$, $R^3$, $R^4$, $R^{10}$, $R^{15}$, $R^{16}$, and $R^{17}$ are each independently substituted with 0 to 3 groups independently chosen from halogens, hydroxyl groups, $C_1$-$C_6$ alkyl groups, —O—($C_1$-$C_6$ alkyl) groups, —NR$^{15}$R$^{16}$, $C_3$-$C_8$ cycloalkyl groups, $C_1$-$C_6$ alkylhydroxy groups, $C_1$-$C_6$ alkylalkoxy groups, benzyl groups, and $C_3$-$C_8$ heterocyclyl groups; and
wherein each $R^a$ is independently substituted with 0 to 3 groups independently chosen from halogens, hydroxyl groups, —NR$^{15}$R$^{16}$, $C_1$-$C_6$ alkyl groups, —(C=O)—($C_1$-$C_6$ alkyl) groups, —(C=O)—($C_1$-$C_6$ alkyl)-($C_3$-$C_{10}$ heterocyclyl groups), and $C_1$-$C_6$ alkylcarboxylic acid groups, each of which is substituted with 0, 1, or 2 groups independently chosen from halogens, hydroxyl groups, —NR$^{15}$R$^{16}$, and $C_1$-$C_3$ alkyl groups; and w is 0, 1, or 2.

In some embodiments, $R^1$ is chosen from absent, hydrogen, $C_1$-$C_4$ alkyl groups, $C_1$-$C_4$ alkylcarboxylic acid groups, and $C_3$-$C_8$ cycloalkyl groups. In some embodiments, $R^1$ is absent. In some embodiments, $R^1$ is hydrogen. In some embodiments, $R^1$ is a $C_1$-$C_4$ alkyl group. In some embodiments, $R^1$ is methyl. In some embodiments, $R^1$ is ethyl.

In some embodiments, $R^1$ is a $C_1$-$C_4$ alkylcarboxylic acid group. In some embodiments, $R^1$ is —CH$_2$CH$_2$CH$_2$CO$_2$H. In some embodiments, $R^1$ is a $C_3$-$C_8$ cycloalkyl group. In some embodiments, $R^1$ is cycloheptyl. In some embodiments, $R^3$ is chosen from hydrogen, $C_1$-$C_4$alkyl groups, $C_1$-$C_4$ alkylalkoxy groups, $C_1$-$C_4$ alkylcarboxylic acid groups, and $C_1$-$C_4$ alkylhydroxy groups. In some embodiments, $R^3$ is chosen from hydrogen and $C_1$-$C_4$ alkylcarboxylic acid groups. In some embodiments, $R^3$ is hydrogen. In some embodiments, $R^3$ is a $C_1$-$C_4$ alkylcarboxylic acid group. In some embodiments, $R^3$ is —CH$_2$CH$_2$CO$_2$H.

In some embodiments, $R^4$ is chosen from hydrogen, hydroxyl groups, —O—($C_1$-$C_4$ alkyl) groups, —O—C(=O)—($C_1$-$C_4$ alkyl) groups, and $C_1$-$C_4$ alkyl groups. In some embodiments, $R^4$ is hydrogen. In some embodiments, $R^4$ is hydroxyl. In some embodiments, $R^4$ is a —O—($C_1$-$C_4$ alkyl) group. In some embodiments, $R^4$ is —OCH$_3$. In some embodiments, $R^4$ is —OCH$_2$CH$_3$. In some embodiments, $R^4$ is a —O—C(=O)—($C_1$-$C_4$ alkyl) group. In some embodiments, $R^4$ is —O—C(=O)—CH$_3$. In some embodiments, $R^4$ is —O—C(=O)—CH$_2$CH$_3$. In some embodiments, $R^4$ is a $C_1$-$C_4$ alkyl group. In some embodiments, $R^4$ is methyl. In some embodiments, $R^4$ is ethyl.

In some embodiments, $R^{10}$ is chosen from 6 to 9 membered carbocycles and 6 to 9 membered heterocycles, each of which is substituted with 0 to 2 $R^a$, wherein each $R^a$ is independently substituted with 0 to 3 groups independently chosen from halogens, hydroxyl groups, $C_1$-$C_6$ alkyl groups, —(C=O)—($C_1$-$C_6$ alkyl) groups, —(C=O)—($C_1$-$C_6$ alkyl)-(3 to 10 membered heterocycle) groups, and $C_1$-$C_5$ alkylcarboxylic acid groups.

In some embodiments, the carbocycle is a phenyl substituted with 0 to 2 $R^a$, wherein each $R^a$ is independently substituted with 0 to 3 groups independently chosen from halogens, hydroxyl groups, $C_1$-$C_6$ alkyl groups, —(C=O)—($C_1$-$C_6$ alkyl) groups, —(C=O)—($C_1$-$C_6$ alkyl)-(3 to 10 membered heterocycle) groups, and $C_1$—C alkylcarboxylic acid groups. In some embodiments, the phenyl is substituted with 2 $R^a$, wherein each $R^a$ is independently substituted with 0 to 3 groups independently chosen from halogens, hydroxyl groups, $C_1$-$C_6$ alkyl groups, —(C=O)—($C_1$-$C_6$ alkyl) groups, —(C=O)—($C_1$-$C_6$ alkyl)-(3 to 10 membered heterocycle) groups, and $C_1$-$C_6$alkylcarboxylic acid groups. In some embodiments, the phenyl is

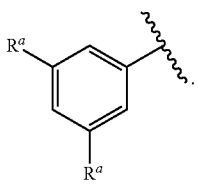

In some embodiments, the heterocycle is a 9 membered heterocycle substituted with 0 to 2 $R^a$, wherein each $R^a$ is independently substituted with 0 to 3 groups independently chosen from halogens, hydroxyl groups, $C_1$-$C_6$ alkyl groups, —(C═O)—($C_1$-$C_6$ alkyl) groups, —(C═O)—($C_1$-$C_6$ alkyl)-(3 to 10 membered heterocycle) groups, and $C_1$-$C_6$ alkylcarboxylic acid groups. In some embodiments, the 9 membered heterocycle is

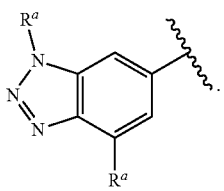

In some embodiments, $R^a$ is chosen from halogens, 3 to 10 membered carbocycles, and 3 to 10 membered heterocycles, wherein each $R^a$ is independently substituted with 0 to 3 groups independently chosen from halogens, hydroxyl groups, $C_1$-$C_6$ alkyl groups, —(C═O)—($C_1$-$C_6$ alkyl) groups, —(C═O)—($C_1$-$C_6$ alkyl)-(3 to 10 membered heterocycle) groups, and $C_1$-$C_6$ alkylcarboxylic acid groups. In some embodiments, $R^a$ is chosen from halogens,

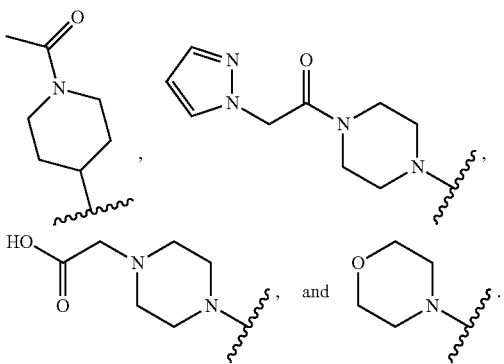

In some embodiments, $R^{15}$ is hydrogen. In some embodiments, $R^{15}$ is $R^{17}$. In some embodiments, $R^{15}$ is —C(═O)—$R^{17}$. In some embodiments, $R^{15}$ is —C(═O)—O—$R^{17}$.

In some embodiments, $R^{16}$ is hydrogen. In some embodiments, $R^{16}$ is $R^{17}$. In some embodiments, $R^{16}$ is —C(═O)—$R^{17}$. In some embodiments, $R^{16}$ is —C(═O)—O—$R^{17}$.

In some embodiments, $R^{17}$ is chosen from hydrogen, $C_1$-$C_4$ alkyl groups, $C_3$-$C_6$ cycloalkyl groups, and $C_3$-$C_8$ heterocyclyl groups. In some embodiments, $R^{17}$ is hydrogen. In some embodiments, $R^{17}$ is a $C_1$-$C_4$ alkyl group. In some embodiments, $R^{17}$ is a $C_1$ alkyl group. In some embodiments, $R^{17}$ is a $C_3$-$C_6$ cycloalkyl group. In some embodiments, $R^{17}$ is a $C_3$ cycloalkyl group. In some embodiments, $R^{17}$ is a $C_4$ cycloalkyl group. In some embodiments, $R^{17}$ is a $C_5$ cycloalkyl group. In some embodiments, $R^{17}$ is a C cycloalkyl group. In some embodiments, $R^{17}$ is a $C_3$-$C_8$ heterocyclyl group. In some embodiments, $R^{17}$ is a $C_3$ heterocyclyl group. In some embodiments, $R^{17}$ is a $C_4$ heterocyclyl group. In some embodiments, $R^{17}$ is a $C_5$ heterocyclyl group. In some embodiments, $R^{17}$ is a C heterocyclyl group. In some embodiments, $R^{17}$ is a $C_7$ heterocyclyl group. In some embodiments, $R^{17}$ is a C heterocyclyl group.

In some embodiments, $R^2$ is a linker. In some embodiments, the linker comprises at least one cleavable peptide moiety. In some embodiments, the at least one cleavable peptide moiety is cleavable by an enzyme. In some embodiments, the linker or cleavable peptide moiety comprises at least one amino acid unit. In some embodiments, the at least one amino acid unit is chosen from arginine, histidine, lysine, aspartic acid, glutamic acid, serine, threonine, asparagine, glutamine, cysteine, selenocysteine, glycine, proline, alanine, valine, isoleucine, methionine, phenylalanine, tyrosine, tryptophan, and citrulline. In some embodiments, the at least one amino acid unit is chosen from alanine, citrulline, and valine. In some embodiments, the linker comprises citrulline and valine. In some embodiments, the linker comprises alanine and valine.

In some embodiments, the linker comprises a moiety chosen from a sulfonamide, a β-glucuronide, a disulfide, and a carbonyl. In some embodiments, the linker comprises a sulfonamide. In some embodiments, the linker comprises a β-glucuronide. In some embodiments, the linker comprises a disulfide. In some embodiments, the linker comprises a carbonyl.

In some embodiments, the linker comprises a spacer unit. In some embodiments, the spacer unit is chosen from alkyl groups and polyethylene glycol (PEG) moieties. In some embodiments, the alkyl group is a $C_1$-$C_{12}$ alkyl group. In some embodiments, the alkyl group is a $C_1$-$C_6$ alkyl group. In some embodiments, the alkyl group is methylene. In some embodiments, the alkyl group is ethylene. In some embodiments, the alkyl group is n-propylene. In some embodiments, the alkyl group is n-butylene. In some embodiments, the alkyl group is n-pentylene. In some embodiments, the alkyl group is n-hexylene. In some embodiments, the PEG moiety comprises -(PEG)$_m$-, wherein m is an integer from 1 to 10. In some embodiments, m is 1. In some embodiments, m is 2. In some embodiments, m is 3. In some embodiments, m is 4. In some embodiments, m is 5. In some embodiments, m is 6.

In some embodiments, the linker comprises a maleimide (Mal) moiety ("Mal-spacer unit"). In some embodiments, the linker comprises a self-immolative spacer unit. In some embodiments, the self-immolative spacer unit is chosen from β-aminobenzyloxycarbonyl (pABC) and β-aminobenzyl (pAB).

In some embodiments, the linker comprises a Mal-spacer unit, an alkyl group, at least one amino acid unit, and a self-immolative spacer. In some embodiments, at least one amino acid unit is chosen from alanine, citrulline, and valine. In some embodiments, the at least one amino acid unit comprises alanine and valine. In some embodiments, the at least one amino acid unit comprises citrulline and valine. In some embodiments, the self-immolative spacer is chosen from pAB and pABC. In some embodiments, the self-immolative spacer comprises pAB. In some embodiments, the self-immolative spacer comprises pABC. In some embodiments, the alkyl group comprises a $C_1$-$C_6$ alkyl group.

In some embodiments, the linker comprises a Mal-spacer unit, PEG moiety, at least one amino acid unit, and a self-immolative spacer. In some embodiments, at least one amino acid unit is chosen from alanine, citrulline, and valine. In some embodiments, the at least one amino acid unit comprises alanine and valine. In some embodiments, the at least one amino acid unit comprises citrulline and valine. In some embodiments, the self-immolative spacer is chosen from pAB and pABC. In some embodiments, the self-immolative spacer comprises pAB. In some embodiments, the self-immolative spacer comprises pABC. In some embodiments, the PEG moiety comprises -(PEG)$_m$-, wherein m is an integer from 1 to 6.

In some embodiments, the drug moiety is a splicing modulator chosen from D1, D2, D3, D4,D4', D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, and D35.

In various embodiments, the drug moiety is a splicing modulator selected from D2 and D1.

In various embodiments, the drug moiety is D2. In various embodiments, the structure of the D2 drug moiety used in the disclosed linker-drug (L–D) compounds is shown below:

D2

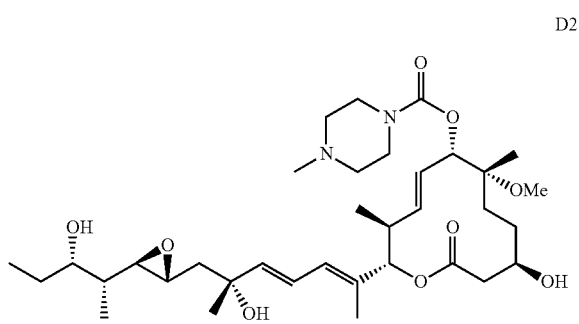 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C)CC2)/C=C/[C@@H]1C]

In various embodiments, the linker in the linker-drug (L–D) compounds described herein covalently attaches to the D2 drug moiety via an amine on the piperazine group. In various embodiments, the drug moiety is a derivative of D2. In various embodiments, the D2 derivative retains at least one biological function or activity as D2 (e.g., SF3b complex binding, in vitro splicing activity, cytotoxicity) but has an altered chemical structure.

In various embodiments, the drug moiety is D1. In various embodiments, the structure of the D1 drug moiety used in the disclosed linker-drug (L–D) compounds is shown below:

D1

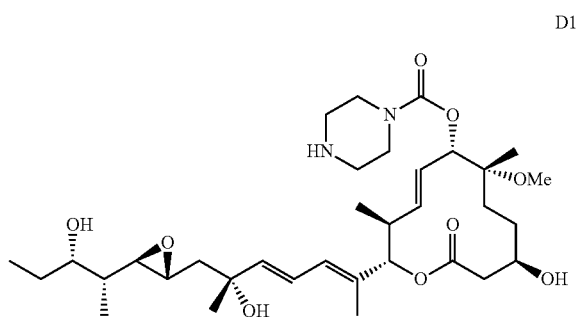 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCNCC2)/C=C/[C@@H]1C]

In various embodiments, the linker in the linker-drug (L–D) compounds described herein covalently attaches to the D1 drug moiety via an amine on the piperazine group. In various embodiments, the drug moiety is a derivative of D1. In various embodiments, the D1 derivative retains at least one biological function or activity as D1 (e.g., SF3b complex binding, in vitro splicing activity, cytotoxicity) but has an altered chemical structure Also disclosed herein are exemplary splicing modulator drug compounds, for use on their own or as drug moieties in the ADCs disclosed herein. The present disclosure, in various embodiments, further provides compositions comprising multiple copies of such compounds, e.g., pharmaceutical compositions comprising a splicing modulator drug compound and a pharmaceutically acceptable carrier.

In various embodiments, the present disclosure provides a compound chosen from a compound of formula (D4)

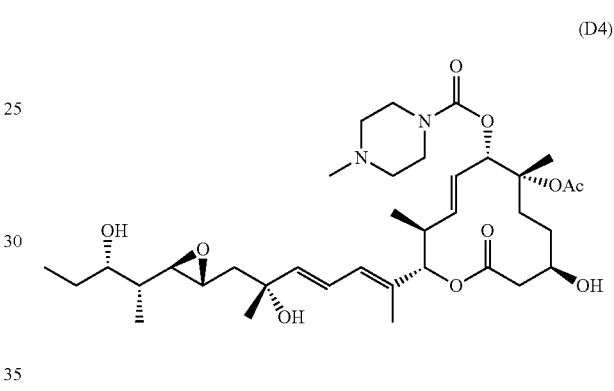

and pharmaceutically acceptable salts thereof.

In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula (D8)

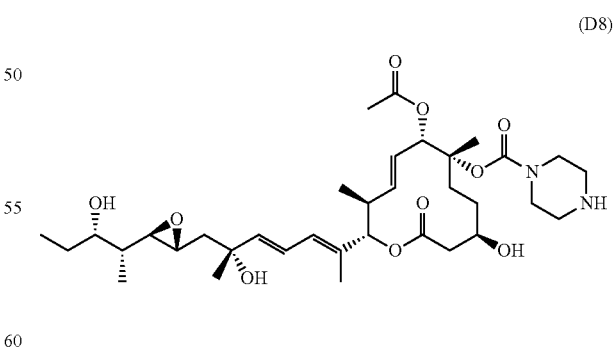

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula

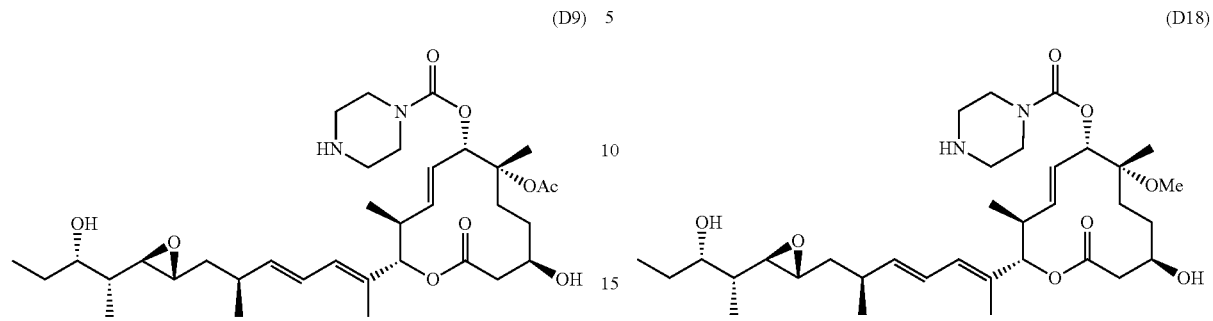

(D9)

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula

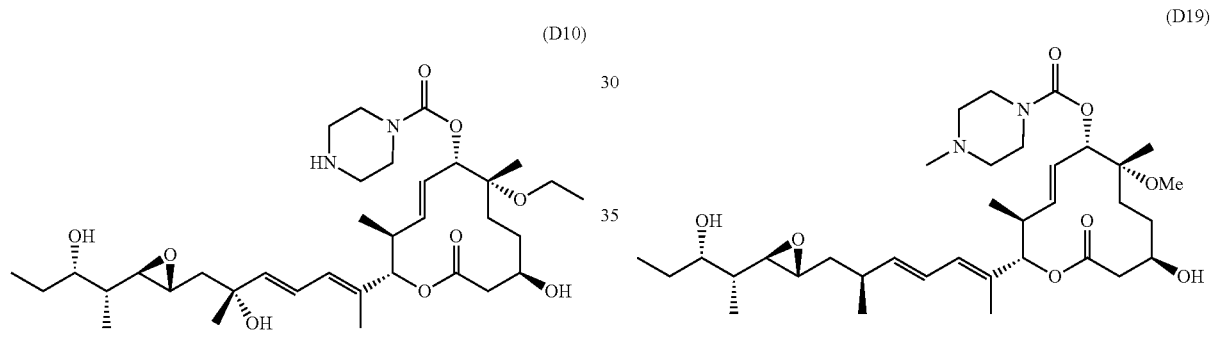

(D10)

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula

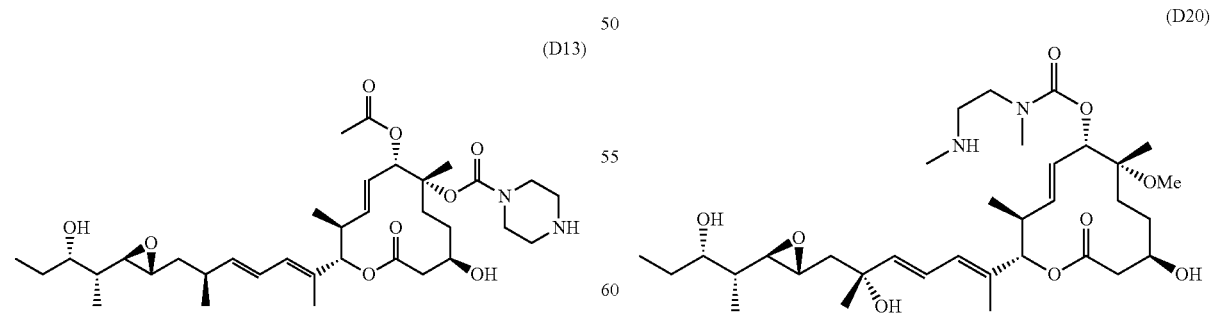

(D13)

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula (D18)

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula (D19)

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula (D20)

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula

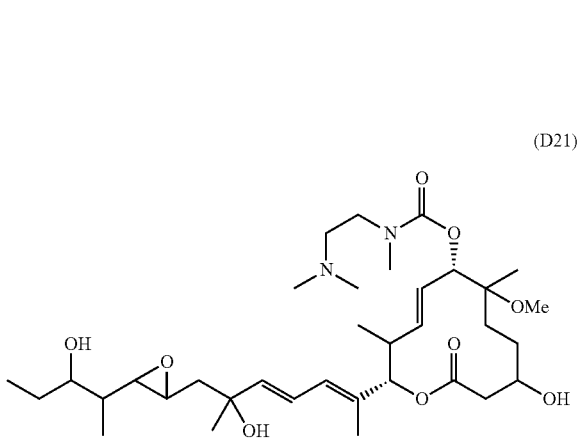 [SMILES: CCC(O)C(C)C1OC1CC(C)(O)/C=C/C=C(\C)[C@H]1OC(=O)CC(O)CCC(C)(OC)[C@@H](OC(=O)N(C)CCN(C)C)/C=C/C1C]

(D21)

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula

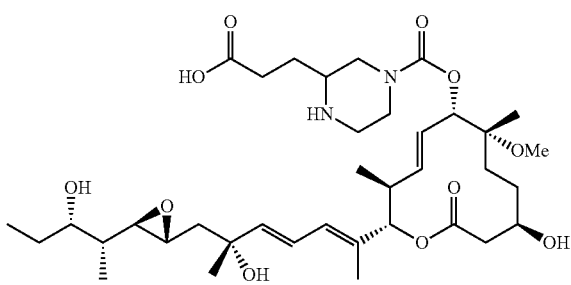

(D22)

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula

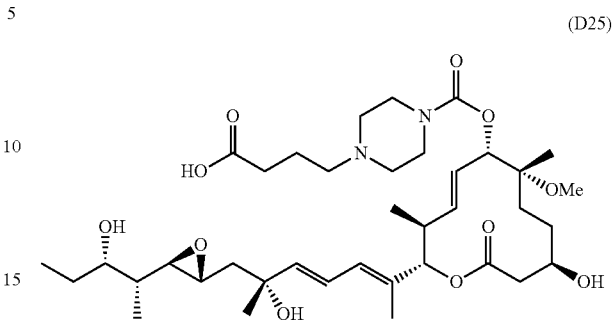

(D25)

and pharmaceutically acceptable salts thereof. In various embodiments, the present disclosure further provides a pharmaceutical composition comprising the compound, or a pharmaceutically acceptable salt thereof, and a pharmaceutically acceptable carrier.

In various other embodiments, the present disclosure provides a compound chosen from a compound of formula

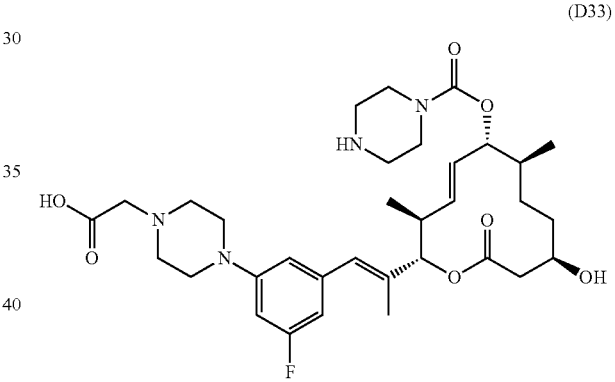

(D33)

and pharmaceutically acceptable salts thereof. In various embodiments, the present disclosure further provides a pharmaceutical composition comprising the compound, or a pharmaceutically acceptable salt thereof, and a pharmaceutically acceptable carrier.

Bioconjugation

Figure 26:
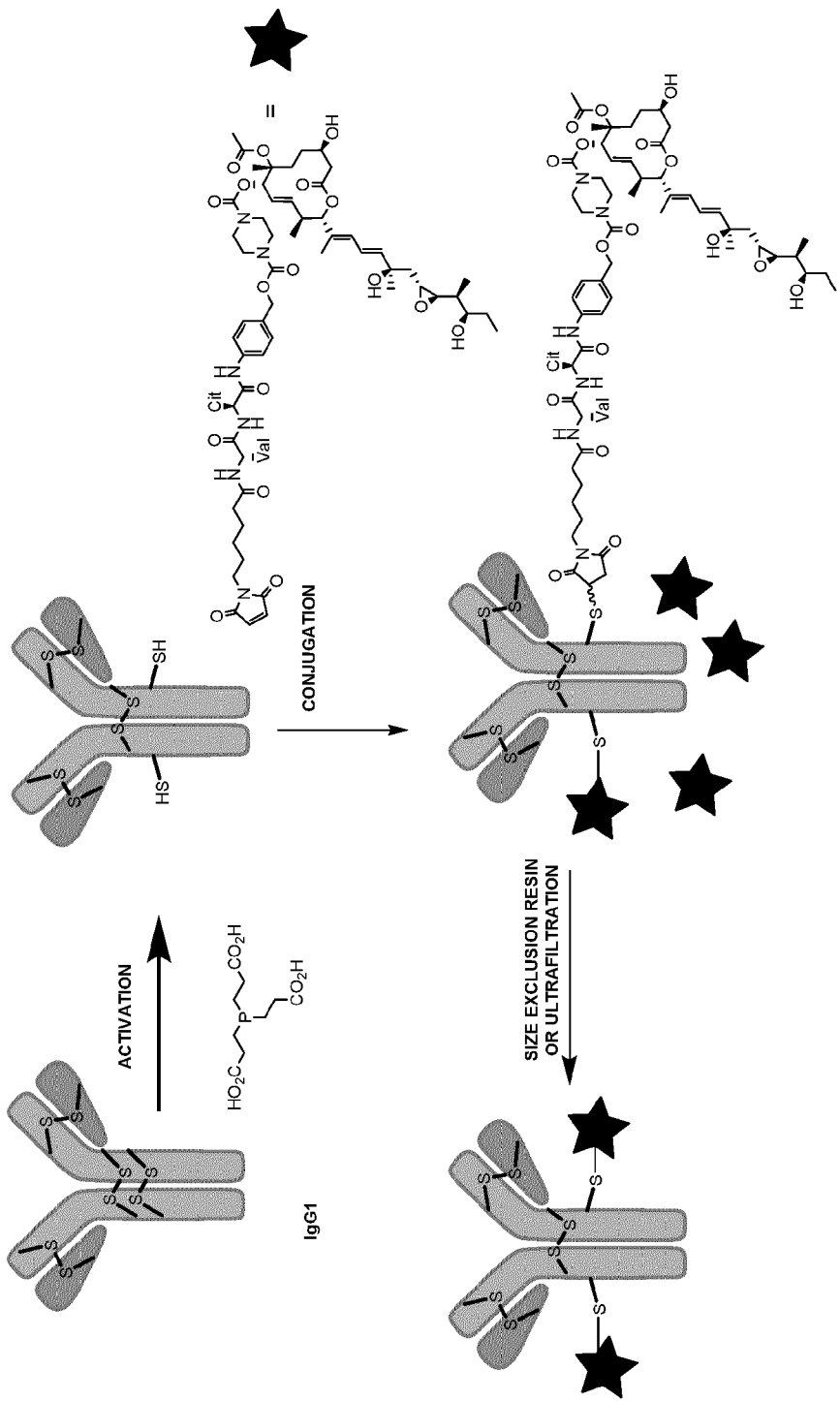
FIG. 26 shows an exemplary bioconjugation scheme for preparation of ADCs using splicing modulators.

In some embodiments, a linker-drug compound may be conjugated to an antibody or antigen binding fragment according to the exemplary scheme depicted in FIG. 26. Briefly, in some embodiments, an antibody or antigen binding fragment may be treated with a reagent, e.g., a reducing agent, e.g., tris(2-carboxyethyl)phosphine, to activate the antibody or antigen binding fragment by reducing one or more disulfide bonds. In some embodiments, the activated antibody or antigen binding fragment is then treated with a linker-drug compound at a predetermined stoichiometry. Subsequently, in some embodiments, the mixture is then subjected to a purification technique, e.g., size exclusion resin or ultrafiltration to afford the desired antibody-drug conjugate.

In some embodiments, provided herein is an antibody-drug conjugate having the structure

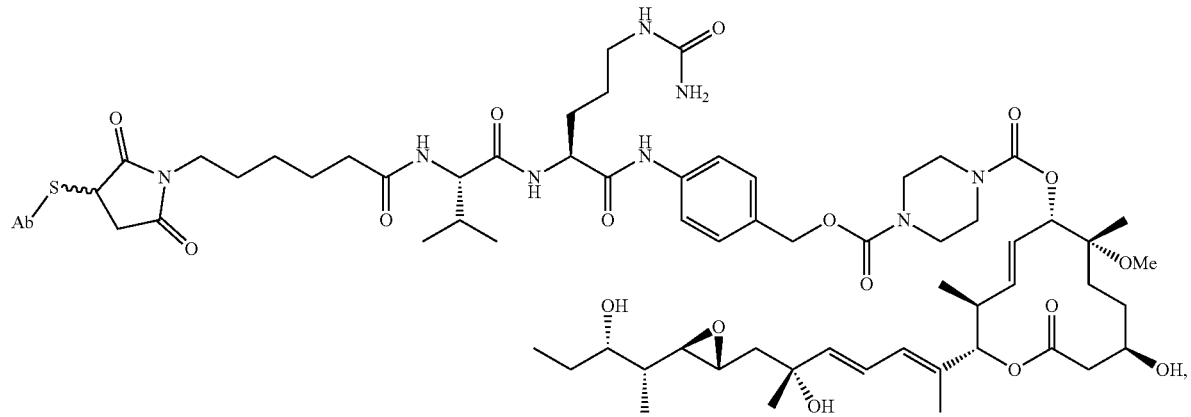

(Ab-ADL1-D1)

wherein Ab is an antibody or antigen binding fragment covalently bound to a maleimide group of the linker-drug compound (ADL1-D1) through the sulfur atom of a thiol group on the antibody or antigen binding fragment.

In some embodiments, provided herein is an antibody-drug conjugate having the structure

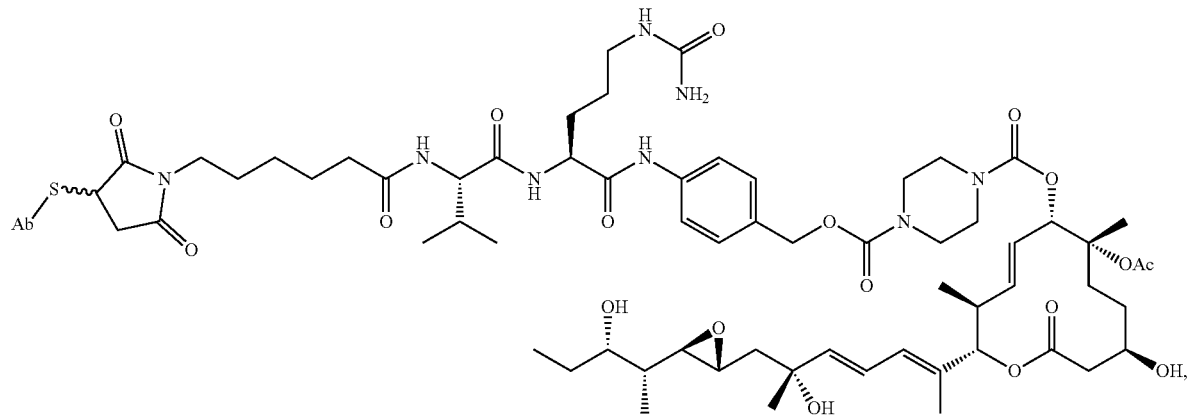

(Ab-ADL1-D4)

wherein Ab is an antibody or antigen binding fragment covalently bound to a maleimide group of the linker-drug compound (ADL1-D4) through the sulfur atom of a thiol group on the antibody or antigen binding fragment.

In some embodiments, provided herein is an antibody-drug conjugate having the structure

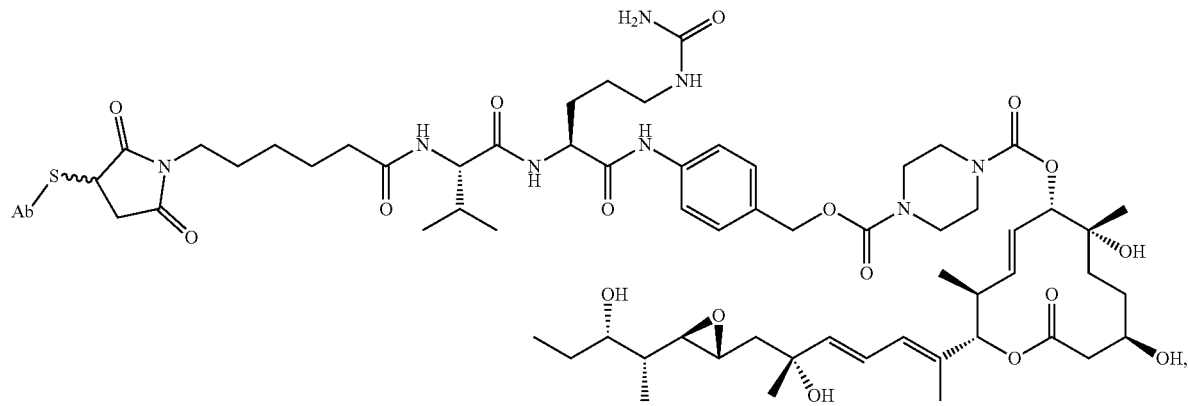

(Ab-ADL1-D12)

wherein Ab is an antibody or antigen binding fragment covalently bound to a maleimide group of the linker-drug compound (ADL1-D12) through the sulfur atom of a thiol group on the antibody or antigen binding fragment.

In some embodiments, provided herein is an antibody-drug conjugate having the structure

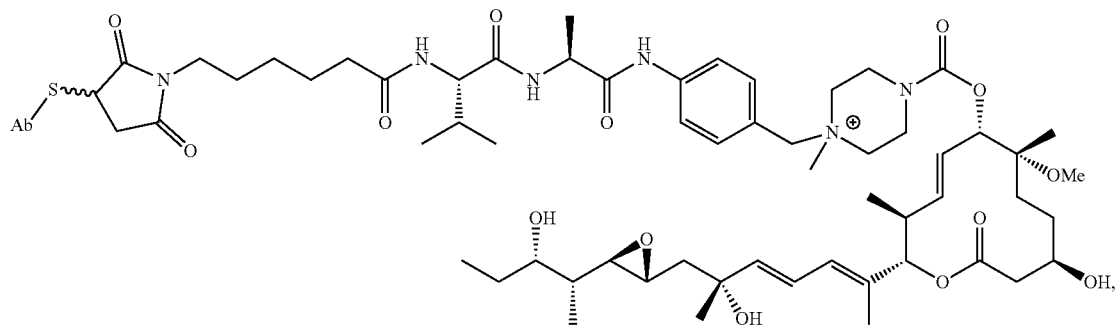

(Ab-ADL5-D2)

wherein Ab is an antibody or antigen binding fragment covalently bound to a maleimide group of the linker-drug compound (ADL5-D2) through the sulfur atom of a thiol group on the antibody or antigen binding fragment.

In some embodiments, provided herein is an antibody-drug conjugate having the structure (Ab-ADL5-D15)

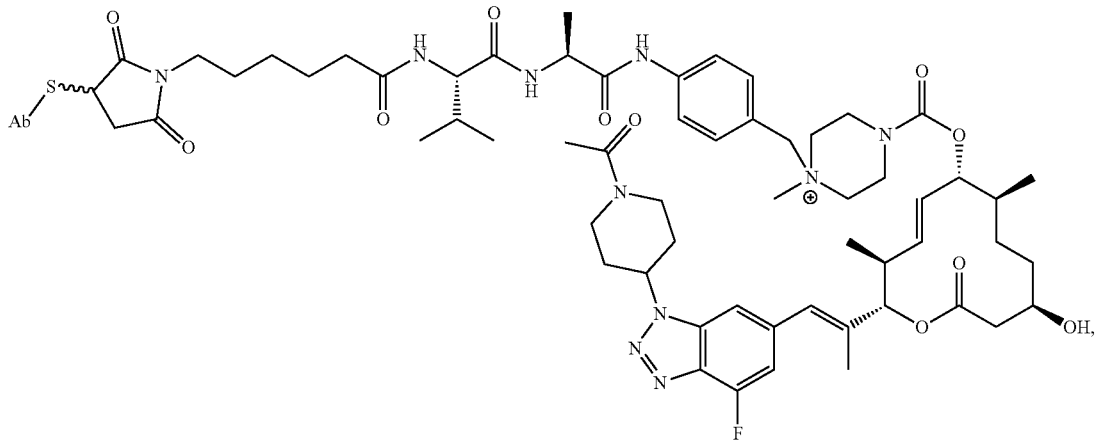

wherein Ab is an antibody or antigen binding fragment covalently bound to a maleimide group of the linker-drug compound (ADL5-D15) through the sulfur atom of a thiol group on the antibody or antigen binding fragment.

In some embodiments, provided herein is an antibody-drug conjugate having the structure (Ab-ADL13-D4)

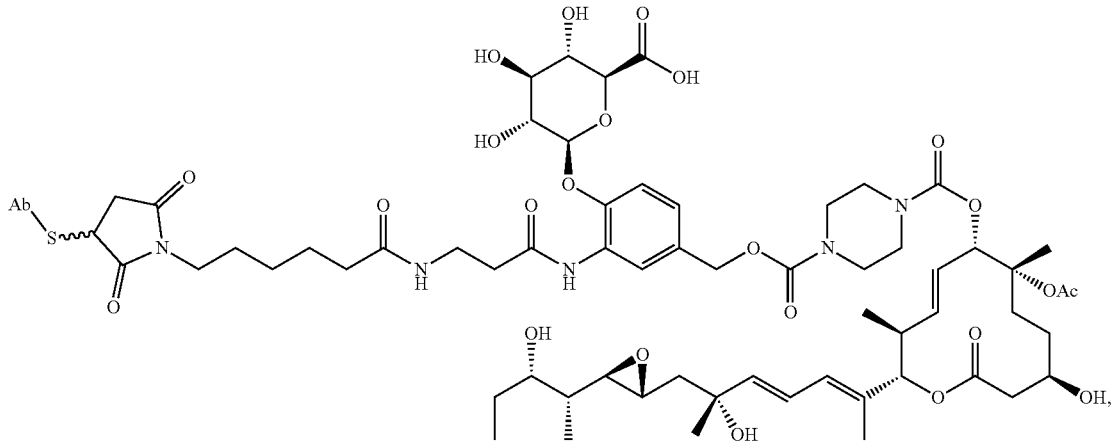

wherein Ab is an antibody or antigen binding fragment covalently bound to a maleimide group of the linker-drug compound (ADL13-D4) through the sulfur atom of a thiol group on the antibody or antigen binding fragment.

In some embodiments, the Ab is an anti-HER2 antibody or an antigen binding fragment thereof. In some embodiments, the Ab binds to HER2 and targets HER2-expressing neoplastic cells (i.e., the ADC targets HER2-expressing neoplastic cells). In some embodiments, the Ab is an internalizing anti-HER2 antibody or internalizing antigen binding fragment thereof.

In some embodiments, the anti-HER2 antibody or antigen binding fragment comprises three heavy chain complementarity determining regions (HCDR1, HCDR2, and HCDR3) comprising amino acid sequences of SEQ ID NO:1 (HCDR1), SEQ ID NO:2 (HCDR2), and SEQ ID NO:3 (HCDR3); and three light chain complementarity determining regions (LCDR1, LCDR2, and LCDR3) comprising amino acid sequences of SEQ ID NO:4 (LCDR1), SEQ ID NO:5 (LCDR2), and SEQ ID NO:6 (LCDR3). In some embodiments, the anti-HER2 antibody or antigen binding fragment is an internalizing antibody or internalizing antigen binding fragment. In some embodiments, the anti-HER2 antibody or antigen binding fragment comprises human framework sequences. In some embodiments, the anti-HER2 antibody or antigen binding fragment comprises a heavy chain variable region comprising an amino acid sequence of SEQ ID NO:19, and a light chain variable region comprising an amino acid sequence of SEQ ID NO:20. In some embodiments, the anti-HER2 antibody or antigen binding fragment comprises a human IgG1 heavy chain constant region. In some embodiments, the anti-HER2 antibody or antigen binding fragment comprises a human Ig kappa light chain constant region.

Drug Loading

Drug loading is represented by p, and is also referred to herein as the drug-to-antibody ratio (DAR). Drug loading may range from 1 to 10 drug moieties per antibody or antigen binding fragment. In some embodiments, p is an integer from 1 to 10. In some embodiments, p is an integer from 1 to 10, 1 to 9, 1 to 8, 1 to 7, 1 to 6, 1 to 5, 1 to 4, 1 to 3, or 1 to 2. In some embodiments, p is an integer from 2 to 10, 2 to 9, 2 to 8, 2 to 7, 2 to 6, 2 to 5, 2 to 4, or 2 to 3. In some embodiments, p is an integer from 1 to 8. In some embodiments, p is an integer from 2 to 4. In other embodiments, p is an integer from 4 to 8. In other embodiments, p is 1, 2, 3, 4, 5, 6, 7, or 8, preferably 4 or 8.

Drug loading may be limited by the number of attachment sites on the antibody or antigen binding fragment. In some embodiments, the linker moiety (L) of the ADC attaches to the antibody or antigen binding fragment through a chemically active group on one or more amino acid residues on the antibody or antigen binding fragment. For example, the linker may be attached to the antibody or antigen binding fragment via a free amino, imino, hydroxyl, thiol, or carboxyl group (e.g., to the N- or C-terminus, to the epsilon amino group of one or more lysine residues, to the free carboxylic acid group of one or more glutamic acid or aspartic acid residues, or to the sulfhydryl group of one or more cysteine residues). The site to which the linker is attached can be a natural residue in the amino acid sequence of the antibody or antigen binding fragment, or it can be introduced into the antibody or antigen binding fragment, e.g., by DNA recombinant technology (e.g., by introducing a cysteine residue into the amino acid sequence) or by protein biochemistry (e.g., by reduction, pH adjustment, or hydrolysis).

In some embodiments, the number of drug moieties that can be conjugated to an antibody or antigen binding fragment is limited by the number of free cysteine residues. For example, where the attachment is a cysteine thiol group, an antibody may have only one or a few cysteine thiol groups, or may have only one or a few sufficiently reactive thiol groups through which a linker may be attached. Generally, antibodies do not contain many free and reactive cysteine thiol groups that may be linked to a drug moiety. Indeed, most cysteine thiol residues in antibodies are involved in either interchain or intrachain disulfide bonds. Conjugation to cysteines can, in some embodiments, therefore require at least partial reduction of the antibody. Over-attachment of linker-toxin to an antibody may destabilize the antibody by reducing the cysteine residues available to form disulfide bonds. Therefore, an optimal drug:antibody ratio should increase potency of the ADC (by increasing the number of attached drug moieties per antibody) without destabilizing the antibody or antigen binding fragment. In some embodiments, an optimal ratio may be 2, 4, 6, or 8.

In some embodiments, an antibody or antigen binding fragment is exposed to reducing conditions prior to conjugation in order to generate one or more free cysteine residues. An antibody, in some embodiments, may be reduced with a reducing agent such as dithiothreitol (DTT) or tris(2-carboxyethyl)phosphine (TCEP), under partial or total reducing conditions, to generate reactive cysteine thiol groups. Unpaired cysteines may be generated through partial reduction with limited molar equivalents of TCEP, which can reduce the interchain disulfide bonds which link the light chain and heavy chain (one pair per H-L pairing) and the two heavy chains in the hinge region (two pairs per H—H pairing in the case of human IgG1) while leaving the intrachain disulfide bonds intact (Stefano et al. (2013) Methods Mol Biol. 1045:145-71). In embodiments, disulfide bonds within the antibodies are reduced electrochemically, e.g., by employing a working electrode that applies an alternating reducing and oxidizing voltage. This approach can allow for on-line coupling of disulfide bond reduction to an analytical device (e.g., an electrochemical detection device, an NMR spectrometer, or a mass spectrometer) or a chemical separation device (e.g., a liquid chromatograph (e.g., an HPLC) or an electrophoresis device (see, e.g., U.S. Publ. No. 20140069822)). In certain embodiments, an antibody is subjected to denaturing conditions to reveal reactive nucleophilic groups on amino acid residues, such as cysteine.

The drug loading of an ADC may be controlled in different ways, e.g., by: (i) limiting the molar excess of drug-linker intermediate or linker reagent relative to antibody; (ii) limiting the conjugation reaction time or temperature; (iii) partial or limiting reductive conditions for cysteine thiol modification; and/or (iv) engineering by recombinant techniques the amino acid sequence of the antibody such that the number and position of cysteine residues is modified for control of the number and/or position of linker-drug attachments.

In some embodiments, free cysteine residues are introduced into the amino acid sequence of the antibody or antigen binding fragment. For example, cysteine engineered antibodies can be prepared wherein one or more amino acids of a parent antibody are replaced with a cysteine amino acid. Any form of antibody may be so engineered, i.e. mutated. For example, a parent Fab antibody fragment may be engineered to form a cysteine engineered Fab referred to as a "ThioFab." Similarly, a parent monoclonal antibody may be engineered to form a "ThioMab." A single site mutation yields a single engineered cysteine residue in a ThioFab, whereas a single site mutation yields two engineered cysteine residues in a ThioMab, due to the dimeric nature of the IgG antibody. DNA encoding an amino acid sequence variant of the parent polypeptide can be prepared by a variety of methods known in the art (see, e.g., the methods described in Intl. Pub. No. WO 2006/034488). These methods include, but are not limited to, preparation by site-directed (or oligonucleotide-mediated) mutagenesis, PCR mutagenesis, and cassette mutagenesis of an earlier prepared DNA encoding the polypeptide. Variants of recombinant antibodies may also be constructed by restriction fragment manipulation or by overlap extension PCR with synthetic oligonucleotides. ADCs of Formula (I) include, but are not limited to, antibodies that have 1, 2, 3, or 4 engineered cysteine amino acids (Lyon et al. (2012) Methods Enzymol. 502:123-38). In some embodiments, one or more free cysteine residues are already present in an antibody or antigen binding fragment, without the use of engineering, in which case the existing free cysteine residues may be used to conjugate the antibody or antigen binding fragment to a drug moiety.

Where more than one nucleophilic group reacts with a drug-linker intermediate or a linker moiety reagent followed by drug moiety reagent, in a reaction mixture comprising multiple copies of the antibody or antigen binding fragment and linker moiety, then the resulting product can be a mixture of ADC compounds with a distribution of one or more drug moieties attached to each copy of the antibody or antigen binding fragment in the mixture. In some embodiments, the drug loading in a mixture of ADCs resulting from a conjugation reaction ranges from 1 to 10 drug moieties attached per antibody or antigen binding fragment. The average number of drug moieties per antibody or antigen binding fragment (i.e., the average drug loading, or average p) may be calculated by any conventional method known in the art, e.g., by mass spectrometry (e.g., reverse-phase LC-MS), and/or high-performance liquid chromatography (e.g., HIC-HPLC). In some embodiments, the average number of drug moieties per antibody or antigen binding fragment is determined by hydrophobic interaction chromatography-high performance liquid chromatography (HIC-HPLC). In some embodiments, the average number of drug moieties per antibody or antigen binding fragment is determined by reverse-phase liquid chromatography-mass spectrometry (LC-MS). In some embodiments, the average number of drug moieties per antibody or antigen binding fragment is from about 1.5 to about 3.5, about 2.5 to about 4.5, about 3.5 to about 5.5, about 4.5 to about 6.5, about 5.5 to about 7.5, about 6.5 to about 8.5, or about 7.5 to about 9.5. In some embodiments, the average number of drug moieties per antibody or antigen binding fragment is from about 2 to about 4, about 3 to about 5, about 4 to about 6, about 5 to about 7, about 6 to about 8, about 7 to about 9, about 2 to about 8, or about 4 to about 8.

In some embodiments, the average number of drug moieties per antibody or antigen binding fragment is about 2. In some embodiments, the average number of drug moieties per antibody or antigen binding fragment is about 1.5, about 1.6, about 1.7, about 1.8, about 1.9, about 2, about 2.1, about 2.2, about 2.3, about 2.4, or about 2.5. In some embodiments, the average number of drug moieties per antibody or antigen binding fragment is 2.

In some embodiments, the average number of drug moieties per antibody or antigen binding fragment is about 4. In some embodiments, the average number of drug moieties per antibody or antigen binding fragment is about 3.5, about 3.6, about 3.7, about 3.8, about 3.9, about 4, about 4.1, about 4.2, about 4.3, about 4.4, or about 4.5. In some embodiments, the average number of drug moieties per antibody or antigen binding fragment is 4.

In some embodiments, the average number of drug moieties per antibody or antigen binding fragment is about 8. In some embodiments, the average number of drug moieties per antibody or antigen binding fragment is about 7.5, about 7.6, about 7.7, about 7.8, about 7.9, about 8, about 8.1, about 8.2, about 8.3, about 8.4, or about 8.5. In some embodiments, the average number of drug moieties per antibody or antigen binding fragment is 8.

In various embodiments, the term "about," as used with respect to the average number of drug moieties per antibody or antigen binding fragment, means plus or minus 10%.

Individual ADC compounds, or "species," may be identified in the mixture by mass spectroscopy and separated by UPLC or HPLC, e.g. hydrophobic interaction chromatography (HIC-HPLC). In certain embodiments, a homogeneous or nearly homogenous ADC product with a single loading value may be isolated from the conjugation mixture, e.g., by electrophoresis or chromatography.

In some embodiments, higher drug loading (e.g., p>8) may cause aggregation, insolubility, toxicity, or loss of cellular permeability of certain antibody-drug conjugates. Higher drug loading may also negatively affect the pharmacokinetics (e.g., clearance) of certain ADCs. In some embodiments, lower drug loading (e.g., p<2) may reduce the potency of certain ADCs against target-expressing cells and/or bystander cells. In some embodiments, the drug loading for an ADC of the present disclosure ranges from about 2 to about 8; from about 2 to about 6; from about 2 to about 5; from about 3 to about 5; from about 2 to about 4; or from about 4 to about 8.

In some embodiments, a drug loading and/or an average drug loading of about 2 is achieved, e.g., using partial reduction of intrachain disulfides on the antibody or antigen binding fragment, and provides beneficial properties. In some embodiments, a drug loading and/or an average drug loading of about 4 is achieved, e.g., using partial reduction of intrachain disulfides on the antibody or antigen binding fragment, and provides beneficial properties. In some embodiments, a drug loading and/or an average drug loading of about 8 is achieved, e.g., using partial reduction of intrachain disulfides on the antibody or antigen binding fragment, and provides beneficial properties. In some embodiments, a drug loading and/or an average drug loading of less than about 2 may result in an unacceptably high level of unconjugated antibody species, which can compete with the ADC for binding to a target antigen and/or provide for reduced treatment efficacy. In some embodiments, a drug loading and/or average drug loading of more than about 8 may result in an unacceptably high level of product heterogeneity and/or ADC aggregation. A drug loading and/or an average drug loading of more than about 8 may also affect stability of the ADC, due to loss of one or more chemical bonds required to stabilize the antibody or antigen binding fragment.

The present disclosure includes methods of producing the described ADCs. Briefly, the ADCs comprise an antibody or antigen binding fragment as the antibody or antigen binding fragment, a drug moiety (e.g., a splicing modulator), and a linker that joins the drug moiety and the antibody or antigen binding fragment. In some embodiments, the ADCs can be prepared using a linker having reactive functionalities for covalently attaching to the drug moiety and to the antibody or antigen binding fragment. For example, in some embodiments, a cysteine thiol of an antibody or antigen binding fragment can form a bond with a reactive functional group of a linker or a drug-linker intermediate (e.g., a maleimide moiety) to make an ADC. The generation of the ADCs can be accomplished by any technique known to the skilled artisan.

In some embodiments, an ADC is produced by contacting an antibody or antigen binding fragment with a linker and a drug moiety (e.g., a splicing modulator) in a sequential manner, such that the antibody or antigen binding fragment is covalently linked to the linker first, and then the pre-formed antibody-linker intermediate reacts with the drug moiety. The antibody-linker intermediate may or may not be subjected to a purification step prior to contacting the drug moiety. In other embodiments, an ADC is produced by contacting an antibody or antigen binding fragment with a linker-drug compound pre-formed by reacting a linker with a drug moiety. The pre-formed linker-drug compound may or may not be subjected to a purification step prior to contacting the antibody or antigen binding fragment. In other embodiments, the antibody or antigen binding fragment contacts the linker and the drug moiety in one reaction mixture, allowing simultaneous formation of the covalent bonds between the antibody or antigen binding fragment and the linker, and between the linker and the drug moiety. This method of producing ADCs may include a reaction, wherein the antibody or antigen binding fragment contacts the antibody or antigen binding fragment prior to the addition of the linker to the reaction mixture, and vice versa. In certain embodiments, an ADC is produced by reacting an antibody or antigen binding fragment with a linker joined to a drug moiety, such as ADL1-splicing modulator (e.g., ADL1-D1) or ADL5-splicing modulator (e.g., ADL5-D2), under conditions that allow conjugation.

The ADCs prepared according to the methods described above may be subjected to a purification step. The purification step may involve any biochemical methods known in the art for purifying proteins, or any combination of methods thereof. These include, but are not limited to, tangential flow filtration (TFF), affinity chromatography, ion exchange chromatography, any charge or isoelectric point-based chromatography, mixed mode chromatography, e.g., CHT (ceramic hydroxyapatite), hydrophobic interaction chromatography, size exclusion chromatography, dialysis, filtration, selective precipitation, or any combination thereof.

Therapeutic Uses and Compositions

Disclosed herein are methods of using the disclosed ADCs and compositions in treating a subject for a disorder, e.g., a neoplastic disorder. ADCs may be administered alone or in combination with a second therapeutic agent, and may be administered in any pharmaceutically acceptable formulation, dosage, and dosing regimen. ADC treatment efficacy may be evaluated for toxicity as well as indicators of efficacy and adjusted accordingly. Efficacy measures include, but are not limited to, a cytostatic and/or cytotoxic effect observed in vitro or in vivo, reduced tumor volume, tumor growth inhibition, and/or prolonged survival.

Methods of determining whether an ADC exerts a cytostatic and/or cytotoxic effect on a cell are known. For example, the cytotoxic or cytostatic activity of an ADC can be measured by: exposing mammalian cells expressing a target protein of the ADC in a cell culture medium; culturing the cells for a period from about 6 hours to about 6 days; and measuring cell viability. Cell-based in vitro assays may also be used to measure viability (proliferation), cytotoxicity, and induction of apoptosis (caspase activation) of the ADC.

For determining whether an ADC exerts a cytostatic effect, a thymidine incorporation assay may be used. For example, cancer cells expressing a target antigen at a density of 5,000 cells/well of a 96-well plated can be cultured for a 72-hour period and exposed to 0.5 µCi of $^3$H-thymidine during the final 8 hours of the 72-hour period. The incorporation of $^3$H-thymidine into cells of the culture is measured in the presence and absence of the ADC.

For determining cytotoxicity, necrosis or apoptosis (programmed cell death) may be measured. Necrosis is typically accompanied by increased permeability of the plasma membrane; swelling of the cell, and rupture of the plasma membrane. Apoptosis can be quantitated, for example, by measuring DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica (1999) No. 2, pp. 34-37 (Roche Molecular Biochemicals).

Apoptosis may also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (Coligan et al., eds. (1992) pp. 3.17.1-3.17.16). Cells also can be labeled with a DNA dye (e.g., acridine orange, ethidium bromide, or propidium iodide) and the cells observed for chromatin condensation and margination along the inner nuclear membrane. Apoptosis may also be determined, in some embodiments, by screening for caspase activity. In some embodiments, a Caspase-Glo® Assay can be used to measure activity of caspase-3 and caspase-7. In some embodiments, the assay provides a luminogenic caspase-3/7 substrate in a reagent optimized for caspase activity, luciferase activity, and cell lysis. In some embodiments, adding Caspase-Glo® 3/7 Reagent in an "add-mix-measure" format may result in cell lysis, followed by caspase cleavage of the substrate and generation of a "glow-type" luminescent signal, produced by luciferase. In some embodiments, luminescence may be proportional to the amount of caspase activity present, and can serve as an indicator of apoptosis. Other morphological changes that can be measured to determine apoptosis include, e.g., cytoplasmic condensation, increased membrane blebbing, and cellular shrinkage. Determination of any of these effects on cancer cells indicates that an ADC is useful in the treatment of cancers.

Cell viability may be measured, e.g., by determining in a cell the uptake of a dye such as neutral red, trypan blue, Crystal Violet, or ALAMAR™ blue (see, e.g., Page et al. (1993) Intl J Oncology 3:473-6). In such an assay, the cells are incubated in media containing the dye, the cells are washed, and the remaining dye, reflecting cellular uptake of the dye, is measured spectrophotometrically. Cell viability may also be measured, e.g., by quantifying ATP, an indicator of metabolically active cells. In certain embodiments, in vitro potency and/or cell viability of prepared ADCs or splicing modulator compounds may be assessed using a CellTiter-Glo® Luminescent Cell Viability Assay, as described in the examples provided herein. In this assay, in certain embodiments, the single reagent (CellTiter-Glo® Reagent) is added directly to cells cultured in serum-supplemented medium. The addition of reagent results in cell lysis and generation of a luminescent signal proportional to the amount of ATP present. The amount of ATP is directly proportional to the number of cells present in culture. The protein-binding dye sulforhodamine B (SRB) can also be used to measure cytotoxicity (Skehan et al. (1990) J Natl Cancer Inst. 82:1107-12).

The disclosed ADCs may also be evaluated for bystander killing activity. Bystander killing activity may be determined, e.g., by an assay employing two cell lines, one positive for a target antigen and one negative for a target antigen. In certain embodiments, the design of the assay allows tracking of only target negative cells. In certain embodiments, cells are plated under three conditions: (i) target negative cells alone (tagged or labeled); (ii) target positive cells alone; and (iii) co-culture of target negative cells and target positive cells. Cells are then treated with an ADC followed by monitoring of cytotoxicity. When plates are read with CellTiter-Glo® Reagent, viability of all cell populations can be monitored. When plates are read with OneGlo® Reagent, only the tagged or labeled target negative cells produce a signal. Killing of the target-negative cells when mixed with target-positive cells is indicative of bystander killing, whereas killing of the target-negative cells in the absence of the target-positive cells is indicative of off-target killing.

In certain aspects, the present disclosure features a method of killing, inhibiting or modulating the growth of, or interfering with the metabolism of, a cancer cell or tissue by disrupting RNA splicing. The method may be used with any subject where disruption of RNA splicing provides a therapeutic benefit. Subjects that may benefit from disrupting RNA splicing include, but are not limited to, those having or at risk of having a neoplastic disorder such as a hematological malignancy or a solid tumor. In certain embodiments, the hematological malignancy is a B-cell malignancy, a cancer of the blood (leukemia), a cancer of plasma cells (myeloma, e.g., multiple myeloma), or a cancer of the lymph nodes (lymphoma). In certain embodiments, the hematological malignancy is acute myelogenous leukemia or multiple myeloma. In certain embodiments, the leukemia is acute lymphoblastic leukemia (ALL), acute myelogenous leukemia (AML), chronic lymphocytic leukemia (CLL), chronic myelogenous leukemia (CML), chronic myelomonocytic leukemia (CMML), or acute monocytic leukemia (AMoL). In certain embodiments, the lymphoma is Hodgkin's lymphoma or non-Hodgkin's lymphoma. In certain embodiments, the hematological malignancy is myelodysplasia syndrome (MDS). In certain embodiments, the solid tumor is a carcinoma such as breast cancer, pancreatic cancer, prostate cancer, colon or colorectal cancer, lung cancer, gastric cancer, cervical cancer, endometrial cancer, ovarian cancer, cholangiocarcinoma, glioma, or melanoma. In certain embodiments, the solid tumor is breast cancer, gastric cancer, prostate cancer, ovarian cancer, lung cancer (e.g., lung adenocarcinoma), uterine cancer (e.g., uterine serous endometrial carcinoma), salivary duct carcinoma, melanoma, colon cancer, cervical cancer, pancreatic cancer, kidney cancer, colorectal cancer, and esophageal cancer. In certain embodiments, the lung cancer is lung adenocarcinoma. In certain embodiments, the uterine cancer is uterine serous endometrial carcinoma.

In various embodiments, the disclosed ADCs may be administered in any cell or tissue that expresses HER2, such as a HER2-expressing neoplastic cell or tissue. An exemplary embodiment includes a method of inhibiting HER2-mediated cell signaling or a method of killing a cell. The method may be used with any cell or tissue that expresses HER2, such as a cancerous cell or a metastatic lesion. Non-limiting examples of HER2-expressing cancers include breast cancer, gastric cancer, bladder cancer, urothelial cell carcinoma, esophageal cancer, lung cancer (e.g., lung adenocarcinoma), uterine cancer (e.g., uterine serous endometrial carcinoma), salivary duct carcinoma, cervical cancer, endometrial cancer, and ovarian cancer (English et al. (2013) Mol Diagn Ther. 17:85-99). Non-limiting examples of HER2-expressing cells include HCC1954 and SKBR3 human breast ductal carcinoma cells, N87 human gastric carcinoma cells, and cells comprising a recombinant nucleic acid encoding HER2 or a portion thereof.

In various embodiments, the disclosed ADCs may be administered in any cell or tissue that expresses CD138, such as a CD138-expressing neoplastic cell or tissue. An exemplary embodiment includes a method of inhibiting CD138-mediated cell signaling or a method of killing a cell. The method may be used with any cell or tissue that expresses CD138, such as a cancerous cell or a metastatic lesion. Non-limiting examples of CD138-expressing cancers include intrathoracic cancer (e.g., lung cancer, mesothelioma), skin cancer (e.g., basal cell carcinoma, squamous cell carcinoma), head and neck cancer (e.g., laryngeal, hypopharynx, nasopharyngeal), breast cancer, urogenital cancer (e.g., cervical cancer, ovarian cancer, endometrial cancer, prostate cancer, bladder cancer, urothelial cancer), hematological malignancies (e.g., myeloma such as multiple myeloma, Hodgkin's lymphoma), and thyroid cancer (Szatmeri et al. (2015) Dis Markers 2015:796052). Non-limiting examples of CD138-expressing cells include MOLP8 human multiple myeloma cells, and cells comprising a recombinant nucleic acid encoding CD138 or a portion thereof.

In various embodiments, the disclosed ADCs may be administered in any cell or tissue that expresses EPHA2, such as an EPHA2-expressing neoplastic cell or tissue. An exemplary embodiment includes a method of inhibiting EPHA2-mediated cell signaling or a method of killing a cell. The method may be used with any cell or tissue that expresses EPHA2, such as a cancerous cell or a metastatic lesion. Non-limiting examples of EPHA2-expressing cancers include breast cancer, brain cancer, ovarian cancer, bladder cancer, pancreatic cancer, esophageal cancer, lung cancer, prostate cancer, melanoma, esophageal cancer, and gastric cancer (Tandon et al. (2011) Expert Opin Ther Targets 15(1):31-51. Non-limiting examples of EPHA2-expressing cells include PC3 human prostate cancer cells, and cells comprising a recombinant nucleic acid encoding EPHA2 or a portion thereof.

Exemplary methods include the steps of contacting a cell with an ADC, as described herein, in an effective amount, i.e., amount sufficient to kill the cell. The method can be used on cells in culture, e.g. in vitro, in vivo, ex vivo, or in situ. For example, cells that express HER2 (e.g., cells collected by biopsy of a tumor or metastatic lesion; cells from an established cancer cell line; or recombinant cells), can be cultured in vitro in culture medium and the contacting step can be affected by adding the ADC to the culture medium. The method will result in killing of cells expressing HER2, including in particular tumor cells expressing HER2. Alternatively, the ADC can be administered to a subject by any suitable administration route (e.g., intravenous, subcutaneous, or direct contact with a tumor tissue) to have an effect in vivo. This approach can be used for antibodies targeting other cell surface antigens (e.g., CD138, EPHA2).

The in vivo effect of a disclosed ADC therapeutic composition can be evaluated in a suitable animal model. For example, xenogeneic cancer models can be used, wherein cancer explants or passaged xenograft tissues are introduced into immune compromised animals, such as nude or SCID mice (Klein et al. (1997) Nature Med. 3:402-8). Efficacy may be predicted using assays that measure inhibition of tumor formation, tumor regression or metastasis, and the like.

In vivo assays that evaluate the promotion of tumor death by mechanisms such as apoptosis may also be used. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

Further provided herein are methods of treating a neoplastic disorder, e.g., a cancer. The ADCs disclosed herein can be administered to a non-human mammal or human subject for therapeutic purposes. The therapeutic methods entail administering to a subject having or suspected of having a neoplastic disorder a therapeutically effective amount of an ADC or composition comprising a splicing modulator linked to a targeting antibody that binds to an antigen expressed, is accessible to binding, or is localized on a cancer cell surface. In some embodiments, treatment with the antibody-drug conjugate or composition induces bystander killing of neoplastic cells which do not express a target antigen but are adjacent to neoplastic cells which express a target antigen.

An exemplary embodiment is a method of delivering a splicing modulator to a cell expressing HER2, comprising conjugating the splicing modulator to an antibody that immunospecifically binds to a HER2 epitope and exposing the cell to the ADC. Exemplary tumor cells that express HER2 for which the ADCs of the present disclosure are indicated include gastric carcinoma cells and breast ductal carcinoma cells.

Another exemplary embodiment is a method of delivering a splicing modulator to a cell expressing CD138, comprising conjugating the splicing modulator to an antibody that immunospecifically binds to a CD138 epitope and exposing the cell to the ADC. Exemplary tumor cells that express CD138 for which the ADCs of the present disclosure are indicated include multiple myeloma cells.

Another exemplary embodiment is a method of delivering a splicing modulator to a cell expressing EPHA2, comprising conjugating the splicing modulator to an antibody that immunospecifically binds to an EPHA2 epitope and exposing the cell to the ADC. Exemplary tumor cells that express EPHA2 for which the ADCs of the present disclosure are indicated include prostate cancer cells.

Another exemplary embodiment is a method of reducing or inhibiting growth of a tumor (e.g., a HER2-expressing tumor, a CD138-expressing tumor, an EPHA2-expressing tumor), comprising administering a therapeutically effective amount of an ADC or composition comprising an ADC. In some embodiments, the treatment is sufficient to reduce or inhibit the growth of the patient's tumor, reduce the number or size of metastatic lesions, reduce tumor load, reduce primary tumor load, reduce invasiveness, prolong survival time, and/or maintain or improve the quality of life. In some embodiments, the tumor is resistant or refractory to treatment with the antibody or antigen binding fragment of the ADC (e.g., an anti-HER2 antibody, an anti-CD138 antibody, an anti-EPHA2 antibody) when administered alone, and/or the tumor is resistant or refractory to treatment with the splicing modulator drug moiety when administered alone In certain aspects, the present disclosure provides a method of reducing or inhibiting growth of a HER2-expressing tumor. In certain embodiments, treatment with the antibody-drug conjugate or composition induces bystander killing of tumor cells which do not express HER2 but that are adjacent to neoplastic tumor cells which do express HER2. Exemplary HER2-expressing tumor types include but are not limited to tumors derived from a HER2-expressing breast cancer, gastric cancer, bladder cancer, urothelial cell carcinoma, esophageal cancer, lung cancer (e.g., lung adenocarcinoma), uterine cancer (e.g., uterine serous endometrial carcinoma), salivary duct carcinoma, cervical cancer, endometrial cancer, and ovarian cancer. In certain embodiments, the HER2-expressing tumor is a tumor derived from a HER2-expressing breast cancer, ovarian cancer, gastric cancer, lung cancer (e.g., lung adenocarcinoma), uterine cancer (e.g., uterine serous endometrial carcinoma), osteosarcoma, or salivary duct carcinoma. In certain embodiments, the HER2-expressing tumor is a lung adenocarcinoma or uterine serous endometrial carcinoma.

In certain aspects, the present disclosure provides a method of reducing or inhibiting growth of a CD138-expressing tumor. In certain embodiments, treatment with the antibody-drug conjugate or composition induces bystander killing of tumor cells which do not express CD138 but that are adjacent to neoplastic tumor cells which do express CD138. Exemplary CD138-expressing tumor types include but are not limited to tumors derived from a CD138-expressing intrathoracic cancer (e.g., lung cancer, mesothelioma), skin cancer (e.g., basal cell carcinoma, squamous cell carcinoma), head and neck cancer (e.g., laryngeal, hypopharynx, nasopharyngeal), breast cancer, urogenital cancer (e.g., cervical cancer, ovarian cancer, endometrial cancer, prostate cancer, bladder cancer, urothelial cancer), and thyroid cancer.

In certain aspects, the present disclosure provides a method of reducing or inhibiting growth of an EPHA2-expressing tumor. In certain embodiments, treatment with the antibody-drug conjugate or composition induces bystander killing of tumor cells which do not express EPHA2 but that are adjacent to neoplastic tumor cells which do express EPHA2. Exemplary EPHA2-expressing tumor types include but are not limited to tumors derived from an EPHA2-expressing breast cancer, brain cancer, ovarian cancer, bladder cancer, pancreatic cancer, esophageal cancer, lung cancer, prostate cancer, melanoma, esophageal cancer, and gastric cancer. In certain embodiments, the EPHA2-expressing tumor is a tumor derived from an EPHA2-expressing breast cancer, prostate cancer, ovarian cancer, lung cancer, melanoma, colon cancer, or esophageal cancer.

Moreover, antibodies of the present disclosure may be administered to a non-human mammal expressing an antigen with which the ADC is capable of binding for veterinary purposes or as an animal model of human disease. Regarding the latter, such animal models may be useful for evaluating the therapeutic efficacy of the disclosed ADCs (e.g., testing of dosages and time courses of administration).

Further provided herein are therapeutic uses of the disclosed ADCs and compositions. An exemplary embodiment is the use of an ADC in the treatment of a neoplastic disorder (e.g., a HER2-expressing cancer, a CD138-expressing cancer, an EPHA2-expressing cancer). Another exemplary embodiment is an ADC for use in the treatment of a neoplastic disorder (e.g., a HER2-expressing cancer, a CD138-expressing cancer, an EPHA2-expressing cancer). Methods for identifying subjects having cancers that express a target antigen (e.g., HER2, CD138, EPHA2, MSLN, FOLH1, CDH6, CEACAM5, CFC1B, ENPP3, FOLR1, HAVCR1, KIT, MET, MUC16, SLC39A6, SLC44A4, STEAP1) are known in the art and may be used to identify suitable patients for treatment with a disclosed ADC.

Another exemplary embodiment is the use of an ADC in a method of manufacturing a medicament for the treatment of a neoplastic disorder (e.g., a HER2-expressing cancer, a CD138-expressing cancer, an EPHA2-expressing cancer).

The therapeutic compositions used in the practice of the foregoing methods may be formulated into pharmaceutical compositions comprising a pharmaceutically acceptable carrier suitable for the desired delivery method. An exemplary embodiment is a pharmaceutical composition comprising an ADC of the present disclosure and a pharmaceutically acceptable carrier. Suitable carriers include any material that, when combined with the therapeutic composition, retains the anti-tumor function of the therapeutic composition and is generally non-reactive with the patient's immune system. Pharmaceutically acceptable carriers include any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol, mesylate salt, and the like, as well as combinations thereof. In many cases, isotonic agents are included, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the ADC.

Therapeutic formulations may be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. Therapeutic protein preparations can be lyophilized and stored as sterile powders, e.g., under vacuum, and then reconstituted in bacteriostatic water (containing for example, benzyl alcohol preservative) or in sterile water prior to injection. Therapeutic formulations may comprise an ADC or a pharmaceutically acceptable salt thereof, e.g., a mesylate salt.

In some embodiments, the ADC is administered to the patient daily, bimonthly, or any time period in between. Dosages and administration protocols for the treatment of cancers using the foregoing methods will vary with the method and the target cancer, and will generally depend on a number of other factors appreciated in the art.

Various delivery systems are known and may be used to administer one or more ADCs of the present disclosure. Methods of administering the ADCs include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration may be employed, e.g., by use of an inhaler or nebulizer, and formulation with an aerosolizing agent. See, e.g., the compositions and methods for pulmonary administration described in U.S. Pat. Nos. 6,019,968, 5,985,320, 5,985,309, 5,934,272, 5,874,064, 5,855,913, 5,290,540, and 4,880,078; and Intl. Publ. Nos. WO 1992/019244, WO 1997/032572, WO 1997/044013, WO 1998/031346, and WO 1999/066903. The ADCs may be administered by any convenient route, for example, by infusion or bolus injection, or by absorption through epithelial or mucocutaneous linings (e.g., oral mucosa, rectal and intestinal mucosa, etc.). Administration can be either systemic or local.

Therapeutic compositions disclosed herein may be sterile and stable under the conditions of manufacture and storage. In some embodiments, one or more of the ADCs, or pharmaceutical compositions, is supplied as a dry sterilized lyophilized powder or water free concentrate in a hermetically sealed container and can be reconstituted (e.g., with water or saline) to the appropriate concentration for administration to a subject. In some embodiments, one or more of the prophylactic or therapeutic agents or pharmaceutical compositions is supplied as a dry sterile lyophilized powder in a hermetically sealed container at a unit dosage of at least 5 mg, at least 10 mg, at least 15 mg, at least 25 mg, at least 35 mg, at least 45 mg, at least 50 mg, at least 75 mg, or at least 100 mg, or any amount in between. In some embodiments, the lyophilized ADCs or pharmaceutical compositions is stored at between 2° C. and 8° C. in the original container. In some embodiments, one or more of the ADCs or pharmaceutical compositions described herein is supplied in liquid form in a hermetically sealed container, e.g., a container indicating the quantity and concentration of the agent. In some embodiments, the liquid form of the administered composition is supplied in a hermetically sealed container of at least 0.25 mg/mL, at least 0.5 mg/mL, at least 1 mg/mL, at least 2.5 mg/mL, at least 5 mg/mL, at least 8 mg/mL, at least 10 mg/mL, at least 15 mg/mL, at least 25 mg/mL, at least 50 mg/mL, at least 75 mg/mL, or at least 100 mg/mL ADC. The liquid form may be stored at between 2° C. and 8° C. in the original container.

In some embodiments, the disclosed ADCs can be incorporated into a pharmaceutical composition suitable for parenteral administration. The injectable solution may be composed of either a liquid or lyophilized dosage form in a flint or amber vial, ampule, or pre-filled syringe, or other known delivery or storage device.

The compositions described herein may be in a variety of forms. These include, for example, liquid, semi-solid, and solid dosage forms, such as liquid solutions (e.g., injectable and infusible solutions), dispersions or suspensions, tablets, pills, powders, liposomes, and suppositories. The preferred form depends on the intended mode of administration and therapeutic application.

In various embodiments, treatment involves single bolus or repeated administration of the ADC preparation via an acceptable route of administration.

Patients may be evaluated for the levels of target antigen in a given sample (e.g. the levels of target antigen expressing cells) in order to assist in determining the most effective dosing regimen, etc. An exemplary embodiment is a method of determining whether a patient will be responsive to treatment with an ADC of the present disclosure, comprising providing a biological sample from the patient and contacting the biological sample with the ADC. Exemplary biological samples include tissue or body fluid, such as an inflammatory exudate, blood, serum, bowel fluid, stool sample, or tumor biopsy (e.g., a tumor biopsy derived from a patient having or at risk of a target antigen-expressing cancer, e.g., a HER2-expressing cancer, a CD138-expressing cancer, an EPHA2-expressing cancer). In some embodiments, a sample (e.g., a tissue and/or body fluid) can be obtained from a subject, and a suitable immunological method can be used to detect and/or measure protein expression of the target antigen (e.g., HER2, CD138, EPHA2, MSLN, FOLH1, CDH6, CEACAM5, CFC1B, ENPP3, FOLR1, HAVCR1, KIT, MET, MUC16, SLC39A6, SLC44A4, STEAP1). Such evaluations are also used for monitoring purposes throughout therapy, and are useful to gauge therapeutic success in combination with the evaluation of other parameters.

In some embodiments, the efficacy of an ADC may be evaluated by contacting a tumor sample from a subject with the ADC and evaluating tumor growth rate or volume. In some embodiments, when an ADC has been determined to be effective, it may be administered to the subject.

The above therapeutic approaches can be combined with any one of a wide variety of additional surgical, chemotherapy, or radiation therapy regimens. In some embodiments, the ADCs or compositions disclosed herein are co-formulated and/or co-administered with one or more additional therapeutic agents, e.g., one or more chemotherapeutic agents. Non-limiting examples of chemotherapeutic agents include alkylating agents, for example, nitrogen mustards, ethyleneimine compounds, and alkyl sulphonates; antimetabolites, for example, folic acid, purine or pyrimidine antagonists; anti-mitotic agents, for example, anti-tubulin agents such as eribulin or eribulin mesylate (Halaven™), vinca alkaloids, and auristatins; cytotoxic antibiotics; compounds that damage or interfere with DNA expression or replication, for example, DNA minor groove binders; and growth factor receptor antagonists. In some embodiments, a chemotherapeutic agent may be a cytotoxic or cytostatic agent. Examples of cytotoxic agents include, but are not limited to, anti-mitotic agents, such as eribulin or eribulin mesylate (Halaven™), auristatins (e.g., monomethyl auristatin E (MMAE), monomethyl auristatin F (MMAF)), maytansinoids (e.g., maytansine), dolastatins, duostatins, cryptophycins, vinca alkaloids (e.g., vincristine, vinblastine), taxanes, taxols, and colchicines; anthracyclines (e.g., daunorubicin, doxorubicin, dihydroxyanthracindione); cytotoxic antibiotics (e.g., mitomycins, actinomycins, duocarmycins (e.g., CC-1065), auromycins, duomycins, calicheamicins, endomycins, phenomycins); alkylating agents (e.g., cisplatin); intercalating agents (e.g., ethidium bromide); topoisomerase inhibitors (e.g., etoposide, tenoposide); radioisotopes, such as $At^{211}$, $I^{131}$, $I^{125}$, $Y^{90}$, $Re^{186}$, $Re^{188}$, $Sm^{153}$, $Bi^{212}$ or $^{213}$, $P^{32}$, and radioactive isotopes of lutetium (e.g., Lu$^{177}$); and toxins of bacterial, fungal, plant or animal origin (e.g., ricin (e.g., ricin A-chain), diphtheria toxin, *Pseudomonas* exotoxin A (e.g., PE40), endotoxin, mitogellin, combrestatin, restrictocin, gelonin, alpha-sarcin, abrin (e.g., abrin A-chain), modeccin (e.g., modeccin A-chain), curicin, crotin, *Sapaonaria officinalis* inhibitor, glucocorticoid).

Also disclosed herein are uses of one or more of the disclosed ADCs in the manufacture of a medicament for treating cancer, e.g., according to the methods described above. In some embodiments, the ADCs disclosed herein are used for treating cancer, e.g., according to the methods described above.

In various embodiments, kits for use in the laboratory and therapeutic applications described herein are within the scope of the present disclosure. Such kits may comprise a carrier, package, or container that is compartmentalized to receive one or more containers such as vials, tubes, and the like, each of the container(s) comprising one of the separate elements to be used in a method disclosed herein, along with a label or insert comprising instructions for use, such as a use described herein. Kits may comprise a container comprising a drug moiety. The present disclosure also provides one or more of the ADCs, or pharmaceutical compositions thereof, packaged in a hermetically sealed container, such as an ampoule or sachette, indicating the quantity of the agent.

Kits may comprise the container described above, and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label may be present on or with the container to indicate that the composition is used for a specific therapy or non-therapeutic application, such as a prognostic, prophylactic, diagnostic, or laboratory application. A label may also indicate directions for either in vivo or in vitro use, such as those described herein. Directions and or other information may also be included on an insert(s) or label(s), which is included with or on the kit. The label may be on or associated with the container. A label may be on a container when letters, numbers, or other characters forming the label are molded or etched into the container itself. A label may be associated with a container when it is present within a receptacle or carrier that also holds the container, e.g., as a package insert. The label may indicate that the composition is used for diagnosing or treating a condition, such as a cancer a described herein.

Neoantigens and Methods of Use

Also disclosed herein, in various embodiments, are methods of treating a patient by inducing neoantigens in tumor cells that can be targeted by the patient's immune system for clearance. Without being bound by theory, in various embodiments, administering a splicing modulator, alone and/or as part of an ADC or composition, may produce neoantigens that induce an immune response, induce a double-stranded RNA immune response, e.g., as a result of re-expressed intron-resident endogenous retroviruses, and/or produce neoantigens that induce immunogenic cell death.

As used herein, the term "neoantigen" refers to any antigen to which the immune system has not previously been exposed that arises from one or more tumor-specific mutations and/or from exposing a tumor to a drug (e.g., any one or more of the splicing modulators disclosed herein, alone and/or as part of an ADC or composition). Tumor-specific mutations can include missense mutations, frameshifts, translocations, and mRNA splicing variants, as well as mutations that influence posttranslational processing, such as phosphorylation and glycosylation. These exemplary mutations, in various embodiments, can be derived from non-synonymous coding changes and/or mutations that alter mRNA processing (e.g., splicing). All of these exemplary mutations, in various embodiments, can result in molecular changes that can be discriminated by an appropriate T-cell receptor. In various preferred embodiments, an exemplary neoantigen is a neoantigen induced by delivery of a splicing modulator, alone and/or as part of an ADC or composition. In various embodiments, delivery of a splicing modulator (e.g., any one or more of the splicing modulators disclosed herein) can induce novel mRNA splicing that results in the translation of proteins containing one or more novel peptide domains to which the immune system has not previously been exposed. In various embodiments, tumor-specific mutations may be mRNA splicing variants resulting from delivery or administration of a splicing modulator, ADC, or composition comprising a splicing modulator or ADC.

Without being bound by theory, in various embodiments, the delivery of splicing modulators, alone and as part of an ADC or composition, may induce novel mRNA splicing (e.g., exon skipping, intron retention) that results in the alteration of the open reading frames and/or coding sequences of various genes. In various embodiments, these altered genes are translated into proteins containing one or more novel peptide domains recognized by the immune system as foreign. In various embodiments, the one or more novel peptide domains do not exist in the proteins or in any other part of the human proteome in the absence of splicing modulator treatment. In various embodiments, the proteins containing the one or more novel peptide domains can be degraded by the proteasome to create novel peptide fragments that act as substrates for the immunopeptide presentation machinery, e.g., via MHC presentation. In various embodiments, the novel peptide fragments representing neoantigens can be presented in the MHC1-bound peptidome, e.g., on tumor cells.

In various embodiments, the delivery of splicing modulators, alone and as part of an ADC or composition, may lead to one or more tumor cell-intrinsic events (e.g., cell growth arrest). In various embodiments, the tumor cell-intrinsic event(s) may lead to (1) enhanced engagement by phagocytic cells (Bracci et al. (2014) Cell Death Differ. 21(1):15-25); (2) the transport of novel peptide fragments to a tumor draining lymph node to engage with antigen-presenting cells; (3) antigen-presenting cells processing novel peptide fragments from a phagocytosed tumor cell and presenting the fragments as neoantigens to circulating naïve T-cell populations; (4) novel peptide fragments interacting with T-cells expressing receptors that recognize the fragments as neoantigens; (5) maturation and activation of effector T-cell responses (e.g., CD4+ and/or CD8+ T-cells; and/or (6) engagement of T-cells with additional tumor cells exposed to the splicing modulator treatment and presenting novel peptide fragments representing neoantigens on their surface MHC1 complexes. In various embodiments, the tumor cell-intrinsic event(s) may result, either directly or indirectly, in T-cell engagement of effector function and/or killing of neoantigen-presenting tumor cells.

Also, without being bound by theory, in various embodiments, the delivery of splicing modulators, alone and as part of an ADC or composition, may cause the re-expression of intron-resident endogenous retroviruses, leading to a double-stranded RNA immune response.

Further, without being bound by theory, in various embodiments, the delivery of splicing modulators, alone and as part of an ADC or composition, may lead to immunogenic cell death triggered by splice modulator-induced release of mutationally-derived neoantigens. In various embodiments, the delivery of splicing modulators, alone and as part of an ADC or composition, may induce a double-stranded RNA immune response. In various embodiments, the double-stranded RNA immune response can result from the re-expression of intron-resident endogenous retroviruses. In various embodiments, the double-stranded RNA immune response can result in tumor cell death. In various embodiments, the delivery of splicing modulators, alone and as part of an ADC or composition, may induce immunogenic cell death. In various embodiments, the immunogenic cell death can result from release of mutational-derived neoantigens and/or a host immune response against tumor cells.

Accordingly, in various embodiments, methods of treatment are disclosed comprising inducing neoantigens by administering one or more splicing modulators and/or ADCs and/or compositions comprising a splicing modulator or ADC, e.g., any splicing modulator, ADC, or composition disclosed herein. In various embodiments, the method comprises administering a reduced dosage of the splicing modulator, ADC, or composition than would be needed absent the induction of neoantigens. In some embodiments, the method comprises administering one or more initial induction doses to produce neoantigens and induce an immune response (e.g., converting naïve T-cells to memory cells), followed by a reduced dosage or administration frequency (i.e., because of the combinatorial effect of the splicing modulator, ADC, or composition and of immune targeting of the neoantigens). In some embodiments, treatment can comprise a combination of administering the splicing modulator, ADC, or composition to induce a neoantigen-based immune response and at least one additional therapy (e.g., a second anti-cancer therapy). For example, in some embodiments, treatment can comprise a combination of administering the splicing modulator, ADC, or composition to induce a neoantigen-based immune response and one or more checkpoint inhibitors. In some embodiments, treatment can comprise a combination of administering the splicing modulator, ADC, or composition to induce a neoantigen-based immune response and one or more cytokines or cytokine analogs. In some embodiments, treatment can comprise a combination of administering the splicing modulator, ADC, or composition to induce a neoantigen-based immune response and one or more neoantigen vaccines. In some other embodiments, treatment can comprise a combination of administering the splicing modulator, ADC, or composition to induce a neoantigen-based immune response and one or more engineered tumor-targeting T-cells (e.g., CAR-T).

In some embodiments, neoantigens can be used to monitor the effectiveness of treatment with a splicing modulator, ADC, or composition. For instance, after administration of a splicing modulator, ADC, or composition, a patient sample (e.g., a tumor biopsy) can be obtained and screened for neoantigens or for identifiers of an immune or inflammatory response. Further treatment can be provided, e.g., at reduced dosage, if a neoantigen and/or immune response is detected.

In various embodiments, methods of treatment are disclosed comprising inducing a double-stranded RNA immune response by administering one or more splicing modulators and/or ADCs and/or compositions comprising a splicing modulator or ADC, e.g., any splicing modulator, ADC, or composition disclosed herein.

In various embodiments, methods of treatment are disclosed comprising inducing immunogenic cell death by administering one or more splicing modulators and/or ADCs and/or compositions comprising a splicing modulator or ADC, e.g., any splicing modulator, ADC, or composition disclosed herein.

In various embodiments, administration of a splicing modulator, ADC, or composition comprising a splicing modulator can be combined with any known anti-cancer therapy. Examples of current immune activating strategies available for oncology treatment include, but are not limited to, treatment with immune checkpoint inhibitor (ICI) molecules, treatment with cytokines or cytokine analogs, vaccination with tumor-associated vaccines, and engineering tumor-targeting T-cells (e.g., expansion of tumor-infiltrating lymphocytes or CAR-T). These technologies are predominantly focused on enhancing or inducing an immune response to already existing tumor antigens (either mutations or aberrant expression of cell-surface proteins). One or more of these strategies may involve one or more mutations that are capable of inducing an antigenic T-cell response. For example, patient responses to checkpoint inhibition may correlate with non-synonymous mutational burden. In addition, cancer vaccine approaches may be used that rely on pre-existing mutations and the antigenicity of these mutations.

Splicing modulators and/or ADCs comprising such modulators may induce broad-ranging changes in the transcriptome that occur in multiple lineages. Translation of these mRNA changes may produce robust and reproducible protein changes that produce MHC1-bound neopeptides with high affinity across multiple HLA isotypes. Without being bound by theory, due to the large number of changes to the transcriptome and proteome, treatment with splicing modulators and/or ADCs may enrich the number of potentially reactive neoantigens for enhanced engagement of the adaptive immune response.

As described herein, the terms "splicing modulator," "spliceosome modulator," or "splice modulator" refer to compounds that have anti-cancer activity by interacting with components of the spliceosome. In some embodiments, a splicing modulator alters the rate or form of splicing in a target cell. Splicing modulators that function as inhibitory agents, for example, are capable of decreasing uncontrolled cellular proliferation. In particular, in some embodiments, the splicing modulators may act by inhibiting the SF3b spliceosome complex. In some embodiments, a splicing modulator is chosen from any one or more of the splicing modulators disclosed herein. In some embodiments, a splicing modulator is used, delivered to a cell, and/or administered to a subject as a stand-alone agent. In some other embodiments, a splicing modulator is used, delivered to a cell, and/or administered to a subject as part of an ADC (e.g., an ADC chosen from any of the exemplary ADCs disclosed herein). In some other embodiments, a splicing modulator is used, delivered to a cell, and/or administered to a subject as part of a composition comprising multiple copies of the splicing modulator or multiple copies of an ADC carrying the splicing modulator. Such compositions are disclosed herein.

In some embodiments, a splicing modulator used, delivered to a cell, and/or administered to a subject as part of an ADC (e.g., an ADC chosen from any of the exemplary ADCs disclosed herein) provides added therapeutic benefits over a splicing modulator used, delivered to a cell, and/or administered to a subject as a stand-alone agent. For example, in some embodiments, a splicing modulator used, delivered to a cell, and/or administered to a subject as part of an ADC provides targeted delivery of the splicing modulator to a neoplastic cell expressing the target antigen (i.e., the antigen targeted by the antibody moiety of the ADC). In some embodiments, such targeted delivery of the splicing modulator reduces off-target treatment and/or off-target cytotoxicity. In some embodiments, such targeted delivery promotes tumor-selective neoantigen presentation on neoplastic cells, but not on healthy cells that do not express the target antigen. In some embodiments, such targeted delivery leads to, e.g., at least 75%, 80%, 85%, 90%, 95%, or 99%, of the alternative splicing and induction of novel mRNAs and MHC-associated peptides representing neoantigens in targeted neoplastic cells rather than off-target cells. Thus, without being bound by theory, in some embodiments, following effector T-cell priming and/or expansion (e.g., using a neoantigen vaccine), the immune system may preferentially attack neoantigen-presenting neoplastic cells rather than healthy cells due to the preferential expression of neoantigens on tumor cells after treatment with an ADC as disclosed herein.

Immune Induction and Treatment Regimen:

In various embodiments, the present disclosure provides a method of inducing at least one neoantigen by contacting a neoplastic cell with an effective amount of a splicing modulator, a splicing modulator-based antibody-drug conjugate (ADC), or a composition comprising a splicing modulator or ADC. In various embodiments, the present disclosure provides a method of inducing a double-stranded RNA immune response by contacting a neoplastic cell with an effective amount of a splicing modulator, a splicing modulator-based antibody-drug conjugate (ADC), or a composition comprising a splicing modulator or ADC. In various embodiments, the present disclosure provides a method of inducing immunogenic cell death by contacting a neoplastic cell with an effective amount of a splicing modulator, a splicing modulator-based antibody-drug conjugate (ADC), or a composition comprising a splicing modulator or ADC.

In some embodiments, the at least one neoantigen comprises an amino acid sequence of any one of SEQ ID NOs: 37-65. In some embodiments, the at least one neoantigen comprises an amino acid sequence of SEQ ID NO: 37. In some embodiments, the at least one neoantigen comprises an amino acid sequence of SEQ ID NO: 39. In some embodiments, the at least one neoantigen comprises an amino acid sequence of any one of SEQ ID NOs: 46-49.

In some embodiments, the neoplastic cell is present in an in vitro cell culture. In some embodiments, the neoplastic cell is obtained from a subject. In some embodiments, the neoplastic cell is present in a subject. In some embodiments, the neoplastic cell is derived from a hematological malignancy or a solid tumor. In some embodiments, the hematological malignancy is selected from a B-cell malignancy, a leukemia, a lymphoma, and a myeloma. In some embodiments, the hematological malignancy is selected from acute myeloid leukemia and multiple myeloma. In some embodiments, the solid tumor is selected from breast cancer (e.g., HER2-positive breast cancer), gastric cancer (e.g., gastric adenocarcinoma), prostate cancer, ovarian cancer, lung cancer (e.g., lung adenocarcinoma), uterine cancer (e.g., uterine serous endometrial carcinoma), salivary duct carcinoma, melanoma, colon cancer, cervical cancer, pancreatic cancer, kidney cancer, colorectal cancer, and esophageal cancer. In some embodiments, the solid tumor is selected from HER2-positive breast cancer, gastric adenocarcinoma, prostate cancer, and osteosarcoma.

In various embodiments, the present disclosure further provides a method of inducing at least one neoantigen and/or a T-cell response in a subject having or suspected of having a neoplastic disorder by administering to the subject an effective amount of a splicing modulator, an ADC, or a composition comprising a splicing modulator or ADC. Also provided herein, in various embodiments, is a method of treating a subject having or suspected of having a neoplastic disorder by administering to the subject an effective amount of a splicing modulator, an ADC, or a composition comprising a splicing modulator or ADC, wherein administration of the splicing modulator, antibody-drug conjugate, or composition induces at least one neoantigen and/or a T-cell response.

In various other embodiments, the present disclosure provides a method of inducing a double-stranded RNA immune response in a subject having or suspected of having a neoplastic disorder by administering to the subject an effective amount of a splicing modulator, an ADC, or a composition comprising a splicing modulator or ADC. Also provided herein, in various embodiments, is a method of treating a subject having or suspected of having a neoplastic disorder by administering to the subject an effective amount of a splicing modulator, an ADC, or a composition comprising a splicing modulator or ADC, wherein administration of the splicing modulator, antibody-drug conjugate, or composition induces a double-stranded RNA immune response.

In still other embodiments, the present disclosure provides a method of inducing immunogenic cell death in a subject having or suspected of having a neoplastic disorder by administering to the subject an effective amount of a splicing modulator, an ADC, or a composition comprising a splicing modulator or ADC. Further provided herein, in various embodiments, is a method of treating a subject having or suspected of having a neoplastic disorder by administering to the subject an effective amount of a splicing modulator, an ADC, or a composition comprising a splicing modulator or ADC, wherein administration of the splicing modulator, antibody-drug conjugate, or composition induces immunogenic cell death.

In some embodiments of the therapeutic methods described herein, the at least one neoantigen comprises an amino acid sequence of any one of SEQ ID NOs: 37-65. In some embodiments, the at least one neoantigen comprises an amino acid sequence of SEQ ID NO: 37. In some embodiments, the at least one neoantigen comprises an amino acid sequence of SEQ ID NO: 39. In some embodiments, the at least one neoantigen comprises an amino acid sequence of any one of SEQ ID NOs: 46-49.

In some embodiments, the present disclosure further provides a method of treating a subject having or suspected of having a neoplastic disorder by administering to the subject an effective amount of a splicing modulator, an ADC, or a composition comprising a splicing modulator or ADC, wherein administration of the splicing modulator, antibody-drug conjugate, or composition induces immunogenic cell death, in combination with one or more additional therapies comprising a second agent.

In some embodiments of the therapeutic methods described herein, the amount of the splicing modulator, antibody-drug conjugate, composition, or second agent administered is reduced due to induction of at least one neoantigen and/or a T-cell response, as compared to a standard dosage of the splicing modulator, antibody-drug conjugate, composition, or second agent. In some embodiments, the administered amount of the splicing modulator, antibody-drug conjugate, composition, or second agent is reduced by 10%, 15%, 20%, 25%, 30%, 35%, 40%, 45%, 50%, 75%, or 90%, as compared to a standard dosage of the splicing modulator, antibody-drug conjugate, composition, or second agent. In some embodiments, the splicing modulator, antibody-drug conjugate, composition, or second agent is administered at least 10%, 15%, 20%, 25%, 30%, 35%, 40%, 45%, 50%, 75%, or 90% less frequently, as compared to a standard dosing regimen of the splicing modulator, antibody-drug conjugate, composition, or second agent. In some embodiments, the administered amount and/or dosage of the splicing modulator, antibody-drug conjugate, composition, or second agent results in lower systemic toxicity and/or improved tolerance.

As used herein, the term "standard dosage" or "standard dosing regimen" refers to any usual or routine dosing regimen for a therapeutic agent, e.g., a regimen proposed by the manufacturer, approved by regulatory authorities, or otherwise tested in human subjects to meet the average patient's needs. In some embodiments, the therapeutic agent is a splicing modulator, an antibody, or an antibody-drug conjugate with anti-cancer activity.

For instance, a standard dosing regimen for trastuzumab, an exemplary anti-HER2 antibody disclosed herein, may be 8 mg/kg administered intravenously over 90 min (week 1) followed by 6 mg/kg administered intravenously over 30-90 min every 3 weeks (week 4 through the end of the therapy cycle) (Herceptin® (trastuzumab) FDA Label Supplement, 2017).

As another example, a standard dosing regimen for ipilimumab, an exemplary anti-CTLA4 checkpoint inhibitor antibody, may be 3 mg/kg administered intravenously over 90 min every 3 weeks for 4 doses (Yervoy® (ipilimumab) FDA Label Supplement, 2018). Another standard dosing regimen for ipilimumab may be 10 mg/kg administered intravenously over 90 min every 3 weeks for 4 doses, followed by 10 mg/kg every 12 weeks for up to 3 years (Yervoy® (ipilimumab) FDA Label Supplement, 2018).

As another example, a standard dosing regimen for nivolumab, an exemplary anti-PD1 checkpoint inhibitor antibody, may be 3 mg/kg administered intravenously over 60 min every 2 weeks (Opdivo® (nivolumab) FDA Label, 2015).

As another example, a standard dosing regimen for atezolizumab, an exemplary anti-PDL1 checkpoint inhibitor antibody, may be 1200 mg administered intravenously over 60 min every 3 weeks (Tecentriq® (atezolizumab) FDA Label Supplement, 2018).

As yet another example, a standard dosing regimen for T-DM1, an exemplary anti-HER2 antibody-drug conjugate, may be 3.6 mg/kg administered intravenously over 90 min every 3 weeks (Kadcyla® (T-DM1) FDA Label Supplement, 2016).

In some embodiments, the methods described herein may further comprise administering at least one additional therapy (e.g., a checkpoint inhibitor, a neoantigen vaccine, a cytokine or cytokine analog, CAR-T, etc.). In some embodiments, the amount of the splicing modulator, antibody-drug conjugate, composition, and/or the at least one additional therapy administered is reduced due to induction of at least one neoantigen and/or a T-cell response, as compared to a standard dosage of the splicing modulator, antibody-drug conjugate, composition, and/or the at least one additional therapy. In some embodiments, the amount of the splicing modulator, antibody-drug conjugate, composition, and/or the at least one additional therapy administered is reduced due to induction of a double-stranded RNA immune response, as compared to a standard dosage of the splicing modulator, antibody-drug conjugate, composition, and/or the at least one additional therapy. In some embodiments, the amount of the splicing modulator, antibody-drug conjugate, composition, and/or the at least one additional therapy administered is reduced due to induction of immunogenic cell death, as compared to a standard dosage of the splicing modulator, antibody-drug conjugate, composition, and/or the at least one additional therapy. In some embodiments, the administered amount of the splicing modulator, antibody-drug conjugate, composition, and/or the at least one additional therapy is reduced by 10%, 15%, 20%, 25%, 30%, 35%, 40%, 45%, 50%, 75%, or 90%, as compared to a standard dosage of the splicing modulator, antibody-drug conjugate, composition, and/or the at least one additional therapy. In some embodiments, the splicing modulator, antibody-drug conjugate, composition, and/or the at least one additional therapy is administered at least 10%, 15%, 20%, 25%, 30%, 35%, 40%, 45%, 50%, 75%, or 90% less frequently, as compared to a standard dosing regimen of the splicing modulator, antibody-drug conjugate, composition, and/or the at least one additional therapy. In some embodiments, the administered amount and/or dosage of the splicing modulator, antibody-drug conjugate, composition, and/or the at least one additional therapy results in lower systemic toxicity and/or improved tolerance.

In some embodiments, administration of the splicing modulator, antibody-drug conjugate, or composition is initiated before administration of the at least one additional therapy. In other embodiments, administration of the splicing modulator, antibody-drug conjugate, or composition is initiated after administration of the at least one additional therapy. In still other embodiments, administration of the splicing modulator, antibody-drug conjugate, or composition is initiated concurrently with administration of the at least one additional therapy.

In some embodiments, administration of the splicing modulator, antibody-drug conjugate, or composition is repeated at least once after initial administration. In some embodiments, the amount of the splicing modulator, antibody-drug conjugate, or composition used for repeated administration is reduced as compared to the amount used for initial administration. In some embodiments, the amount of the splicing modulator, antibody-drug conjugate, or composition used for repeated administration is reduced as compared to a standard dosage of the splicing modulator, antibody-drug conjugate, or composition. In some embodiments, the amount of the splicing modulator, antibody-drug conjugate, or composition used for repeated administration is reduced by 10%, 15%, 20%, 25%, 30%, 35%, 40%, 45%, 50%, 75%, or 90%, as compared to a standard dosage or initial dosage of the splicing modulator, antibody-drug conjugate, or composition.

In some embodiments, administration of the at least one additional therapy is repeated at least once after initial administration. In some embodiments, the amount of the at least one additional therapy used for repeated administration is reduced as compared to the amount used for initial administration. In some embodiments, the amount of the at least one additional therapy used for repeated administration is reduced as compared to a standard dosage of the at least one additional therapy. In some embodiments, the amount of the at least one additional therapy used for repeated administration is reduced by 10%, 15%, 20%, 25%, 30%, 35%, 40%, 45%, 50%, 75%, or 90%, as compared to a standard dosage or initial dosage of the at least one additional therapy.

In some embodiments, repeated administration of the splicing modulator, antibody-drug conjugate, or composition is concurrent with repeated administration of the at least one additional therapy. In some embodiments, administration of the splicing modulator, antibody-drug conjugate, or composition is sequential or staggered with repeated administration of the at least one additional therapy.

In some embodiments, the at least one additional therapy comprises administering a checkpoint inhibitor, e.g., any checkpoint inhibitor disclosed herein. In some embodiments, the subject is intolerant, non-responsive, or poorly responsive to the checkpoint inhibitor when administered alone. In some embodiments, the checkpoint inhibitor is targeted at PD1/PDL1, CTLA4, OX40, CD40, LAG3, TIM3, GITR, and/or KIR. In some embodiments, the checkpoint inhibitor is targeted at CTLA4, OX40, CD40, and/or GITR. In some embodiments, the checkpoint inhibitor is an antibody having inhibitory or agonist activity to its target. In some embodiments, a checkpoint inhibitor is targeted with an inhibitory antibody or other similar inhibitory molecule. In other embodiments, a checkpoint inhibitor is targeted with an agonist antibody or other similar agonist molecule.

In some other embodiments, the at least one additional therapy comprises administering a neoantigen vaccine, e.g., any neoantigen vaccine disclosed herein. In some embodiments, the splicing modulator, ADC, or composition is administered before administration of the neoantigen vaccine. In some embodiments, the splicing modulator, ADC, or composition is administered after administration of the neoantigen vaccine. In some embodiments, the splicing modulator, ADC, or composition is administered concurrently with administration of the neoantigen vaccine. In some embodiments, administration of the splicing modulator, ADC, or composition is repeated at least once after initial administration. In some embodiments, the amount of the splicing modulator, ADC, or composition used for repeated administration is reduced as compared to the amount used for initial administration.

In some embodiments, the neoantigen vaccine comprises at least one neoantigen peptide. In some embodiments, the at least one neoantigen peptide ranges from about 10 to about 50 amino acids in length. In some embodiments, the at least one neoantigen peptide ranges from about 10 to about 35 amino acids in length. In some embodiments, the at least one neoantigen peptide ranges from about 15 to about 25 amino acids in length. In some embodiments, the at least one neoantigen peptide comprises one or more than one neoantigen sequence.

In some embodiments, the neoantigen sequence comprises an amino acid sequence of any one of SEQ ID NOs: 37-65. In some embodiments, the neoantigen sequence comprises an amino acid sequence of SEQ ID NO: 37. In some embodiments, the neoantigen sequence comprises an amino acid sequence of SEQ ID NO: 39. In some embodiments, the neoantigen sequence comprises an amino acid sequence of any one of SEQ ID NOs: 46-49.

In some other embodiments, the neoantigen sequence comprises an amino acid sequence of any one of SEQ ID NOs: 66-93, or an antigenic portion of any one of SEQ ID NOs: 66-93. In some embodiments, the neoantigen sequence comprises an amino acid sequence of SEQ ID NO: 66, or an antigenic portion of SEQ ID NO: 66. In some embodiments, the neoantigen sequence comprises an amino acid sequence of any one of SEQ ID NOs: 74-77, or an antigenic portion of any one of SEQ ID NOs: 74-77. In some embodiments, the neoantigen sequence and/or antigenic portion ranges from about 10 to about 50 amino acids in length. In some embodiments, the neoantigen sequence and/or antigenic portion ranges from about 10 to about 35 amino acids in length. In some embodiments, the neoantigen sequence and/or antigenic portion ranges from about 15 to about 25 amino acids in length. In some embodiments, the neoantigen sequence and/or antigenic portion ranges from about 10 to about 20 amino acids in length. In some embodiments, the neoantigen sequence and/or antigenic portion does not exclusively overlap or consist of the canonical peptide sequence (e.g., any of the exemplary canonical peptide sequences underlined in Table 21).

The term "antigenic portion" or "antigenic fragment" of a neoantigen sequence, as used herein, refers to one or more fragments of a neoantigen sequence that retain the ability to induce a T-cell response (e.g., antigen-specific expansion and/or maturation of effector T-cell population(s)). An antigenic portion, in some embodiments, may also retain the ability to be internalized, processed, and/or presented by antigen-presenting cells (e.g., dendritic cells). In some embodiments, an antigenic portion also retains T-cell priming function. In some embodiments, an antigenic portion of a neoantigen sequence ranges from about 10 to about 50 amino acids in length. In some embodiments, an antigenic portion of a neoantigen sequence ranges from about 10 to about 35 amino acids in length. In some embodiments, an antigenic portion of a neoantigen sequence ranges from about 15 to about 25 amino acids in length. In some embodiments, an antigenic portion of a neoantigen sequence ranges from about 10 to about 20 amino acids in length. In some embodiments, an antigenic portion of a neoantigen sequence (e.g., an antigenic portion of any one of SEQ ID NOs: 66-93), or its encoding mRNA, is formulated as a neoantigen vaccine.

An exemplary embodiment of an antigenic portion is the region(s) flanking amino acids 45-53 of SEQ ID NO: 66. Another exemplary embodiment of an antigenic portion is the region(s) flanking amino acids 82-90 of SEQ ID NO: 66. In some embodiments, the antigenic portion is capable of binding to at least one HLA allele expressed in a subject (e.g., HLA-A*02:01). In some other embodiments, the antigenic portion is capable of binding to at least one HLA allele expressed in at least 10%, at least 15%, at least 20%, at least 25%, at least 30%, at least 35%, at least 40%, or at least 45% of subjects in a population of subjects suffering from a neoplastic disorder. In some embodiments, the antigenic portion is capable of eliciting a T-cell response against a tumor present in at least 1%, at least 5%, or at least 10% of a population of subjects suffering from a neoplastic disorder.

In some embodiments, an antigenic portion does not exclusively overlap or consist of a canonical peptide sequence. The term "canonical peptide sequence," as used herein, refers to any contiguous peptide sequence present in the human proteome in the absence of contact with a splicing modulator (e.g., in the absence of contact with a splicing modulator alone and/or as part of an ADC or composition), and/or to which the immune has previously been exposed. In some embodiments, the canonical peptide sequence is derived from and/or encoded by the canonical transcript open reading frame. Exemplary canonical peptide sequences are underlined in Table 21.

In some embodiments, when a splicing modulator is administered (e.g., alone and/or as part of an ADC or composition), a canonical peptide sequence may be derived from and/or encoded by the immediate 5' in-frame 24 nucleotides preceding an aberrant splicing event induced by the splicing modulator. Thus, in some embodiments, the canonical peptide sequence comprises or consists of the 8 amino acids immediately N-terminal to the neoantigen sequence induced by the splicing modulator. In some embodiments, when a 5' exon sequence terminates with a terminal nucleotide of a codon, the canonical peptide sequence terminates at the end of the exon. In some other embodiments, when a 5' exon sequence terminates with one or two of the three nucleotides of a codon, the canonical peptide sequence is derived from and/or encoded by the 24 nucleotides preceding the incomplete codon. In some embodiments, mRNA sequences 3' of the aberrant splicing event may be translated in the same open reading frame derived from the 5' exon until reaching a stop codon, whereupon translation may terminate. In some embodiments, when the aberrant splicing event (e.g., exon skipping) results in a conservation of the canonical transcript open reading frame, the C-terminal sequence may be translated for an additional 24 nucleotides, encoding 8 C-terminal amino acids. In this context, in some embodiments, only the region across the aberrant exon junction may encode a neoantigen sequence. In some embodiments, when the open reading frame is shifted (e.g., intron retention), the complete C-terminal sequence (encoded by the 3' mRNA) may encode a neoantigen sequence.

In some embodiments, an antigenic portion of a neoantigen sequence is chosen by comparing the neoantigen sequence to the canonical peptide sequence; and selecting a portion of the neoantigen sequence that does not exclusively overlap, consist of, and/or align with the canonical peptide sequence. An antigenic portion of a neoantigen sequence, in some embodiments, can be screened for antigenicity and/or T-cell priming function in the same manner as are full-length neoantigen sequences (e.g., the neoantigen sequence from which the antigenic portion is derived). In some embodiments, an antigenic portion of a neoantigen sequence is evaluated for antigenicity and/or T-cell priming function using a T-cell priming assay, such as the exemplary T-cell priming experiments described herein.

In some embodiments, the neoantigen sequence is a neoantigen sequence specific to the subject. In some embodiments, the neoantigen sequence is a personalized neoantigen vaccine for the subject. In some embodiments, the neoantigen sequence used to create a personalized neoantigen vaccine for a subject is capable of binding to at least one HLA allele expressed in the subject. In some embodiments, a personalized neoantigen vaccine is selected by identifying neoantigens expressed in a subject's tumor, e.g., after administration of a splicing modulator or ADC, and selecting a vaccine comprising a neoantigen sequence observed in the patient's tumor, e.g., a vaccine comprising an amino acid sequence of any one of SEQ ID NOs: 37-65 that is observed in the tumor.

The term "personalized" when used to describe a neoantigen vaccine refers to a vaccine created by identifying one or more neoantigens produced in a patient, preferably one identified in the patient after an exposure to a splicing modulator, ADC, or composition, and then using one or more of those neoantigens as the basis of the vaccine for the same patient. Accordingly, in some embodiments, a patient is given a splicing modulator, ADC, or composition and screened for neoantigens produced by the treatment. In some embodiments, the selected neoantigen vaccine comprises a neoantigen peptide or mRNA disclosed herein and confirmed to be present in the patient after exposure to the splicing modulator, ADC, or composition. In some embodiments, the splicing modulator, ADC, or composition and/or peptide or mRNA vaccine may be administered to the patient once or repeatedly. Subsequently, in some embodiments, one or more of those neoantigens are used to create a personalized vaccine that is given to the patient. In some embodiments, the one or more neoantigens used to create a personalized vaccine possess binding affinity for one or more patient-specific HLA alleles. In some embodiments, the patient expresses one or more MHC1 alleles that bind to the one or more neoantigens. The prediction of whether a given neoantigen will bind to a specific MHC1 allele can be determined using any computational prediction method known in the art. Exemplary computational prediction methods are disclosed, e.g., in Meydan et al. (2013) BMC Bioinformatics 14(Suppl. 2):S13, which is incorporated herein by reference for such methods.

In some other embodiments, the neoantigen sequence is a universal neoantigen sequence. In some embodiments, the neoantigen sequence is a universal neoantigen vaccine.

The term "universal" when used to describe a neoantigen vaccine refers to a vaccine having a peptide or mRNA sequence that is based on common or known neoantigen(s) observed by sequencing neoantigens produced in multiple patients and/or patient tissue samples, preferably after an exposure to a splicing modulator, ADC, or composition. The peptide or mRNA sequence used in the vaccine need not be present in every patient but rather be observed in at least several patients or patient tissue samples. In some embodiments, the splicing modulator, ADC, or composition and/or peptide or mRNA vaccine may be administered to the patient once or repeatedly. Subsequently, in some embodiments, that peptide or mRNA sequence is used for vaccinating further patients. In some embodiments, a patient is given a splicing modulator, ADC, or composition, and then given a peptide or mRNA vaccine of known neoantigen to enhance immune response to the neoantigens produced by the splicing modulator, ADC, or composition. In some embodiments, a patient is given a universal peptide or mRNA vaccine and then given a splicing modulator, ADC, or composition once or repeatedly. In some embodiments, the neoantigen sequence (or sequences) used to create a universal neoantigen vaccine is selected based on overall MHC1 allele frequency in a given patient population (Maiers et al. (2007) Hum. Immunol. 68(9):779-88).

In some embodiments, the neoantigen (e.g., a universal neoantigen) sequence is capable of binding to at least one HLA allele expressed in at least 10%, at least 15%, at least 20%, at least 25%, at least 30%, at least 35%, at least 40%, or at least 45% of subjects in a population of subjects suffering from the neoplastic disorder. In some embodiments, the neoantigen sequence is capable of eliciting a T-cell response against a tumor present in at least 1%, at least 5%, or at least 10% of a population of subjects suffering from the neoplastic disorder.

In some embodiments, the neoantigen sequence has been identified by sequencing at least one neoantigen peptide, or its encoding mRNA, induced in the subject by administering an effective amount of the splicing modulator, antibody-drug conjugate, or composition. In some embodiments, the at least one neoantigen peptide comprises a neoantigen sequence induced by contacting a neoplastic cell with an effective amount of the splicing modulator, antibody-drug conjugate, or composition. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen peptide and a pharmaceutically acceptable carrier (e.g., any of the exemplary carriers described herein). In some embodiments, the at least one neoantigen peptide is linked to the pharmaceutically acceptable carrier. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine. In some embodiments, the neoantigen peptide and the pharmaceutically acceptable carrier are covalently attached via a linker. In some embodiments, the neoantigen peptide and the pharmaceutically acceptable carrier are expressed as a fusion protein. In some embodiments, the neoantigen vaccine comprises at least one neoantigen peptide and a pharmaceutically acceptable diluent. In some embodiments, the neoantigen vaccine comprises at least one neoantigen peptide and a pharmaceutically acceptable adjuvant.

In some embodiments, the neoantigen vaccine comprises at least one neoantigen mRNA. In some embodiments, the at least one neoantigen mRNA encodes one or more than one neoantigen sequence. In some embodiments, the neoantigen sequence comprises an amino acid sequence of any one of SEQ ID NOs: 37-65. In some embodiments, the neoantigen sequence comprises an amino acid sequence of SEQ ID NO: 37. In some embodiments, the neoantigen sequence comprises an amino acid sequence of SEQ ID NO: 39. In some embodiments, the neoantigen sequence comprises an amino acid sequence of any one of SEQ ID NOs: 46-49.

In some other embodiments, the neoantigen sequence comprises an amino acid sequence of any one of SEQ ID NOs: 66-93, or an antigenic portion of any one of SEQ ID NOs: 66-93. In some embodiments, the neoantigen sequence comprises an amino acid sequence of SEQ ID NO: 66, or an antigenic portion of SEQ ID NO: 66. In some embodiments, the neoantigen sequence comprises an amino acid sequence of any one of SEQ ID NOs: 74-77, or an antigenic portion of any one of SEQ ID NOs: 74-77. In some embodiments, the neoantigen sequence and/or antigenic portion ranges from about 10 to about 50 amino acids in length. In some embodiments, the neoantigen sequence and/or antigenic portion ranges from about 10 to about 35 amino acids in length. In some embodiments, the neoantigen sequence and/or antigenic portion ranges from about 15 to about 25 amino acids in length. In some embodiments, the neoantigen sequence and/or antigenic portion ranges from about 10 to about 20 amino acids in length. In some embodiments, the neoantigen sequence and/or antigenic portion does not exclusively overlap or consist of the canonical peptide sequence (e.g., any of the exemplary canonical peptide sequences underlined in Table 21).

In some embodiments, the neoantigen sequence is a neoantigen sequence specific to the subject. In some embodiments, the neoantigen sequence is a personalized neoantigen vaccine for the subject. In some embodiments, the neoantigen sequence is capable of binding to at least one HLA allele expressed in the subject.

In some other embodiments, the neoantigen sequence is a universal neoantigen sequence. In some embodiments, the neoantigen sequence is a universal neoantigen vaccine. In some embodiments, the neoantigen sequence is capable of binding to at least one HLA allele expressed in at least 10%, at least 15%, at least 20%, at least 25%, at least 30%, at least 35%, at least 40%, or at least 45% of subjects in a population of subjects suffering from the neoplastic disorder. In some embodiments, the neoantigen sequence is capable of eliciting a T-cell response against a tumor present in at least 1%, at least 5%, or at least 10% of a population of subjects suffering from the neoplastic disorder.

In some embodiments, the neoantigen sequence has been identified by sequencing the protein sequence of at least one neoantigen. In some embodiments, the neoantigen sequence has been identified by sequencing at least one mRNA encoding a neoantigen induced in the subject by administering an effective amount of the splicing modulator, antibody-drug conjugate, or composition. In some embodiments, the at least one neoantigen mRNA encodes a neoantigen sequence induced by contacting a neoplastic cell with an effective amount of the splicing modulator, antibody-drug conjugate, or composition. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen mRNA and a pharmaceutically acceptable carrier (e.g., any of the exemplary carriers described herein). In some embodiments, the at least one neoantigen mRNA is linked to the pharmaceutically acceptable carrier. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine. In some embodiments, the neoantigen vaccine comprises at least one neoantigen mRNA and a pharmaceutically acceptable diluent. In some embodiments, the neoantigen vaccine comprises at least one neoantigen mRNA and a pharmaceutically acceptable adjuvant. In some embodiments, the neoantigen mRNA is encapsulated by an encapsulating agent. In some embodiments, the encapsulating agent is a liposome. In some embodiments, the encapsulating agent is a nanoparticle.

In some embodiments, the at least one additional therapy comprises administering a cytokine or cytokine analog, e.g., any cytokine or cytokine analog disclosed herein. In some embodiments, the subject is intolerant, non-responsive, or poorly responsive to the cytokine or cytokine analog when administered alone. In some embodiments, the cytokine or cytokine analog comprises a T-cell enhancer. In some embodiments, the cytokine or cytokine analog comprises IL-2, IL-10, IL-12, IL-15, IFNγ, and/or TNFα. In some embodiments, the cytokine or cytokine analog comprises IL-2, IL-10, IL-12, and/or IL-15. In some embodiments, administering the cytokine or cytokine analog enhances T-cell priming following administration of a splicing modulator, antibody-drug conjugate, or composition due to the induction and presentation of neoantigens.

In some embodiments, the at least one additional therapy comprises administering engineered tumor-targeting T-cells (i.e., CAR-T), e.g., any CAR-T therapy disclosed herein.

In some embodiments, the methods described herein may further comprise detecting one or more neoantigens and/or a T-cell response in the subject after administration of the splicing modulator, antibody-drug conjugate, or composition, and, optionally, continuing administration of the splicing modulator, antibody-drug conjugate, or composition if one or more neoantigens and/or a T-cell response is detected. In some embodiments, detecting one or more neoantigens and/or a T-cell response in the subject indicates efficacy of treatment with the splicing modulator, antibody-drug conjugate, or composition. In some embodiments, treatment with the additional therapy, along with splicing modulator, antibody-drug conjugate, or composition, is continued if one or more neoantigens and/or a T-cell response is detected. In some embodiments, treatment is continued at a reduced dosage and/or frequency if one or more neoantigens and/or a T-cell response is detected.

In some embodiments, the methods described herein may further comprise detecting a double-stranded RNA immune response in the subject after administration of the splicing modulator, antibody-drug conjugate, or composition, and, optionally, continuing administration of the splicing modulator, antibody-drug conjugate, or composition if a double-stranded RNA immune response is detected. In some embodiments, detecting a double-stranded RNA immune response in the subject indicates efficacy of treatment with the splicing modulator, antibody-drug conjugate, or composition. In some embodiments, treatment with the additional therapy, along with splicing modulator, antibody-drug conjugate, or composition, is continued if a double-stranded RNA immune response is detected. In some embodiments, treatment is continued at a reduced dosage and/or frequency if a double-stranded RNA immune response is detected.

In some embodiments, the methods described herein may further comprise detecting immunogenic cell death in the subject after administration of the splicing modulator, antibody-drug conjugate, or composition, and, optionally, continuing administration of the splicing modulator, antibody-drug conjugate, or composition if immunogenic cell death is detected. In some embodiments, detecting immunogenic cell death in the subject indicates efficacy of treatment with the splicing modulator, antibody-drug conjugate, or composition. In some embodiments, treatment with the additional therapy, along with splicing modulator, antibody-drug conjugate, or composition, is continued if immunogenic cell death is detected. In some embodiments, treatment is continued at a reduced dosage and/or frequency if immunogenic cell death is detected.

In some embodiments, the subject has a non-synonymous mutational burden of about 150 mutations or less. In some embodiments, the subject has a non-synonymous mutational burden of about 100 mutations or less. In some embodiments, the subject has a non-synonymous mutational burden of about 50 mutations or less. In some embodiments, the subject has or is suspected of having a neoplastic disorder, e.g., a hematological malignancy or a solid tumor. In some embodiments, the hematological malignancy is selected from a B-cell malignancy, a leukemia, a lymphoma, and a myeloma. In some embodiments, the hematological malignancy is selected from acute myeloid leukemia and multiple myeloma. In some embodiments, the solid tumor is selected from breast cancer, gastric cancer, prostate cancer, ovarian cancer, lung cancer, uterine cancer, salivary duct carcinoma, melanoma, colon cancer, cervical cancer, pancreatic cancer, kidney cancer, colorectal cancer, and esophageal cancer. In some embodiments, the solid tumor is selected from HER2-positive breast cancer, gastric adenocarcinoma, prostate cancer, and osteosarcoma.

In various embodiments, the present disclosure further provides a method of treating a subject having or suspected of having a neoplastic disorder, comprising: (a) administering to the subject an effective amount of a splicing modulator, an ADC, or composition comprising a splicing modulator or ADC, wherein administration of the splicing modulator, antibody-drug conjugate, or composition induces at least one neoantigen and/or a T-cell response; (b) detecting one or more neoantigens and/or a T-cell response in the subject after administration of the splicing modulator, antibody-drug conjugate, or composition; and (c) continuing administration of the splicing modulator, antibody-drug conjugate, or composition if one or more neoantigens and/or a T-cell response is detected. In some embodiments, detecting one or more neoantigens and/or a T-cell response in the subject indicates efficacy of treatment with the splicing modulator, antibody-drug conjugate, or composition. In some embodiments, the one or more neoantigens comprise an amino acid sequence of any one of SEQ ID NOs: 37-65.

In some embodiments, the one or more neoantigens comprise an amino acid sequence of SEQ ID NO: 37. In some embodiments, the one or more neoantigens comprise an amino acid sequence of SEQ ID NO: 39. In some embodiments, the one or more neoantigens comprise an amino acid sequence of any one of SEQ ID NOs: 46-49.

Combination of Splicing Modulator/ADC and Immune Checkpoint Inhibition:

In various embodiments, a patient having a cancer as described herein can be treated with a combination of a splicing modulator, ADC, or composition and a checkpoint inhibitor therapy. Immune checkpoints are inhibitory pathways that slow down or stop immune reactions and prevent excessive tissue damage from uncontrolled activity of immune cells. As used herein, the term "checkpoint inhibitor" is meant to refer to any therapeutic agent, including any small molecule chemical compound, antibody, nucleic acid molecule, or polypeptide, or any fragments thereof, that inhibits one or more of the inhibitory pathways, thereby allowing more extensive immune activity.

Treatment of patients with immune checkpoint inhibition has been shown to have robust efficacy in certain clinical indications. Recently, the FDA approved use of a checkpoint inhibitor in patients with tumors exhibiting high microsatellite instability, agnostic to the tissue lineage. This approval was based, in part, on the observation that response rates correlate positively with mutational burden (Rizvi et al. (2015) Science 348(6230):124-8; Hellmann et al. (2018) Cancer Cell 33(5):853-861). Estimates from the literature vary in absolute numbers and by lineage, but generally support that above a threshold of -150-250 mutations, the probability of response rises. Analysis of TCGA data shows that a large percentage of adult-onset tumor lineages have comparatively low non-synonymous mutational burden (Vogelstein et al. (2013) Science 339:1549-58). Most lineages have median non-synonymous mutational rates of -30-80 per patient, well below the thresholds for improved odds of response to checkpoint inhibitors.

For instance, HER2-positive breast cancer has been shown to have a median of ~60 non-synonymous mutations present per patient sample. However, the threshold for checkpoint inhibitor treatment efficacy, as mentioned above, is estimated to be in the range of −150-250 non-synonymous mutations, i.e., patients above this threshold are more likely to show complete remission, partial remission, and/or stable disease, whereas patients below this threshold are more likely to exhibit progressive disease. Strategies to enhance the apparent number of non-synonymous mutations and/or neoantigens being presented on tumor cells are therefore desirable, and may enhance the overall probability of response, e.g., to checkpoint inhibitor therapies. As cytokines (and analogs thereof) act via a similar mechanism of action, such strategies may also enhance the overall probability of response to cytokine-based therapies.

Current response rates in HER2-positive breast cancer are -15-25% (CTI NCT02129556). In various embodiments disclosed herein, treatment with a splicing modulator, ADC, or composition in combination with a checkpoint inhibitor and/or cytokine therapy may improve such response rates. In various embodiments, treatment with a splicing modulator, ADC, or composition in combination with a checkpoint inhibitor and/or cytokine therapy may apply to any adult-onset tumor, particularly those in which the median non-synonymous mutational rate is below the estimated ~150 mutations threshold. In various embodiments, exemplary cancer types suitable for treatment with a splicing modulator, ADC, or composition of the present disclosure, alone or in combination with an additional therapy (e.g., a checkpoint inhibitor therapy, a cytokine therapy) include but are not limited to esophageal cancer, non-Hodgkin's lymphoma, colorectal cancer, head and neck cancer, gastric cancer, endometrial cancer, pancreatic adenocarcinoma, ovarian cancer, prostate cancer, hepatocellular cancer, glioblastoma, breast cancer (e.g., HER2-positive breast cancer), lung cancer (e.g., non-small cell lung cancer), chronic lymphocytic leukemia, and acute myeloid leukemia. Other exemplary suitable cancer types are identified, e.g., in Vogelstein et al. (2013) Science 339:1549-58, which is incorporated herein by reference in its entirety.

As many checkpoint inhibitor therapies are based on chronic expression of tumor-associated antigens, regular treatment boosts are required for efficacy and for "re-boosting" reactive T-cell populations. The inducible nature of splicing modulator or ADC-derived neoantigens described herein provide for therapeutic dosing regimens that may be designed to enhance the immune response of neoantigen-reactive T-cells, while limiting T-cell exhaustion often caused by chronic antigen stimulation. For instance, in some embodiments, an initial dose of a splicing modulator, ADC, or composition is administered to a subject to trigger aberrant splicing and production of neoantigen peptides. After a period of time to allow for protein production and antigen presentation, in some embodiments, the subject is then administered an initial dose of a checkpoint inhibitor to boost and/or enhance effector T-cell priming and expansion. In some embodiments, the wait period between doses of splicing modulator, ADC, or composition and checkpoint inhibitor is about 2, about 3, about 4, about 5, about 6, or about 7 days. In some embodiments, the wait period is between about 3 days and about 5 days. In some embodiments, the checkpoint inhibitor is targeted at CTLA4, OX40, CD40, and/or GITR. In some embodiments, the combination therapeutic benefit of a splicing modulator, ADC, or composition and a checkpoint inhibitor may be additive or superadditive.

In some embodiments, after a period to allow for T-cell priming and expansion, the subject is then administered a second or subsequent dose of the splicing modulator, ADC, or composition to trigger re-presentation of neoantigen peptides. In some embodiments, the wait period between an initial dose of a checkpoint inhibitor and a second or subsequent dose of a splicing modulator, ADC, or composition is about 2, about 3, about 4, or about 5 weeks. In some embodiments, the wait period is about 3 weeks. Following a second or subsequent dose of the splicing modulator, ADC, or composition, in some embodiments, the immune system may engage with the neoantigen-presenting tumor cells and/or elicit tumor cell killing. In some embodiments, the subject is then administered a second or subsequent dose of the checkpoint inhibitor to further expand the memory effector T-cell population, after allowing for secondary T-cell priming and expansion.

In some embodiments, dosing of the splicing modulator, ADC, or composition following this exemplary initial treatment regimen can be pulsatile, i.e., the splicing modulator, ADC, or composition may be dosed at prolonged intervals (e.g., about every 4 weeks, about every 5 weeks, about every 6 weeks) to allow for antigen presentation, T-cell engagement and/or tumor cell killing, and/or recovery of the memory T-cell population. At later timepoints, in some embodiments, the splicing modulator, ADC, or composition treatment may be combined with one or more checkpoint inhibitors targeted to restore effector functionality to exhausted T-cell populations. For example, in some embodiments, at later timepoints, the splicing modulator, ADC, or composition treatment may be combined with one or more checkpoint inhibitors targeted at PD1/PDL1, LAG3, and/or TIM3. In some embodiments, the pulsed nature of neoantigen presentation and priming may allow a checkpoint inhibitor and/or a splicing modulator, ADC, or composition to be administered less frequently and/or at lower doses. In some embodiments, the pulsed nature of neoantigen presentation may provide one or more treatment benefits for a checkpoint inhibitor (e.g., an anti-CTLA4 antibody such as ipilimumab), as compared to the checkpoint inhibitor when administered without concurrent splicing modulator, ADC, or composition treatment, for example, by lowering the potential risk of adverse reactions often observed with the checkpoint inhibitor's standard dosing regimen.

In certain embodiments, the checkpoint inhibitor is an inhibitor of the cytotoxic T-lymphocyte-associated antigen (CTLA4) pathway. CTLA4, also known as CD152, is a protein receptor that downregulates immune responses. CTLA4 is constitutively expressed in regulatory T-cells, but only upregulated in conventional T-cells after activation. As used herein, the term "CTLA4 inhibitor" is meant to refer to any inhibitor of CTLA4 and/or the CTLA4 pathway. Exemplary CTLA4 inhibitors include but are not limited to anti-CTLA4 antibodies. CTLA4 blocking antibodies for use in humans were developed based on the pre-clinical activity seen in mouse models of anti-tumor immunity. Exemplary anti-CTLA4 antibodies include but are not limited to ipilimumab (MDX-010) and tremelimumab (CP-675,206), both of which are fully human. Ipilimumab is an IgG1 with a plasma half-life of approximately 12-14 days; tremelimumab is an IgG2 with a plasma half-life of approximately 22 days. See, e.g., Phan et al. (2003) Proc Natl Acad Sci USA. 100:8372-7; Ribas et al. (2005) J Clin Oncol. 23:8968-77; Weber et al. (2008) J Clin Oncol. 26:5950-6. In some embodiments, the anti-CTLA4 antibody is ipilimumab.

In certain embodiments, the checkpoint inhibitor is an inhibitor of the programmed death-1 (PD1) pathway. The programmed cell death 1 (PD1) pathway represents a major immune control switch which may be engaged by tumor cells to overcome active T-cell immune surveillance. The ligands for PD1 (PDL1 and PDL2) are constitutively expressed or can be induced in various tumors. High expression of PDL1 on tumor cells (and to a lesser extent of PDL2) has been found to correlate with poor prognosis and survival in various other solid tumor types. Furthermore, PD1 has been suggested to regulate tumor-specific T-cell expansion in patients with malignant melanoma. These observations suggest that the PD1/PDL1 pathway plays a critical role in the tumor immune evasion and may be considered an attractive target for therapeutic intervention. As used herein, the term "PD1 inhibitor" is meant to refer to any inhibitor of PD1 and/or the PD1 pathway. Exemplary PD1 inhibitors include but are not limited to anti-PD1 and anti-PDL1 antibodies. In certain embodiments, the checkpoint inhibitor is an anti-PD1 antibody. Exemplary anti-PD1 antibodies include but are not limited to nivolumab and pembrolizumab (MK-3475). Nivolumab, for example, is a fully human immunoglobulin G4 (IgG4) PD1 immune checkpoint inhibitor antibody that disrupts the interaction of the PD1 receptor with its ligands PDL1 and PDL2, thereby inhibiting the cellular immune response (Guo et al. (2017) J Cancer 8(3):410-6). In some embodiments, the anti-PD1 antibody is nivolumab. Pembrolizumab, for example, is a potent and highly-selective humanized mAb of the IgG4/kappa isotype designed to directly block the interaction between PD1 and its ligands, PDL1 and PDL2.

Pembrolizumab strongly enhances T lymphocyte immune responses in cultured blood cells from healthy human donors, cancer patients, and primates. Pembrolizumab has also been reported to modulate the level of interleukin-2 (IL-2), tumor necrosis factor alpha (TNFα), interferon gamma (IFNγ), and other cytokines. Exemplary anti-PDL1 antibodies include but are not limited to atezolizumab, avelumab, and durvalumab. Atezolizumab, for example, is an IgG1 humanized mAb that is reported to block the PD1/PDL1 interaction, by targeting the expressed PDL1 on numerous kinds of malignant cells. This blockage of the PD1/PDL1 pathway may stimulate the immune defense mechanisms against tumors (Abdin et al. (2018) Cancers (Basel) 10(2):32). In some embodiments, the anti-PDL1 antibody is atezolizumab.

In certain embodiments, the checkpoint inhibitor is targeted at PD1/PDL1, CTLA4, OX40, CD40, LAG3, TIM3, GITR, and/or KIR. In certain embodiments, the checkpoint inhibitor is targeted at CTLA4, OX40, CD40, and/or GITR. In certain embodiments, a checkpoint inhibitor is targeted with an inhibitory antibody or other similar inhibitory molecule (e.g., an inhibitory anti-CTLA4 or anti-PD1/PDL1 antibody). In certain other embodiments, a checkpoint inhibitor is targeted with an agonist for the target; examples of this class include the stimulatory targets OX40, CD40, and/or GITR. In some embodiments, the checkpoint inhibitor targeted at OX40, CD40, and/or GITR is an agonist antibody. Agonist antibodies directed against OX40 may have a dual role, inhibiting regulatory T-cell suppression, while enhancing effector T-cell functions. Agonist anti-GITR antibodies have also been shown to make effector T-cells more resistant to the inhibition induced by regulatory T-cells (Karaki et al. (2016) Vaccines (Basel) 4(4):37). Likewise, agonist CD40 antibodies demonstrate T-cell-dependent anti-tumor activity. Activation of CD40 on dendritic cells increases cross-presentation of tumor antigens and consequently the number of activated tumor-directed effector T-cells (Ellmark et al. (2015) Oncoimmunol. 4(7): e1011484).

In certain embodiments, the checkpoint inhibitor is targeted at CTLA4 (e.g., an anti-CTLA4 antibody). In certain embodiments, targeting CTLA4 facilitates priming and activation of naïve T-cells. In certain embodiments, the checkpoint inhibitor is targeted at OX40 (e.g., an anti-OX40 antibody). In certain embodiments, targeting OX40 enhances expansion of effector T-cells. In certain embodiments, the checkpoint inhibitor is targeted at CD40 (e.g., an anti-CD40 antibody). In certain embodiments, targeting CD40 inhibits "tolerogenic" priming of T-cells and/or formation of regulatory T-cells. In certain embodiments, the checkpoint inhibitor is targeted at GITR (e.g., an anti-GITR antibody). In certain embodiments, targeting GITR inhibits activity of regulatory T-cells. In certain embodiments, the benefit of combination therapy (e.g., the effect on at least one symptom or the risk/rate of disease progression) with a splicing modulator, ADC, or composition and a CTLA4-, OX40-, CD40-, and/or GITR-targeted agent is additive. In some embodiments, the benefit of combination therapy with a splicing modulator, ADC, or composition and a CTLA4-, OX40-, CD40-, and/or GITR-targeted agent is superadditive (i.e., synergistic).

Checkpoint inhibitor treatment strategies are based on the hypothesis that treatment facilitates and/or enhances priming of T-cell responses to weakly or poorly antigenic tumors (e.g., CTLA4) or that treatment restores and/or reinvigorates T-cells that respond to tumor antigens, but have become "exhausted" due to the chronic nature of the antigen presentation (e.g., PD1, PDL1) (Chen and Mellman (2013) Immunity 39(1):1-10). Examples of suitable checkpoint inhibition therapies and agents, e.g., anti-PD1, anti-PDL1, or anti-CTLA4 antibodies, are known in the art. See, e.g., WO 2001/014424 WO 2013/173223, WO 2016/007235.

Combining these primed T-cell responses following checkpoint inhibitor therapy with treatment to induce neoantigens in tumor cells to which the primed immune system can react may provide beneficial synergy. As the splicing modulator or ADC-derived neoantigens have not yet been presented for T-cell priming, combination with a CTLA4 inhibitor may be particularly beneficial. In some embodiments, treatment comprises administering one or more splicing modulator, ADC, or composition to induce the production of neoantigens, followed before, concurrently, or thereafter by an initial administration of a CTLA4 inhibitor to stimulate CD8 T-cell priming. In some embodiments, additional administrations of an CTLA4 inhibitor are provided to the patient, e.g., to further stimulate priming and/or activation of neoantigen-reactive CD8 populations. In some embodiments, additional administrations of splicing modulator, ADC, or composition can be given to the patient to increase neoantigen presentation by the tumor. Repeat administrations of splicing modulator, ADC, or composition and checkpoint inhibitor therapy can occur concurrently or in staggered intervals. In some embodiments, treatment further comprises administering a PD1/PDL1 inhibitor co-treatment, e.g., to restore effector function of exhausted neoantigen-targeted T-cells within the tumor microenvironment.

The terms "combination" or "combination therapy," as used herein, refer to the administration of one or more splicing modulator, ADC, or composition together with an additional agent or therapy (e.g., a checkpoint inhibitor, a cytokine or cytokine analog, a neoantigen vaccine, CAR-T), as part of a treatment regimen intended to provide a beneficial (i.e., additive or synergistic) effect from the co-action of one or more of the administered agents. In some embodiments, the combination may also include one or more additional agents, including but not limited to chemotherapeutic agents, anti-angiogenesis agents, and agents that reduce immune-suppression (e.g., a second checkpoint inhibitor). The beneficial effect of the combination includes, but is not limited to, pharmacokinetic or pharmacodynamic co-action resulting from the combination of therapeutic agents. Administration of these therapeutic agents in combination typically is carried out over a defined time period (for example, minutes, hours, days, or weeks, depending upon the combination selected).

Administered "in combination" or "co-administration," as used herein, means that two or more different treatments are delivered to a subject during the subject's affliction with a medical condition (e.g., a neoplastic disorder). For example, in some embodiments, the two or more treatments are delivered after the subject has been diagnosed with a disease or disorder, and before the disease or disorder has been cured or eliminated, or when a subject is identified as being at risk but before the subject has developed symptoms of the disease. In some embodiments, the delivery of one treatment is still occurring when the delivery of the second treatment begins, so that there is overlap. In some embodiments, the first and second treatment are initiated at the same time. These types of delivery are sometimes referred to herein as "simultaneous," "concurrent," or "concomitant" delivery. In other embodiments, the delivery of one treatment ends before delivery of the second treatment begins. This type of delivery is sometimes referred to herein as "successive" or "sequential" delivery.

In some embodiments, the two treatments (e.g., a splicing modulator, ADC, or composition and a checkpoint inhibitor) are comprised in the same composition. Such compositions may be administered in any appropriate form and by any suitable route. In other embodiments, the two treatments (e.g., a splicing modulator, ADC, or composition and a checkpoint inhibitor) are administered in separate compositions, in any appropriate form and by any suitable route. For example, in some embodiments, a composition comprising a splicing modulator or ADC and a composition comprising a checkpoint inhibitor may be administered concurrently or sequentially, in any order at different points in time; in either case, they should be administered sufficiently close in time so as to provide the desired therapeutic or prophylactic effect.

In embodiments of either simultaneous or sequential delivery, treatment may be more effective because of combined administration. In some embodiments, the first treatment is more effective, e.g., an equivalent effect is seen with less of the first treatment (e.g., with a lower dose), than would be seen if the first treatment were administered in the absence of the second treatment. In some embodiments, the first treatment is more effective such that the reduction in a symptom, or other parameter associated with the disease or disorder, is greater than what would be observed with the first treatment delivered in the absence of the second treatment. In other embodiments, an analogous situation is observed with the second treatment. In some embodiments, the benefit of combination therapy (e.g., the effect on at least one symptom or the risk/rate of disease progression) is additive. In some embodiments, the benefit of combination therapy is superadditive.

In various embodiments, the present disclosure provides a method of treating a subject having or suspected of having a neoplastic disorder by administering to the subject an effective amount of a splicing modulator, an ADC, or a composition comprising a splicing modulator or ADC; and at least one additional therapy (e.g., a checkpoint inhibitor therapy, a cytokine or cytokine analog, a neoantigen vaccine, CAR-T). In some embodiments, administration of the splicing modulator, ADC, or composition induces at least one neoantigen and/or a T-cell response. In some embodiments, administration of the splicing modulator, ADC, or composition induces a double-stranded RNA immune response. In some embodiments, administration of the splicing modulator, ADC, or composition induces immunogenic cell death. In some embodiments, the at least one additional therapy may comprise at least one, at least two, at least three, at least four, or at least five additional therapies. For example, in some embodiments, a splicing modulator, ADC, or composition may be administered in combination with two checkpoint therapies, i.e., using two different checkpoint inhibitors. In some other embodiments, a splicing modulator, ADC, or composition may be administered in combination with a checkpoint inhibitor therapy and a neoantigen vaccine.

In some embodiments of combination therapy, the administered amount of the splicing modulator, antibody-drug conjugate, or composition and/or the at least one additional therapy is reduced by 10%, 15%, 20%, 25%, 30%, 35%, 40%, 45%, 50%, 75%, or 90%, as compared to a standard dosage of the splicing modulator, antibody-drug conjugate, or composition and/or the at least one additional therapy. In some embodiments, the splicing modulator, antibody-drug conjugate, or composition and/or the at least one additional therapy is administered at least 10%, 15%, 20%, 25%, 30%, 35%, 40%, 45%, 50%, 75%, or 90% less frequently, as compared to a standard dosing regimen of the splicing modulator, antibody-drug conjugate, or composition and/or the at least one additional therapy. In some embodiments, the administered amount and/or dosage of the splicing modulator, antibody-drug conjugate, or composition and/or the at least one additional therapy results in lower systemic toxicity and/or improved tolerance.

In some embodiments, administration of the splicing modulator, antibody-drug conjugate, or composition is initiated before administration of the at least one additional therapy. In some embodiments, administration of the splicing modulator, antibody-drug conjugate, or composition is initiated after administration of the at least one additional therapy. In some embodiments, administration of the splicing modulator, antibody-drug conjugate, or composition is initiated concurrently with administration of the at least one additional therapy.

In some embodiments, administration of the splicing modulator, antibody-drug conjugate, or composition is repeated at least once after initial administration. In some embodiments, the amount of the splicing modulator, antibody-drug conjugate, or composition used for repeated administration is reduced as compared to the amount used for initial administration. In some embodiments, the amount of the splicing modulator, antibody-drug conjugate, or composition used for repeated administration is reduced as compared to a standard dosage of the splicing modulator, antibody-drug conjugate, or composition. In some embodiments, the amount of the splicing modulator, antibody-drug conjugate, or composition used for repeated administration is reduced by 10%, 15%, 20%, 25%, 30%, 35%, 40%, 45%, 50%, 75%, or 90%, as compared to a standard dosage of the splicing modulator, antibody-drug conjugate, or composition.

In some embodiments, administration of the at least one additional therapy is repeated at least once after initial administration. In some embodiments, the amount of the at least one additional therapy used for repeated administration is reduced as compared to the amount used for initial administration. In some embodiments, the amount of the at least one additional therapy used for repeated administration is reduced as compared to a standard dosage of the at least one additional therapy. In some embodiments, the amount of the at least one additional therapy used for repeated administration is reduced by 10%, 15%, 20%, 25%, 30%, 35%, 40%, 45%, 50%, 75%, or 90%, as compared to a standard dosage of the at least one additional therapy.

In some embodiments, repeated administration of the splicing modulator, antibody-drug conjugate, or composition is concurrent with repeated administration of the at least one additional therapy. In some embodiments, repeated administration of the splicing modulator, antibody-drug conjugate, or composition is sequential or staggered with repeated administration of the at least one additional therapy.

In various embodiments, the present disclosure provides a method of treating a subject having or suspected of having a neoplastic disorder by administering to the subject an effective amount of a splicing modulator, an ADC, or a composition comprising a splicing modulator or ADC; and a checkpoint inhibitor therapy. In some embodiments, the checkpoint inhibitor therapy comprises administering at least one checkpoint inhibitor. In some embodiments, the subject is intolerant, non-responsive, or poorly responsive to the at least one checkpoint inhibitor when administered alone. In some embodiments, a subject may be considered non-responsive or poorly responsive to the at least one checkpoint inhibitor as determined using, e.g., the immune-related Response Criteria (irRC) and/or the immune-related Response Evaluation Criteria in Solid Tumors (irRECIST). See, e.g., Wolchok et al. (2009) Clin Cancer Res. 15(23): 7412-20; Bohnsack et al. "Adaptation of the Immune-Related Response Criteria:irRECIST" (Abstract 4958) ESMO 2014. Exemplary criteria may include those used in the art to define when tumors in cancer patients improve ("respond"), remain the same ("stabilize"), or worsen ("progress") during treatment, when the treatment being evaluated is an immune-oncology drug (e.g., a checkpoint inhibitor). In some embodiments, a subject may be considered intolerant to the at least one checkpoint inhibitor if the subject presents with one or more than one adverse (grade 2+) event identified for the respective checkpoint inhibitor (e.g., ipilimumab). In some embodiments, for example, a subject may be considered intolerant to ipilimumab treatment if the subject presents with one or more adverse events selected from enterocolitis, hepatitis, dermatitis (including toxic epidermal necrolysis), neuropathy, and endocrinopathy (Yervoy® (ipilimumab) FDA Label Supplement, 2018).

In some embodiments, the checkpoint inhibitor is targeted at PD1/PDL1, CTLA4, OX40, CD40, LAG3, TIM3, GITR, and/or KIR. In some embodiments, the checkpoint inhibitor is targeted at CTLA4, OX40, CD40, and/or GITR. In some embodiments, the checkpoint inhibitor is targeted with an inhibitory antibody or other similar inhibitory molecule. In some other embodiments, the checkpoint inhibitor is targeted with an agonist antibody or other similar agonist molecule. In some embodiments, the checkpoint inhibitor comprises a cytotoxic T-lymphocyte-associated antigen 4 pathway (CTLA4) inhibitor. In some embodiments, the CTLA4 inhibitor is an anti-CTLA4 antibody. In some embodiments, the anti-CTLA4 antibody is ipilimumab. In some embodiments, the checkpoint inhibitor comprises a programmed death-1 pathway (PD1) inhibitor. In some embodiments, the PD1 inhibitor is an anti-PD1 antibody. In some embodiments, the anti-PD1 antibody is nivolumab. In some embodiments, the PD1 inhibitor is an anti-PDL1 antibody. In some embodiments, the anti-PDL1 antibody is atezolizumab. In some embodiments, the checkpoint inhibitor comprises a CTLA4 inhibitor and a PD1 inhibitor. In some embodiments, the checkpoint inhibitor is targeted at OX40. In some embodiments, the checkpoint inhibitor is targeted at CD40. In some embodiments, the checkpoint inhibitor is targeted at GITR. In some embodiments, the benefit of combination therapy (e.g., the effect on at least one symptom or the risk/rate of disease progression) with a splicing modulator, ADC, or composition and a checkpoint inhibitor (e.g., a CTLA4-, PD1/PDL1-, OX40-, CD40-, and/or GITR-targeted antibody or molecule) is additive. In some embodiments, the benefit of combination therapy with a splicing modulator, ADC, or composition and a checkpoint inhibitor (e.g., a CTLA4-, PD1/PDL1, OX40-, CD40-, and/or GITR-targeted antibody or molecule) is superadditive (i.e., synergistic).

In various embodiments, the present disclosure provides a method of treating a subject having or suspected of having a neoplastic disorder by administering to the subject an effective amount of a splicing modulator, an ADC, or a composition comprising a splicing modulator or ADC; and a cytokine or cytokine analog therapy. In some embodiments, the cytokine or cytokine analog therapy comprises administering at least one cytokine or cytokine analog. In some embodiments, the subject is intolerant, non-responsive, or poorly responsive to the at least one cytokine or cytokine analog when administered alone.

In some embodiments, the cytokine or cytokine analog comprises a T-cell enhancer. In some embodiments, the cytokine or cytokine analog comprises IL-2, IL-10, IL-12, IL-15, IFNγ, and/or TNFα. In some embodiments, the cytokine or cytokine analog comprises IL-2, IL-10, IL-12, and/or IL-15. In some embodiments, administering the cytokine or cytokine analog enhances T-cell priming following administration of a splicing modulator, antibody-drug conjugate, or composition due to induction and presentation of neoantigens.

In some embodiments, the cytokine or cytokine analog comprises IL-2. In some embodiments, IL-2 boosts signals to effector cells promoting their expansion (Rosenberg (2014) J Immunol. 192(12):5451-8). In some embodiments, the cytokine or cytokine analog comprises IL-10. In some embodiments, IL-10 boosts CD8+ T-cell priming and activation (Mumm et al. (2011) Cancer Cell 20(6):781-96). In some embodiments, the cytokine or cytokine analog comprises IL-12. In some embodiments, IL-12 links the innate and adaptive immune responses to boost antigen-specific priming and targeting (Tugues et al. (2015) Cell Death Differ. 22(2):237-46). In some embodiments, the cytokine or cytokine analog comprises IL-15. In some embodiments, IL-15 boosts T-effector (CD8) cell priming and/or activation. In some embodiments, the cytokine or cytokine analog comprises IFNγ. In some embodiments, IFNγ supplements T-effector cell secretion of IFNγ. In some embodiments, the cytokine or cytokine analog comprises TNFα. In some embodiments, TNFα supplements T-effector cell secretion of TNFα.

In some embodiments, an initial dose of a splicing modulator, ADC, or composition is administered to a subject to trigger aberrant splicing and production of neoantigen peptides. After a period to allow for protein production and antigen presentation, in some embodiments, the subject is then administered an initial dose of a cytokine or cytokine analog to boost and/or enhance effector T-cell priming and expansion. In some embodiments, the wait period between doses of splicing modulator, ADC, or composition and cytokine or cytokine analog is about 2, about 3, about 4, about 5, about 6, or about 7 days. In some embodiments, the wait period is between about 3 days and about 5 days. In some embodiments, the cytokine or cytokine analog is IL-2, IL-10, IL-12, IL-15, IFNγ, and/or TNFα. In some embodiments, the combination therapeutic benefit of a splicing modulator, ADC, or composition and a cytokine or cytokine analog may be additive or superadditive.

In some other embodiments, an initial dose of a cytokine or cytokine analog is administered to a subject to boost and/or enhance effector T-cell priming and expansion. After a wait period, in some embodiments, the subject is then administered an initial dose of a splicing modulator, ADC, or composition to trigger aberrant splicing and production of neoantigen peptides. In some embodiments, the wait period between doses of cytokine or cytokine analog and splicing modulator, ADC, or composition is about 2, about 3, about 4, about 5, about 6, or about 7 days. In some embodiments, the wait period is between about 3 days and about 5 days. In some embodiments, the cytokine or cytokine analog is IL-2, IL-10, IL-12, IL-15, IFNγ, and/or TNFα. In some embodiments, the combination therapeutic benefit of a cytokine or cytokine analog and a splicing modulator, ADC, or composition may be additive or superadditive.

In some embodiments, after a period to allow for T-cell priming and expansion, the subject is then administered a second or subsequent dose of the splicing modulator, ADC, or composition to trigger re-presentation of neoantigen peptides. In some embodiments, the wait period between an initial dose of a cytokine or cytokine analog and a second or subsequent dose of a splicing modulator, ADC, or composition is about 2, about 3, about 4, or about 5 weeks. In some embodiments, the wait period is about 3 weeks. In some embodiments, subsequent doses of the cytokine or cytokine analog may be administered, e.g., interspersed between subsequent doses of the splicing modulator, ADC, or composition. Following a second or subsequent dose of the splicing modulator, ADC, or composition, in some embodiments, the immune system may engage with the neoantigen-presenting tumor cells and/or elicit tumor cell killing. In some embodiments, dosing of the splicing modulator, ADC, or composition following this exemplary initial treatment regimen can be pulsatile, i.e., the splicing modulator, ADC, or composition may be dosed at prolonged intervals (e.g., about every 4 weeks, about every 5 weeks, about every 6 weeks) to allow for antigen presentation, T-cell engagement and/or tumor cell killing, and/or recovery of the memory T-cell population.

In some embodiments, the subject has a non-synonymous mutational burden of about 150 mutations or less. In some embodiments, the subject has a non-synonymous mutational burden of about 100 mutations or less. In some embodiments, the subject has a non-synonymous mutational burden of about 50 mutations or less. In some embodiments, the subject has or is suspected of having a neoplastic disorder, e.g., a hematological malignancy or a solid tumor. In some embodiments, the hematological malignancy is selected from a B-cell malignancy, a leukemia, a lymphoma, and a myeloma. In some embodiments, the hematological malignancy is selected from acute myeloid leukemia and multiple myeloma. In some embodiments, the solid tumor is selected from breast cancer, gastric cancer, prostate cancer, ovarian cancer, lung cancer, uterine cancer, salivary duct carcinoma, melanoma, colon cancer, cervical cancer, pancreatic cancer, kidney cancer, colorectal cancer, and esophageal cancer. In some embodiments, the solid tumor is selected from HER2-positive breast cancer, gastric adenocarcinoma, prostate cancer, and osteosarcoma.

Combination of Splicing Modulator/ADC and Neoantigen Vaccine:

In various embodiments, a patient having a cancer as described herein can be treated with a combination of a splicing modulator, ADC, or composition and a neoantigen vaccine. Without being bound by theory, vaccines, used alone or in combination with immune checkpoint inhibitor (ICI) molecules, have shown promise in early trials (Ott et al. (2017) Nature 547(7662):217-21; Sahin et al. (2017) Nature 547(7662):222-6), but generally require sequencing of patient tumor mutations (Ott et al. (2017) Nature 547 (7662):217-21; Aldous and Dong (2018) Bioorg. Med. Chem. 26(10):2842-9). As such, vaccines are often dependent on sufficient numbers of non-synonymous mutations that are antigenic. In general, tumors with very low mutation burden provide few candidate antigens, and those with rapid growth provide limited time to identify and produce patient-specific vaccines.

To date, attempts to develop vaccines that would be broadly immunogenic across a large percentage of patients have focused on proteins that are either frequently mutated, ectopically overexpressed, or amplified, and/or that exist as "self" proteins within the organism. In addition, these proteins are often expressed in immunologically restricted tissues (e.g., neuronal markers expressed in neuroendocrine tumor types), while others may be normally expressed during embryogenesis (e.g., oncofetal antigens). Thus, utility of vaccines using such proteins as antigens is often limited to specific tumor lineages or subsets where one or more of the antigens are presented. Vaccine utility would also need to be confirmed by sequencing of patient tumor samples, which can be time-consuming.

Moreover, if these antigens exist as "self" proteins, the immune system would likely be primed to recognize these as "self" and thus, not respond. Or, alternatively, if the immune system is able to mount an effector response to these antigens, it may lead to on-target side effects in tissues where the antigen may be expressed. In both of these cases, one of the key challenges is that most antigenic peptides are derived from "passenger" genes (i.e., genes that are mutated or amplified in the course of tumorigenesis, but that do not play a critical role in the continued survival or proliferation of the tumor itself). As such, these genes may be silenced without significant consequence to the tumor progression, and thus would allow a tumor to "escape" an immune response against these antigens. Without wishing to be bound by theory, this mechanism may play a role in tumor evolution, where random mutations that are strongly antigenic are often "selected against" by the tumor during the early stages of tumorigenesis (Dunn et al. (2004) Annu. Rev. Immunol. 22:329-60).

In addition, certain evidence also indicates that chronic antigen presentation and immune stimulation may lead to immune cell anergy and exhaustion (Pardoll (2012) Nat. Rev. Cancer 12(4):252-64). These phenotypes underlie the therapeutic rationale behind current ICI treatments, as ICI has been shown to either repress the exhausted immune cell phenotype (α-PD1/PD-L1) or to facilitate additional immune cell responses (α-CTLA4). Notably, with α-CTLA4 therapy, a certain subset of patients have been reported to exhibit severe immune-related adverse events that may be ascribed to the promotion of T-cell activation and a break of the immune tolerance mechanisms that restrain self-reactive immune responses.

Both of these approaches (i.e., triggering or enhancing de novo immune responses to neoantigens or derepressing the anergy or exhaustion of existing immune responses) are linked to a chronic immune activation. As such, these approaches are sensitive to anergy, editing, and other tumor-mediated mechanisms designed to suppress immune engagement.

In contrast, treatment with a splicing modulator, ADC, or composition disclosed herein may induce an immune response to novel sequences representing neoantigens. In some embodiments, presentation of neoantigens provides the adaptive immune system with more divergent targets with which to engage and activate. In some embodiments, the ability of a splicing modulator, ADC, or composition to acutely induce alternative splicing and the resulting neoantigens may reduce the risk of immune system fatigue due to chronic exposure to mutation-driven neoantigens and/or limit the ability of tumor cells to adapt to evade therapy. In some embodiments, administering a splicing modulator, ADC, or composition in combination with a neoantigen vaccine enhances the immune response to the neoantigens produced by the splicing modulator, ADC, or composition. In some embodiments, the splicing modulator, ADC, or composition is administered before, during, or after vaccination. In some embodiments, the splicing modulator, ADC, or composition and/or vaccine may be administered once or more than once during the course of treatment. In some embodiments, the vaccine is administered once and the splicing modulator, ADC, or composition is administered more than once during the course of treatment. In some embodiments, the vaccine is administered once and then one or more boosters are administered during the course of treatment.

As used herein, the term "neoantigen vaccine" refers to a pooled sample of one or more immunogenic neoantigen peptides or mRNAs, for example at least two, at least three, at least four, at least five, or more neoantigen peptides. The term "vaccine" refers to a composition for generating immunity for the prophylaxis and/or treatment of a disease (e.g., a neoplastic disorder, e.g., a hematological malignancy or solid tumor). Accordingly, vaccines are medicaments which comprise immunogenic agents and are intended to be used in humans or animals for generating specific immune defenses and protective substances after vaccination. A neoantigen vaccine can additionally include a pharmaceutically acceptable carrier, diluent, excipient, and/or adjuvant.

As used herein, the term "immunogenic" refers to any agent or composition that can elicit an immune response, e.g., a T-cell response. The immune response can be antibody- or cell-mediated, or both.

In some embodiments, a patient is given a splicing modulator, ADC, or composition and then given a peptide or mRNA vaccine of known neoantigen to enhance immune response to the neoantigens produced by the splicing modulator, ADC, or composition. In some other embodiments, a patient is given a splicing modulator, ADC, or composition and screened for neoantigens produced by the treatment. Subsequently, one or more of those neoantigens are used to create a personalized vaccine that is given to the patient. In either of these embodiments, the splicing modulator, ADC, or composition and/or peptide or mRNA vaccine may be administered to the patient once or repeatedly.

In various embodiments, a suitable neoantigen for a vaccine can be identified by screening a panel of transcripts with altered splicing and robust expression from one or more tissue samples in a patient (e.g., from a tumor biopsy). In some embodiments, variant protein sequences are identified in the screened sample based on translation across the aberrantly spliced mRNA junction while retaining portions of the protein sequence (up to 12 amino acids) flanking the junction-spanning amino acid changes. In some embodiments, these junction-spanning peptide fragments are scanned for high affinity binding to MHC1 alleles, e.g., using a tool such as NetMHC1 (Nielsen et al. (2003) Protein Sci 12(5):1007-17; Andreatta and Neilsen (2016) Bioinformatics 32(4):511-7). These results allow for filtering of the neopeptides to those that are predicted high affinity binders for a unique patient HLA allele makeup as well as assembly of pools of neopeptides predicted to be broadly binding to HLA alleles that are present with high frequencies in different populations (Maiers et al. (2007) Hum Immunol 68(9):779-88). In various embodiments, the identified neopeptides are then formulated as a vaccine, e.g., by conjugation to a suitable carrier or adjuvant (Ott et al. (2017) Nature 547(7662):217-21), or for delivery as an mRNA (Sahin et al. (2017) Nature 547(7662):222-6).

In some embodiments, the selected neoantigen is based on a screen of an individual patent's tumor response to the splicing modulator, ADC, or composition to identify one or more neoantigens resulting from treatment to use in subsequent vaccination. In other embodiments, a neoantigen is chosen, e.g., based on screening a panel of samples from different patients to identify common neoantigens produced by the splicing modulator, ADC, or composition and then used as a universal vaccine for future patients.

Without being bound by theory, in some embodiments, use of a universal neoantigen vaccine would avoid the need to sequence and analyze the unique mutation status of each patient's tumor because the chosen neoantigens are not dependent on tumor mutation but rather mimic a neoantigen produced by a splicing modulator, ADC, or composition and generally recognized by the body as foreign. In addition, in some embodiments, use of a neoantigen vaccine may be particularly effective since a patient's tumor cells may be more likely to mutate away from producing one or more neoantigens that are dependent on tumor mutation, as compared to those that mimic a neoantigen produced by a splicing modulator, ADC, or composition. This may allow for the formulation of a bulk vaccine that would be broadly immunogenic across a large percentage of patients, expediting the initiation of a treatment regime. Patients may be vaccinated according to the schedules outlined herein and, prior to following completion of the vaccination, could be further treated with a splicing modulator, ADC, or composition, e.g., to induce expression of the neoantigen peptides. In some embodiments, patients may be administered a splicing modulator, ADC, or composition before, at the same time as, or after vaccination. In some embodiments, patients are administered a splicing modulator, ADC, or composition, screened for one or more neoantigens found in a panel of universal neoantigens, and vaccinated with a universal neoantigen vaccine comprising at least one universal neoantigen identified in the subject. In some embodiments, patients may be administered a splicing modulator, ADC, or composition once or more than once after vaccination. Splicing modulator or ADC or composition and/or vaccine may be administered once or more than once during the course of treatment.

In various embodiments, a vaccine may comprise one or more than one neoantigen peptide or mRNA. In various embodiments, a vaccine may comprise one or more than one long neoantigen peptide. Such "long" neoantigen peptides, in various embodiments, undergo efficient internalization, processing, and cross-presentation in professional antigen-presenting cells such as dendritic cells. Similarly, long vaccine peptides have been shown, in other contexts, to induce cytotoxic T-cells in humans (Melief and van der Burg (2008) Nat Rev Cancer 8(5):351-60). In various embodiments, a neoantigen peptide is extended to comprise the neoantigen peptide sequence itself in addition to flanking amino acid sequences. In various embodiments, the extended peptide sequence facilitates the uptake of protein by antigen-presenting cells, e.g., dendritic cells. In various embodiments, the extended peptide sequence enables efficient antigen presentation and T-cell priming in models with different HLA isotypes. In various embodiments, a longer neoantigen peptide and/or extended peptide sequence exhibits increased uptake by antigen-presenting cells (e.g., dendritic cells), increased antigen presentation, and/or increased T-cell priming, as compared to a shorter neoantigen peptide and/or shorter peptide sequence (e.g., a peptide sequence less than about 10 or less than about 5 amino acids in length). In some embodiments, a long neoantigen peptide ranges from about 5 to about 50 amino acids in length. In some embodiments, a long neoantigen peptide ranges from about 10 to about 50 amino acids in length. In some embodiments, a long neoantigen peptide ranges from about 10 to about 35 amino acids in length. In some embodiments, a long neoantigen peptide ranges from about 15 to about 25 amino acids in length. Amino acid sequences of exemplary long neoantigen peptides are set forth in Table 21.

As used herein, a neoantigen peptide or mRNA vaccine encompasses using a fragment of a neoantigen peptide or its encoding mRNA, so long as that fragment retains immunogenic potential.

In some embodiments, a neoantigen vaccine comprises at least one neoantigen peptide. In some embodiments, a neoantigen vaccine comprises at least 2, at least 3, at least 4, at least 5, at least 6, at least 7, at least 8, at least 9, at least 10, at least 12, at least 15, or at least 20 neoantigen peptides. In some embodiments, the neoantigen peptide(s) range from about 5 to about 50 amino acids in length. In some embodiments, the neoantigen peptide(s) range from about 10 to about 50 amino acids in length. In some embodiments, the neoantigen peptide(s) range from about 10 to about 35 amino acids in length. In some embodiments, the neoantigen peptide(s) range from about 15 to about 25 amino acids in length.

In various embodiments, the present disclosure provides a method of treating a subject having or suspected of having a neoplastic disorder by administering to the subject an effective amount of a splicing modulator, an ADC, or a composition comprising a splicing modulator or ADC; and a neoantigen vaccine. A neoantigen vaccine may be, e.g., a peptide or mRNA neoantigen vaccine. In some embodiments, the splicing modulator, ADC, or composition is administered before administration of the neoantigen vaccine. In some embodiments, the splicing modulator, ADC, or composition is administered after administration of the neoantigen vaccine. In some embodiments, the splicing modulator, ADC, or composition is administered concurrently with administration of the neoantigen vaccine. In some embodiments, administration of the splicing modulator, ADC, or composition is repeated at least once after initial administration. In some embodiments, the amount of the splicing modulator, ADC, or composition used for repeated administration is reduced as compared to the amount used for initial administration.

In various embodiments, the present disclosure further provides a combination comprising a splicing modulator, an ADC, or a composition comprising a splicing modulator or ADC; and a neoantigen vaccine (e.g., a universal neoantigen vaccine) for use in treating a subject having or suspected of having a neoplastic disorder. In some embodiments, the neoantigen vaccine is a peptide or mRNA neoantigen vaccine. In some embodiments, the combination further comprises at least one additional therapy. In some embodiments, the at least one additional therapy comprises at least one, at least two, at least three, at least four, or at least five additional therapies.

In various embodiments, the present disclosure further provides a method of treating a subject having or suspected of having a neoplastic disorder by (a) administering to the subject an effective amount of a splicing modulator, an ADC, or a composition comprising a splicing modulator or ADC; (b) detecting one or more neoantigens in the subject after administration of the splicing modulator, ADC, or composition; (c) comparing the one or more neoantigens to a panel of universal neoantigens; and (d) administering to the subject a universal neoantigen vaccine comprising at least one universal neoantigen present in the subject. In some embodiments, the universal neoantigen vaccine is administered alone or in combination with at least one additional therapy. In some embodiments, the at least one additional therapy comprises at least one, at least two, at least three, at least four, or at least five additional therapies.

In some embodiments, the at least one additional therapy comprises repeated administration of the splicing modulator, ADC, or composition. In some embodiments, repeated administration of the splicing modulator, ADC, or composition is initiated before administration of the universal neoantigen vaccine. In some embodiments, repeated of the splicing modulator, ADC, or composition is initiated after administration of the universal neoantigen vaccine. In some embodiments, repeated administration of the splicing modulator, ADC, or composition is initiated concurrently with administration of the universal neoantigen vaccine. In some embodiments, the amount of the splicing modulator, ADC, or composition used for repeated administration is reduced as compared to the amount used for initial administration. In some embodiments, the amount of the splicing modulator, ADC, or composition used for the initial and/or repeated administration is reduced as compared to a standard dosage of the splicing modulator, ADC, or composition when used without a vaccine treatment. In some embodiments, the amount of the splicing modulator, ADC, or composition used for initial and/or repeated administration is reduced by 10%, 15%, 20%, 25%, 30%, 35%, 40%, 45%, 50%, 75%, or 90%, as compared to a standard dosage of the splicing modulator, ADC, or composition.

In some embodiments, the at least one additional therapy comprises administering a checkpoint inhibitor (e.g., any of the exemplary checkpoint inhibitors described herein). In some embodiments, administration of the checkpoint inhibitor is initiated before administration of the universal neoantigen vaccine and/or repeated administration of the splicing modulator, ADC, or composition. In some embodiments, administration of the checkpoint inhibitor is initiated after administration of the universal neoantigen vaccine and/or repeated of the splicing modulator, ADC, or composition. In some embodiments, administration of the checkpoint inhibitor is initiated concurrently with administration of the universal neoantigen vaccine and/or repeated administration of the splicing modulator, ADC, or composition. In some embodiments, administration of the checkpoint inhibitor is repeated at least once after initial administration. In some embodiments, the amount of the checkpoint inhibitor used for repeated administration is reduced as compared to the amount used for initial administration. In some embodiments, the amount of the checkpoint inhibitor used for repeated administration is reduced as compared to a standard dosage of the checkpoint inhibitor. In some embodiments, the amount of the checkpoint inhibitor used for repeated administration is reduced by 10%, 15%, 20%, 25%, 30%, 35%, 40%, 45%, 50%, 75%, or 90%, as compared to a standard dosage of the checkpoint inhibitor. In some embodiments, the subject is intolerant, non-responsive, or poorly responsive to the checkpoint inhibitor when administered alone.

Also provided herein, in various embodiments, are neoantigen vaccines comprising at least one neoantigen peptide or at least one neoantigen mRNA. In some embodiments, a neoantigen vaccine comprises at least one neoantigen peptide. In some other embodiments, a neoantigen vaccine comprises at least one neoantigen mRNA.

Also provided herein, in various embodiments, are kits comprising a splicing modulator, an ADC, or a composition comprising a splicing modulator or ADC; and a neoantigen vaccine (e.g., a universal neoantigen vaccine). In some embodiments, the neoantigen vaccine is a peptide or mRNA neoantigen vaccine. In some embodiments, the kit further comprises one or more additional components, including but not limited to: instructions for use; other agents, e.g., one or more additional therapeutic agents; devices, containers, or other materials for preparing the splicing modulator, ADC, composition, and/or neoantigen vaccine for therapeutic administration; pharmaceutically acceptable carriers; and devices, containers, or other materials for administering the splicing modulator, ADC, composition, and/or neoantigen vaccine to a patient. Instructions for use can include guidance for therapeutic applications including suggested dosages and/or modes of administration, e.g., in a patient having or suspected of having a neoplastic disorder. In various embodiments, the kit further contains instructions for therapeutic use, e.g., use of the splicing modulator, ADC, or composition, and the neoantigen vaccine to treat or prevent a neoplastic disorder in a patient. In various embodiments, the kit further contains at least one additional therapeutic agent (e.g., for administering together with the splicing modulator, ADC, or composition, and the neoantigen vaccine, e.g., a checkpoint inhibitor). In various embodiments, the splicing modulator, ADC, composition, and/or neoantigen vaccine is formulated as a pharmaceutical composition.

In some embodiments of the methods and compositions disclosed herein, the neoantigen vaccine comprises at least one neoantigen peptide. In some embodiments, the at least one neoantigen peptide ranges from about 10 to about 50 amino acids in length. In some embodiments, the at least one neoantigen peptide ranges from about 10 to about 35 amino acids in length. In some embodiments, the at least one neoantigen peptide ranges from about 15 to about 25 amino acids in length.

In some embodiments, the at least one neoantigen peptide comprises one or more than one neoantigen sequence. In some embodiments, the neoantigen sequence comprises an amino acid sequence of any one of SEQ ID NOs: 37-65. In some embodiments, the neoantigen sequence comprises an amino acid sequence of SEQ ID NO: 37. In some embodiments, the neoantigen sequence comprises an amino acid sequence of SEQ ID NO: 39. In some embodiments, the neoantigen sequence comprises an amino acid sequence of any one of SEQ ID NOs: 46-49.

In some other embodiments, the neoantigen sequence comprises an amino acid sequence of any one of SEQ ID NOs: 66-93, or an antigenic portion of any one of SEQ ID NOs: 66-93. In some embodiments, the neoantigen sequence comprises an amino acid sequence of SEQ ID NO: 66, or an antigenic portion of SEQ ID NO: 66. In some embodiments, the neoantigen sequence comprises an amino acid sequence of any one of SEQ ID NOs: 74-77, or an antigenic portion of any one of SEQ ID NOs: 74-77. In some embodiments, the neoantigen sequence and/or antigenic portion ranges from about 10 to about 50 amino acids in length. In some embodiments, the neoantigen sequence and/or antigenic portion ranges from about 10 to about 35 amino acids in length. In some embodiments, the neoantigen sequence and/or antigenic portion ranges from about 15 to about 25 amino acids in length. In some embodiments, the neoantigen sequence and/or antigenic portion ranges from about 10 to about 20 amino acids in length. In some embodiments, the neoantigen sequence and/or antigenic portion does not exclusively overlap or consist of the canonical peptide sequence (e.g., any of the exemplary canonical peptide sequences underlined in Table 21).

In some embodiments, the neoantigen sequence is a neoantigen sequence specific to the subject. In some embodiments, the neoantigen sequence is a personalized neoantigen vaccine for the subject. In some embodiments, the neoantigen sequence is capable of binding to at least one HLA allele expressed in the subject.

In some other embodiments, the neoantigen sequence is a universal neoantigen sequence. In some embodiments, the neoantigen sequence is a universal neoantigen vaccine. In some embodiments, the neoantigen sequence is capable of binding to at least one HLA allele expressed in at least 10%, at least 15%, at least 20%, at least 25%, at least 30%, at least 35%, at least 40%, or at least 45% of subjects in a population of subjects suffering from the neoplastic disorder. In some embodiments, the neoantigen sequence is capable of eliciting a T-cell response against a tumor present in at least 1%, at least 5%, or at least 10% of a population of subjects suffering from the neoplastic disorder.

In some embodiments, the neoantigen sequence has been identified by sequencing at least one neoantigen peptide induced in the subject by administering an effective amount of the splicing modulator, antibody-drug conjugate, or composition. In some embodiments, the at least one neoantigen peptide comprises a neoantigen sequence induced by contacting a neoplastic cell with an effective amount of the splicing modulator, antibody-drug conjugate, or composition. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen peptide or mRNA and a pharmaceutically acceptable carrier. In various embodiments, a neoantigen peptide or mRNA can be linked to a suitable carrier to help elicit an immune response. Exemplary carriers for linking to immunogenic agents (e.g., a neoantigen peptide or mRNA) include serum albumins, keyhole limpet hemocyanin, immunoglobulin molecules, thyroglobulin, ovalbumin, tetanus toxoid, or a toxoid from other pathogenic bacteria, such as diphtheria, E. coli, cholera, or H. pylori, or an attenuated toxin derivative. Other carriers for stimulating or enhancing an immune response include cytokines such as IL-1, IL-1α and β peptides, IL-2, γINF, IL-10, GM-CSF, and chemokines, such as M1P1α and β and RANTES. Immunogenic agents can also be linked to peptides that enhance transport across tissues, as described, e.g., in WO 97/17613 and WO 97/17614. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine.

In some embodiments, the neoantigen peptide or mRNA may be linked to the pharmaceutically acceptable carrier. Immunogenic agents can be linked to carriers by chemical crosslinking. Techniques for linking an immunogenic peptide to a carrier include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the epsilon-amino on a lysine, or other free amino group in other amino acids. A variety of such disulfide/amide-forming agents are described in Jansen et al. ((1982) Immun Rev. 62:185). Other bifunctional coupling agents form a thioether rather than a disulfide linkage. Many of these thioether-forming agents are commercially available and include reactive esters of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt. In some embodiments, the neoantigen peptide and the pharmaceutically acceptable carrier are covalently attached via a linker.

Neoantigen and other such immunogenic peptides can also be expressed as fusion proteins with carriers. The immunogenic peptide can be linked at the amino terminus, the carboxyl terminus, or at a site anywhere within the peptide (internally) to the carrier. In some embodiments, multiple repeats of the immunogenic peptide can be present in the fusion protein. In some embodiments, the neoantigen peptide and the pharmaceutically acceptable carrier are expressed as a fusion protein.

In some embodiments, the neoantigen vaccine comprises at least one neoantigen peptide or its encoding mRNA and a pharmaceutically acceptable diluent. In some embodiments, the neoantigen vaccine comprises at least one neoantigen peptide or its encoding mRNA and a pharmaceutically acceptable adjuvant (e.g., an adjuvant as described herein).

In some embodiments of the methods and compositions disclosed herein, the neoantigen vaccine comprises at least one neoantigen mRNA. In some embodiments, the at least one neoantigen mRNA encodes one or more than one neoantigen sequence. In some embodiments, the neoantigen sequence comprises an amino acid sequence of any one of SEQ ID NOs: 37-65. In some embodiments, the neoantigen sequence comprises an amino acid sequence of SEQ ID NO: 37. In some embodiments, the neoantigen sequence comprises an amino acid sequence of SEQ ID NO: 39. In some embodiments, the neoantigen sequence comprises an amino acid sequence of any one of SEQ ID NOs: 46-49.

In some other embodiments, the neoantigen sequence comprises an amino acid sequence of any one of SEQ ID NOs: 66-93, or an antigenic portion of any one of SEQ ID NOs: 66-93. In some embodiments, the neoantigen sequence comprises an amino acid sequence of SEQ ID NO: 66, or an antigenic portion of SEQ ID NO: 66. In some embodiments, the neoantigen sequence comprises an amino acid sequence of any one of SEQ ID NOs: 74-77, or an antigenic portion of any one of SEQ ID NOs: 74-77. In some embodiments, the neoantigen sequence and/or antigenic portion ranges from about 10 to about 50 amino acids in length. In some embodiments, the neoantigen sequence and/or antigenic portion ranges from about 10 to about 35 amino acids in length. In some embodiments, the neoantigen sequence and/or antigenic portion ranges from about 15 to about 25 amino acids in length. In some embodiments, the neoantigen sequence and/or antigenic portion ranges from about 10 to about 20 amino acids in length. In some embodiments, the neoantigen sequence and/or antigenic portion does not exclusively overlap or consist of the canonical peptide sequence (e.g., any of the exemplary canonical peptide sequences underlined in Table 21).

In some embodiments, the neoantigen sequence is a neoantigen sequence specific to the subject. In some embodiments, the neoantigen sequence is a personalized neoantigen vaccine for the subject. In some embodiments, the neoantigen sequence is capable of binding to at least one HLA allele expressed in the subject.

In some other embodiments, the neoantigen sequence is a universal neoantigen sequence. In some embodiments, the neoantigen sequence is a universal neoantigen vaccine. In some embodiments, the neoantigen sequence is capable of binding to at least one HLA allele expressed in at least 10%, at least 15%, at least 20%, at least 25%, at least 30%, at least 35%, at least 40%, or at least 45% of subjects in a population of subjects suffering from the neoplastic disorder. In some embodiments, the neoantigen sequence is capable of eliciting a T-cell response against a tumor present in at least 1%, at least 5%, or at least 10% of a population of subjects suffering from the neoplastic disorder.

In some embodiments, the neoantigen sequence has been identified by sequencing at least one neoantigen mRNA induced in the subject by administering an effective amount of the splicing modulator, antibody-drug conjugate, or composition. In some embodiments, the at least one neoantigen mRNA encodes a neoantigen sequence induced by contacting a neoplastic cell with an effective amount of the splicing modulator, antibody-drug conjugate, or composition. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen mRNA and a pharmaceutically acceptable carrier. In some embodiments, the at least one neoantigen mRNA is linked to the pharmaceutically acceptable carrier. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine.

In some embodiments, the neoantigen vaccine comprises at least one neoantigen mRNA and a pharmaceutically acceptable diluent. In some embodiments, the neoantigen vaccine comprises at least one neoantigen mRNA and a pharmaceutically acceptable adjuvant (e.g., an adjuvant as described herein).

In some embodiments, the neoantigen mRNA is encapsulated by an encapsulating agent. In some embodiments, the encapsulating agent protects the neoantigen mRNA from degradation and improves vaccine delivery (McNamara et al. (2015) J Immunol Res. 2015:794528). In some embodiments, the encapsulating agent is a liposome. In some embodiments, the liposome is a cationic liposome such as N-[1-(2,3-dioleoloxy)propyl]-N,N,N-trimethyl ammonium chloride 1 (DOTAP). In some embodiments, the encapsulating agent is a nanoparticle. In some embodiments, the nanoparticle protects the neoantigen mRNA from nuclease degradation and/or enhances cell uptake and/or delivery efficiency. In some embodiments, the nanoparticle may be engineered to be fully degradable. In some embodiments, the nanoparticle is a biodegradable core-shell structured nanoparticle with a pH responsive poly-(b-amino ester) (PBAE) core enveloped by a phospholipid shell (Su et al. (2011) Mol Pharm. 8(3):774-87). In some embodiments, such nanoparticles are particularly efficient in delivering mRNA in vivo and eliciting an anti-tumor immune response.

In some embodiments, the subject has a non-synonymous mutational burden of about 150 mutations or less. In some embodiments, the subject has a non-synonymous mutational burden of about 100 mutations or less. In some embodiments, the subject has a non-synonymous mutational burden of about 50 mutations or less. In some embodiments, the subject has or is suspected of having a neoplastic disorder, e.g., a hematological malignancy or a solid tumor. In some embodiments, the hematological malignancy is selected from a B-cell malignancy, a leukemia, a lymphoma, and a myeloma. In some embodiments, the hematological malignancy is selected from acute myeloid leukemia and multiple myeloma. In some embodiments, the solid tumor is selected from breast cancer, gastric cancer, prostate cancer, ovarian cancer, lung cancer, uterine cancer, salivary duct carcinoma, melanoma, colon cancer, cervical cancer, pancreatic cancer, kidney cancer, colorectal cancer, and esophageal cancer. In some embodiments, the solid tumor is selected from HER2-positive breast cancer, gastric adenocarcinoma, prostate cancer, and osteosarcoma.

As used herein, "adjuvant" refers to a substance that is capable of increasing, amplifying, or modulating an immune response to an accompanying immunogenic agent, e.g., a neoantigen peptide or mRNA. In certain embodiments, a neoantigen of the present disclosure can be administered in combination with adjuvants, i.e., substances that do not themselves cause adaptive immune responses, but amplify or modulate the response to an accompanying neoantigen. A variety of adjuvants can be used in combination with the disclosed neoantigens, in order to elicit an immune response. In some embodiments, the adjuvant(s) are chosen to augment the intrinsic response to the neoantigen without causing conformational changes in the neoantigen that would affect the qualitative form of the response. In some embodiments, the adjuvant(s) are chosen to enhance T-effector (e.g., CD8) cell priming and/or activation.

In certain embodiments, the adjuvant is an aluminum salt (alum), such as aluminum hydroxide, aluminum phosphate, and aluminum sulphate. Such adjuvants can be used with or without other specific immunostimulating agents, such as 3 de-O-acylated monophosphoryl lipid A (MPL) or 3-DMP, polymeric or monomeric amino acids, such as polyglutamic acid or polylysine. Such adjuvants can be used with or without other specific immunostimulating agents, such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-AI-D-isoglu-L-Ala-dipalmitoxy propylamide (DTP-DPP)), or other bacterial cell wall components. Other adjuvants are oil-in-water emulsions and include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi$^T$M adjuvant system (RAS), (Ribi ImmunoChem) containing 2% squalene, 0.2% Tween 80, and one or more bacterial cell wall components from the group consisting of monophosphoryllipid A (MPL), trehalose dimycolate (TDM), and cell wall skeleton (CWS), for example MPL-FCWS (Detox™). In some embodiments, the adjuvant is a saponin, such as Stimulon™ (QS21) or particles generated therefrom such as ISCOMs (immunostimulating complexes) and ISCOMATRIX. Other adjuvants include Complete Freund's Adjuvant (CFA) and Incomplete Freund's Adjuvant (IFA), cytokines, such as interleukins (IL-1, IL-2, and IL-12), macrophage colony stimulating factor (M-CSF), and tumor necrosis factor (TNF).

An adjuvant can be administered with an immunogenic agent (e.g., a neoantigen peptide or mRNA) as a single composition, or can be administered before, concurrent with, or after administration of the immunogenic agent. In some embodiments, the immunogenic agent and adjuvant can be packaged and supplied in the same vial or can be packaged in separate vials and mixed before use. In some embodiments, the immunogenic agent and adjuvant can be packaged with a label, indicating the intended therapeutic application. In some embodiments, if the immunogenic agent and adjuvant are packaged separately, the packaging can include instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. However, alum, MPL or Incomplete Freund's adjuvant (Chang et al. (1998) Adv Drug Deliv Rev. 32:173-186) alone or optionally in combination with any of alum, QS21, and MPL and all combinations thereof are suitable for human administration.

In various embodiments, the present disclosure further provides methods of screening for and identifying at least one neoantigen. More specifically, in various embodiments, the present disclosure provides a method of identifying at least one neoantigen by (a) contacting a neoplastic cell with an effective amount of a splicing modulator, an ADC, or a composition comprising a splicing modulator or ADC; (b) detecting at least one alternatively-spliced mRNA transcript after contacting the neoplastic cell with the splicing modulator, ADC, or composition; (c) predicting translation of the at least one alternatively-spliced mRNA transcript into at least one peptide; and (d) comparing the at least one peptide to a reference proteome, wherein at least one neoantigen is identified if the at least one peptide does not match any peptides in the reference proteome. In various embodiments, the method further comprises contacting one or more additional neoplastic cells to identify at least one universal neoantigen. In various embodiments, the method is repeated on one or more additional neoplastic cells or samples (e.g., a tissue biopsy) to confirm suitable neoantigens (e.g., for use in a neoantigen vaccine) and/or to identify one or more universal neoantigens.

In various other embodiments, the present disclosure provides a method of identifying at least one neoantigen by (a) contacting a neoplastic cell with an effective amount of a splicing modulator, an ADC, or a composition comprising a splicing modulator or ADC; (b) detecting at least one peptide comprising a potential neoantigen sequence after contacting the neoplastic cell with the splicing modulator, ADC, or composition; and (c) comparing the at least one peptide to a reference proteome, wherein at least one neoantigen is identified if the at least one peptide does not match any peptides in the reference proteome. In various embodiments, the method further comprises contacting one or more additional neoplastic cells to identify at least one universal neoantigen. In various embodiments, the method is repeated on one or more additional neoplastic cells or samples (e.g., a tissue biopsy) to confirm suitable neoantigens (e.g., for use in a neoantigen vaccine) and/or to identify one or more universal neoantigens.

In some embodiments of the neoantigen identification methods described herein, detecting at least one alternatively-spliced mRNA transcript comprises RNAseq. In some embodiments, predicting translation of the at least one alternatively-spliced mRNA transcript comprises quantifying the change in percent spliced in (dPSI) value for the at least one transcript. In some embodiments, predicting translation of the at least one alternatively-spliced mRNA transcript comprises RiboSeq and/or ribosomal profiling.

In some embodiments of the neoantigen identification methods described herein, the methods further comprise evaluating the at least one peptide for predicted major histocompatibility complex (MHC) binding. In some embodiments, predicted MHC binding is determined by measuring raw affinity predicted binding strength of the at least one peptide. In some embodiments, a raw affinity predicted binding strength of about 500 nM or higher indicates MHC binding. In some embodiments, predicted MHC binding is determined by identifying a distribution of predicted binding strengths for a series of random peptides; and comparing predicted binding strength of the at least one peptide to the distribution. In some embodiments, a predicted binding strength in the top 2.0% of the distribution indicates weak MHC binding. In some embodiments, a predicted binding strength in the top 0.5% of the distribution indicates strong MHC binding.

In some embodiments of the neoantigen identification methods described herein, the neoplastic cell is present in an in vitro cell culture. In some embodiments, the neoplastic cell is obtained from the subject. In some embodiments, the neoplastic cell is present in the subject.

Also provided herein, in various embodiments, are methods of making a neoantigen vaccine by (a) identifying at least one neoantigen (e.g., at least one neoantigen peptide or its encoding mRNA) using any of the exemplary identification methods disclosed herein; and (b) formulating the at least one neoantigen together with a pharmaceutically acceptable carrier, diluent, or adjuvant (e.g., any of the pharmaceutically acceptable carriers, diluents, or adjuvants described herein). In some embodiments, the at least one neoantigen used in the vaccine comprises an amino acid sequence of any one of SEQ ID NOs: 37-65. In some embodiments, the at least one neoantigen used in the vaccine comprises an amino acid sequence of SEQ ID NO: 37. In some embodiments, the at least one neoantigen used in the vaccine comprises an amino acid sequence of SEQ ID NO: 39. In some embodiments, the at least one neoantigen used in the vaccine comprises an amino acid sequence of any one of SEQ ID NOs: 46-49.

In some other embodiments, the at least one neoantigen used in the vaccine comprises an amino acid sequence of any one of SEQ ID NOs: 66-93, or an antigenic portion of any one of SEQ ID NOs: 66-93. In some embodiments, the at least one neoantigen used in the vaccine comprises an amino acid sequence of SEQ ID NO: 66, or an antigenic portion of SEQ ID NO: 66. In some embodiments, the at least one neoantigen used in the vaccine comprises an amino acid sequence of any one of SEQ ID NOs: 74-77, or an antigenic portion of any one of SEQ ID NOs: 74-77. In some embodiments, the at least one neoantigen and/or antigenic portion ranges from about 10 to about 50 amino acids in length. In some embodiments, the at least one neoantigen and/or antigenic portion ranges from about 10 to about 35 amino acids in length. In some embodiments, the at least one neoantigen and/or antigenic portion ranges from about 15 to about 25 amino acids in length. In some embodiments, the at least one neoantigen and/or antigenic portion ranges from about 10 to about 20 amino acids in length. In some embodiments, the at least one neoantigen and/or antigenic portion does not exclusively overlap or consist of the canonical peptide sequence (e.g., any of the exemplary canonical peptide sequences underlined in Table 21).

In some embodiments, the at least one neoantigen used in the vaccine is linked to the pharmaceutically acceptable carrier. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine.

Combination of Splicing Modulator/ADC and Engineered T-Cells (CAR-T):

In various embodiments, a patient having a cancer as described herein can be treated with a combination of a splicing modulator, ADC, or composition and one or more engineered tumor-targeting T-cells (i.e., CAR-T). Thus, in various embodiments, the present disclosure provides a method of treating a subject having or suspected of having a neoplastic disorder by administering to the subject an effective amount of a splicing modulator, an ADC, or a composition comprising a splicing modulator or ADC; and engineered tumor-targeting T-cells (i.e., CAR-T). In various embodiments, a chimeric T-cell receptor can be engineered using antigen recognition sequences that are reactive with an identified neoantigen.

For instance, in various embodiments, in order to target splicing modulator- or ADC-induced changes in the extracellular domains of cell surface proteins, a chimeric antigen-reactive T-cell receptor (CAR) may be engineered by first identifying antibodies that recognize a cell surface-expressed neoantigen protein domain. The antigen recognition sequences of such antibodies can then be fused to a T-cell receptor domain for selective targeting and activation.

In various other embodiments, a strategy integrating the antigen presentation machinery of tumor cells together with splicing modulator- or ADC-derived neoantigens is employed. In some embodiments, cells containing known and frequently represented HLA alleles (e.g., HLA-A*02:01) can be treated with a splicing modulator, ADC, or composition and MHC1-bound neoantigens are identified by ligandomics. In some embodiments, these peptides can be used to prime and/or expand T-cells from healthy donors expressing the same HLA allele. Such T-cells, in some embodiments, can be isolated and the T-cell receptor (TCR) α and β chains sequenced to identify the cognate antigen recognition/variable regions. In some embodiments, a cognate CAR can then be engineered.

In some embodiments, the CAR sequences are cloned into patient-derived T-cell populations and expanded using currently available protocols. In some embodiments, the engineered T-cells are then transfused back into the patient's circulation, following treatment with a splicing modulator, ADC, or composition. After treatment with the splicing modulator, ADC, or composition, in some embodiments, the tumor cells may begin to present antigen. In some embodiments, the engineered T-cell population can engage with and kill antigen presenting tumor cells.

It will be readily apparent to those skilled in the art that other suitable modifications and adaptations of the methods of the disclosure described herein are obvious and may be made using suitable equivalents without departing from the scope of the disclosure or the embodiments disclosed herein. Having now described the disclosure in detail, the same will be more clearly understood by reference to the following examples, which are included for purposes of illustration only and are not intended to be limiting.

EXAMPLES

Example 1

Synthesis methods for payloads, linkers, and conjugatable linker-payload (linker-drug, L–D) compounds, having the structures shown in Tables 7-9, are described. Conjugatable linker-payloads were used in the preparation of antibody-drug conjugates (ADCs). Exemplary ADCs are described in Examples 3-5.

1.1 Reagents and Materials

The starting materials used in the following synthesis methods are either commercially available or can be readily prepared by standard methods from known materials. The disclosed conjugatable linker-payloads can be prepared using the reactions and techniques described herein. In the description of the synthetic methods described below, it is to be understood that all proposed reaction conditions, including choice of solvent, reaction atmosphere, reaction temperature, duration of the experiment, and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions are apparent to one skilled in the art, and alternate methods are therefore indicated herein.

Preparative liquid chromatography-mass spectrometry (LC/MS) was conducted using a Waters AutoPurification System and an XTerra MS $C_{18}$ column (5 pm, 19 mm×100 mm) under acidic mobile phase conditions. Nuclear magnetic resonance (NMR) spectra were recorded at 400 MHz using a Varian instrument (Agilent Technologies). Microwave heating was performed using a Biotage Emrys Liberator or Initiator microwave. Column chromatography was carried out using a Teledyne Isco Combiflash Rf200d. Solvent removal was carried out using either a BQchi rotary evaporator or a Genevac centrifugal evaporator.

Terms/Abbreviations: As used herein, the term "inerted" refers to replacement of the air in a reactor (e.g., a reaction vessel, a flask, a glass reactor) with an essentially moisture-free, inert gas, such as nitrogen or argon. The following abbreviations are used herein: DCM=dichloromethane, DMF=dimethylformamide, HPLC=high performance liquid chromatography, KHMDS=potassium bis(trimethylsilyl) amide, LC/MS=liquid chromatography-mass spectrometry, MeOH=methanol, RT=room temperature, TBSCl=tert-butyldimethylsilyl chloride, THF=tetrahydrofuran, TLC=thin-layer chromatography. Multiplicities are indicated using the following abbreviations: s=singlet, d=doublet, t=triplet, q=quartet, quint=quintet, sxt=sextet, m=multiplet, dd=doublet of doublets, ddd=doublet of doublets of doublets, dt=doublet of triplets, br s=a broad singlet.

LC/MS: Mobile phases=A (0.1% formic acid in H2O) and B (0.1% formic acid in acetonitrile). Gradient=B 5% to 95% in 1.8 min. Column=Waters Acquity BEH 018 column (1.7 μm, 2.1×50 mm).

References: U.S. Pat. Nos. 7,884,128 and 7,816,401 describe exemplary methods of synthesizing pladienolide B and D and are each incorporated herein by reference for such methods. Synthesis of pladienolide B and D may also be performed using the exemplary methods described in Kanada et al. ((2007) Angew Chem Int Ed. 46:4350-5). Kanada et al. and Intl. Pub. No. WO 2003/099813 describe exemplary methods for synthesizing E7107 (D11) (Compound 45 of WO 2003/099813) from Pladienolide 0 (111070 of WO 2003/099813). A corresponding U.S. Pat. No. is 7,550,503 to Kotake et al. Each of these references is incorporated herein for the described synthesis methods.

TABLE 7

Structures of exemplary drug moieties (payloads)

Payload Structure/ID (Payload Series)

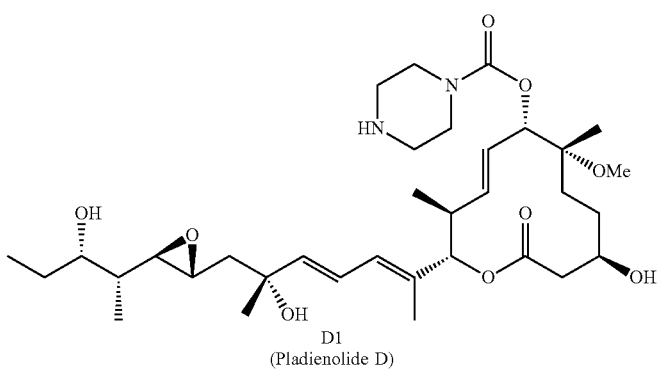

D1
(Pladienolide D)

TABLE 7-continued
Structures of exemplary drug moieties (payloads)
Payload Structure/ID
(Payload Series)
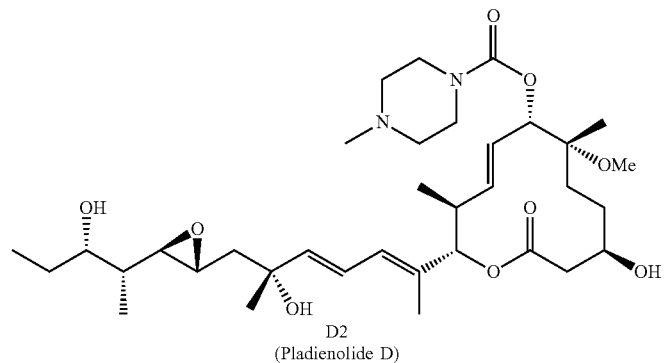
D2
(Pladienolide D)
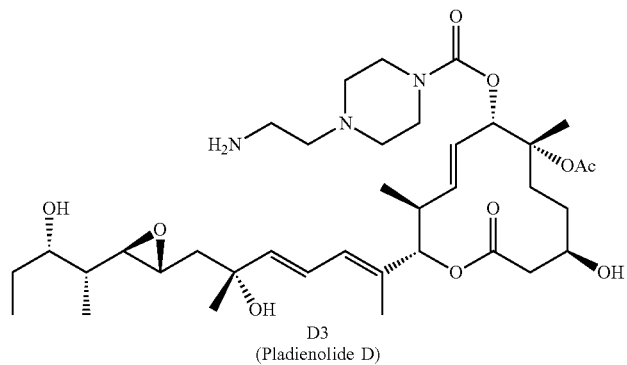
D3
(Pladienolide D)
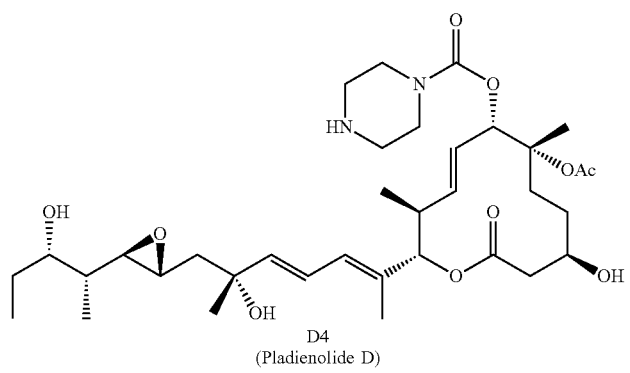
D4
(Pladienolide D)
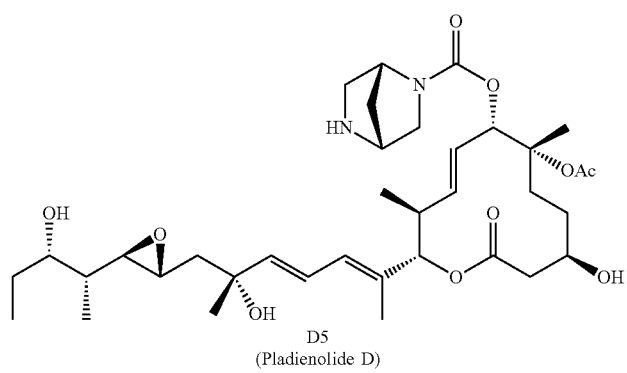
D5
(Pladienolide D)

TABLE 7-continued
Structures of exemplary drug moieties (payloads)
Payload Structure/ID
(Payload Series)
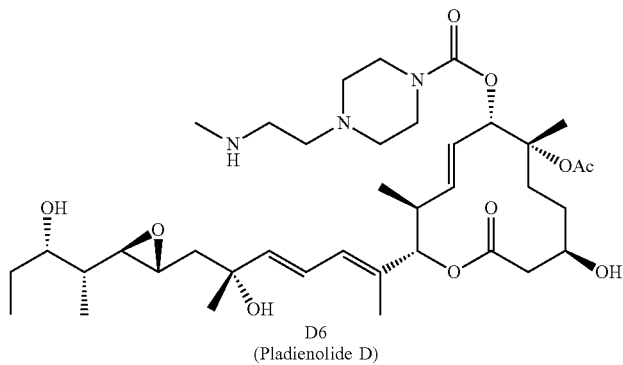
D6
(Pladienolide D)
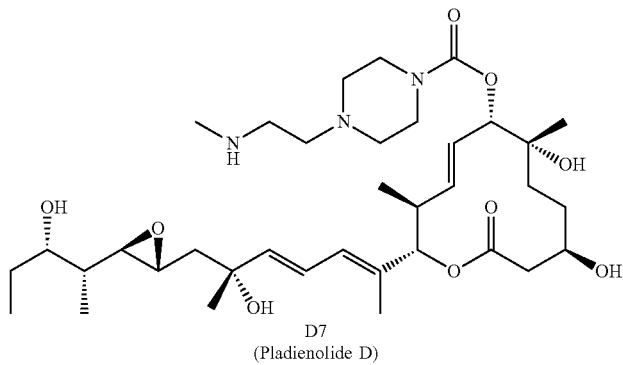
D7
(Pladienolide D)
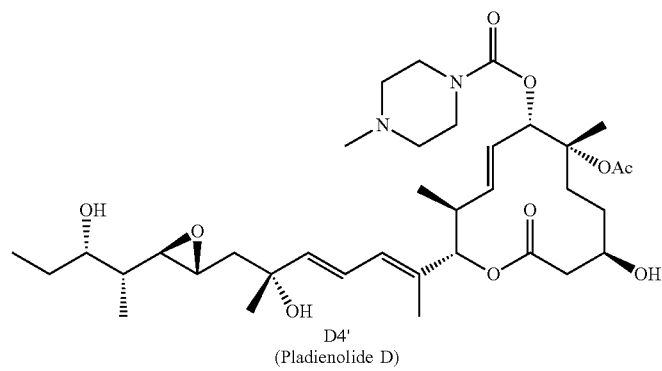
D4'
(Pladienolide D)
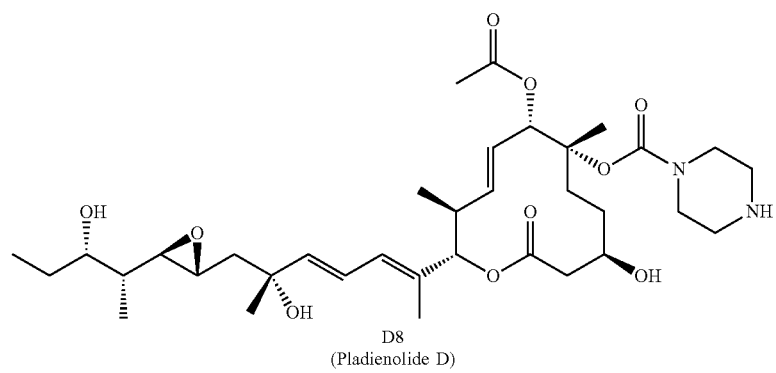
D8
(Pladienolide D)

TABLE 7-continued
Structures of exemplary drug moieties (payloads)
Payload Structure/ID
(Payload Series)
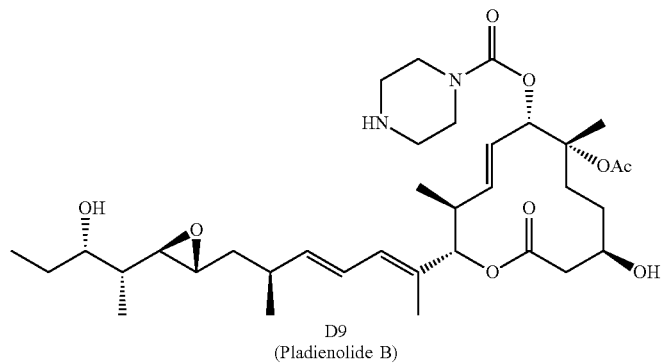
D9
(Pladienolide B)
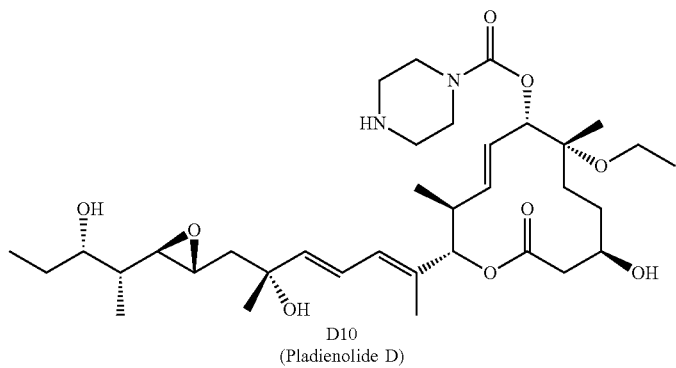
D10
(Pladienolide D)
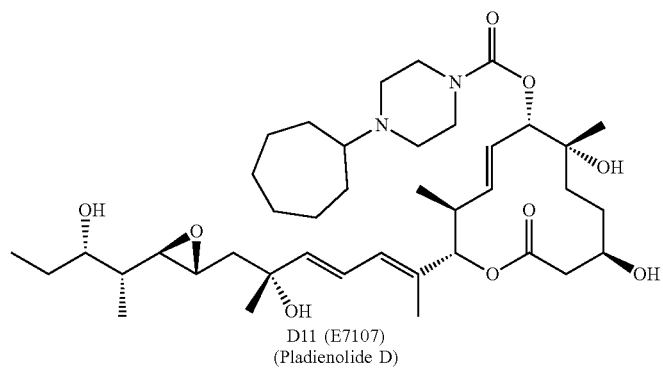
D11 (E7107)
(Pladienolide D)
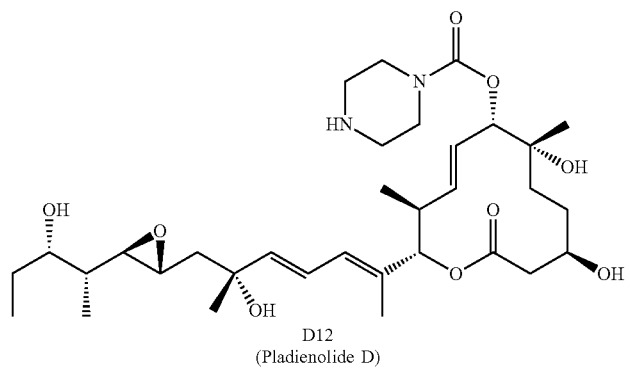
D12
(Pladienolide D)

TABLE 7-continued
Structures of exemplary drug moieties (payloads)
Payload Structure/ID
(Payload Series)
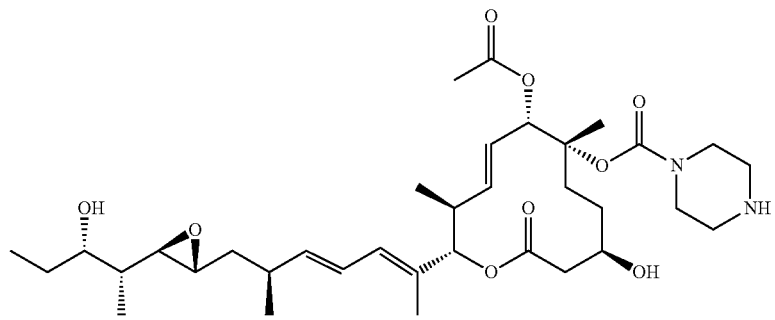 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC(=O)N2CCNCC2)[C@@H](OC(C)=O)/C=C/[C@@H]1C]
D13
(Pladienolide B)
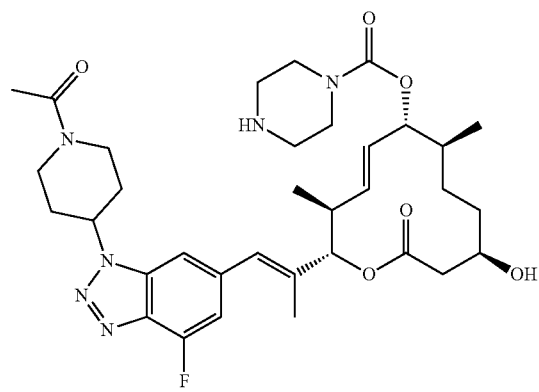 [SMILES: CC(=O)N1CCC(n2nnc3c(F)cc(/C=C(\C)[C@H]4OC(=O)C[C@H](O)CC[C@H](C)[C@@H](OC(=O)N5CCNCC5)/C=C/[C@@H]4C)cc32)CC1]
D14
(Aryl Pladienolide)
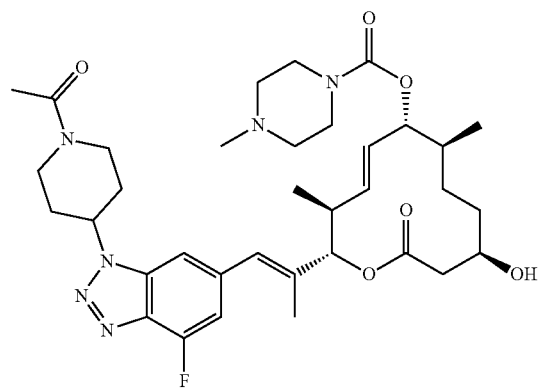 [SMILES: CC(=O)N1CCC(n2nnc3c(F)cc(/C=C(\C)[C@H]4OC(=O)C[C@H](O)CC[C@H](C)[C@@H](OC(=O)N5CCN(C)CC5)/C=C/[C@@H]4C)cc32)CC1]
D15
(Aryl Pladienolide)

TABLE 7-continued
Structures of exemplary drug moieties (payloads)
Payload Structure/ID
(Payload Series)
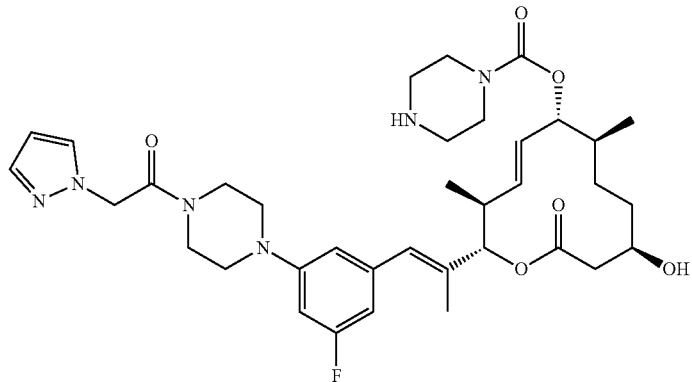 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CCNCC2)/C=C/[C@@H]1C]
D16
(Aryl Pladienolide)
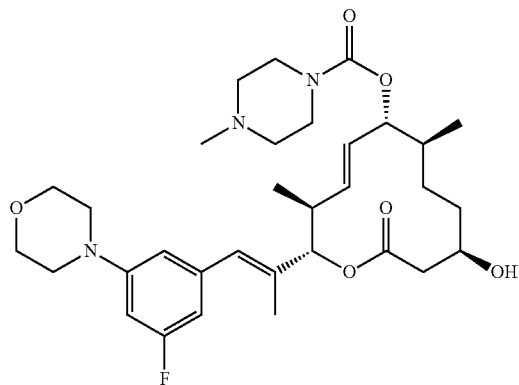 [SMILES: C/C(=C\c1cc(F)cc(N2CCOCC2)c1)[C@H]1OC(=O)C[C@H](O)CC[C@H](C)[C@@H](OC(=O)N2CCN(C)CC2)/C=C/[C@@H]1C]
D17
(Aryl Pladienolide)
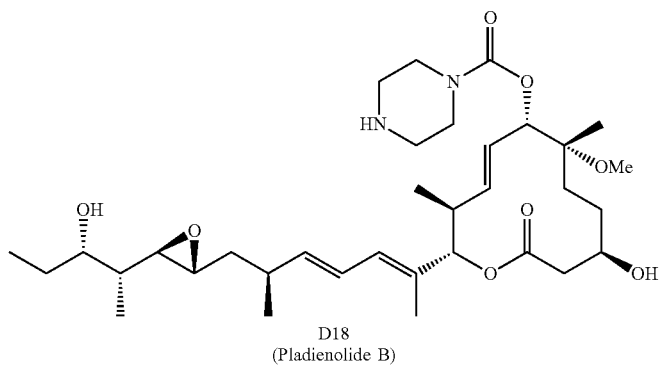
D18
(Pladienolide B)

TABLE 7-continued
Structures of exemplary drug moieties (payloads)
Payload Structure/ID
(Payload Series)
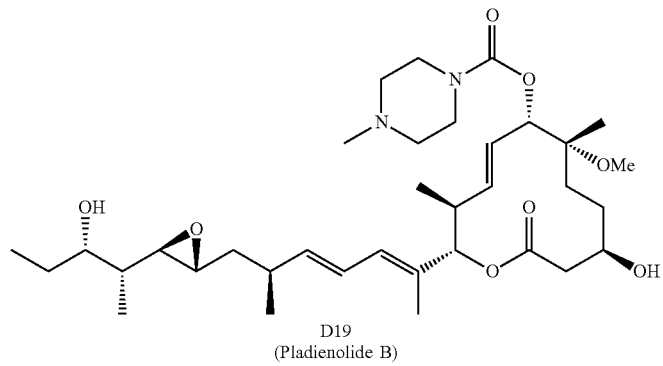
D19
(Pladienolide B)
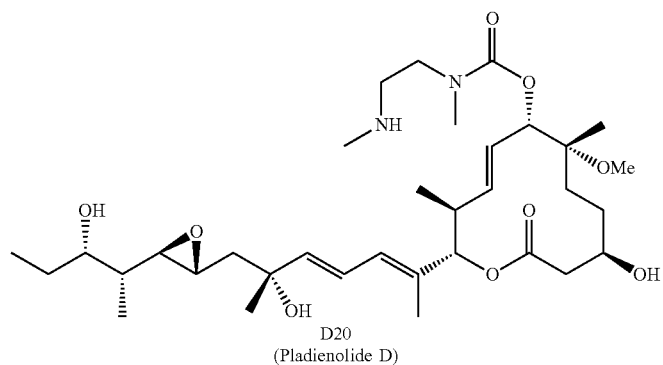
D20
(Pladienolide D)
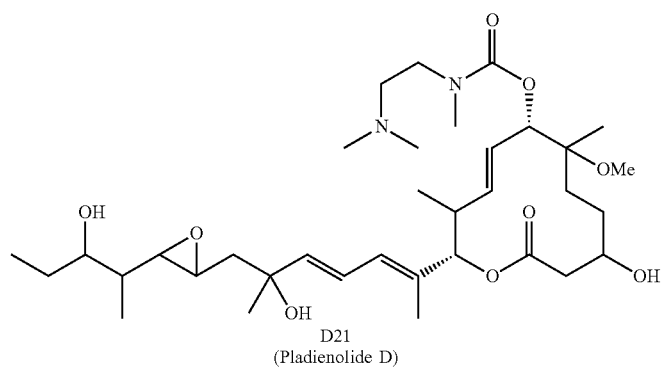
D21
(Pladienolide D)
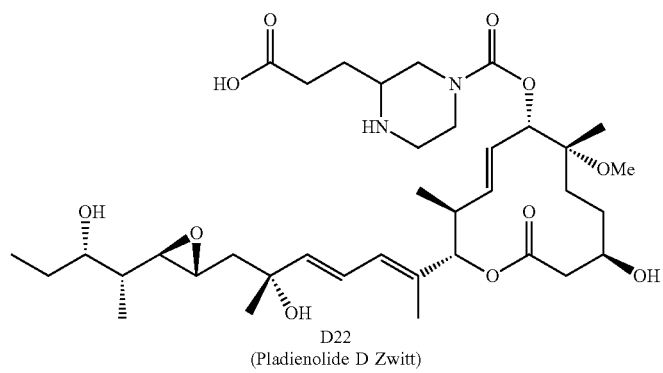
D22
(Pladienolide D Zwitt)

TABLE 7-continued
Structures of exemplary drug moieties (payloads)
Payload Structure/ID
(Payload Series)
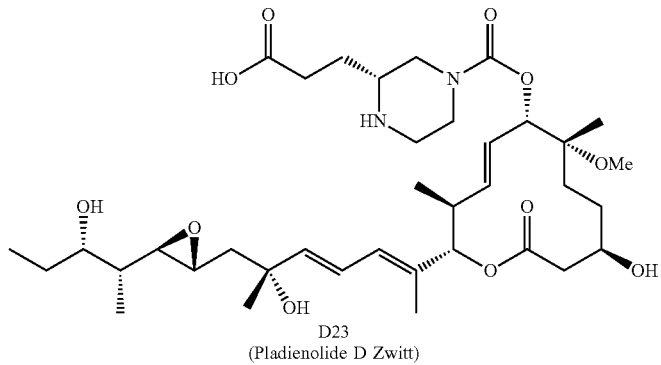
D23
(Pladienolide D Zwitt)
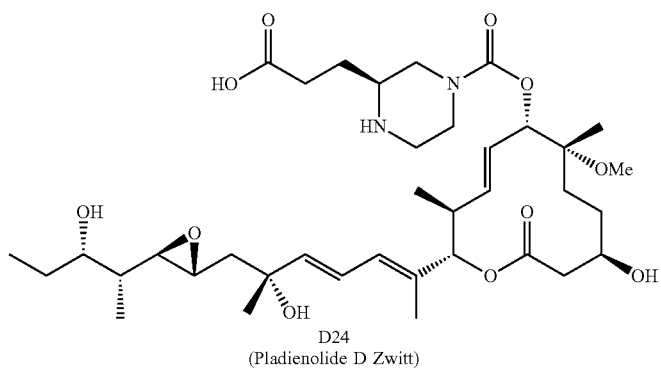
D24
(Pladienolide D Zwitt)
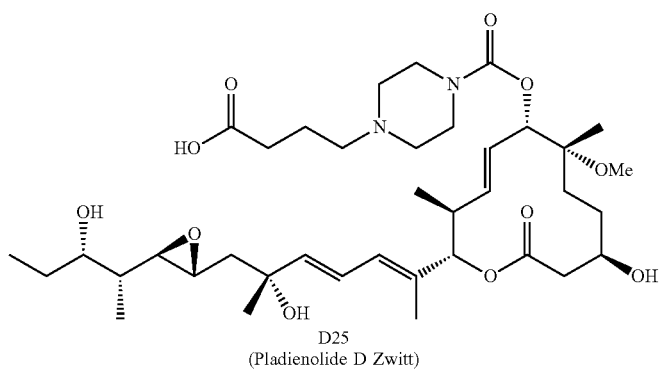
D25
(Pladienolide D Zwitt)
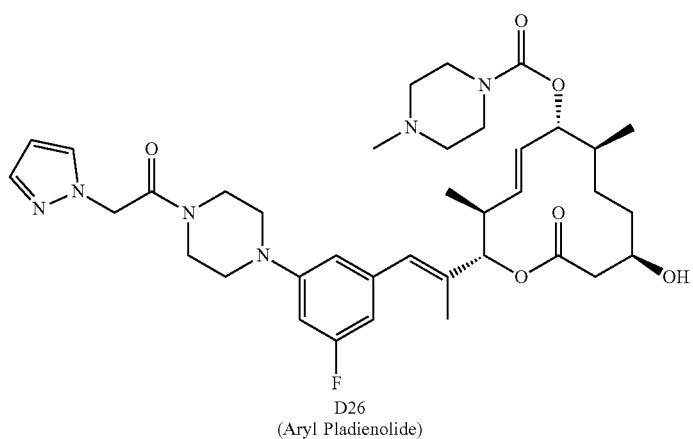
D26
(Aryl Pladienolide)

TABLE 7-continued
Structures of exemplary drug moieties (payloads)
Payload Structure/ID
(Payload Series)
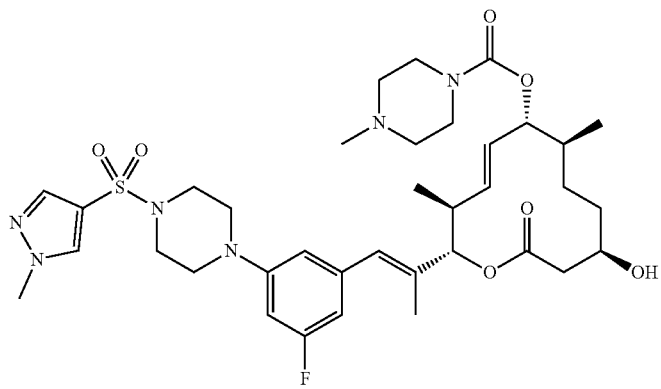 [SMILES: C/C(=C\c1cc(F)cc(N2CCN(S(=O)(=O)c3cnn(C)c3)CC2)c1)[C@H]1OC(=O)C[C@H](O)CC[C@H](C)[C@@H](OC(=O)N2CCN(C)CC2)/C=C/[C@@H]1C]
D27
(Aryl Pladienolide)
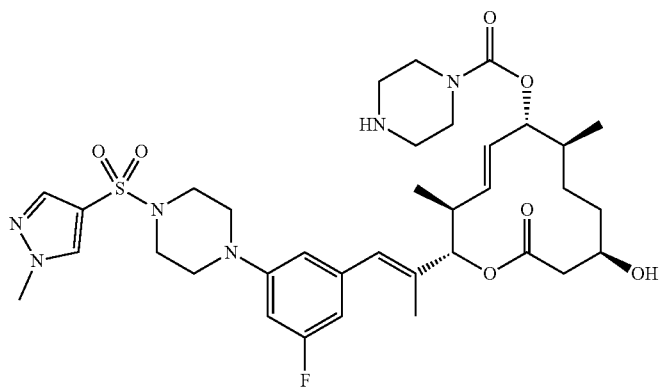 [SMILES: C/C(=C\c1cc(F)cc(N2CCN(S(=O)(=O)c3cnn(C)c3)CC2)c1)[C@H]1OC(=O)C[C@H](O)CC[C@H](C)[C@@H](OC(=O)N2CCNCC2)/C=C/[C@@H]1C]
D28
(Aryl Pladienolide)
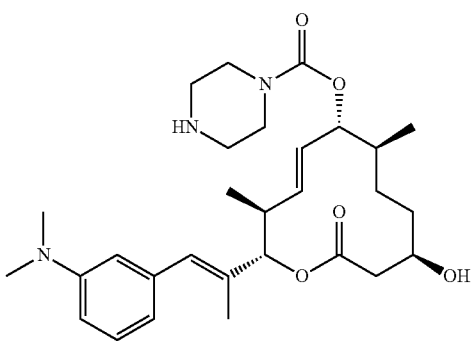 [SMILES: C/C(=C\c1cccc(N(C)C)c1)[C@H]1OC(=O)C[C@H](O)CC[C@H](C)[C@@H](OC(=O)N2CCNCC2)/C=C/[C@@H]1C]
D29
(Aryl Pladienolide)

TABLE 7-continued
Structures of exemplary drug moieties (payloads)
Payload Structure/ID
(Payload Series)
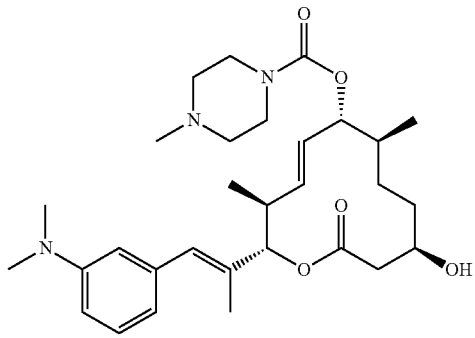 [SMILES: C/C(=C\c1cccc(N(C)C)c1)[C@H]1OC(=O)C[C@H](O)CC[C@H](C)[C@@H](OC(=O)N2CCN(C)CC2)/C=C/[C@@H]1C]
D30
(Aryl Pladienolide)
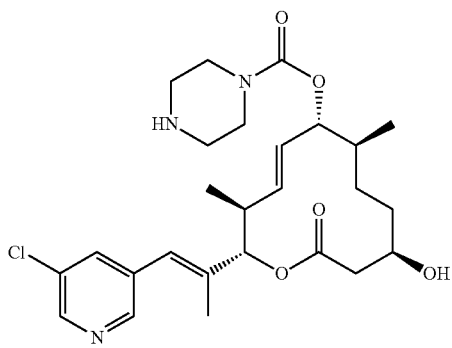 [SMILES: C/C(=C\c1cncc(Cl)c1)[C@H]1OC(=O)C[C@H](O)CC[C@H](C)[C@@H](OC(=O)N2CCNCC2)/C=C/[C@@H]1C]
D31
(Aryl Pladienolide)
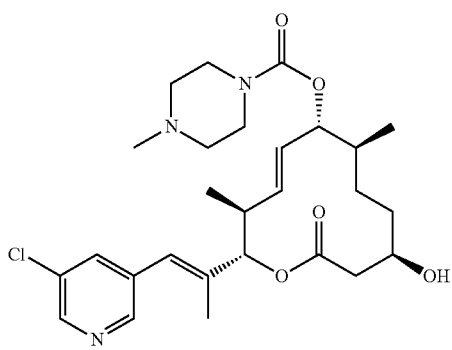 [SMILES: C/C(=C\c1cncc(Cl)c1)[C@H]1OC(=O)C[C@H](O)CC[C@H](C)[C@@H](OC(=O)N2CCN(C)CC2)/C=C/[C@@H]1C]
D32
(Aryl Pladienolide)

TABLE 7-continued
Structures of exemplary drug moieties (payloads)
Payload Structure/ID
(Payload Series)
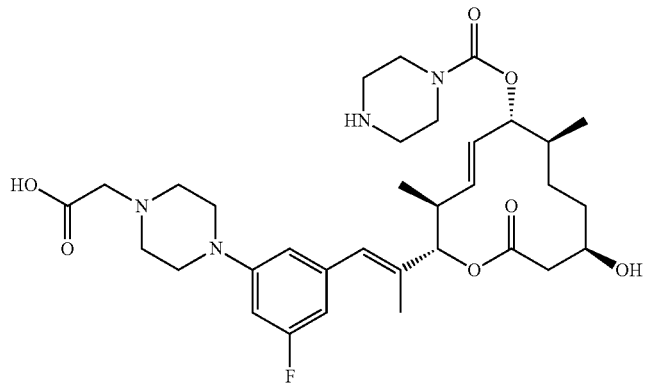 [SMILES: C/C(=C\c1cc(F)cc(N2CCN(CC(=O)O)CC2)c1)[C@H]1OC(=O)C[C@H](O)CC[C@H](C)[C@@H](OC(=O)N2CCNCC2)/C=C/[C@@H]1C]
D33
(Aryl Pladienolide Zwitt)
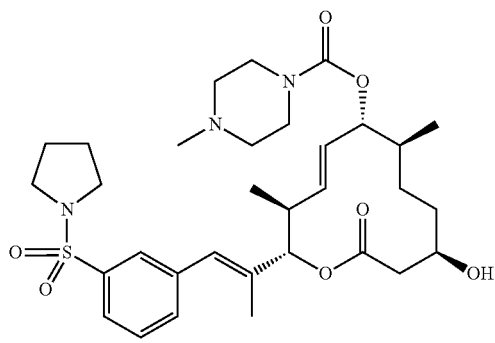 [SMILES: C/C(=C\c1cccc(S(=O)(=O)N2CCCC2)c1)[C@H]1OC(=O)C[C@H](O)CC[C@H](C)[C@@H](OC(=O)N2CCN(C)CC2)/C=C/[C@@H]1C]
D34
(Aryl Pladienolide Zwitt)
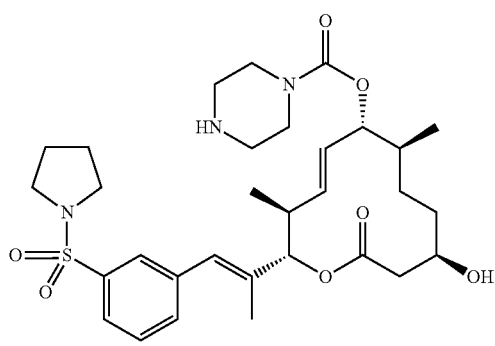 [SMILES: C/C(=C\c1cccc(S(=O)(=O)N2CCCC2)c1)[C@H]1OC(=O)C[C@H](O)CC[C@H](C)[C@@H](OC(=O)N2CCNCC2)/C=C/[C@@H]1C]
D35
(Aryl Pladienolide Zwitt)

TABLE 8

Structures of exemplary linkers
Linker Structure/ID
(IUPAC Name)

ADL1 - "MC-Val-Cit-pABC"
({4-[(2S)-5-(carbamoylamino)-2-[(2S)-2-[6-(2,5-dioxo-2,5-dihydro-1H-pyrrol-1-yl)hexanamido]-3-methylbutanamido]pentanamido]phenyl}methyl formate)

ADL2 - "MC-(PEG)$_2$-CO"
(3-{2-[2-(2,5-dioxo-2,5-dihydro-1H-pyrrol-1-yl)ethoxy]ethoxy}propanal)

ADL5 - "MC-Val-Ala-pAB"
(6-(2,5-dioxo-2,5-dihydro-1H-pyrrol-1-yl)-N-[(1S)-2-methyl-1-{[(1S)-1-[(4-methylphenyl)carbamoyl]ethyl]carbamoyl}propyl]hexanamide)

ADL6 - "MC-Val-Ala-pABC"
({4-[(2S)-2-[(2S)-2-[6-(2,5-dioxo-2,5-dihydro-1H-pyrrol-1-yl)hexanamido]-3-methylbutanamido]propanamido]phenyl}methyl formate)

ADL7 - "MC-Val-Cit-pAB"
(N-[(1S)-1-{[(1S)-4-(carbamoylamino)-1-[(4-methylphenyl)carbamoyl]butyl]carbamoyl}-2-methylpropyl]-6-(2,5-dioxo-2,5-dihydro-1H-pyrrol-1-yl)hexanamide)

253 254
TABLE 8-continued

Structures of exemplary linkers
Linker Structure/ID
(IUPAC Name)

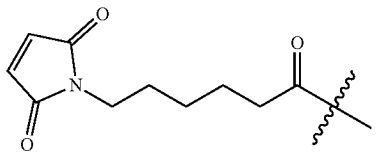 [SMILES: *C(=O)CCCCCN1C(=O)C=CC1=O]

ADL10 - "MC"
(6-(2,5-dioxo-2,5-dihydro-1H-pyrrol-1-yl)hexanal)

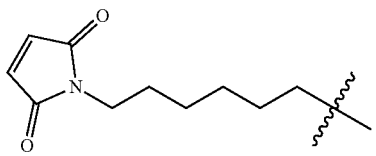 [SMILES: *CCCCCCN1C(=O)C=CC1=O]

ADL12 - "Mal-Hex"
(1-hexyl-2,5-dihydro-1H-pyrrole-2,5-dione)

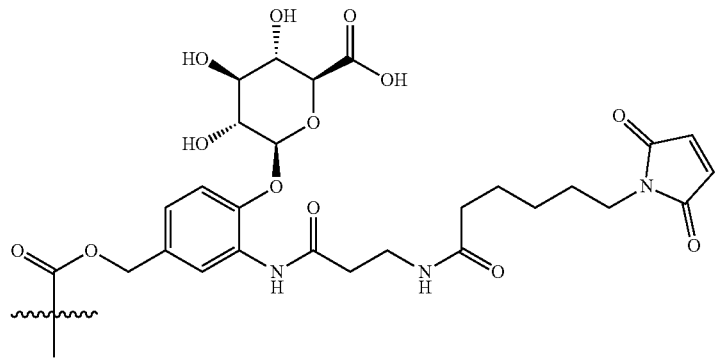 [SMILES: *C(=O)OCc1ccc(O[C@@H]2O[C@H](C(=O)O)[C@@H](O)[C@H](O)[C@H]2O)c(NC(=O)CCNC(=O)CCCCCN2C(=O)C=CC2=O)c1]

ADL13 - "MC-β-glucuronide"
((2S,3S,4S,5R,6S)-6-(2-{3-[6-(2,5-dioxo-2,5-dihydro-1H-pyrrol-1-
yl)hexanamido]propanamido}-4-[(formyloxy)methyl]phenoxy)-3,4,5-trihydroxyoxane-2-
carboxylic acid)

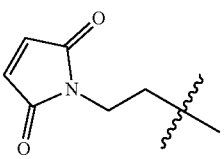 [SMILES: *CCN1C(=O)C=CC1=O]

ADL14 - "Mal-Et"
(1-ethyl-2,5-dihydro-1H-pyrrole-2,5-dione)

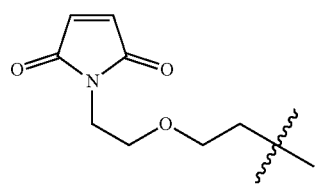 [SMILES: *CCOCCN1C(=O)C=CC1=O]

ADL15 - "Mal-Et-O-Et"
(1-(2-ethoxyethyl)-2,5-dihydro-1H-pyrrole-2,5-dione)

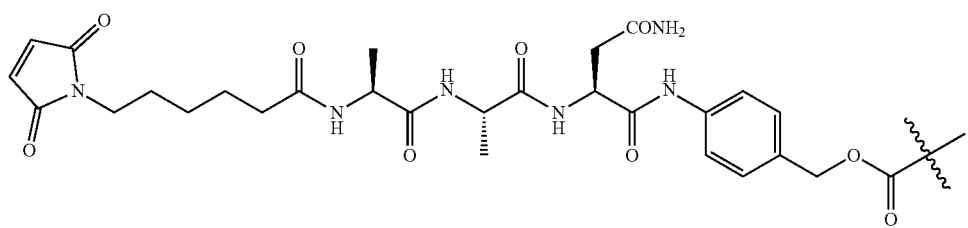 [SMILES: *C(=O)OCc1ccc(NC(=O)[C@H](CC(N)=O)NC(=O)[C@H](C)NC(=O)[C@H](C)NC(=O)CCCCCN2C(=O)C=CC2=O)cc1]

ADL21 - "MC-Ala-Ala-Asp-pABC"

TABLE 8-continued
Structures of exemplary linkers
Linker Structure/ID
(IUPAC Name)
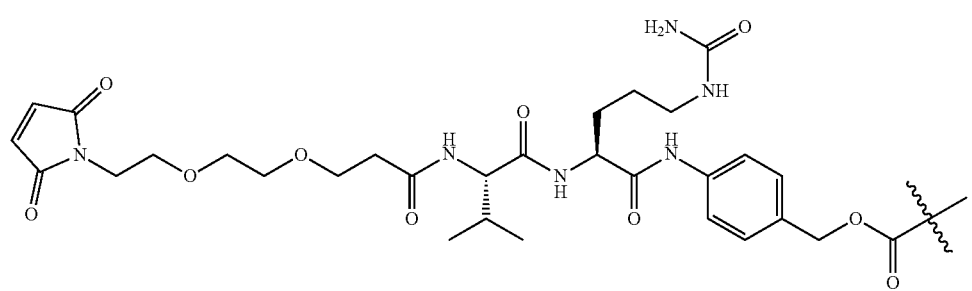 [SMILES: *C(=O)OCc1ccc(NC(=O)[C@H](CCCNC(N)=O)NC(=O)[C@@H](NC(=O)CCOCCOCCN2C(=O)C=CC2=O)C(C)C)cc1]
ADL22 - "Mc-PEG2-Val-Cit-pABC"
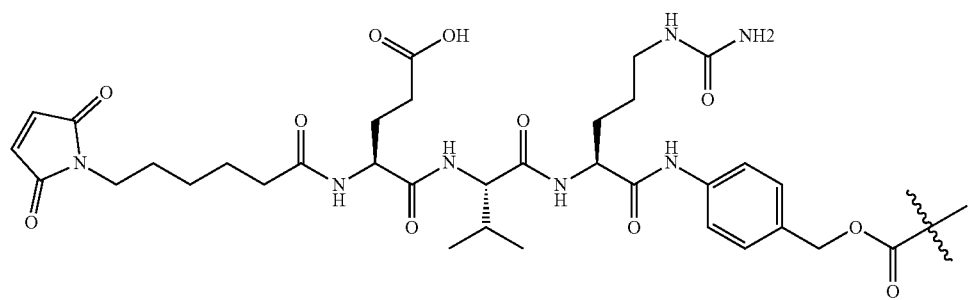 [SMILES: *C(=O)OCc1ccc(NC(=O)[C@H](CCCNC(N)=O)NC(=O)[C@@H](NC(=O)[C@H](CCC(=O)O)NC(=O)CCCCCN2C(=O)C=CC2=O)C(C)C)cc1]
ADL23 - "MC-Glu-Val-Cit-pABC"
TABLE 9
Structures of exemplary conjugatable linker-payload (L-D) compounds
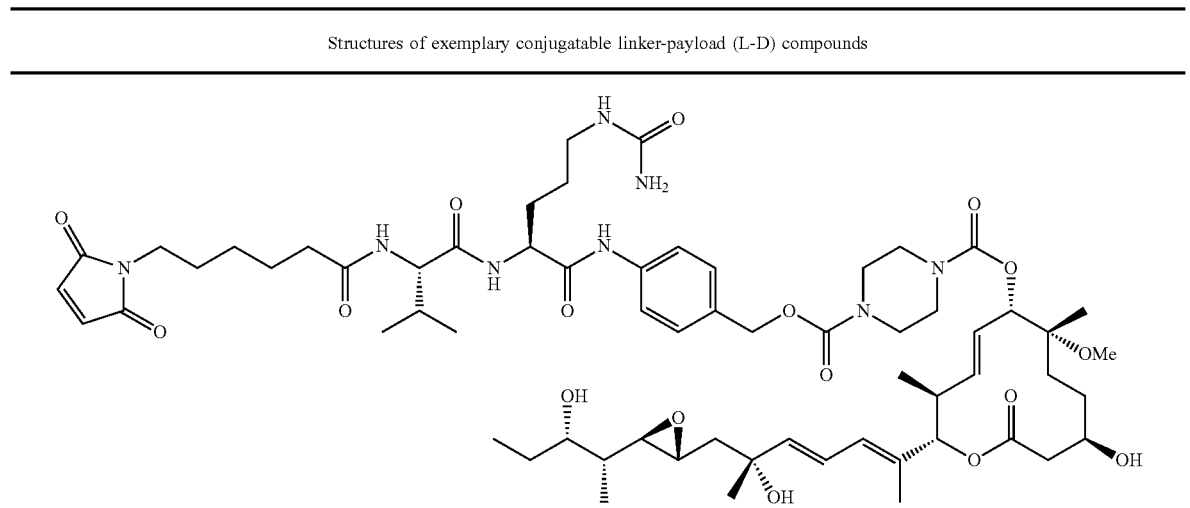
Chemical Formula: $C_{63}H_{94}N_8O_{17}$
Exact Mass: 1234.67
Molecular Weight: 1235.48
ADL1-D1

TABLE 9-continued
Structures of exemplary conjugatable linker-payload (L-D) compounds
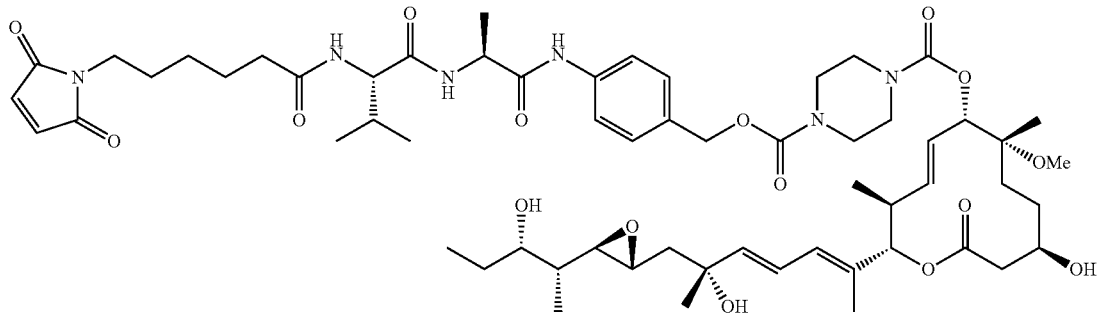 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)OCc3ccc(NC(=O)[C@H](C)NC(=O)[C@@H](NC(=O)CCCCCN4C(=O)C=CC4=O)C(C)C)cc3)CC2)/C=C/[C@@H]1C]
Chemical Formula: $C_{60}H_{88}N_6O_{16}$
Exact Mass: 1148.63
Molecular Weight: 1149.39
ADL6-D1
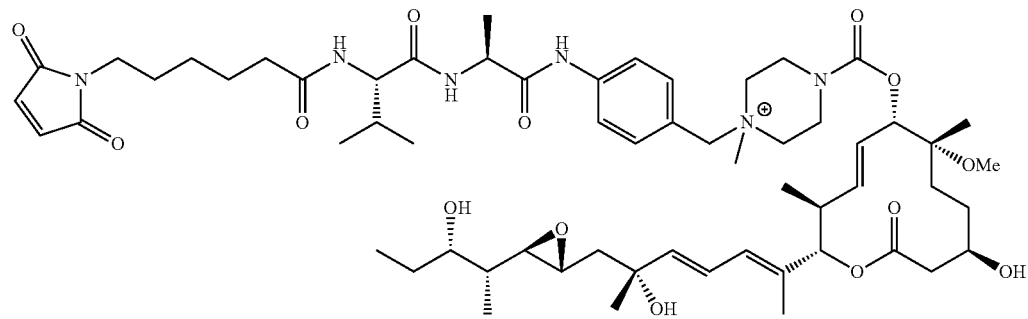 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]
Chemical Formula: $C_{60}H_{91}N_6O_{14}^+$
Exact Mass: 1119.66
Molecular Weight: 1120.42
ADL5-D2
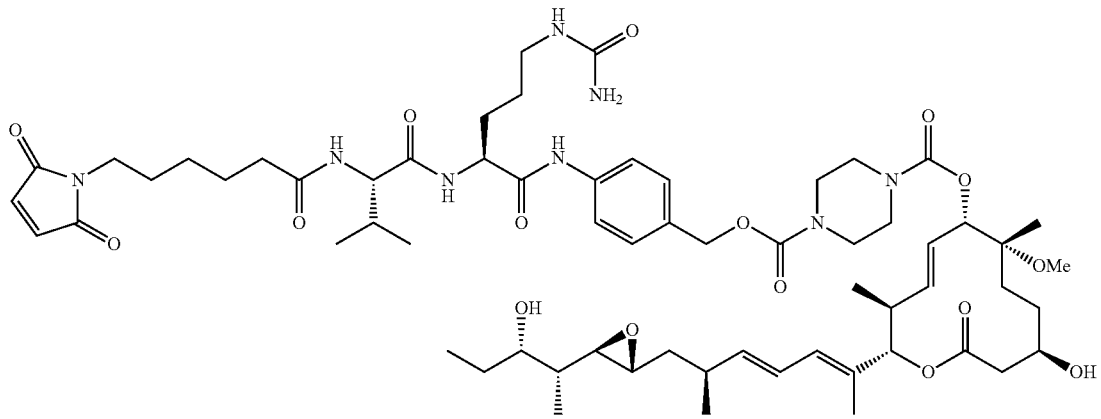 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]
Chemical Formula: $C_{63}H_{94}N_8O_{16}$
Exact Mass: 1218.68
Molecular Weight: 1219.49
ADL1-D18

TABLE 9-continued
Structures of exemplary conjugatable linker-payload (L-D) compounds
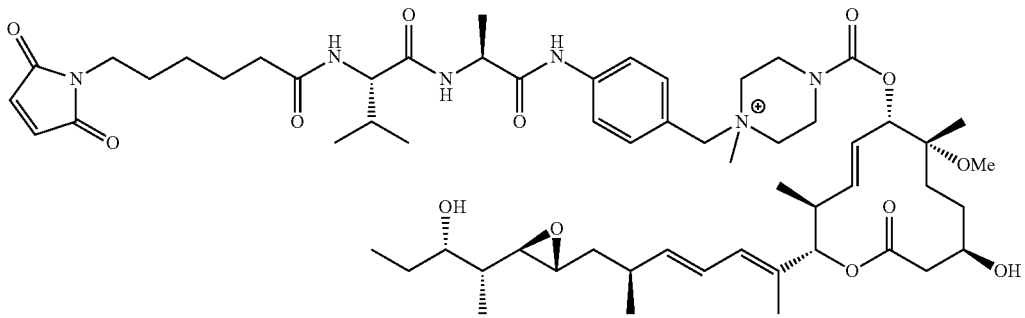 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]
Chemical Formula: $C_{60}H_{91}N_6O_{13}^+$
Exact Mass: 1103.66
Molecular Weight: 1104.42
ADL5-D19
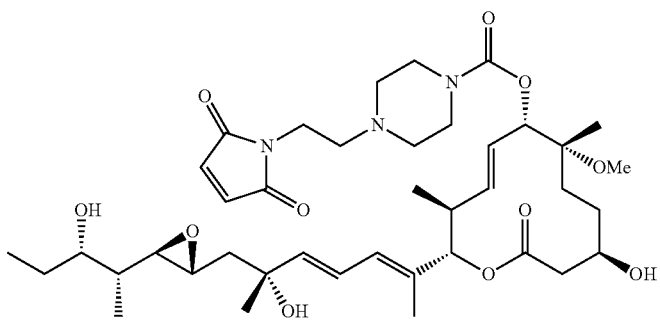 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(CCN3C(=O)C=CC3=O)CC2)/C=C/[C@@H]1C]
Chemical Formula: $C_{40}H_{61}N_3O_{11}$
Exact Mass: 759.43
Molecular Weight: 759.94
ADL14-D1
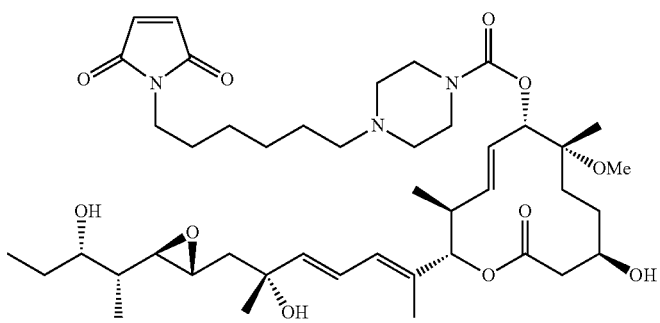 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(CCCCCCN3C(=O)C=CC3=O)CC2)/C=C/[C@@H]1C]
Chemical Formula: $C_{44}H_{69}N_3O_{11}$
Exact Mass: 815.49
Molecular Weight: 816.05
ADL12-D1
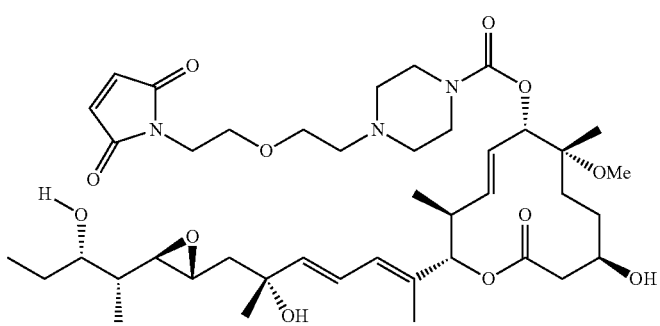 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(CCOCCN3C(=O)C=CC3=O)CC2)/C=C/[C@@H]1C]
Chemical Formula: $C_{42}H_{65}N_3O_{12}$
Exact Mass: 803.46
Molecular Weight: 803.99
ADL15-D1

TABLE 9-continued
Structures of exemplary conjugatable linker-payload (L-D) compounds
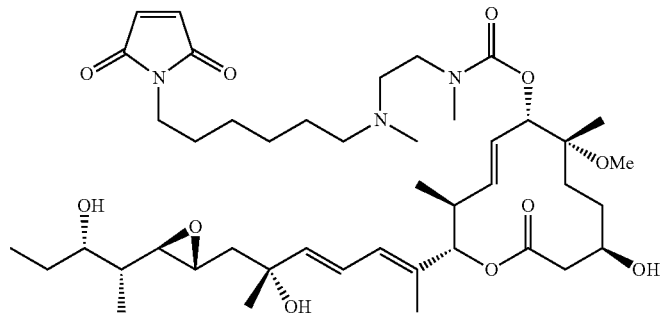 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N(C)CCN(C)CCCCCCN2C(=O)C=CC2=O)/C=C/[C@@H]1C]
Chemical Formula: $C_{44}H_{71}N_3O_{11}$
Exact Mass: 817.51
Molecular Weight: 818.06
ADL12-D20
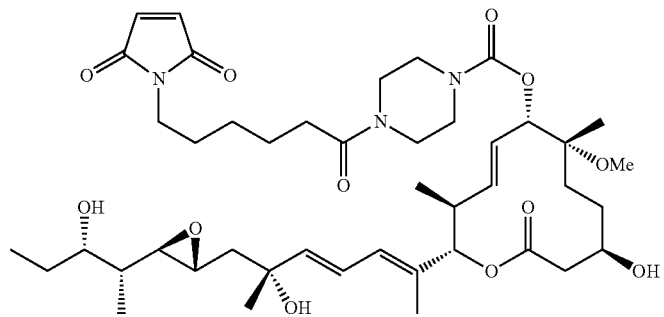 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)CCCCCN3C(=O)C=CC3=O)CC2)/C=C/[C@@H]1C]
Chemical Formula: $C_{44}H_{67}N_3O_{12}$
Exact Mass: 829.47
Molecular Weight: 830.03
ADL10-D1
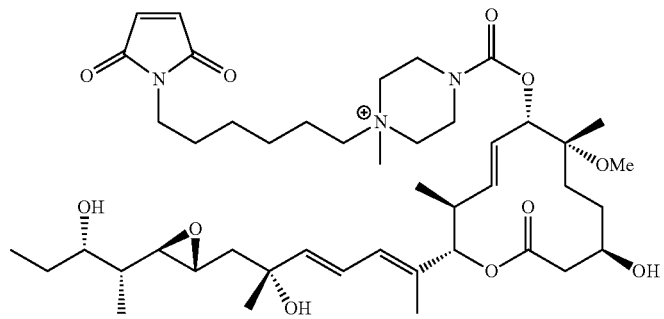 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CC[N+](C)(CCCCCCN3C(=O)C=CC3=O)CC2)/C=C/[C@@H]1C]
Chemical Formula: $C_{45}H_{72}N_3O_{11}^+$
Exact Mass: 830.52
Molecular Weight: 831.08
ADL12-D2

TABLE 9-continued
Structures of exemplary conjugatable linker-payload (L-D) compounds
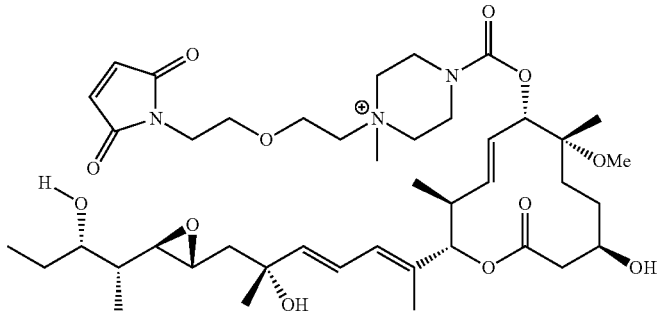 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CC[N+](C)(CCOCCN3C(=O)C=CC3=O)CC2)/C=C/[C@@H]1C]
Chemical Formula: $C_{43}H_{68}N_3O_{12}{}^+$
Exact Mass: 818.48
Molecular Weight: 819.03
ADL15-D2
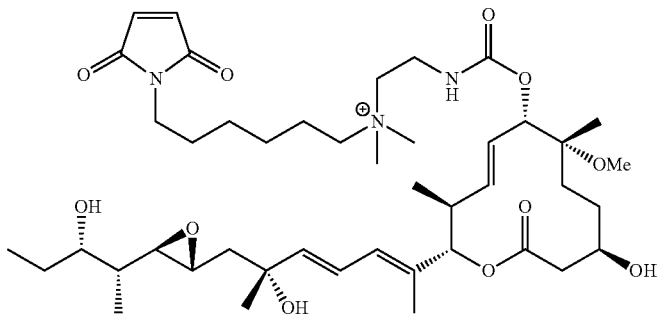 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)NCC[N+](C)(C)CCCCCCN2C(=O)C=CC2=O)/C=C/[C@@H]1C]
Chemical Formula: $C_{44}H_{72}N_3O_{11}{}^+$
Exact Mass: 818.52
Molecular Weight: 819.07
ADL12-D21
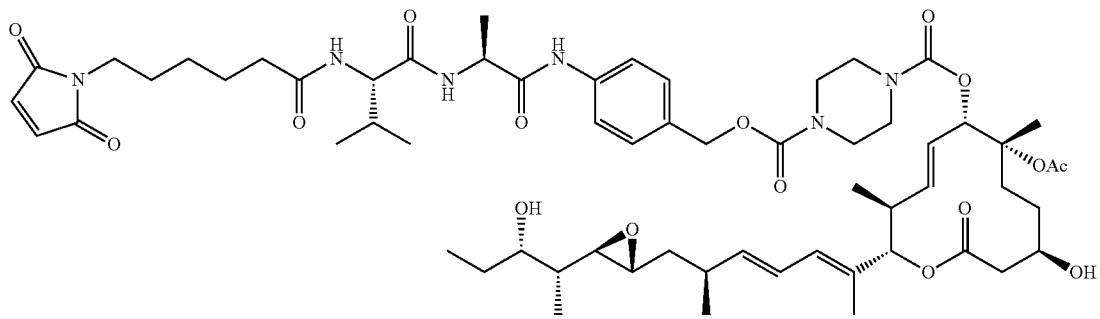 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC(C)=O)[C@@H](OC(=O)N2CCN(C(=O)OCc3ccc(NC(=O)[C@H](C)NC(=O)[C@@H](NC(=O)CCCCCN4C(=O)C=CC4=O)C(C)C)cc3)CC2)/C=C/[C@@H]1C]
Chemical Formula: $C_{61}H_{88}N_6O_{16}$
Exact Mass: 1160.63
Molecular Weight: 1161.40
ADL6-D9

TABLE 9-continued
Structures of exemplary conjugatable linker-payload (L-D) compounds
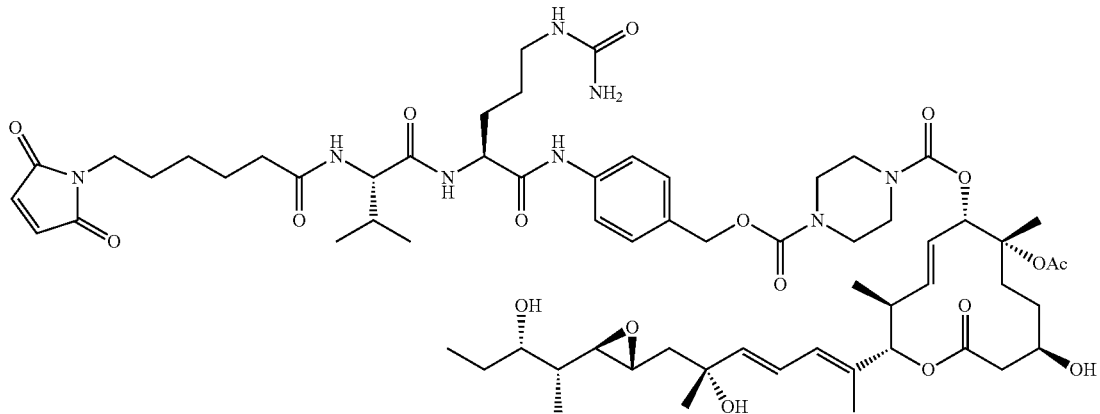 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]
Chemical Formula: $C_{64}H_{94}N_8O_{18}$
Exact Mass: 1262.67
Molecular Weight: 1263.49
ADL1-D4
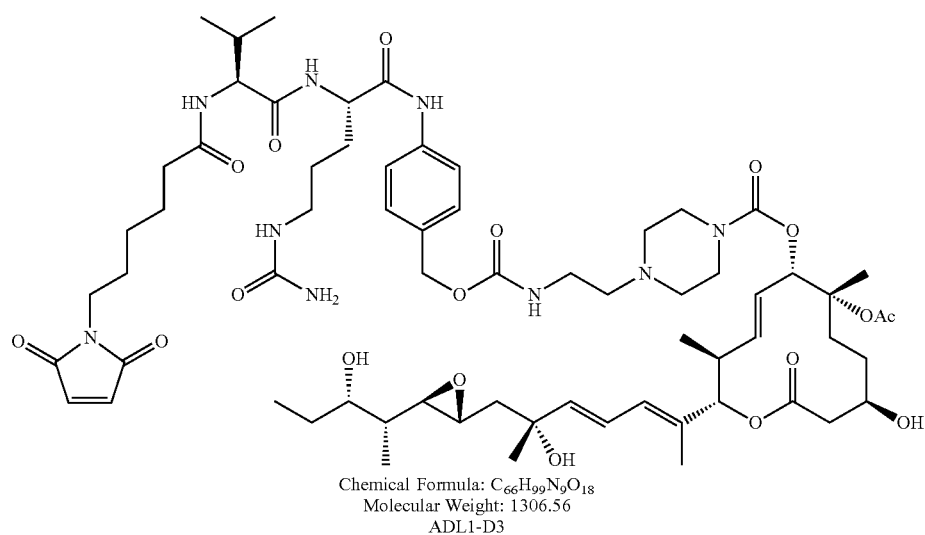
Chemical Formula: $C_{66}H_{99}N_9O_{18}$
Molecular Weight: 1306.56
ADL1-D3
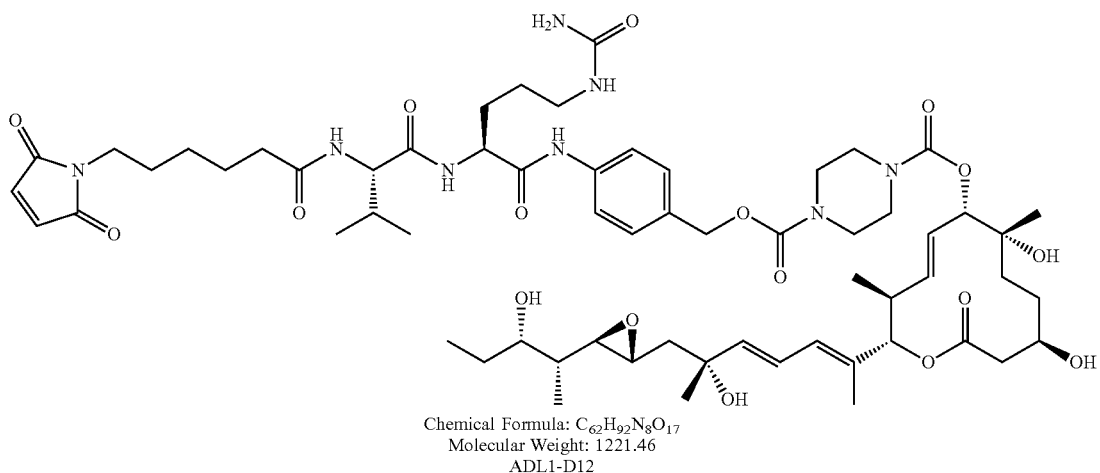
Chemical Formula: $C_{62}H_{92}N_8O_{17}$
Molecular Weight: 1221.46
ADL1-D12

TABLE 9-continued
Structures of exemplary conjugatable linker-payload (L-D) compounds
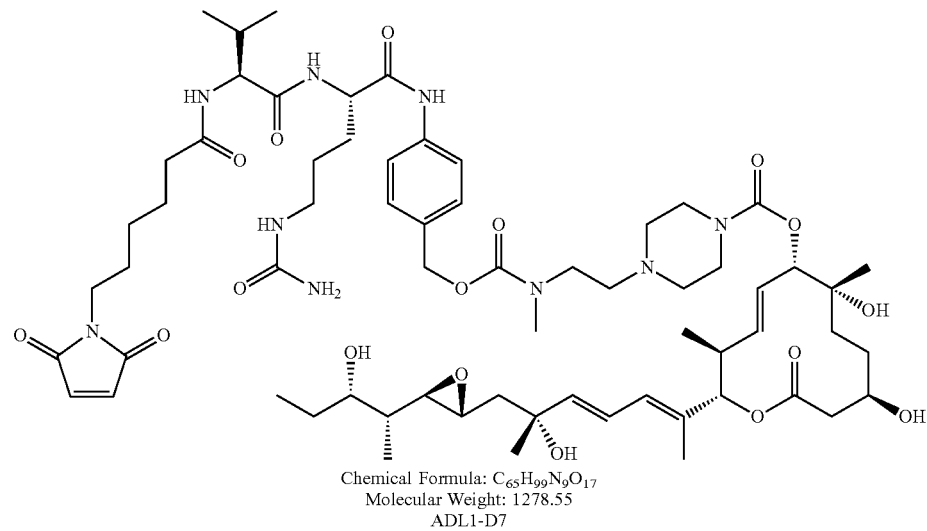
Chemical Formula: C$_{65}$H$_{99}$N$_{9}$O$_{17}$
Molecular Weight: 1278.55
ADL1-D7
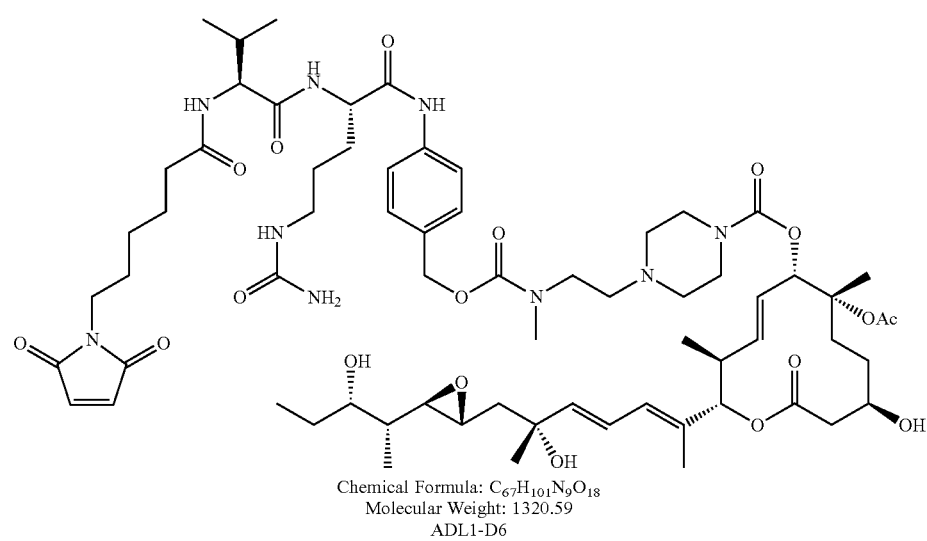
Chemical Formula: C$_{67}$H$_{101}$N$_{9}$O$_{18}$
Molecular Weight: 1320.59
ADL1-D6
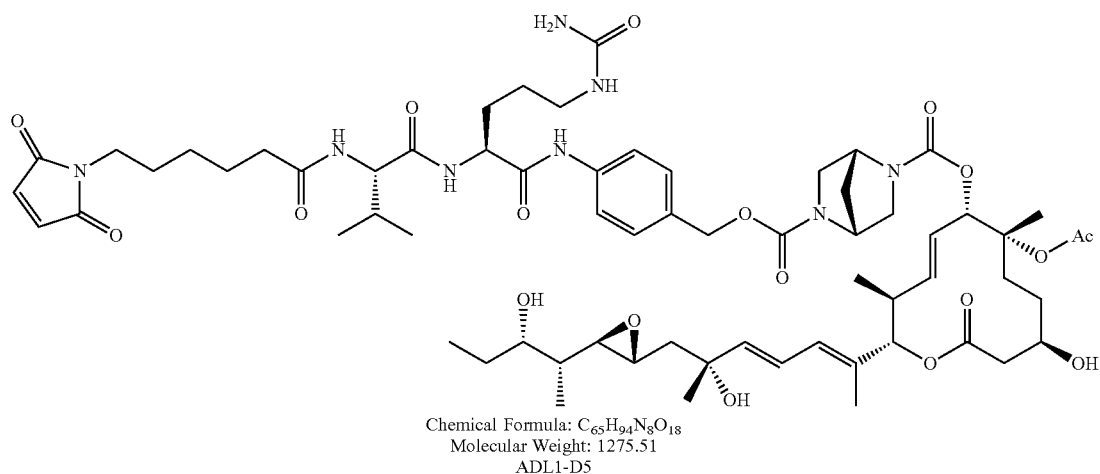
Chemical Formula: C$_{65}$H$_{94}$N$_{8}$O$_{18}$
Molecular Weight: 1275.51
ADL1-D5

TABLE 9-continued
Structures of exemplary conjugatable linker-payload (L-D) compounds
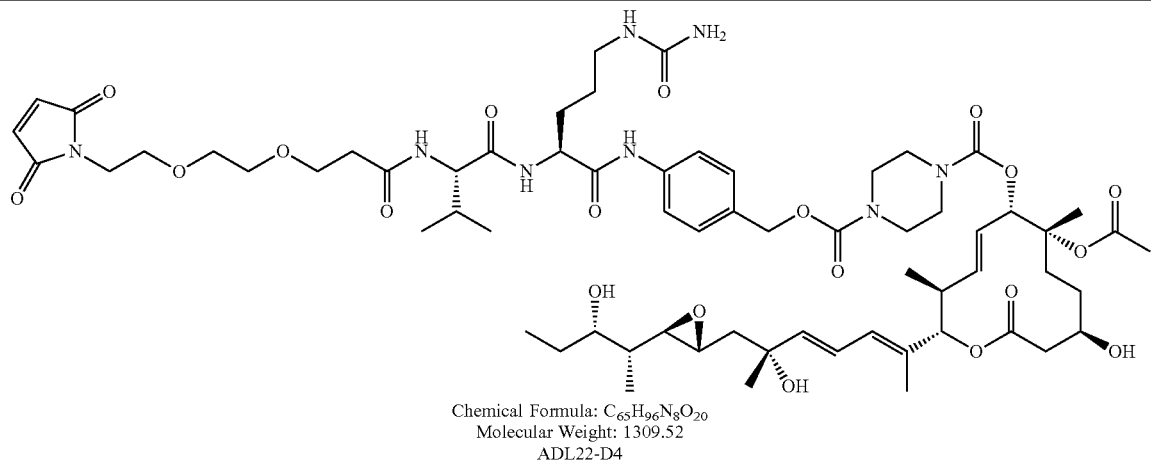
Chemical Formula: $C_{65}H_{96}N_8O_{20}$
Molecular Weight: 1309.52
ADL22-D4
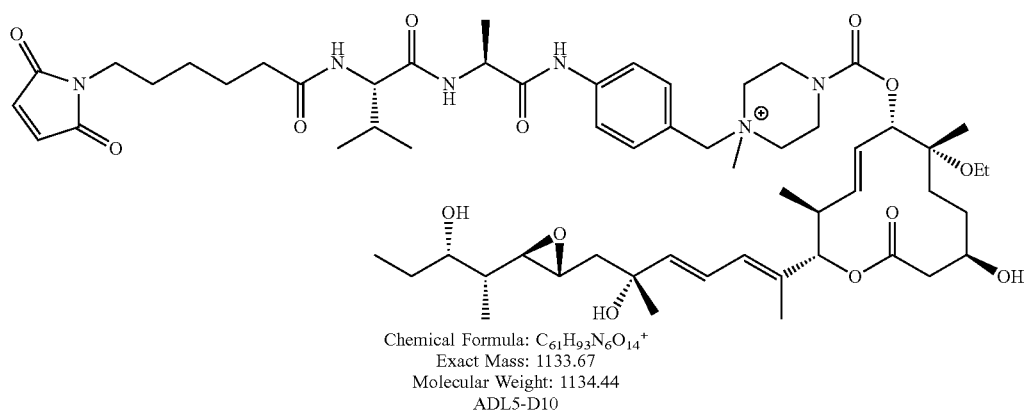
Chemical Formula: $C_{61}H_{93}N_6O_{14}^+$
Exact Mass: 1133.67
Molecular Weight: 1134.44
ADL5-D10
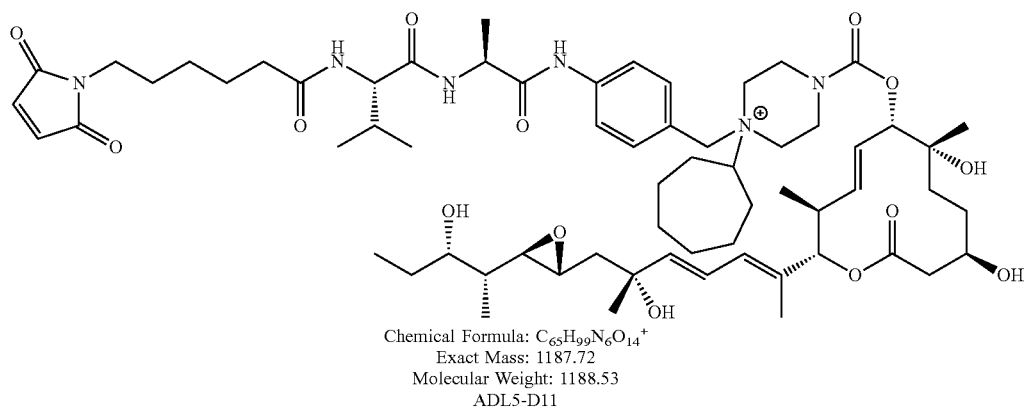
Chemical Formula: $C_{65}H_{99}N_6O_{14}^+$
Exact Mass: 1187.72
Molecular Weight: 1188.53
ADL5-D11
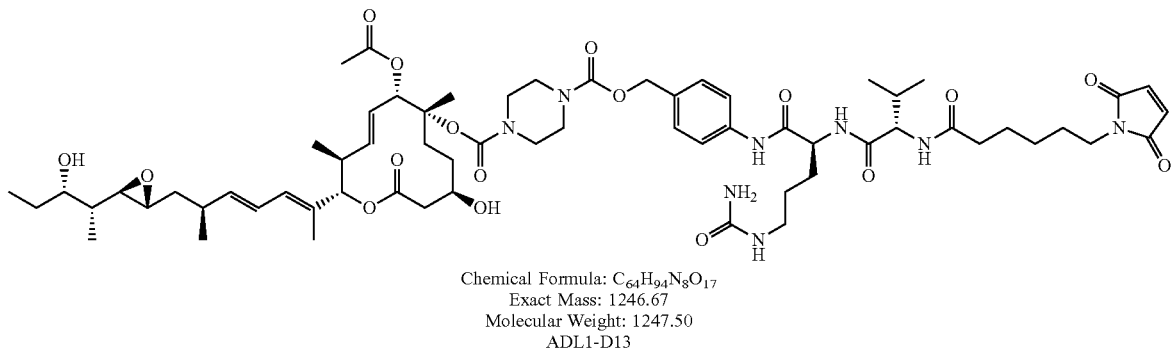
Chemical Formula: $C_{64}H_{94}N_8O_{17}$
Exact Mass: 1246.67
Molecular Weight: 1247.50
ADL1-D13

TABLE 9-continued
Structures of exemplary conjugatable linker-payload (L-D) compounds
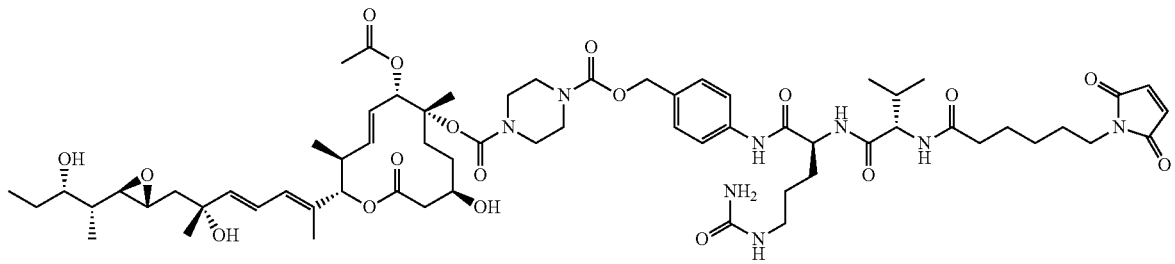 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)[C@@H](OC(C)=O)/C=C/[C@@H]1C]
ADL1-110978
Chemical Formula: $C_{64}H_{94}N_8O_{18}$
Exact Mass: 1262.67
Molecular Weight: 1263.49
ADL1-D8
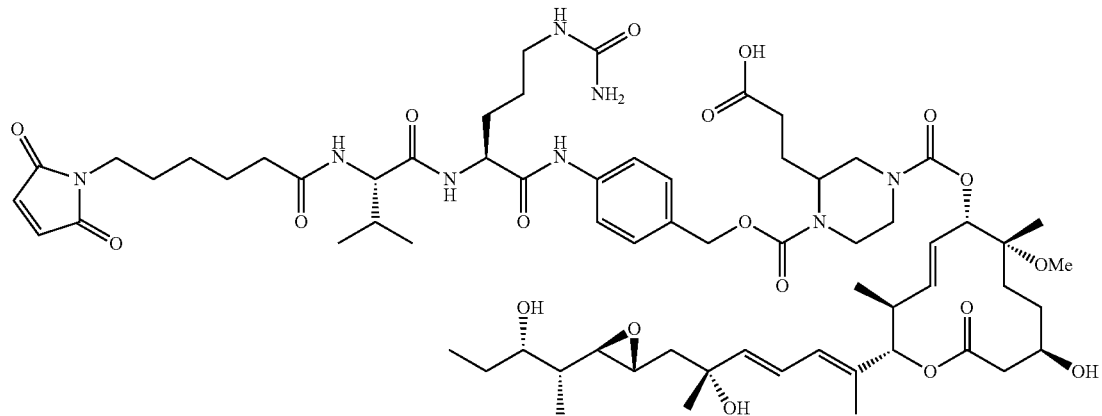 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)C(CCC(=O)O)C2)/C=C/[C@@H]1C]
Chemical Formula: $C_{66}H_{98}N_8O_{19}$
Exact Mass: 1306.69
Molecular Weight: 1307.55
ADL1-D22
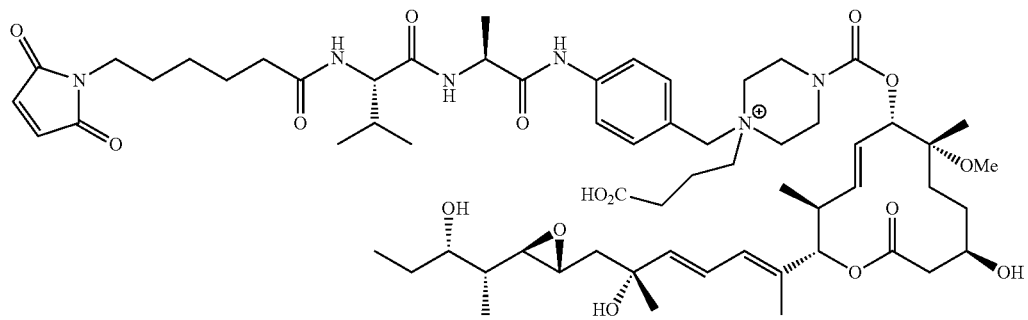 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CC[N+](CCCC(=O)O)(Cc3ccc(NC(=O)[C@H](C)NC(=O)[C@@H](NC(=O)CCCCCN4C(=O)C=CC4=O)C(C)C)cc3)CC2)/C=C/[C@@H]1C]
Chemical Formula: $C_{63}H_{95}N_6O_{16}^+$
Exact Mass: 1191.68
Molecular Weight: 1192.48
ADL5-D25

TABLE 9-continued
Structures of exemplary conjugatable linker-payload (L-D) compounds
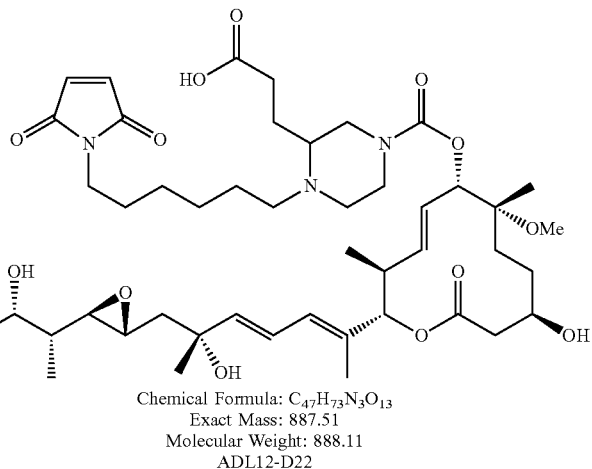
Chemical Formula: $C_{47}H_{73}N_3O_{13}$
Exact Mass: 887.51
Molecular Weight: 888.11
ADL12-D22
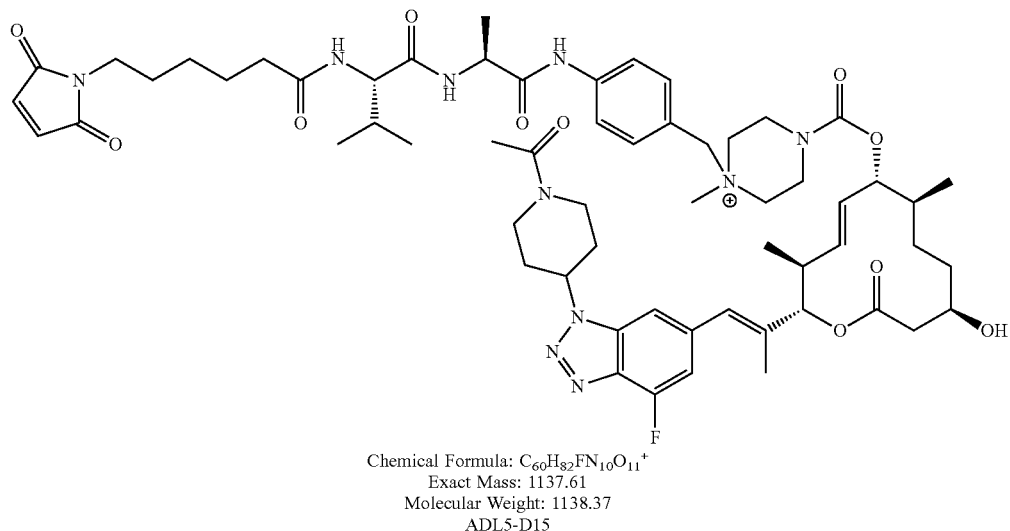
Chemical Formula: $C_{60}H_{82}FN_{10}O_{11}^+$
Exact Mass: 1137.61
Molecular Weight: 1138.37
ADL5-D15
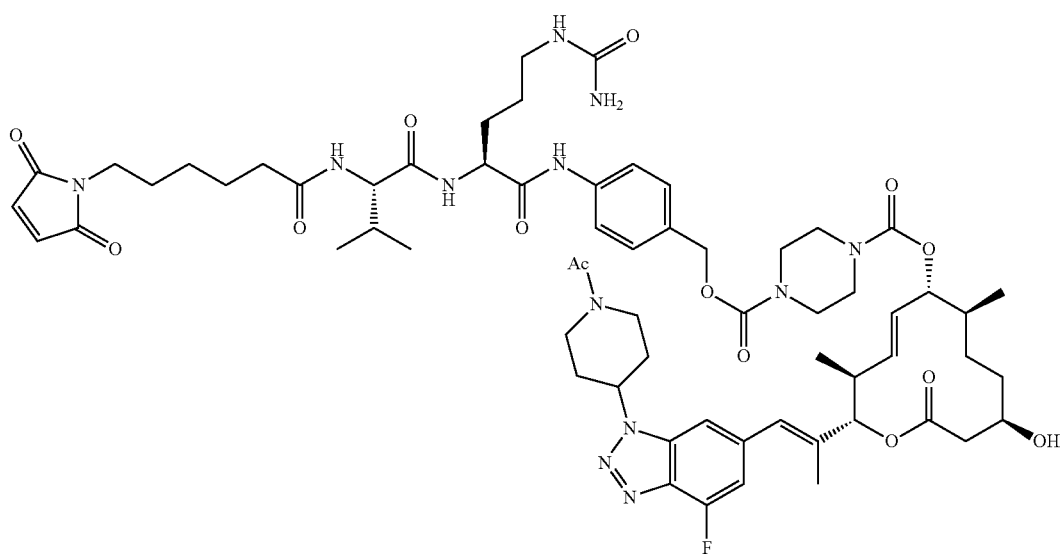 [SMILES: CC(=O)N1CCC(n2nnc3c(F)cc(/C=C(\C)[C@H]4OC(=O)C[C@H](O)CC[C@H](C)[C@@H](OC(=O)N5CCN(C(=O)OCc6ccc(NC(=O)[C@H](CCCNC(N)=O)NC(=O)[C@@H](NC(=O)CCCCCN7C(=O)C=CC7=O)C(C)C)cc6)CC5)/C=C/[C@@H]4C)cc32)CC1]
Chemical Formula: $C_{63}H_{85}FN_{12}O_{14}$
Exact Mass: 1252.63
Molecular Weight: 1253.44
ADL1-D14

TABLE 9-continued
Structures of exemplary conjugatable linker-payload (L-D) compounds
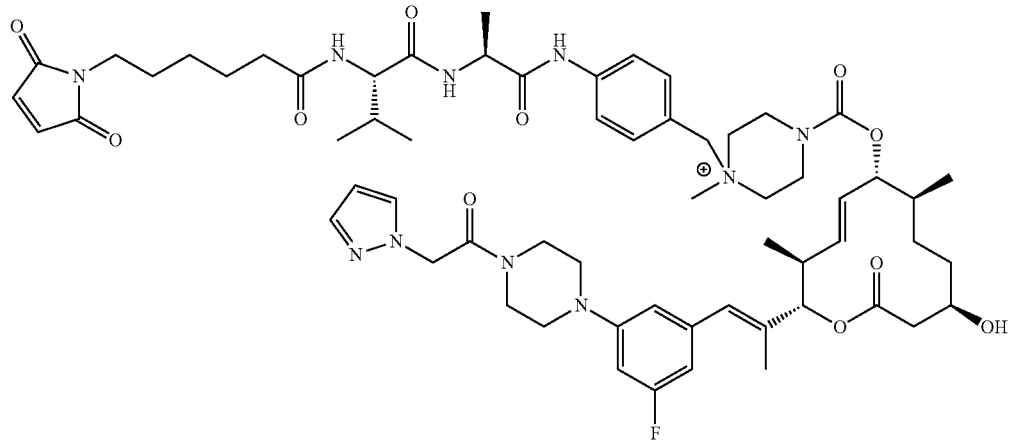 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]
Chemical Formula: $C_{62}H_{84}FN_{10}O_{11}{}^{+}$
Exact Mass: 1163.63
Molecular Weight: 1164.41
ADL5-D26
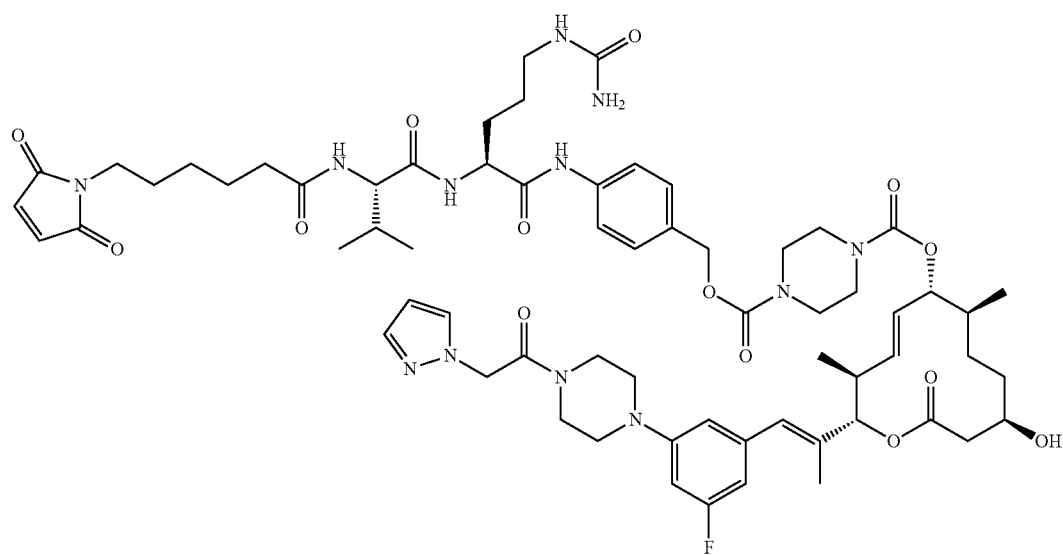 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]
Chemical Formula: $C_{65}H_{87}FN_{12}O_{14}$
Exact Mass: 1278.64
Molecular Weight: 1279.48
ADL1-D16

TABLE 9-continued
Structures of exemplary conjugatable linker-payload (L-D) compounds
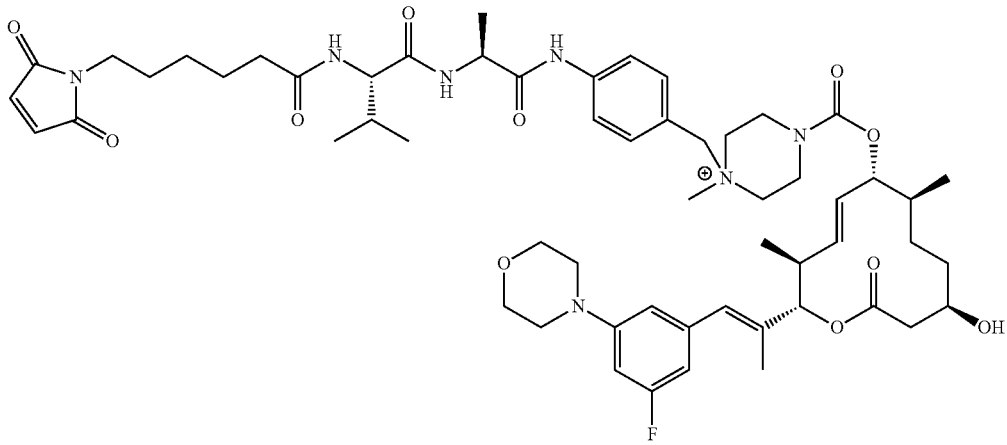 [SMILES: C/C(=C\c1cc(F)cc(N2CCOCC2)c1)[C@H]1OC(=O)C[C@H](O)CC[C@H](C)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]
Chemical Formula: $C_{57}H_{79}FN_7O_{11}^+$
Exact Mass: 1056.58
Molecular Weight: 1057.29
ADL5-D17
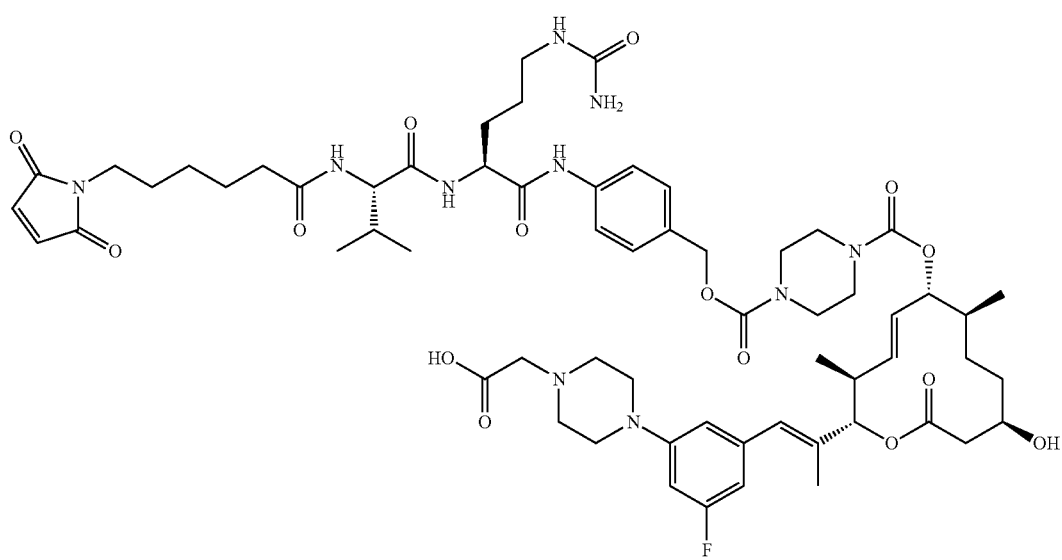 [SMILES: C/C(=C\c1cc(F)cc(N2CCN(CC(=O)O)CC2)c1)[C@H]1OC(=O)C[C@H](O)CC[C@H](C)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]
Chemical Formula: $C_{62}H_{85}FN_{10}O_{15}$
Exact Mass: 1228.62
Molecular Weight: 1229.42
ADL1-D33

TABLE 9-continued
Structures of exemplary conjugatable linker-payload (L-D) compounds
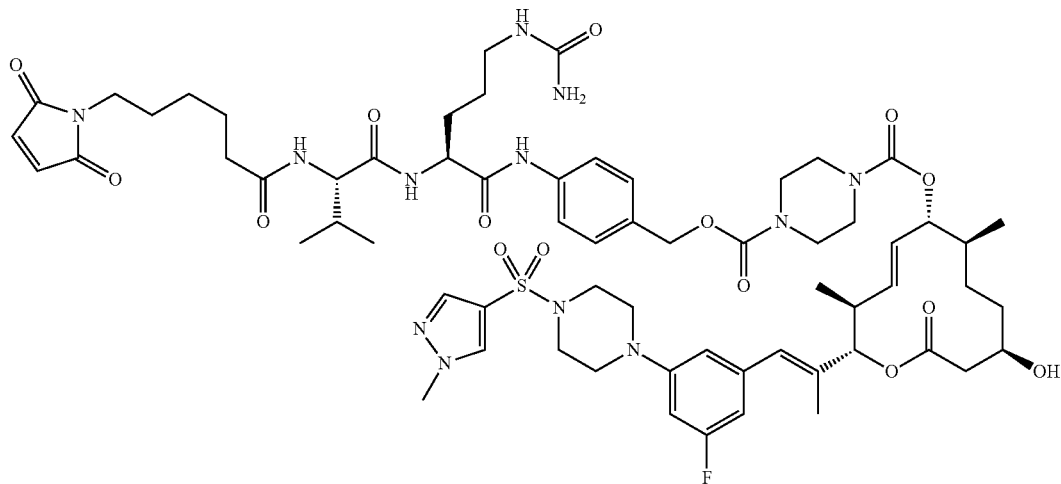 [SMILES: C/C(=C\c1cc(F)cc(N2CCN(S(=O)(=O)c3cnn(C)c3)CC2)c1)[C@H]1OC(=O)C[C@H](O)CC[C@H](C)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]
Chemical Formula: $C_{64}H_{87}FN_{12}O_{15}S$
Molecular Weight: 1315.53
ADL1-D28
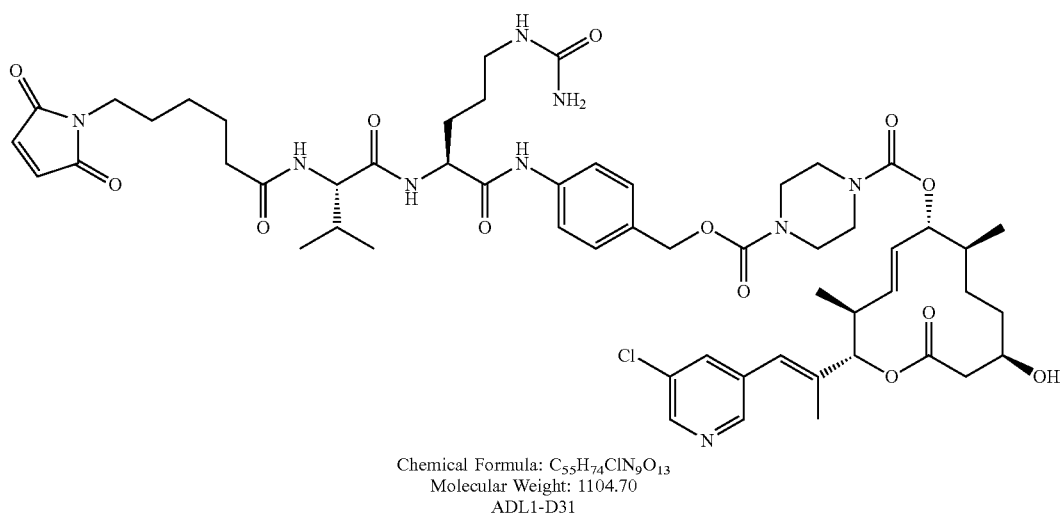
Chemical Formula: $C_{55}H_{74}ClN_9O_{13}$
Molecular Weight: 1104.70
ADL1-D31
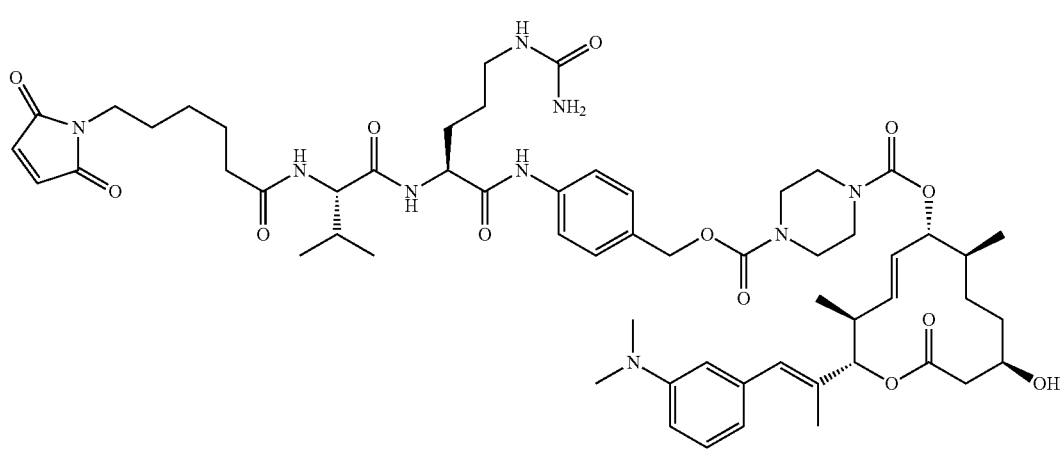 [SMILES: C/C(=C\c1cccc(N(C)C)c1)[C@H]1OC(=O)C[C@H](O)CC[C@H](C)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]
Chemical Formula: $C_{58}H_{81}N_9O_{13}$
Molecular Weight: 1112.34
ADL1-D29

TABLE 9-continued
Structures of exemplary conjugatable linker-payload (L-D) compounds
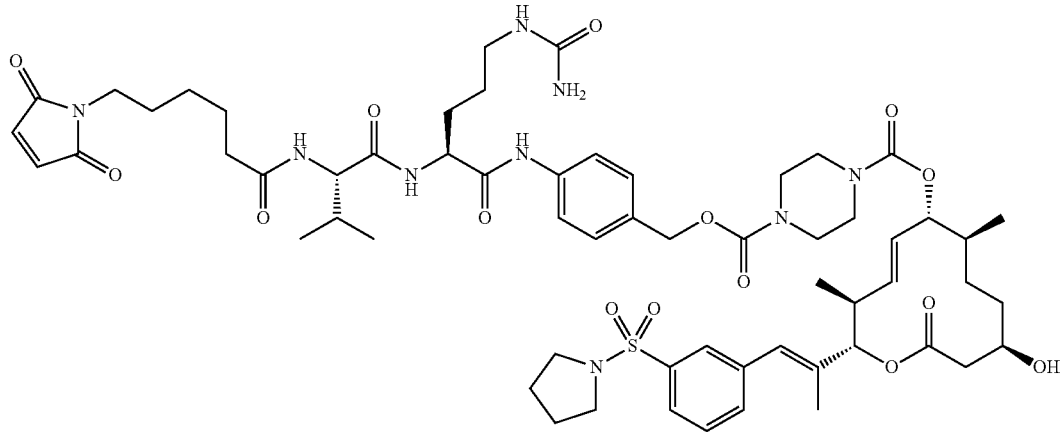 [SMILES: C/C(=C\c1cccc(S(=O)(=O)N2CCCC2)c1)[C@H]1OC(=O)C[C@H](O)CC[C@H](C)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]
Chemical Formula: $C_{60}H_{83}N_9O_{15}S$
Molecular Weight: 1202.43
ADL1-D35
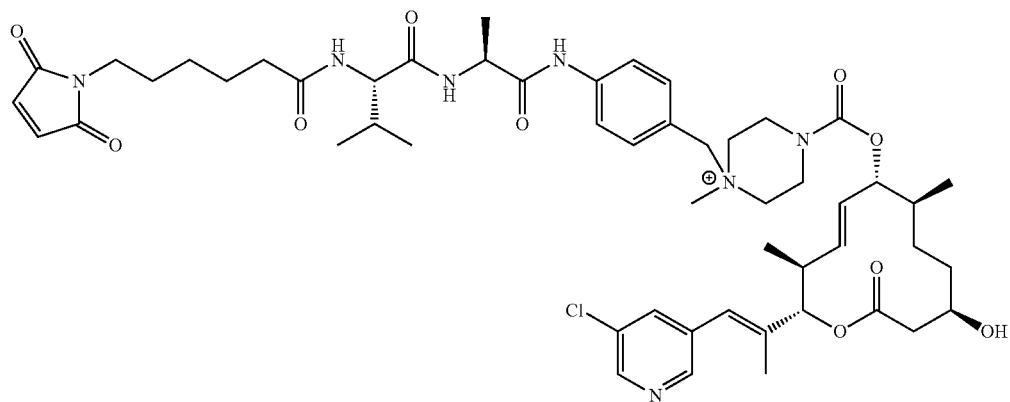 [SMILES: C/C(=C\c1cncc(Cl)c1)[C@H]1OC(=O)C[C@H](O)CC[C@H](C)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]
Chemical Formula: $C_{52}H_{71}ClN_7O_{10}^+$
Molecular Weight: 989.63
ADL5-D32
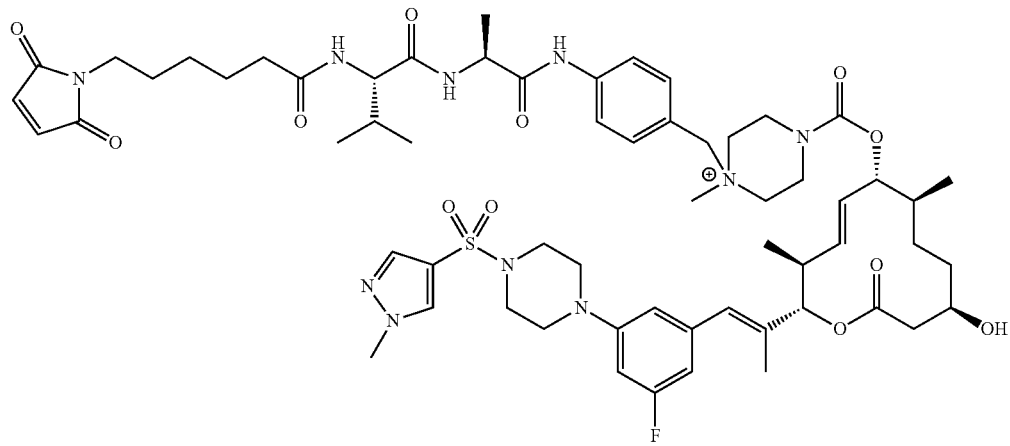 [SMILES: C/C(=C\c1cc(F)cc(N2CCN(S(=O)(=O)c3cnn(C)c3)CC2)c1)[C@H]1OC(=O)C[C@H](O)CC[C@H](C)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]
Chemical Formula: $C_{61}H_{84}FN_{10}O_{12}S^+$
Molecular Weight: 1200.46
ADL5-D27

TABLE 9-continued
Structures of exemplary conjugatable linker-payload (L-D) compounds
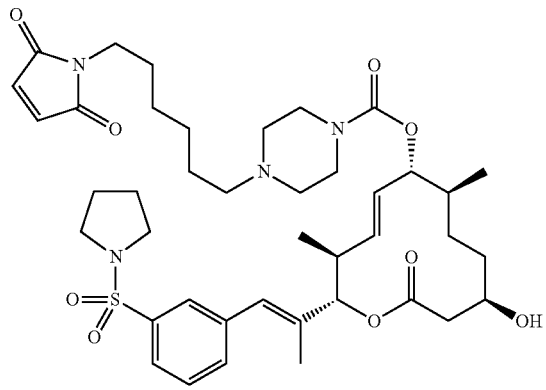 [SMILES: C/C(=C\c1cccc(S(=O)(=O)N2CCCC2)c1)[C@H]1OC(=O)C[C@H](O)CC[C@H](C)[C@@H](OC(=O)N2CCN(CCCCCCN3C(=O)C=CC3=O)CC2)/C=C/[C@@H]1C]
Chemical Formula: $C_{41}H_{58}N_4O_9S$
Molecular Weight: 782.99
ADL12-D35
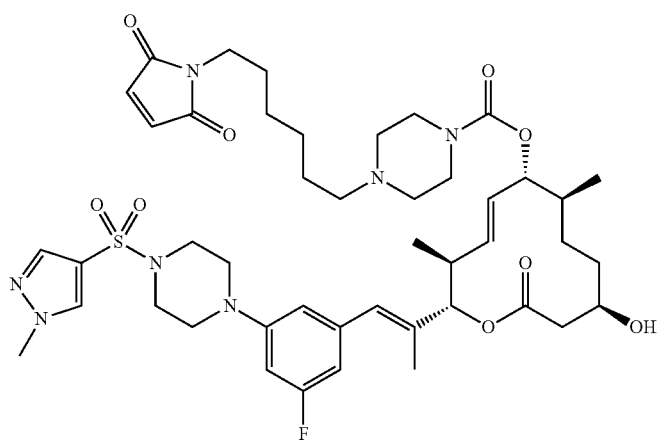 [SMILES: C/C(=C\c1cc(F)cc(N2CCN(S(=O)(=O)c3cnn(C)c3)CC2)c1)[C@H]1OC(=O)C[C@H](O)CC[C@H](C)[C@@H](OC(=O)N2CCN(CCCCCCN3C(=O)C=CC3=O)CC2)/C=C/[C@@H]1C]
Chemical Formula: $C_{45}H_{64}FN_7O_9S$
Molecular Weight: 898.11
ADL12-D28
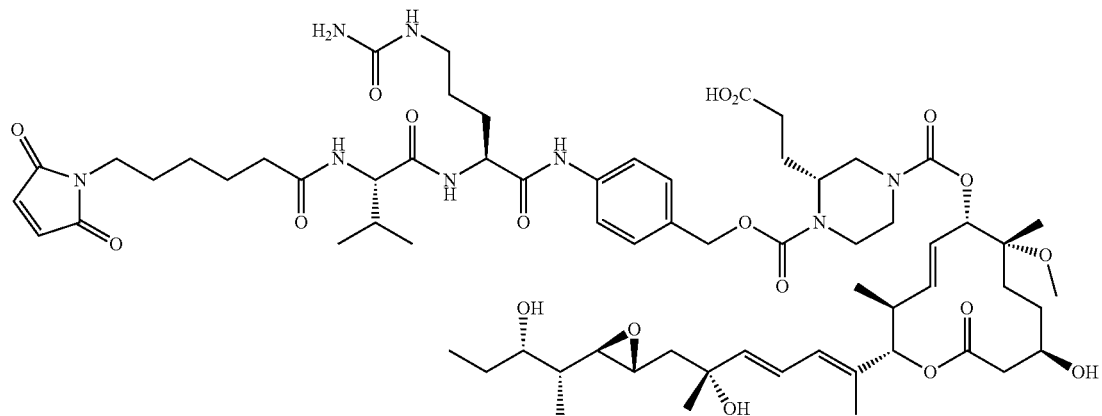 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)[C@H](CCC(=O)O)C2)/C=C/[C@@H]1C]
Chemical Formula: $C_{66}H_{98}N_8O_{19}$
Molecular Weight: 1307.55
ADL1-D23

TABLE 9-continued
Structures of exemplary conjugatable linker-payload (L-D) compounds
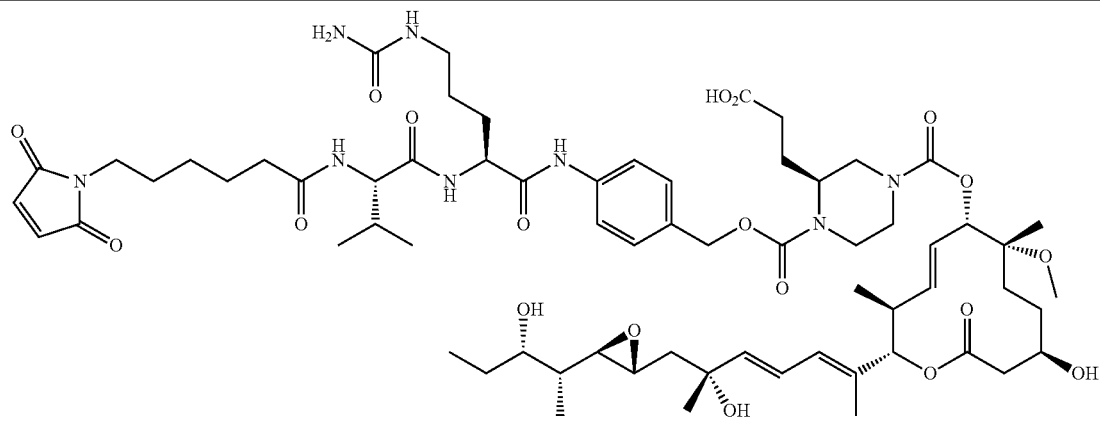
Chemical Formula: $C_{66}H_{98}N_8O_{19}$
Molecular Weight: 1307.55
ADL1-D24
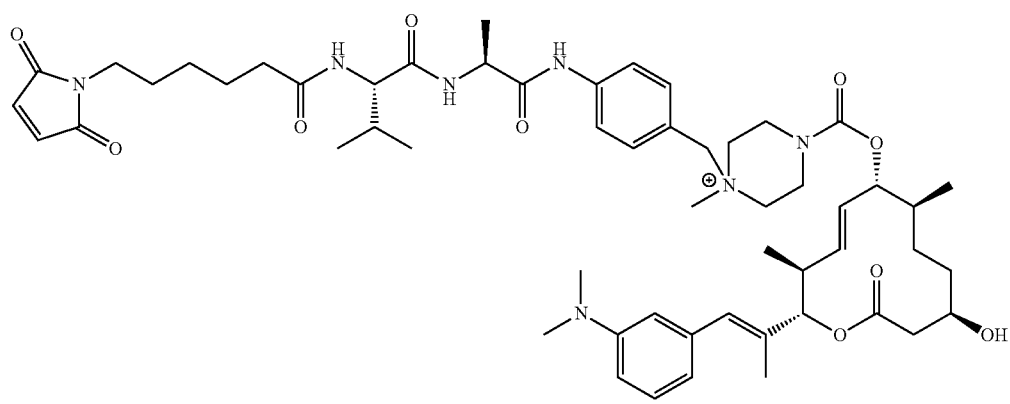 [SMILES: C/C(=C\c1cccc(N(C)C)c1)[C@H]1OC(=O)C[C@H](O)CC[C@H](C)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]
ADL5-D30
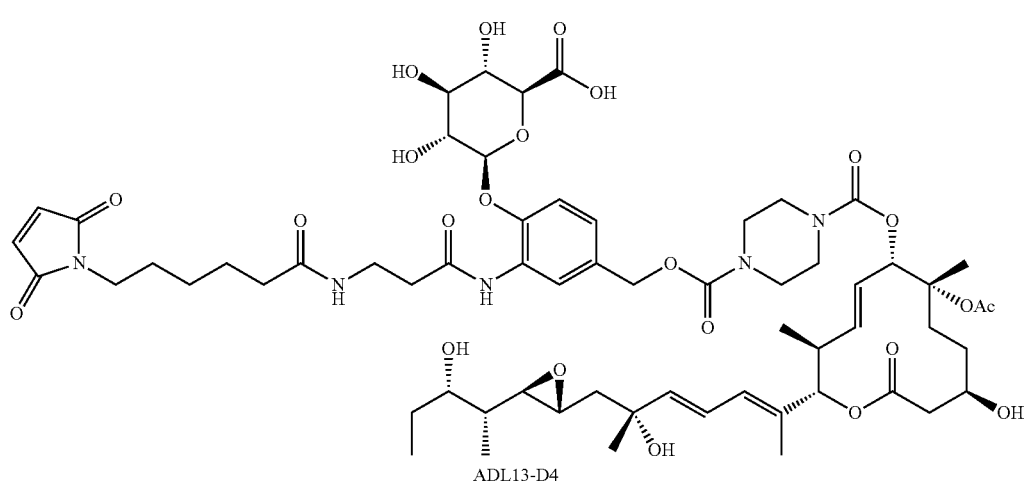
ADL13-D4
1.2 Preparation of Pladienolide-Based Payloads
1.2.1 Overview—General Procedure 1

Scheme 1
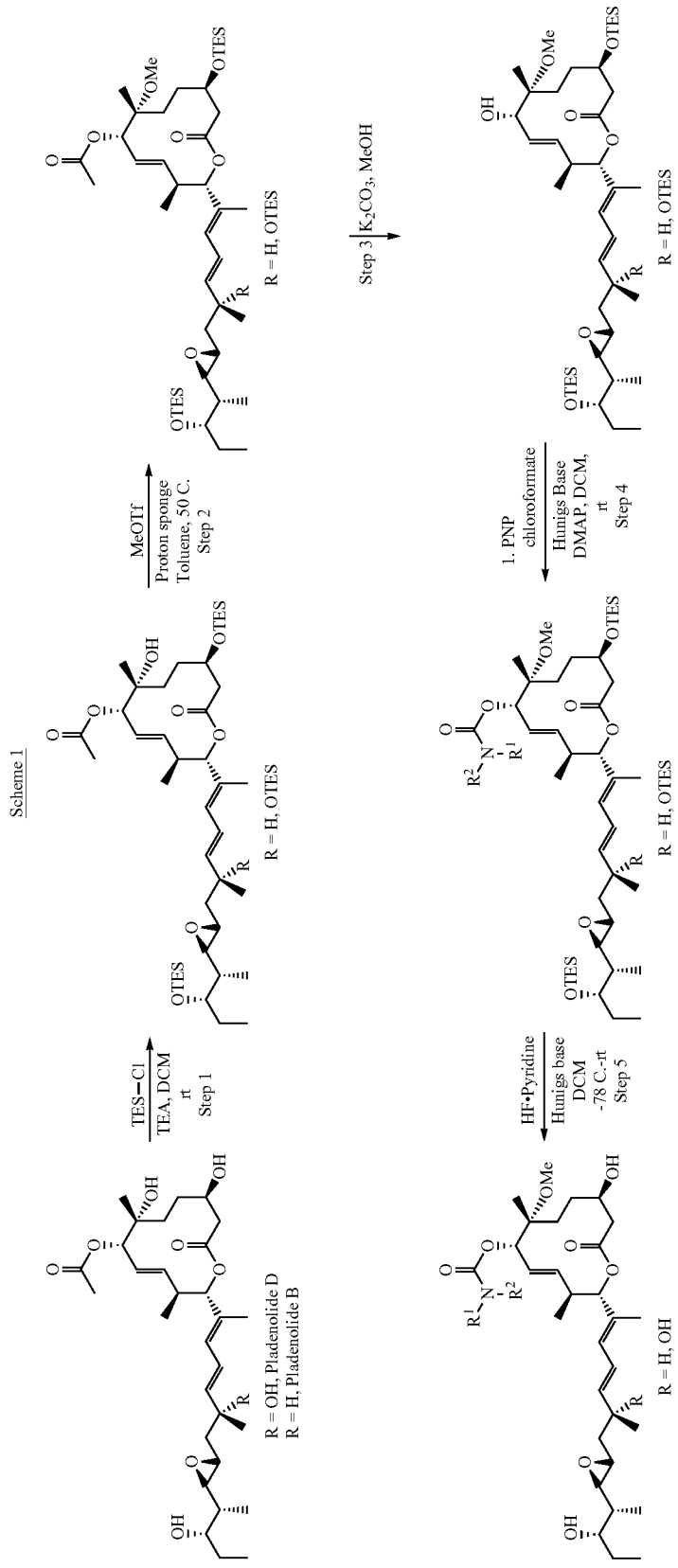

Step 1: (2S,3S,6S,7R,10R,E)-7,10-dihydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-3,7-dimethyl-12-oxooxacyclododec-4-en-6-yl acetate (1.7 g, 3.154 mmol), triethylamine (4.40 mL, 31.536 mmol), 1,2-dichloroethane (31.5 mL, 3.154 mmol) were combined and stirred at RT. Chlorotriethylsilane (2.1 mL, 12.615 mmol) was added and stirred overnight. Brine was poured into the reaction mix and stirred for 30 min and the organic layer separated. The aqueous layer was back extracted with DCM (3×). The organic layers were combined, dried (an. Na$_2$SO$_4$), concentrated to dryness, and chromatographed to afford (2S,3S,6S,7R,10R,E)-7-hydroxy-3,7-dimethyl-2-((R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl acetate (1.274 g, 1.423 mmol, 45.1% yield).

$^1$H-NMR (400 MHz, DMSO-d6): δ ppm 0.51-0.64 (m, 18H) 0.74-0.84 (m, 9H) 0.90-0.97 (m, 26H) 1.04 (s, 3H) 1.18 (s, 4H) 1.37 (s, 3H) 1.41-1.57 (m, 4H) 1.69 (s, 3H) 1.84-1.93 (m, 1H) 2.00-2.05 (m, 3H) 2.24-2.35 (m, 1H) 2.38-2.45 (m, 1H) 2.72-2.80 (m, 1H) 3.28-3.30 (m, 1H) 3.62-3.70 (m, 1H) 3.80-3.90 (m, 1H) 4.56 (s, 1H) 4.81-4.93 (m, 2H) 5.41-5.52 (m, 1H) 5.63-5.73 (m, 1H) 5.77-5.87 (m, 1H) 6.01-6.12 (m, 1H) 6.42 (dd, J=15.12, 11.11 Hz, 1H).

Step 2: To a solution of (2S,3S,6S,7R,10R,E)-7-hydroxy-3,7-dimethyl-2-((R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl acetate (0.7 g, 0.782 mmol) in toluene (4.16 mL, 39.085 mmol) was added 1,8-Naphthalenediamine, N,N,N',N'-tetramethyl-(1.173 g, 5.472 mmol), followed by methyl trifluoromethanesulfonate (0.354 mL, 3.127 mmol) at 0° C. The reaction mixture was then warmed up to 50° C. and heated for 3 hours. Solvent was evaporated. Purification by column chromatography afforded (2S,3S,6S,7R,10R,E)-7-methoxy-3,7-dimethyl-2-((R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl acetate (467 mg, 0.513 mmol, 65.7% yield) as a colorless oil.

$^1$H-NMR (400 MHz, MeOH-d4): δ ppm 0.62-0.70 (m, 18H) 0.83-0.95 (m, 13H) 0.99-1.07 (m, 27H) 1.22 (s, 3H) 1.24-1.36 (m, 2H) 1.28-1.28 (m, 1H) 1.45 (s, 3H) 1.47-1.65 (m, 8H) 1.78 (d, J=0.88 Hz, 3H) 1.91-2.00 (m, 1H) 2.07 (s, 3H) 2.37-2.45 (m, 1H) 2.51-2.68, (m, 3H) 2.88-2.92 (m, 1H) 3.20-3.24 (m, 1H) 3.35 (s, 3H) 3.74-3.82 (m, 1H) 3.93-4.02 (m, 1H) 4.94-4.99 (m, 1H) 5.08-5.14 (m, 1H), 5.53-5.64 (m, 1H) 5.70-5.79 (m, 1H) 5.81-5.88 (m, 1H) 6.12-6.18 (m, 1H) 6.47-6.58 (m, 1H).

Step 3: (2S,3S,6S,7R,10R,E)-7-hydroxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl acetate (500 mg, 0.558 mmol) was dissolved in MeOH (6009 μL, 148.524 mmol) and potassium carbonate (232 mg, 1.675 mmol) was added. The reaction mixture was stirred at RT for 1 hour and showed the reaction complete. The reaction mixture was diluted with water and extracted with EtOAc (3×). The combined organics were washed with brine, dried over sodium sulfate, filtered, and concentrated. Purification by column chromatography afforded (4R,7R,8S,11S,12S,E)-7,8-dihydroxy-7,11-dimethyl-12-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-4-((triethylsilyl)oxy)oxacyclododec-9-en-2-one (305 mg, 0.357 mmol, 64.0% yield).

$^1$H-NMR (400 MHz, MeOH-d4): δ ppm 0.61-0.72 (m, 18H) 0.82-0.92 (m, 7H) 0.92-1.06 (m, 30H) 1.19-1.40 (m, 7H) 1.42-1.66 (m, 8H) 1.51-1.52 (m, 1H) 1.75-1.81 (m, 3H) 1.91-2.01 (m, 1H) 2.34-2.45 (m, 1H) 2.51-2.61 (m, 2H) 2.61-2.69 (m, 1H) 2.86-2.94 (m, 1H) 3.67-3.73 (m, 1H) 3.73-3.80 (m, 1H) 3.89-3.96 (m, 1H) 4.08-4.17 (m, 1H) 4.93-4.99 (m, 1H) 5.36-5.47 (m, 1H) 5.67-5.78 (m, 1H) 5.80-5.88 (m, 1H) 6.10-6.19 (m, 1H) 6.47-6.58 (m, 1H).

Step 4: (4R,7R,8S,11S,12S,E)-8-hydroxy-7-methoxy-7,11-dimethyl-12-((R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-4-((triethylsilyl)oxy)oxacyclododec-9-en-2-one (0.386 g, 0.445 mmol), DCM (0.1 M), DMAP (1.0 equiv.), Hunig's base (5.0 equiv.), 4-Nitrophenyl chloroformate (1.8 equiv.) were combined and stirred overnight. The reaction mixture was then extracted with 1N NaOH. The organic layer was dried (an. Na$_2$SO$_4$) and concentrated to dryness. The residue was mixed with DCM (0.1 M), Hunig's base (5.0 equiv.), amine (2.0 equiv.), which were combined and stirred for 1 hour. The reaction mixture was concentrated and chromatographed to afford the triTES-Pladienolide carbamate.

Step 5: triTES-Pladienolide carbamate (1 equiv.), DCM (0.04 M), and DIPEA (191 equiv.) were combined and cooled to −78° C. Hydrogen fluoride-pyridine (6.2 equiv.) was added and the reaction was allowed to warm to RT and stirred overnight. The reaction mixture was cooled in an ice bath, then sat. NaHCO$_3$ was added, stirred, and extracted with DCM. The organic layers were combined, dried over an. Na$_2$SO$_4$, concentrated, and chromatographed to afford the pladienolide carbamate.

1.2.1.1 D1

General procedure 1 (outlined in section 1.2.1) was employed to synthesize D1.

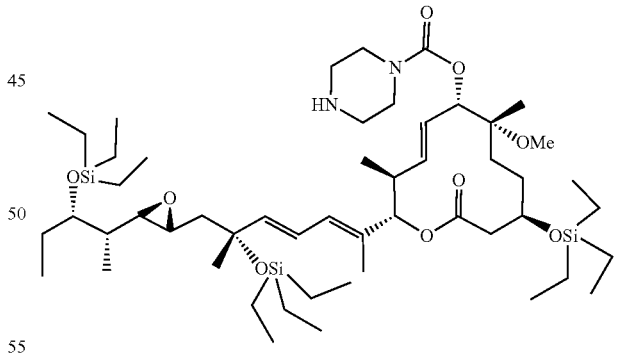

(2S,3S,6S,7R,10R,E)-7-methoxy-3,7-dimethyl-2-((R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl piperazine-1-carboxylate (240 mg, 0.245 mmol, 55.1% yield). LC/MS (ESI, m/z), 980.4 [M+H]$^+$.

$^1$H-NMR (400 MHz, CDCl$_3$-d): δ ppm 0.56-0.66 (m, 18H) 0.78-0.91 (m, 9H) 0.96 (t, J=7.91 Hz, 27H) 1.18-1.22 (m, 3H) 1.23-1.28 (m, 1H) 1.37-1.41 (m, 3H) 1.41-1.63 (m, 7H) 1.69-1.74 (m, 3H) 1.89 (dd, J=13.87, 4.96 Hz, 1H) 2.33-2.62 (m, 4H) 2.78-2.89 (m, 5H) 3.35 (s, 3H) 3.43-3.52

(m, 4H) 3.73 (td, J=6.40, 3.51 Hz, 1H) 3.86 (br dd, J=7.84, 3.95 Hz, 1H) 4.94-5.13 (m, 2H) 5.58-5.76 (m, 3H) 6.12, (br d, J=0.75 Hz, 1H) 6.41 (dd, J=15.06, 11.04 Hz, 1H).

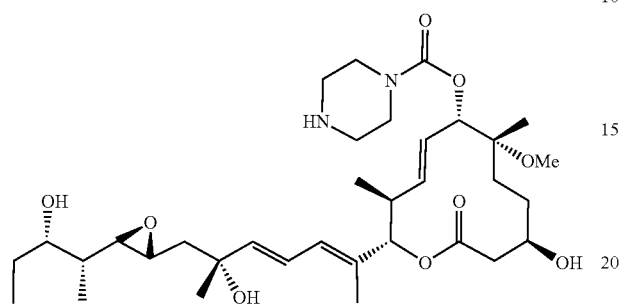

D1

(2S,3S,6S,7R,10R,E)-7-methoxy-3,7-dimethyl-2-((R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl piperazine-1-carboxylate (240 mg, 0.245 mmol, 55.1% yield). LC/MS (ESI, m/z), 637.6 [M+H]⁺.

¹H-NMR (400 MHz, MeOH-d4): δ ppm 0.83-1.01 (m, 10H) 1.23 (s, 3H) 1.25-1.32 (m, 1H) 1.35 (s, 3H) 1.40-1.61 (m, 6H) 1.61-1.71 (m, 2H) 1.79 (d, J=0.75 Hz, 3H) 1.84-1.93 (m, 1H) 2.45-2.63 (m, 3H) 2.63-2.72 (m, 1H) 2.77-2.85 (m, 4H) 2.86-2.94 (m, 1H) 3.33-3.37 (m, 3H) 3.40-3.57 (m, 5H) 3.77-3.89 (m, 1H) 4.38-4.42 (m, 1H) 5.01-5.12 (m, 2H) 5.52-5.65 (m, 1H) 5.69-5.80 (m, 1H) 5.84-5.92 (m, 1H) 6.09-6.18 (m, 1H) 6.49-6.60 (m, 1H).

1.2.1.2 D2

General procedure 1 (outlined in section 1.2.1) was employed to synthesize D2.

(2S,3S,6S,7R,10R,E)-7-methoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl 4-methylpiperazine-1-carboxylate (413 mg, 0.416 mmol, 90% yield). LC/MS (ESI, m/z), 994 [M+H]⁺.

¹H-NMR (400 MHz, MeOH-d4): δ ppm 0.61-0.71 (m, 18H) 0.83-0.94 (m, 9H) 0.98-1.07 (m, 28H) 1.23 (s, 3H) 1.41-1.48 (m, 3H) 1.48-1.65 (m, 7H) 1.72-1.81 (m, 3H) 1.93-1.99 (m, 1H) 2.03 (s, 3H) 2.32 (s, 3H) 2.38-2.48 (m, 5H) 2.52-2.67 (m, 3H) 2.87-2.93 (m, 1H) 3.47-3.61 (m, 4H) 3.72-3.81 (m, 1H) 3.96-4.04 (m, 1H) 4.53-4.62 (m, 1H) 4.93-5.07 (m, 2H) 5.51-5.64 (m, 1H) 5.69-5.79 (m, 1H) 5.81-5.92 (m, 1H) 6.09-6.21 (m, 1H) 6.46-6.60 (m, 1H).

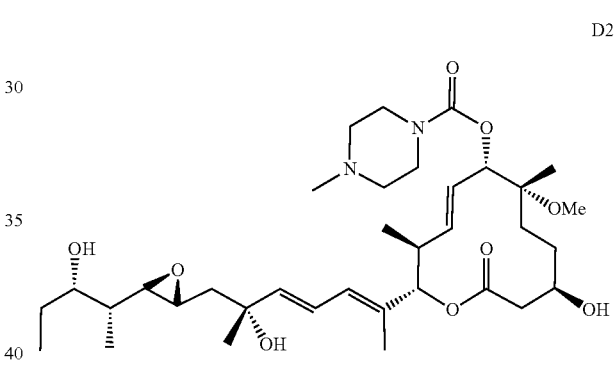

D2

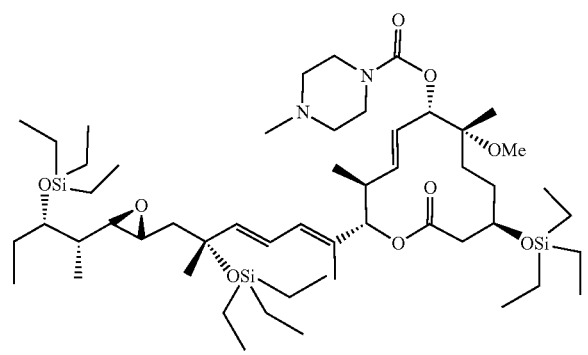

(2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-methylpiperazine-1-carboxylate (37.8 mg, 0.058 mmol, 24.05% yield). LC/MS (ESI, m/z), 651.69 [M+H]*.

¹H-NMR (400 MHz, DMSO-d6): δ ppm 0.76-0.89 (m, 9H) 1.10 (s, 3H) 1.20-1.26 (m, 3H) 1.30-1.42 (m, 4H) 1.42-1.55 (m, 2H) 1.66-1.75 (m, 3H) 1.75-1.82 (m, 1H) 2.13-2.21 (m, 3H) 2.25 (br s, 4H) 2.31-2.41 (m, 2H) 2.54-2.60 (m, 2H) 2.72-2.82 (m, 1H) 3.22 (s, 3H) 3.36-3.40 (m, 3H) 3.66-3.76 (m, 3H) 4.36-4.46 (m, 1H) 4.53-4.60 (m, 1H) 4.78-4.85 (m, 1H) 4.86-4.96 (m, 2H) 5.36-5.50 (m, 1H) 5.60-5.74 (m, 1H) 5.80-5.92 (m, 1H) 6.02-6.11 (m, 1H) 6.34-6.46 (m, 1H).

1.3 Preparation of MC-Val-Cit-pABC Linker-Payloads 1.3.1 Overview—General Procedure 1

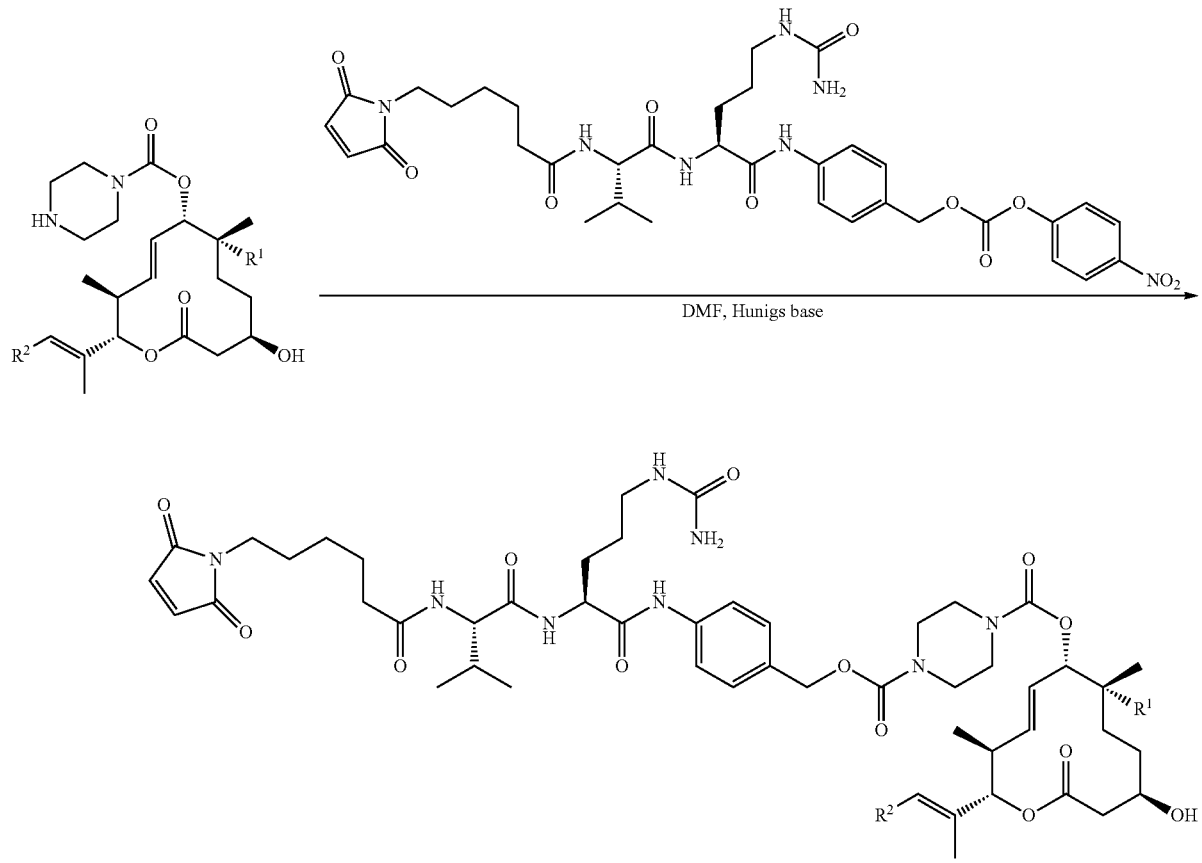

Scheme 2

Payload (1.0 equiv.), Hunig's base (3.0 equiv.), DMF (0.1 M), and 4-((S)-2-((S)-2-(6-(2,5-dioxo-2,5-dihydro-1H-pyrrol-1-yl)hexanamido)-5-ureidopentanamido)-3-methylbutanamido)benzyl (4-nitrophenyl) carbonate (1.2 equiv.) were combined and stirred at RT overnight. The reaction mixture was then concentrated and purified via column chromatography (MeOH in DCM) or reverse-phase HPLC to afford the product.

1.3.1.1 ADL1-D1

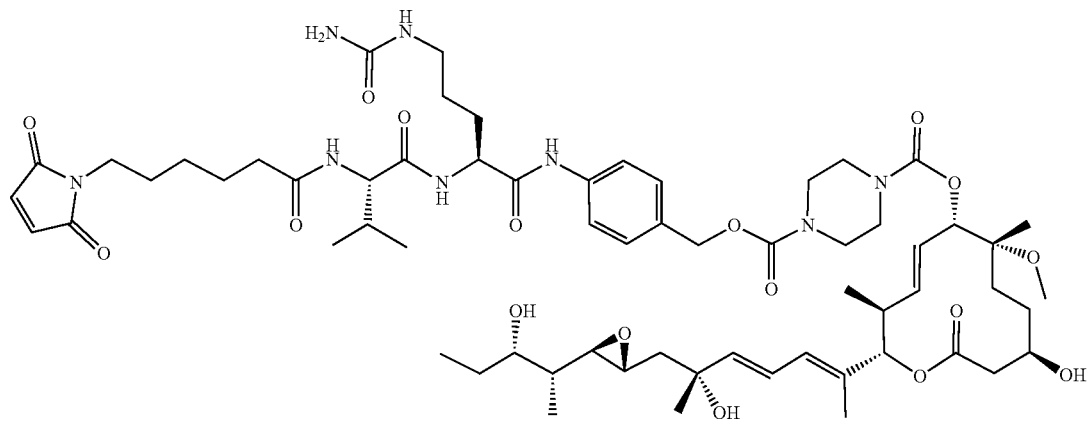 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]

Linker-Payload (ADL1-D1): General procedure 1 (outlined in section 1.3.1) was employed to synthesize 1-(4-((S)-2-((S)-2-((((9H-fluoren-9-yl)methoxy)carbonyl)amino)-3-methylbutanamido)-5-ureidopentanamido)benzyl) 4-((2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl) piperazine-1,4-dicarboxylate (50 mg, 0.040 mmol, 42% yield). LC/MS (ESI, m/z), 1258.5 [M+Na]+.

(2S,3S,6S,7R,10R,E)-10-hydroxy-2-((S,2E,4E)-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl piperazine-1-carboxylate (205 mg, 0.330 mmol, 77% yield). LC/MS (ESI, m/z), 621.6 [M+H]+.

¹H-NMR (400 MHz, MeOH-d4): δ ppm 0.88-0.99 (m, 9H) 1.10 (d, J=6.78 Hz, 3H) 1.24 (s, 4H) 1.42-1.69 (m, 8H) 1.77 (d, J=0.88 Hz, 3H) 2.43-2.63 (m, 4H) 2.64-2.70 (m, 1H) 2.71-2.82 (m, 5H) 3.34 (br s, 3H) 3.37 (s, 2H) 3.42-3.57 (m, 5H) 3.79-3.89 (m, 1H) 5.06 (s, 2H), 5.54-5.63 (m, 1H) 5.64-5.80 (m, 2H) 6.07-6.16 (m, 1H) 6.29-6.40 (m, 1H).

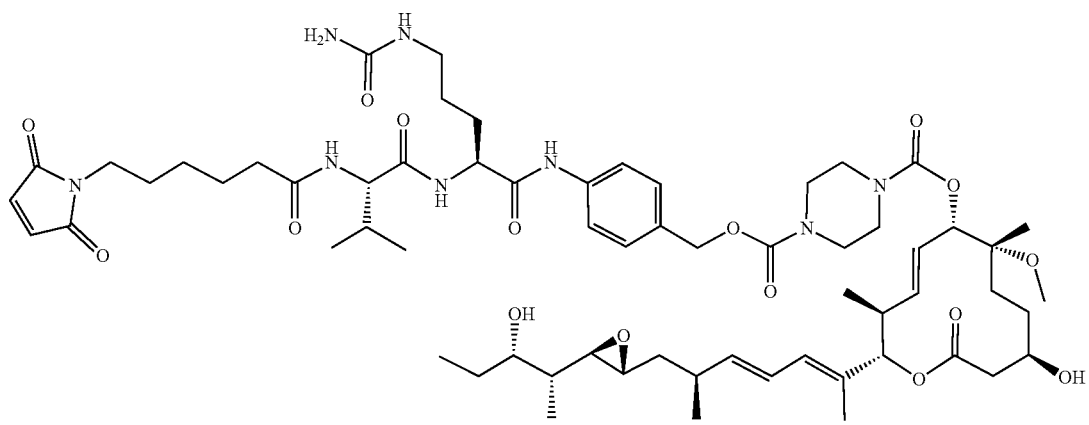

¹H-NMR (400 MHz, MeOH-d4): δ ppm 0.85-1.04 (m, 16H) 1.18-1.26 (m, 3H) 1.26-1.38 (m, 6H) 1.40-1.71 (m, 14H) 1.80 (s, 3H) 1.85-1.98 (m, 2H) 2.02-2.15 (m, 1H) 2.24-2.34 (m, 2H) 2.44-2.64 (m, 3H) 2.65-2.72 (m, 1H) 2.87-2.96 (m, 1H) 3.06-3.27 (m, 2H) 3.37 (s, 6H) 3.43-3.61 (m, 12H) 3.79-3.90 (m, 1H) 4.12-4.21 (m, 1H) 4.48-4.55 (m, 1H) 5.02-5.14 (m, 4H) 5.55-5.65 (m, 1H), 5.69-5.81 (m, 1H) 5.85-5.93 (m, 1H) 6.12-6.19 (m, 1H) 6.49-6.60 (m, 1H) 6.81 (s, 2H) 7.29-7.38 (m, 2H) 7.57-7.65 (m, 2H).

1.3.1.2 ADL1-D18

The payload D18 was prepared using procedures outlined in section 1.2.1, employing pladienolide B as the starting material (SM) (R=H; Scheme 1).

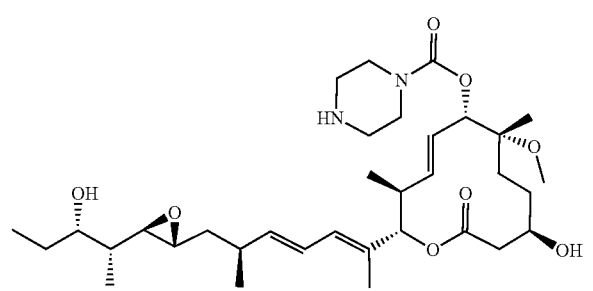 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC)[C@@H](OC(=O)N2CCNCC2)/C=C/[C@@H]1C]

Linker-Payload (ADL1-D18): General procedure 1 (outlined in section 1.3.1) was employed to synthesize 1-(4-((S)-2-((S)-2-(6-(2,5-dioxo-2,5-dihydro-1H-pyrrol-1-yl)hexanamido)-5-ureidopentanamido)-3-methylbutanamido)benzyl) 4-((2S,3S,6S,7R,10R,E)-10-hydroxy-2-((S,2E,4E)-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl) piperazine-1,4-dicarboxylate (72 mg, 0.059 mmol, 54.7% yield). LC/MS (ESI, m/z), 1220.08 [M+H]+.

¹H-NMR (400 MHz, MeOH-d4): δ ppm 0.87-1.02 (m, 15H) 1.10 (d, J=6.78 Hz, 3H) 1.23 (s, 4H) 1.29-1.38 (m, 2H) 1.44-1.68 (m, 13H), 1.54-1.55 (m, 1H) 1.77 (d, J=0.75 Hz, 4H) 1.87-1.95 (m, 1H) 2.05-2.15 (m, 1H) 2.24-2.32 (m, 2H) 2.45-2.62 (m, 4H) 2.65-2.70 (m, 1H), 2.71-2.78 (m, 1H) 3.13-3.18 (m, 2H) 3.46-3.58 (m, 11H) 3.79-3.90 (m, 1H) 4.13-4.21 (m, 1H) 4.47-4.56 (m, 1H) 5.11 (s, 4H) 5.53-5.81 (m, 3H) 6.06-6.16 (m, 1H) 6.29-6.40 (m, 1H) 6.81 (s, 2H) 7.34 (d, J=8.53 Hz, 2H) 7.60 (d, J=8.53 Hz, 2H).

1.3.1.3 ADL1-D8 & ADL6-D8

The payload D8 was synthesized according to the procedure outlined below:

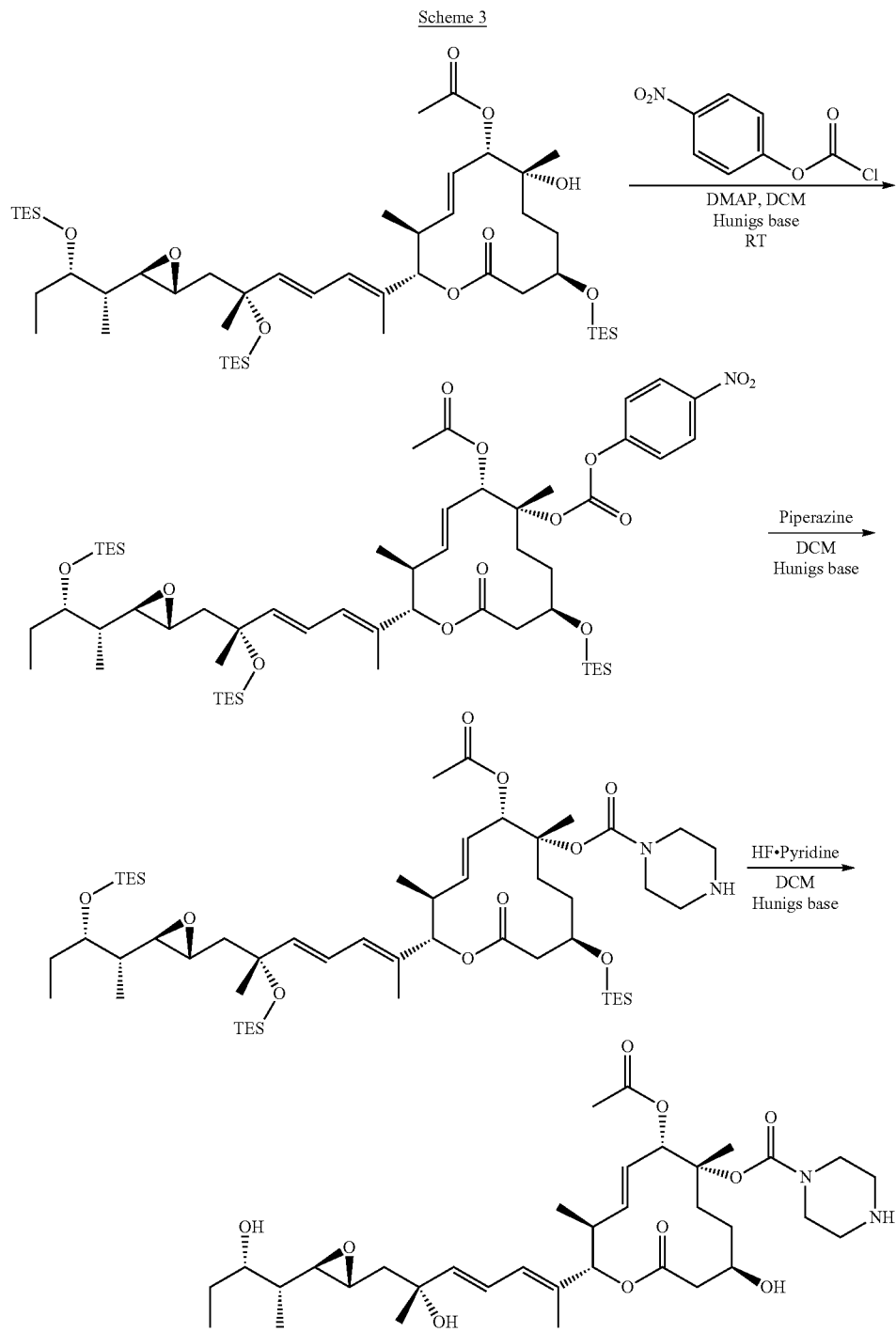

Scheme 3

Step 1: To a solution of tri-TES-Pladienolide D (200 mg, 0.223 mmol) in dichloromethane (2 mL) at 0° C. was added DMAP (409 mg, 3.35 mmol) and 4-nitrophenyl chloroformate (338 mg, 1.675 mmol). The reaction mixture was stirred at RT for 7 days, diluted with EtOAc and water, then the layers were separated. The aqueous layer was extracted with EtOAc (2×), and the combined organic extracts were washed with brine. The combined organic layers were dried over $Na_2SO_4$, filtered and concentrated in vacuo. Flash chromatography afforded (2S,3S,6S,7R,10R,E)-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2- yl)hepta-2,4-dien-2-yl)-7-(((4-nitrophenoxy)carbonyl)oxy)-12-oxo-10-((triethylsilyl)oxy)oxacyclododec-4-en-6-yl acetate. (170 mg, 72% yield).

$^1$H-NMR (400 MHz, CHCl$_3$-d): δ ppm 0.54-0.67 (m, 18H) 0.78-1.03 (m, 36H) 1.19-1.32 (m, 1H) 1.39 (s, 3H) 1.43-1.52 (m, 3H) 1.55-1.63 (m, 3H) 1.64 (s, 3H) 1.74 (s, 3H) 1.88 (dd, J=13.80, 5.02 Hz, 1H) 2.13 (s, 3H) 2.23-2.37 (m, 1H) 2.39-2.48 (m, 2H) 2.51-2.63 (m, 2H) 2.84 (s, 1H) 3.69-3.77 (m, 1H) 3.82-4.00 (m, 1H) 5.04 (d, J=10.79 Hz, 1H) 5.24 (d, J=9.03 Hz, 1H) 5.67-5.84 (m, 3H) 6.12 (d, J=10.16 Hz, 1H) 6.42 (dd, J=15.06, 11.04 Hz, 1H) 7.42 (d, J=9.29 Hz, 2H) 8.29 (d, J=9.16 Hz, 2H).

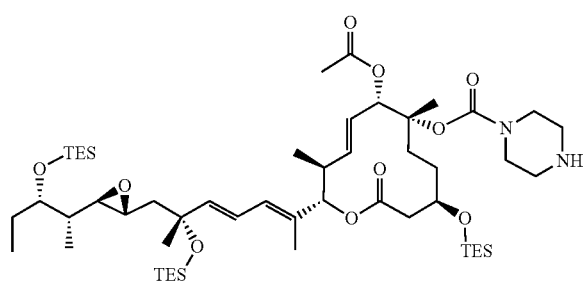

Step 2: To a solution of (2S,3S,6S,7R,10R,E)-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-7-(((4-nitrophenoxy)carbonyl)oxy)-12-oxo-10-((triethylsilyl)oxy)oxacyclododec-4-en-6-yl acetate (100 mg, 0.094 mmol) in DCM was added piperazine and DMAP. The resulting yellowish suspension was stirred for 6 hours. The reaction mixture was concentrated to give the crude product. Flash chromatography afforded (2S,3S,6S,7R,10R,E)-6-acetoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-7-yl piperazine-1-carboxylate (95 mg, 100%). LC/MS (ESI, m/z), 1008.8 [M+H]$^+$.

$^1$H-NMR (400 MHz, CHCl$_3$-d): δ ppm 0.42-0.70 (m, 22H) 0.79-0.84 (m, 7H) 0.86-0.91 (m, 4H) 0.92-1.03 (m,

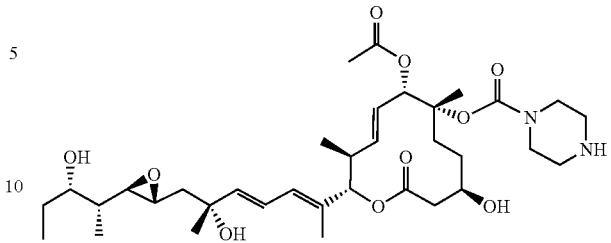

Step 3: To a solution of (2S,3S,6S,7R,10R,E)-6-acetoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-7-yl piperazine-1-carboxylate in (95 mg, 0.094 mmol) in THF (3 mL) was added TBAF (0.424 mL, 1 M, 0.424 mmol) and stirred at RT for 10 hours. The mixture as concentrated and diluted with EtOAc, washed with water and brine. The organic layer was separated and dried with Na$_2$SO$_4$, filtered and concentrated in vacuo. HPLC purification afforded (2S,3S,6S,7R,10R,E)-6-acetoxy-10-hydroxy-2-((R,2E,4E)-6-hydroxy-7-((2R,3R)-3-((2S,3S)-3-hydroxypentan-2-yl)oxiran-2-yl)-6-methyl-hepta-2,4-dien-2-yl)-3,7-dimethyl-12-oxooxacyclododec-4-en-7-yl piperazine-1-carboxylate (16 mg, 26%). LC/MS (ESI, m/z), 665.6 [M+H]$^+$.

$^1$H-NMR (400 MHz, CHCl$_3$-d): δ ppm 0.90 (dd, J=6.84, 2.20 Hz, 6H) 0.94 (t, J=7.40 Hz, 3H) 1.20-1.30 (m, 1H) 1.34 (s, 3H) 1.39-1.54 (m, 3H) 1.55 (s, 3H) 1.59 -1.73 (m, 3H) 1.78 (d, J=0.88 Hz, 3H) 1.86 (dd, J=13.99, 5.46 Hz, 1H) 2.05 (s, 3H) 2.39-2.53 (m, 3H) 2.55-2.65 (m, 1H) 2.67 (dd, J=8.03, 2.26 Hz, 1H) 2.89 (s, 1H) 3.22 (br s, 4H) 3.50-3.57 (m, 1H) 3.58-3.90 (m, 5H) 5.08 (d, J=10.67 Hz, 1H) 5.18 (d, J=9.03 Hz, 1H) 5.58-5.78 (m, 2H) 5.88 (d, J=15.31 Hz, 1H) 6.10-6.23 (m, 1H) 6.53 (dd, J=15.25, 10.98 Hz, 1H).

Step 4

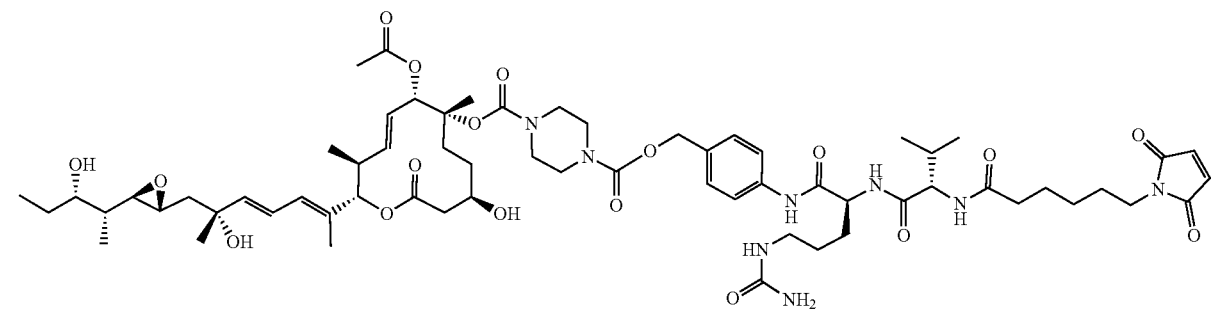 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)[C@@H](OC(C)=O)/C=C/[C@@H]1C]

30H) 1.15-1.30 (m, 2H) 1.37-1.42 (m, 3H) 1.44-1.52 (m, 3H) 1.56-1.62 (m, 2H) 1.62-1.68 (m, 1H) 1.71-1.76 (m, 3H) 1.83-1.93 (m, 1H) 2.03-2.11 (m, 4H) 2.36-2.45 (m, 2H) 2.45-2.53 (m, 2H) 2.54-2.64 (m, 1H) 2.78-2.86 (m, 1H) 2.86-3.07 (m, 4H) 3.32-3.45 (m, 1H) 3.45-3.64 (m, 3H) 3.69-3.78 (m, 1H) 3.79-3.94 (m, 1H) 5.00 (d, J=10.54 Hz, 1H) 5.18 (s, 1H) 5.54-5.79 (m, 3H) 5.98-6.21 (m, 1H) 6.33-6.57 (m, 1H) 6.84-6.96 (m, 3H) 8.02-8.35 (m, 2H) 8.06-8.08 (m, 1H).

Linker-Payload (ADL1-D8): 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (7.5 mg, 10.166 µmol) in DMF (315 µL, 4.066 mmol) was added Hunig's base (5.33 µL, 0.03 mmol). The reaction was cooled to 0° C., and added (2S,3S,6S,7R,10R,E)-6-acetoxy-10-hydroxy-2-((R,2E,4E)-6-hydroxy-7-((2R,3R)--

3-((2R,3S)-3-hydroxypentan-2-yl)oxiran-2-yl)-6-methyl-hepta-2,4-dien-2-yl)-3,7-dimethyl-12-oxooxacyclododec-4-en-7-yl piperazine-1-carboxylate (7.50 mg, 0.011 mmol). The reaction mixture was stirred at RT until consumption of starting material. The reaction mixture was concentrated in vacuo. Flash chromatography afforded ADL1-D8 (7.2 mg, 5.70 µmol, 56.1% yield). LC/MS (ESI, m/z), 1263.8 [M+H]*. General procedure 1 (1.3.1) can also be employed for the preparation of ADL1-110987.

$^1$H-NMR (400 MHz, CHLOROFORM-d): δ ppm 0.80-1.02 (m, 16H) 1.20-1.35 (m, 6H) 1.38-1.48 (m, 2H) 1.57-1.69 (m, 7H) 1.74-1.81 (m, 4H) 1.86-1.96 (m, 2H) 2.00-2.11 (m, 4H) 2.31 (br d, J=6.02 Hz, 2H) 2.45-2.55 (m, 2H) 2.59-2.74 (m, 2H) 2.85-2.96 (m, 1H) 3.05-3.25 (m, 5H) 3.40-3.59 (m, 9H) 3.62-3.88 (m, 1H) 4.15 (d, J=7.53 Hz, 1H) 5.05-5.22 (m, 5H) 5.56-5.77 (m, 2H) 5.84-5.98 (m, 1H) 6.11-6.22 (m, 1H) 6.47-6.61 (m, 1H) 7.31-7.40 (m, 2H) 7.56-7.65 (m, 2H).

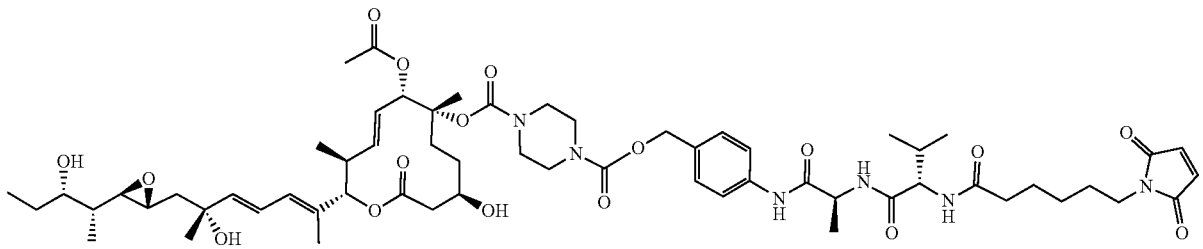 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(=O)N2CCN(C(=O)OCc3ccc(NC(=O)[C@H](C)NC(=O)[C@@H](NC(=O)CCCCCN4C(=O)C=CC4=O)C(C)C)cc3)CC2)[C@@H](OC(C)=O)/C=C/[C@@H]1C]

Linker-Payload (ADL6-D8): 4-((S)-2-((S)-2-(6-(2,5-dioxo-2,5-dihydro-1H-pyrrol-1-yl)hexanamido)-3-methylbutanamido)propanamido)benzyl (4-nitrophenyl) carbonate (5 mg, 7.673 µmol) in DMF (238 µL, 3.069 mmol) was added Hunig's base (4.02 µL, 0.023 mmol). The reaction mixture was cooled to 0° C., and added (2S,3S,6S,7R,10R,E)-6-acetoxy-10-hydroxy-2-((R,2E,4E)-6-hydroxy-7-((2R,3R)-3-((2R,3S)-3-hydroxypentan-2-yl)oxiran-2-yl)-6-methyl-hepta-2,4-dien-2-yl)-3,7-dimethyl-12-oxooxacyclododec-4-en-7-yl piperazine-1-carboxylate. The reaction mixture was stirred at RT until consumption of starting material. The reaction mixture was concentrated in vacuo. HPLC purification afforded ADL6-D8 (1.2 mg, 1.019 µmol, 13.28% yield). LC/MS (ESI, m/z), 1199.9 [M+Na]$^+$.

$^1$H NMR (400 MHz, CHCl$_3$-d): δ ppm 0.78-1.04 (m, 18H) 1.15-1.52 (m, 58H) 1.64-1.72 (m, 3H) 1.78 (d, J=6.53 Hz, 4H) 2.04-2.19 (m, 3H) 2.21-2.30 (m, 1H) 2.44-2.67 (m, 4H) 2.76 (dd, J=6.09, 2.95 Hz, 1H) 2.90-3.02 (m, 1H) 3.42-3.57 (m, 8H) 3.61-3.70 (m, 1H) 3.77 (br s, 1H) 4.10-4.27 (m, 1H) 4.58 (br d, J=6.65 Hz, 1H) 5.01-5.26 (m, 4H) 5.52-5.70 (m, 2H) 5.88 (s, 1H) 5.93-6.02 (m, 1H) 6.08-6.18 (m, 1H) 6.47-6.58 (m, 1H) 7.29-7.35 (m, 2H) 7.55 (d, J=8.66 Hz, 1H).

1.3.1.4 ADL1-D4

ADL1-D4 was synthesized using the procedures outlined below.

Scheme 4

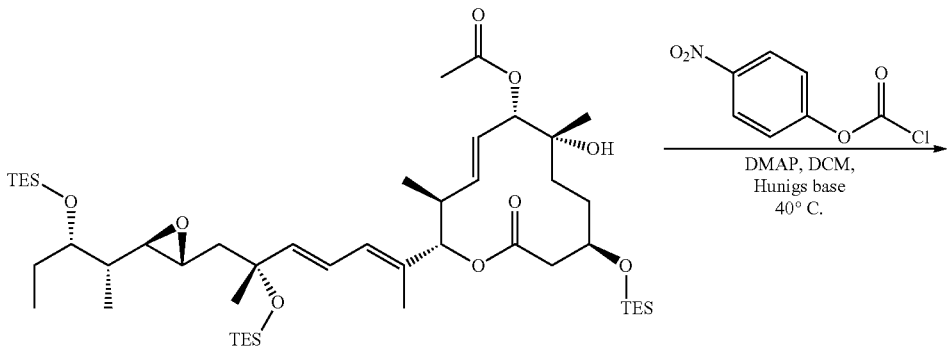

-continued
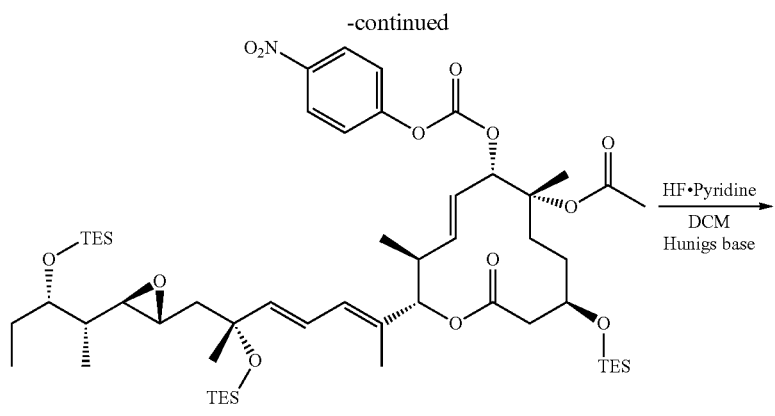
HF·Pyridine
DCM
Hunigs base
⟶
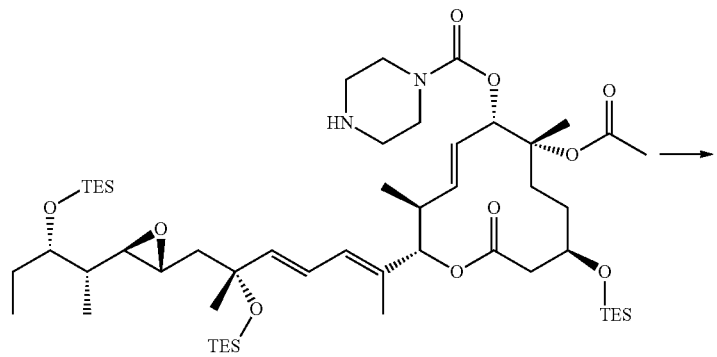
⟶
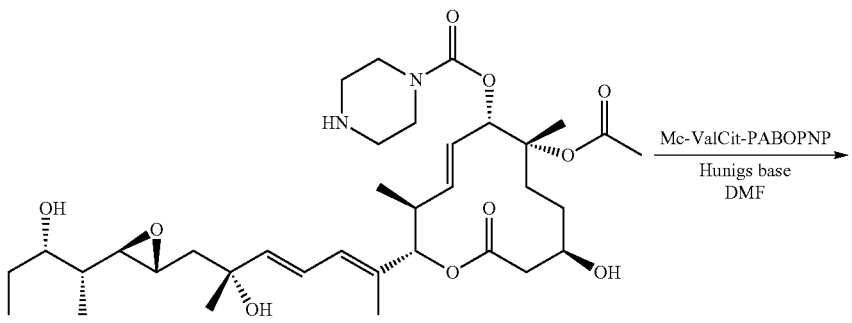
Mc-ValCit-PABOPNP
Hunigs base
DMF
⟶
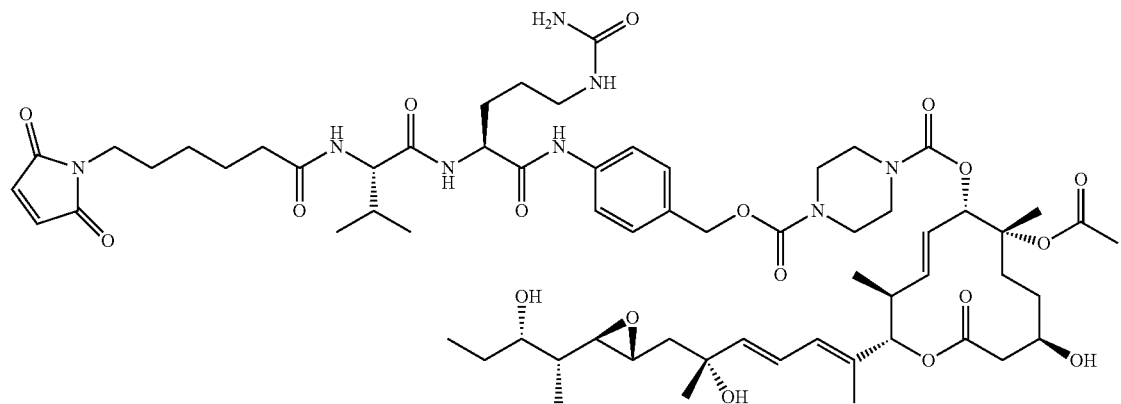

Step 1: (2S,3S,6S,7R,10R, E)-3,7-dimethyl-2-((R,2E, 4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-6-(((4-nitrophenoxy)carbonyl)oxy)-12-oxo-10-((triethylsilyl)oxy)oxacyclododec-4-en-7-yl acetate.

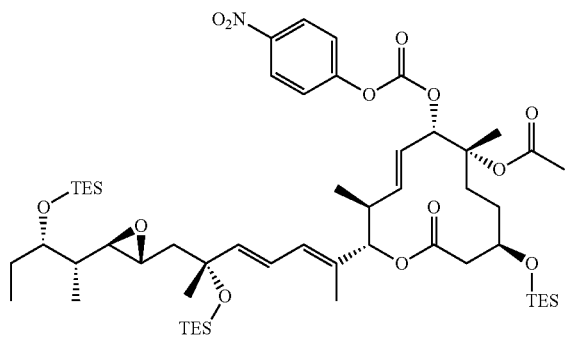

To a solution of tri-TES Pladienolide D (160 mg, 0.179 mmol) in 1,2-dichloroethane (5 mL) at 20° C. was added DMAP (32.7 mg, 0.268 mmol), triethyl amine (0.75 mL, 5.36 mmol) and 4-nitrophenyl chloroformate (360 mg, 1.787 mmol). The reaction mixture was stirred at 40° C. for 4 days, and at 60° C. for 2 hours. The reaction mixture was diluted with EtOAc and washed with water, then the layers were separated. The aqueous layer was extracted with EtOAc (2×). The combined organic extracts were successively washed with water and brine, dried over MgSO$_4$, filtered, and concentrated in vacuo. Flash chromatography afforded (2S,3S,6S,7R,10R,E)-7-acetoxy-3,7-dimethyl-2-((R,2E, 4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl piperazine-1-carboxylate (150 mg, 79% yield).

$^1$H-NMR (400 MHz, CHCl$_3$-d): δ ppm 0.48-0.71 (m, 24H) 0.78-0.85 (m, 7H) 0.86-0.93 (m, 5H) 0.94-1.03 (m, 34H) 1.18-1.22 (m, 2H) 1.22-1.26 (m, 2H) 1.35-1.43 (m, 4H) 1.43-1.52 (m, 4H) 1.54 (s, 4H) 1.56-1.65 (m, 3H) 1.68-1.72 (m, 3H) 1.75 (br d, J=0.75 Hz, 2H) 1.84-1.95 (m, 1H) 2.01-2.06 (m, 2H) 2.09 (s, 2H) 2.11 (s, 2H) 2.33-2.52 (m, 4H) 2.57 (dd, J=8.09, 2.07 Hz, 2H) 2.80-2.90 (m, 1H) 3.66-3.80 (m, 1H) 3.82-3.93 (m, 2H) 4.92-5.13 (m, 2H) 5.63-5.68 (m, 1H) 5.69-5.74 (m, 1H) 5.75-5.83 (m, 2H) 6.12 (br d, J=10.67 Hz, 1H) 6.41 (ddd, J=15.15, 11.01, 5.08 Hz, 1H) 7.50 (d, J=9.41 Hz, 2H) 8.35 (d, J=9.29 Hz, 2H).

Step 2: (2S,3S,6S,7R,10R,E)-7-acetoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl piperazine-1-carboxylate.

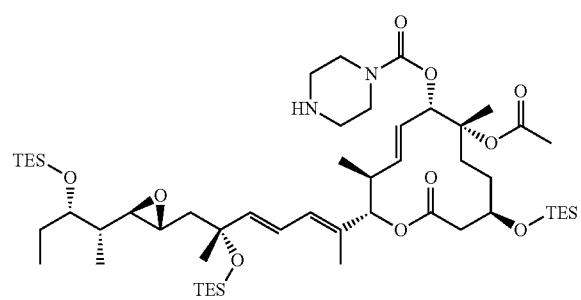

To a solution of (2S,3S,6S,7R,10R,E)-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-6-(((4-nitrophenoxy)carbonyl)oxy)-12-oxo-10-((triethylsilyl)oxy)oxacyclododec-4-en-7-yl acetate in DCM (1 mL) was added piperazine (0.447 g, 5.195 mmol) and Hunig's base (0.9 mL, 5.195 mmol). The resulting yellowish suspension was stirred for 6 hours. Reaction mixture was concentrated and chromatographed over silica gel to afford (2S,3S,6S,7R,10R,E)-7-acetoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl piperazine-1-carboxylate (1.0 g, 0.844 mmol, 81% yield). LC/MS (ESI, m/z), 1008.1 [M+H]$^+$.

D4

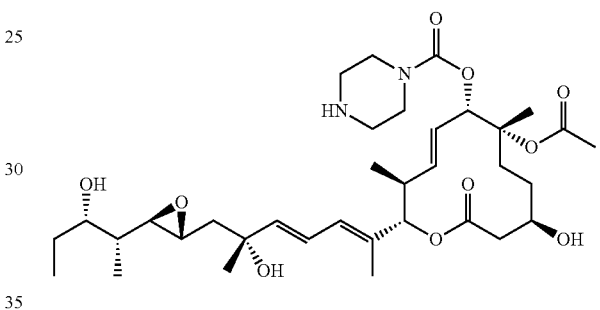

Step 3: (2S, 3S,6S,7R,10R,E)-7-acetoxy-3,7-dimethyl-2-((R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl piperazine-1-carboxylate (1.09 g, 0.92 mmol), DCM (20.71 mL, 321.826 mmol), and DIPEA (19.91 mL, 114.018 mmol) were combined and cooled to −78° C. Hydrogen fluoride-pyridine (0.518 g, 5.232 mmol) was added and the reaction allowed to warm to RT and stirred overnight. LC/MS suggested desilylation. The reaction mixture was cooled in an ice bath. Saturated NaHCO$_3$ was added and stirred and extracted with DCM. The organic layers were combined, dried over an. Na$_2$SO$_4$ and concentrated and chromatographed to afford (2S,3S,6S,7R,10R,E)-7-acetoxy-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate (225 mg, 36.8%). LC/MS (ESI, m/z), 665.6 [M+H]$^+$.

$^1$H-NMR (400 MHz, CHCl$_3$-d): δ ppm 0.87-0.92 (m, 6H) 0.94 (t, J=7.40 Hz, 3H) 1.16-1.31 (m, 1H) 1.35 (s, 3H) 1.40-1.56 (m, 4H) 1.59 (s, 3H) 1.66 (br dd, J=14.68, 7.03 Hz, 3H) 1.76-1.80 (m, 3H) 1.87 (dd, J=14.12, 5.46 Hz, 1H) 2.05 (s, 3H) 2.30-2.41 (m, 1H) 2.50 (d, J=3.76 Hz, 2H) 2.56-2.72 (m, 2H) 2.90 (br d, J=2.01 Hz, 1H) 3.19 (br t, J=5.14 Hz, 4H) 3.50-3.59 (m, 1H) 3.71 (br s, 4H) 3.77-3.89 (m, 1H) 5.01 -5.13 (m, 2H) 5.58-5.71 (m, 1H) 5.71-5.81 (m, 1H) 5.88 (d, J=15.31 Hz, 1H) 6.15 (br d, J=10.79 Hz, 1H) 6.53 (dd, J=15.18, 10.92 Hz, 1H).

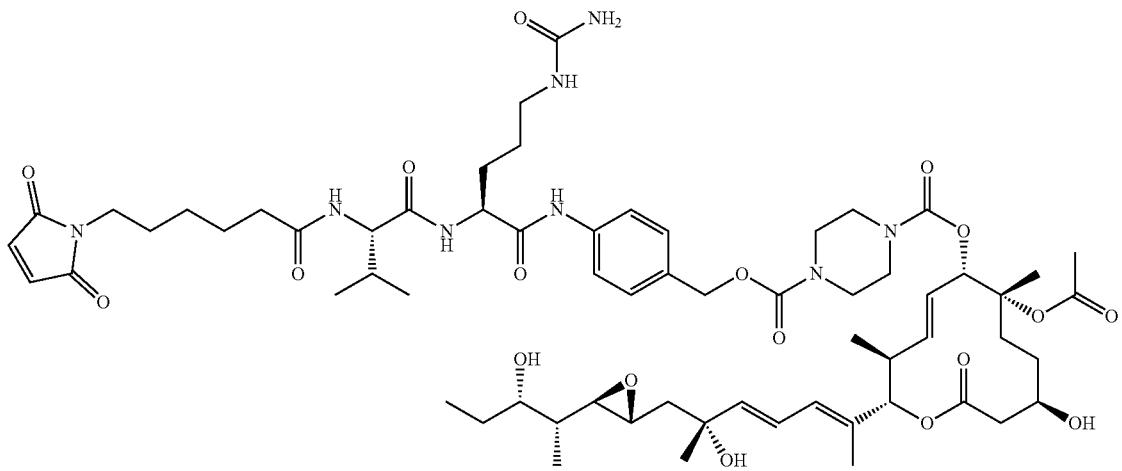 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]

To 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (23 mg, 0.031 mmol) in DMF (966 μL) in a round-bottom flask was added Hunig's base (16.33 μL, 0.094 mmol). The reaction mixture was cooled to 0° C., and D4 (22.80 mg, 0.034 mmol) was added and stirred at RT. The reaction mixture was concentrated in vacuo. Flash chromatography afforded ADL1-D4 (30.5 mg, 0.024 mmol, 77% yield). LC/MS (ESI, m/z), 1263.8 [M+H]*.

$^{1}$H-NMR (400 MHz, MeOH-d$_4$): δ ppm 0.87-0.93 (m, 7H) 0.93-1.01 (m, 8H) 1.19-1.34 (m, 4H) 1.50 (s, 3H) 1.57 (s, 5H) 1.58-1.70 (m, 6H) 1.70-1.77 (m, 1H) 1.78 (s, 3H) 1.83-1.95 (m, 2H) 2.04 (s, 3H) 2.05-2.13 (m, 1H) 2.27 (t, J=7.40 Hz, 2 H) 2.32-2.42 (m, 1H) 2.50 (d, J=3.64 Hz, 2H) 2.55-2.74 (m, 2H) 2.90 (td, J=5.83, 2.26 Hz, 1H) 3.03-3.26 (m, 2H) 3.35 (s, 13H) 3.42-3.61 (m, 11H) 3.80 (br dd, J=9.85, 3.58 Hz, 1H) 4.16 (d, J=7.40 Hz, 1H) 4.50 (dd, J=8.91, 5.14 Hz, 1H) 4.56 (s, 1H) 5.05 (dd, J=14.37, 10.10 Hz, 2H) 5.09 (s, 2H) 5.49 (s, 1H) 5.59-5.69 (m, 1H) 5.72-5.80 (m, 1H) 5.87 (d, J=15.18 Hz, 1H) 6.09-6.22 (m, 1H) 6.44-6.60 (m, 1H) 7.32 (d, J=8.66 Hz, 2H) 7.58 (d, J=8.53 Hz, 2H).

1.3.1.5 ADL1-D9, ADL6-D9, & ADL1-D13

D9 & D13

D9 and D13 were synthesized as a 3:1 mixture of isomers employing procedures outlined in the synthesis of D4 (Scheme 4) utilizing tri-TES Pladienolide B.

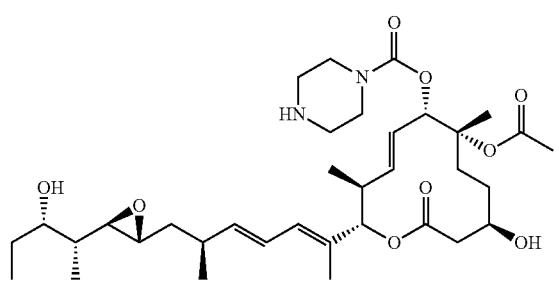 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC(C)=O)[C@@H](OC(=O)N2CCNCC2)/C=C/[C@@H]1C]

Payload (D9): LC/MS (ESI, m/z), 649.7 [M+H]$^+$.

$^{1}$H-NMR (400 MHz, CHCl$_3$-d): δ ppm 0.87-1.01 (m, 10H) 1.08 (d, J=6.78 Hz, 3 H) 1.27-1.63 (m, 12H) 1.66-1.74 (m, 1H) 1.76 (s, 3H) 1.97-2.10 (m, 3H) 2.35-2.57 (m, 5H) 2.58-2.65 (m, 1H) 2.65-2.71 (m, 1H) 2.77 (td, J=5.93, 2.32 Hz, 1H) 2.89-3.05 (m, 4H) 3.07-3.34 (m, 8H) 3.50-3.68 (m, 5H) 3.72-3.88 (m, 1H) 4.88-5.09 (m, 1H) 5.18 (d, J=10.67 Hz, 1H) 5.50-5.84 (m, 3H) 6.01-6.13 (m, 1H) 6.19-6.36 (m, 1H).

Payload (D13): LC/MS (ESI, m/z), 649.6 [M+H]$^+$.

$^{1}$H NMR (400 MHz, CHCl$_3$-d) δ ppm 0.84-1.01 (m, 11H) 1.08 (d, J=6.78 Hz, 3 H) 1.29-1.64 (m, 10H) 1.63-1.73 (m, 1H) 1.76 (s, 3H) 1.94-2.12 (m, 4H) 2.37-2.58 (m, 4H) 2.59-2.65 (m, 1H) 2.68 (dd, J=7.40, 2.26 Hz, 1H) 2.77 (td, J=5.93, 2.32 Hz, 1H) 3.01-3.30 (m, 4H) 3.49 (s, 1H) 3.54-3.67 (m, 2H) 3.69-3.92 (m, 5H) 4.13 -4.78 (m, 11H) 5.13-5.24 (m, 2H) 5.48-5.61 (m, 1H) 5.62-5.74 (m, 2H) 6.04-6.13 (m, 1H) 6.18-6.32 (m, 1H).

ADL1-D9

General procedure 1 (outlined in section 1.3.1) was employed to synthesize ADL1-D9.

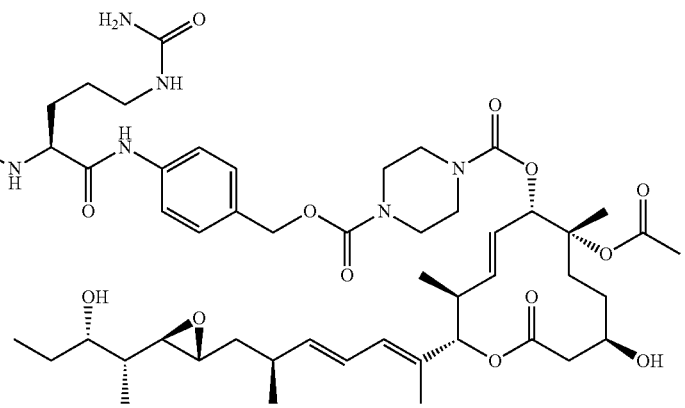

Linker-Payload (ADL1-D9): (30.5 mg, 0.024 mmol, 77% yield). LC/MS (ESI, m/z), 1263.8 [M+H]$^+$.

$^1$H-NMR (400 MHz, MeOH-d$_4$): δ ppm 0.87-0.93 (m, 7H) 0.93-1.01 (m, 8H) 1.19-1.34 (m, 4H) 1.50 (s, 3H) 1.57 (s, 5H) 1.58-1.70 (m, 6H) 1.70-1.77 (m, 1H) 1.78 (s, 3H) 1.83-1.95 (m, 2H) 2.04 (s, 3H) 2.05-2.13 (m, 1H) 2.27 (t, J=7.40 Hz, 2 H) 2.32-2.42 (m, 1H) 2.50 (d, J=3.64 Hz, 2H) 2.55-2.74 (m, 2H) 2.90 (td, J=5.83, 2.26 Hz, 1H) 3.03-3.26 (m, 2H) 3.35 (s, 13H) 3.42-3.61 (m, 11H) 3.80 (br dd, J=9.85, 3.58 Hz, 1H) 4.16 (d, J=7.40 Hz, 1H) 4.50 (dd, J=8.91, 5.14 Hz, 1H) 4.56 (s, 1H) 5.05 (dd, J=14.37, 10.10 Hz, 2H) 5.09 (s, 2H) 5.49 (s, 1H) 5.59-5.69 (m, 1H) 5.72 -5.80 (m, 1H) 5.87 (d, J=15.18 Hz, 1H) 6.09-6.22 (m, 1H) 6.44-6.60 (m, 1H) 7.32 (d, J=8.66 Hz, 2H) 7.58 (d, J=8.53 Hz, 2H).

ADL6-D9

General procedure 1 (outlined in section 1.3.1) was employed to synthesize

Linker-Payload (ADL6-D9): To diluted 4-((S)-2-((S)-2-(6-(2,5-dioxo-2,5-dihydro-1H-pyrrol-1-yl)hexanamido)-3-methylbutanamido)propanamido)benzyl (4-nitrophenyl) carbonate (16.5 mg, 0.025 mmol) in DMF (784 µL) was added Hunig's Base (13.27 µL, 0.076 mmol). The reaction mixture was cooled to 0° C., and D9 was added. The reaction mixture was stirred at RT until LC/MS showed the reaction complete. The reaction mixture was concentrated in vacuo. Flash chromatography of the residue on silica gel with DCM/MeOH gave the titled compound (16.7 mg, 57% yield). LC/MS (ESI, m/z), 1184.6 [M+Na]$^+$.

$^1$H-NMR (400 MHz, MeOH-d$_4$): δ ppm 0.80-1.02 (m, 16H) 1.05-1.12 (m, 4H) 1.13-1.34 (m, 5H) 1.38-1.51 (m, 7H) 1.53-1.68 (m, 11H) 1.71-1.80 (m, 4H) 1.97-2.16 (m, 4H) 2.24-2.32 (m, 2H) 2.32-2.42 (m, 1H) 2.43-2.55 (m, 3H) 2.56-2.69 (m, 3H) 2.73 (br d, J=2.13 Hz, 1H) 3.07-3.18 (m, 1H) 3.42-3.61 (m, 17H) 3.75-3.91 (m, 1H) 4.11-4.24 (m, 1H) 4.43 (s, 2H) 5.59-5.88 (m, 4H) 6.06-6.17 (m, 1H) 6.29-6.39 (m, 1H) 7.24-7.39 (m, 2H) 7.52-7.64 (m, 2H).

ADL6-D9

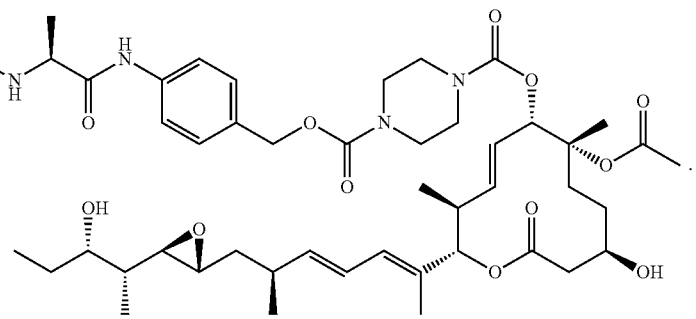

ADL1-D13

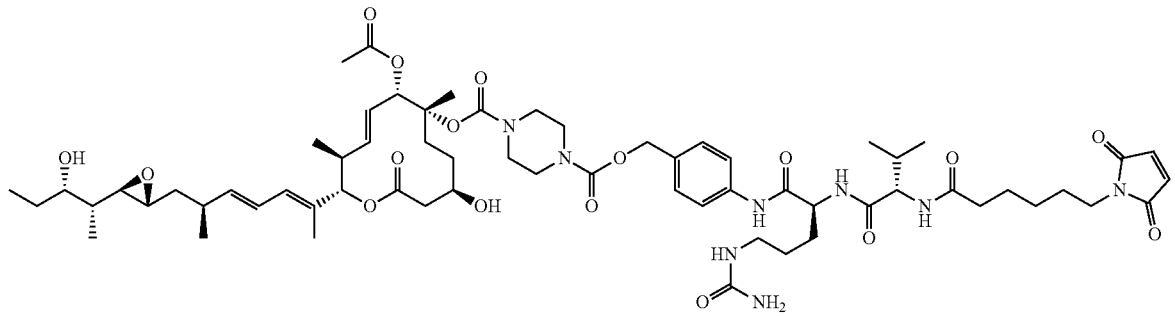

Linker-Payload (AD1-D13): 4-((S)-2-((S)-2-(6-(2,5-dioxo-2,5-dihydro-1H-pyrrol-1-yl)hexanamido)-3-methylbutanamido)-5ureidopentanamido)benzyl (4-nitrophenyl) carbonate (4.2 mg, 5.693 µmol) in DMF (176 µL, 2.277 mmol) was added Hunig's base (2.98 µL, 0.017 mmol). The reaction mixture was cooled to 0° C., and D13 was added (4.06 mg, 6.262 µmol). The reaction mixture was stirred at RT until LC/MS showed the reaction complete. The reaction mixture was concentrated in vacuo. Flash chromatography of the residue on silica gel with DCM/MeOH gave the title compound (4.8 mg, 68% yield). LC/MS (ESI, m/z), 1248.0 [M+H]$^+$.

$^1$H-NMR (400 MHz, CHCl$_3$-d): δ ppm 0.58-0.98 (m, 10H) 0.99-1.06 (m, 2H) 1.11-1.31 (m, 6H) 1.57-1.75 (m, 3H) 2.11-2.26 (m, 1H) 2.30-2.73 (m, 2H) 3.28-3.80 (m, 7H) 4.14-4.33 (m, 1H) 4.44-4.55 (m, 1H) 4.63-4.81 (m, 1H) 4.92-5.06 (m, 1H) 5.09 (s, 1H) 5.49-5.74 (m, 1H) 5.88-6.09 (m, 1H) 6.14-6.36 (m, 1H) 6.99 -7.08 (m, 1H) 7.21-7.38 (m, 2H) 7.53-7.67 (m, 1H) 7.95 (s, 1H).

1.3.1.6 ADL1-D14

General procedure 1 (outlined in section 1.3.1) was employed to synthesize 1-((2S,3S,6R,7S,10R,E)-2-((E)-1-(1-(1-acetylpiperidin-4-yl)-4-fluoro-1H-benzo[d][1,2,3]triazol-6-yl)prop-1-en-2-yl)-10-hydroxy-3,7-dimethyl-12-oxooxacyclododec-4-en-6-yl) 4-(4-((S)-2-((S)-2-(6-(2,5-dioxo-2,5-dihydro-1H-pyrrol-1-yl)hexanamido)-3-methylbutanamido)-5-ureidopentanamido)benzyl) piperazine-1,4-dicarboxylate (30 mg, 0.024 mmol, 39.2% yield). LC/MS (ESI, m/z), 1254.5 [M+H]$^+$.

$^1$H-NMR (400 MHz, DMSO-d6): δ ppm 0.75-1.00 (m, 12H), 1.06-1.26 (m, 4 H), 1.26-1.77 (m, 13H), 1.75-2.02 (m, 7H), 2.08 (s, 8H), 2.23-2.35 (m, 2H), 2.54-2.70 (m, 2H), 2.78-3.10 (m, 4H), 3.36 (br s, 13H), 3.66-3.79 (m, 1H), 3.95-4.08 (m, 1H), 4.11-4.25 (m, 1H), 4.28-4.46 (m, 1H), 4.46-4.58 (m, 1H), 4.58-4.66 (m, 1H), 4.66-4.77 (m, 1H), 5.01 (s, 3H), 5.14-5.27 (m, 1H), 5.39 (s, 4H), 5.71-5.79 (m, 1H), 5.87-6.00 (m, 1H), 6.63-6.75 (m, 1H), 6.99 (s, 2H), 7.13-7.24 (m, 1H), 7.24-7.34 (m, 2H), 7.52-7.62 (m, 2H), 7.65-7.74 (m, 1H), 7.75-7.82 (m, 1H), 7.98 -8.13 (m, 1H).

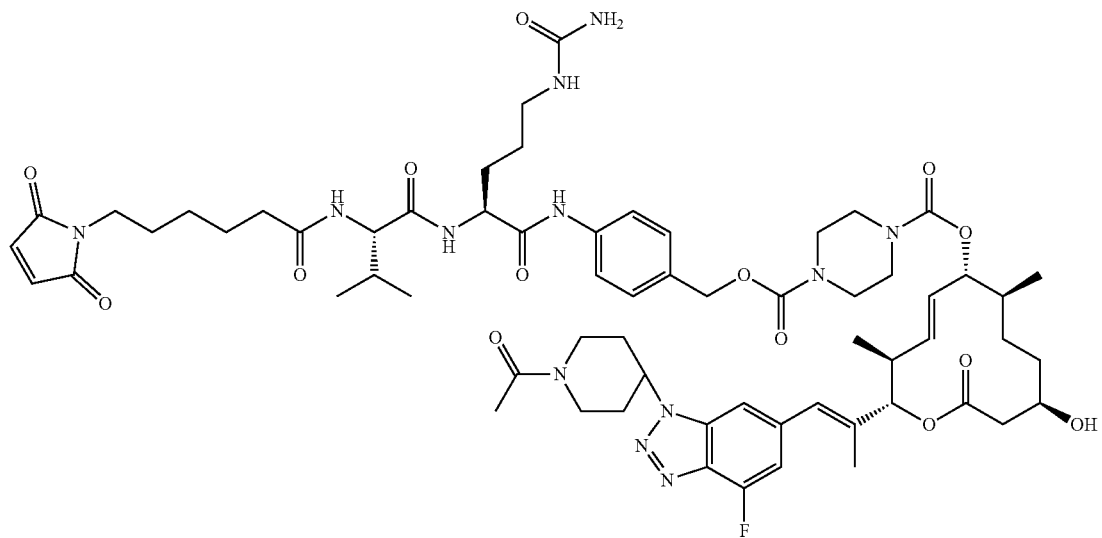 [SMILES: CC(=O)N1CCC(n2nnc3c(F)cc(/C=C(\C)[C@H]4OC(=O)C[C@H](O)CC[C@H](C)[C@@H](OC(=O)N5CCN(C(=O)OCc6ccc(NC(=O)[C@H](CCCNC(N)=O)NC(=O)[C@@H](NC(=O)CCCCCN7C(=O)C=CC7=O)C(C)C)cc6)CC5)/C=C/[C@@H]4C)cc32)CC1]

1.3.1.7 ADL1-D33

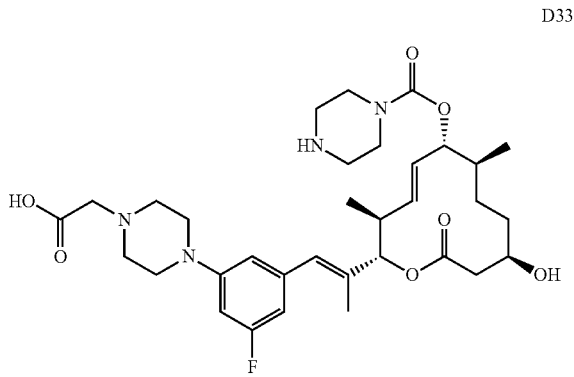 [SMILES: C/C(=C\c1cc(F)cc(N2CCN(CC(=O)O)CC2)c1)[C@H]1OC(=O)C[C@H](O)CC[C@H](C)[C@@H](OC(=O)N2CCNCC2)/C=C/[C@@H]1C]

D33

To a stirred solution of (2S,3S,6R,7S,10R,E)-2-((E)-1-(3-fluoro-5-(4-(2-methoxy-2-oxoethyl)piperazin-1-yl)phenyl)prop-1-en-2-yl)-10-hydroxy-3,7-dimethyl-12-oxooxacyclododec-4-en-6-yl piperazine-1-carboxylate (27 mg, 0.042 mmol) in THF/H$_2$O (3 mL/1 mL) at 0° C. was added LiOH, and the reaction mixture was allowed to slowly warm to 25° C. (2S,3S,6R,7S,10R,E)-2-((E)-1-(3-fluoro-5-(4-(2-methoxy-2-oxoethyl)piperazin-1-yl)phenyl)prop-1-en-2-yl)-10-hydroxy-3,7-dimethyl-12-oxooxacyclododec-4-en-6-yl piperazine-1-carboxylate was synthesized using procedures outlined in International Application No. PCT/US2019/026992 (see, e.g., Procedures 17 and 19), which is incorporated herein by reference. After 6 hours, the reaction mixture was neutralized with phosphate buffer (NaH$_2$PO$_4$, 1.0 M, 3 mL) and the phases were separated. The aqueous layer was extracted with ethyl acetate (3×2 mL), and the combined organic layers were dried with anhydrous sodium sulfate and concentrated in vacuo. Reversed phase column chromatography afforded the titled compound (19.4 mg, 0.031 mmol, 73.4% yield). LC/MS (ESI, m/z), 631.4 [M+H]$^+$.

$^1$H-NMR (400 MHz, CHCl$_3$-d): δ ppm 0.85-1.16 (m, 2H) 1.23-1.52 (m, 1H) 1.57-1.77 (m, 1H) 1.87 (s, 1H) 1.92-2.13 (m, 1H) 2.35-2.55 (m, 1H) 2.50-2.74 (m, 1H) 3.11 (br s, 1H) 3.36-3.54 (m, 2H) 3.64 (br d, J=10.42 Hz, 2H) 3.77-3.90 (m, 1H) 4.76 (br s, 4H) 5.07-5.19 (m, 1H) 5.38-5.68 (m, 1H) 6.40-6.76 (m, 1H) 8.02-8.66 (m, 1H).

ADL1-D33

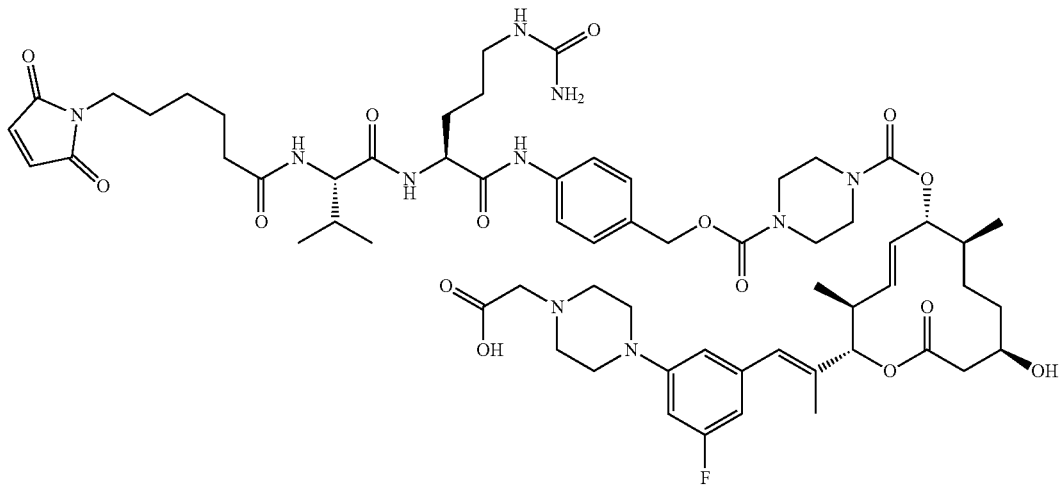

Linker-Payload (ADL1-D33): To 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (17 mg, 0.023 mmol) in DMF (714 μL, 9.217 mmol) was added Hunig's base (12.07 μL, 0.069 mmol). The reaction mixture was cooled to 0° C., and added 2-(4-(3-fluoro-5-((E)-2-((2S,3S,6R,7S,10R,E)-10-hydroxy-3,7-dimethyl-12-oxo-6-((piperazine-1-carbonyl)oxy)oxacyclododec-4-en-2-yl)prop-1-en-1-yl)phenyl)piperazin-1-yl) acetic acid (16.71 mg, 0.026 mmol). The reaction mixture was stirred at RT until LC/MS showed the reaction complete. The reaction mixture was concentrated in vacuo. Flash chromatography on silica gel and further HPLC purification gave the titled compound (13.5 mg, 10.98 μmol, 47.7% yield). LC/MS (ESI, m/z), 1229.5 [M+H]$^+$.

$^1$H-NMR (400 MHz, MeOH-d$_4$): δ ppm 0.92-0.99 (m, 10H) 1.01 (d, J=6.78 Hz, 3 H) 1.24-1.46 (m, 9H) 1.52-1.70 (m, 10H) 1.70-1.82 (m, 1H) 1.87 (d, J=1.00 Hz, 4 H) 1.89-2.00 (m, 2H) 2.01-2.23 (m, 2H) 2.27 (t, J=7.40 Hz, 2H) 2.46 (dd, J=14.31, 5.27 Hz, 1H) 2.57-2.71 (m, 2H) 2.86 (d, J=0.63 Hz, 1H) 3.00 (s, 1H) 3.06-3.27 (m, 4H) 3.35 (s, 5H) 3.41-3.53 (m, 19H) 3.66 (s, 2H) 3.76-3.90 (m, 1H) 4.07-4.21 (m, 1H) 4.39-4.69 (m, 37H) 5.09 (s, 3H) 5.13 (d, J=10.54 Hz, 1H) 5.52 (dd, J=14.56, 9.03 Hz, 2H) 6.55 (br s, 2H) 6.69 (d, J=1.38 Hz, 2H) 7.33 (d, J=8.66 Hz, 2H) 7.59 (d, J=8.53 Hz, 2H) 7.88-8.04 (m, 1H) 8.16-8.33 (m, 1H).

1.3.2 ADL1-D4, ADL1-D5, ADL21-D4, ADL22-D4, ADL23-D4, ADL13-D4

1.3.2.1 General Procedure for Preparation of D4 and D5

The 4-step procedure outlined below was employed to synthesize the title compounds.

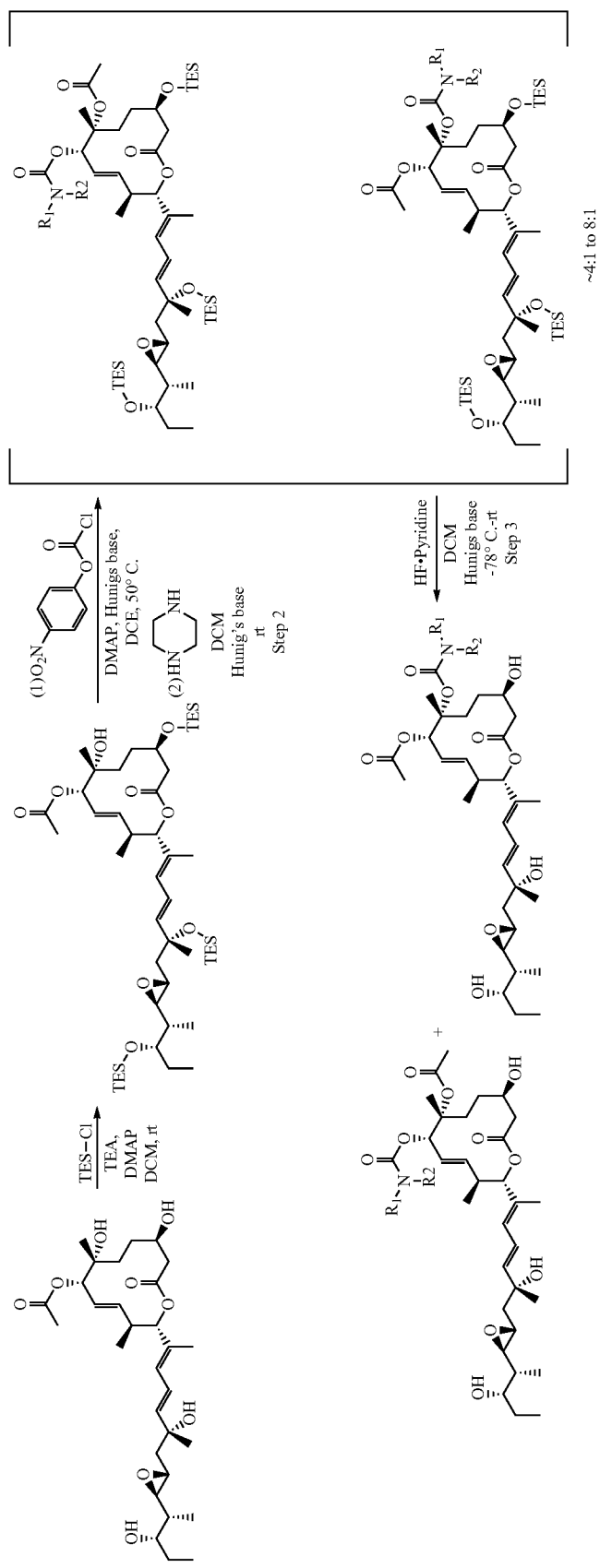

Step 2

To a solution of tri-TES Pladenolide D (1.0 equiv.) in 1,2-dichloroethane (0.2 M) at 20° C. was added DMAP (1.5 equiv.), triethylamine (30 equiv.) and 4-Nitrophenyl chloroformate (10 equiv.). The mixture was stirred at 40° C. for 4 days, and then for 2 h at 60° C. The reaction mixture was diluted with EtOAc and washed with water, then the layers were separated, and the aqueous layer was extracted with EtOAc (2×). The combined organic extracts were successively washed with water and brine, dried over magnesium sulfate, filtered and concentrated in vacuo. The resulting residue was purified by silica gel chromatography (EtOAc in Hexane) to afford the intermediate carbonate. Carbonate (1.0 equiv.), DCM (0.2M), triethylamine (3.0 equiv.), and amine (2.0 equiv.) were combined and stirred at RT for 1 hour. The resulting mixture was concentrated in vacuo and chromatographed (DCM/MeOH) to afford the carbamate intermdiate as a mixture of regioisomers.

Step 3

The mixture of regioisomeric carbamates obtained in Step 2 (1.0 equiv.) was dissolved in DCM (0.04 M). Hunig's base (124 equiv.) was added and the resulting mixture was cooled to −78° C. HF·Pyridine (30 equiv.) was added dropwise and the mixture was warmed to rt and stirred overnight at rt. The mixture was then cooled to −78° C. and saturated sodium bicarbonate was added dropwise to the reaction mixture and the mixture was warmed to rt. The organic layers were partioned and the aqueous layer was extracted with DCM (3×). The combined organic layers were dried over anhydrous sodium sulfate, filtered, and concentrated in vacuo. The resulting residue was subjected to reverse-phase HPLC purification to afford each of desired regioisomeric products.

D5

The title compound was prepared using 2,5-diazabicyclo [2.2.1]heptane in step 2 via the general procedure 1.3.2.1 step 2 & 3

Step 2

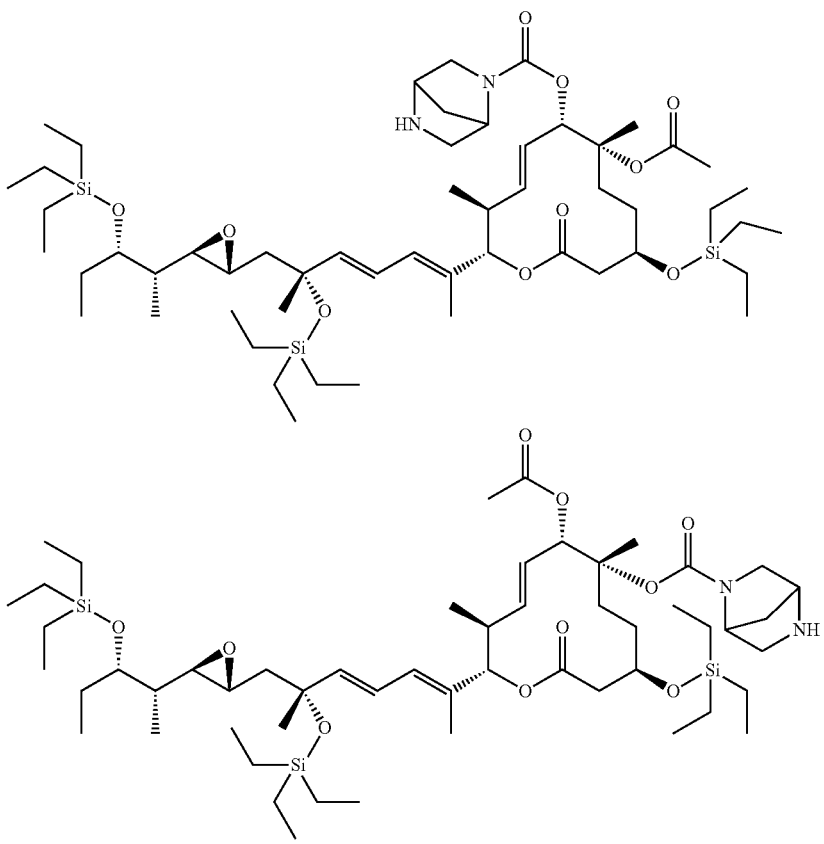

A mixture of (2S,3S,6S,7R,10R,E)-7-acetoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy) oxacyclododec-4-en-6-yl 2,5-diazabicyclo[2.2.1]heptane-2-carboxylate and (2S,3S,6S,7R,10R,E)-6-acetoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl) oxiran-2-yl)hepta-2,4-dien-2-yl)-12-oxo-10-((triethylsilyl) oxy)oxacyclododec-4-en-7-yl 2,5-diazabicyclo[2.2.1] heptane-2-carboxylate was obtained (21.7 mg, 45.1%) as a Colorless oil. LCMS (ESI, m/z), [M+H]*1020.6

$^1$H NMR (400 MHz, METHANOL-d) δ ppm 0.61-0.70 (m, 19H) 0.82-0.95 (m, 10H) 0.95-1.04 (m, 29H) 1.23 (br dd, J=7.15, 4.64 Hz, 1H)1.30 (s, 1H) 1.42-1.64 (m, 12H) 1.78 (s, 4H) 1.88-2.01 (m, 2H) 2.06 (br d, J=10.92 Hz, 3H) 2.14 (br s, 1H) 2.43 (br d, J=4.64 Hz, 2H) 2.49 (br s, 1H) 2.63 (dd, J=8.16, 2.13 Hz, 2H) 2.86-2.91 (m, 1H) 3.47-3.66

(m, 2H) 3.76 (td, J=6.37, 3.33 Hz, 1H) 3.95 (br d, J=4.27 Hz, 1H) 4.34 (br s, 1H) 6.15 (br d, J=10.92 Hz, 1H) 6.52 (dd, J=15.12, 10.98 Hz, 1H)

Step 3

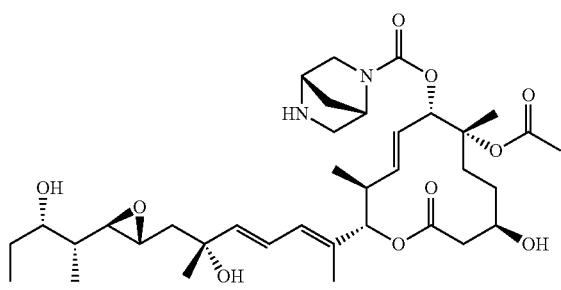

HPLC purification afforded (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl (1S,4S)-2,5-diazabicyclo[2.2.1]heptane-2-carboxylate (5 mg, 34.7%) as a white solid. LCMS (ESI, m/z), [M+H]+ 677.6

1H NMR (400 MHz, METHANOL-d4) δ ppm 0.85-0.98 (m, 9H) 1.25 (td, J=7.40, 4.14 Hz, 1H) 1.34 (s, 3H) 1.42-1.69 (m, 9H) 1.79 (s, 4H) 1.82-1.96 (m, 2H) 2.04 (d, J=9.29 Hz, 3H) 2.33 (br d, J=10.04 Hz, 1H) 2.47-2.54 (m, 2H) 2.57-2.72 (m, 2H) 2.87-2.92 (m, 1H) 3.03 (br s,2 H) 3.33-3.43 (m, 2H) 3.43-3.57 (m, 2H) 3.77-3.84 (m, 1H) 3.86-3.94 (m, 1H) 4.50 (br s, 1H) 4.97-5.11 (m, 2H) 5.60-5.68 (m, 1H) 5.73-5.82 (m, 1H) 5.88 (d, J=15.31 Hz, 1H) 6.15 (br d, J=11.04 Hz, 1H) 6.53 (dd, J=15.25, 10.98 Hz, 1H) 8.54 (s, 1H)

D4

The title compound was prepared using piperazine in step 2 via the general procedure 1.3.2.1 step 2 & 3

Step 2

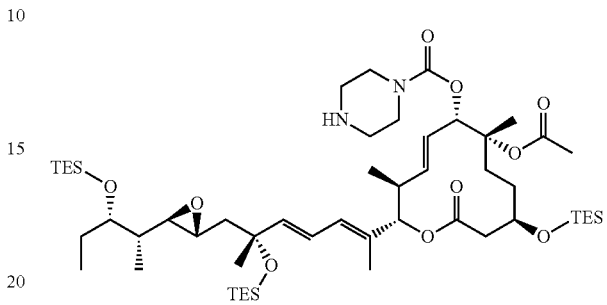

General procedure 1.3.2.1, step 2 employing piperazine afforded (2S,3S,6S,7R,10R,E)-7-acetoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl) hepta-2,4-dien-2-yl)-12-oxo-10-((triethylsilyl)oxy) oxacyclododec-4-en-6-yl piperazine-1-carboxylate (1.0 g, 0.844 mmol, 81% yield). LC/MS (ESI, m/z), 1008.1 [M+H]+.

Step 3

D4

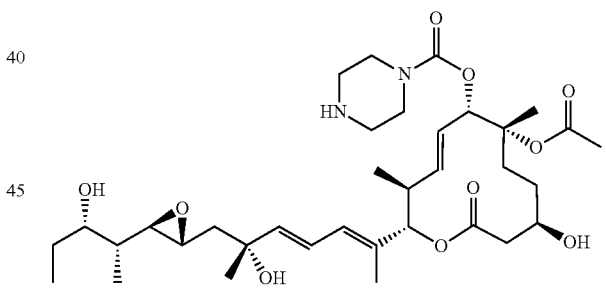

HPLC purification afforded (2S,3S,6S,7R,10R,E)-7-acetoxy-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate (225 mg, 36.8%). LC/MS (ESI, m/z), 665.6 [M+H]+.

1H-NMR (400 MHz, CHCl3-d): δ ppm 0.87-0.92 (m, 6H) 0.94 (t, J=7.40 Hz, 3H) 1.16-1.31 (m, 1H) 1.35 (s, 3H) 1.40-1.56 (m, 4H) 1.59 (s, 3H) 1.66 (br dd, J=14.68, 7.03 Hz, 3H) 1.76-1.80 (m, 3H) 1.87 (dd, J=14.12, 5.46 Hz, 1H) 2.05 (s, 3H) 2.30-2.41 (m, 1H) 2.50 (d, J=3.76 Hz, 2H) 2.56-2.72 (m, 2H) 2.90 (br d, J=2.01 Hz, 1H) 3.19 (br t, J=5.14 Hz, 4H) 3.50-3.59 (m, 1H) 3.71 (br s, 4H) 3.77-3.89 (m, 1H) 5.01 -5.13 (m, 2H) 5.58-5.71 (m, 1H) 5.71-5.81 (m, 1H) 5.88 (d, J=15.31 Hz, 1H) 6.15 (br d, J=10.79 Hz, 1H) 6.53 (dd, J=15.18, 10.92 Hz, 1H).

ADL1-D4

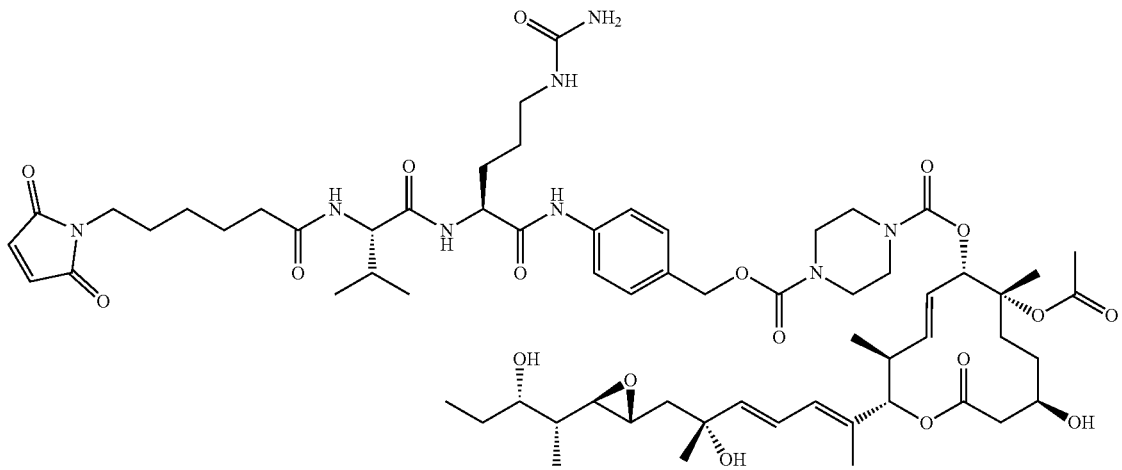

General procedure 1 (1.3.1) was employed for the preparation of ADL1-D4. Flash chromatography afforded ADL1-D4 (30.5 mg, 0.024 mmol, 77% yield).

LC/MS (ESI, m/z), 1263.8 [M+H]$^+$.

$^1$H-NMR (400 MHz, MeOH-d$_4$): δ ppm 0.87-0.93 (m, 7H) 0.93-1.01 (m, 8H) 1.19-1.34 (m, 4H) 1.50 (s, 3H) 1.57 (s, 5H) 1.58-1.70 (m, 6H) 1.70-1.77 (m, 1H) 1.78 (s, 3H) 1.83-1.95 (m, 2H) 2.04 (s, 3H) 2.05-2.13 (m, 1H) 2.27 (t, J=7.40 Hz, 2 H) 2.32-2.42 (m, 1H) 2.50 (d, J=3.64 Hz, 2H) 2.55-2.74 (m, 2H) 2.90 (td, J=5.83, 2.26 Hz, 1H) 3.03-3.26 (m, 2H) 3.35 (s, 13H) 3.42-3.61 (m, 11H) 3.80 (br dd, J=9.85, 3.58 Hz, 1H) 4.16 (d, J=7.40 Hz, 1H) 4.50 (dd, J=8.91, 5.14 Hz, 1H) 4.56 (s, 1H) 5.05 (dd, J=14.37, 10.10 Hz, 2H) 5.09 (s, 2H) 5.49 (s, 1H) 5.59-5.69 (m, 1H) 5.72-5.80 (m, 1H) 5.87 (d, J=15.18 Hz, 1H) 6.09-6.22 (m, 1H) 6.44-6.60 (m, 1H) 7.32 (d, J=8.66 Hz, 2H) 7.58 (d, J=8.53 Hz, 2H).

General procedure 1 (1.3.1) was employed for the preparation of ADL1-D5 using D5. Flash chromatography afforded (14 mg, 51.6% yield). LCMS (ESI, m/z), 1276.43 [M+H]+

1H NMR (400 MHz, METHANOL-d4) δ ppm 0.86-1.00 (m, 16H) 1.23-1.40 (m, 7H) 1.42-1.69 (m, 16H) 1.73-1.80 (m, 4H) 1.84-1.96 (m, 4H) 1.98-2.10 (m, 4H) 2.27 (t, J=7.40 Hz, 2H) 2.31-2.41 (m, 1H) 2.50 (br d, J=3.39 Hz, 2H) 2.56-2.64 (m, 1H) 2.64-2.72 (m, 1H) 2.80-2.93 (m, 1H) 3.12 (br d, J=6.90 Hz, 1H) 3.16-3.26 (m, 1H) 3.35-3.56 (m, 7H) 3.76-3.86 (m, 1H) 4.16 (d, J=7.40 Hz, 1H) 4.48-4.58 (m, 3H) 4.93-5.16 (m, 4H) 5.65 (br d, J=9.91 Hz, 1H) 5.70-5.82 (m, 1H) 5.88 (d, J=15.18 Hz, 1H) 6.14 (br d, J=11.04 Hz, 1H) 6.50-6.58 (m, 1H), 6.79 (s, 2H) 7.26-7.36 (m, 2H) 7.56-7.63 (m, 2H)

ADL1-D5

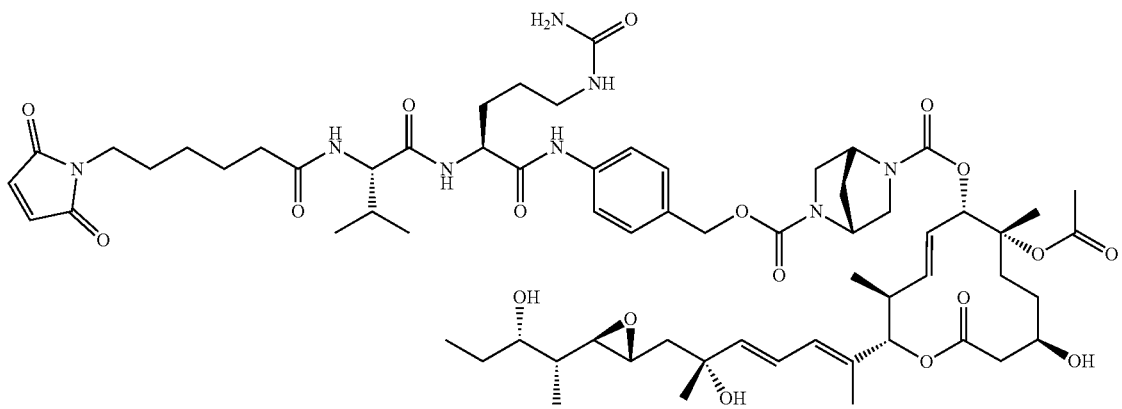

1.3.3 Synthesis of ADL22-D4

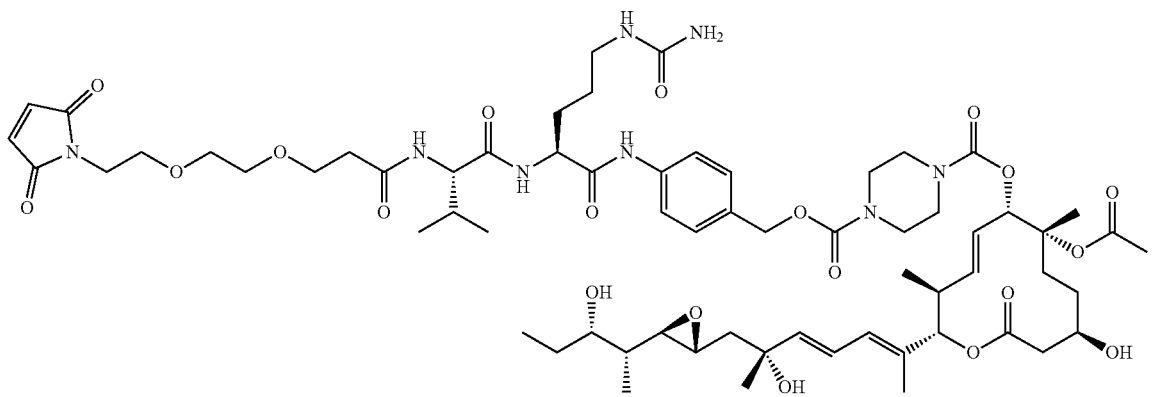 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2CCN(C(=O)OCc3ccc(NC(=O)[C@H](CCCNC(N)=O)NC(=O)[C@@H](NC(=O)CCOCCOCCN4C(=O)C=CC4=O)C(C)C)cc3)CC2)/C=C/[C@@H]1C]

To a solution of (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate (12 mg, 0.018 mmol) in DMF (2 mL) was added 4-((2S,5S)-15-(2,5-dioxo-2,5-dihydro-1H-pyrrol-1-yl)-5-isopropyl-4,7-dioxo-2-(3-ureidopropyl)-10,13-dioxa-3,6-diazapentadecanamido)benzyl (4-nitrophenyl) carbonate (16.98 mg, 0.022 mmol) and Hunig's base (7.00 mg, 0.054 mmol). The mixture was stirred for 1 h at 200 C. The mixture was concentrated in vacuo directly on to silica gel and purified by column chromatography (MeOH/DCM 0-20%) to provide 1-((2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl) 4-(4-((2S,5S)-15-(2,5-dioxo-2,5-dihydro-1H-pyrrol-1-yl)-5-isopropyl-4,7-dioxo-2-(3-ureidopropyl)-10,13-dioxa-3,6-diazapentadecanamido)benzyl) piperazine-1,4-dicarboxylate (12 mg, 9.16 μmol, 50.8% yield) as a white solid. LCMS (ESI, m/z), 1310.2 [M+H]+

Chemical Formula: $C_{65}H_{96}N_8O_{20}$ Molecular Weight: 1309.52

1H NMR (400 MHz, DMSO-d6) δ ppm 0.73-0.89 (m, 17H) 1.03-1.13 (m, 1H) 1.21-1.25 (m, 4H) 1.25-1.40 (m, 5H) 1.42-1.47 (m, 4H) 1.48, (br s, 3H) 1.69 (s, 4H) 1.73-1.83 (m, 1H) 1.99 (s, 2H) 2.10-2.25 (m, 1H) 2.36 (br s, 3H) 2.40-2.48 (m, 2H) 2.54-2.66 (m, 2H) 2.72-2.80, (m, 1H) 2.88-3.08 (m, 2H) 3.34-3.44 (m, 9H) 3.44-3.48 (m, 3H) 3.48-3.52 (m, 2H) 3.52-3.59 (m, 3H) 3.64-3.75 (m, 1H) 4.24 (s, 1H), 4.40 (br d, J=5.65 Hz, 2H) 4.62 (d, J=5.02 Hz, 1H) 4.80-4.85 (m, 1H) 4.90 (br d, J=9.03 Hz, 2H) 5.01 (s, 2H) 5.40 (s, 2H) 5.48-5.57 (m, 1H), 5.66-5.76 (m, 1H) 5.81-5.91 (m, 1H) 5.94-6.01 (m, 1H) 6.02-6.11 (m, 1H) 6.36-6.45 (m, 1H) 7.02 (s, 2H) 7.27-7.33 (m, 2H) 7.58 (s, 2H) 7.81-7.89 (m, 1H) 8.11 (br d, J=7.40 Hz, 1H) 9.96-10.02 (m, 1H)

1.3.4 General Procedure for Synthesis of ADL21-D12, ADL21-D1, ADL21-D4

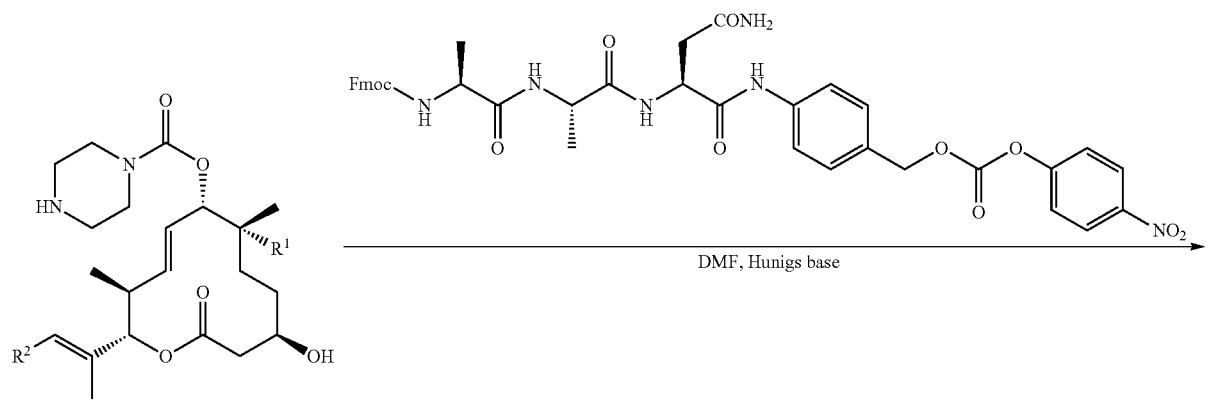

-continued

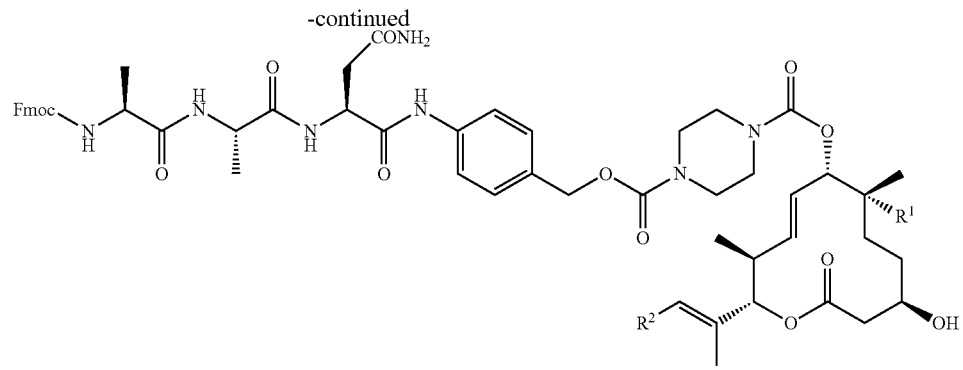

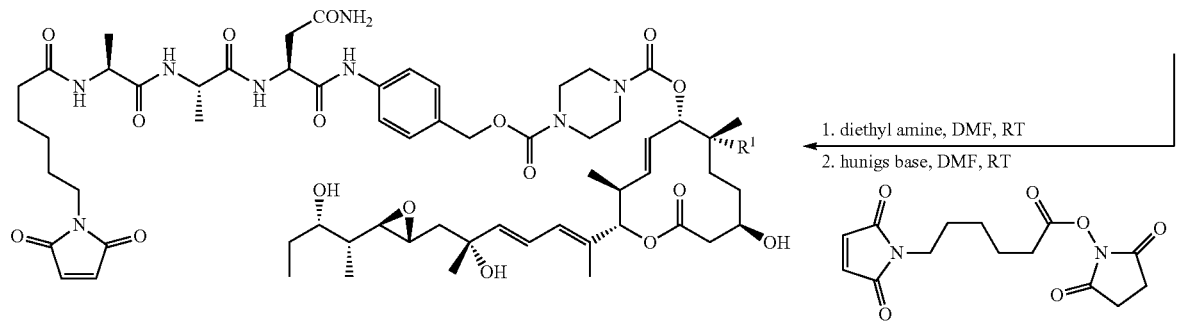

Step 1

The Payload (1.0 equiv) and (9H-fluoren-9-yl)methyl ((S)-1-(((S)-1-(((S)-4-amino-1-((4-(((((4-nitrophenoxy)carbonyl)oxy)methyl)phenyl)amino)-1,4-dioxobutan-2-yl)amino)-1-oxopropan-2-yl)amino)-1-oxopropan-2-yl)carbamate (1.0 equiv.) were dissolved in DMF (0.1M) and Hunig's Base (3.0 euiv.) was added. The reaction mixture was stirred at RT for 30 minutes after which the reaction was concetrated to in vacuo and the resulting residue was chromatographed (MeOH/DCM) to afford the desired product.

Step 2 and 3 fmoc-Ala-Ala-Aspargine PABC payload (1.0 equiv.), was dissolved in N,N-dimethylformamide (0.05 M), then diethylamine (6.0 equiv.) was added. The reaction was stirred at RT for 1 hour and the mixture evaporated to dryness. The crude product was diluted with N,N-dimethylformamide (0.05 M). 2,5-dioxopyrrolidin-1-yl 6-(2,5-dioxo-2,5-dihydro-1H-pyrrol-1-yl)hexanoate (1.2 equiv.) and Hunig's base (2.5 equiv.) were added to the mixture and stirred at RT for 1 ixture was then concentrated in vacuo and the resulting residue was purified via reverse-phour. The mhase HPLC to afford the desired Maleimidocaprolyl Ala-Ala-Aspargine PABC linker payload.

1.3.4.1 ADL21-D1

Step 1

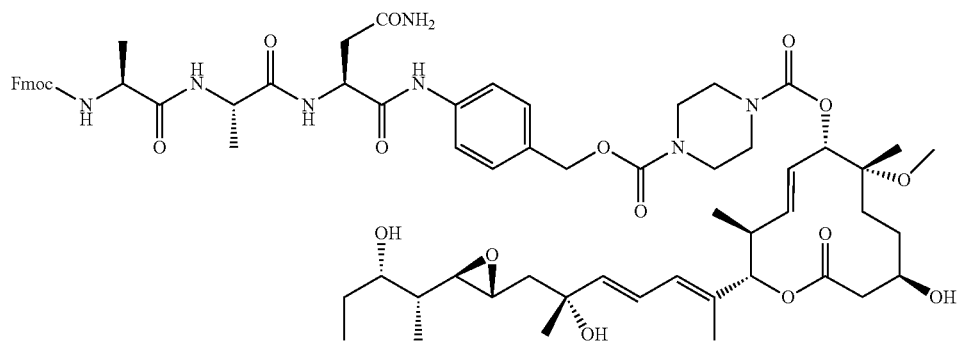

1-(4-(((5S,8S,11S)-11-(2-amino-2-oxoethyl)-1-(9H-fluoren-9-yl)-5,8-dimethyl-3,6,9-trioxo-2-oxa-4,7,10-triazadodecan-12-amido)benzyl) 4-((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl) piperazine-1,4-dicarboxylate (140.2 mg, 71.9%) LCMS (ESI, m/z) 1265.6 [M+H]+

Chemical Formula: $C_{67}H_{89}N_7O_{17}$
Molecular Weight: 1264.48

Steps 2 and 3:

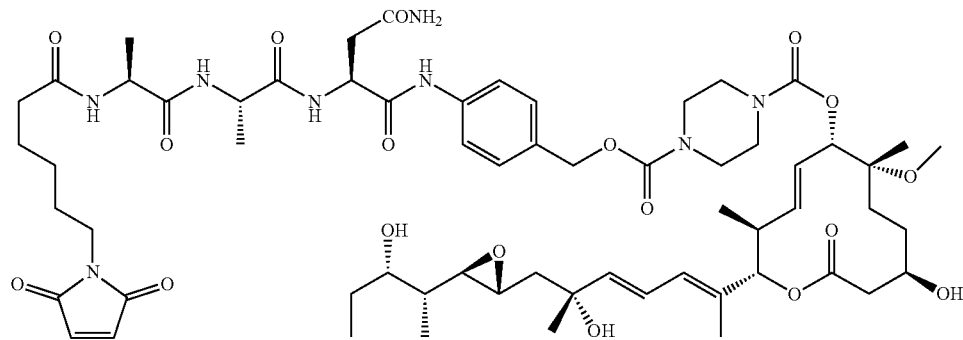 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)OCc3ccc(NC(=O)[C@H](CC(N)=O)NC(=O)[C@H](C)NC(=O)[C@H](C)NC(=O)CCCCCN4C(=O)C=CC4=O)cc3)CC2)/C=C/[C@@H]1C]

1-(4-(((S)-4-amino-2-((S)-2-((S)-2-(6-(2,5-dioxo-2,5-dihydro-1H-pyrrol-1-yl)hexanamido)propanamido)propanamido)-4-oxobutanamido)benzyl) 4-((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl) piperazine-1,4-dicarboxylate (49.1 mg, 35.8%) LCMS (ESI, m/z) 1258.19 [M+Na]+

$^1$H NMR (400 MHz, METHANOL-d4) δ ppm 0.85-0.98 (m, 10H) 1.22 (s, 4H) 1.26-1.45 (m, 14H) 1.45-1.69 (m, 12H) 1.79 (s, 3H) 1.90 (s, 2H) 2.20-2.27 (m, 2H) 2.52 (br dd, J=10.10, 3.70 Hz, 3H) 2.67 (br d, J=2.13 Hz, 1H) 2.85 (t, J=6.15 Hz, 3H) 3.14 (t, J=1.57 Hz, 1H) 3.41-3.57, (m, 14H) 3.78-3.88 (m, 1H) 4.27 (dd, J=12.36, 7.09 Hz, 2H) 4.77 (s, 1H) 4.97-5.13 (m, 6H) 5.51-5.64 (m, 1H) 5.72 (br d, J=9.66 Hz, 1H), 5.88 (d, J=15.43 Hz, 1H) 6.12-6.17 (m, 1H) 6.47-6.61 (m, 1H) 6.79 (s, 2H) 7.33 (m, J=8.66 Hz, 2H), 7.68 (m, J=8.66 Hz, 2H)

1.3.4.2 ADL21-D4 Step 1

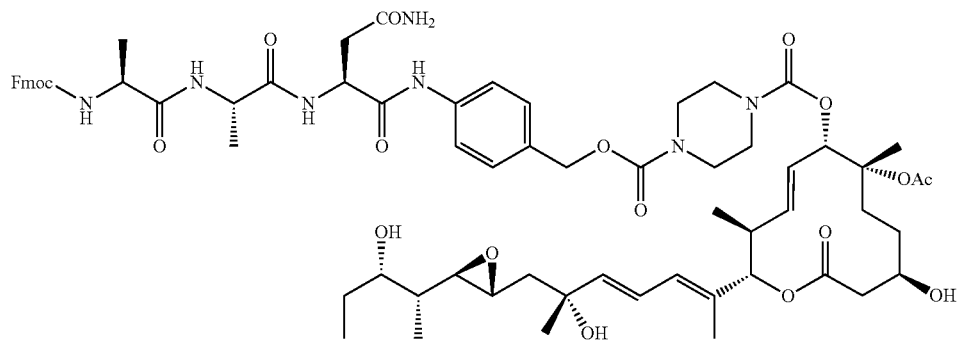

1-((2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl) 4-(4-((5S,8S,11S)-11-(2-amino-2-oxoethyl)-1-(9H-fluoren-9-yl)-5,8-dimethyl-3,6,9-trioxo-2-oxa-4,7,10-triazadodecan-12-amido)benzyl) piperazine-1,4-dicarboxylate (125 mg, 85.6%) LCMS (ESI, m/z) 1293.4 [M+H]+

Steps 2 and 3

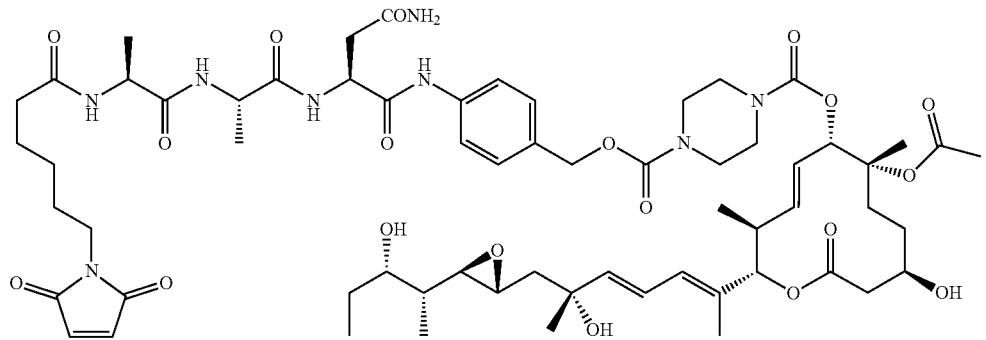 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2CCN(C(=O)OCc3ccc(NC(=O)[C@H](CC(N)=O)NC(=O)[C@H](C)NC(=O)[C@H](C)NC(=O)CCCCCN4C(=O)C=CC4=O)cc3)CC2)/C=C/[C@@H]1C]

1-((2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl) 4-(4-((S)-4-amino-2-((S)-2-((S)-2-(6-(2,5-dioxo-2,5-dihydro-1H-pyrrol-1-yl)hexanamido)propanamido)propanamido)-4-oxobutanamido)benzyl) piperazine-1,4-dicarboxylate (35 mg, 80%) LCMS (ESI, m/z) 1285.0 [M+Na]+

$^1$H NMR (400 MHz, DMSO-d6) δ ppm 0.71-0.87 (m, 9H) 1.04-1.12 (m, 1H) 1.14-1.26 (m, 13H) 1.27-1.40 (m, 3H) 1.40-1.52 (m, 9H) 1.52-1.62 (m, 1H) 1.69 (s, 3H) 1.74-1.83 (m, 1H) 1.99 (d, J=4.27 Hz, 4H) 2.03-2.14 (m, 2H) 2.15-2.26 (m, 1H) 2.31-2.41 (m, 2H) 2.54-2.65 (m, 4H) 2.72-2.80 (m, 1H) 3.17 (d, J=5.27 Hz, 3H) 3.36 (br s, 9H) 3.63-3.74 (m, 1H) 3.99-4.12 (m, 2H) 4.14-4.22 (m, 1H) 4.23-4.30 (m, 1H) 4.40 (d, J=5.65 Hz, 1H) 4.55-4.65 (m, 2H) 4.82 (s, 1H) 4.87-4.93 (m, 2H) 5.01 (s, 2H) 5.47-5.57 (m, 1H) 5.66-5.77 (m, 1H) 6.01-6.09 (m, 1H) 6.35-6.45 (m, 1H) 6.89-6.96 (m, 1H) 6.99 (s, 2H) 7.30 (d, J=8.66 Hz, 2H) 7.36-7.42 (m, 1H) 7.62 (s, 2H) 7.97-8.21 (m, 3H), 9.62-9.72 (m, 1H).

1.3.5 ADL21-D12

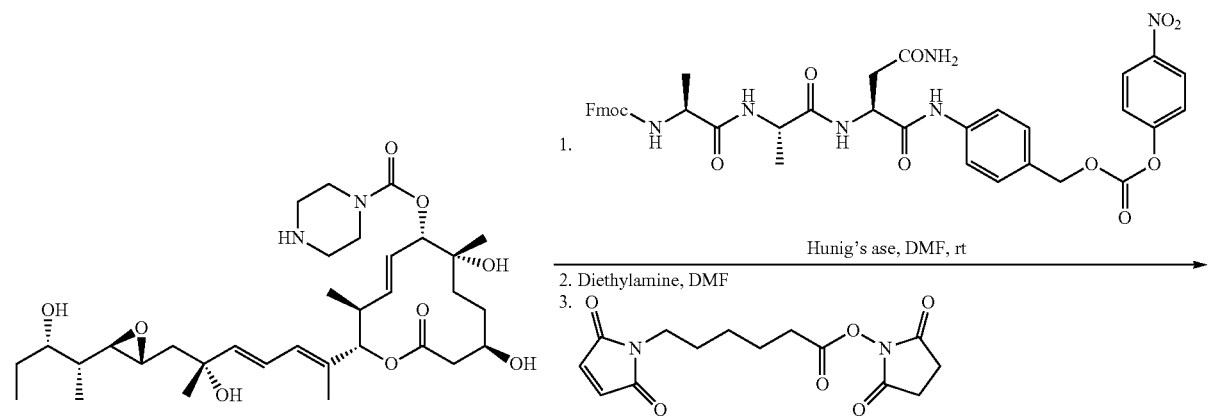

-continued

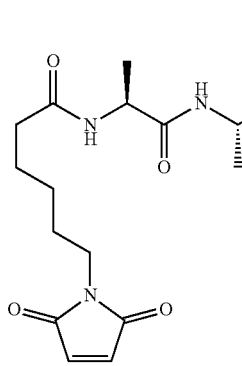
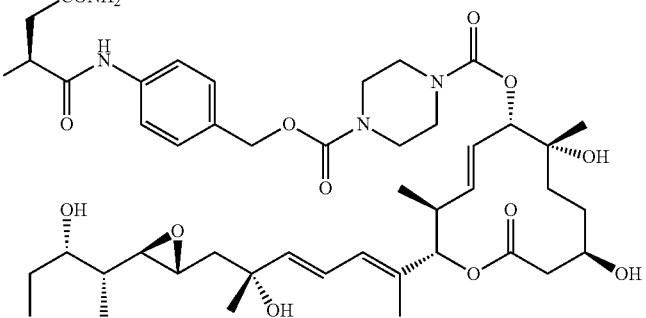

To a solution of (2S,3S,6S,7R,10R,E)-7,10-dihydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate (50 mg, 0.08 mmol) in DMF (1 mL) was added (9H-fluoren-9-yl)methyl ((S)-1-(((S)-1-(((S)-4-amino-1-((4-((((4-nitrophenoxy)carbonyl)oxy)methyl)phenyl)amino)-1,4-dioxobutan-2-yl)amino)-1-oxopropan-2-yl)amino)-1-oxopropan-2-yl)carbamate (73.9 mg, 0.096 mmol) followed by N-ethyl-N-isopropylpropan-2-amine (104 mg, 0.803 mmol). The reaction mixture was stirred for 1h. The reaction mixture was concentrated to dryness and purified by silica gel column chromatography. The fractions containing the desired compound were concentrated to provide a clear oil that was carried on directly to the following step assuming 100% yield. The oil obtained was then dissolved in DMF (2 mL) and charged with diethylamine (58.7 mg, 0.803 mmol). The resulting mixture was stirred 1h at 200C and concentrated in vacuo. The residue residue was re-dissolved in DMF (1 mL) and then 2,5-dioxopyrrolidin-1-yl 6-(2,5-dioxo-2,5-dihydro-1H-pyrrol-1-yl)hexanoate (32.2 mg, 0.104 mmol) and N-ethyl-N-isopropylpropan-2-amine (104 mg, 0.803 mmol) were added. The resulting mixure was stirred for 1h. The reaction mixture was concentrated to dryness and purified under reverse-phase HPLC to furnish 1-(4-((S)-4-amino-2-((S)-2-((S)-2-(6-(2,5-dioxo-2,5-dihydro-1H-pyrrol-1-yl)hexanamido)propanamido)propanamido)-4-oxobutanamido)benzyl) 4-((2S,3S,6S,7R,10R,E)-7,10-dihydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl) piperazine-1,4-dicarboxylate (7.5 mg, 6.14 μmol, 7.65% yield) as a white solid. LCMS (ESI, m/z) 1222.28 [M+H]+

1.3.6 ADL21-D8

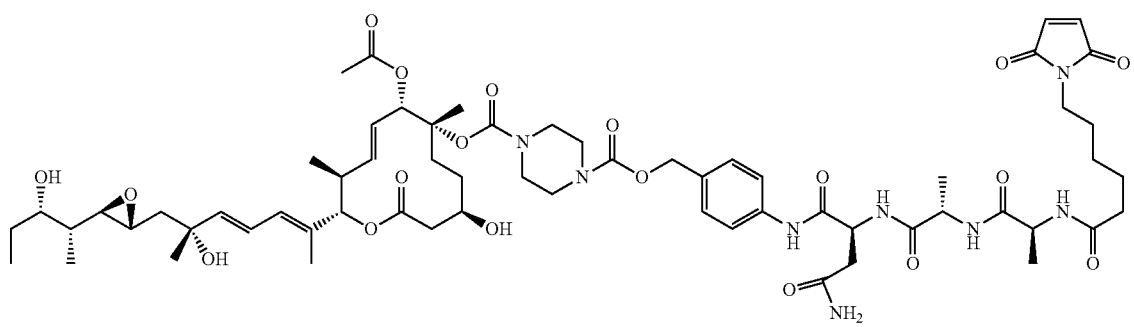 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(=O)N2CCN(C(=O)OCc3ccc(NC(=O)[C@H](CC(N)=O)NC(=O)[C@H](C)NC(=O)[C@H](C)NC(=O)CCCCCN4C(=O)C=CC4=O)cc3)CC2)[C@@H](OC(C)=O)/C=C/[C@@H]1C]

To a solution of (2S,3S,6S,7R,10R,E)-6-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-7-yl piperazine-1-carboxylate (27.0 mg, 0.041 mmol) in DMF was added (9H-fluoren-9-yl)methyl ((S)-1-(((S)-1-(((S)-4-amino-1-((4((((4nitrophenoxy)carbonyl)oxy)methyl)phenyl)amino)-1,4-dioxobutan-2-yl)amino)-1-oxopropan-2-yl)amino)-1-oxopropan-2-yl)carbamate (40.5 mg, 0.053 mmol) followed Hunig's base (36.2 µl, 0.203 mmol). After stirring for 20 minutes at rt, the mixture was then concentrated in vacuo and the resulting residue was purified by column chromatography (0-20% MeOH/DCM) to afford the desired intermediate. The residue was then combined with DMF (2 mL) and diethylamine (29.7 mg, 0.406 mmol) and stirred for 20 minutes at rt. Subsequently, the mixture was concentrated in vacuo and the resulting residue was re-dissolved in DMF (2 ml) and treated with 2,5-dioxopyrrolidin-1-yl 6-(2,5-dioxo-2,5-dihydro-1H-pyrrol-1-yl)hexanoate (16.28 mg, 0.053 mmol) and Hunig's base (36.2 µl, 0.203 mmol). The resulting mixture was stirred for 20 minutes before concentrating to dryness and purifying the resulting residue by column chromatography with the intermediate eluting in a 0-20% MeOH/DCM gradient. The residue obtained was then subjected to reverese phase HPLC purification to afford 1-((2S,3S,6S,7R,10R,E)-6-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-7-yl) 4-(4-((S)-4-amino-2-((S)-2-((S)-2-(6-(2,5-dioxo-2,5-dihydro-1 H-pyrrol-1-yl)hexanamido)propanamido)propanamido)-4-oxobutanamido)benzyl) piperazine-1,4-dicarboxylate (3.5 mg, 2.77 µmol, 6.82% yield) isolated as a white solid. 1-((2S,3S,6S,7R,10R,E)-6-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-7-yl) 4-(4-((S)-4-amino-2-((S)-2-((S)-2-(6-(2,5-dioxo-2,5-dihydro-1 H-pyrrol-1-yl)hexanamido)propanamido)propanamido)-4-oxobutanamido)benzyl) piperazine-1,4-dicarboxylate (3.5 mg, 6.8%) LCMS (ESI, m/z) 1285.60 [M+Na]+

$^1$H NMR: 0.68-0.90 (m, 11H) 1.03-1.13 (m, 2H) 1.15-1.26 (m, 14H) 1.24-1.38 (m, 4H) 1.40-1.63 (m, 12H), 1.69 (s, 3H) 1.74-1.83 (m, 1H) 2.03 (s, 3H) 2.06-2.12 (m, 2H) 2.24-2.41 (m, 3H) 2.53-2.63 (m, 4H), 3.79-3.80 (m, 1H) 4.13-4.30 (m, 2H) 4.32-4.33 (m, 1H) 4.33-4.47 (m, 1H) 4.44-4.48 (m, 1H) 4.52-4.73 (m, 2H) 4.74-4.97 (m, 2H) 5.03 (s, 3H) 5.47-5.61 (m, 1H) 5.65-5.77 (m, 1H) 5.79-5.92 (m, 1H) 5.98-6.12 (m, 1H) 6.30-6.46 (m, 1H) 6.75-6.85 (m, 1H) 6.90-6.95 (m, 1H) 6.99 (s, 1H) 7.26-7.36 (m, 2H) 7.37-7.46 (m, 1H) 7.56-7.73 (m, 2H) 7.90-8.09 (m, 1H) 8.07-8.22 (m, 2H) 8.46 (s, 1H) 9.59-9.78 (m, 1H)

1.3.7 Preparation of DBCO-Val-Cit-pABC linker-payload, ADL25-D4

To a solution of 3-amino-1-(11,12-dihydrodibenzo[b,f]azocin-5(6H)-yl)propan-1-one (19.36 mg, 0.07 mmol) in DCM (5 mL) at 0° C. was added Hunig's base (10.26 mg, 0.079 mmol) followed by 4-nitrophenyl carbonochloridate (14.12 mg, 0.07 mmol). The reaction was warmed to 20° C. and stirred for 2 h. The mixture was then concentrated to dryness and diluted with DMF. The resulting mixture was charged Hunig's base (10.26 mg, 0.079 mmol) and 1-((2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl) 4-(4-((S)-2-((S)-2-amino-3-methylbutanamido)-5-ureidopentanamido)benzyl) piperazine-1,4-dicarboxylate (50 mg, 0.047 mmol) and stirred for 1h. The mixture was then concentrated to dryness and purified by column chromatography followed by reverese-phase purification to afford 1-((2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl) 4-(4-((9S,12S)-9-isopropyl-3,7,10-trioxo-12-(3-ureidopropyl)-2,6,8,11-tetraazatridecan-13-dibenzenecyclooctyneamido)benzyl) piperazine-1,4-dicarboxylate (5.3 mg, 8.27%) LCMS (ESI, m/z) 1372.7 [M]$^+$

1.3.8. Preparation of Maleimido-Glu-Val-Cit-pABC Linker-Payload

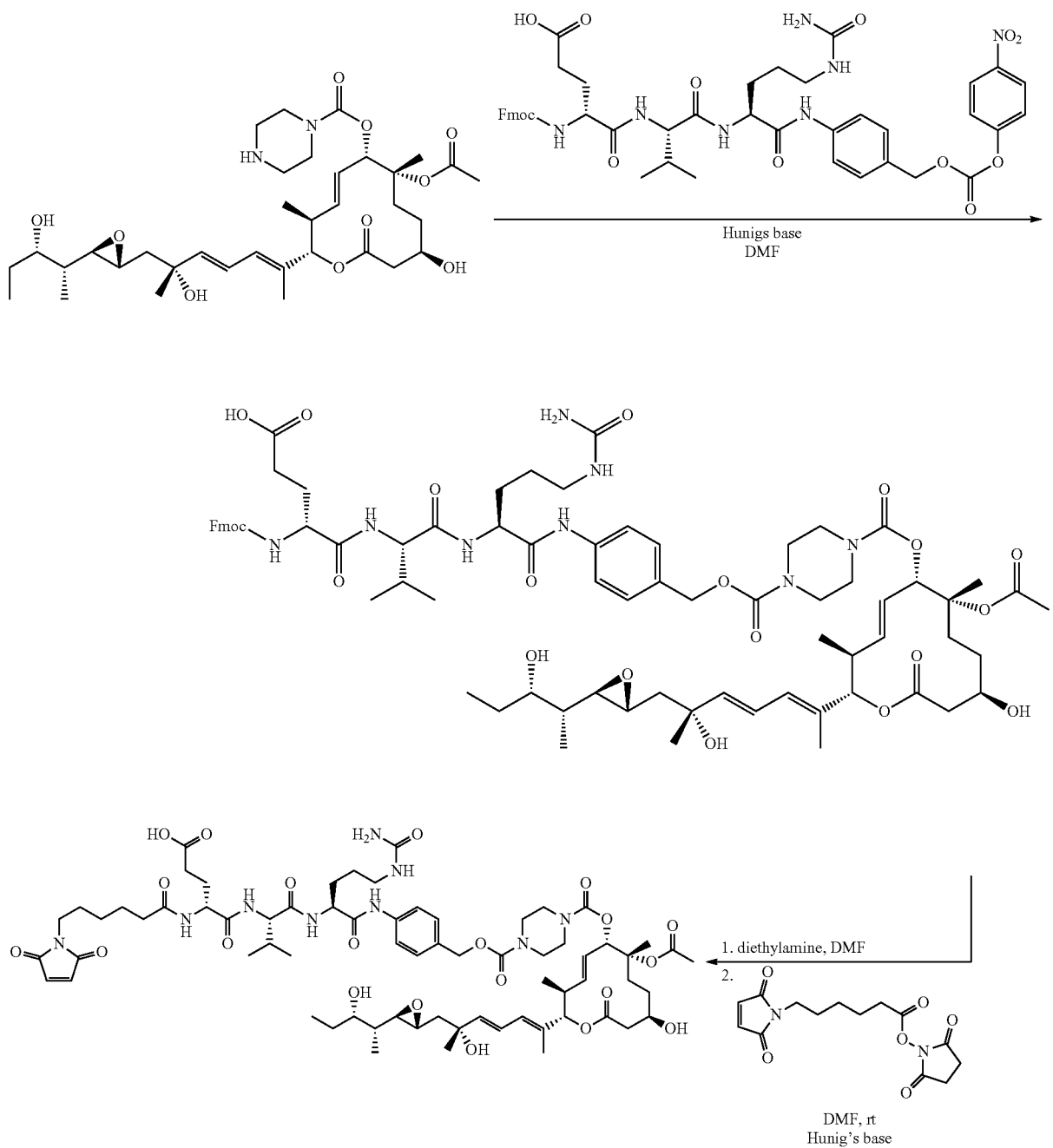

To a solution of (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate (20 mg, 0.03 mmol) in DMF (1 mL) was added (S)-4-((((9H-fluoren-9-yl)methoxy)carbonyl)amino)-5-(((S)-3-methyl-1-(((S)-1-((4-((((4-nitrophenoxy)carbonyl)oxy)methyl)phenyl)amino)-1-oxo-5-ureidopentan-2-yl)amino)-1-oxobutan-2-yl)amino)-5-oxopentanoic acid (32.3 mg, 0.036 mmol) and Hunig's base (11.66 mg, 0.09 mmol) and stirred 1h at 20° C. Diethylamine (110 mg, 1.504 mmol) was then added and the mixture was stirred for an additional 30 min at 20° C. The mixture was then diluted with ethyl acetate and concentrated in vacuo. The resulting residue was diluted with DMF (1 mL), 2,5-dioxopyrrolidin-1-yl-6-(2,5-dioxo-2,5-dihydro-1H-pyrrol-1-yl)hexanoate (13.91 mg, 0.045 mmol) and Hunig's base (11.66 mg, 0.09 mmol) and the reaction stirred 50 minutes. The reaction mixture was then diluted with ethyl acetate, concentrated to dryness and purified using reverse-phase HPLC to furnish (S)-5-(((S)-1-(((S)-1-((4-(((4-((((2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl)oxy)carbonyl)piperazine-1-carbonyl)oxy)methyl)phenyl)amino)-1-oxo-5-ureidopentan-2-yl)amino)-3-methyl-1-oxobutan-2-yl)amino)-4-(6-(2,5-dioxo-2,5-dihydro-1H-pyrrol-1-yl)hexanamido)-5-oxopentanoic acid (9.3 mg, 6.68 µmol, 22.20% yield) as a white solid; LCMS (ESI, m/z) 1393.4 [M+H]+

¹H NMR (400 MHz, DMSO-d6) δ ppm 0.74-0.89 (m, 16H) 1.03-1.66 (m, 25H) 1.69 (s, 4H) 1.74-1.94 (m, 2H) 2.00 (s, 4H) 2.09 (br d, J=4.39 Hz, 2H) 2.21 (br d, J=7.53 Hz, 3H) 2.31-2.42 (m, 2H) 2.53-2.84 (m, 3H) 2.89-3.09 (m, 2H) 3.34-3.48 (m, 10H) 3.65-3.74 (m, 1H) 4.19, (dd, J=8.47, 6.59 Hz, 1H) 4.26-4.45 (m, 3H) 4.57 -4.64 (m, 1H) 4.79-4.85 (m, 1H) 4.90 (br d, J=9.03 Hz, 2H) 5.01 (s, 2H) 5.43 (br s, 2 H), 5.47-5.59 (m, 1H) 5.67-5.80 (m, 1H) 5.81-5.93 (m, 1H) 5.94-6.14 (m, 2H) 6.35-6.47 (m, 1H) 6.99 (s, 2H) 7.30 (d, J=8.66 Hz, 2H) 7.58, (d, J=8.53 Hz, 2H) 7.63 -7.71 (m, 1H) 7.98-8.06 (m, 1H) 8.15-8.27 (m, 1H) 9.99-10.09 (m, 1H)

1.3.10. ADL1-D3, ADL10-D3

The payload D3 was prepared via the procedure given below

D3

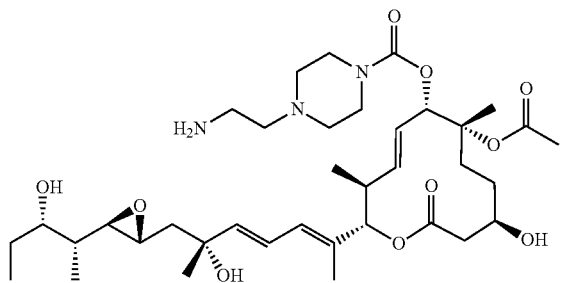

To a mixture of (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate (55 mg, 0.083 mmol) in DCM (3 mL) was added (9H-fluoren-9-yl)methyl (2-oxoethyl)carbamate (46.5 mg, 0.165 mmol) and Sodium triacetoxy borohydride (52.6 mg, 0.248 mmol). The reaction was stirred for 20 minutes at rt. The reaction mixture was then concentrated to dryness and purified by silica gel column chromatography (0-10% MeOH/DCM). The purified material was dissolved in DMF (3 mL). The mixture was then charged with diethylamine (121 mg, 1.655 mmol) and stirred at rt. The mixture was then concentrated in vacuo and purified via reverse phase HPLC purification to afford (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-aminoethyl)piperazine-1-carboxylate (6 mg, 8.48 µmol, 10.25% yield) as a white solid.

LCMS (ESI, m/z), 708.2 [M+H]+

¹H NMR (400 MHz, DMSO-d6) δ ppm 0.74-0.86 (m, 9H) 1.04-1.15 (m, 1H) 1.23 (s, 3H) 1.26-1.40 (m, 3H) 1.45 (s, 4H) 1.47-1.51 (m, 1H), 1.52-1.63 (m, 1H) 1.69 (s, 3H) 1.73-1.82 (m, 1H) 1.99 (s, 3H) 2.13-2.42 (m, 9H) 2.53-2.65 (m, 4H) 2.72-2.80 (m, 1H), 3.35-3.41 (m, 3H) 3.65-3.76 (m, 1H) 4.36-4.46 (m, 1H) 4.57-4.66 (m, 1H) 4.79-4.85 (m, 1H) 4.87-4.95 (m, 2H) 5.43-5.56 (m, 1H) 5.64-5.77 (m, 1H) 5.80-5.91 (m, 1H) 6.01-6.12 (m, 1H) 6.33-6.49 (m, 1H).

1.3.10.1 ADL10-D3

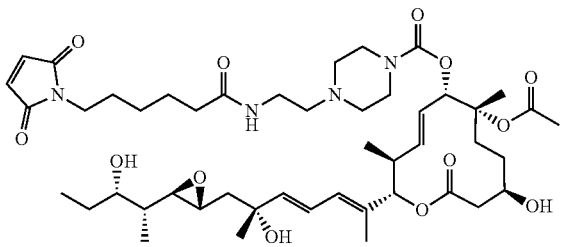 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2CCN(CCNC(=O)CCCCCN3C(=O)C=CC3=O)CC2)/C=C/[C@@H]1C]

To a solution of (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-aminoethyl)piperazine-1-carboxylate (40 mg, 0.057 mmol) in DMF (2 mL) was added 2,5-dioxopyrrolidin-1-yl 6-(2,5-dioxo-2,5-dihydro-1H-pyrrol-1-yl)hexanoate (27.9 mg, 0.09 mmol) followed by Hunig'a base (36.5 mg, 0.283 mmol) and stirred for 20 minutes. The resulting mixture was then concentrated onto silica gel and purified via column chromatography (0-20% MeOH/DCM) to provide (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-(6-(2,5-dioxo-2,5-dihydro-1H-pyrrol-1-yl)hexanamido)ethyl)piperazine-1-carboxylate (22 mg, 43.2% yield) as a yellowish solid.

LCMS (ESI, m/z) 902.1 [M+H]+

¹H NMR (400 MHz, DMSO-d6) δ ppm 0.73-0.89 (m, 10H) 0.99-1.29 (m, 10H) 1.30-1.38 (m, 2H) 1.40-1.49 (m, 9H) 1.52-1.64 (m, 1H), 1.69 (s, 3H) 1.74-1.83 (m, 1H) 1.93-2.07 (m, 5H) 2.34 (br d, J=16.94 Hz, 9H) 2.59 (s, 3H) 3.07-3.21 (m, 2H) 3.36 (br d, J=14.05 Hz, 3H) 3.66-3.78 (m, 1H) 3.47-4.45 (m, 1H) 4.57-4.66 (m, 1H) 4.79-4.86 (m, 1H) 4.87-4.97 (m, 2H) 5.46-5.57 (m, 1H) 5.66-5.75 (m, 1H) 5.81-5.91 (m, 1H) 5.99-6.13 (m, 1H) 6.31-6.47 (m, 1H) 7.00 (s, 2H) 7.62-7.71 (m, 1H)

1.3.10.2 ADL1-D3

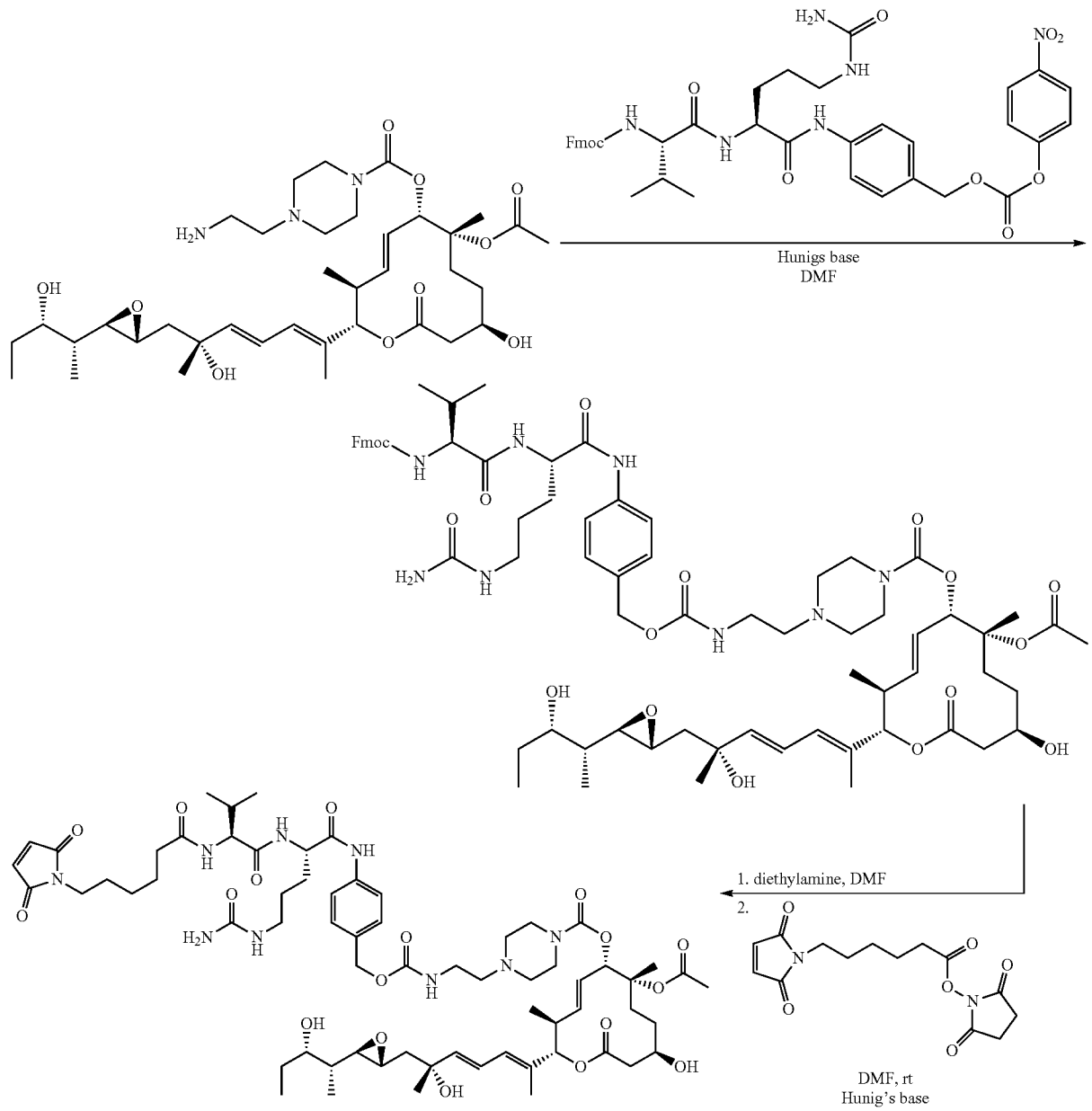

To a solution of (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-aminoethyl)piperazine-1-carboxylate (30 mg, 0.042 mmol) in DMF (2 mL) was added (9H-fluoren-9-yl)methyl ((S)-3-methyl-1-(((S)-1-((4-((((4-nitrophenoxy)carbonyl)oxy)methyl)phenyl)amino)-1-oxo-5-ureidopentan-2-yl)amino)-1-oxobutan-2-yl)carbamate (35.7 mg, 0.047 mmol) followed by Hunig's base (16.43 mg, 0.127 mmol) and mixture allowed to stirfor 1 h. The resulting mixture was concentrated directly on to silica gel and purified by silica gel column chromatography to provide (2S,3S,6S,7R,10R, E)-7-acetoxy-10-hydroxy-2-((R,2E,4E)-6-hydroxy-7-((2R, 3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-((((4-((S)-2-((S)-2-((((9H-fluoren-9-yl)methoxy)carbonyl)amino)-3-methylbutanamido)-5-ureidopentanamido)benzyl)oxy)carbonyl)amino)ethyl)piperazine-1-carboxylate which was carried on directly to following step directly. To a solution of (2S,3S,6S,7R,10R, E)-7-acetoxy-10-hydroxy-2-((R,2E,4E)-6-hydroxy-7-((2R, 3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-((((4-((S)-2-((S)-2-((((9H-fluoren-9-yl)methoxy)carbonyl)amino)-3-methylbutanamido)-5-ureidopentanamido)benzyl)oxy)carbonyl)amino)ethyl)piperazine-1-carboxylate (30 mg, 0.022 mmol) in DMF (2 mL) was added diethylamine (82 mg, 1.123 mmol) and mixture allowed to stir 1 h at 20° C. The resulting mixture was diluted with ethyl acetate and concentrated in vacuo. The resulting residue was then re-dissolved in DMF and charged with 2,5-dioxopyrrolidin-1-yl 6-(2,5-dioxo-2,5-dihydro-1H-pyrrol-1-yl)hexanoate (8.31 mg, 0.027 mmol) and Hunig's base (8.71 mg, 0.067 mmol). The resulting mixture stirred 1h at 20° C. The solution was then concentrated on to silica gel and purified by column chromatography (0-20% MeOH/DCM) to provide (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)amino)ethyl)piperazine-1-carboxylate (25 mg, 0.019 mmol, 85% yield) as a white solid; LC/MS (ESI, m/z), 1306.2 [M]$^+$.

$^1$H NMR (400 MHz, DMSO-d$_6$) δ ppm 0.75-0.89 (m, 18H) 1.05-1.12 (m, 1H) 1.15-1.20 (m, 1H) 1.21-1.26 (m, 4H) 1.26-1.39 (m, 5H) 1.40-1.40 (m,1 H) 1.42-1.47 (m, 5H) 1.57 (br s, 3H) 1.69 (s, 4H) 1.73-1.81 (m, 1H) 1.92-1.98 (m, 1H) 1.99 (d, J=4.39 Hz, 4H) 2.14-2.26 (m, 1H) 2.29-2.42 (m, 4H) 2.42-2.47 (m, 1H) 2.53-2.64 (m, 2H) 2.73-2.78 (m, 1H) 2.88-3.08 (m, 2H) 3.35-3.60 (m, 19H) 3.65-3.75 (m, 1H) 4.22 (dd, J=8.47, 6.71 Hz, 1H) 4.32-4.45 (m, 2H) 4.60-4.65 (m, 1H) 4.79-4.85 (m, 1H) 4.90 (br d, J=9.03 Hz, 2H) 5.01 (s, 2H) 5.40 (s, 2H) 5.47-5.58 (m, 1H) 5.66-5.77 (m, 1H) 5.87 (s, 1H) 5.97 (s, 1H) 6.03-6.13 (m, 1H) 6.35-6.45 (m, 1H) 7.02 (s, 2H) 7.30 (d, J=8.53 Hz, 2H) 7.59 (d, J=8.53 Hz, 2H) 7.81-7.88 (m, 1H), 8.09 -8.15 (m, 1H) 9.90-10.09 (m, 1H)

1.3.11 ADL1-D6 and ADL1-D7 were Prepared Via the General Procedure Below

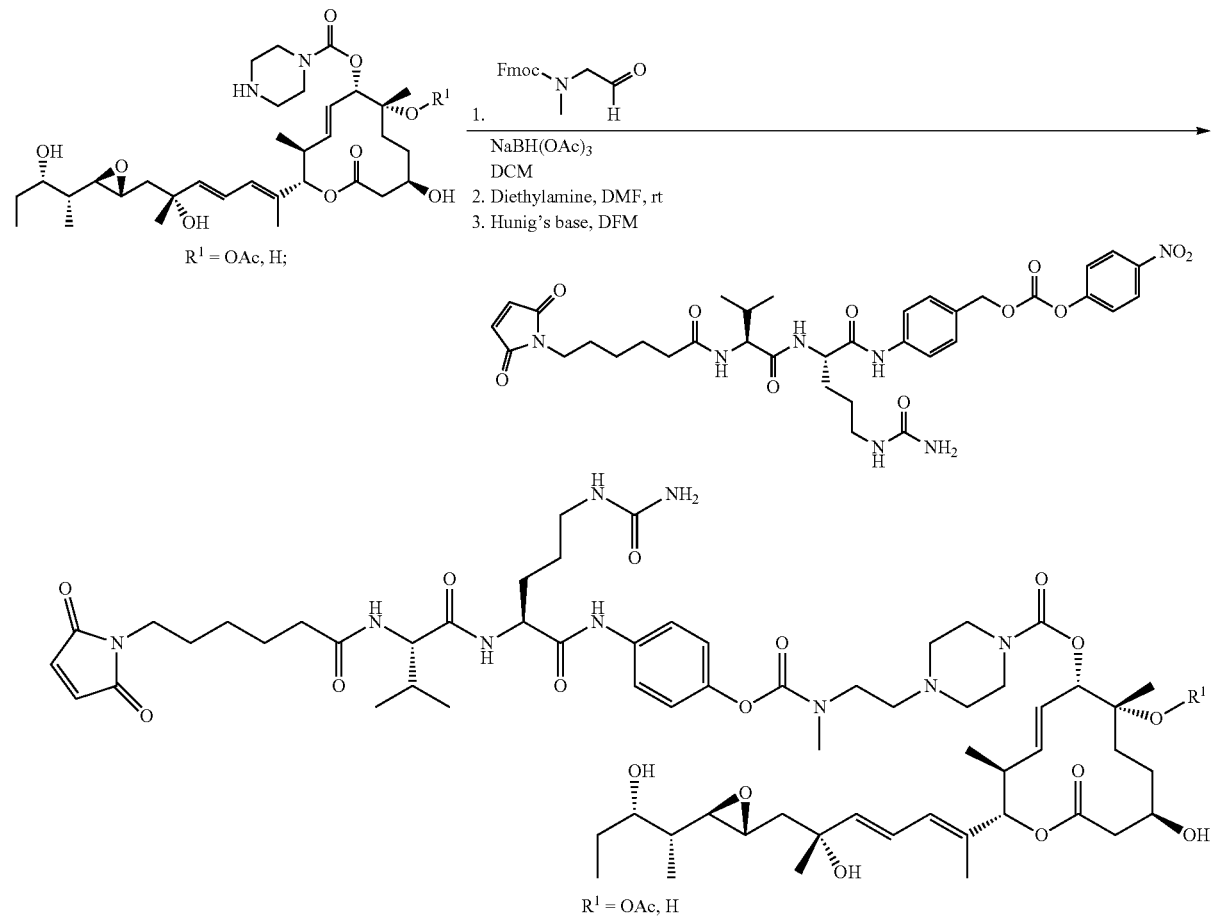

To a solution of (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate (30 mg, 0.045 mmol) in DCM (0.1 M) was added (9H-fluoren-9-yl)methyl methyl(2-oxoethyl) carbamate (5 equiv.) and sodium triacetoxy borohydride (10 equiv.) and stirred for 30 minutes. The mixture then diluted with ethyl acetate and washed with water and brine. The organic layer was dried over anhydrous Na$_2$SO$_4$, concentrated and purified by column chromatography (0-10% MeOH/DCM gradient) to isolate the desired product. The resulting material was then diluted with DMF (0.1M), charged with diethylamine (20 equiv.) and stirred for 20 minutes. The mixture was then concentrated to dryness and diluted again in DMF and charged with 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (1.2 equiv.), then Hunig's base (3.0 equiv.). The mixture was stirred for 30 minutes, concentrated in vacuo, and purified via preparative HPLC purification to afford target product.

1.3.11.2 ADL1-D7
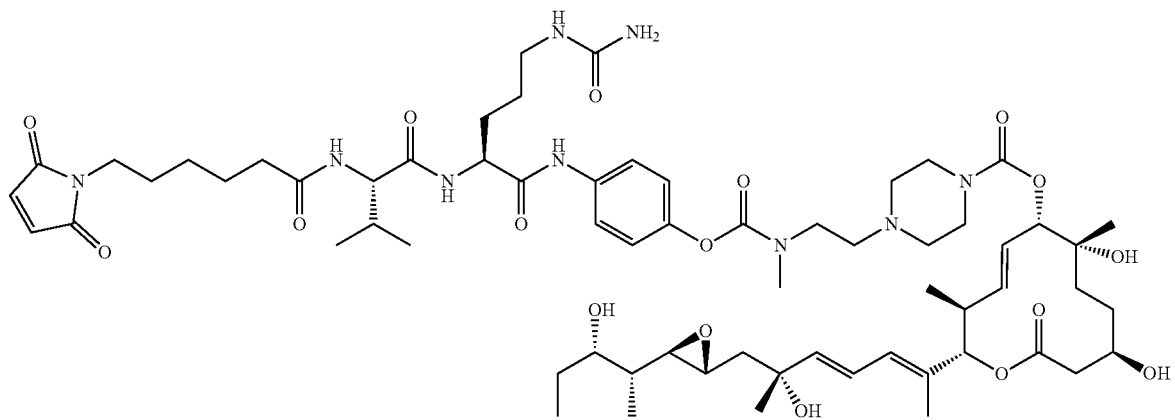 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(O)[C@@H](OC(=O)N2CCN(CCN(C)C(=O)Oc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]
General procedure 1 (1.3.11) afforded (2S,3S,6S,7R,10R,E)-7,10-dihydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-(((4-((S)-2-((S)-2-(6-(2,5-dioxo-2,5-dihydro-1H-pyrrol-1-yl)hexanamido)-3-methylbutanamido)-5-ureidopentanamido)phenoxy)carbonyl)(methyl)amino)ethyl)piperazine-1-carboxylate (3.1 mg, 5.03% yield). LC/MS (ESI, m/z), 1278.4 [M+H]$^+$.
1.3.11.2 ADL1-D6
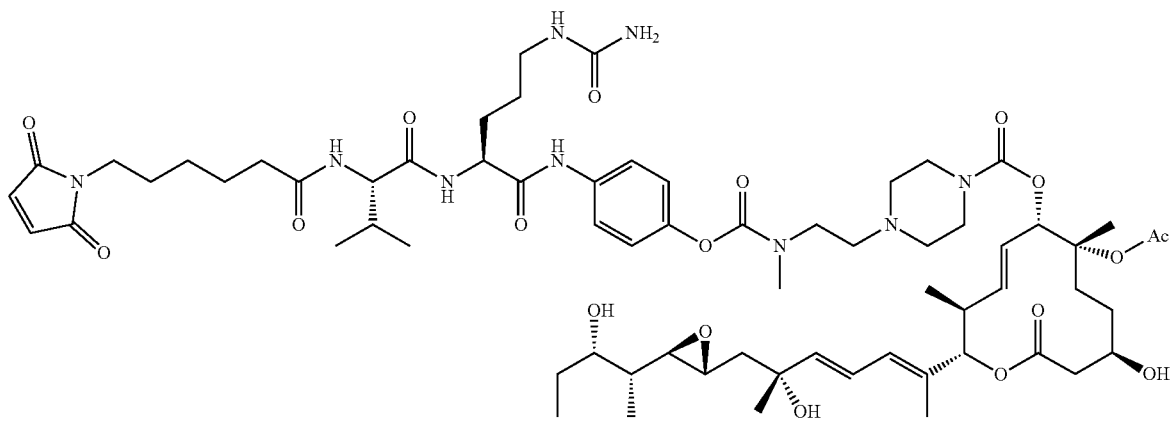 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2CCN(CCN(C)C(=O)Oc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]

General procedure 1 (1.3.11) afforded (2S,3S,6S,7R,10R,E)-7,10-dihydroxy-2-((R,2E,4E)-6-hydroxy-7-((2R,3R)-3-((2R,3S)-3-hydroxypentan-2-yl)oxiran-2-yl)-6-methyl-hepta-2,4-dien-2-yl)-3,7-dimethyl-12-oxooxacyclododec-4-en-6-yl 4-(2-(((4-((S)-2—((S)-2-(6-(2,5-dioxo-2,5-dihydro-1H-pyrrol-1-yl)hexanamido)-3-methylbutanamido)-5-ureidopentanamido)phenoxy)carbonyl)(methyl)amino)ethyl)piperazine-1-carboxylate (2 mg, 3.36% yield LC/MS (ESI, m/z), 1321.37 [M+H]+.

1.3.1.5 ADL1-D9, ADL6-D9, & ADL1-D13

D9 & D13

D9 and D13 were synthesized as a 3:1 mixture of isomers employing procedures outlined in the synthesis of D4 (Scheme 4) utilizing tri-TES Pladienolide B.

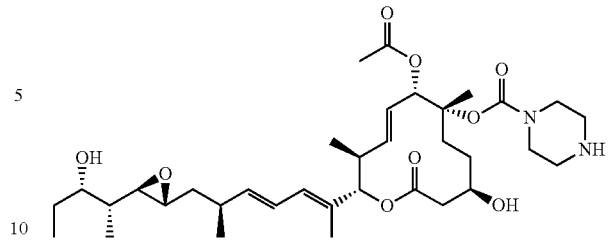

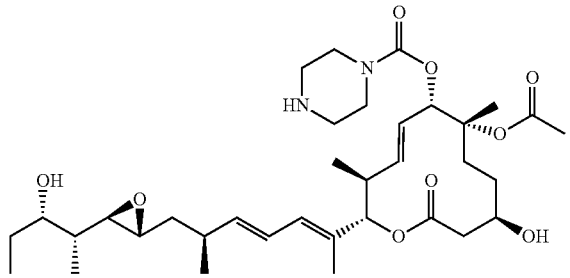 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC(C)=O)[C@@H](OC(=O)N2CCNCC2)/C=C/[C@@H]1C]

Payload (D13): LC/MS (ESI, m/z), 649.6 [M+H]*.

$^1$H NMR (400 MHz, CHCl$_3$-d) δ ppm 0.84-1.01 (m, 11H) 1.08 (d, J=6.78 Hz, 3 H) 1.29-1.64 (m, 10H) 1.63-1.73 (m, 1H) 1.76 (s, 3H) 1.94-2.12 (m, 4H) 2.37-2.58 (m, 4H) 2.59-2.65 (m, 1H) 2.68 (dd, J=7.40, 2.26 Hz, 1H) 2.77 (td, J=5.93, 2.32 Hz, 1H) 3.01-3.30 (m, 4H) 3.49 (s, 1H) 3.54-3.67 (m, 2H) 3.69-3.92 (m, 5H) 4.13 -4.78 (m, 11H) 5.13-5.24 (m, 2H) 5.48-5.61 (m, 1H) 5.62-5.74 (m, 2H) 6.04-6.13 (m, 1H) 6.18-6.32 (m, 1H).

ADL1-D9

General procedure 1 (outlined in section 1.3.1) was employed to synthesize ADL1-D9.

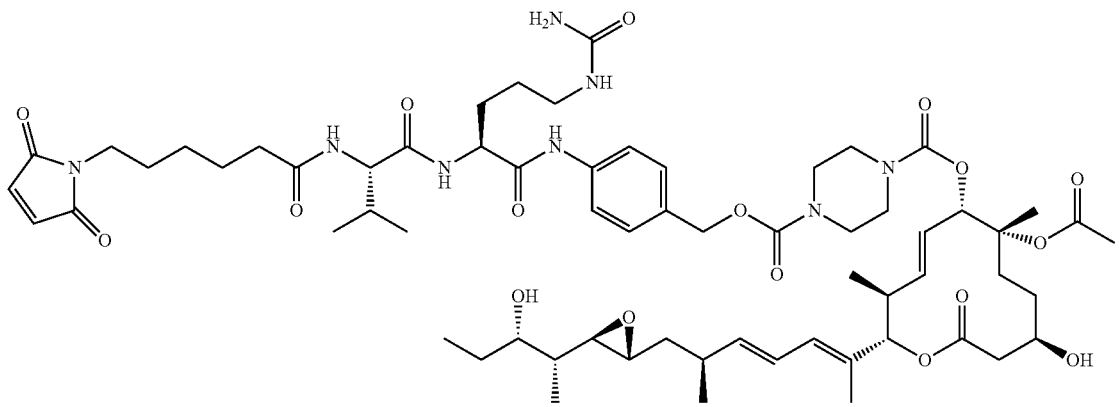 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC(C)=O)[C@@H](OC(=O)N2CCN(C(=O)OCc3ccc(NC(=O)[C@H](CCCNC(N)=O)NC(=O)[C@@H](NC(=O)CCCCCN4C(=O)C=CC4=O)C(C)C)cc3)CC2)/C=C/[C@@H]1C]

Payload (D9): LC/MS (ESI, m/z), 649.7 [M+H]+.

$^1$H-NMR (400 MHz, CHCl$_3$-d): δ ppm 0.87-1.01 (m, 10H) 1.08 (d, J=6.78 Hz, 3 H) 1.27-1.63 (m, 12H) 1.66-1.74 (m, 1H) 1.76 (s, 3H) 1.97-2.10 (m, 3H) 2.35-2.57 (m, 5H) 2.58-2.65 (m, 1H) 2.65-2.71 (m, 1H) 2.77 (td, J=5.93, 2.32 Hz, 1H) 2.89-3.05 (m, 4H) 3.07-3.34 (m, 8H) 3.50-3.68 (m, 5H) 3.72-3.88 (m, 1H) 4.88-5.09 (m, 1H) 5.18 (d, J=10.67 Hz, 1H) 5.50-5.84 (m, 3H) 6.01-6.13 (m, 1H) 6.19-6.36 (m, 1H).

Linker-Payload (ADL1-D9): (30.5 mg, 0.024 mmol, 77% yield). LC/MS (ESI, m/z), 1263.8 [M+H]+.

$^1$H-NMR (400 MHz, MeOH-d$_4$): δ ppm 0.87-0.93 (m, 7H) 0.93-1.01 (m, 8H) 1.19-1.34 (m, 4H) 1.50 (s, 3H) 1.57 (s, 5H) 1.58-1.70 (m, 6H) 1.70-1.77 (m, 1H) 1.78 (s, 3H) 1.83-1.95 (m, 2H) 2.04 (s, 3H) 2.05-2.13 (m, 1H) 2.27 (t, J=7.40 Hz, 2 H) 2.32-2.42 (m, 1H) 2.50 (d, J=3.64 Hz, 2H) 2.55-2.74 (m, 2H) 2.90 (td, J=5.83, 2.26 Hz, 1H) 3.03-3.26 (m, 2H) 3.35 (s, 13H) 3.42-3.61 (m, 11H) 3.80 (br dd, J=9.85, 3.58 Hz, 1H) 4.16 (d, J=7.40 Hz, 1H) 4.50 (dd, J=8.91, 5.14 Hz, 1H) 4.56 (s, 1H) 5.05 (dd, J=14.37, 10.10 Hz, 2H) 5.09 (s, 2H) 5.49 (s, 1H) 5.59-5.69 (m, 1H) 5.72 -5.80 (m, 1H) 5.87 (d, J=15.18 Hz, 1H) 6.09-6.22 (m, 1H) 6.44-6.60 (m, 1H) 7.32 (d, J=8.66 Hz, 2H) 7.58 (d, J=8.53 Hz, 2H).

ADL6-D9

General procedure 1 (outlined in section 1.3.1) was employed to synthesize ADL6-D9.

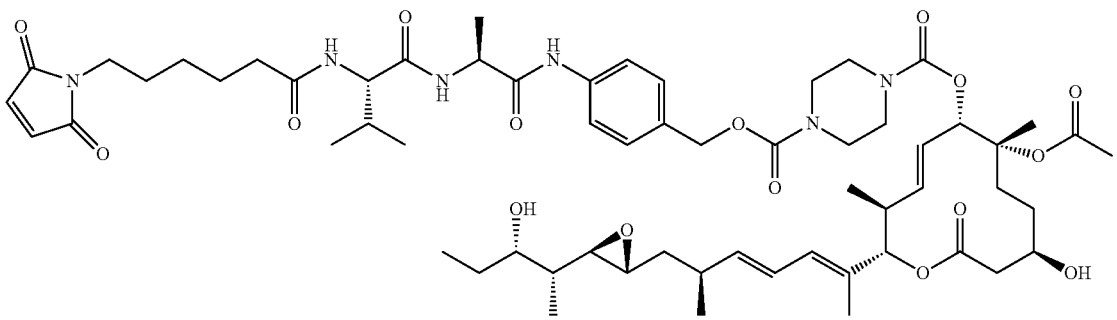 [SMILES: CC[C@H](O)[C@@H](C)[C@H]1O[C@@H]1C[C@H](C)/C=C/C=C(\C)[C@H]1OC(=O)C[C@H](O)CC[C@@](C)(OC(C)=O)[C@@H](OC(=O)N2CCN(C(=O)OCc3ccc(NC(=O)[C@H](C)NC(=O)[C@@H](NC(=O)CCCCCN4C(=O)C=CC4=O)C(C)C)cc3)CC2)/C=C/[C@@H]1C]

Linker-Payload (ADL6-D9): To diluted 4-((S)-2-((S)-2-(6-(2,5-dioxo-2,5-dihydro-1 H-pyrrol-1-yl)hexanamido)-3-methylbutanamido)propanamido)benzyl (4-nitrophenyl) carbonate (16.5 mg, 0.025 mmol) in DMF (784 μL) was added Hunig's Base (13.27 μL, 0.076 mmol). The reaction mixture was cooled to 0° C., and D9 was added. The reaction mixture was stirred at RT until LC/MS showed the reaction complete. The reaction mixture was concentrated in vacuo. Flash chromatography of the residue on silica gel with DCM/MeOH gave the titled compound (16.7 mg, 57% yield). LC/MS (ESI, m/z), 1184.6 [M+Na]$^+$.

$^1$H-NMR (400 MHz, MeOH-d$_4$): δ ppm 0.80-1.02 (m, 16H) 1.05-1.12 (m, 4H) 1.13-1.34 (m, 5H) 1.38-1.51 (m, 7H) 1.53-1.68 (m, 11H) 1.71-1.80 (m, 4H) 1.97-2.16 (m, 4H) 2.24-2.32 (m, 2H) 2.32-2.42 (m, 1H) 2.43-2.55 (m, 3H) 2.56-2.69 (m, 3H) 2.73 (br d, J=2.13 Hz, 1H) 3.07-3.18 (m, 1H) 3.42-3.61 (m, 17H) 3.75-3.91 (m, 1H) 4.11-4.24 (m, 1H) 4.43 (s, 2H) 5.59-5.88 (m, 4H) 6.06-6.17 (m, 1H) 6.29-6.39 (m, 1H) 7.24-7.39 (m, 2H) 7.52-7.64 (m, 2H).

ADL1-D13

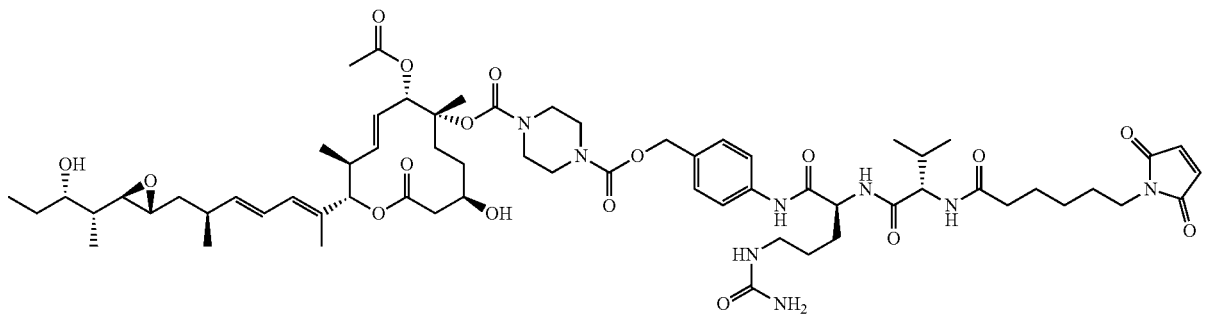

Linker-Payload (AD1-D13): 4-((S)-2-((S)-2-(6-(2,5-di-oxo-2,5-dihydro-1H-pyrrol-1-yl)hexanamido)-3-methylbutanamido)-5ureidopentanamido)benzyl (4-nitrophenyl) carbonate (4.2 mg, 5.693 μmol) in DMF (176 μL, 2.277 mmol) was added Hunig's base (2.98 μL, 0.017 mmol). The reaction mixture was cooled to 0° C., and D13 was added (4.06 mg, 6.262 μmol). The reaction mixture was stirred at RT until LC/MS showed the reaction was complete. The reaction mixture was concentrated in vacuo. Flash chromatography of the residue on silica gel with DCM/MeOH gave the titled compound (4.8 mg, 68% yield). LC/MS (ESI, m/z), 1248.0 [M+H]$^+$.

$^1$H-NMR (400 MHz, CHCl$_3$-d): δ ppm 0.58-0.98 (m, 10H) 0.99-1.06 (m, 2H) 1.11-1.31 (m, 6H) 1.57-1.75 (m, 3H) 2.11-2.26 (m, 1H) 2.30-2.73 (m, 2H) 3.28-3.80 (m, 7H) 4.14-4.33 (m, 1H) 4.44-4.55 (m, 1H) 4.63-4.81 (m, 1H) 4.92-5.06 (m, 1H) 5.09 (s, 1H) 5.49-5.74 (m, 1H) 5.88-6.09 (m, 1H) 6.14-6.36 (m, 1H) 6.99 -7.08 (m, 1H) 7.21-7.38 (m, 2H) 7.53-7.67 (m, 1H) 7.95 (s, 1H).

1.3.1.6 ADL1-D14

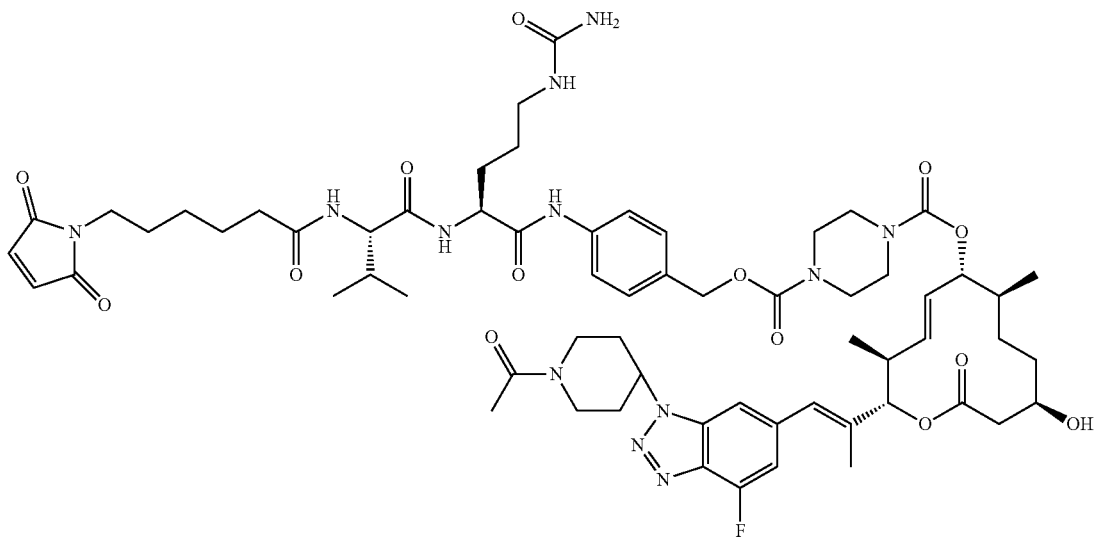 [SMILES: CC(=O)N1CCC(n2nnc3c(F)cc(/C=C(\C)[C@H]4OC(=O)C[C@H](O)CC[C@H](C)[C@@H](OC(=O)N5CCN(C(=O)OCc6ccc(NC(=O)[C@H](CCCNC(N)=O)NC(=O)[C@@H](NC(=O)CCCCCN7C(=O)C=CC7=O)C(C)C)cc6)CC5)/C=C/[C@@H]4C)cc32)CC1]

General procedure 1 (outlined in section 1.3.1) was employed to synthesize 1-((2S,3S,6R,7S,10R,E)-2-((E)-1-(1-(1-acetylpiperidin-4-yl)-4-fluoro-1H-benzo[d][1,2,3]triazol-6-yl)prop-1-en-2-yl)-10-hydroxy-3,7-dimethyl-12-oxooxacyclododec-4-en-6-yl) 4-(4-((S)-2-((S)-2-(6-(2,5-dioxo-2,5-dihydro-1 H-pyrrol-1-yl)hexanamido)-3-methylbutanamido)-5-ureidopentanamido)benzyl) piperazine-1,4-dicarboxylate (30 mg, 0.024 mmol, 39.2% yield). LC/MS (ESI, m/z), 1254.5 [M+H]$^+$.

$^1$H-NMR (400 MHz, DMSO-d$_6$): δ ppm 0.75-1.00 (m, 12H), 1.06-1.26 (m, 4H), 1.26-1.77 (m, 13H), 1.75-2.02 (m, 7H), 2.08 (s, 8H), 2.23-2.35 (m, 2H), 2.54-2.70 (m, 2H), 2.78-3.10 (m, 4H), 3.36 (br s, 13H), 3.66-3.79 (m, 1H), 3.95-4.08 (m, 1H), 4.11-4.25 (m, 1H), 4.28-4.46 (m, 1H), 4.46-4.58 (m, 1H), 4.58-4.66 (m, 1H), 4.66-4.77 (m, 1H), 5.01 (s, 3H), 5.14-5.27 (m, 1H), 5.39 (s, 4H), 5.71-5.79 (m, 1H), 5.87-6.00 (m, 1H), 6.63-6.75 (m, 1H), 6.99 (s, 2H), 7.13-7.24 (m, 1H), 7.24-7.34 (m, 2H), 7.52-7.62 (m, 2H), 7.65-7.74 (m, 1H), 7.75-7.82 (m, 1H), 7.98 -8.13 (m, 1H).

1.3.1.7 ADL1-D33

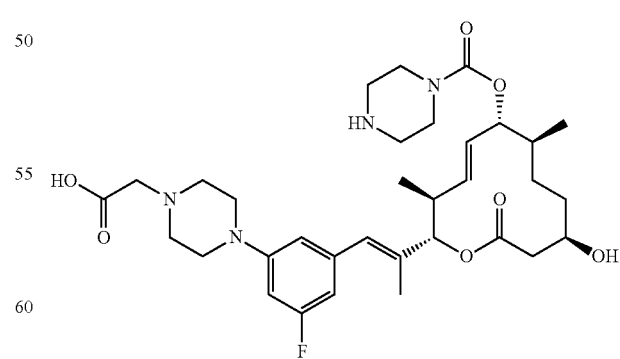

D33

To a stirred solution of (2S,3S,6R,7S,10R,E)-2-((E)-1-(3-fluoro-5-(4-(2-methoxy-2-oxoethyl)piperazin-1-yl)phenyl)prop-1-en-2-yl)-10-hydroxy-3,7-dimethyl-12-oxooxacyclododec-4-en-6-yl piperazine-1-carboxylate (27 mg, 0.042 mmol) in THF/H₂O (3 mL/1 mL) at 00C was added LiOH, and the reaction mixture was allowed to slowly warm to 25° C. (2S,3S,6R,7S,10R,E)-2-((E)-1-(3-fluoro-5-(4-(2-methoxy-2-oxoethyl)piperazin-1-yl)phenyl)prop-1-en-2-yl)-10-hydroxy-3,7-dimethyl-12-oxooxacyclododec-4-en-6-yl piperazine-1-carboxylate was synthesized using procedures outlined in International Application No. PCT/US2019/026992 (see, e.g., Procedures 17 and 19), which is incorporated herein by reference. After 6 hours, the reaction mixture was neutralized with phosphate buffer (NaH₂PO₄, 1.0 M, 3 mL) and the phases were separated. The aqueous layer was extracted with ethyl acetate (3×2 mL), and the combined organic layers were dried with anhydrous sodium sulfate and concentrated in vacuo. Reversed phase column chromatography afforded the titled compound (19.4 mg, 0.031 mmol, 73.4% yield). LC/MS (ESI, m/z), 631.4 [M+H]⁺.

¹H-NMR (400 MHz, CHCl₃-d): δ ppm 0.85-1.16 (m, 2H) 1.23-1.52 (m, 1H) 1.57-1.77 (m, 1H) 1.87 (s, 1H) 1.92-2.13 (m, 1H) 2.35-2.55 (m, 1H) 2.50-2.74 (m, 1H) 3.11 (br s, 1H) 3.36-3.54 (m, 2H) 3.64 (br d, J=10.42 Hz, 2H) 3.77-3.90 (m, 1H) 4.76 (br s, 4H) 5.07-5.19 (m, 1H) 5.38-5.68 (m, 1H) 6.40-6.76 (m, 1H) 8.02-8.66 (m, 1H).

nyl) carbonate (17 mg, 0.023 mmol) in DMF (714 μL, 9.217 mmol) was added Hunig's base (12.07 μL, 0.069 mmol). The reaction mixture was cooled to 0° C., and added 2-(4-(3-fluoro-5-((E)-2-((2S,3S,6R,7S,10R,E)-10-hydroxy-3,7-dimethyl-12-oxo-6-((piperazine-1-carbonyl)oxy)oxacyclododec-4-en-2-yl)prop-1-en-1-yl)phenyl)piperazin-1-yl) acetic acid (16.71 mg, 0.026 mmol). The reaction mixture was stirred at RT until LC/MS showed the reaction was complete. The reaction mixture was then concentrated in vacuo. Flash chromatography on silica gel and further HPLC purification gave the titled compound (13.5 mg, 10.98 μmol, 47.7% yield). LC/MS (ESI, m/z), 1229.5 [M+H]⁺.

¹H-NMR (400 MHz, MeOH-d₄): δ ppm 0.92-0.99 (m, 10H) 1.01 (d, J=6.78 Hz, 3 H) 1.24-1.46 (m, 9H) 1.52-1.70 (m, 10H) 1.70-1.82 (m, 1H) 1.87 (d, J=1.00 Hz, 4 H) 1.89-2.00 (m, 2H) 2.01-2.23 (m, 2H) 2.27 (t, J=7.40 Hz, 2H) 2.46 (dd, J=14.31, 5.27 Hz, 1H) 2.57-2.71 (m, 2H) 2.86 (d, J=0.63 Hz, 1H) 3.00 (s, 1H) 3.06-3.27 (m, 4H) 3.35 (s, 5H) 3.41-3.53 (m, 19H) 3.66 (s, 2H) 3.76-3.90 (m, 1H) 4.07-4.21 (m, 1H) 4.39-4.69 (m, 37H) 5.09 (s, 3H) 5.13 (d, J=10.54

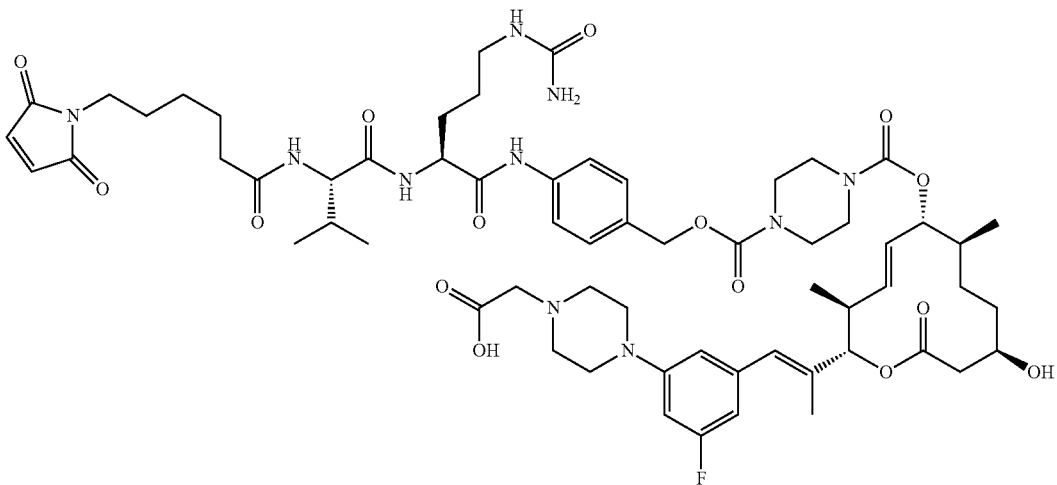

ADL1-D33

Linker-Payload (ADL1-D33): To 4-((S)-2-((S)-2-(6-(2,5-dioxo-2,5-dihydro-1 H-pyrrol-1-yl)hexanamido)-3-methylbutanamido)-5-ureidopentanamido)benzyl (4-nitrophe- Hz, 1H) 5.52 (dd, J=14.56, 9.03 Hz, 2H) 6.55 (br s, 2H) 6.69 (d, J=1.38 Hz, 2H) 7.33 (d, J=8.66 Hz, 2H) 7.59 (d, J=8.53 Hz, 2H) 7.88-8.04 (m, 1H) 8.16-8.33 (m, 1H).

ADL1-D28

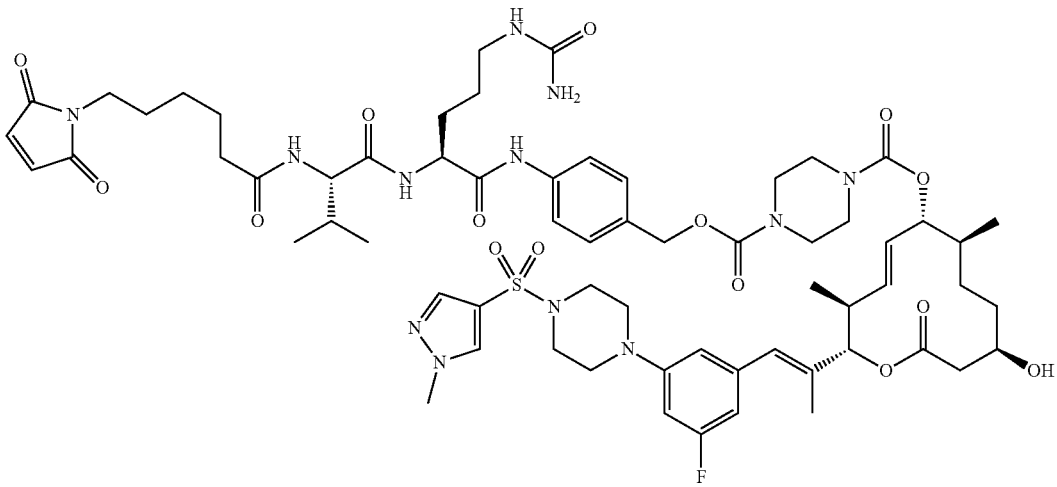

4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (6.17 mg, 8.37 µmol) and (2S,3S,6R,7S,10R,E)-2-((E)-1-(3-fluoro-5-(4-((1-methyl-1H-imidazol-4-yl)sulfonyl)piperazin-1-yl)phenyl)prop-1-en-2-yl)-10-hydroxy-3,7-dimethyl-12-oxooxacyclododec-4-en-6-yl piperazine-1-carboxylate (6 mg, 8.37 µmol) were dissolved in DMF (0.3 ml) and Hunig's Base (4.39 µL, 0.025 mmol) was added. The reaction mixture was stirred at rt overnight. The solvent was evaporated and subjected to reverse-phase HPLC purification to afford (4-((S)-2-((S)-2-(6-(2,5-dioxo-2,5-dihydro-1H-pyrrol-1-yl)hexanamido)-3-methylbutanamido)-5-ureidopentanamido)benzyl) 4-((2S,3S,6R,7S,10R,E)-2-((E)-1-(3-fluoro-5-(4-((1-methyl-1H-imidazol-4-yl)sulfonyl)piperazin-1-yl)phenyl)prop-1-en-2-yl)-10-hydroxy-3,7-dimethyl-12-oxooxacyclododec-4-en-6-yl) piperazine-1,4-dicarboxylate (1.5 mg, 13.6%). LC/MS (ESI, m/z), 1315.66 [M+H]⁺.

¹H NMR (400 MHz, METHANOL-d4) δ ppm 0.85-0.93 (m, 12H) 1.16-1.31 (m, 6H) 1.43-1.57 (m, 9H) 1.62-1.70 (m, 1H) 1.75 (s, 3H) 1.77-1.90 (m, 2H) 1.96-2.03 (m, 1H) 2.13-2.20 (m, 2H) 2.31-2.40 (m, 1H) 2.46-2.55 (m, 2H) 2.97-3.06 (m, 2H) 3.08-3.10 (m, 1H) 3.15 (br d, J=6.27 Hz, 9H) 3.33-3.43 (m, 10H) 3.71 (s, 4H) 4.03-4.09 (m, 1H) 4.37-4.44 (m, 1H) 4.44-4.53 (m, 1H) 4.96-5.06 (m, 3H) 5.33-5.51 (m, 2H) 6.36-6.44 (m, 2H) 6.45-6.53 (m, 2H) 6.69 (s, 2H) 7.19-7.25 (m, 2H) 7.47-7.52 (m, 2H) 7.63-7.70 (m, 2H)

ADL1-D31

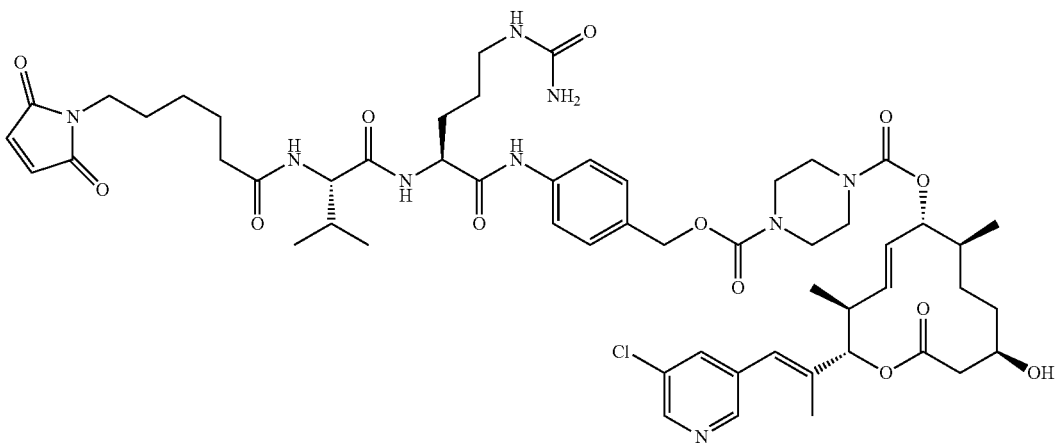

4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (13.12 mg, 0.018 mmol) and (2S,3S,6R,7S,10R,E)-2-((E)-1-(5-chloropyridin-3-yl)prop-1-en-2-yl)-10-hydroxy-3,7-dimethyl-12-oxooxacyclododec-4-en-6-yl piperazine-1-carboxylate (9 mg, 0.018 mmol) were dissolved in DMF (179 µl, 2.312 mmol) and Hunig's Base (9.32 µl, 0.053 mmol) was added. The reaction mixture was stirred at rt overnight. The solvent was evaporated and purified via reverse-phase HPLC to afford 1-((2S,3S,6R,7S,10R,E)-2-((E)-1-(5-chloropyridin-3-yl)prop-1-en-2-yl)-10-hydroxy-3,7-dimethyl-12-oxooxacyclododec-4-en-6-yl) 4-(4-((S)-2-((S)-2-(6-(2,5-dioxo-2,5-dihydro-1H-pyrrol-1-yl)hexanamido)-3- methylbutanamido)-5-ureidopentanamido)benzyl) piperazine-1,4-dicarboxylate (6.9 mg, 34.09%). LC/MS (ESI, m/z), 1105.59 [M+H]$^+$.

1H NMR (400 MHz, METHANOL-d4) δ ppm 0.88 (s, 12H) 1.17-1.31 (m, 4H) 1.43-1.57 (m, 8H) 1.61-1.70 (m, 1H) 1.80 (d, J=1.25 Hz, 5H), 1.92-2.01 (m, 1H) 2.14-2.20 (m, 2H) 2.32-2.42 (m, 1H) 2.48-2.59 (m, 2H) 2.96-3.14 (m, 3H) 3.38 (s, 10H) 3.36-3.36 (m, 1H) 3.38-3.40 (m, 3H) 3.67-3.75 (m, 1H) 4.03-4.07 (m, 1H) 4.37-4.42 (m, 1H) 4.97-5.01 (m, 2H) 5.04-5.11 (m, 1H) 5.35-5.51 (m, 2H) 6.46-6.52, (m, 1H) 6.69 (s, 2H) 7.18-7.26 (m, 2H) 7.45-7.54 (m, 2H) 7.68-7.74 (m, 1H) 8.29-8.34 (m, 2H).

ADL1-D29

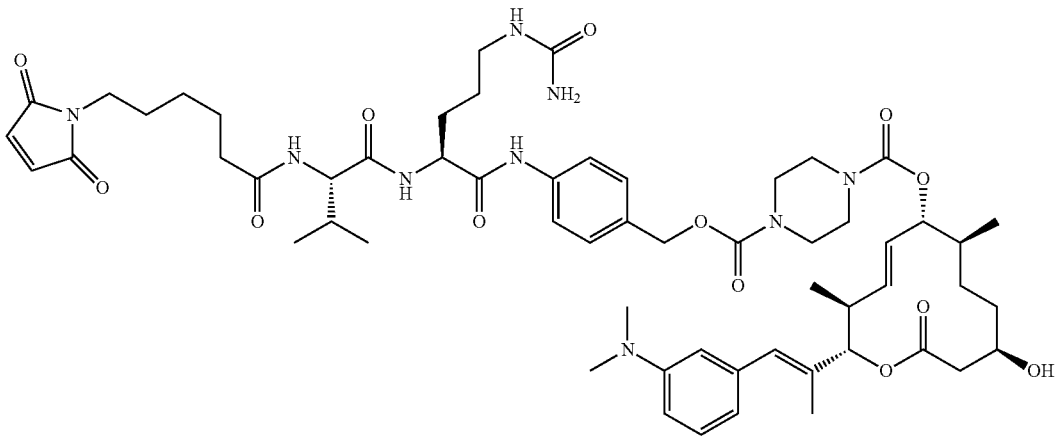

4-((S)-2-((S)-2-(6-(2,5-dioxo-2,5-dihydro-1 H-pyrrol-1-yl)hexanamido)-3-methylbutanamido)-5-ureidopentanamido)benzyl (4-nitrophenyl) carbonate (8.62 mg, 0.012 mmol) and (2S,3S,6R,7S,10R, E)-2-((E)-1-(3-(dimethylamino)phenyl)prop-1-en-2-yl)-10-hydroxy-3,7-dimethyl-12-oxooxacyclododec-4-en-6-yl piperazine-1-carboxylate (6 mg, 0.012 mmol) were dissolved in DMF (118 µl, 1.518 mmol) and Hunig'sBase (6.12 µl, 0.035 mmol). The reaction mixture was stirred at rt overnight. The solvent was evaporated and purified via reverse-phase HPLC to afford 1-((2S, 3S,6R,7S,10R,E)-2-((E)-1-(3-(dimethylamino)phenyl)prop-1-en-2-yl)-10-hydroxy-3,7-dimethyl-12-oxooxacyclododec-4-en-6-yl) 4-(4-((S)-2-((S)-2-(6-(2,5-dioxo-2,5-dihydro-1 H-pyrrol-1-yl)hexanamido)-3-methylbutanamido)-5-ureidopentanamido)benzyl) piperazine-1,4-dicarboxylate (4.0 mg, 30.79%). LC/MS (ESI, m/z), 1112.59 [M+H]$^+$.

$^1$H NMR (400 MHz, METHANOL-d$_4$) δ ppm 0.87 (s, 12H) 1.17-1.23 (m, 3H) 1.26-1.32 (m, 1H) 1.44-1.57 (m, 8H) 1.63-1.69 (m, 1H) 1.74-1.81 (m, 4H) 1.83-1.88 (m, 1H) 1.93-2.03 (m, 1H) 2.13-2.20 (m, 2H) 2.34-2.42 (m, 1H) 2.48-2.57 (m, 2H) 2.81 (s, 5H) 2.98-3.05 (m, 2H) 3.08-3.14 (m, 1H) 3.38 (br s, 9H) 3.65-3.75 (m, 1H) 4.03-4.07 (m, 1H) 4.35-4.43 (m, 1H) 4.44-4.52 (m, 1H) 4.96-5.01 (m, 2H) 5.02-5.08 (m, 1H) 5.34-5.51 (m, 2H) 6.43-6.48 (m, 1H) 6.51-6.61 (m, 3H) 6.69 (s, 2H) 7.03-7.10 (m, 1H) 7.20-7.26 (m, 2H) 7.46-7.51 (m, 2H).

ADL1-D35

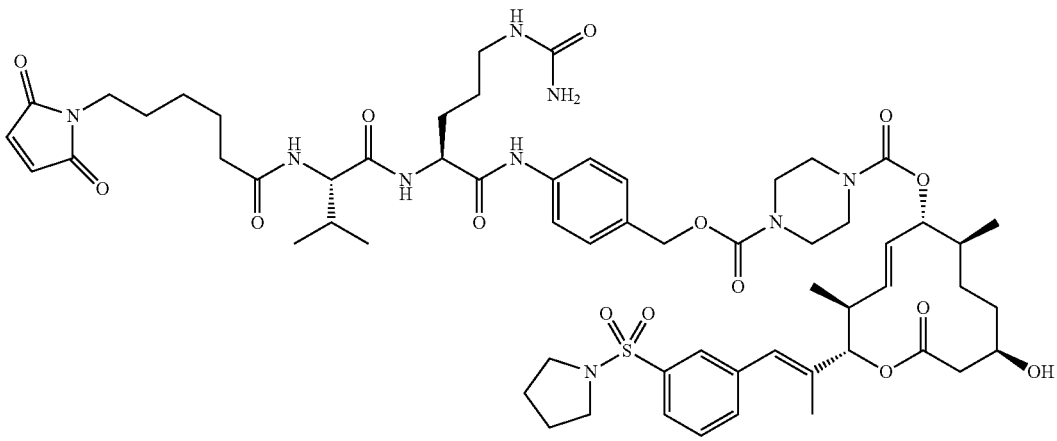

4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (9.78 mg, 0.013 mmol) and (2S,3S,6R,7S,10R,E)-10-hydroxy-3,7-dimethyl-12-oxo-2-((E)-1-(3-(pyrrolidin-1-ylsulfonyl)phenyl)prop-1-en-2-yl)oxacyclododec-4-en-6-yl piperazine-1-carboxylate (8 mg, 0.013 mmol) were dissolved in DMF (133 μl, 1.722 mmol) and Hunig's Base (6.94 μl, 0.04 mmol) [two drops] was added. The resulting mixture was stirred at rt overnight, 4.96-5.02 (m, 2H) 5.04-5.11 (m, 1H) 5.35-5.51 (m, 2H) 6.59 (s, 1H) 6.69 (s, 2H) 7.20-7.27 (m, 2H) 7.45-7.52 (m, 4H) 7.58-7.65 (m, 2H).

1.4 Preparation of MC-Val-Ala-pABC linker-payloads

1.4.1 Overview

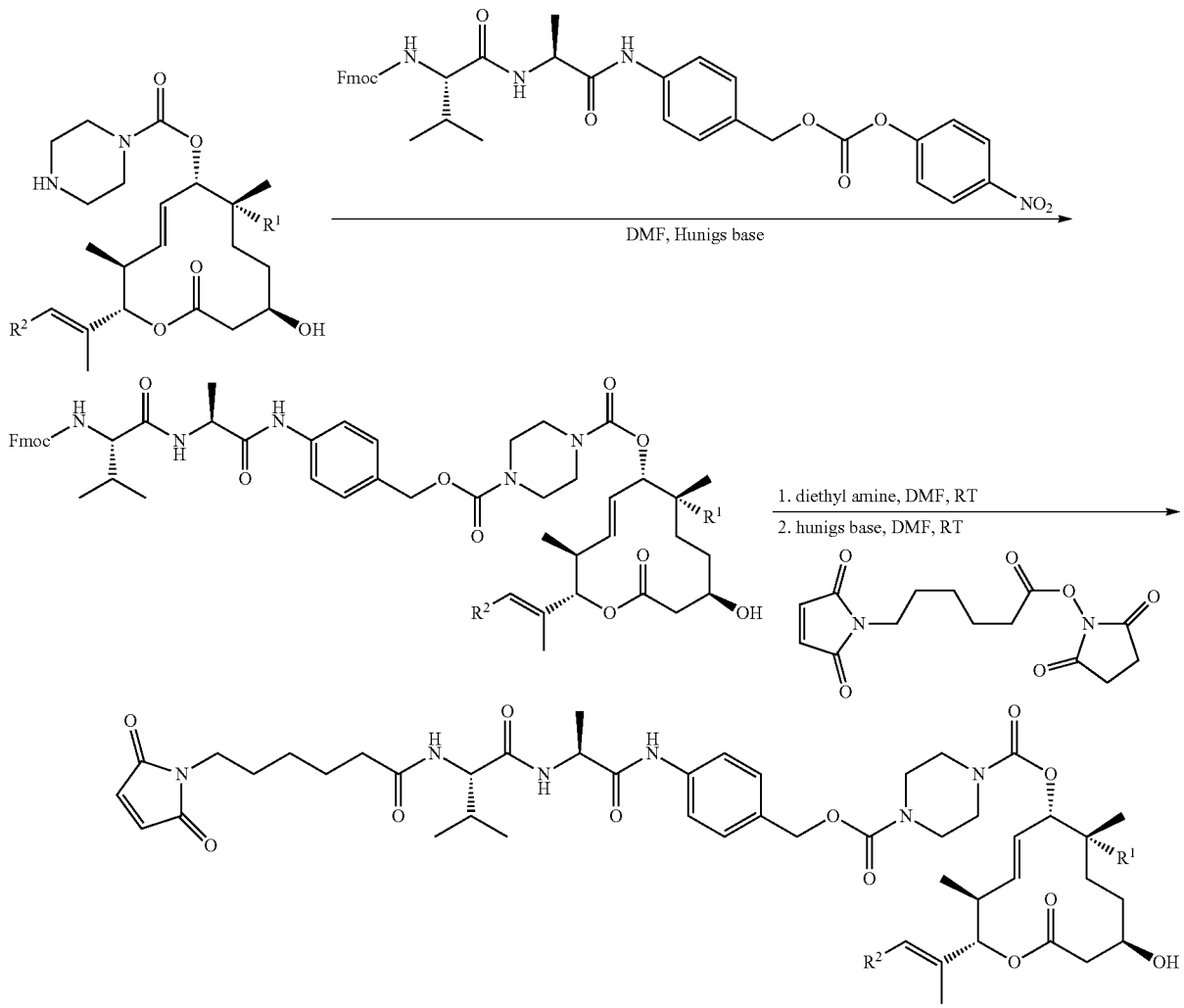

Scheme 5 concentrated in vacuo, and purified via reverse-phase HPLC to afford product 1-(4-((S)-2-((S)-2-(6-(2,5-dioxo-2,5-dihydro-1 H-pyrrol-1-yl)hexanamido)-3-methylbutanamido)-5-ureidopentanamido)benzyl) 4-((2S,3S,6R,7S,10R,E)-10-hydroxy-3,7-dimethyl-12-oxo-2-((E)-1-(3-(pyrrolidin-1-ylsulfonyl)phenyl)prop-1-en-2-yl)oxacyclododec-4-en-6-yl) piperazine-1,4-dicarboxylate (8.2 mg, 51.47%). LC/MS (ESI, m/z), 1203.53 [M+H]⁺.

1H NMR (400 MHz, METHANOL-d4) δ ppm 0.85-0.93 (m, 12H) 1.17-1.34 (m, 4H) 1.42-1.57 (m, 8H) 1.61-1.69 (m, 5H) 1.79 (s, 4H) 1.83-1.90 (m, 1H) 1.94-2.03 (m, 1H) 2.12-2.20 (m, 2H) 2.33-2.43 (m, 1H) 2.48-2.59 (m, 2H) 2.96-3.05 (m, 2H) 3.06-3.17 (m, 6H) 3.31-3.41 (m, 10H) 3.67-3.77 (m, 1H) 4.02-4.10 (m, 1H) 4.36-4.43 (m, 1H)

Step 1: Macrocycle payload (1.0 equiv.), DMF (0.1 M), (9H-fluoren-9-yl)methyl ((S)-3-methyl-1-(((S)-1-((4-((((4-nitrophenoxy)carbonyl)oxy)methyl)phenyl)amino)-1-oxopropan-2-yl)amino)-1-oxobutan-2-yl)carbamate (1.5 equiv.; prepared using the procedure described in WO 2012/153193), and Hunig's base (3.0 equiv.) were combined and stirred overnight. The reaction mix was concentrated to dryness and chromatographed to afford fmocVal-Ala-pABC-payload.

Step 2: Ammonium fmoc-Val-Ala-pABC payload (1.0 equiv.), dissolved in DMF (0.1 M), and diethylamine (10 equiv.) were combined and stirred for 30 min. The reaction mix was concentrated to dryness under high vacuum. The crude product was dissolved in DMF (0.1 M), and Hunig's base (2 equiv.) was added, after which 2,5-dioxopyrrolidin-1-yl 6-(2,5-dioxo-2,5-dihydro-1H-pyrrol-1-yl)hexanoate (3 equiv.) was added and stirred overnight. The reaction mix was then concentrated to dryness and chromatographed (0-30% MeOH in DCM) to afford the desired MC-Val-Ala-pABC-payload.

1.4.1.1 ADL6-D1

Scheme 5 -Step 1: General procedure outlined above (section 1.4.1) was followed to afford 1-(4-((S)-2-((S)-2-(((((9H-fluoren-9-yl)methoxy)carbonyl)amino)-3-methylbutanamido)propanamido)benzyl) 4-((2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl) piperazine-1,4-dicarboxylate (32 mg, 0.027 mmol, 27.9% yield). LC/MS (ESI, m/z), [M+Na]$^+$1200.5.

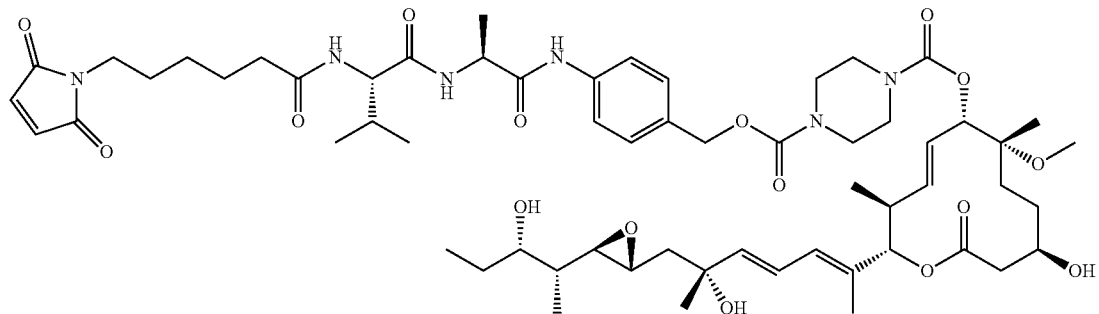 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)OCc3ccc(NC(=O)[C@H](C)NC(=O)[C@@H](NC(=O)CCCCCN4C(=O)C=CC4=O)C(C)C)cc3)CC2)/C=C/[C@@H]1C]

Scheme 5 -Step 2: General procedure outlined above (section 1.4.1) was followed to afford 1-(4-((S)-2-((S)-2-(6-(2,5-dioxo-2,5-dihydro-1H-pyrrol-1-yl)hexanamido)-3-methylbutanamido)propanamido)benzyl) 4-((2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl) piperazine-1,4-dicarboxylate (24 mg, 0.021 mmol, 77% yield). LC/MS (ESI, m/z), 1149.2 [M+H]$^+$.

$^1$H-NMR (400 MHz, MeOH-d4): δ ppm 0.85-1.02 (m, 16H), 1.20-1.23 (m, 3H) 1.23-1.32 (m, 3H) 1.34 (s, 3H) 1.41-1.46 (m, 4H) 1.46-1.72 (m, 11H) 1.78 (s, 3H) 1.87 (dd, J=14.05, 5.40 Hz, 1H) 2.08 (dq, J=13.77, 6.83 Hz, 1H) 2.27 (t, J=7.40 Hz, 2 H) 2.43-2.63 (m, 3H) 2.64-2.70 (m, 1H) 2.90 (td, J=5.83, 2.26 Hz, 1H) 3.32-3.33 (m, 4H) 3.42-3.57 (m, 11H) 3.82 (br dd, J=8.66, 3.89 Hz, 1H) 4.15 (d, J=7.15 Hz, 1 H), 4.47 (q, J=7.15 Hz, 1H) 4.99-5.12 (m, 4H) 5.57 (dd, J=15.18, 9.79 Hz, 1H) 5.69-5.78 (m, 1H) 5.87 (d, J=15.18 Hz, 1H) 6.13 (d, J=10.92 Hz, 1H), 6.53 (dd, J=15.31, 10.92 Hz, 1H) 6.78 (s, 2H) 7.32 (d, J=8.53 Hz, 2H) 7.58 (d, J=8.53 Hz, 2H).

1.4.1.2 ADL6-D16

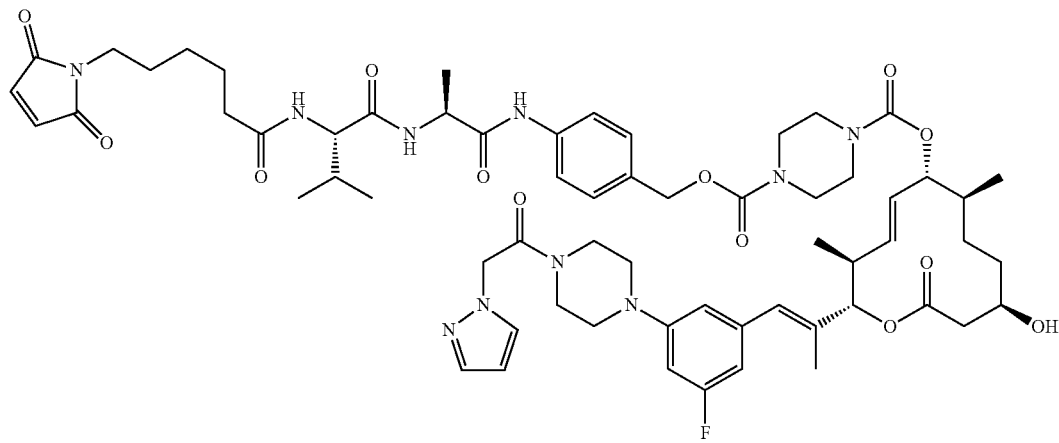 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CCN(C(=O)OCc3ccc(NC(=O)[C@H](C)NC(=O)[C@@H](NC(=O)CCCCCN4C(=O)C=CC4=O)C(C)C)cc3)CC2)/C=C/[C@@H]1C]

Scheme 5 —Step 1: General procedure outlined above (section 1.4.1) was followed to afford 1-((2S,3S,6R,7S,10R, E)-2-((E)-1-(3-(4-(2-(1H-pyrazol-1-yl)acetyl)piperazin-1-yl)-5-fluorophenyl)prop-1-en-2-yl)-10-hydroxy-3,7-dimethyl-12-oxooxacyclododec-4-en-6-yl) 4-(4-((S)-2-((S)-2-(((((9H-fluoren-9-yl)methoxy)carbonyl)amino)-3-methylbutanamido)propanamido)benzyl) piperazine-1,4-dicarboxylate (0.060 g, 0.049 mmol, 60.8% yield). LC/MS (ESI, m/z), 1223.68 [M+H].

Scheme 5—Step 2: General procedure outlined above (section 1.4.1) was followed to afford 1-((2S,3S,6R,7S,10R, E)-2-((E)-1-(3-(4-(2-(1H-pyrazol-1-yl)acetyl)piperazin-1-yl)-5-fluorophenyl)prop-1-en-2-yl)-10-hydroxy-3,7-dimethyl-12-oxooxacyclododec-4-en-6-yl) 4-(4-((S)-2-((S)-2-(6-(2,5-dioxo-2,5-dihydro-1 H-pyrrol-1-yl)hexanamido)-3-methylbutanamido)propanamido)benzyl) piperazine-1,4-dicarboxylate (11.50 mg, 9.64 μmol, 12.05% yield). LC/MS (ESI, m/z),1194.82 [M+H]$^+$.

$^1$H-NMR (400 MHz, CHCl$_3$-d): δ ppm 0.97 (br d, J=1.25 Hz, 12H), 1.24-1.41 (m, 5H), 1.41-1.47 (m, 3H), 1.52-1.69 (m, 6H), 1.84-1.90 (m, 3H), 1.92-2.01 (m, 1 H), 2.02-2.16 (m, 1H), 2.23-2.30 (m, 2H), 2.42-2.51 (m, 1H), 2.57-2.65 (m, 2H), 3.19-3.28 (m, 4H), 3.35 (s, 4H), 3.40-3.54 (m, 11H), 3.69-3.77 (m, 4H), 3.78-3.85 (m, 1H), 4.12-4.18 (m, 1H), 4.43-4.51 (m, 1H), 5.07-5.16 (m, 3H), 5.20 (s, 2 H), 5.42-5.62 (m, 2H), 6.29-6.38 (m, 1H), 6.46-6.58 (m, 2H), 6.59-6.68 (m, 2H), 7.28-7.37 (m, 2H), 7.50-7.67 (m, 4H).

1.5 Preparation of MC-Val-Ala-pAB Linker-Payloads 1.5.1 Overview

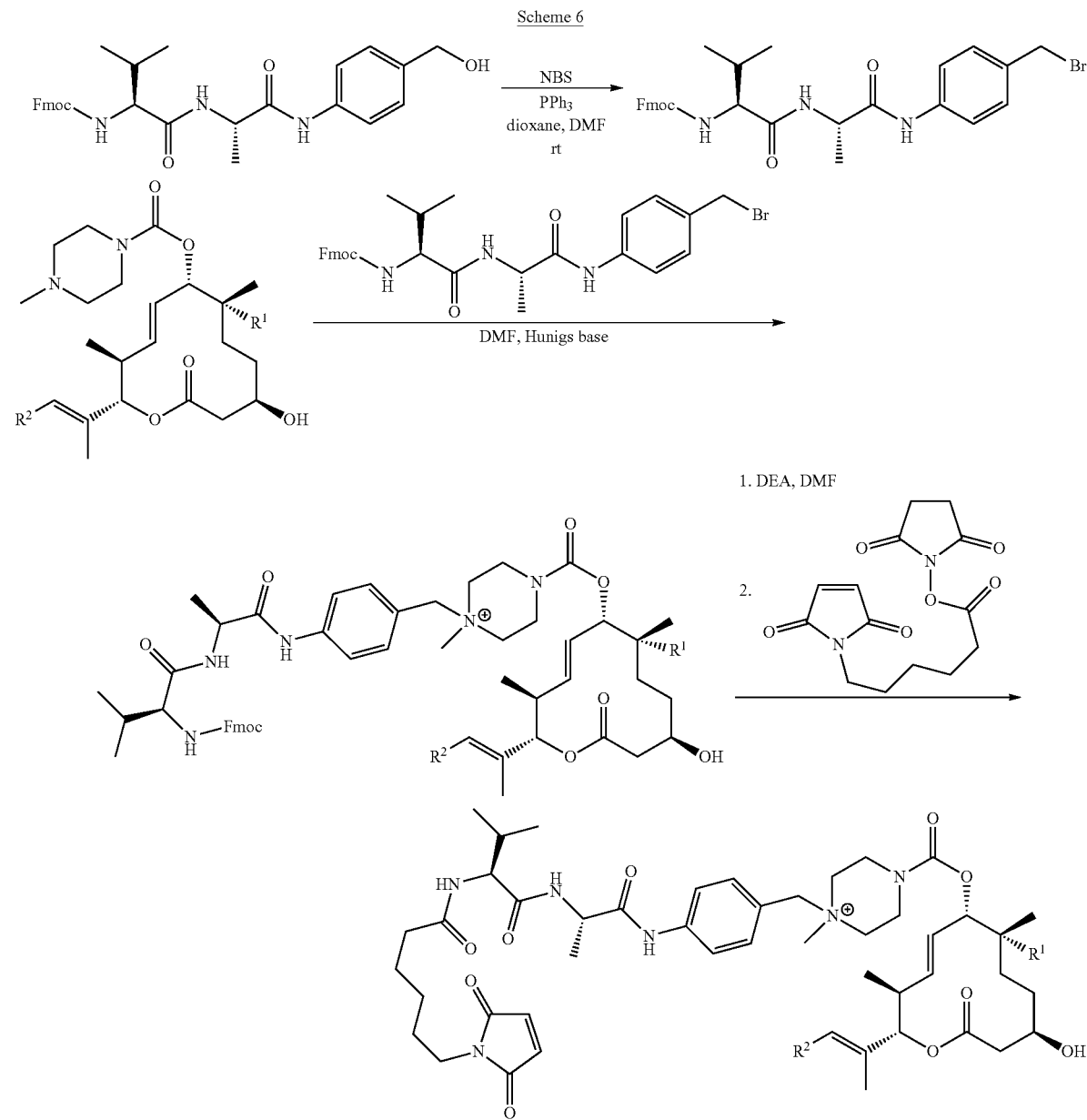

Step 1: (9H-fluoren-9-yl)methyl ((S)-1-(((S)-1-((4-(hydroxymethyl)phenyl)amino)-1-oxopropan-2-yl)amino)-3-methyl-1-oxobutan-2-yl)carbamate (0.5 g, 0.97 mmol), 1,4-dioxane (9.70 mL, 0.97 mmol), triphenylphosphine (0.509 g, 1.939 mmol), N-bromosuccinimide (0.345 g, 1.939 mmol), and DMF (2.424 mL, 0.97 mmol) were combined and stirred for 3 hours at RT. The reaction mix was concentrated and chromatographed to afford (9H-fluoren-9-yl)methyl ((S)-1-(((S)-1-((4-(bromomethyl)phenyl)amino)-1-oxopropan-2-yl)amino)-3-methyl-1-oxobutan-2-yl)carbamate (116 mg, 0.201 mmol, 20.68% yield). LC/MS (ESI, m/z), 580.14 [M+H].

Step 2: The payload (1.0 equiv.), (9H-fluoren-9-yl)methyl ((S)-1-(((S)-1-((4-(bromomethyl)phenyl)amino)-1-oxopropan-2-yl)amino)-3-methyl-1-oxobutan-2-yl)carbamate (0.069 g, 0.12 mmol), N,N-dimethylformamide (0.1 M), and Hunig's base (1.5 equiv.) were combined and stirred overnight. The reaction mix was concentrated to dryness and chromatographed (0-10% MeOH in DCM) to afford the quaternary ammonium fmoc-Val-Ala-pAB payload.

Step 3: Quaternary ammonium fmoc-Val-Ala-pAB payload (1.0 equiv.), dissolved in DMF (0.1 M), and diethylamine (10 equiv.) were combined and stirred for 30 min. The reaction mix was concentrated to dryness under high vacuum. The crude product was dissolved in DMF (0.1 M) and Hunig's base (2 equiv.) was added, after which 2,5-dioxopyrrolidin-1-yl 6-(2,5-dioxo-2,5-dihydro-1H-pyrrol-1-yl)hexanoate (3 equiv.) was added and stirred overnight. The reaction mix was then concentrated to dryness and chromatographed (0-30% MeOH in DCM) to afford the desired quaternary ammonium linker-payload.

1.5.1.1 ADL5-D2

Scheme 6—Step 2: 1-(4-((S)-2-((S)-2-((((9H-fluoren-9-yl)methoxy)carbonyl)amino)-3-methylbutanamido)propanamido)benzyl)-4-(((((2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)-1-methylpiperazin-1-ium bromide (30 mg, 0.024 mmol, 26.5% yield). LC/MS (ESI, m/z), 1149.77 [M+H]+.

Scheme 6—Step 3: mono(1-(4-((S)-2-((S)-2-(6-(2,5-dioxo-2,5-dihydro-1H-pyrrol-1-yl)hexanamido)-3-methylbutanamido)propanamido)benzyl)-4-(((((2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)-1-methylpiperazin-1-ium-2-ylium) monobromide (4.8 mg, 15.33% yield). LC/MS (ESI, m/z), 1120.99 [M+H]+.

1H-NMR (400 MHz, MeOH-d4): δ ppm 0.88 (s, 15H), 1.09-1.26 (m, 9H), 1.31-1.58 (m, 14H), 1.42-1.44 (m, 1H), 1.68 (s, 3H), 1.73-1.81 (m, 1H), 1.91-2.03 (m, 1 H), 2.14-2.22 (m, 2H), 2.35-2.52 (m, 3H), 2.53-2.60 (m, 1H), 2.74-2.83 (m, 1H), 2.97 (s, 3H), 3.25 (s, 1H), 3.28-3.46 (m, 8H), 3.52-3.66 (m, 2H), 3.70-3.78 (m, 1 H), 3.97-4.11 (m, 3H), 4.32-4.41 (m, 1H), 4.45-4.54 (m, 2H), 4.91-5.01 (m, 2H), 5.44-5.55 (m, 1H), 5.57-5.70 (m, 1H), 5.72-5.82 (m, 1H), 6.00-6.08 (m, 1H), 6.43 (dd, J=15.25, 10.98 Hz, 1H), 6.69 (s, 2H), 7.36-7.47 (m, 2H), 7.67-7.75 (m, 2H).

1.5.1.2 ADL5-D19

General procedure outlined above (section 1.5.1) was employed to synthesize ADL5-D19. The payload D19 was synthesized using procedures outlined in section 1.2.1.

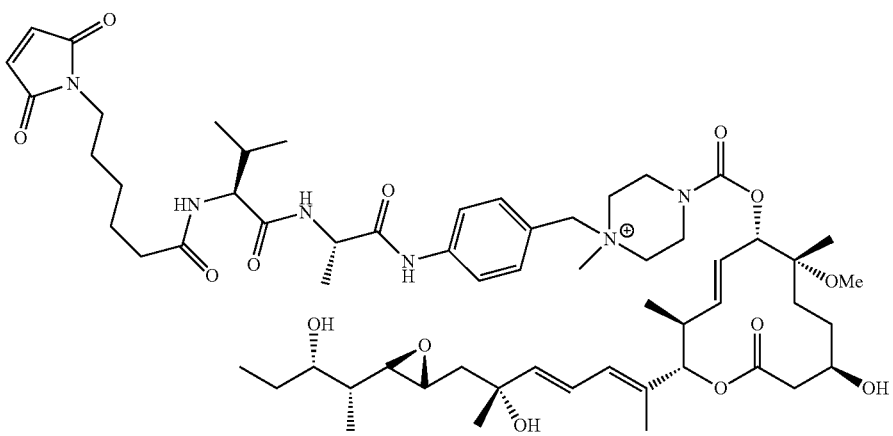

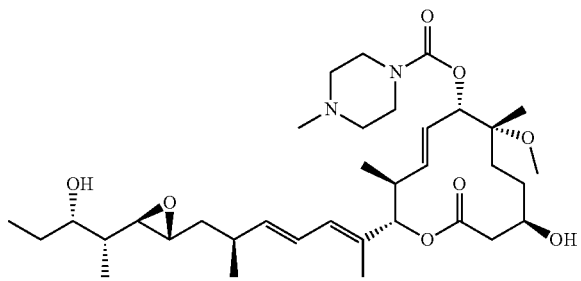

D19 methylhepta-2,4-dien-2-yl)-7-methoxy-3,7-dimethyl-12-oxooxacyclododec-4-en-6-yl)oxy)carbonyl)-1-methylpiperazin-1-ium (25 mg, 45.6%). LC/MS (ESI, m/z), 1133.1 [M+]*.

$^1$H-NMR (400 MHz, MeOH-d4): δ ppm 0.94 (br dd, J=18.45, 7.15 Hz, 18H) 1.10 (d, J=6.78 Hz, 3H) 1.25 (s, 4H) 1.28-1.35 (m, 1H) 1.46 (br d, J=7.03 Hz, 9H) 1.59-1.70 (m, 2H) 1.77 (s, 3H) 2.05-2.12 (m, 1H) 2.44-2.60 (m, 4H) 2.63-2.72 (m, 1H) 2.70-2.77 (m, 1H) 3.06 (s, 3H) 3.40-3.44 (m, 1H) 3.50 (br d, J=1.63 Hz, 4H) 3.64-3.75 (m, 1H) 3.80-3.88 (m, 1H) 3.91-3.99 (m, 1H) 4.04-4.20 (m, 1H) 4.21-4.28 (m, 1H) 4.37-4.43 (m, 1H) 4.59 (br s, 2H) 4.93-4.95 (m, 2H) 5.06-5.08 (m, 2H) 5.57-5.80 (m, 4H) 6.05-6.16 (m, 1H) 6.27-6.41 (m, 1H) 7.28-7.37 (m, 2H) 7.38-7.45 (m, 2H) 7.47-7.53 (m, 2H) 7.65-7.72 (m, 2H) 7.74-7.86 (m, 4H).

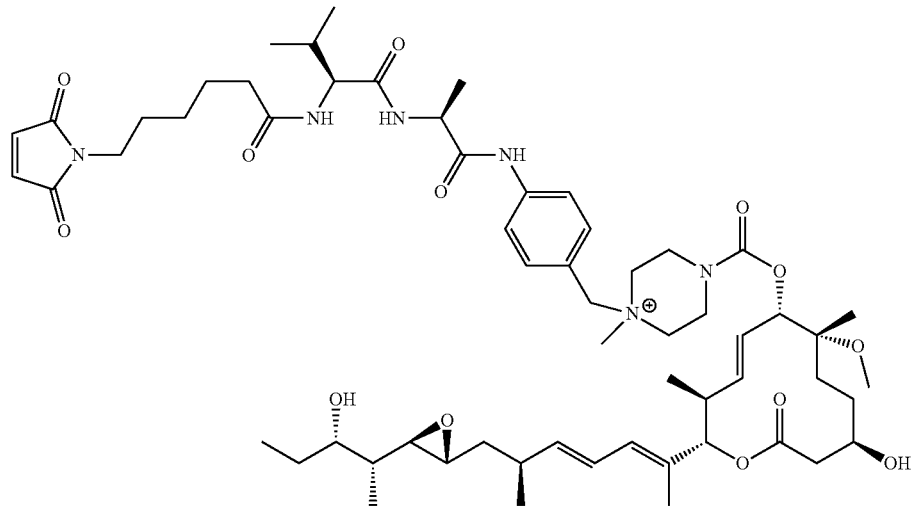

ADL5-D19

(2S,3S,6S,7R,10R,E)-10-hydroxy-2-((S,2E,4E)-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-methylpiperazine-1-carboxylate (114.2 mg, 0.180 mmol, 82% yield). LC/MS (ESI, m/z), 635.8 [M+H].

$^1$H-NMR (400 MHz, MeOH-d4): δ ppm 0.88-1.00 (m, 9H) 1.10 (d, J=6.65 Hz, 3 H) 1.16-1.27 (m, 4H) 1.40-1.70 (m, 8H) 1.77 (d, J=0.88 Hz, 3H) 2.28-2.36 (m, 3H) 2.42 (br t, J=5.08 Hz, 3H) 2.47-2.61 (m, 4H) 2.68 (dd, J=8.22, 2.20 Hz, 1H) 2.74 (td, J=5.99, 2.20 Hz, 1H) 3.13-3.17 (m, 1H) 3.34-3.38 (m, 3H) 3.47-3.58 (m, 5H) 3.81-3.87 (m, 1H) 5.01-5.10 (m, 2H) 5.54-5.81 (m, 3H) 6.06-6.15 (m, 1H) 6.34 (dd, J=15.00, 10.98 Hz, 1H).

1-(4-((S)-2-((S)-2-(((((9H-fluoren-9-yl)methoxy)carbonyl)amino)-3-methylbutanamido)propanamido)benzyl)-4-(((((2S,3S,6S,7R,10R,E)-10-hydroxy-2-((S,2E,4E)-7-((2R,3R)-3-((2R,3S)-3-hydroxypentan-2-yl)oxiran-2-yl)-6-

Linker-Payload (ADL5-D19): 1-(4-((S)-2-((S)-2-(6-(2,5-dioxo-2,5-dihydro-1 H-pyrrol-1-yl)hexanamido)-3-methylbutanamido)propanamido)benzyl)-4-(((((2S,3S,6S,7R, 10R, E)-10-hydroxy-2-((S,2E,4E)-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)-1-methylpiperazin-1-ium (19.4 mg, 0.018 mmol, 80% yield). LC/MS (ESI, m/z), 1105.9 [M+H].

$^1$H NMR (400 MHz, MeOH-d4): δ ppm 0.85-1.03 (m, 16H) 1.10 (d, J=6.78 Hz, 3H) 1.17-1.27 (m, 4H) 1.29-1.37 (m, 3H) 1.44-1.70, (m, 15H) 1.74-1.80 (m, 3H) 2.04-2.14 (m, 1H) 2.30 (t, J=7.47 Hz, 2H) 2.44-2.61 (m, 4H) 2.64-2.69 (m, 1H) 2.72-2.78 (m, 1H) 3.09 (s, 3H) 3.40-3.59 (m, 9H) 3.62-3.77 (m, 2H) 3.82-3.89 (m, 1H) 4.12-4.21 (m, 3H) 4.40-4.55 (m, 1H) 4.56-4.66 (m, 3H) 5.03-5.12 (m, 2H) 5.55-5.81 (m, 3H) 6.06-6.16 (m, 1H) 6.26-6.41 (m, 1H) 6.81 (s, 2H) 7.48-7.57 (m, 2H) 7.78-7.86 (m, 2H).

1.5.1.3 ADL5-D17

General procedure outlined above (section 1.5.1) was employed to synthesize ADL5-D17. The payload D17 was synthesized using procedures outlined in International Application No. PCT/US2019/026992 (see, e.g., Procedure 2, Procedure 3, and Procedure 4 or 5), which is incorporated herein by reference.

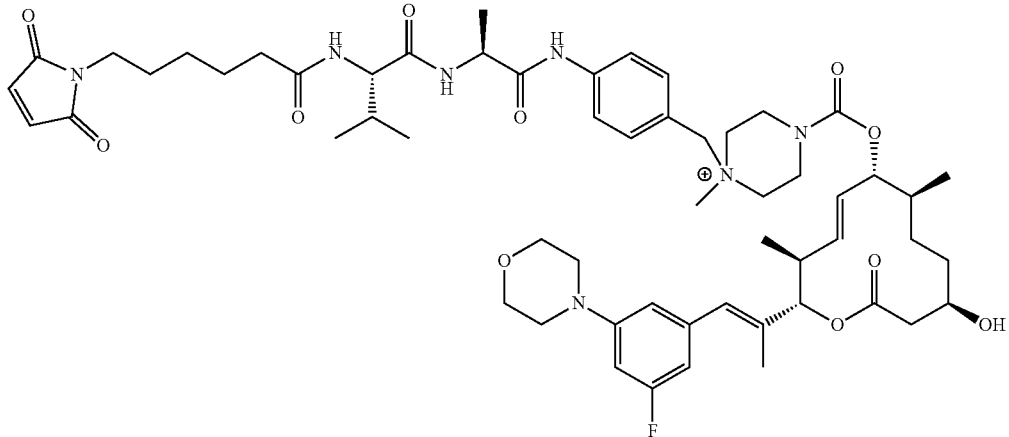 [SMILES: C/C(=C\c1cc(F)cc(N2CCOCC2)c1)[C@H]1OC(=O)C[C@H](O)CC[C@H](C)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]

Step 1: 1-(4-((S)-2-((S)-2-((((9H-fluoren-9-yl)methoxy)carbonyl)amino)-3-methylbutanamido)propanamido)benzyl)-4-(((((2S,3S,6R,7S,10R,E)-2-((E)-1-(3-fluoro-5-morpholinophenyl)prop-1-en-2-yl)-10-hydroxy-3,7-dimethyl-12-oxooxacyclododec-4-en-6-yl)oxy)carbonyl)-1-methylpiperazin-1-ium (12.9 mg, 69.8%). LC/MS (ESI, m/z), 1086.43 [M+H].

$^1$H-NMR (400 MHz, MeOH-d4): δ ppm 0.96-1.07 (m, 12H), 1.27-1.42 (m, 3 H), 1.46 (d, J=7.15 Hz, 3H), 1.62-1.72 (m, 2H), 1.88 (d, J=1.13 Hz, 3H), 1.97-2.06 (m, 1H), 2.04-2.14 (m, 1H), 2.44-2.53 (m, 1H), 2.58-2.69 (m, 2H), 3.08 (s, 3H), 3.13-3.19 (m, 4H), 3.38-3.56 (m, 4H), 3.61-3.75 (m, 2H), 3.79-3.88 (m, 5H), 3.90 -3.98 (m, 1H), 4.07-4.18 (m, 2H), 4.20-4.29 (m, 1H), 4.35-4.45 (m, 2H), 4.45-4.54 (m, 1H), 4.61 (s, 2H), 4.86-4.92 (m, 2H), 5.15 (d, J=10.67 Hz, 1H), 5.46-5.65 (m, 2H), 6.46-6.67 (m, 4H), 7.28-7.37 (m, 2H), 7.37-7.45 (m, 2H), 7.47-7.53 (m, 2H), 7.66-7.71 (m, 2H), 7.74-7.84 (m, 4H).

Step 2: 1-(4-((R)-2-((R)-2-(6-(2,5-dioxo-2,5-dihydro-1H-pyrrol-1-yl)hexanamido)-3-methylbutanamido)propanamido)benzyl)-4-(((((2S,3S,6R,7S,10R,E)-2-((E)-1-(3-fluoro-5-morpholinophenyl)prop-1-en-2-yl)-10-hydroxy-3,7-dimethyl-12-oxooxacyclododec-4-en-6-yl)oxy)carbonyl)-1-methylpiperazin-1-ium bromide (7.6 mg, 60.5% yield). LC/MS (ESI, m/z), 1057.62 [M+H].

$^1$H-NMR (400 MHz, MeOH-d4): δ ppm 0.95-1.08 (m, 12H), 1.24-1.42 (m, 5 H), 1.47 (d, J=7.15 Hz, 3H), 1.52-1.71 (m, 6H), 1.89 (d, J=1.13 Hz, 3H), 1.95-2.05 (m, 1H), 2.05-2.15 (m, 1H), 2.26-2.34 (m, 2H), 2.46-2.53 (m, 1H), 2.58-2.69 (m, 2H), 3.07-3.12 (m, 3H), 3.14-3.19 (m, 4H), 3.39-3.58 (m, 6H), 3.61-3.76 (m, 2H), 3.80-3.86 (m, 5H), 4.09-4.18 (m, 3H), 4.43-4.51 (m, 1H), 4.62 (s, 2H), 4.87-4.93 (m, 2H), 5.12-5.19 (m, 1H), 5.46-5.65 (m, 2H), 6.47-6.66 (m, 4H), 6.80 (s, 2H), 7.53 (d, J=8.66 Hz, 2H), 7.82 (d, J=8.66 Hz, 2H).

1.5.1.4 ADL5-D10

General procedure outlined above (section 1.5.1) was employed to synthesize ADL5-D10. The payload D10 was synthesized using procedures outlined in section 1.2.1

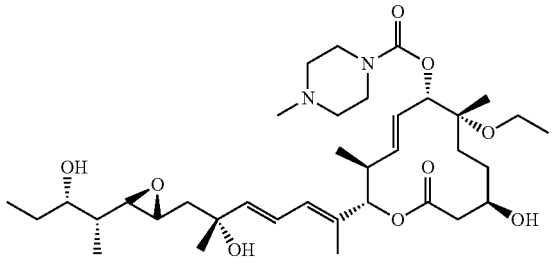

(2S,3S,6S,7R,10R,E)-7-ethoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-methylpiperazine-1-carboxylate (16.6 mg, 0.025 mmol, 38.7% yield). LC/MS (ESI, m/z), 665.7 [M+H]$^+$.

$^1$H-NMR (400 MHz, METHANOL-d): δ ppm 0.76-0.87 (m, 9H), 1.03-1.09 (m, 3H), 1.10-1.13 (m, 3H) 1.13-1.19 (m, 1H) 1.20-1.27 (m, 3H), 1.29-1.48 (m, 6H) 1.51-1.59 (m, 1H) 1.65-1.71 (m, 3H) 1.73-1.81 (m, 1H) 2.20 (s, 3H), 2.27-2.34 (m, 4H) 2.34-2.44 (m, 2H) 2.44-2.53 (m, 1H) 2.53-2.59 (m, 1H) 2.76-2.83 (m, 1H) 3.23-3.26 (m, 1H) 3.34-3.52 (m, 7H) 3.67-3.75 (m, 1H) 4.86-4.92 (m, 1H) 4.92 -4.99 (m,1 H), 5.41-5.51 (m, 1H), 5.60-5.71 (m, 1H), 5.72-5.82 (m, 1H), 6.00 -6.07 (m, 1H), 6.37-6.48 (m, 1H)

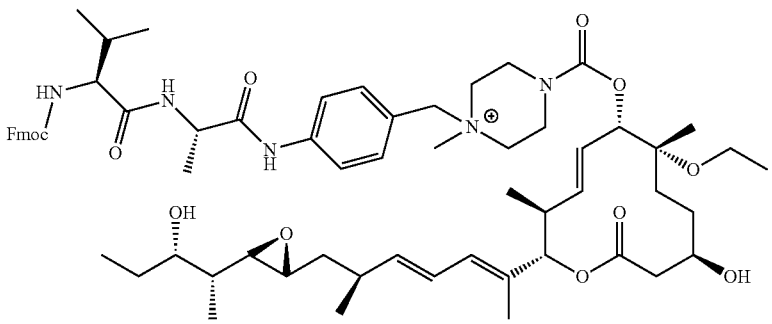

Step 1: 1-(4-((S)-2-((S)-2-((((9H-fluoren-9-yl)methoxy)carbonyl)amino)-3-methylbutanamido)propanamido)benzyl)-4-(((((2S,3S,6S,7R,10R,E)-7-ethoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl)oxy)carbonyl)-1-methylpiperazin-1-ium (18.6 mg, 0.016 mmol, 87% yield) as a colorless glaze. LC/MS (ESI, m/z), 1163.01 [M]+.

$^1$H-NMR (400 MHz, MeOH-d4): δ ppm 0.86-1.03 (m, 16H), 1.20 (s, 3H), 1.25 (s, 4H), 1.36 (s, 3H), 1.43-1.72 (m, 10H), 1.81 (s, 3H), 1.84-1.92 (m, 1H), 2.06-2.14 (m, 1H), 2.46-2.63 (m, 3H), 2.67-2.72 (m, 1H), 2.88-2.94 (m, 1H), 3.03-3.09 (m, 3H), 3.38-3.45 (m, 3H), 3.54 (s, 6H), 3.63-3.79 (m, 2H), 3.81-3.88 (m, 1H), 3.92-3.98 (m, 1H), 4.07-4.18 (m, 2H), 4.21-4.28 (m, 1H), 4.36-4.44 (m, 2H), 4.47-4.53 (m, 1H), 4.55-4.63 (m, 3H), 5.02-5.11 (m, 3H), 5.56-5.66 (m, 1H), 5.75-5.84 (m, 1H), 5.86-5.92 (m, 1H), 6.12-6.19 (m, 1H), 6.49-6.61 (m, 1H), 7.29-7.36 (m, 2H), 7.38-7.44 (m, 2H), 7.47-7.53 (m, 2H), 7.64-7.71 (m, 2H), 7.80 (dd, J=15.06, 7.91 Hz, 4H).

$^1$H-NMR (400 MHz, MeOH-d4): δ ppm 0.87-1.03 (m, 15H), 1.20 (s, 3H), 1.22-1.29 (m, 4H), 1.37 (s, 6H), 1.45-1.72 (m, 14H), 1.81 (s, 3H), 1.84-1.95 (m, 1H), 2.05-2.16 (m, 1H), 2.26-2.36 (m, 2H), 2.47-2.62 (m, 3H), 2.66-2.74 (m, 1H), 2.86-2.95 (m, 1H), 3.11 (s, 3H), 3.42-3.51 (m, 4H), 3.51-3.62 (m, 5H), 3.64-3.78 (m, 2H), 3.81-3.89 (m, 1H), 4.09-4.20 (m, 3H), 4.43-4.52 (m, 1H), 4.54-4.59 (m, 1H), 4.55-4.67 (m, 2H), 4.60-4.68 (m, 2H), 5.01-5.12 (m, 2H), 5.54-5.65 (m, 1H), 5.75-5.86 (m, 1H), 5.86-5.94 (m, 1H), 6.10-6.21 (m, 1H), 6.47-6.62 (m, 1H), 6.81 (s, 2H), 7.49-7.60 (m, 2H) 7.76-7.89 (m, 2H).

1.5.1.5 ADL5-D15

General procedure outlined above (section 1.5.1) was employed to synthesize ADL5-D15. The payload D15 was synthesized using procedures outlined in International Application No. PCT/US2019/026992, which is incorporated herein by reference.

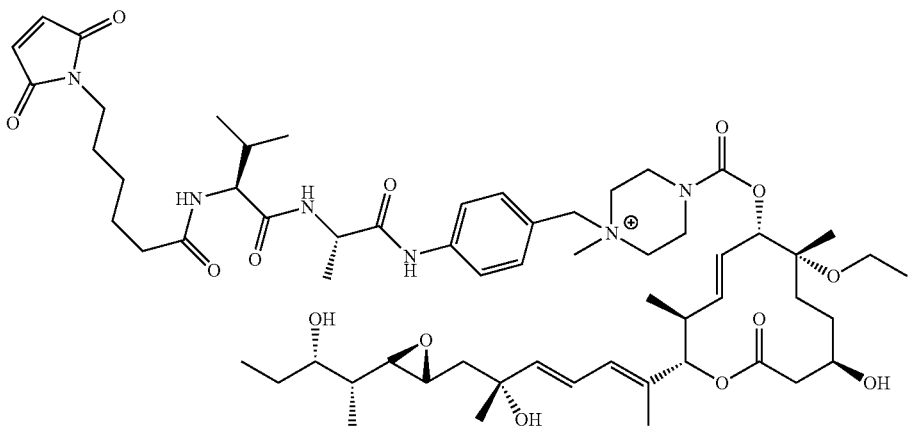

Step 2: 1-(4-((S)-2-((S)-2-(6-(2,5-dioxo-2,5-dihydro-1H-pyrrol-1-yl)hexanamido)-3-methylbutanamido)propanamido)benzyl)-4-(((((2S,3S,6S,7R,10R,E)-7-ethoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl)oxy)carbonyl)-1-methylpiperazin-1-ium (14.09 mg, 82% yield). LC/MS (ESI, m/z), 1057.62 [M+H]+.

Step 1: 1-(4-((S)-2-((S)-2-((((9H-fluoren-9-yl)methoxy)carbonyl)amino)-3-methylbutanamido)propanamido)benzyl)-4-(((((2S,3S,6R,7S,10R,E)-2-((E)-1-(1-(1-acetylpiperidin-4-yl)-4-fluoro-1 H-benzo[d][1,2,3]triazol-6-yl)prop-1-en-2-yl)-10-hydroxy-3,7-dimethyl-12-oxooxacyclododec-4-en-6-yl)oxy)carbonyl)-1-methylpiperazin-1-ium (100 mg, 0.086 mmol, 57.3% yield). LC/MS (ESI, m/z), 1167.76 [M+H].

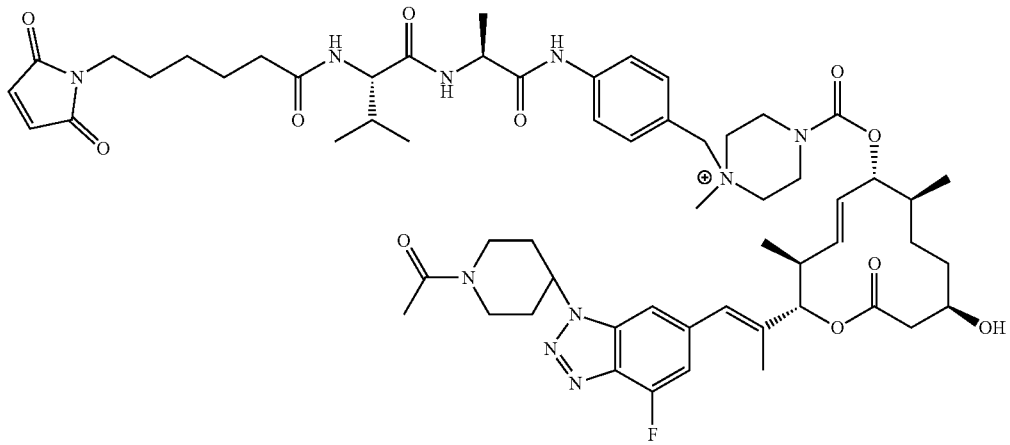 [SMILES: CC(=O)N1CCC(n2nnc3c(F)cc(/C=C(\C)[C@H]4OC(=O)C[C@H](O)CC[C@H](C)[C@@H](OC(=O)N5CC[N+](C)(Cc6ccc(NC(=O)[C@H](C)NC(=O)[C@@H](NC(=O)CCCCCN7C(=O)C=CC7=O)C(C)C)cc6)CC5)/C=C/[C@@H]4C)cc32)CC1]

Step 2: 4-(((((2S,3S,6R,7S,10R,E)-2-((E)-1-(1-(1-acetylpiperidin-4-yl)-4-fluoro-1H-benzo[d][1,2,3]triazol-6-yl)prop-1-en-2-yl)-10-hydroxy-3,7-dimethyl-12-oxooxacyclododec-4-en-6-yl)oxy)carbonyl)-1-(4-((S)-2-((S)-2-(6-(2,5-dioxo-2,5-dihydro-1H-pyrrol-1-yl)hexanamido)-3-methylbutanamido)propanamido)benzyl)-1-methylpiperazin-1-ium (32 mg, 0.028 mmol, 32.8% yield). LC/MS (ESI, m/z), 1138.64 [M+H].

$^1$H-NMR (400 MHz, MeOH-d4): δ ppm 0.99 (s, 10H), 1.26-1.40 (m, 5H), 1.42-1.49 (m, 3H), 1.67 (br s, 6H), 1.96 (d, J=1.00 Hz, 3H), 2.00-2.13 (m, 2H), 2.16-2.42 (m, 7H), 2.44-2.55 (m, 1H), 2.59-2.76 (m, 2H), 2.98-3.26 (m, 4H), 3.38-3.59 (m, 7H), 3.60-3.76 (m, 2H), 3.78-3.90 (m, 1H), 4.13 (br d, J=7.15 Hz, 3H), 4.41-4.52 (m, 1H), 4.53-4.71 (m, 3H), 4.89-4.97 (m, 1H), 5.10-5.27 (m, 2H), 5.48-5.67 (m, 2H), 6.79 (s, 2H) 7.07-7.17 (m, 1H), 7.48-7.61 (m, 3H), 7.78-7.84 (in, 2H).

1.5.1.5 ADL5-D32

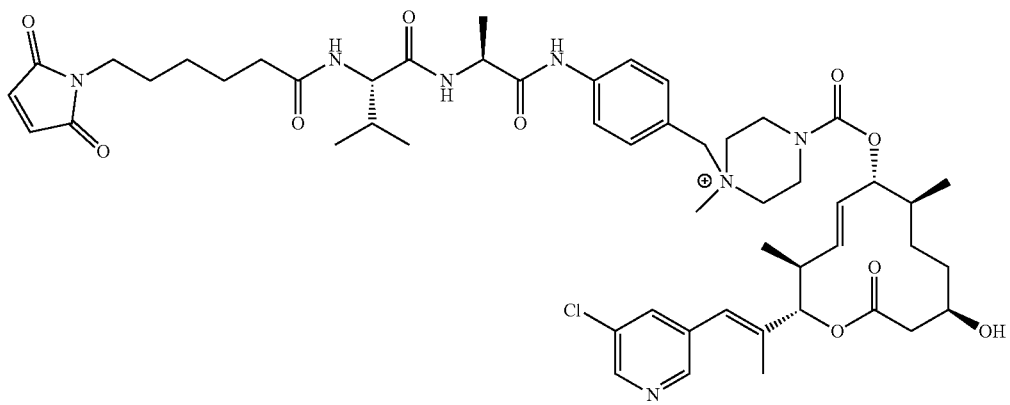 [SMILES: C/C(=C\c1cncc(Cl)c1)[C@H]1OC(=O)C[C@H](O)CC[C@H](C)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]

General procedure outlined above (section 1.5.1) was employed to synthesize ADL5-D32. The payload 015 was synthesized using procedures outlined in International Application No. PCT/US2019/026992, which is incorporated herein by reference.

Step 1: 1-(4-((S)-2-((S)-2-(((((9H-fluoren-9-yl)methoxy)carbonyl)amino)-3-methylbutanamido)propanamido)benzyl)-4-(((((2S,3S,6R,7S,10R,E)-2-((E)-1-(5-chloropyridin-3-yl)prop-1-en-2-yl)-10-hydroxy-3,7-dimethyl-12-oxooxacyclododec-4-en-6-yl)oxy)carbonyl)-1-methylpiperazin-1-ium (15 mg, 0.015 mmol, 69.6% yield) LC/MS (ESI, m/z), 1018.4 [M]*

1H NMR (400 MHz, METHANOL-d4) δ ppm 0.99 (s, 14H) 1.29-1.41 (m, 3H) 1.44-1.49 (m, 3H) 1.61-1.71 (m, 2H) 1.92 (d, J=1.25 Hz, 3H), 1.95-2.13 (m, 2H) 2.45-2.53 (m, 1H) 2.60-2.70 (m, 2H) 3.04-3.09 (m, 3H) 3.37 (s, 3H) 3.39-3.47 (m, 1H) 3.47-3.54 (m, 2H) 3.61-3.75, (m, 2H) 3.78-3.87 (m, 1H) 3.93-3.99 (m, 1H) 4.08-4.18 (m, 2H) 4.22-4.29 (m, 1H) 4.39-4.45 (m, 2H) 4.45-4.53 (m, 1H) 4.56 -4.63 (m,3 H) 5.17-5.23 (m, 1H) 5.48-5.64 (m, 2H) 6.57-6.64 (m, 1H) 7.28 -7.36 (m,2 H) 7.37-7.45 (m, 2H) 7.47-7.54 (m, 2H) 7.64-7.70 (m, 2H) 7.75-7.84 (m, 5H) 8.41-8.48 (m, 2H)

Step 2: 4-(((((2S,3S,6R,7S,10R,E)-2-((E)-1-(5-chloropyridin-3-yl)prop-1-en-2-yl)-10-hydroxy-3,7-dimethyl-12-oxooxacyclododec-4-en-6-yl)oxy)carbonyl)-1-(4-((S)-2-((S)-2-(6-(2,5-dioxo-2,5-dihydro-1H-pyrrol-1-yl) hexanamido)-3-methylbutanamido)propanamido)benzyl)-1-methylpiperazin-1-ium (6.2 mg, 42.5% yield). LC/MS (ESI, m/z), 990.34 [M+H].

1H NMR (400 MHz, METHANOL-d4) δ ppm 0.97-1.09 (m, 12H) 1.24-1.41 (m, 5H) 1.47 (d, J=7.15 Hz, 3H) 1.55-1.71 (m, 6H) 1.92 (d, J=1.13 Hz, 3H) 1.98-2.15 (m, 2H) 2.27-2.36 (m, 2H) 2.46-2.53 (m, 1H) 2.60-2.71 (m, 2H) 3.06-3.13 (m, 3H) 3.35-3.38 (m, 1H) 3.41-3.58 (m, 6H) 3.62-3.76 (m, 2H) 3.80-3.88 (m, 1H) 4.08-4.19 (m, 3H)

4.43-4.52 (m, 1H) 4.57-4.66 (m, 2H) 5.16-5.24 (m, 1H) 5.49 -5.68, (m, 2H) 6.62 (s, 1H) 6.81 (s, 2H) 7.49-7.57 (m, 2H) 7.76-7.87 (m, 3H) 8.39-8.49 (m, 2H)

1.5.1.5 ADL5-D30

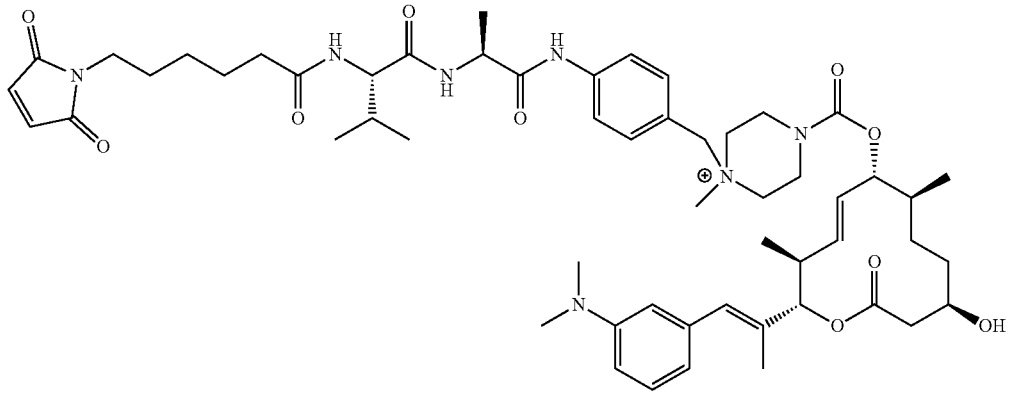 [SMILES: C/C(=C\c1cccc(N(C)C)c1)[C@H]1OC(=O)C[C@H](O)CC[C@H](C)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]

General procedure outlined above (section 1.5.1) was employed to synthesize ADL5-D30. The payload D30 was synthesized using procedures outlined in International Application No. PCT/US2019/026992, which is incorporated herein by reference.

Step 1: 1-(4-((S)-2-((S)-2-(((((9H-fluoren-9-yl)methoxy)carbonyl)amino)-3-methylbutanamido)propanamido)benzyl)-4-((((2S,3S,6R,7S,10R,E)-2-((E)-1-(3-(dimethylamino)phenyl)prop-1-en-2-yl)-10-hydroxy-3,7-dimethyl-12-oxooxacyclododec-4-en-6-yl)oxy)carbonyl)-1-methylpiperazin-1-ium (16 mg, 0.016 mmol, 51.4% yield) LC/MS (ESI, m/z), 1027.50 [M+H]+

1H NMR (400 MHz, METHANOL-$d_4$) δ ppm 0.95-1.07 (m, 13H) 1.31-1.42 (m, 2H) 1.44-1.50 (m, 3H) 1.63-1.71 (m, 2H) 1.84-1.92 (m, 3H) 1.98-2.14 (m, 2H) 2.47-2.56 (m, 1H) 2.60-2.67 (m, 2H) 2.93 (s, 6H) 3.03-3.09 (m, 3H) 3.37 (s, 4H) 3.47-3.56 (m, 2H) 3.63-3.75 (m, 2H) 3.79-3.88 (m, 1H) 3.92-3.98 (m, 1H) 4.08-4.19 (m, 2H) 4.21-4.27 (m, 1H) 4.37-4.44 (m, 2H) 4.45-4.54 (m, 1H) 4.57-4.62 (m, 2H) 4.91-4.94 (m, 2H) 5.15-5.20 (m, 1H) 5.47-5.55 (m, 1H) 5.56-5.65 (m, 1H) 6.58 (s, 1H) 6.67 (d, J=1.51 Hz, 3H) 7.15-7.24 (m, 1H), 7.28-7.36 (m, 2H) 7.38-7.45 (m, 2H) 7.47-7.54 (m, 2H) 7.64-7.73 (m, 2H) 7.75-7.85 (m, 4H)

Step 2: 4-((((2S,3S,6R,7S,10R,E)-2-((E)-1-(5-chloropyridin-3-yl)prop-1-en-2-yl)-10-hydroxy-3,7-dimethyl-12-oxooxacyclododec-4-en-6-yl)oxy)carbonyl)-1-(4-((S)-2-((S)-2-(6-(2,5-dioxo-2,5-dihydro-1H-pyrrol-1-yl)hexanamido)-3-methylbutanamido)propanamido)benzyl)-1-methylpiperazin-1-ium (6.2 mg, 42.5% yield). LC/MS (ESI, m/z), 990.34 [M+H].

1H NMR (400 MHz, METHANOL-d4) δ ppm 0.88 (d, J=6.65 Hz, 12H) 1.16-1.30 (m, 4H) 1.32-1.38 (m, 3H) 1.43-1.58 (m, 6H) 1.75-1.80, (m, 3H) 1.84-1.92 (m, 1H) 1.93-2.02 (m, 1H) 2.14-2.21 (m, 2H) 2.35-2.42 (m, 1H) 2.48-2.57 (m, 2H) 2.82 (s, 6H) 2.94-3.02 (m, 3H), 3.27-3.32 (m, 1H) 3.35-3.45 (m, 4H) 3.50-3.64 (m, 2H) 3.68-3.76 (m, 1H) 3.97-4.07 (m, 3H) 4.31-4.40 (m, 1H) 4.47-4.53 (m, 2H) 5.03-5.09 (m, 1H) 5.35-5.44 (m, 1H) 5.45-5.55 (m, 1H) 6.42-6.50 (m, 1H) 6.51 -6.62 (m, 3H) 6.69 (s, 2H) 7.03-7.12 (m, 1H) 7.38-7.44 (m, 2H) 7.66-7.75 (m, 2H) 8.42-8.47 (m, 1H).

1.5.1.5 ADL5-D27

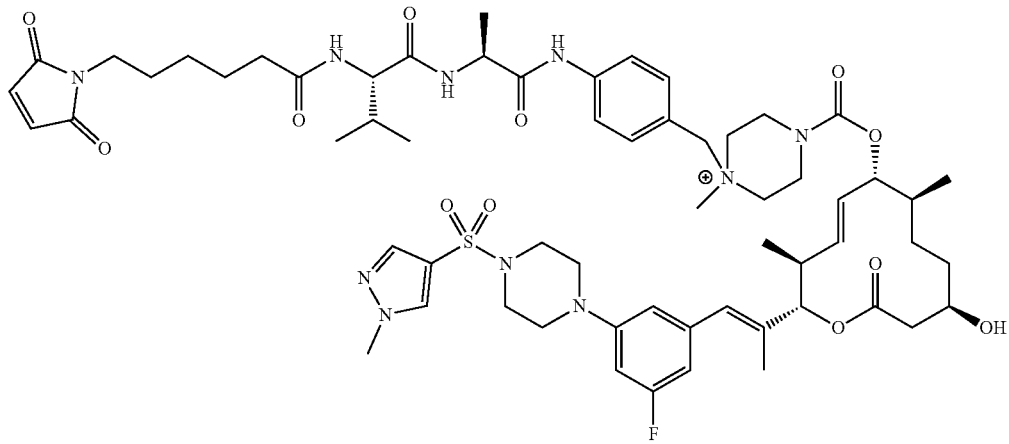 [SMILES: C/C(=C\c1cc(F)cc(N2CCN(S(=O)(=O)c3cnn(C)c3)CC2)c1)[C@H]1OC(=O)C[C@H](O)CC[C@H](C)[C@@H](OC(=O)N2CC[N+](C)(Cc3ccc(NC(=O)[C@H](C)NC(=O)[C@@H](NC(=O)CCCCCN4C(=O)C=CC4=O)C(C)C)cc3)CC2)/C=C/[C@@H]1C]

General procedure outlined above (section 1.5.1) was employed to synthesize ADL5-D27. The payload D27 was synthesized using procedures outlined in International Application No. PCT/US2019/026992, which is incorporated herein by reference.

Step 1: 1-(4-((S)-2-((S)-2-((((9H-fluoren-9-yl)methoxy)carbonyl)amino)-3-methylbutanamido)propanamido)benzyl)-4-((((2S,3S,6R,7S,10R,E)-2-((E)-1-(3-fluoro-5-(4-((1-methyl-1 H-pyrazol-4-yl)sulfonyl)piperazin-1-yl)phenyl)prop-1-en-2-yl)-10-hydroxy-3,7-dimethyl-12-oxooxacyclododec-4-en-6-yl)oxy)carbonyl)-1-methylpiperazin-1-ium (25.2 mg, 0.020 mmol, 83% yield). LC/MS (ESI, m/z), 1230.54 [M+H]+

Step 2: 1-(4-((S)-2-((S)-2-(6-(2,5-dioxo-2,5-dihydro-1 H-pyrrol-1-yl)hexanamido)-3-methylbutanamido)propanamido)benzyl)-4-((((2S,3S,6R,7S,10R,E)-2-((E)-1-(3-fluoro-5-(4-((1-methyl-1 H-pyrazol-4-yl)sulfonyl)piperazin-1-yl)phenyl)prop-1-en-2-yl)-10-hydroxy-3,7-dimethyl-12-oxooxacyclododec-4-en-6-yl)oxy)carbonyl)-1-methylpiperazin-1-ium (5.2 mg, 4.33 µmol, 21.13% yield). LC/MS (ESI, m/z), 1201.68 [M+H]+

$^1$H NMR (400 MHz, METHANOL-$d_4$) δ ppm 0.87 (d, J=6.78 Hz, 12H) 1.13-1.29 (m, 4H) 1.31-1.38 (m, 3H) 1.43-1.59 (m, 6H) 1.71-1.79, (m, 3H) 1.83-2.02 (m, 2H) 2.14-2.21 (m, 2H) 2.34-2.41 (m, 1H) 2.56 (s, 8H) 2.94-3.01 (m, 3H) 3.12-3.18 (m, 8H) 3.28-3.45 (m, 5H), 3.48-3.63 (m, 2H) 3.70 (s, 4H) 3.97-4.07 (m, 3H) 4.29 -4.41 (m, 1H) 4.49 (s, 2H) 4.98-5.06 (m, 1H) 5.34-5.54 (m, 2H) 6.37-6.45 (m, 2H) 6.51 (s, 2H) 6.69 (s, 2H) 7.37-7.43 (m, 2H) 7.63-7.73 (m, 4H)

1.5.1.6 ADL10-D1

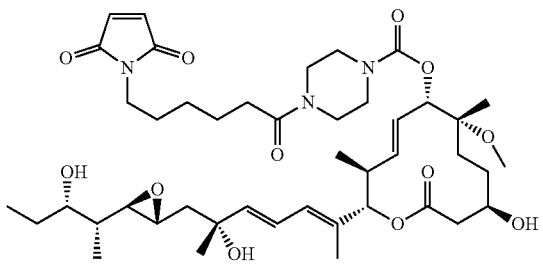 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(C(=O)CCCCCN3C(=O)C=CC3=O)CC2)/C=C/[C@@H]1C]

(2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl piperazine-1-carboxylate (0.012 g, 0.019 mmol), 2,5-dioxopyrrolidin-1-yl 6-(2,5-dioxo-2,5-dihydro-1H-pyrrol-1-yl)hexanoate (0.012 g, 0.038 mmol), and DCM (0.188 ml, 0.019 mmol) were combined and stirred overnight. The mixture was directly loaded onto a silica gel column and chromatographed to afford (2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-(6-(2,5-dioxo-2,5-dihydro-1 H-pyrrol-1-yl)hexanoyl)piperazine-1-carboxylate (8.4 mg, 10.12 µmol, 53.7% yield). LC/MS [M+Na]853.5.

$^1$H-NMR (400 MHz, MeOH-d4): δ ppm 0.89 (s, 9H) 1.21-1.39 (m, 9H) 1.41-1.56 (m, 5H) 1.57-1.71 (m, 6H) 1.69-1.71 (m, 1H) 1.79, (d, J=0.88 Hz, 3H) 1.82-1.90 (m, 1H) 2.34-2.43 (m, 1H) 2.41-2.41 (m, 1H) 2.46-2.63 (m, 3H) 2.65-2.68 (m, 2H) 2.68 (s, 3H) 2.86-2.92 (m, 1H) 3.33 (s, 3H) 3.51 (br d, J=7.03 Hz, 6H) 3.54-3.60 (m, 5H) 3.77-3.88 (m, 1H) 5.06 (s, 2H) 5.53-5.63 (m, 1H) 5.70-5.80 (m, 1H), 5.83-5.94 (m, 1H) 6.08-6.19 (m, 1H) 6.47-6.59 (m, 1H) 6.80 (s, 2H).

1.6 Preparation of ADL12-D1, ADL14-D1, and ADL15-D1

1.6.1 Overview—General Procedure 1

Scheme 7

Step 1

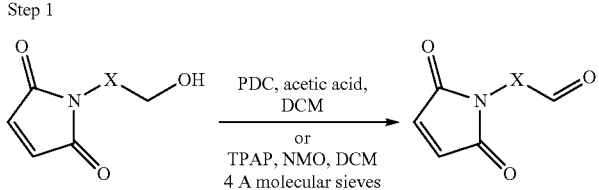

PDC, acetic acid, DCM
or
TPAP, NMO, DCM
4 A molecular sieves

Step 2

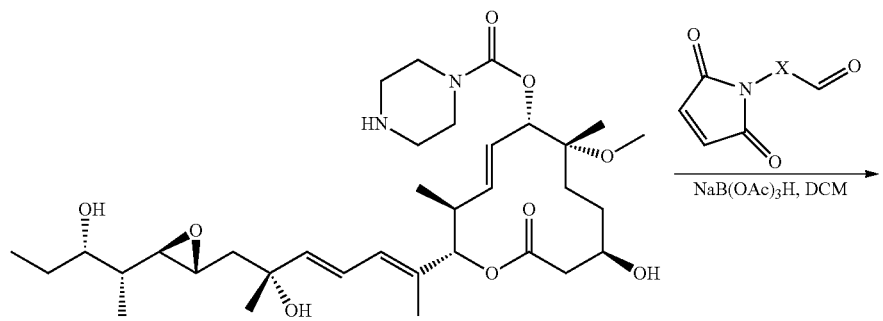

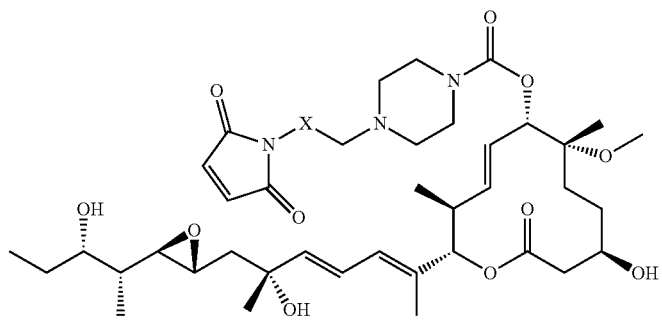

For ADL12-D1—Step 1: To a stirred solution of 1-(6-hydroxyhexyl)-1H-pyrrole-2,5-dione (0.200 g, 1.014 mmol) in DCM (20.28 mL, 1.014 mmol) was added PDC (3.81 g, 10.14 mmol) and acetic acid (0.1 mL). The reaction mixture was stirred for 3 hours at RT. The reaction mixture was then filtered through a silica pad and concentrated to dryness to afford 6-(2,5-dioxo-2,5-dihydro-1H-pyrrol-1-yl)hexanal (40 mg, 0.205 mmol, 20.21% yield).

For ADL14-D1 and ADL15-D1—Step 1: To a stirred solution of maleimide alcohol (1.0 equiv.) in DCM (0.05 M) was added pre-activated powdered MS-4A 2.6 mg per 1 mg of alcohol, N-methylmorpholine-N-oxide (1.2 equiv.), and TPAP (0.1 equiv.) in that order. The reaction mixture was stirred for 60 min at RT. The reaction mixture was then filtered through a silica gel pad and concentrated to dryness. Unpurified product was taken forward to the next step (Step 2).

Step 2: (2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl piperazine-1-carboxylate (1.0 equiv.), 2-(2,5-dioxo-2,5-dihydro-1H-pyrrol-1-yl)acetaldehyde (2.0-3.0 equiv.), DCM (0.1 M), sodium triacetoxyborohydride (3.0 equiv.) were mixed and stirred for 10 min. The reaction mixture was then loaded directly onto a silica gel column and chromatographed to afford the desired linker-payload.

1.6.1.1 ADL12-D1

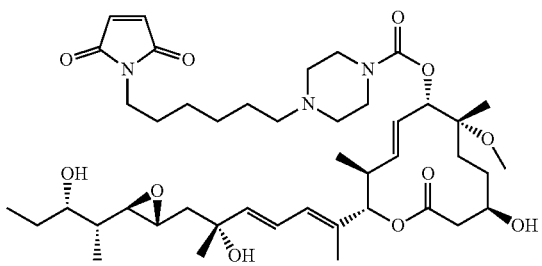 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CCN(CCCCCCN3C(=O)C=CC3=O)CC2)/C=C/[C@@H]1C]

Linker-Payload (ADL12-D1): General procedure outlined in section 1.6.1 was employed to synthesize (2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methyl-hepta-2,4-dien-2-yl)-7-methoxy-3,7-dimethyl-12-oxooxacyclododec-4-en-6-yl 4-(6-(2,5-dioxo-2,5-dihydro-1H-pyrrol-1-yl)hexyl)piperazine-1-carboxylate (41 mg, 0.050 mmol, 80% yield). LC/MS [M+]*816.75.

$^1$H-NMR (400 MHz, MeOH-d4): δ ppm 0.86-0.98 (m, 9H) 1.20-1.23 (m, 3H) 1.23-1.40 (m, 8H) 1.41-1.70 (m, 12H) 1.79 (d, J=0.63 Hz, 3H) 1.83-1.91 (m, 1H) 2.33-2.40 (m, 2H) 2.43 (br t, J=4.77 Hz, 4H) 2.48-2.64 (m, 3H) 2.65-2.69 (m, 1H) 2.87-2.92 (m, 1H) 3.32 (s, 3H) 3.41-3.60 (m, 7H) 3.79-3.87 (m, 1H) 5.04 (dd, J=19.39, 10.23 Hz, 2H) 5.57 (dd, J=15.18, 9.79 Hz, 1H) 5.69-5.79 (m, 1H) 5.87 (d, J=15.31 Hz, 1H) 6.11-6.17 (m, 1H) 6.49-6.58 (m, 1H) 6.80 (s, 2H).

1.6.1.X ADL12-D28

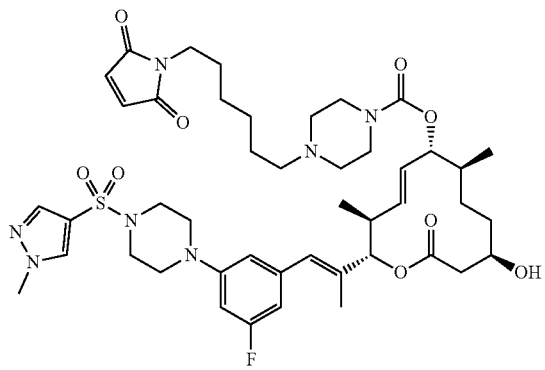 [SMILES: C/C(=C\c1cc(F)cc(N2CCN(S(=O)(=O)c3cnn(C)c3)CC2)c1)[C@H]1OC(=O)C[C@H](O)CC[C@H](C)[C@@H](OC(=O)N2CCN(CCCCCCN3C(=O)C=CC3=O)CC2)/C=C/[C@@H]1C]

Linker-Payload (ADL12-D28): General procedure outlined in section 1.6.1 was employed to synthesize (2S,3S,6R,7S,10R,E)-2-((E)-1-(3-fluoro-5-(4-((1-methyl-1H-pyrazol-4-yl)sulfonyl)piperazin-1-yl)phenyl)prop-1-en-2-yl)-10-hydroxy-3,7-dimethyl-12-oxooxacyclododec-4-en-6-yl 4-(6-(2,5-dioxo-2,5-dihydro-1H-pyrrol-1-yl)hexyl)piperazine-1-carboxylate (2.3 mg, 30.7%). LC/MS [M+]$^+$897.32

$^1$H NMR (400 MHz, METHANOL-d$_4$) δ ppm 0.85-0.93 (m, 6H) 1.16-1.34 (m, 6H) 1.37-1.58 (m, 6H) 1.72-1.77 (m, 3H) 1.80-1.88 (m, 1H), 2.23-2.41 (m, 7H) 2.47-2.57 (m, 2H) 3.08-3.19 (m, 9H) 3.33-3.42 (m, 5H) 3.70 (s, 4H) 4.67-4.72 (m, 1H) 4.98-5.07 (m, 1H) 5.33-5.50 (m, 2H) 6.36-6.43 (m, 2H) 6.44-6.53 (m, 2H) 6.70 (s, 2H) 7.62-7.69 (m, 2H)

1.6.1.X ADL12-D35

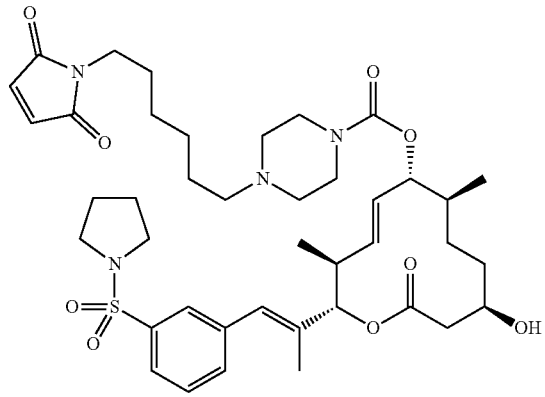 [SMILES: C/C(=C\c1cccc(S(=O)(=O)N2CCCC2)c1)[C@H]1OC(=O)C[C@H](O)CC[C@H](C)[C@@H](OC(=O)N2CCN(C(C)CCCCCN3C(=O)C=CC3=O)CC2)/C=C/[C@@H]1C]

Linker-Payload (ADL12-D35): General procedure outlined in section 1.6.1 was employed to synthesize (2S,3S,6R,7S,10R,E)-10-hydroxy-3,7-dimethyl-12-oxo-2-((E)-1-(3-(pyrrolidin-1-ylsulfonyl)phenyl)prop-1-en-2-yl)oxacyclododec-4-en-6-yl 4-(6-(2,5-dioxo-2,5-dihydro-1H-pyrrol-1-yl)hexyl)piperazine-1-carboxylate (4.0 mg, 5.11 μmol, 28.8% yield). LC/MS [M+H]$^+$ 783.5

1H NMR (400 MHz, METHANOL-d4) δ ppm 0.91 (dd, J=6.78, 2.51 Hz, 6H) 1.17 -1.33 (m, 6H) 1.38-1.59 (m, 6H) 1.65 (s, 4H) 1.80 (s, 3H), 1.82-1.91 (m, 1H) 2.23-2.41 (m, 7H) 2.49-2.61 (m, 2H) 3.14 (s, 4H) 3.38 (br d, J=7.15 Hz, 6H) 3.67-3.76 (m, 1H) 4.68-4.73 (m, 1H) 5.03-5.11 (m, 1H) 5.34-5.52 (m, 2H) 6.55-6.62 (m, 1H) 6.70 (s, 2H) 7.46-7.54 (m, 2H) 7.58-7.65 (m, 2H)

1.6.1.X ADL12-D22 (R)

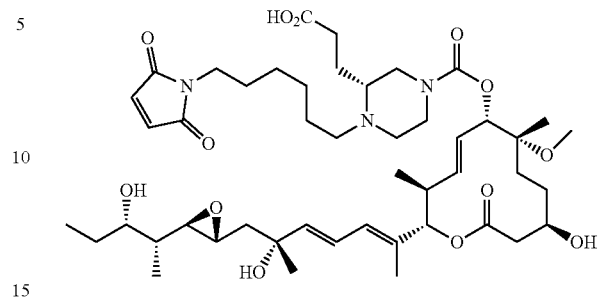

Linker-Payload (ADL12-D28): General procedure outlined in section 1.6.1 was employed to synthesize 3-((R)-1-(6-(2,5-dioxo-2,5-dihydro-1H-pyrrol-1-yl)hexyl)-4-((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)piperazin-2-yl) propanoic acid (3.2 mg, 3.60 μmol, 15.39% yield). LC/MS [M+]$^+$888.5

1.6.1.X ADL12-D22 (S)

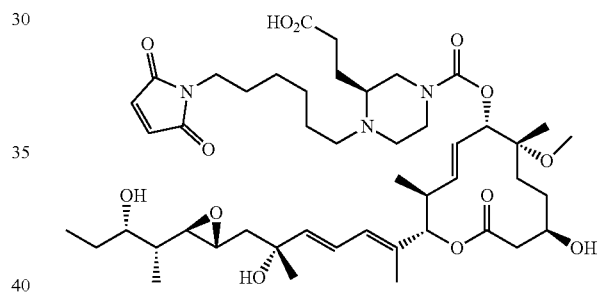

Linker-Payload (ADL12-D28): General procedure outlined in section 1.6.1 was employed to synthesize 3-((S)-1-(6-(2,5-dioxo-2,5-dihydro-1 H-pyrrol-1-yl)hexyl)-4-((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)piperazin-2-yl) propanoic acid (3.6 mg, 3.60 μmol, 28.7% yield). LC/MS [M+]$^+$888.56

1.6.1.2 ADL14-D1

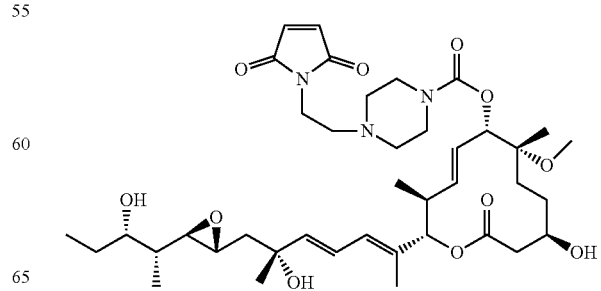

Linker-Payload (ADL14-D1): General procedure outlined in section 1.6.1 was employed to synthesize (2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methyl-hepta-2,4-dien-2-yl)-7-methoxy-3,7-dimethyl-12-oxooxacyclododec-4-en-6-yl 4-(2-(2,5-dioxo-2,5-dihydro-1H-pyrrol-1-yl)ethyl)piperazine-1-carboxylate (8 mg, 10.53 µmol, 33.5% yield). LC/MS [M+H] 760.3.

¹H-NMR (400 MHz, MeOH-d4): δ ppm 0.85-1.01 (m, 9H), 1.17-1.33 (m, 5H), 1.36 (s, 3H), 1.41-1.71 (m, 7H), 1.80 (s, 3H), 1.83-1.95 (m, 1H), 2.48 (br s, 10H), 2.89-2.98 (m, 1H), 3.40-3.57 (m, 5H), 3.61-3.72 (m, 2H), 3.78-3.91 (m, 1H), 4.98-5.14 (m, 2H), 5.50-5.52 (m, 1H), 5.52-5.65 (m, 1H), 5.69-5.82 (m, 1H), 5.86-5.96 (m, 1H), 6.09-6.21 (m, 1H), 6.47-6.60 (m, 1H), 6.79-6.90 (m, 2H).

1.6.1.3 ADL15-D1

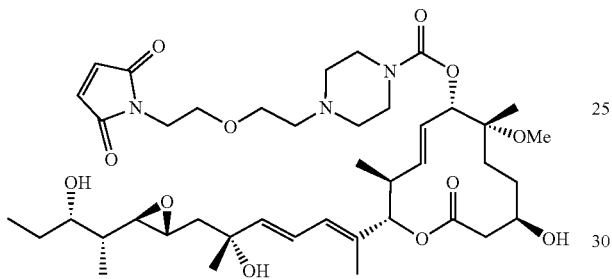

Linker-Payload (ADL15-D1): General procedure outlined in section 1.6.1 was employed to synthesize (2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methyl-hepta-2,4-dien-2-yl)-7-methoxy-3,7-dimethyl-12-oxooxacyclododec-4-en-6-yl 4-(2-(2-(2,5-dioxo-2,5-dihydro-1H-pyrrol-1-yl)ethoxy)ethyl)piperazine-1-carboxylate (7 mg, 8.71 µmol, 23.10% yield).

LC/MS [M=+H] 804.1.

¹H-NMR (400 MHz, MeOH-d4): δ ppm 0.85-1.02 (m, 9H), 1.18-1.32 (m, 4H), 1.36 (s, 3H), 1.40-1.72 (m, 7H), 1.78-1.83 (m, 3H), 1.85-1.93 (m, 1H), 2.42-2.65 (m, 9H), 2.67-2.73 (m, 1H), 2.89-2.96 (m, 1H), 3.37 (s, 5H), 3.41-3.58 (m, 5H), 3.59-3.67 (m, 4H), 3.68-3.75 (m, 2H), 3.81-3.89 (m, 1H), 4.94-5.15 (m, 2H), 5.61 (br d, J=10.04 Hz, 1H), 5.69-5.82 (m, 1H), 5.89 (br d, J=15.18 Hz, 1H), 6.16 (br d, J=10.92 Hz, 1H), 6.56 (br s, 1H), 6.77-6.91 (m, 2H).

1.7 ADL12-D2

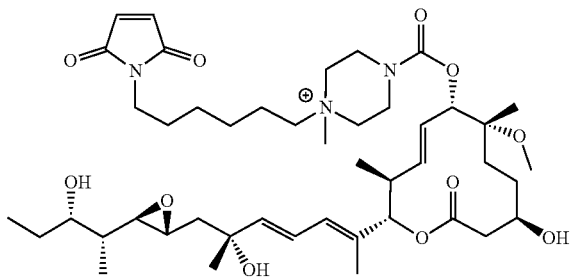 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](OC(=O)N2CC[N+](C)(CCCCCCN3C(=O)C=CC3=O)CC2)/C=C/[C@@H]1C]

(2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-(6-(2,5-dioxo-2,5-dihydro-1H-pyrrol-1-yl)hexyl)piperazine-1-carboxylate (26 mg, 0.032 mmol), acetonitrile (319 µL, 0.032 mmol), iodomethane (19.92 µL, 0.319 mmol) were combined and stirred overnight. The reaction mix was concentrated to dryness and chromatographed (0-30% MeOH in DCM) to afford 1-(6-(2,5-dioxo-2,5-dihydro-1H-pyrrol-1-yl)hexyl)-4-((((2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)-1-methylpiperazin-1-ium (14 mg, 0.017 mmol, 52.9% yield). LC/MS [M+] 831.6.

¹H-NMR (400 MHz, MeOH-d4): δ ppm 0.86-0.98 (m, 9H) 1.26 (s, 4H) 1.36 (s, 3H) 1.40-1.58 (m, 9H) 1.60-1.71 (m, 4H) 1.80 (d, J=0.88 Hz, 4H) 1.85-1.91 (m, 1H) 1.87-1.88 (m, 1H) 2.48-2.63 (m, 3H) 2.65-2.72 (m, 1H) 2.88-2.94 (m, 1H) 3.18 (s, 3H) 3.34-3.41 (m, 3H) 3.53 (s, 10H) 3.73-3.90 (m, 3H) 3.90-4.06 (m, 2H) 5.02-5.11 (m, 2H) 5.56-5.66 (m, 1H) 5.70-5.81 (m, 1H) 5.84-5.94 (m, 1H) 6.11-6.20 (m, 1H) 6.50-6.60 (m, 1H) 6.83 (s, 2H).

1.8 ADL15-D2

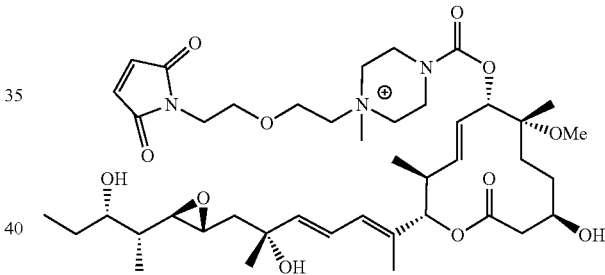

(2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-(2-(2-(2,5-dioxo-2,5-dihydro-1H-pyrrol-1-yl)ethoxy)ethyl)piperazine-1-carboxylate (6 mg, 7.463 µmol), iodomethane (0.467 µL, 7.463 µmol), and acetonitrile (0.390 µL, 7.463 µmol) were combined and stirred at RT. The reaction mixture was concentrated to dryness to afford (2S,3S,6S,7R,10R,E)-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-(2-(2-(2,5-dioxo-2,5-dihydro-1H-pyrrol-1-yl)ethoxy)ethyl)-4-methyl-414-piperazine-1-carboxylate (6 mg, 7.33 µmol, 98% yield). LC/MS [M+]⁺819.28.

¹H-NMR (400 MHz, MeOH-d4): δ ppm 0.74-0.88 (m, 9H) 1.18 (br d, J=4.27 Hz, 5H) 1.23-1.27 (m, 3H) 1.28-1.49 (m, 5H) 1.51-1.61 (m, 2H) 1.66-1.71 (m, 3H) 1.73-1.80 (m, 1H) 2.36-2.53 (m, 3H) 2.55-2.60 (m, 1H) 2.78-2.83 (m, 1H) 3.10-3.14 (m, 3H) 3.23-3.25 (m, 3H) 3.32-3.51 (m, 5H) 3.52-3.67 (m, 6H) 3.67-3.87 (m, 7H) 4.93-5.01 (m, 2H) 5.44-5.55 (m, 1H) 5.61-5.70 (m, 1H) 6.00-6.07 (m, 1H) 6.38-6.48 (m, 1H) 6.75 (s, 2H).

1.9 ADL5-D25
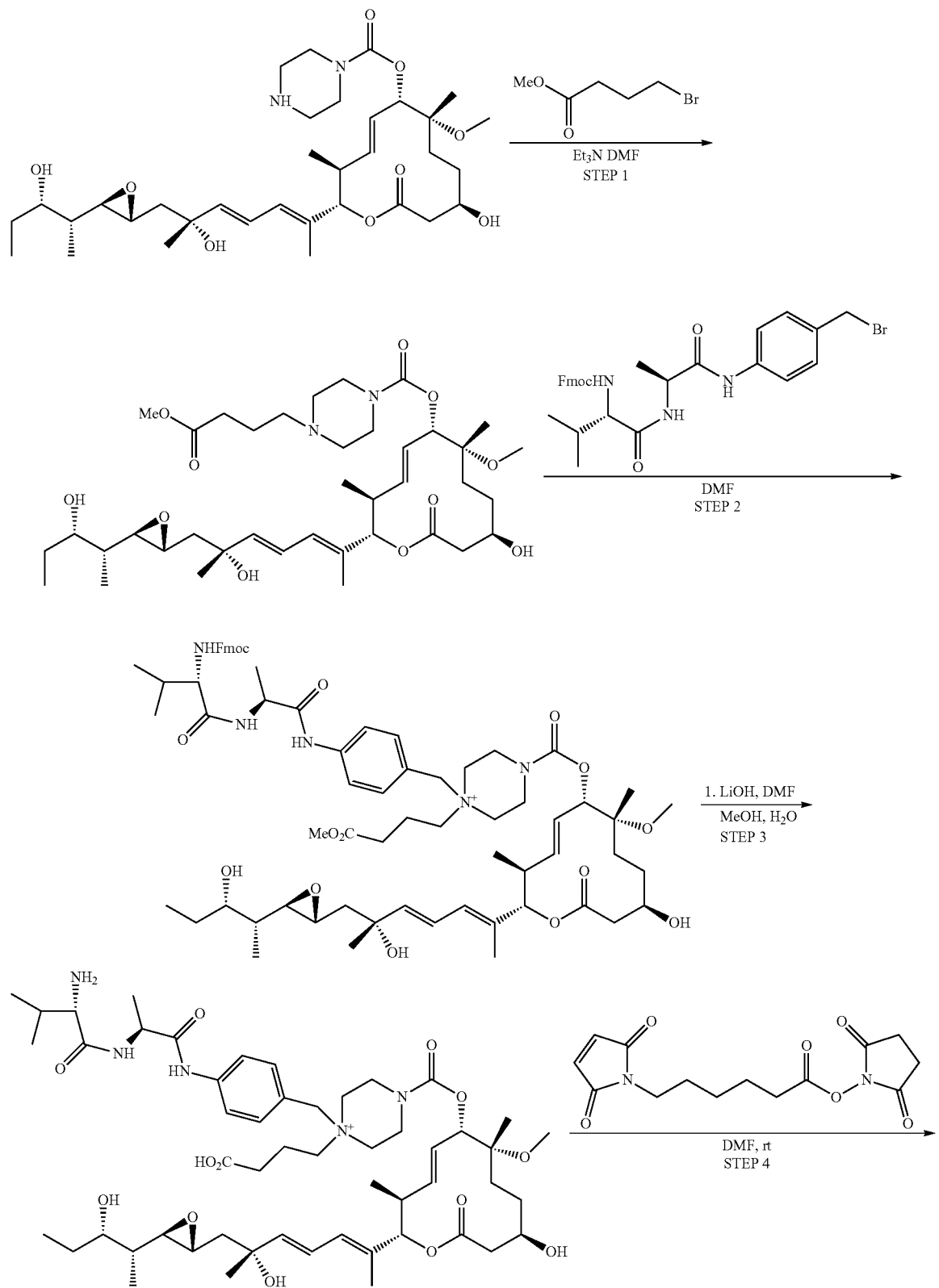
Scheme 8

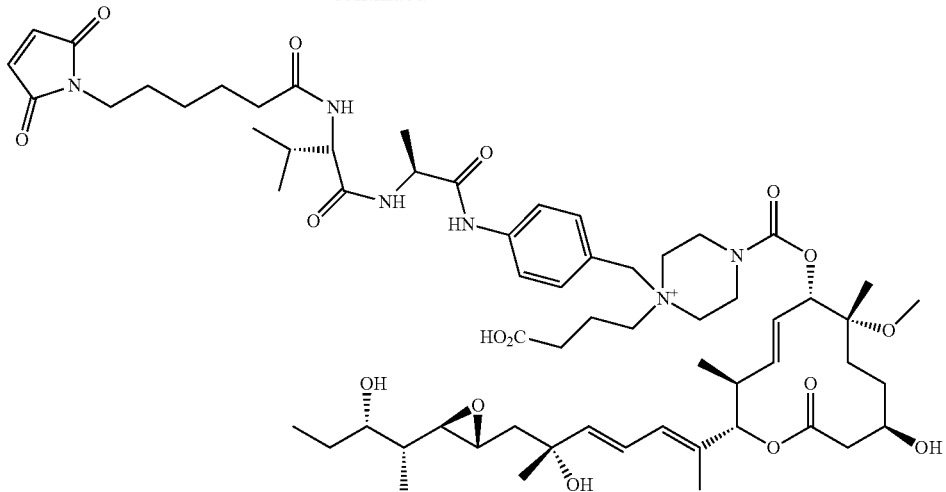

Step 1: D1 (40 mg, 0.063 mmol) was dissolved in N,N-dimethylformamide (730 μl, 9.422 mmol) and methyl-bromobutarate (23.69 μL, 0.188 mmol) was added followed by triethylamine (35.0 μL, 0.251 mmol). The solution was stirred at RT for 2 days. The solvent was evaporated. Purification by column chromatography afforded (2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-(4-methoxy-4-oxobutyl)piperazine-1-carboxylate (51 mg, 0.069 mmol, ~100% yield) as a colorless oil. LC/MS (ESI, m/z), 737.4 [M+H]*.

¹H-NMR (400 MHz, MeOH-d4): δ ppm 0.76-0.86 (m, 9H), 1.12 (s, 3H), 1.14-1.19 (m, 1H), 1.24 (s, 3H), 1.34-1.50 (m, 5H), 1.52-1.60 (m, 1H), 1.69 (s, 6H), 2.27 (s, 8H), 2.37-2.49 (m, 3H), 2.54-2.61 (m, 1H), 2.77-2.83 (m, 1H), 3.35-3.47 (m, 5H), 3.56 (s, 3H), 3.67-3.76 (m, 1H), 4.46 (s, 3H), 4.89-5.00 (m, 3H), 5.42-5.52 (m, 1H), 5.57-5.70 (m, 1H), 5.73-5.81 (m, 1H), 5.98-6.08 (m, 1H), 6.43 (dd, J=15.25, 10.98 Hz, 1H).

Step 2: Fmoc-ValAla-PAB bromide (88 mg, 0.152 mmol) and (2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl 4-(4-methoxy-4-oxobutyl)piperazine-1-carboxylate (51 mg, 0.069 mmol) were suspended in N,N-dimethylformamide (670 μL, 8.651 mmol).

The reaction was stirred at RT overnight. The solvent was evaporated. Purification by column chromatography afforded 1-(4-((S)-2-((S)-2-(((((9H-fluoren-9-yl)methoxy)carbonyl)amino)-3-methylbutanamido)propanamido)benzyl)-4-(((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)-1-(4-methoxy-4-oxobutyl)piperazin-1-ium (42 mg, 0.034 mmol, 49.1% yield) as a waxy solid. LC/MS (ESI, m/z), 1235.4 [M]*.

Step 3: 1-(4-((S)-2-((S)-2-(((((9H-fluoren-9-yl)methoxy)carbonyl)amino)-3-methylbutanamido)propanamido)benzyl)-4-(((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)-1-(4-methoxy-4-oxobutyl)piperazin-1-ium (42 mg, 0.034 mmol) was dissolved in a 5:2:1 ratio of THF (600 μL, 7.322 mmol), MeOH (250 μL, 6.179 mmol), water (125 μL, 6.939 mmol), and lithium hydroxide (1.221 mg, 0.051 mmol) was added. The mixture was stirred at RT for 1 hour. The mixture was quenched with acetic acid (5.84 μL, 0.102 mmol) and the solvent was evaporated and purified by RP HPLC to afford 1-(4-((S)-2-((S)-2-amino-3-methylbutanamido)propanamido)benzyl)-1-(3-carboxypropyl)-4-(((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)piperazin-1-ium as a waxy solid (18.4 mg, 0.018 mmol, 54.2% yield). LC/MS (ESI, m/z), 998.5 [M]*.

Step 4: 1-(4-((S)-2-((S)-2-amino-3-methylbutanamido)propanamido)benzyl)-1-(3-carboxypropyl)-4-(((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)piperazin-1-ium (18.4 mg, 0.018 mmol) was dissolved in N,N-dimethylformamide (356 μL, 4.603 mmol) and 2,5-dioxopyrrolidin-1-yl 6-(2,5-dioxo-2,5-dihydro-1H-pyrrol-1-yl)hexanoate (6.81 mg, 0.022 mmol) was added followed by Hunig's base (8.04 μL, 0.046 mmol). The reaction solution was stirred at RT for 30 min. The solvent was evaporated and the crude residue was purified by RP HPLC to afford (1-(3-carboxypropyl)-1-(4-((S)-2-((R)-2-(6-(2,5-dioxo-2,5-dihydro-1 H-pyrrol-1-yl)hexanamido)-3-methylbutanamido)propanamido)benzyl)-4-(((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)piperazin-1-ium (8.8 mg, 7.38 μmol, 40.1% yield) as a white lyophilized solid. LC/MS (ESI, m/z), 1191.5 [M]⁺.

¹H-NMR (400 MHz, DMSO-d6): δ ppm 0.68-0.81 (m, 18H), 0.98-1.07 (m, 4H), 1.07-1.14 (m, 3H), 1.16 (br d, J=3.89 Hz, 5H), 1.22-1.33 (m, 8H), 1.36-1.47 (m, 7H), 1.62 (s, 3H) 1.66-1.73 (m, 1H), 1.83-1.92 (m, 5H), 1.98-2.13 (m, 2H), 2.26 (dt, J=3.54, 1.80 Hz, 1H), 2.27-2.33 (m, 1H), 2.47-2.51 (m, 2H), 2.58-2.62 (m, 1H), 2.66-2.72 (m, 1H), 3.15 (s, 3H) 3.45-3.58 (m, 3H), 3.60-3.68 (m, 2H) 3.77-3.86 (m, 2H), 4.06-4.13 (m, 1H), 4.27-4.37 (m, 2H), 4.46-4.54 (m, 3H), 4.72-4.78 (m, 1H), 4.80-4.87 (m, 2H), 5.32-5.48

(m, 1H), 5.53-5.67 (m, 1H), 5.73-5.86 (m, 1H), 5.93-6.05 (m, 1H), 6.16-6.26 (m, 1H), 6.20 (s, 1H), 6.23-6.41 (m, 1H), 6.27-6.38 (m, 1H), 6.93 (s, 2H), 6.98-7.06 (m, 2H), 7.43-7.50 (m, 2H), 7.62-7.69 (m, 2H), 7.74-7.80 (m, 1H), 8.22-8.27 (m, 1H), 8.44-8.49 (m, 4H), 10.15-10.22 (m, 1H).

1.10 ADL12-D20 & ADL12-D21

General procedure 1 outlined in section 1.2.1 was employed to synthesize D20.

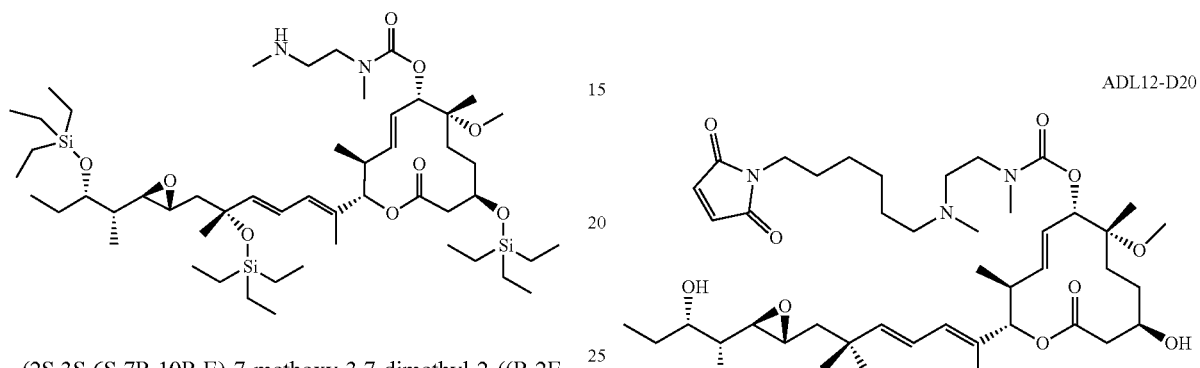

(2S,3S,6S,7R,10R,E)-7-methoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl methyl(2-(methylamino)ethyl)carbamate (43 mg, 0.044 mmol, 90% yield) as a colorless oil.

LC/MS (ESI, m/z), 981.4 [M+H]$^+$.

$^1$H-NMR (400 MHz, MeOH-d4): δ ppm 0.62-0.73 (m, 18H), 0.82-0.93 (m, 9H), 0.95-1.06 (m, 27H), 1.24 (br s, 4H), 1.45 (br s, 10H), 1.78 (br s, 3H), 1.92-2.00 (m, 1 H), 2.46 (br s, 4H), 2.51-2.67 (m, 3H), 2.76-2.84 (m, 2H), 2.86-2.93 (m, 1H), 2.93-3.02 (m, 3H), 3.34-3.38 (m, 3H), 3.43-3.49 (m, 2H), 3.72-3.82 (m, 1H), 3.93-4.04 (m, 1H), 4.94-5.07 (m, 2H), 5.53-5.64 (m, 1H), 5.72-5.89 (m, 2H), 6.07-6.21 (m, 1H), 6.44-6.61 (m, 1H).

$^1$H-NMR (400 MHz, MeOH-d4): δ ppm 0.92 (br d, J=6.53 Hz, 9H), 1.25 (br s, 4 H), 1.36 (s, 3H), 1.41-1.74 (m, 6H), 1.45-1.59 (m, 1H), 1.64-1.72 (m, 1H), 1.80 (s, 3 H), 1.85-1.94 (m, 1H), 2.42 (s, 3H), 2.50-2.63 (m, 3H), 2.65-2.73 (m, 1H), 2.73-2.80 (m, 2H), 2.88-3.01 (m, 4H), 3.35-3.38 (m, 3H), 3.35-3.40 (m, 3H), 3.41-3.48 (m, 2H), 3.52-3.57 (m, 1H), 3.78-3.89 (m, 1H), 5.00-5.13 (m, 2H), 5.53-5.64 (m, 1H), 5.71-5.82 (m, 1H), 5.84-5.94 (m, 1H), 6.12-6.19 (m, 1H), 6.49-6.61 (m, 1H).

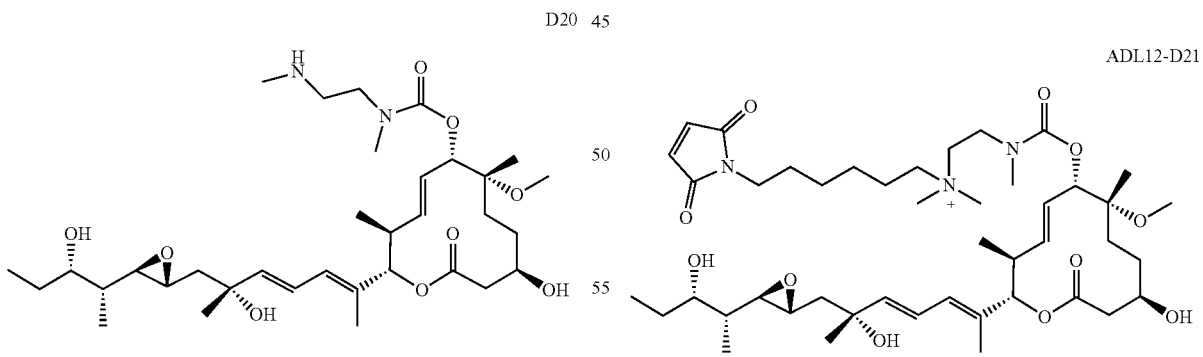

ADL12-D20

General procedure outlined in section 1.6.1 was employed to synthesize ALD12-D20 and afforded (13.0 mg, 0.016 mmol, 67.7%) as a colorless oil. LC/MS (ESI, m/z), 818.3 [M+H]$^+$.

$^1$H-NMR (400 MHz, MeOH-d4): δ ppm 0.91 (br s, 9H), 1.21-1.31 (m, 4H), 1.36 (br s, 7H), 1.46-1.73 (m, 11H), 1.80 (s, 3H), 1.84-1.93 (m, 1H), 2.50-2.72 (m, 7H), 2.75-2.85 (m, 1H), 2.87-3.09 (m, 7H), 3.48-3.68 (m, 6H) 3.80-3.89 (m, 1H), 5.02-5.13 (m, 2H), 5.55-5.66 (m, 1H), 5.71-5.82 (m, 1H), 5.85-5.94 (m, 1H), 6.11-6.22 (m, 1H), 6.49-6.61 (m, 1H), 6.83 (br d, J=1.13 Hz, 2H).

D20

ADL12-D21

(2S,3S,6S,7R,10R,E)-10-hydroxy-2-((R,2E,4E)-6-hydroxy-7-((2R,3R)-3-((2S,3S)-3-hydroxypentan-2-yl)oxiran-2-yl)-6-methylhepta-2,4-dien-2-yl)-7-methoxy-3,7-dimethyl-12-oxooxacyclododec-4-en-6-yl methyl(2-(methylamino)ethyl)carbamate (16.4 mg, 0.026 mmol, 58.6% yield) as a colorless oil. LC/MS (ESI, m/z), 639.7 [M+H]$^+$.

((2S,3S,6S,7R,10R,E)-10-hydroxy-2-((R,2E,4E)-6-hydroxy-7-((2R,3R)-3-((2S,3S)-3-hydroxypentan-2-yl)oxiran-2-yl)-6-methylhepta-2,4-dien-2-yl)-7-methoxy-3,7-dimethyl-12-oxooxacyclododec-4-en-6-yl (2-((6-(2,5-dioxo-2,5-dihydro-1 H-pyrrol-1-yl)hexyl)(methyl)amino)ethyl) (methyl)carbamate (7 mg, 8.557 μmol) was dissolved in N,N-dimethylformamide (99 μl, 1.284 mmol) and methyl iodide (2.68 μL, 0.043 mmol) was added. The solution was stirred at rt o/n. The solvent was evaporated. Purification by column chromatography afforded 6-(2,5-dioxo-2,5-dihydro-1 H-pyrrol-1-yl)-N-(2-(((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)(methyl)amino)ethyl)-N,N-dimethylhexan-1-aminium (7 mg, 8.40 μmol, 98% yield). LC/MS (ESI, m/z), 832.7 [M+H]⁺.

¹H-NMR (400 MHz, MeOH-d4): δ ppm 0.75-0.87 (m, 9H), 1.14 (s, 4H), 1.25 (s, 3H), 1.27-1.45 (m, 9H), 1.48-1.61 (m, 4H), 1.69 (s, 4H), 1.72-1.79 (m, 2H), 2.35-2.53 (m, 3H), 2.53-2.60 (m, 1H), 2.75-2.83 (m, 1H), 2.85-2.95 (m, 3H), 3.06 (br d, J=10.42 Hz, 6H), 3.15-3.20 (m, 2H), 3.25 (br d, J=2.38 Hz, 3H), 3.42 (br d, J=6.90 Hz, 5H), 3.53-3.69 (m, 2H), 3.69-3.78 (m, 1H), 4.88-5.01 (m, 2H), 5.44-5.56 (m, 1H), 5.59-5.72 (m, 1H), 5.73-5.83 (m, 1H), 5.99-6.10 (m, 1H), 6.40 (s, 1H), 6.72 (s, 2H).

1.11 ADL12-D22

General procedure 1 outlined in section 1.2.1 was employed to synthesize D22.

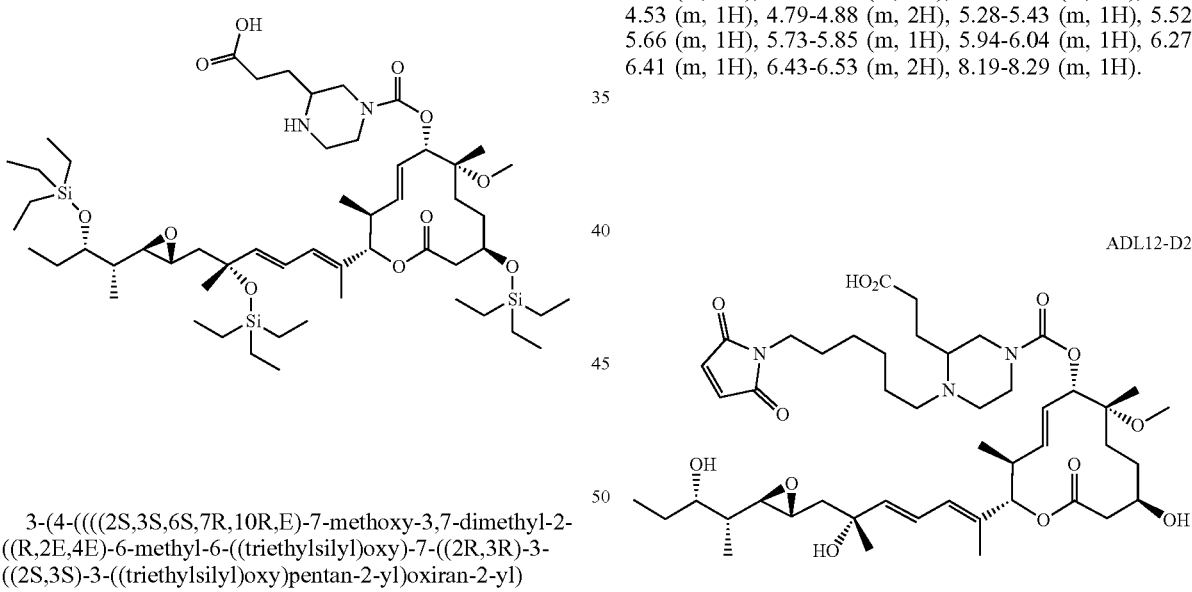

3-(4-(((((2S,3S,6S,7R,10R,E)-7-methoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl)oxy)carbonyl)piperazin-2-yl)propanoic acid (48 mg, 0.046 mmol, 34.4% yield) as a colorless oil. LC/MS (ESI, m/z), 1051.4 [M+H]⁺.

¹H-NMR (400 MHz, MeOH-d4): δ ppm 0.62-0.70 (m, 18H), 0.82-0.94 (m, 9H), 1.01 (tt, J=7.92, 3.18 Hz, 27H), 1.22-1.28 (m, 4H), 1.45 (s, 3H), 1.47-1.66 (m, 7H), 1.76-1.87 (m, 5H), 1.92-1.99 (m, 1H), 2.36-2.47 (m, 3H), 2.50-2.68 (m, 3H), 2.86-2.93 (m, 1 H), 2.98-3.08 (m, 2H), 3.10-3.18 (m, 1H), 3.18-3.26 (m, 2H), 3.27-3.31 (m, 1H), 3.34-3.36 (m, 3H), 3.36-3.37 (m, 1H) 3.72-3.81 (m, 1H), 3.95-4.19 (m, 3H), 4.93-5.00 (m, 1 H), 5.01-5.07 (m, 1H), 5.54-5.66 (m, 1H) 5.72-5.81 (m, 1H) 5.81-5.90 (m, 1H), 6.12-6.19 (m, 1H), 6.47-6.58 (m, 1H).

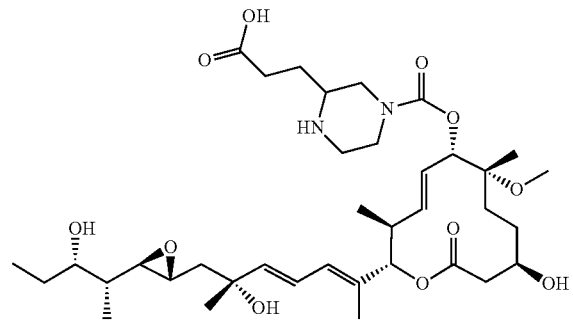

D22

N-ethyl-N-isopropylpropan-3-(4-(((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)piperazin-2-yl)propanoic acid (23.5 mg, 0.031 mmol, 68.2% yield).

LC/MS (ESI, m/z), 709.5 [M+H]⁺.

¹H-NMR (400 MHz, DMSO-d6): δ ppm 0.71-0.77 (m, 9H), 1.03 (s, 5H), 1.14-1.20 (m, 6H), 1.23-1.33 (m, 5H), 1.36-1.48 (m, 5H), 1.63 (s, 3H), 1.67-1.75 (m, 1H), 2.13-2.24 (m, 4H), 2.58-2.64 (m, 1H), 2.68-2.81 (m, 2H), 3.20-3.20 (m, 3H), 3.61-3.77 (m, 4H), 4.28-4.39 (m, 1H), 4.44-4.53 (m, 1H), 4.79-4.88 (m, 2H), 5.28-5.43 (m, 1H), 5.52-5.66 (m, 1H), 5.73-5.85 (m, 1H), 5.94-6.04 (m, 1H), 6.27-6.41 (m, 1H), 6.43-6.53 (m, 2H), 8.19-8.29 (m, 1H).

ADL12-D22

General procedure outlined in section 1.6.1 was employed to synthesize ADL12-D22 (3.6 mg, 4.05 μmol, 34.4% yield). LC/MS (ESI, m/z), 888.7 [M+H]⁺.

¹H-NMR (400 MHz, MeOH-d4): δ ppm 0.77-0.89 (m, 9H), 1.08-1.31 (m, 13H), 1.35-1.60 (m, 12H), 1.69 (s, 3H), 1.73-1.83 (m, 1H), 1.85-1.97 (m, 1H), 2.15-2.27 (m, 1H), 2.27-2.83 (m, 11H), 2.84-2.98 (m, 1H), 3.39 (s, 7H), 3.67-3.77 (m, 1H), 4.89-5.01 (m, 2H), 5.40-5.53 (m, 1H), 5.59-5.69 (m, 1H), 5.72-5.83 (m, 1H), 5.99-6.11 (m, 1H), 6.37-6.49 (m, 1H), 6.69 (s, 2H).

ADL1-D22

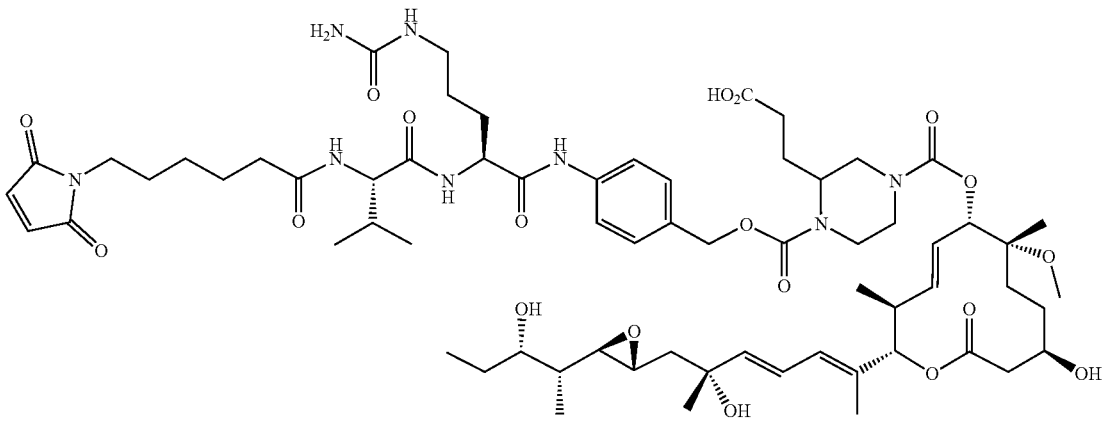

General procedure 1 outlined in section 1.2.1 was employed to synthesize ADL1-D22 (4.7 mg, 3.59 μmol, 38.6% yield) as a white lyophilized solid. LC/MS (ESI, m/z), 1307.6 [M+H]+.

$^1$H NMR (400 MHz, DMSO-d6): δ ppm 0.68-0.79 (m, 16H), 1.03 (s, 3H), 1.16 (s, 5H), 1.23-1.44 (m, 13H), 1.48-1.55 (m, 1H), 1.62 (s, 4H), 1.68-1.74 (m, 1H), 1.86-1.93 (m, 1H), 2.02 (s, 4H), 2.24-2.37 (m, 3H), 2.46-2.51 (m, 2H), 2.66-2.73 (m, 1H), 2.79-2.99 (m, 4H), 3.15 (s, 3H), 3.21-3.22 (m, 2H), 3.30 (s, 4H), 3.61-3.67 (m, 1H), 3.73-3.88 (m, 3H), 4.01-4.08 (m, 1H), 4.09-4.16 (m, 1H), 4.29-4.38 (m, 2H), 4.43-4.51 (m, 1H), 4.73-4.78 (m, 1H), 4.79-4.88 (m, 2H), 4.91-4.98 (m, 2H), 5.29-5.43 (m, 3H), 5.54-5.67 (m, 1H), 5.74-5.83 (m, 1H), 5.95-6.07 (m, 1H), 6.28-6.40 (m, 1H), 6.54-6.62 (m, 1H), 6.93 (s, 2H), 7.17-7.26 (m, 2H), 7.44-7.57 (m, 2H), 7.66-7.76 (m, 1H), 7.95-8.03 (m, 1H), 8.42-8.49 (m, 1H), 9.89-9.96 (m, 1H).

ADL1-D23

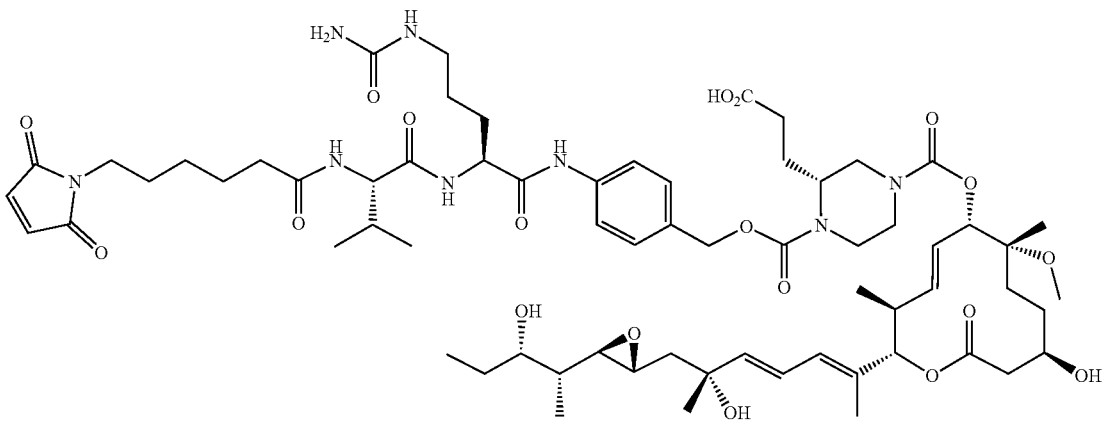

4-((S)-2-((S)-2-(6-(2,5-dioxo-2, 5-dihydro-1 H-pyrrol-1-yl)hexanamido)-3-methylbutanamido)-5-ureidopentanamido)benzyl (4-nitrophenyl) carbonate (16.76 mg, 0.023 mmol) and 3-((R)-4-((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl) oxy)carbonyl)piperazin-2-yl)propanoic acid (16.1 mg, 0.023 mmol) were dissolved in DMF (229 μl, 2.953 mmol) and Hunig's Base (11.90 μl, 0.068 mmol) was added. The reaction mixture was stirred overnight at rt. The solvent was then evaporated and subjected to reverse-phase HPLC purification to afford 3-((R)-1-(((4-((S)-2-((S)-2-(6-(2,5-dioxo-2,5-dihydro-1 H-pyrrol-1-yl)hexanamido)-3-methylbutanamido)-5-ureidopentanamido)benzyl)oxy)carbonyl)-4-((((2S,3S,6S,7R,10R,E)-10-hydroxy-2-((R,2E,4E)-6-hydroxy-7-((2R,3R)-3-((2R,3S)-3-hydroxypentan-2-yl) oxiran-2-yl)-6-methylhepta-2,4-dien-2-yl)-7-methoxy-3,7-dimethyl-12-oxooxacyclododec-4-en-6-yl)oxy)carbonyl) piperazin-2-yl)propanoic acid (3.9 mg, 2.98 μmol, 13.13% yield). LC/MS (ESI, m/z), 1308.6 [M+H]*.

ADL1-D24 (S)

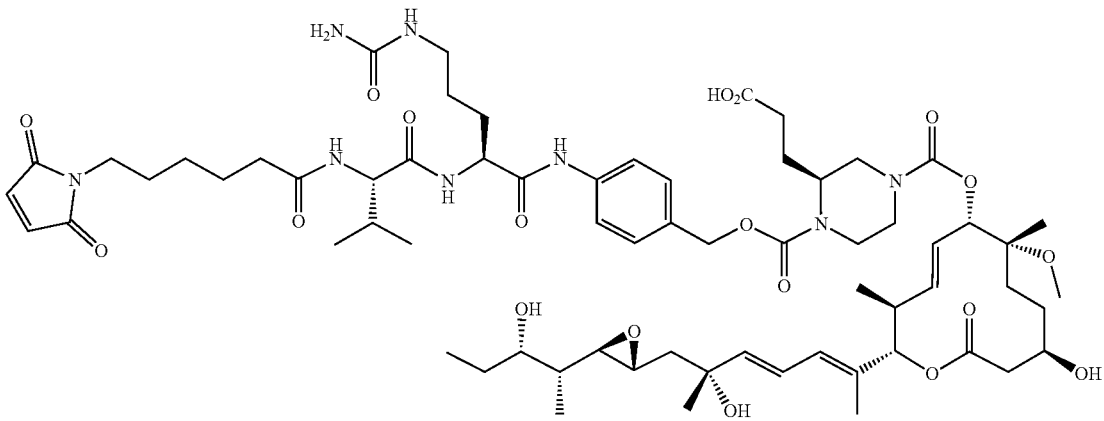

3-((S)-4-((((2S,3S,6S,7R,10R,E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl) piperazin-2-yl)propanoic acid (10 mg, 0.014 mmol), N,N-dimethylformamide (141 µl, 0.014 mmol), Hunig's base (5 µl, 0.028 mmol), 4-((S)-2-((S)-2-(6-(2,5-dioxo-2,5-dihydro-1 H-pyrrol-1-yl)hexanamido)-3-methylbutanamido)-5-ureidopentanamido)benzyl (4-nitrophenyl) carbonate (20.8 mg, 0.028 mmol) were combined and stirred for 2 hours. chromatograoged (MeOH/CH$_2$Cl$_2$) to afford 3-((S)-1-(((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)-4-((((2S,3S,6S,7R,10R, E)-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-7-methoxy-3,7-dimethyl-12-oxooxacyclododec-4-en-6-yl)oxy)carbonyl)piperazin-2-yl)propanoic acid (5 mg, 3.82 µmol, 27.1% yield). LC/MS (ESI, m/z), 1308.4 [M+H]$^+$.

Example 2

Exemplary spliceosome modulator payloads used in the preparation of ADCs were profiled. Payloads were evaluated for binding to the SF3b complex, in vitro splicing activity, and ability to inhibit cell growth.

2.1 SF3B1 Binding/Scintillation Proximity Assay (SPA)

A scintillation proximity assay was performed to measure the binding affinity of compounds ("payloads") to the SF3b complex. Batch immobilization of anti-SF3B1 antibody (MBL) to anti-mouse PVT SPA scintillation beads (PerkinElmer) was prepared as follows: for every 2.5 mg of nuclear extracts, 5 µg of anti-SF3B1 antibody and 1.5 mg of beads were mixed in 150 µL PBS. The antibody-bead mixture was incubated for 30 min at RT and centrifuged at 18,000g for 5 min. 150 µL PBS was used to resuspend every 1.5 mg antibody-bead mixture. The beads were suspended and added to the prepared nuclear extracts. The slurry was incubated for 2 hours at 4° C. with gentle mixing. The beads were then collected by centrifuging at 18,000g for 5 min, and washed twice with PBS+0.1% Triton X-100. After a final centrifugation step, every 1.5 mg of beads was suspended with 150 µL of PBS. SF3b complexes were tested for [$^3$H]-labeled pladienolide B probe binding ([$^3$H]—PB), synthesized as previously described (Kotake et al. (2007) Nat Chem Biol. 3(9):570-5). 100 µL binding reactions were prepared with 50 µL bead slurry and by adding varying concentrations of PB or PB—OH, and after 30 min preincubation, 2.5 nM of [$^3$H]—PB was added. The mixture was incubated for 30 min, and luminescence signals were read using a MicroBeta2 Plate Counter (PerkinElmer). Prism 7 (Graphpad) was used for non-linear regression curve fitting of the data.

Similar binding profiles were observed for all tested payloads (FIG. 1). In general, specific binding was in the low nanomolar range, suggesting that all tested payloads are potent SF3b complex binders and promising candidate compounds for use in ADCs.

2.2 In Vitro Splicing (IVS)

To evaluate payload activity in a cell-free system, an in vitro splicing assay was performed. The payloads were incubated with nuclear extracts and pre-mRNA substrate minigenes.

HeLa nuclear extract preparation: HeLa S3 cell pellets were resuspended in hypotonic buffer (10 mM HEPES pH 7.9, 1.5 mM MgCl$_2$, 10 mM KCl, 0.2 mM PMSF, 0.5 mM DTT) and the suspension was brought up to a total of 5 packed cell volume (PCV). After centrifugation, the supernatant was discarded, and the cells were brought up to 3 PCV with hypotonic buffer and incubated on ice for 10 min. Cells were lysed using a dounce homogenizer and then centrifuged. The supernatant was discarded, and the pellet was resuspended with % packed nuclear volume (PNV) of low salt buffer (20 mM HEPES pH 7.9, 1.5 mM MgCl$_2$, 20 mM KCl, 0.2 mM EDTA, 25% glycerol, 0.2 mM PMSF, 0.5 mM DTT), followed by % PNV of high salt buffer (same as low salt buffer except 1.4 M KCl). The nuclei were gently mixed for 30 min before centrifuging. The supernatant (nuclear extract) was then dialyzed into storage buffer (20 mM HEPES pH 7.9, 100 mM KCl, 0.2 mM EDTA, 20% glycerol, 0.2 mM PMSF, 0.5 mM DTT). Protein concentration was determined using NanoDrop 8000 UV-Vis spectrophotometer (ThermoFisher Scientific).

Figure 2:
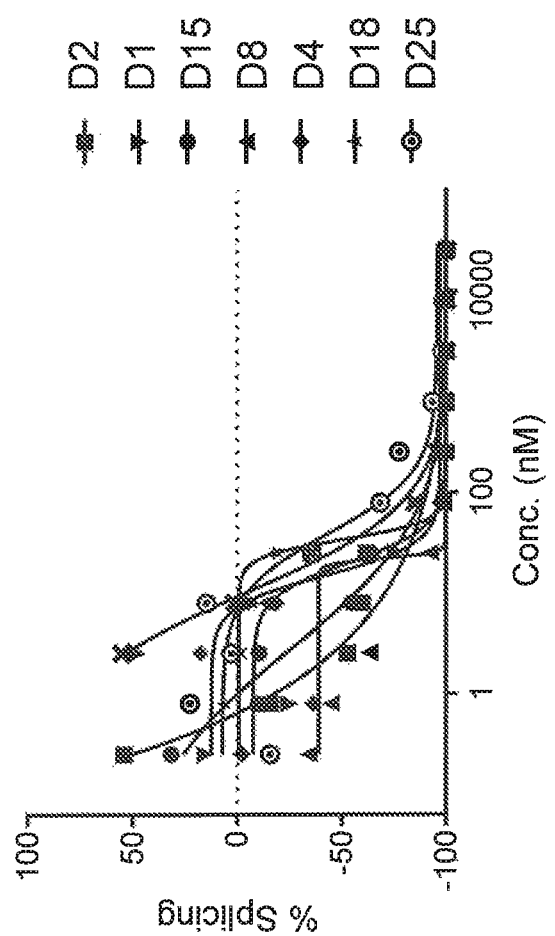
FIG. 2 shows modulation of splicing by exemplary payload compounds in an in vitro splicing assay. Nuclear extracts from HeLa S3 cells were incubated with Ad2.2 pre-mRNA and increasing concentrations of compound, followed by quantification of splicing modulation via RT-PCR. The Ad2.2 sequence is derived from the adenoviral Ad2 pre-mRNA substrate with modifications around the branch point sequence. The y-axis represents the percent change (% response) of splicing relative to the DMSO control (0%). Data are represented as mean±SD.

IVS: All Ad2-derived sequences (Pellizzoni et al. (1998) Cell 95(5):615-24) were cloned into pcDNA3.1(+) vector (Promega) using 5' EcoRI and 3' XbaI restriction sites. The plasmids were linearized using XbaI and used as DNA templates in in vitro transcription reactions. The FtzΔi intron-less plasmid (Luo and Reed (1999) 96(26):14937-42) was linearized using EcoRI. All RNAs were in vitro transcribed and then purified using MEGAScript T7 (Invitrogen) and MegaClear (Invitrogen) kits, respectively. For splicing reactions using Ad2 variant pre-mRNAs, 1 µL reactions were prepared using 8 µg nuclear extracts prepared from HeLa S3, 2 ng pre-mRNA, 0.2 ng FTZΔi, and varying concentrations of compounds or DMSO. After a 15 min pre-incubation at 30° C., 1 µL splicing activation buffer (0.5 mM ATP, 20 mM creatine phosphate, 1.6 mM $MgCl_2$) was added, and the reactions were incubated for 90 min at 30° C. The reactions were then quenched with 13 µL DMSO, and 25 nL was used for RT-qPCR. RT-qPCR reactions were prepared using TaqMan RNA-to-$C_T$ 1-step kit (Life Technologies), RNA from splicing reactions, Ad2 (forward: ACTCTCTTCCGCATCGCTGT; reverse: CCGACGGGTTTCCGATCCAA; probe: CTGTTGGGCTCGCGGTTG) and Ftz (forward: TGGCATCAGATTGCAAAGAC; reverse: ACGCCGGGTGATGTATCTAT; probe: CGAAACGCACCCGTCAGACG) mRNA primer-probe sets. Prism 7 (Graphpad) was used for non-linear regression curve fitting of the formed spliced product and normalized to the control (DMSO) sample. Given that all tested payloads specifically bind to the SF3b complex and demonstrate similar binding profiles (FIG. 1), it was hypothesized that all payloads should also modulate splicing to a comparable degree. All payloads significantly modulated splicing of Ad2.2 pre-mRNA (FIG. 2). In the presence of payload, a decrease in the amount of spliced product was observed.

2.3 Cell Viability

HCC1954 (American Type Culture Collection (ATCC)) breast ductal carcinoma cells were plated at 2000 cells/well in flat bottom 96-well tissue culture plates (Corning) in a total volume of 90 µL tissue culture medium supplemented with 10% fetal bovine serum (ThermoFisher Scientific). Cells were treated with a 3-fold serial dilution of compound from 200 nM to 0.03 nM. Each concentration was tested in triplicate. At the time of treatment, a plate of untreated cells was evaluated using CellTiter-Glo®2.0 Luminescent Cell Viability Assay according to the manufacturer's recommendations (Promega; #G9241). CellTiter-Glo® 2.0 reagent was added to the medium, incubated, and assayed on an EnVision Multilabel Reader (PerkinElmer). Values represent time zero (T0). The number of viable cells following 144 hours (T144) of compound treatment was also determined using the CellTiter-Glo®2.0 Luminescent Cell Viability Assay. Using the luminescence value at time zero (T0), DMSO control growth (C), and test growth in the presence of compound (T144), the percentage growth was calculated at each of the compound concentrations levels. Percentage growth inhibition was calculated as: [(T144-T0)/(C-T0)]×100 for concentrations for which T144>/=T0 or [(T144-T0)/T0]×100 for concentrations for which T144<T0. The dose response curve plots were generated using Prism 7 (Graphpad) and fit using nonlinear regression analysis and the log(inhibitor) versus response-variable slope (four parameters).

Figure 3:
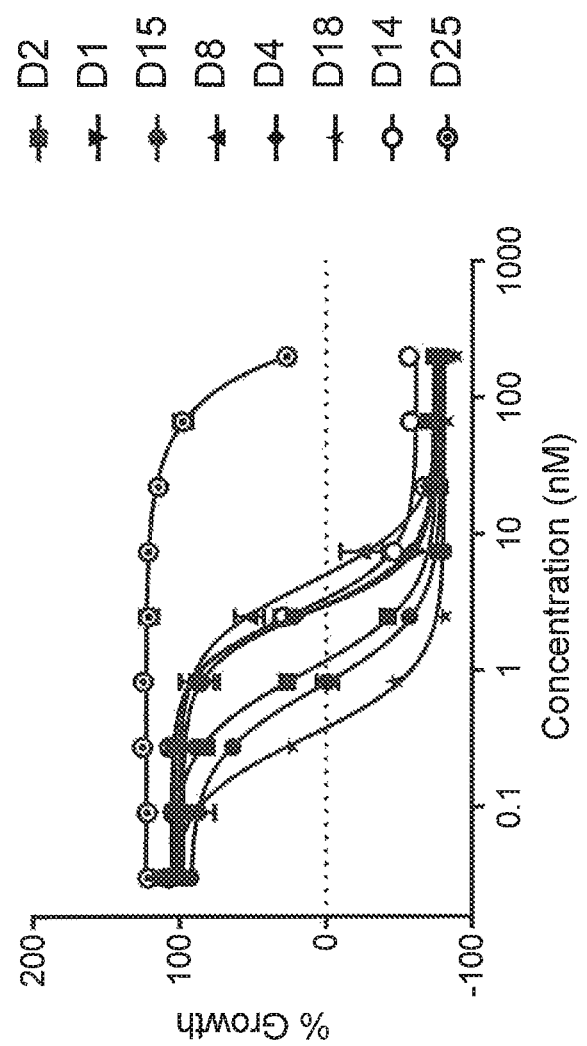
FIG. 3 shows viability dose response of exemplary payload compounds in HER2-amplified breast cancer cells (HCC1954). Cells were incubated with compound for 144 hours (6 days) and viability was read in CellTiter-Glo® reagent. Data are represented as mean±SD.

Cell viability dose response was determined for all payloads in HER2-amplified HCC1954 breast cancer cells. Most of the tested payloads exhibited $GI_{50}$ values (i.e., concentration of compound to cause 50% reduction in cell proliferation) in the single digit nanomolar range, with the exception of poorly permeable payloads such as D25 (FIG. 3). Exemplary permeability data is shown in Table 14.

Example 3

Exemplary payloads evaluated in Example 2 were conjugated to an exemplary anti-HER2 antibody (trastuzumab) via cysteine residues on the antibody. The preparation and evaluation of exemplary anti-HER2 ADCs is described below.

3.1 Antibody

Trastuzumab antibody ("AB185") (Molina et al. (2001) Cancer Res. 61(12):4744-9) was used for the preparation of anti-HER2 ADCs (also referred to herein as SMLAs).

3.2 Bioconjugation

Antibody (trastuzumab) at 10 mg/mL in PBS buffer (pH 7.0) was mixed with 5 mM TCEP (2-4 molar equivalents) (ThermoFisher Scientific; #77720) to break interchain disulfide bonds. The reaction was gently mixed at 22° C. for 3 hours. Propylene glycol (15% v/v) was then added followed by 8 molar equivalents of linker-payload (6 mM stock in DMSO), and the solution was mixed thoroughly. The reaction was placed onto a rotary plate in an incubator at 22° C. After a 2-hour conjugation, the reaction mixture was purified to remove unconjugated payload by AKTA GE M150 (HiTrap™ 26/10 desalting column; flow rate: 3 mL/min) (GE Healthcare Bio-Sciences) into DPBS (pH 7.5). The resulting conjugate was concentrated via Amicon ultrafiltration (30 kDa, Ultra-4) (EMD Millipore) and submitted to sterile filtration through a 0.22 m PVDF disposable filter (EMD Millipore). The final clear solution was measured by UV-VIS to determine antibody concentration ([mAb]; mole/L) and conjugated payload concentration ([LD]; mole/L) according to the Beer-Lambert law (A=E*c*I) and the following equations:

$$A280 \text{ nm} = E^{mAb}_{280nm} *[mAb]*I + E^{LD}_{280nm}*[LD]*I$$

$$A_{252nm} = E^{mAb}_{252 \ nm} *[mAb]*I + E^{LD}_{252 \ nm}*[LD]*I$$

$$E^{mAb}_{280 \ nm} : B - B4 = 224{,}320 \text{ cm}^{-1}M^{-1}$$

$$1C_{1=215,380} \text{ cm}^{-1}M^{-1}$$

$$E^{mAb}_{252nm} : B - B4 = 83{,}670 \text{ cm}^{-1}M^{-1}$$

$$1C_{1=80,337} \text{ cm}^{-1}M^{-1};$$

$$E^{LD}_{280nm} = 800 \text{ cm}^{-1}M^{-1}$$

$$E^{LD}_{252 \ nm} = 31{,}000 \text{ cm}^{-1}M^{-1}$$

Abbreviations: c—molar concentration; I—light path length (Nanodrop: 0.1 cm); E—molar extinction coefficient; A—absorbance.

3.3 Biophysical Characterization

The drug-to-antibody ratio (DAR), percent aggregation, and percent unconjugated payload was analyzed for exemplary anti-HER2 ADCs by liquid chromatography-mass spectrometry (LC/MS), size exclusion chromatography (SEC), and reverse-phase high-performance liquid chromatography (HPLC), respectively. In general, conjugates contained less than 2% free drug and contained less than 10% aggregate.

3.3.1 LC/MS Analysis—DAR

LC/MS analysis was performed using an Agilent 1290 UPLC system interfaced to an Agilent G6224A Accurate Mass TOF mass spectrometer. Conjugate was deglycosylated with PNGase F (New England Biolabs; #P0705L) for 4 hours at 37° C., denatured with 8 M Gdn-HCl (Sigma; #G9284), and finally separated into light and heavy chain domains using DTT (5 mM final concentration) (Promega; #V3151). The prepared sample was injected onto an Agilent PLRP-S column (2.1×150 mm, 8 μm) and eluted with a gradient of 25% B to 50% B over 28 min at room temperature (RT). Mobile phase A was water with 0.05% TFA, mobile phase B was acetonitrile with 0.04% TFA, and the flow rate was 1 mL/min. DAR was calculated from the deconvoluted mass spectrum by weighted averaging the intensities of the unconjugated and drug conjugated peaks for the light chain (L0 or L1) and heavy chain ($H_0$, $H_1$, $H_2$, and $H_3$). The total DAR of the intact conjugate was calculated using the equation: $(DAR_{LC}*2)+(DAR_{HC}*2)$=total DAR. DAR values for exemplary anti-HER2 ADCs are reported in Tables 10-14.

3.3.2 SEC Analysis—Aggregation

Size exclusion chromatography was performed using a TOSON-G3000SWXL (#008541) column in 0.2 M potassium phosphate (pH 7) with 0.25 mM potassium chloride and 15% (v/v) IPA at a flow rate of 0.75 mL/min. The peak area absorbance at 280 nm was determined for the high molecular weight and monomeric conjugate components by area under the curve integration. Percent monomer for exemplary anti-HER2 ADCs is reported in Table 10.

3.3.3 HPLC Analysis—Free Drug

Conjugate was precipitated with 10 volumes of acetonitrile on ice for 2 hours and spun down. Supernatants containing residual unconjugated payload were then injected onto an Agilent Poroshell 120 SB—$C_{18\ 120}$A column (4.6× 100 mm, 2.7 μm) and eluted with a gradient of 45% B to 70% B over 10 min at RT. Mobile phase A was 100% water, mobile phase B was 100% acetonitrile, and the flow rate was 0.6 mL/min with detection at 252 nm. The amount of residual free drug was quantified via UV detection with comparison to the external standard curve of unconjugated linker-payload. Percent free drug for exemplary anti-HER2 ADCs is reported in Table 10.

3.4 Binding Characterization

3.4.1 FACS Binding to Target-positive Cells

Binding of unconjugated anti-HER2 antibody and anti-HER2 ADCs to target-positive cells was evaluated by flow-cytometry using indirect immunofluorescence. JIMT1 cells (DSMZ), a breast cancer cell line that endogenously expresses HER2, were plated ($5\times10^4$ cells/well) in a v-bottom 96-well plate (Greiner Bio-One) and incubated for 2 hours at 4° C. with the test compounds diluted to various concentrations in assay medium (RPMI-1640 supplemented with 10% (w/v) fetal bovine serum albumin (Thermo Fisher Scientific)). The cells were then washed with PBS+2% FBS (FACS buffer), and stained with phycoerythrin-labeled (PE) goat anti-human immunoglobulin G (IgG) antibody (Invitrogen) for 40 min at 4° C. in the dark. Cells were washed with cold FACS buffer and fixed with FluroFix buffer (Biolegend) for 30 min at room temperature. Fixative was washed off with FACS buffer. Fixed cells were analyzed for the geometric mean fluorescence of PE using an LSR-Fortessa flow cytometer (BD Bioscience). Trastuzumab and T-DM1 (DM1 conjugated to trastuzumab) were included as controls.

Figure 4:
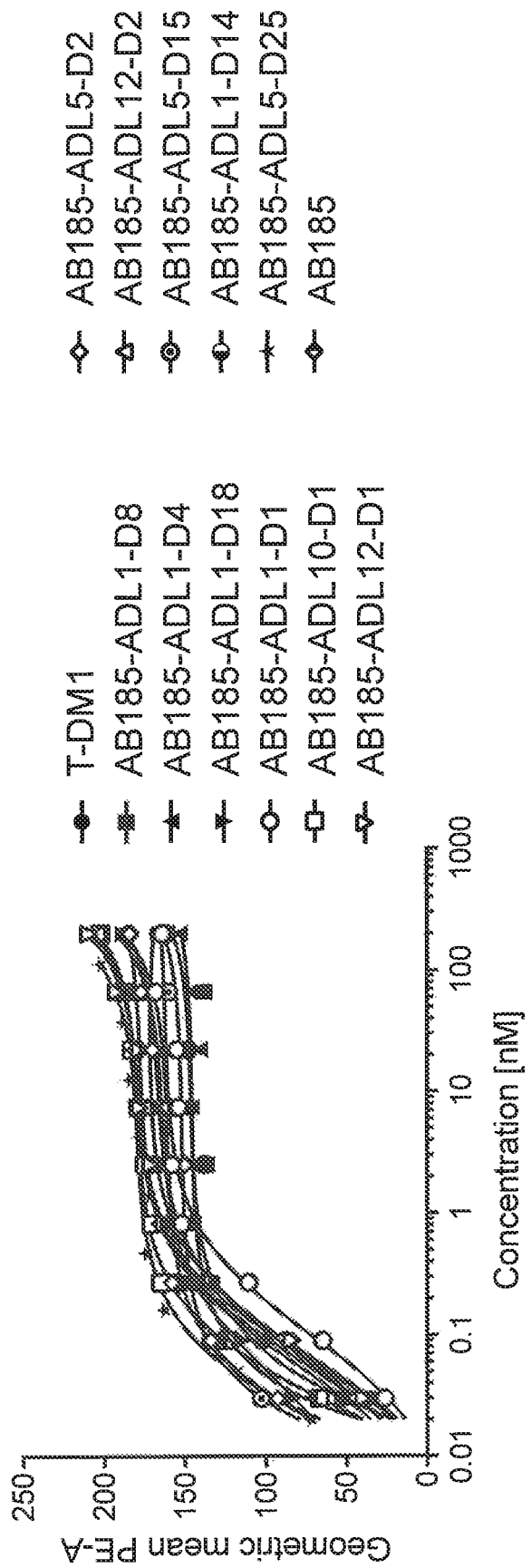
FIG. 4 shows the results of a cell binding assay. Binding of exemplary HER2-ADCs to JIMT1 cells was assessed by flow cytometry. Mean fluorescence intensity values were measured to determine binding of conjugates, followed by PE-labelled secondary. Data are represented as mean±SD.

All anti-HER2 ADCs demonstrated robust binding to HER2 in JIMT1 cells. ADC binding was comparable to binding of trastuzumab and T-DM1 (FIG. 4). This suggests that conjugation to payload does not affect antigen binding affinity of the antibody.

3.5 In Vitro Analysis 3.5.1 Cell Viability

Anti-HER2 ADCs were tested in several HER2-amplified cell lines for their ability to inhibit cell growth. HCC1954 (ATCC), 2000 cells/well), N87 (ATCC, 4000 cells/well), SKBR3 (ATCC, 3000 cells/well), and MCF7 (ATCC, 1500 cells/well) cell lines were used. Cell viability analysis was performed as described in section 2.3.

Figure 5A:
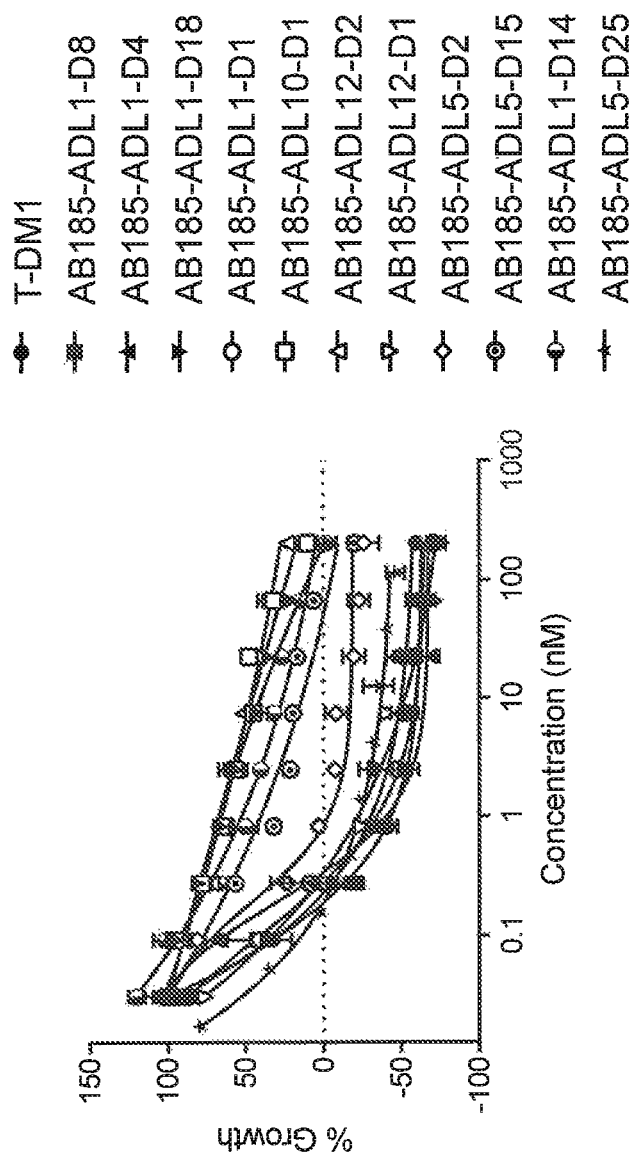
FIG. 5A shows viability dose response of exemplary HER2-ADCs in HER2-amplified breast cancer cells (HCC1954).
Figure 5B:
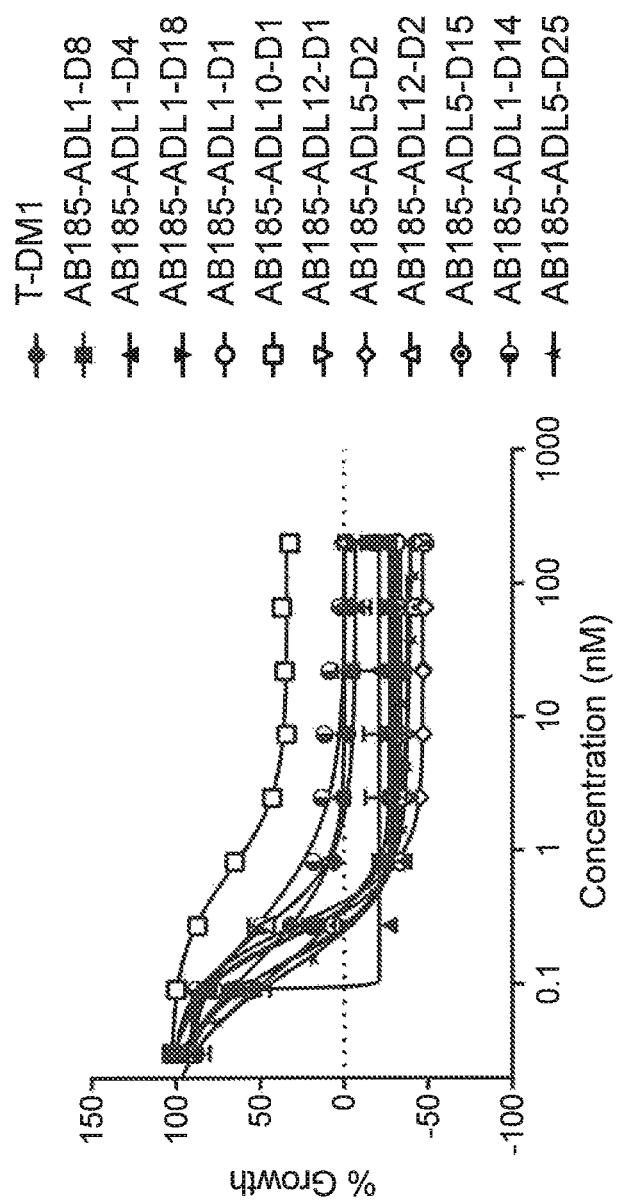
FIG. 5B shows viability dose response of exemplary HER2-ADCs in HER2-amplified gastric cancer cells (N87).
Figure 5C:
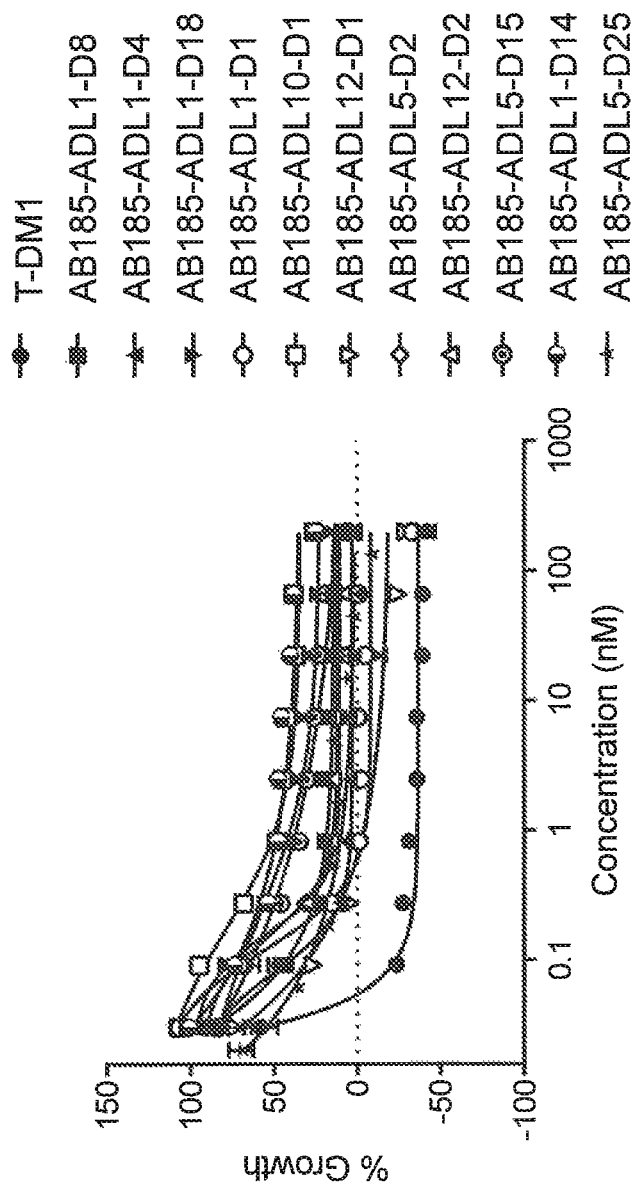
FIG. 5C shows viability dose response of exemplary HER2-ADCs in HER2-amplified breast cancer cells (SKBR3). Cells were incubated with conjugates for 144 hours (6 days) and viability was read in CellTiter-Glo® reagent. Data are represented as mean±SD.

Surprisingly, not all ADCs were active in HCC1954 cells, despite having similar binding profiles (FIG. 1) and payloads with similar biochemical properties. ADCs with certain linkers (e.g., ADL10) and/or certain payloads (e.g., D14) were less capable of inhibiting cell growth, whereas ADCs with alternate linkers (ADL1, ADL5, ADL12) and/or payloads (e.g., D1, D25, D2, D4) were more potent in HCC1954 cells (FIG. 5A and Tables 10, 11, and 14). These trends were generally observed across cell lines (HCC1954, N87, and SKBR3) and indications (HCC1954 and SKBR3 are high HER2 breast cancer lines; N87 is a high HER2 gastric cancer line) (FIG. 5B-C and Tables 11 and 12). Moreover, in general, traditional non-cleavable linkers such as ADL10 did not deliver splicing modulator payloads efficiently. However, small modifications in length to the same linkers rendered ADCs much more potent, e.g., compare cell viability dose response of AB185-ADL10-D1 to AB185-ADL12-D1 (FIG. 5A-C).

Figure 6:
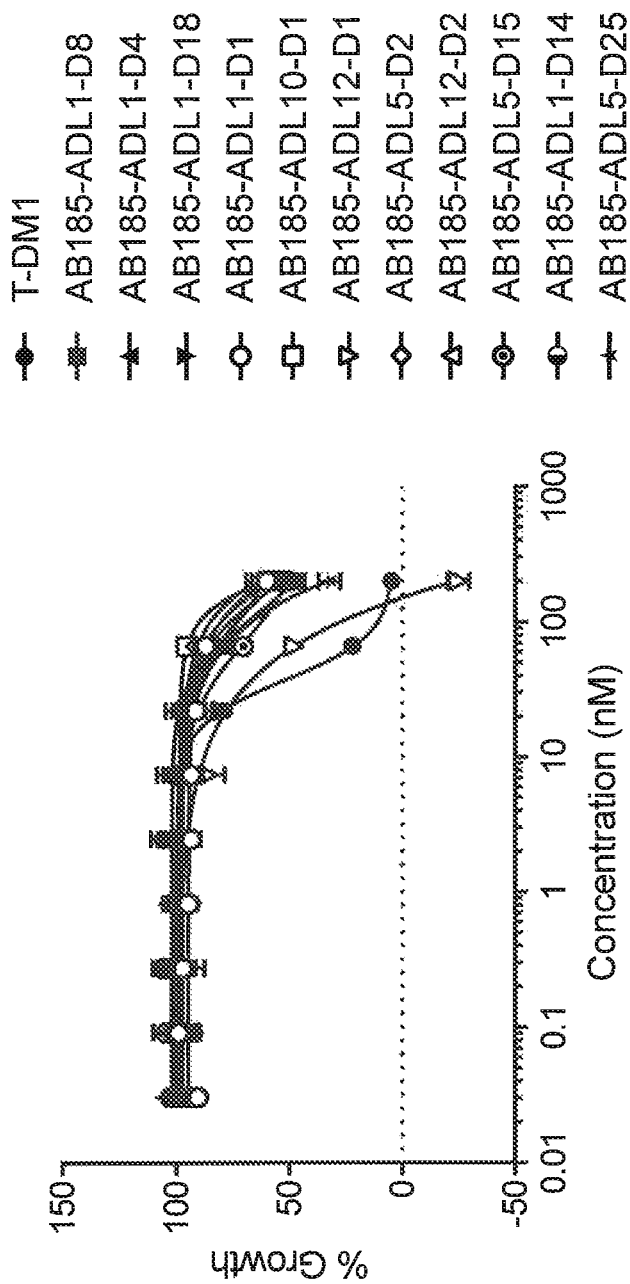
FIG. 6 shows viability dose response of exemplary HER2-ADCs in non-HER2 expressing breast cancer cells (MCF7). Cells were incubated with conjugates for 144 hours (6 days) and viability was read in CellTiter-Glo® reagent. Data are represented as mean±SD.

To ensure activity of anti-HER2 ADCs is antigen-dependent, HER2-negative MCF7 cells were treated. None of the tested ADCs were active at the same concentrations that robustly targeted HER2-positive cells (FIG. 6 and Table 13). This suggests that anti-HER2 ADC activity is antigen-dependent.

TABLE 10

Characterization of exemplary anti-HER2 ADCs

| SMLA Batch ID | Payload Class | Linker | Linker Name | DAR | Percent Monomer | Free Drug (%) | Concentration (mg/ml) | CTGlo GMean GI50 (nM) HCC 1954.1 | CTGlo GMean LD50 (nM) HCC 1954.1 | CTGlo Mean MinResponse % HCC 1954.1 |
|---|---|---|---|---|---|---|---|---|---|---|
| AB185-ADL10-D8 | Plad D | ADL0010-01 | maleimido caproyl | 2.000 | 99.000 | <1 | 0.730 | >200.000 | >200.000 | 58.601 |
| AB185-ADL10-D1 | Plad D | ADL0010-01 | maleimido caproyl | 3.600 | 97.000 | <1 | 3.600 | 25.502 | >200.000 | 23.963 |

TABLE 10-continued

| | | | | | | | | | |
|---|---|---|---|---|---|---|---|---|---|
| AB185-ADL5-D17 | ArylPlad | ADL0005-01 | mc-Val-Ala-PAB (Qamine) | 3.960 | 98.000 | <1 | 1.400 | 2.668 | >160.000 | 14.873 |
| AB185-ADL1-D16 | ArylPlad | ADL0001-01 | mc-Val-Cit-PABC | 4.400 | 95.000 | <1 | 0.550 | 2.086 | 158.245 | |
| AB185-ADL5-D26 | ArylPlad | ADL0005-01 | mc-Val-Ala-PAB (Qamine) | 4.400 | 98.000 | <1 | 1.200 | 0.943 | >200.000 | |
| AB185-ADL1-D14 | ArylPlad | ADL0001-01 | mc-Val-Cit-PABC | 4.340 | 88.000 | <1 | 4.200 | 0.925 | >200.000 | 1.271 |
| AB185-ADL5-D15 | ArylPlad | ADL0005-01 | mc-Val-Ala-PAB (Qamine) | 4.000 | 98.000 | <1 | 0.780 | 0.912 | >200.000 | -45.388 |
| AB185-ADL5-D15 | Plad D | ADL0005-01 | mc-Val-Ala-PAB (Qamine) | 3.700 | 96.000 | <1 | 0.880 | 0.806 | >93.000 | -30.929 |
| AB185-ADL1-D33 | ArylPlad | ADL0001-01 | mc-Val-Cit-PABC | 8.000 | 95.000 | <1 | 0.570 | 0.466 | >200.000 | -25.859 |
| AB185-ADL1-D22 | Plad D | ADL0001-01 | mc-Val-Cit-PABC | 3.000 | 99.000 | <1 | 0.840 | 0.443 | >200.000 | -7.520 |
| AB185-ADL12-D2 | Plad D | ADL0012-01 | mal-(CH2)6-(non-cleavable) | 3.600 | 98.600 | <1 | 1.060 | 0.432 | >200.000 | 18.569 |
| AB185-ADL1-D13 | Plad B | ADL0001-01 | mc-Val-Cit-PABC | 5.000 | 98.000 | <1 | 1.200 | 0.289 | 18.948 | -94.860 |
| AB185-ADL5-D19 | Plad B | ADL0005-01 | mc-Val-Ala-PAB (Qamine) | 6.600 | 97.000 | <1 | 3.230 | 0.278 | >200.000 | -47.381 |
| AB185-ADL5-D10 | Plad D | ADL0005-01 | mc-Val-Ala-PAB (Qamine) | 4.020 | 97.000 | <1 | 0.650 | 0.254 | >200.000 | -2.273 |
| AB185-ADL6-D9 | Plad D | ADL0006-01 | mc-Val-Ala-PABC | 5.200 | 98.000 | <1 | 0.500 | 0.244 | 4.206 | -94.511 |
| AB185-ADL5-D2 | Plad D | ADL0005-01 | mc-Val-Ala-PAB (Qamine) | 4.140 | 99 | <1 | 4.5 | 0.206 | >200.000 | -12.239 |
| AB185-ADL1-D8 | Plad D | ADL0001-01 | mc-Val-Cit-PABC | 7.200 | 97.000 | <1 | 3.410 | 0.188 | >200.000 | -55.079 |
| AB185-ADL5-D2 | Plad D | ADL0005-01 | mc-Val-Ala-PAB (Qamine) | 4.300 | 99.000 | <1 | 5.440 | 0.179 | >200.000 | -18.586 |
| AB185-ADL15-D2 | Plad D | ADL0015-01 | O—CH2CH2—(non-cleavable) | 3.300 | 98.800 | <1 | 1.600 | 0.170 | >200.000 | -23.513 |
| AB185-ADL12-D20 | Plad D | ADL0012-01 | mal-(CH2)6-(non-cleavable) | 3.200 | 98.600 | <1 | 1.390 | 0.142 | >200.000 | -57.399 |
| AB185-ADL12-D1 | Plad D | ADL0012-01 | mal-(CH2)6-(non-cleavable) | 3.300 | 98.800 | <1 | 1.620 | 0.126 | >200.000 | -34.649 |
| T-DM1 | DM1 | ADL0019-01 | SMCC | 3.300 | 98.000 | <1 | 3.300 | 0.118 | 2.759 | -47.952 |
| AB185-ADL5-D9 | Plad D | ADL0005-01 | mc-Val-Ala-PAB (Qamine) | 8.500 | 98 | <1 | 5.1 | 0.086 | 2.918 | -63.909 |
| AB185-ADL6-D1 | Plad D | ADL0006-01 | mc-Val-Ala-PABC | 8.000 | 97.000 | <1 | 1.200 | 0.081 | 2.877 | -85.692 |
| AB185-ADL12-D1 | Plad D | ADL0012-01 | mal-(CH2)6-(non-cleavable) | 3.000 | 98.000 | <1 | 2.860 | 0.081 | 2.148 | -68.999 |
| AB185-ADL12-D22 | Plad D | ADL0012-01 | mal-(CH2)6-(non-cleavable) | 4.300 | 97.000 | <1 | 0.120 | 0.078 | >80.000 | 28.071 |
| AB185-ADL1-D4 | Plad D | ADL0001-01 | mc-Val-Cit-PABC | 8.000 | 98.000 | <1 | 3.600 | 0.073 | 1.949 | -67.199 |
| AB185-ADL15-D1 | Plad D | ADL0015-01 | mal-CH2CH2—O—CH2CH2—(non-cleavable) | 3.200 | 98.800 | <1 | 0.950 | 0.062 | >200.000 | -57.829 |
| AB185-ADL14-D1 | Plad D | ADL0014-01 | mal-(CH2)6-(non-cleavable) | 3.500 | 98.600 | <1 | 0.740 | 0.055 | >200.000 | -56.889 |
| AB185-ADL1-D4 | Plad D | ADL0001-01 | mc-Val-Cit-PABC | 2.800 | 98.000 | <1 | 1.200 | 0.050 | >200.000 | -57.212 |
| AB185-ADL1-D1 | Plad D | ADL0001-01 | mc-Val-Cit-PABC | 3.900 | 99 | <1 | 5.2 | 0.046 | 0.374 | -78.519 |
| AB185-ADL1-D1 | Plad D | ADL0001-01 | mc-Val-Cit-PABC | 4.000 | 98.000 | <1 | 3.500 | 0.042 | 0.447 | -77.970 |
| AB185-ADL5-D25 | Plad D | ADL0005-01 | mc-Val-Ala-PAB (Qamine) | 6.000 | 98.000 | <1 | 0.170 | 0.038 | >113.000 | -46.265 |
| AB185-ADL1-D1 | Plad D | ADL0001-01 | mc-Val-Cit-PABC | 7.700 | 98.000 | <1 | 4.200 | 0.034 | 0.120 | -87.001 |

TABLE 11

Exemplary anti-HER2 ADCs-HCC1954 cells

| | | ADC | | | Payload | | |
|---|---|---|---|---|---|---|---|
| Sample | DAR | GI50 (nM) | LD50 (nM) | Rmin (%) | GI50 (nM) | LD50 (nM) | Rmin (%) |
| AB185-ADL12-D1 | 3.1 | 0.064 | 4.86 | -78.393 | 1.853 | 5.485 | -75.579 |
| AB185-ADL1-D8 | 7.2 | 0.075 | 1.01 | -72.765 | 2.638 | 11.175 | -80.463 |
| T-DM1 | 3.3 | 0.083 | >200 | -64.227 | | | |

TABLE 11-continued

Exemplary anti-HER2 ADCs-HCC1954 cells

| | | ADC | | | Payload | | |
|---|---|---|---|---|---|---|---|
| Sample | DAR | GI50 (nM) | LD50 (nM) | Rmin (%) | GI50 (nM) | LD50 (nM) | Rmin (%) |
| AB185-ADL1-D1 | 4.04 | 0.089 | 2.078 | −74.165 | 1.853 | 5.485 | −75.579 |
| AB185-ADL1-D4 | 4.9 | 0.145 | 1.217 | −75.638 | 1.699 | 6.374 | −81.34 |
| AB185-ADL5-D2 | 4.1 | 0.18 | >200 | −36.513 | 0.6 | 2.758 | −78.732 |
| AB185-ADL5-D16 | 4 | 0.503 | >200 | −20.387 | 0.358 | 2.037 | −84.412 |
| AB185-ADL1-D18 | 3.8 | 5.994 | >200 | −8.011 | 0.208 | 0.787 | −90.055 |
| AB185-ADL12-D2 | 3.6 | 6.129 | >200 | 18.763 | 0.6 | 2.758 | −78.732 |
| AB185-ADL10-D1 | 3.5 | 6.642 | >200 | 8.138 | 1.853 | 5.485 | −78.579 |
| AB185-ADL5-D25 | 6.3 | 0.038 | >113.000 | −51.503 | 167.54 | >200 | 26.882 |
| AB185 | N/A | >200 | >200 | 76.916 | | | |

TABLE 12

Exemplary anti-HER2 ADCs-N87 cells

| | | SMLA | | | Payload | | |
|---|---|---|---|---|---|---|---|
| Sample | DAR | GI50 (nM) | LD50 (nM) | Rmin (%) | GI50 (nM) | LD50 (nM) | Rmin (%) |
| AB185-ADL1-D4 | 4.9 | 0.093 | >200 | −40.056 | 3.241 | 38.774 | −81.775 |
| AB185-ADL5-D16 | 4 | 0.106 | >200 | −50.886 | 0.41 | >200 | −68.045 |
| AB185-ADL5-D25 | 6.3 | 0.11 | 133 | −43.398 | >200 | >200 | 40.364 |
| AB185-ADL12-D1 | 3.1 | 0.111 | >200 | −41.228 | 7.041 | >200 | −40.041 |
| AB185-ADL1-D18 | 3.8 | 0.113 | >200 | −39.509 | 0.275 | 2.993 | −92.127 |
| AB185-ADL1-D1 | 4.04 | 0.163 | >200 | −41.075 | 7.041 | >200 | −40.041 |
| T-DM1 | 3.3 | 0.168 | >200 | −20.785 | | | |
| AB185-ADL1-D8 | 7.2 | 0.172 | >200 | −31.708 | 8.844 | >200 | −34.052 |
| AB185-ADL5-D2 | 4.1 | 0.206 | >200 | −51.328 | 0.749 | >200 | −72.706 |
| AB185-ADL12-D2 | 3.6 | 0.243 | >200 | −9.79 | 0.749 | >200 | −72.706 |
| AB185-ADL1-D14 | 4.3 | 0.296 | >200 | −26.143 | 2.925 | >200 | −52.662 |
| AB185-ADL10-D1 | 3.5 | 1.531 | >200 | 30.759 | 7.041 | >200 | −40.041 |
| AB185 | N/A | >200 | >200 | 77.029 | | | |

TABLE 13

Exemplary anti-HER2 ADCs-MCF7 cells

| | | SMLA | | | Payload | | |
|---|---|---|---|---|---|---|---|
| Sample | DAR | GI50 (nM) | LD50 (nM) | Rmin (%) | GI50 (nM) | LD50 (nM) | Rmin (%) |
| T-DM1 | 3.3 | 38.503 | >200 | 3.876 | | | |
| AB185-ADL12-D1 | 3.1 | 57.818 | >200 | −30.172 | 16.998 | 135.42 | −63.414 |
| AB185-ADL5-D25 | 6.3 | 80.856 | 113 | 28.12 | >200 | >200 | 65.639 |
| AB185-ADL1-D4 | 4.9 | 189.392 | >200 | 43.848 | 11.416 | 96.46 | −60.923 |
| AB185-ADL5-D2 | 4.1 | >200 | >200 | 56.182 | 2.851 | 30.318 | −66.915 |
| AB185-ADL1-D8 | 7.2 | >200 | >200 | 61.169 | 29.614 | 181.521 | −62.957 |
| AB185-ADL1-D18 | 3.8 | >200 | >200 | 48.851 | 0.883 | 7.697 | −68.226 |
| AB185-ADL5-D15 | 4 | >200 | >200 | 49.619 | 0.961 | 130.398 | −68.503 |
| AB185-ADL12-D2 | 3.6 | >200 | >200 | 48.868 | 2.851 | 30.318 | −66.915 |
| AB185-ADL10-D1 | 3.5 | >200 | >200 | 52.699 | 16.998 | 135.42 | −63.414 |
| AB185-ADL1-D14 | 4.3 | >200 | >200 | 49.325 | 5.288 | 77.198 | −61.886 |
| AB185-ADL1-D1 | 4.04 | >200 | >200 | 59.181 | 16.998 | 135.42 | −63.414 |
| AB185 | N/A | >200 | >200 | 72.747 | | | |

3.5.2 Caco-2 Permeability of ADC Payload

Caco-2 cells were cultured for 21 days in transwell 24-well plates at 37° C., 95% humidity, 5% $CO_2$. Integrity of cell monolayer was confirmed by TEER (transepithelial electrical resistance) and Lucifer yellow. Payloads were spiked in duplicate at 10 μM, separately, on both sides of the cell monolayer. Permeability rates from the apical to basolateral (A-B) direction and the basolateral to apical (B-A) direction were determined by sampling aliquots from both chambers immediately after treatment (t=0) and following incubation for 2 hours. Samples were protein precipitated with organic solvent containing internal standard and analyzed by LC-MS/MS (SCIEX; API 5500). The area ratio responses of payload/internal standard over time in both directions were used to generate permeability (cm/see) values. Efflux ratio was calculated by dividing B-A/A-B. Control compounds for low and high permeability and efflux behaved as expected. Permeability values are reported in Table 14.

3.5.3 Chemical Stability of ADC Payload

Payloads were incubated in Mcilvane (Citrate-Phosphate) buffer, pH 5.5 (Boston Bioproducts; #BB-2466) at a final concentration of 20 μM (less than 0.5% DMSO from stock solution). The payload solution and the internal standard were pipetted into 96-well plates, ran on UPLC (Waters Aquity H class), and analyzed for initial chromatographic signal (t=0). The column was a Waters UPLC HSS T3 1.8 μm 2.1×50 mm column (#186003538). A gradient of mobile phase A from 95% to 10% was employed over 1 min, where A was 0.1% formic acid in water and mobile phase B was 0.1% formic acid in acetonitrile (flow rate 0.9 mL/min). The remainder of the payload solution was kept in a plate shaker at 37° C. (Eppendorf ThermoMixer). Sample analyses by UPLC were repeated at 24, 72, and 96 hours post-incubation at 37° C. The area ratio response of the payload and internal standard was determined for three time points: time 0, day 1, and either day 3 or day 4. Time 0 was set to 100. The area ratio responses of the later time points were compared to time 0. Percent remaining was calculated as follows: (Area Ratio day X/Area Ratio time 0)*100=% remaining. The slope of the line was calculated in Excel comparing the log of % remaining and time point. Half-lives were calculated in Excel by ln(2)/slope and are reported in Table 14.

TABLE 14

Characterization of exemplary anti-HER2 ADCs and corresponding payloads

| | | | SMLA activity | | | | | Payload SF381 binding and mRNA splice modulation | | |
|---|---|---|---|---|---|---|---|---|---|---|
| SMLA Batch ID | Linker | DAR | CT Glo GMean GI50 (nM) HCC1954.1 | CTGlo GMean LD50 (nM) HCC1954.1 | Rmin (%) (max lethality) | Payload Class | Mass | SPA-AT S GMean IC50 (nM) SF381 (WT) HELA.2 | qPCR-IVS-AT S GMean IC50 (nm) Ad2.1 HELA.2 | qPCR-IVS-AT S GMean IC50 (nM) Ad2.2 HELA.2 |
| AB185-ADL5-D25 | ADL0005-01 | 6.3 | 0.038 | >113.000 | −51.503 | Plad D Zwitt | 722.917 | 14.567 | 243.749 | 50.858 |
| AB185-ADL1-D1 | ADL0001-01 | 4 | 0.042 | 0.447 | −78.554 | Plad D | 636.827 | 6.085 | 17.568 | 15.853 |
| AB185-ADL14-D4 | ADL0001-01 | 2.8 | 0.05 | >200.000 | −75.774 | Plad D | 664.837 | 8.778 | 20.887 | 17.321 |
| AB185-ADL14-D1 | ADL0014-01 | 3.5 | 0.055 | >200.000 | −60.34 | Plad D | 636.827 | 6.085 | 17.568 | 15.853 |
| AB185-ADL15-D1 | ADL0015-01 | 3.2 | 0.062 | >200.000 | −60.34 | Plad D | 636.827 | 6.085 | 17.568 | 15.853 |
| AB185-ADL1-D8 | ADL0001-01 | 7.2 | 0.075 | 1.01 | −72.765 | Plad D | 664.83 | 5.921 | 11.403 | 9.034 |
| AB185-ADL12-D22 | ADL0012-01 | 4.3 | 0.078 | >80.000 | 27.157 | Plad D Zwitt | 708.89 | 29.188 | 66.293 | 49.131 |
| AB185-ADL12-D1 | ADL0012-01 | 3.1 | 0.081 | 2.148 | −85.136 | Plad D | 636.827 | 6.085 | 17.568 | 15.853 |
| AB185-ADL6-D1 | ADL0006-01 | 3.8 | 0.081 | 2.877 | −86.59 | Plad D | 636.827 | 6.085 | 17.568 | 15.853 |
| T-DM1 | SMCC | 3.3 | 0.118 | 2.759 | −56 | DM1 | 738.29 | >1200.000 | >25000.000 | <25000.000 |
| AB185-ADL12-D21 | ADL0012-01 | 3.3 | 0.126 | >200.000 | −39.556 | Plad D | 652.87 | | | |
| AB185-ADL12-D20 | ADL0012-01 | 3.2 | 0.142 | >200.000 | −61.497 | Plad D | 638.843 | 18.251 | 10.929 | 8.748 |
| AB185-ADL15-D2 | ADL0015-01 | 3.3 | 0.17 | >200.000 | −25.778 | Plad D | 650.854 | 15.533 | 19.133 | 15.342 |
| AB185-ADL5-D2 | ADL0005-01 | 4.1 | 0.179 | >200.000 | −19.945 | Plad D | 650.854 | 15.533 | 19.33 | 15.342 |
| AB185-ADL6-D9 | ADL0006-01 | 5.2 | 0.244 | 4.206 | −95.509 | Plad B | 648.838 | 2.177 | 20.224 | 18.121 |
| AB185-ADL5-D10 | ADL0005-01 | 4 | 0.254 | >200.000 | −7.125 | Plad D | 664.881 | 9.228 | 16.317 | 14.658 |
| AB185-ADL1-D13 | ADL0001-01 | 5 | 0.289 | 18.948 | −95.484 | Plad B | 648.838 | 2.085 | 11.287 | 8.816 |
| AB185-ADL12-D2 | ADL0012-01 | 3.6 | 0.432 | >200.000 | 17.824 | Plad D | 650.854 | 15.533 | 19.133 | 15.342 |
| AB185-ADL1-D22 | ADL0001-01 | 2.9 | 0.443 | >200.000 | 27.157 | Plad D Zwitt | 708.89 | 29.188 | 66.293 | 49.131 |
| AB185-ADL1-D33 | ADL0001-01 | 8 | 0.466 | >200.000 | −34.274 | ArPlad Zwitt | 630.758 | 35.694 | 33.402 | 72.404 |
| AB185-ADL5-D11 | ADL0005-01 | 3.7 | 0.806 | >93.000 | −57.844 | Plad D | 718.973 | 5.99 | 10.545 | 9.364 |
| AB185-ADL5-D15 | ADL0005-01 | 4 | 0.912 | >200.000 | −50.337 | ArPlad | 668.811 | 1.648 | 4.632 | 4.928 |
| AB185-ADL1-D14 | ADL0001-01 | 4.3 | 0.925 | >200.000 | 3.753 | ArPlad | 654.784 | 1.924 | 10.022 | 8.586 |
| AB185-ADL5-D26 | ADL0005-01 | 4.3 | 0.943 | >200.000 | −29 | ArPlad | 694.849 | 5.505 | 18.838 | 14.314 |
| AB185-ADL1-D16 | ADL0001-01 | 4.3 | 2.086 | 158.245 | −55 | ArPlAD | 680.822 | 5.564 | 16.01 | 15.144 |
| AB185-ADL5-D17 | ADL0005-01 | 4 | 2.668 | >100.000 | 12.42 | ArPlad | 587.733 | 1.82 | 17.943 | 9.44 |
| AB185-ADL1-D18 | ADL0001-01 | 3.8 | 5.994 | >200 | −8.011 | Plad B | 620.828 | 0.99 | 12.686 | 12.709 |
| AB185-ADL10-D1 | ADL0010-01 | 3.5 | 6.642 | >200 | 8.138 | Plad D | 636.827 | 6.085 | 17.568 | 15.853 |

Characterization of exemplary anti-HER2 ADCs and corresponding payloads

| | | | Payload cell potency and lethality | | | Payload cell permeability | | | Payload chemical stability |
|---|---|---|---|---|---|---|---|---|---|
| SMLA Batch ID | Linker | DAR | CTGlo-AT S GMean GI50 (nM) Ad2.2 HELA.2 | CTGlo-AT S GMean LD50 (nM) 72 h THP1.1 | CTGlo-AT S Mean MinResponse % 72 h THP1.1 | Perme-ability Mean Caco-2 A-B Perm (10e-6 cm/s) | Perme-ability Mean Caco-2 B-A Perm (10e-Gcm/s) | Eflux ratio | Stability Mean Sta-bility t1/2 pH5.5 (d) |
| AB 185-ADL5-D25 | ADL0005-01 | 6.3 | 348.114 | 2076.811 | −77.246 | 0.137 | 0.349 | 2.547 | 5 |
| AB185-ADL1-D1 | ADL0001-01 | 4 | 11.085 | 41.408 | −100.615 | 0.14 | 2.05 | 14.643 | 3.95 |
| AB185-ADL14-D4 | ADL0001-01 | 2.8 | 10.943 | 33.329 | −99.957 | 0.1 | 1.79 | 17.9 | 4.4 |
| AB185-ADL14-D1 | ADL0014-01 | 3.5 | 11.085 | 41.408 | −100.615 | 0.14 | 2.05 | 14.643 | 3.95 |
| AB 185-ADL15-D1 | ADL0015-01 | 3.2 | 11.085 | 41.408 | −100.615 | 0.14 | 2.05 | 14.643 | 3.95 |

TABLE 14-continued

| | | | | | | | | | |
|---|---|---|---|---|---|---|---|---|---|
| AB185-ADL1-D8 | ADL0001-01 | 7.2 | 8.745 | 38.969 | −99.92 | 0.128 | 2.027 | 15.875 | 3.525 |
| AB185-ADL12-D22 | ADL0012-01 | 4.3 | 223.348 | 1594.636 | −78.119 | 0.14 | 0.18 | 1.143 | |
| AB185-ADL12-D1 | ADL0012-01 | 3.1 | 11.085 | 41.408 | −100.615 | 0.14 | 2.05 | 14.643 | 3.95 |
| AB185-ADL6-D1 | ADL0006-01 | 3.8 | 11.085 | 41.408 | −100.615 | 0.14 | 2.05 | 14.643 | 3.95 |
| T-DM1 | SMCC | 3.3 | 0.503 | 3.287 | −93.785 | 0.38 | 28.6 | 75.263 | 1.3 |
| AB185-ADL12-D21 | ADL0012-01 | 3.3 | | | | | | | |
| AB185-ADL12-D20 | ADL0012-01 | 3.2 | 28.336 | 113.557 | −100.664 | 0.16 | 0.38 | 2.375 | >7.000 |
| AB185-ADL15-D2 | ADL0015-01 | 3.3 | 2015 | 11.708 | −100.218 | 0.624 | 14.2 | 22.756 | 4 |
| AB185-ADL5-D2 | ADL0005-01 | 4.1 | 2015 | 11.708 | −100.218 | 0.624 | 14.2 | 22.756 | 4 |
| AB185-ADL6-D9 | ADL0006-01 | 5.2 | 0.87 | 3.56 | −99.938 | 1.15 | 16.11 | 14.009 | <1.000 |
| AB185-ADL5-D10 | ADL0005-01 | 4 | 1.819 | 8.454 | −99.951 | 1.81 | 23.5 | 12.983 | >7.000 |
| AB185-ADL1-D13 | ADL0001-01 | 5 | 0.892 | 3.358 | −99.941 | 0.9 | 17.17 | 19.078 | <1.000 |
| AB185-ADL12-D2 | ADL0012-01 | 3.6 | 2.015 | 11.708 | −100.218 | 0.624 | 14.2 | 22.756 | 4 |
| AB185-ADL1-D22 | ADL0001-01 | 2.9 | 223.348 | 1594.636 | −78.119 | 0.14 | 0.16 | 1.143 | |
| AB185-ADL1-D33 | ADL0001-01 | 8 | 195.752 | 5202.992 | 53.128 | 0.13 | 0.53 | 4.077 | |
| AB185-ADL5-D11 | ADL0005-01 | 3.7 | 1.352 | 8.086 | −100.481 | 0.87 | 10.56 | 12.138 | 3.75 |
| AB185-ADL5-D15 | ADL0005-01 | 4 | 1.017 | 11.038 | −99.595 | 3.43 | 26.9 | 7.843 | >7.000 |
| AB185-ADL1-D14 | ADL0001-01 | 4.3 | 3.584 | 25.594 | −99.209 | 0.06 | 12.13 | 202.167 | >7.000 |
| AB185-ADL5-D26 | ADL0005-01 | 4.3 | 3.719 | 28.483 | 99.401 | 15.955 | 41.125 | 2.578 | >7.000 |
| AB185-ADL1-D16 | ADL0001-01 | 4.3 | 2.975 | 21.46 | −99.681 | 0.72 | 23.3 | 32.361 | >7.000 |
| AB185-ADL5-D17 | ADL0005-01 | 4 | 2.827 | 24.908 | −99.033 | 20.25 | 18.18 | 0.896 | |
| AB185-ADL1-D18 | ADL0001-01 | 3.8 | 0.863 | 4.355 | −99.621 | 1.19 | 27.4 | 23.025 | |
| AB185-ADL10-D1 | ADL0010-01 | 3.5 | 11.085 | 41.408 | −100.615 | 0.14 | 2.05 | 14.643 | 3.95 |

3.5.4 In-Cell Splicing PD Assay

To interrogate the mechanism of action of exemplary anti-HER2 ADCs, splicing of the SLC25A19 mature transcript was examined in HCC1954 cells treated with increasing concentrations of ADC.

HCC1954 cells (ATCC) were plated in phenol-red free RPMI+10% FBS media (ATCC) at $1\times10^5$ cells per well at 90 µL per well. Cells were treated with conjugates in a 3-fold dilution dose-response. After 24 hours or 6 hours, respectively, cells were lysed with 50 µL of CL buffer (IgePal CA-630, 5M NaCl, 1M Tris HCl 1M pH 7.4 in water) containing 25 µL/mL of RNAsin (Promega) and incubated for 45 min at RT on a rocker. Resulting mixture (0.5 µL) was used to assess splicing modulation in a Taqman Fast Virus 1-Step MasterMix (Applied Biosystems) reverse transcription PCR reaction with the following Taqman primers according to the manufacturer's recommendations: SLC25A19 (Invitrogen, Hs00222265_m1); RPLPO (Invitrogen, Hs99999902_m1); 18S (Invitrogen, Hs99999901_s1).

Figure 7:
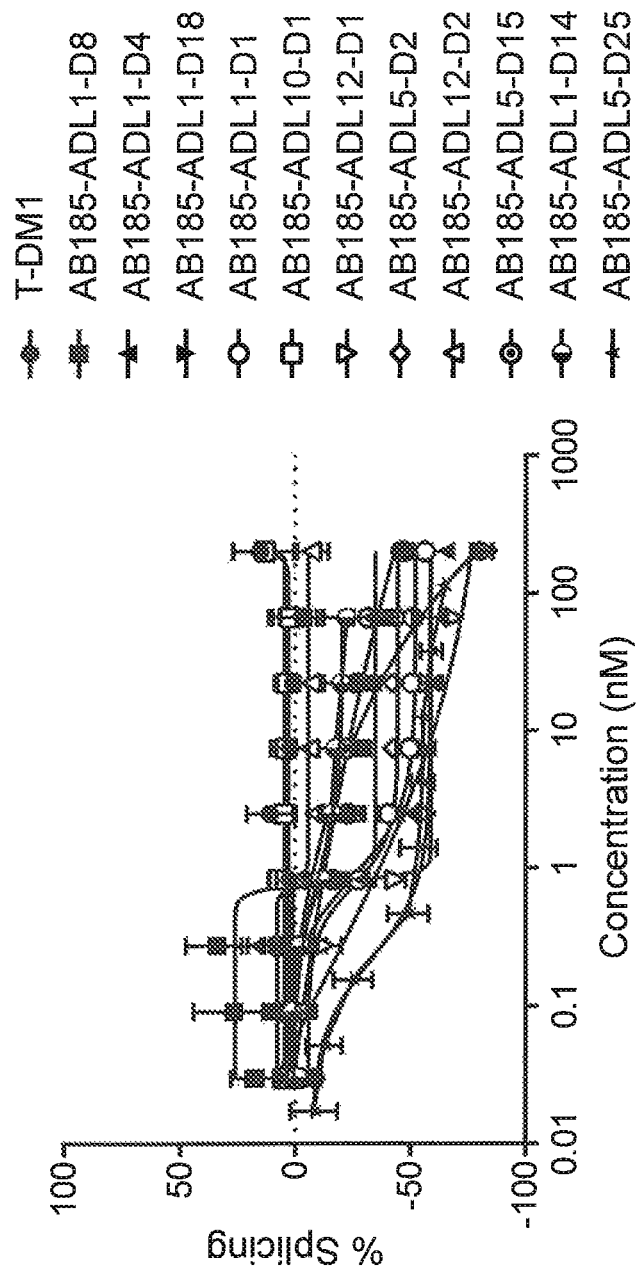
FIG. 7 shows the results of a SLC25A19 splicing assay in HER2-amplified breast cancer cells (HCC1954). Cells were incubated with conjugates for 24 hours and splicing of SLC25A19 transcript was measured in a real time qPCR reaction with a specific Taqman primer-probe set. The y-axis represents the percent (%) response relative to the DMSO control (0%). Data are represented as mean±SD.

T-DM1 control (trastuzumab with a microtubule disrupting agent as payload) did not affect SLC25A19 splicing (FIG. 7). In contrast, anti-HER2 ADCs that demonstrated potent growth inhibition activity in different tested cell lines (FIG. 5) also demonstrated potent splicing modulation, indicating an on-target mechanism of action (FIG. 7). Likewise, anti-HER2 ADCs that exhibited lower potency in cell viability assays were less potent in terms of splicing modulation.

3.5.5 Bystander Cell Killing Assay

The ability of exemplary anti-HER2 conjugates to kill both target-positive cells and neighboring target-negative cells was measured in a bystander cell killing assay. NCI-$H_{1568}$, non-small cell lung cancer cells (ATCC) were engineered to express luciferase. cDNA was synthesized at GeneArt (ThermoFisher Scientific) and cloned into a pLVX-EF1a destination vector (ThermoFisher Scientific). Separately, NCI-$H_{1568}$ were engineered to express human HER2 (cloned into pLenti6.3/V5-DEST, ThermoFisher Scientific) utilizing the TransIT® viral transfection system according to manufacturer's instructions (Mirus Bio LLC; #MIR6003). To assess the bystander activity of conjugates, 2000 target-positive (HER2-transduced) NCI-$H_{1568}$ cells and 2000 target-negative (luc-tagged) NCI-$H_{1568}$ cells were plated together in clear 96-well round bottom plates (Corning) and incubated with conjugates dosed at a 3-fold serial dilution in triplicate, 30-0.005 nM. At the time of treatment, a plate of untreated cells was assayed using OneGlo® Luciferase Assay System (Promega) and CellTiter-Glo®2.0 Luminescent Cell Viability Assay System (Promega) according to the manufacturer's recommendations, to establish a time zero (T0). After 6 days in culture, the remaining cell population was analyzed by OneGlo® Luciferase Assay System (Promega) to measure the fraction of target-negative cells surviving. Overall viability was measured by CellTiter-Glo®2.0 Luminescent Cell Viability Assay System (T144). Dose response curves were calculated as described in section 2.3.

The design of the bystander killing assay allows tracking of only target-negative cells, the elimination of which relies on uptake of the catabolite released by neighboring target-positive cells. As discussed above, cells are plated under three conditions: (1) target-negative (luc-tagged) cells alone; (2) target-positive cells alone; and (3) co-culture of target-negative and target-positive cells. When the plates are read with CellTiter-Glo® reagent, viability of all cell populations can be tracked to confirm antigen-dependent ADC activity. In contrast, when OneGlo® reagent is used, only the target-negative (luc-tagged) cells will have a signal.

Figure 8:
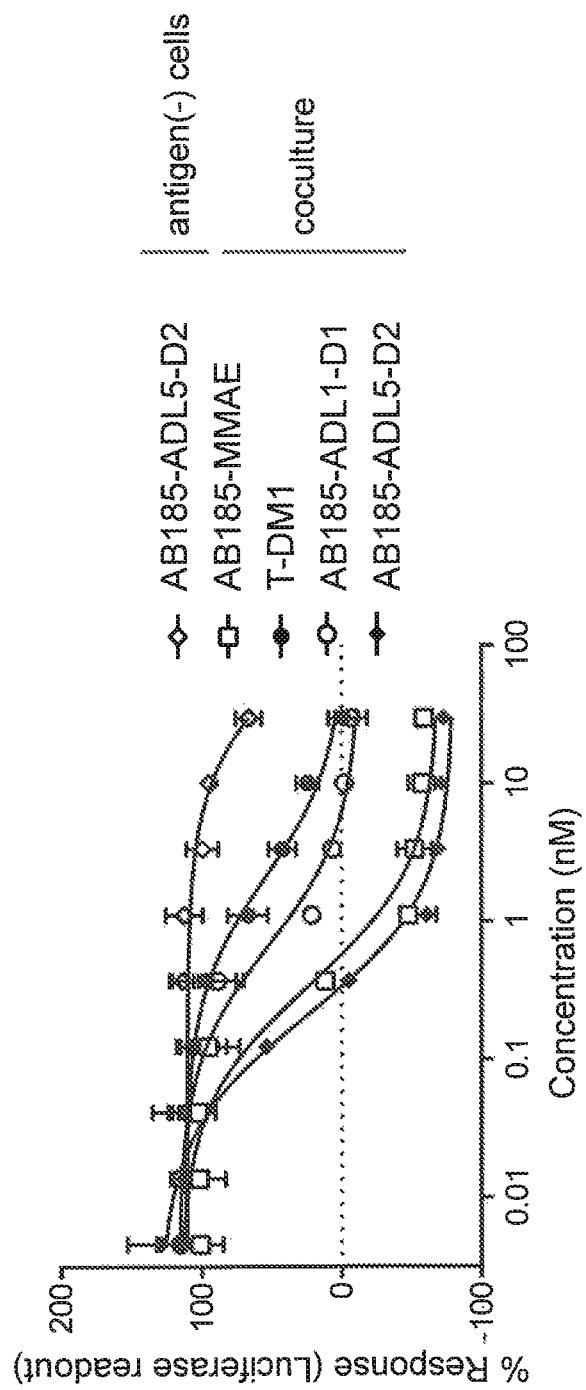
FIG. 8 shows the results of a bystander killing assay. H1568 cells overexpressing HER2 (target-positive) or H1568 cells tagged with luciferase (target-negative) plated either alone or incubated together in co-culture for 144 hours (6 days) were treated with exemplary HER2-ADCs. Plates were read with OneGlo® reagent. The y-axis represents the percent (%) response relative to the PBS control (100%). Data are represented as mean±SD.

Target-negative (luc-tagged) cells were not sensitive to treatment with anti-HER2 ADCs when cultured on their own (FIG. 8). However, when target-negative cells were cultured with target-positive cells, treatment with anti-HER2 ADCs resulted in increased killing of target-negative cells. These data suggest that target-negative cells are killed more effectively by anti-HER2 ADCs when co-cultured with target-positive cells, referred to herein as bystander killing. Bystander killing is distinguishable from off-target killing, which is defined as the killing of target (antigen)-negative cells on their own, in the absence of and independent of co-culturing with target-positive cells.

In this experiment, AB185-ADL5-D2 demonstrated an increased ability to kill an antigen heterogenous cancer cell population as compared to AB185-ADL1-D1. Without wishing to be bound by theory, this difference in potency may be due to the addition of one methyl group in D2, which gives a three-fold increase in payload cell potency and permeability as compared to D1 (see Table 14). The D2 ADC treated an antigen heterogenous cancer cell population as effectively as the AB185-MC-Val-Cit-MMAE control ADC.

3.6 In Vivo Analysis

Exemplary anti-HER2 ADCs that exhibited potent splicing modulation and cell growth inhibition were assessed in vivo.

3.6.1 HCC1954 Xenograft Efficacy Study

To investigate the efficacy of exemplary anti-HER2 ADCs in a mouse xenograft model, HCC1954 (ATCC) breast ductal carcinoma cells ($10 \times 10^6$ cells/100 µL/1:1 RPMI: Matrigel volume) were subcutaneously implanted into the flank of female CB17-SCID mice. Mice were treated with single bolus IV doses of conjugates (formulated in DPBS, pH 7.4) or vehicle control. The animals were dosed at the amounts indicated in FIG. 9. All animals were monitored for tumor growth and body weight twice weekly until they reached either of the following endpoints: (1) excessive tumor volume (calculated by using the ellipsoid formula: (length×width$^2$)/2); or (2) development of any health problems such as excessive body weight loss. All animal studies were carried out according to the $H_3$ Biomedicine Guide for the Care and Use of Laboratory Animals.

Figure 9:
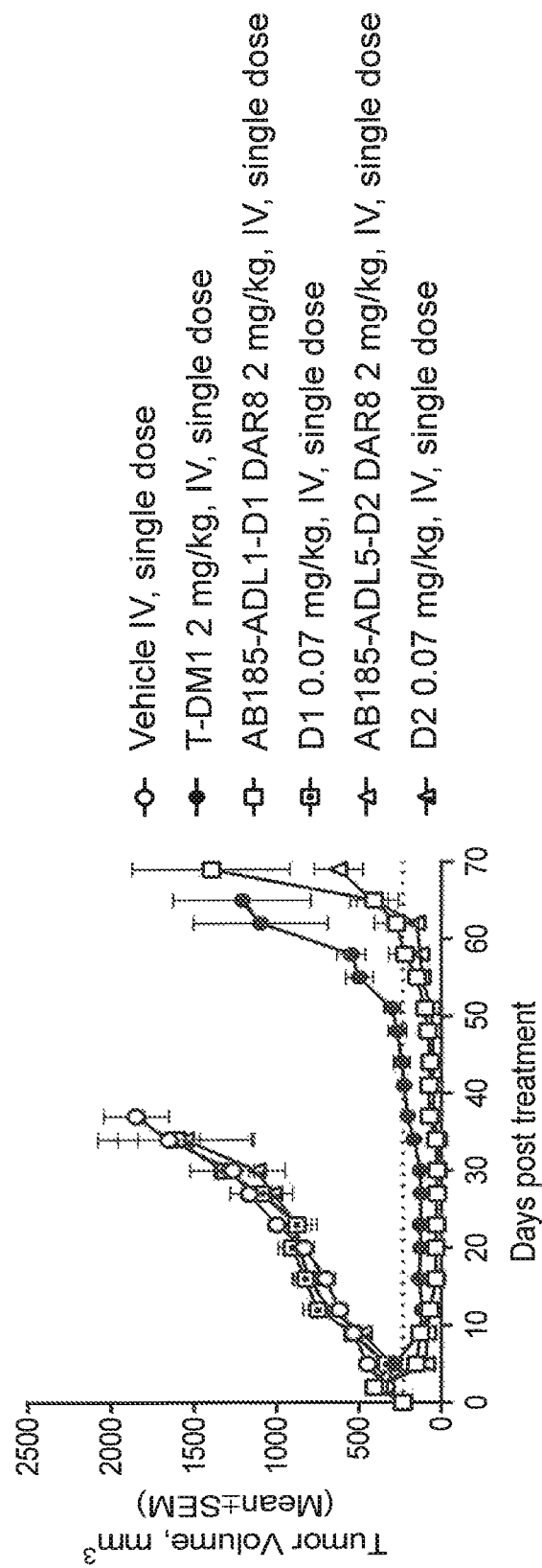
FIG. 9 shows tumor growth kinetics for each group of HCC1954-implanted CB17-SCID mice treated with a single intravenous dose of an exemplary HER2-ADC or corresponding dose-matched payload (6-10 animals per group). Tumor volumes were measured twice weekly after treatment. Data are represented as mean±standard error of the mean (SEM).

Treatment with anti-HER2 ADC (AB185-ADL5-D2 or AB185-ADL1-D1) at a single dose as low as 2 mg/kg resulted in significant tumor regression (FIG. 9). A dose response for the conjugated payload was also observed, such that anti-HER2 ADCs with higher DAR values (DAR -4) demonstrated increased efficacy and slower tumor regrowth relative to dose-matched antibody T-DM1 control. Additionally, payload targeted to the tumor via an ADC was more potent relative to the corresponding unconjugated payload.

Example 4

To determine whether the properties of the exemplary anti-HER2 ADCs described in Example 3 could be extrapolated to other ADCs targeting alternate antigens and/or indications, select payloads were conjugated to an exemplary anti-CD138 antibody (B—B4) and an exemplary anti-EPH2A antibody ($1C_1$). CD138 is expressed on malignant plasma cells, e.g., in multiple myeloma, while EPH2A is more generally expressed in a variety of malignancies. The preparation and evaluation of exemplary anti-CD138 and anti-EPH2A ADCs is described below.

4.1 Antibodies

B—B4 antibody ("AB205") (Tassone et al. (2004) Blood 104:3688-96) and $1C_1$ antibody ("AB206") (Jackson et al. (2008) Cancer Res. 68(22):9367-74) were used for the preparation of anti-CD138 ADCs and anti-EPH2A ADCs, respectively.

4.2 Bioconjugation

Antibody (B—B4 or $1C_1$) at 10 mg/mL in PBS buffer (pH 7.0) was mixed with 5 mM TCEP (2-4 molar equivalents) (ThermoFisher Scientific; #77720) to break interchain disulfide bonds. The reaction was gently mixed at 22° C. for 3 hours. Propylene glycol (15% v/v) was then added followed by 8 molar equivalents of linker-payload (6 mM stock in DMSO), and the solution was mixed thoroughly. The reaction was placed onto a rotary plate in an incubator at 22° C. After a 2-hour conjugation, the reaction mixture was purified to remove unconjugated payload by AKTA GE M150 (HiTrap™ 26/10 desalting column; flow rate: 3 mL/min) (GE Healthcare Bio-Sciences) into DPBS (pH 7.5). The resulting conjugate was concentrated via Amicon ultrafiltration (30 kDa, Ultra-4) (EMD Millipore) and submitted to sterile filtration through a 0.22 m PVDF disposable filter (EMD Millipore). The final clear solution was measured by UV-VIS to determine antibody concentration ([mAb]; mole/L) and conjugated payload concentration ([LD]; mole/L) according to the Beer-Lambert law ($A = E*c*I$) and the following equations:

$$A280 \text{ nm} = E^{mAb}_{280nm}*[mAb]*I + E^{LD}_{280nm}*[LD]*I$$

$$A_{252nm} = E^{mAb}_{252 \text{ nm}}*[mAb]*I + E^{LD}_{252 \text{ nm}}*[LD]*I$$

$$E^{mAb}_{280 \text{ nm}}: B-B4 = 224{,}320 \text{ cm}^{-1}M^{-1}$$

$$1C_{1=215{,}380} \text{ cm}^{-1}M^{-1}$$

$$E^{mAb}_{252nm}: B-B4 = 83{,}670 \text{ cm}^{-1}M^{-1}$$

$$1C_{1=80{,}337} \text{ cm}^{-1}M^{-1};$$

$$E^{LD}_{280nm} = 800 \text{ cm}^{-1}M^{-1}$$

$$E^{LD}_{252 \text{ nm}} = 31{,}000 \text{ cm}^{-1}M^{-1}$$

Abbreviations: c—molar concentration; I—light path length (Nanodrop: 0.1 cm); E—molar extinction coefficient; A—absorbance.

4.3 Biophysical Characterization

DAR, percent aggregation, and percent unconjugated payload was analyzed for exemplary anti-CD138 and anti-EPHA2 ADCs by liquid chromatography-mass spectrometry (LC/MS), size exclusion chromatography (SEC), and reverse-phase high-performance liquid chromatography (HPLC), respectively. All conjugates described herein contained less than 2% free drug and contained less than 10% aggregate.

4.3.1 LC/MS Analysis—DAR

LC/MS analysis was performed as described in section 3.3.1. DAR values for exemplary anti-CD138 and anti-EPHA2 ADCs are reported in Tables 15-18.

4.3.2 SEC Analysis—Aggregation

SEC analysis was performed as described in section 3.3.2. Percent monomer for exemplary anti-CD138 and anti-EPHA2 ADCs is reported in Tables 15 and 17.

4.3.3 HPLC Analysis—Free Drug

HPLC analysis was performed as described in section 3.3.3. Percent free drug for exemplary anti-CD138 and anti-EPHA2 ADCs is reported in Tables 15 and 17.

4.4 In Vitro Analysis

4.4.1 Cell Viability

Anti-CD138 ADCs were tested in the CD138-expressing MOLP8 multiple myeloma cell line. Similarly, anti-EPHA2 ADCs were tested in the EPHA2-expressing PC3 prostate cancer cell line. Cell viability analysis was performed as described in section 2.3.

Figure 10:
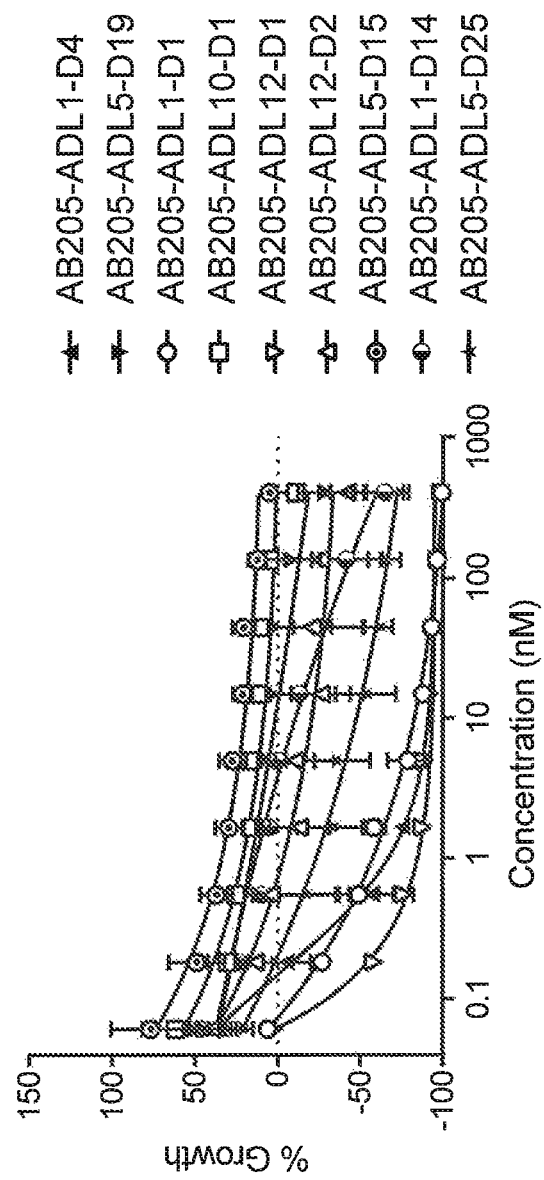
FIG. 10 shows viability dose response of exemplary CD138-ADCs in a CD138-expressing multiple myeloma cell line. MOLP8 cells were incubated with conjugates for 144 hours (6 days) and viability was read in CellTiter-Glo® reagent. Data are represented as mean±SD.
Figure 11:
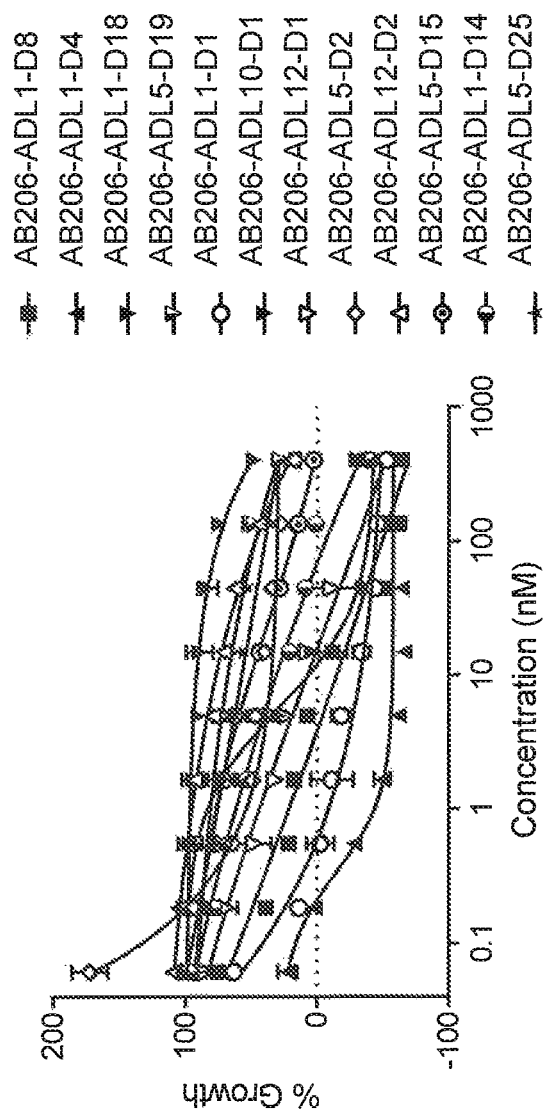
FIG. 11 shows viability dose response of exemplary EPH2A-ADCs in an EPHA2-expressing prostate cancer cell line. PC3 cells were incubated with conjugates for 144 hours (6 days) and viability was read in CellTiter-Glo® reagent. Data are represented as mean±SD.

Payload conjugation to anti-CD138 antibody (FIG. 10 and Table 16) and anti-EPHA2 antibody (FIG. 11 and Table 18) resulted in similar trends as those discussed in section 3.5.1 for anti-HER2 ADCs. In particular, ADCs with certain linkers (e.g., ADL12) and/or payloads (e.g., D1, D25, D4) demonstrated the highest potency in antigen-expressing cells. Consistently, alternate payloads (e.g., D14) were less capable of inhibiting cell growth via antibody-mediated delivery, despite being potent small molecules.

TABLE 15

Characterization of exemplary anti-CD138 ADCs

| SMLA Batch ID | Payload Class | Linker | DAR | Percent Monomer | Free Drug (%) | Concentration (mg/ml) |
|---|---|---|---|---|---|---|
| AB205-ADL1-D14 | Aryl Plad | ADL0001 | 2.900 | 92.000 | <2 | 1.010 |
| AB205-ADL5-D15 | Aryl Plad | ADL0005 | 2.800 | 95.000 | <2 | 1.060 |
| AB205-ADL5-D19 | Plad B | ADL0005 | 4.900 | 95.000 | <2 | 0.880 |
| AB205-ADL1-D1 | Plad D | ADL0001 | 5.000 | 98.000 | <2 | 0.620 |
| AB205-ADL1-D4 | Plad D | ADL0001 | 4.800 | 98.000 | <2 | 1.010 |
| AB205-ADL5-D25 | Plad D Zwitt | ADL0005 | 6.400 | 98.000 | <2 | 0.890 |
| AB205-ADL10-D1 | Plad D | ADL0010 | 3.400 | 96.000 | <2 | 0.750 |
| AB205-ADL12-D1 | Plad D | ADL0012 | 3.800 | 97.000 | <2 | 0.830 |
| AB205-ADL12-D2 | Plad D | ADL0012 | 3.300 | 97.000 | <2 | 0.970 |

TABLE 16

Exemplary anti-CD138 ADCs-MOLP8 cells

| Sample | DAR | GI50 (nM) | LD50 (nM) | Rmin (%) | GI50 (nM) | LD50 (nM) | Rmin (%) |
|---|---|---|---|---|---|---|---|
| AB205-ADL1-D1 | 5 | >0.061 | 0.656 | −100.099 | 6.885 | 25.712 | −100.248 |
| AB205-ADL5-D15 | 2.8 | 0.268 | >400 | 2.419 | 0.776 | 9.178 | −100.198 |
| AB205-ADL5-D19 | 4.9 | <0.061 | >400 | −46.23 | 0.84 | 4.58 | −62.2 |
| AB205-ADL10-D1 | 3.4 | 0.08 | >400 | −25.099 | 6.885 | 25.712 | −100.248 |
| AB205-ADL12-D1 | 3.8 | <0.061 | 0.168 | −99.851 | 6.885 | 25.712 | −100.248 |
| AB208-ADL12-D2 | 3.3 | <0.061 | >400 | −53.125 | 0.316 | 5.035 | −100.198 |
| AB205-ADL1-D14 | 3 | <0.061 | >400 | −74.008 | 1.9 | 8.5 | −61 |
| AB205-ADL1-D4 | 4.8 | <0.061 | 0.535 | −99.306 | 1.151 | 12.99 | −101.935 |
| AB205-ADL5-D25 | 6.4 | <0.061 | 11.669 | −76.736 | 149.874 | >400 | 5.94 |

TABLE 17

Characterization of exemplary anti-EPHA2 ADCs

| SMLA Batch ID | Payload Class | Linker | DAR | Percent Monomer | Free Drug (%) | Concentration (mg/ml) |
|---|---|---|---|---|---|---|
| AB20S-ADL1-D1 | Plad D | ADL0001 | 6.600 | 99.000 | <2 | 2.060 |
| AB206-ADL5-D2 | Plad D | ADL0005 | 6.300 | 99.000 | <2 | 1.900 |
| AB206-ADL1-D4 | Plad D | ADL0001 | 6.000 | 95.000 | <2 | 1.140 |
| AB206-ADL1-D8 | Plad D | ADL0001 | 6.500 | 95.000 | <2 | 1.660 |
| AB206-ADL1-D14 | Aryl Plad | ADL0001 | 3.600 | 80.000 | <2 | 1.620 |
| AB206-ADL5-D19 | Plad B | ADL0005 | 4.600 | 97.000 | <2 | 0.960 |
| AB206-ADL5-D15 | Aryl Plad | ADL0005 | 4.200 | 96.000 | <2 | 0.820 |
| AB206-ADL5-D25 | Plad D Zwitt | ADL0005 | 6.000 | 96.000 | <2 | 1.130 |
| AB206-ADL10-D1 | Plad D | ADL0010 | 2.700 | 97.000 | <2 | 1.620 |
| AB206-ADL12-D1 | Plad D | ADL0012 | 6.400 | 90.000 | <2 | 0.870 |
| AB206-ADL12-D2 | Plad D | ADL0012 | 6.300 | 80.000 | <2 | 0.850 |

TABLE 18

Exemplary anti-EPHA2 ADCs-PC3 cells

| Sample | DAR | SMLA | | | Payload | | |
|---|---|---|---|---|---|---|---|
| | | GI50 (nM) | LD50 (nM) | Rmin (%) | GI50 (nM) | LD50 (nM) | Rmin (%) |
| AB206-ADL1-D8 | 6.5 | 0.175 | 95.5 | −68.678 | 16.622 | 177.783 | −68.37 |
| AB206-ADL1-D4 | 6 | <0.061 | 2.732 | −69.096 | 11.057 | >400 | −55.97 |
| AB206-ADL1-D14 | 3.6 | 3.046 | >400 | −49.267 | 3.877 | >400 | −79.835 |
| AB206-ADL12-D1 | 6.4 | 0.808 | >400 | −64.516 | 13.291 | >400 | −71.987 |
| AB206-ADL12-D2 | 6.3 | 78.977 | >400 | 17.376 | 2.391 | >400 | −68.803 |
| AB206-ADL5-D18 | 4.6 | 71.73 | >400 | 19.765 | 1.41 | >400 | −29.33 |
| AB206-ADL10-D1 | 2.7 | >400 | >400 | 43.796 | 13.291 | >400 | −71.987 |
| AB206-ADL5-D15 | 4.2 | 9.959 | >400 | 2.441 | 3.877 | >400 | −79.835 |
| AB206-ADL5-D28 | 5 | 28.078 | >400 | 20.041 | >400 | >400 | 77.524 |
| AB206-ADL1-D1 | 5.6 | <0.061 | >400 | −59.643 | 13.291 | >400 | −71.987 |
| AB206-ADL5-D2 | 6.3 | 1.003 | >400 | 16.465 | 2.391 | >400 | −68.803 |

Example 5

The in vitro and/or in vivo stability of exemplary anti-HER2 ADCs was assessed as described below.

5.1 Total Antibody and Conjugated Payload of AB185-ADL1-D1 in Plasma

Following in vitro treatment (section 5.1.1) or in vivo treatment (section 5.1.2) with AB185-ADL1-D1, levels of total antibody (TAb) and conjugated payload (CP) were quantified in plasma by immunoprecipitation LC/MS/MS technique. Quantitation fit was linear with $1/x^2$ weighting from 0.5-100 μg/mL, and 0.5-500 ng/ml, in mouse plasma for TAb and CP, respectively. Plasma samples were mixed with stable-isotope labeled universal monoclonal human antibody internal standard (Slu™MAB, Sigma, St. Louis, MO) and 10 mM PBS, PH 7.4 and incubated at room temperature for one hour. Dynabeads® MyOne™ Streptavidin T1 magnetic beads (ThermoFisher Scientific) were added to the mixture and incubated for an additional 30 min at room temperature. A magnetic stand was used to bind beads, which were sequentially washed with CHAPS buffer and then PBS buffer. Analytes of interest were eluted from the beads with 30 mM HCl. Separate eluent aliquots were used to quantify TAb or CP. For TAb, Tris-HCl, pH 8.3 was added, followed by trypsin and allowed to incubate overnight at 37° C. For the CP, 1M ammonium acetate was added, followed by deuterated payload internal standard, and cathepsin B, and allowed to incubate overnight at 25° C. Samples were analyzed by LC/MS/MS and quantified using area ratio of analyte to internal standard and compared against respective calibration curve. To calculate CP concentration, the concentration of TAb was corrected for molecular weights of payload, molecular weight of AB185-ADL1-D1 and DAR (drug-to-antibody ratio).

5.1.1 In Vitro Stability of AB185-ADL1-D1 in Mouse, Rat, and Monkey Plasma

Pooled plasma (Bioreclamation) from mouse, rat, and monkey, and PBS were spiked with AB185-ADL1-D1 (4.81 mg/mL) to achieve a final concentration of 50 μg/mL. Samples were incubated at 37° C., 95% humidity, 5% $CO_2$ for 4 days in a manner to stabilize pH and minimize non-specific binding and evaporation. Aliquots were removed at 4, 24, 48, 72, and 96 hours and stored at −70° C. until processing. Samples were thawed and processed for bioanalysis using methods described above (section 5.1) for total antibody and conjugated payload. Time 0 was set to 100% for each matrix. The area ratio responses of the later time points were compared to time 0 separately for each matrix. Percent remaining was calculated as follows: (Area Ratio day X/Area Ratio time 0)*100=% remaining. The slope of the line was calculated in Excel comparing the log of % remaining and time point. Half-life was calculated in Excel by In(2)/slope.

Figure 12A:
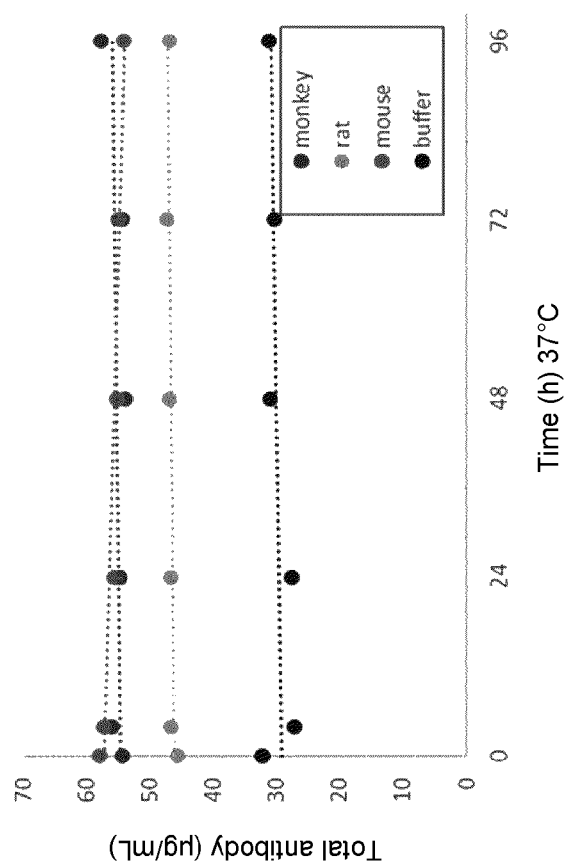
FIG. 12A and FIG. 12B show the results of an in vitro stability assay for an exemplary anti-HER2 ADC, AB185-ADL1-D1. The y-axis represents concentration of total antibody (FIG. 12A) and conjugated (intact) payload (FIG. 12B); the x-axis represents time as measured in hours at 37° C.
Figure 12B:
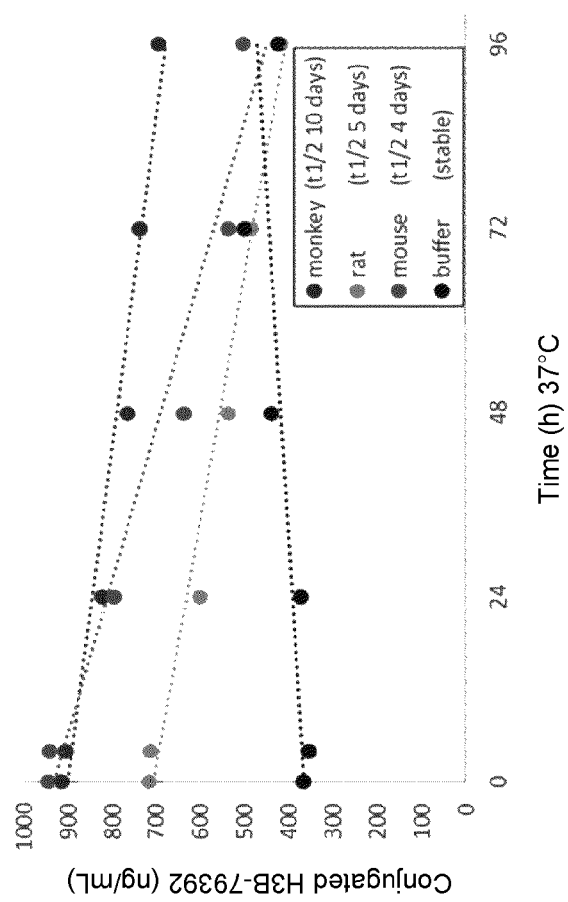

Total antibody from AB185-ADL1-D1 was found to be stable in buffer and in all species of plasma, exhibiting only modest precipitation over 4 days (FIG. 12A). Conjugated (intact) payload D1 levels were maintained over 4 days (FIG. 12B).

5.1.2 Snapshot Pharmacokinetics (PK) in Mouse Plasma Following Single IV Dose of AB185-ADL1-D1

Mice (CB17-SCID) were treated with a single IV dose of AB185-ADL1-D1 at 10 mg/kg or 20 mg/kg, followed by terminal collections (cardiac puncture) in Lithium-Heparin tubes (n=3 per time point per dose group) at 24, 48, and 72 hours post dose. Blood was centrifuged for 5 min at 5000 rpm at 4° C. to remove red blood cells and the plasma was stored at −80° C. until processing. Samples were thawed and processed for bioanalysis using methods described above (section 5.1) for total antibody and conjugated payload.

Figure 13:
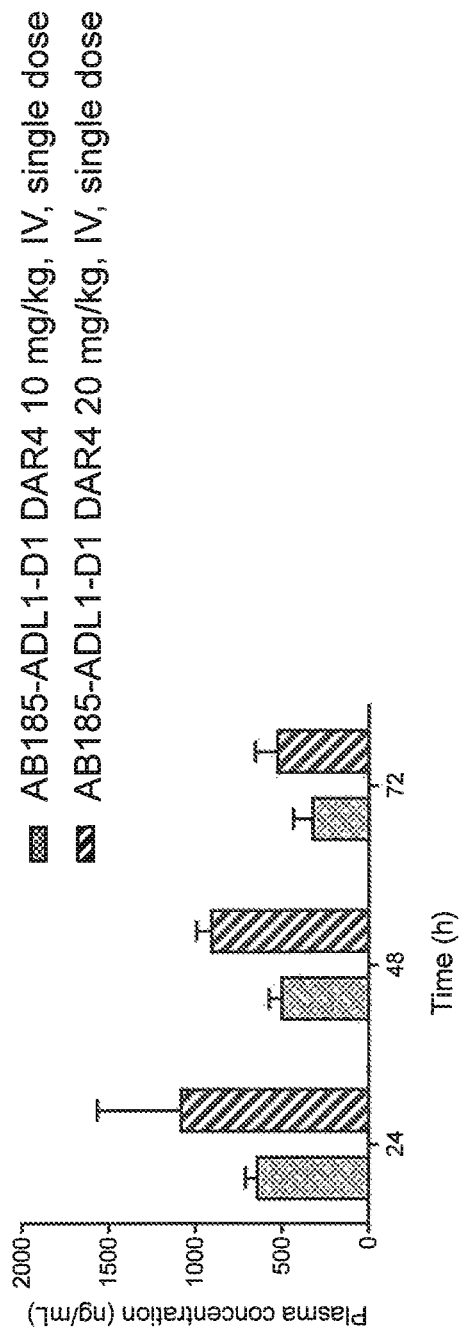
FIG. 13 shows plasma concentrations of an exemplary anti-HER2 ADC, AB185-ADL1-D1, following a single intravenous dose in CD17-SCID N87 tumor-bearing mice.

Following a single IV dose of AB185-ADL1-D1, more than 400 ng/mL of intact D1 payload remained conjugated to AB185 antibody at 72 hours post dose (FIG. 13). The AB185-ADL1-D1 ADC demonstrated improved stability as compared to an alternate ADC carrying a payload with a similar mechanism of action. The thailanstatin A-based ADC reported in Puthenveetil et al. (Bioconjugate Chem. (2016) 27:1880-8) is relatively less stable, and shows complete bioconversion of payload by 72 hours (i.e., acetate is completely hydrolyzed).

5.2 Accelerated Stability Testing of AB185-ADL14-D1 and AB185-ADL5-D25

Freshly produced SMLAs (~1 mg each in Eppendorf tubes, 4-5 mg/mL) were centrifuged and measured by UV absorption (NanoDrop) at 280 nm to determine the protein concentrations. Samples were then incubated in a 37° C. waterbath and sampled at four time points, 0 (freshly prepared), 1 day, 2 days, and 4 days. Samples taken at different time points were stored at −80° C. until the last sampling was completed. After thawing at 22° C., samples were analyzed with SEC, hydrophobic interaction chromatography (HIC), and reverse-phase-MS (RP-HPLC) for quantification of antibody aggregation/fragments, and DAR. Percent aggregation, concentration, and DAR values (HIC and RP-HPLC) for AB185-ADL14-D1 and AB185-ADL5-D25 at four time points are shown in Table 19.

TABLE 19

Accelerated stability testing of select anti-HER2 ADCs

| ADC | Storage Buffer | Days @ 37 C. | Aggregation (%) | Concentration (mg/mL) | DAR HIC | DAR RP-HPLC |
|---|---|---|---|---|---|---|
| AB185-ADL14-01 | DPBS(pH7.5) | 0 | 0.68 | 4.99 | 4.3 | 4.32 |
| | | 1 | 1.18 | 4.98 | 4.29 | 4.31 |
| | | 2 | 1.31 | 5.12 | 4.33 | 4.32 |
| | | 4 | 2.08 | 5.02 | 4.28 | 4.27 |
| AB185-ADL5-D25 | DPBS(pH7.5) | 0 | 0.84 | 5.05 | 4.54 | 4.22 |
| | | 1 | 1.14 | 4.16 | 4.44 | 4.19 |
| | | 2 | 1.41 | 4.52 | 4.74 | 4.19 |
| | | 4 | 2.43 | 3.98 | 4.64 | 4.12 |

Example 6

To determine whether cells treated with splicing modulator-based ADCs (i.e., the exemplary ADCs described herein) could produce neoantigens suitable to prime naïve T-cells to transition to effector cells (i.e., effector cells capable of targeting such neoantigens), the following experiments were performed.

6.1 RNA Sequencing and Protein Ligandome Experiment 6.1.1 Overview

Changes in the transcriptome were interrogated following ADC treatment. Two HER2-overexpressing cell lines, one engineered non-small-cell lung cancer line (NCI-$H_{1568}$) and one HER2-amplified breast cancer line (HCC1954) were treated with ADC (AB185-ADL1-D1) at concentrations intended to trigger robust aberrant mRNA splicing (4 nM and 1.3 nM, respectively). RNAseq experiments were performed at 24 hours post treatment. These experiments demonstrated that multiple mRNA transcripts exhibited altered splicing patterns.

To then interrogate whether the identified transcripts could be translated and presented as neoantigens on tumor cell MHC1 complexes, a timepoint that would allow for translation of the mRNA transcripts, but that would precede extensive cytotoxicity effects (as those may impair collection of cell material for analysis) was selected. NCI-$H_{1568}$ and HCC1954 cell lines were then treated with ADC at 3 nM for 48 hours and the MHC1-bound peptidome was analyzed by LC-MS/MS. Peptidome data was filtered by primary peptide size to 8-14 amino acid fragments (defined as the size limit criteria for binding to MHC1) and then filtered against known human proteins. The identified peptides were characterized as self antigens, regardless of under which conditions and in which cell line they were detected. All remaining peptide sequences were mapped against 3-frame translations of the RNAseq data. Using stringent criteria for evaluating the peptide sequences (including exclusion of: any peptide identified in any untreated sample, any peptide that was not encoded in the canonical open reading frame, and any peptide that was not encoded by an exon-junction-spanning portion of the mRNA where the exon junctions were altered by treatment with AB185-ADL1-D1), four MHC1-bound neopeptides were identified. For a schematic of an exemplary RNA sequencing and protein ligandome experiment, see FIG. 14.

6.1.2 Detailed Methods 6.1.2.1 RNA Sequencing of ADC-Treated Cells

HCC1954 and HER2 overexpressing NCI-$H_{1568}$ (ATCC) cells were plated at $1 \times 10^5$ cells per individual well of a 6-well tissue culture plate (Corning). Cells were treated with phosphate-buffered saline or AB185-ADL1-D1 at 1.3 nM and 4 nM, respectively, for 24 hours. Total RNA was extracted from cells using an RNAeasy Mini kit (Qiagen), and assessed for quality and quantity (RNA 6000 Nano LabChip kit on a 2100 Bioanalyzer, both from Agilent). Poly-A selected RNA-Seq libraries were prepared according to standard Illumina protocols. cDNA libraries were checked for quality and quantified using the DNA-1000 kit on a 2100 Bioanalyzer (both from Agilent). Libraries were pooled and sequenced on a HiSeq2000 (Illumina) to obtain 101-base paired-end reads.

Raw sequence reads were aligned to the human reference sequence hg19 by STAR 2.4.2a using two-pass alignment35, and isoform quantification was performed using Kallisto 0.42.4 (Bray et al. (2016) Nat Biotechnol. 34(5):525-7) against GENCODE annotation v 25 mapped to GRCh37. Estimation of the retained intron count was performed by defining 6 nt (−3 nt from the splice site and +3 following the splice site) exon-intron boundary regions and counting alignments, which fully overlapped the regions. All raw junction counts, including those from exon-intron boundaries, were pooled over all technical replicates per cohort. Differential junction usage was assessed using a binomial z test for differences in proportion between treated and untreated sample pools. Proportions were calculated on the basis of all splice junctions (and exon-intron boundaries) which shared a splice site, similar to the percent spliced in (PSI) measurement. In order to preserve Gaussian assumptions, only those shared splice sites with total junction count (sum raw count over all junctions sharing that splice site) greater than or equal to 10 reads in both treated and untreated cohorts were considered for analysis. z-scores corresponding to a false discovery rate (FDR)-corrected q value of ≤0.05 for treated ('aberrant') junctions and ≤0.20 for untreated ('canonical') junctions were considered significant.

Two or more splice junctions that share a splice site and have at least one junction that is significantly upregulated in treated samples or at least one junction significantly upregulated in untreated samples were considered aberrant or canonical junctions, respectively. Both aberrant and canonical junctions were required to be present in an event for it to be considered differential splicing. In the case of intron-retention events, both exon-intron boundaries (5' and 3' splice sites) as well as the junction bridging the two were required to be significant.

6.1.2.2 MHC1-Bound Peptidome of ADC-Treated Cells

Figure 14:
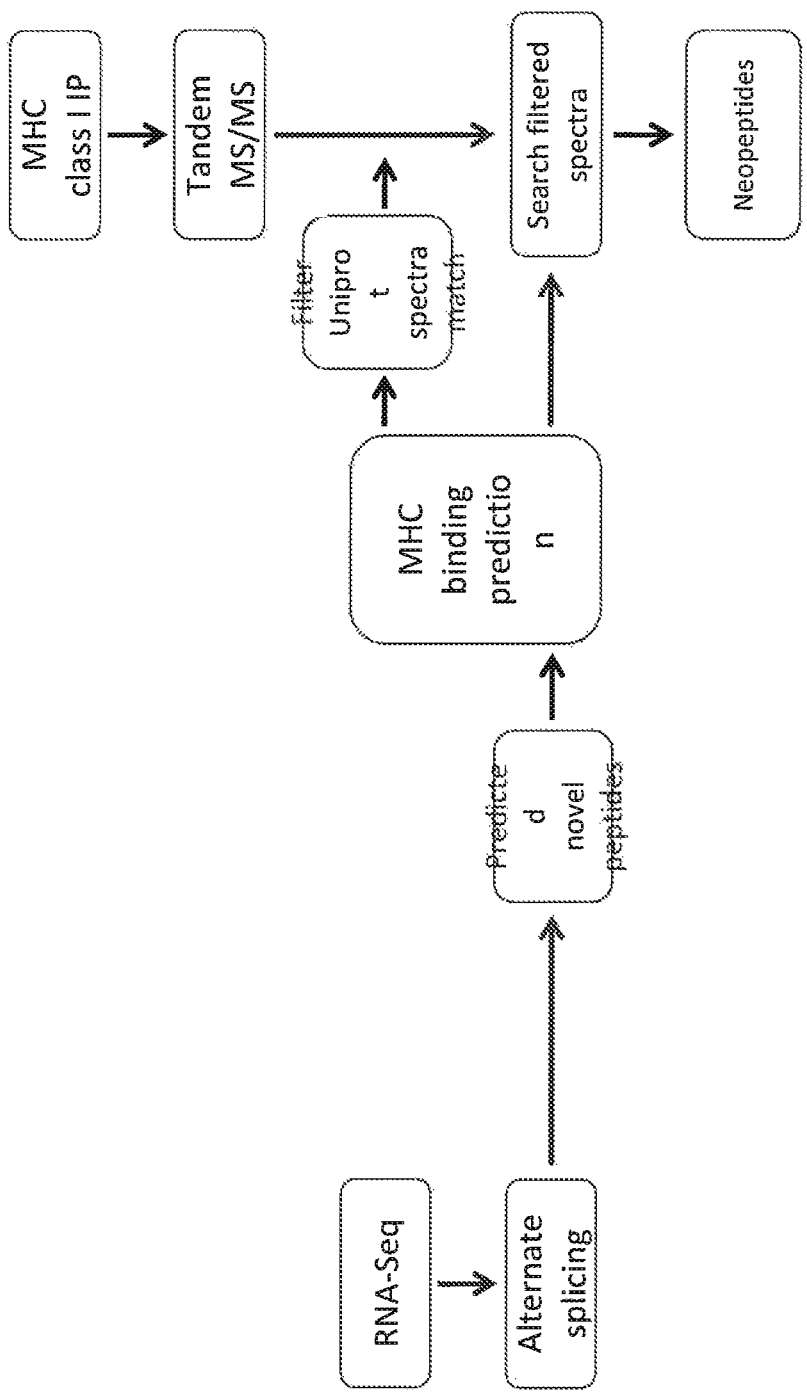
FIG. 14 shows a schematic diagram of an exemplary RNA sequencing and protein ligandome experiment.

HCC1954 and HER2 overexpressing NCI-$H_{1568}$ (ATCC) cells were plated at $1 \times 10^8$ cells on 15 $cm^2$ tissue culture plates (Corning). Cells were treated with phosphate-buffered saline or AB185-ADL1-D1 at 3 nM for 48 hours. Cells were mechanically removed from the plates and processed as per Bassani-Sternberg et al. ((2015) Mol Cell Proteomics 14(3): 658-73). Briefly, the procedure involved solubilization of the MHC-1 protein complexes from cellular membranes, enrichment of MHC-1 protein together with its bound peptides by immunoprecipitation, selective elution and purification of bound peptides, and identification and quantification of peptides by LC/MS/MS analysis. For immunoprecipitation the monoclonal antibody W6/32 purified from its hybridoma cell line HB-95TM was used. Mass spectrometric analyses were performed on a Q Exactive HF instrument. Raw files acquired in this study were processed with the MaxQuant software suite (version 1.5.7.13) for peptide and protein identification and quantification using a human protein sequence database (version 22017). In addition to this database, predicted transcript variants based on RNAseq experiments of AB185-ADL1-D1-treated HCC1954 and NCI-$H_{1568}$ cells were included. MaxQuant performs 6-frame translation and integrates obtained peptide sequences for matching with $MS^2$ spectra. Data were further manually filtered for peptide sequences unique to AB185-ADL1-D1-treated samples as well as for peptides encoded by mRNA splice junctions modulated by AB185-ADL1-D1 treatment (FIG. 14). Four neopeptides were identified by a high-stringency filtering of the RNAseq and MHC-1-bound ligandome data. These were encoded by four genes. The protein sequences of the four neopeptides, referred to herein as Neoantigen 1, Neoantigen 2, Neoantigen 3, and Neoantigen 4, were extended for the following experiments on triggering immune cell priming. The extended protein sequence incorporates both the neopeptide sequence itself in addition to flanking amino acid sequences. The extended protein sequence better facilitates the uptake of protein by dendritic cells and enables antigen presentation and T-cell priming in models with different HLA isotypes.

6.2 T-Cell Priming Experiment

6.2.1 Overview

This experiment was an in vitro reconstitution of the interactions that occur in normal human secondary lymphatic organs (e.g., tumor draining lymph nodes). In this experiment, monocytes were isolated from peripheral blood mononuclear cells (PBMC) and were induced to differentiate into dendritic cells (DC) through culturing in a cytokine cocktail. Following differentiation to mature DC, the mature DC were cultured with extended neoantigen sequences. During culturing, the mature DC take up the peptides, process them into fragments, and present them on MHC1 for priming of CD8 T-cells. The DC were then mixed with additional PBMC from the same donor and incubated for approximately 2 weeks in a cocktail of cytokines to stimulate the activation of CD8 T-cells. Following incubation, the cells were transferred to an ELISpot plate that had been re-coated with the peptides used for priming and re-stimulation of CD8 T-cells was monitored by secretion of IFNγ. The ELISpot plate was then processed and imaged, and the IFNγ spots were counted to estimate the number of active CD8 T-cells. For a schematic of an exemplary T-cell priming experiment, see FIG. 15.

6.2.2 Detailed Methods

6.2.2.1 Neoantigen-Mediated T-Cell Priming and Activation ELISpot

Figure 15:
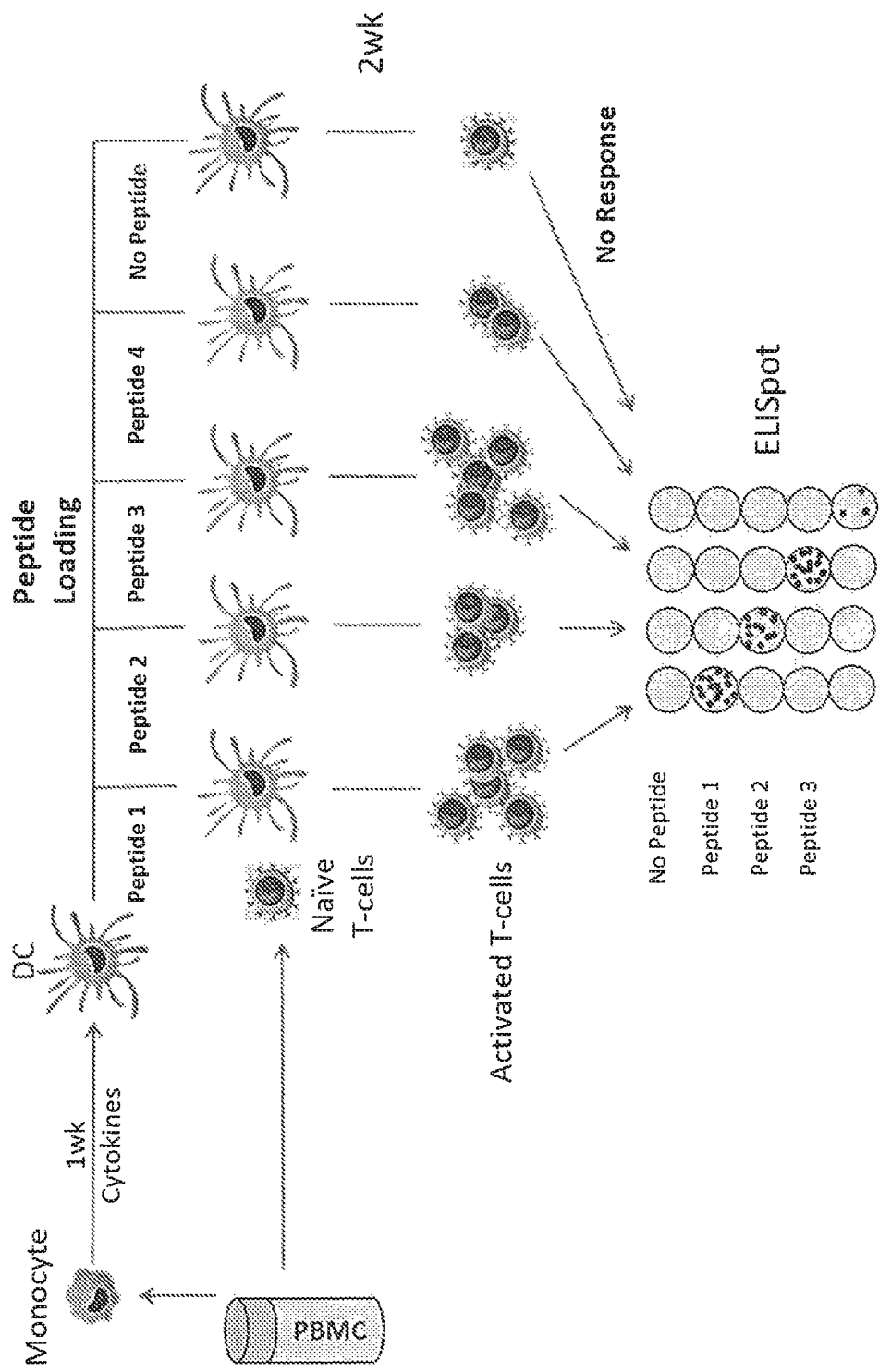
FIG. 15 shows a schematic diagram of an exemplary T-cell priming experiment.
Figure 16:
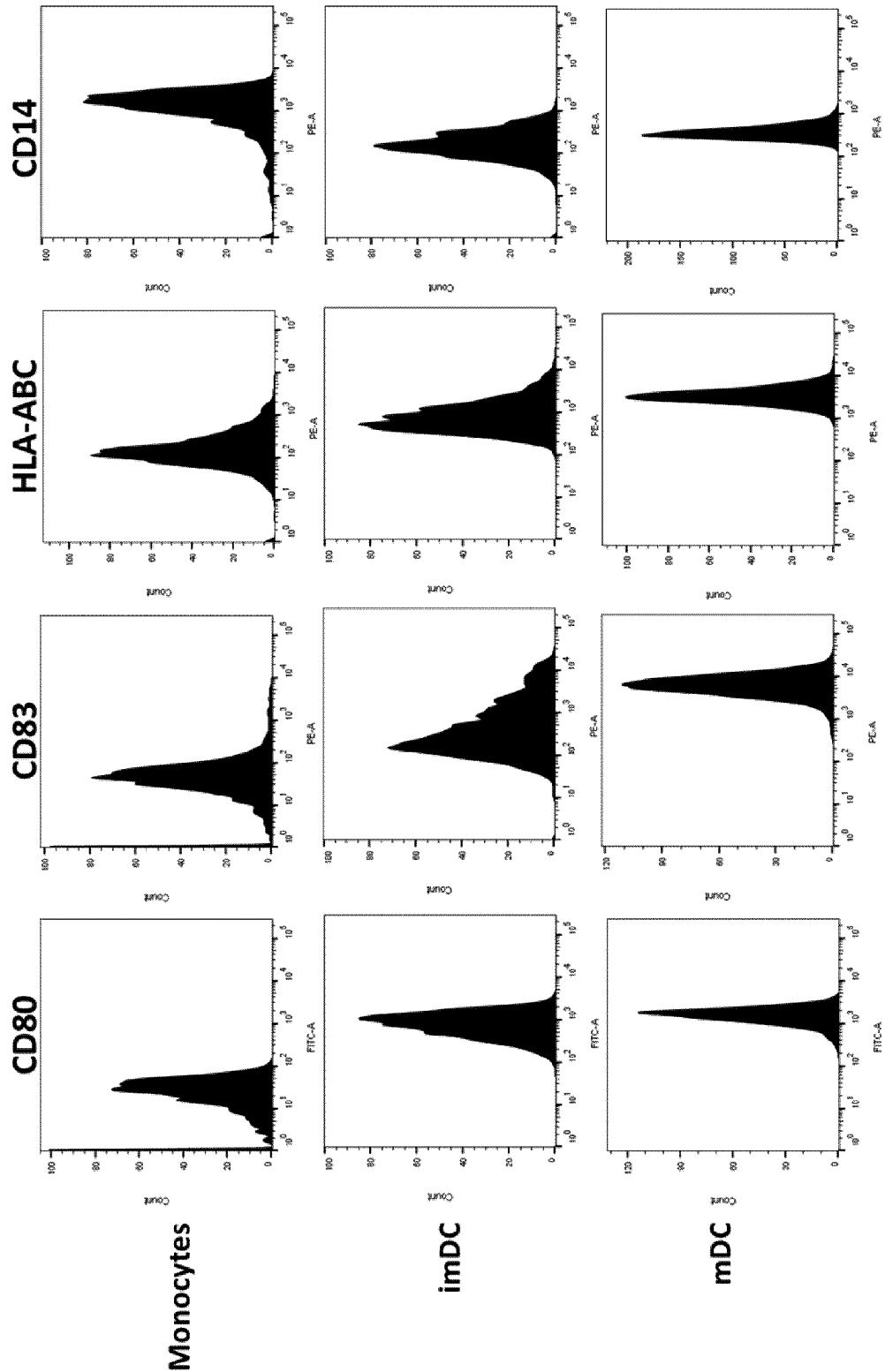
FIG. 16 shows the results of a FACS analysis. Monocytes were isolated from peripheral blood mononuclear cells (PBMC) and were induced to differentiate into dendritic cells (DC) through culturing in a cytokine cocktail. FACS was performed to validate the maturation of DC from monocytes.
Figure 17A:
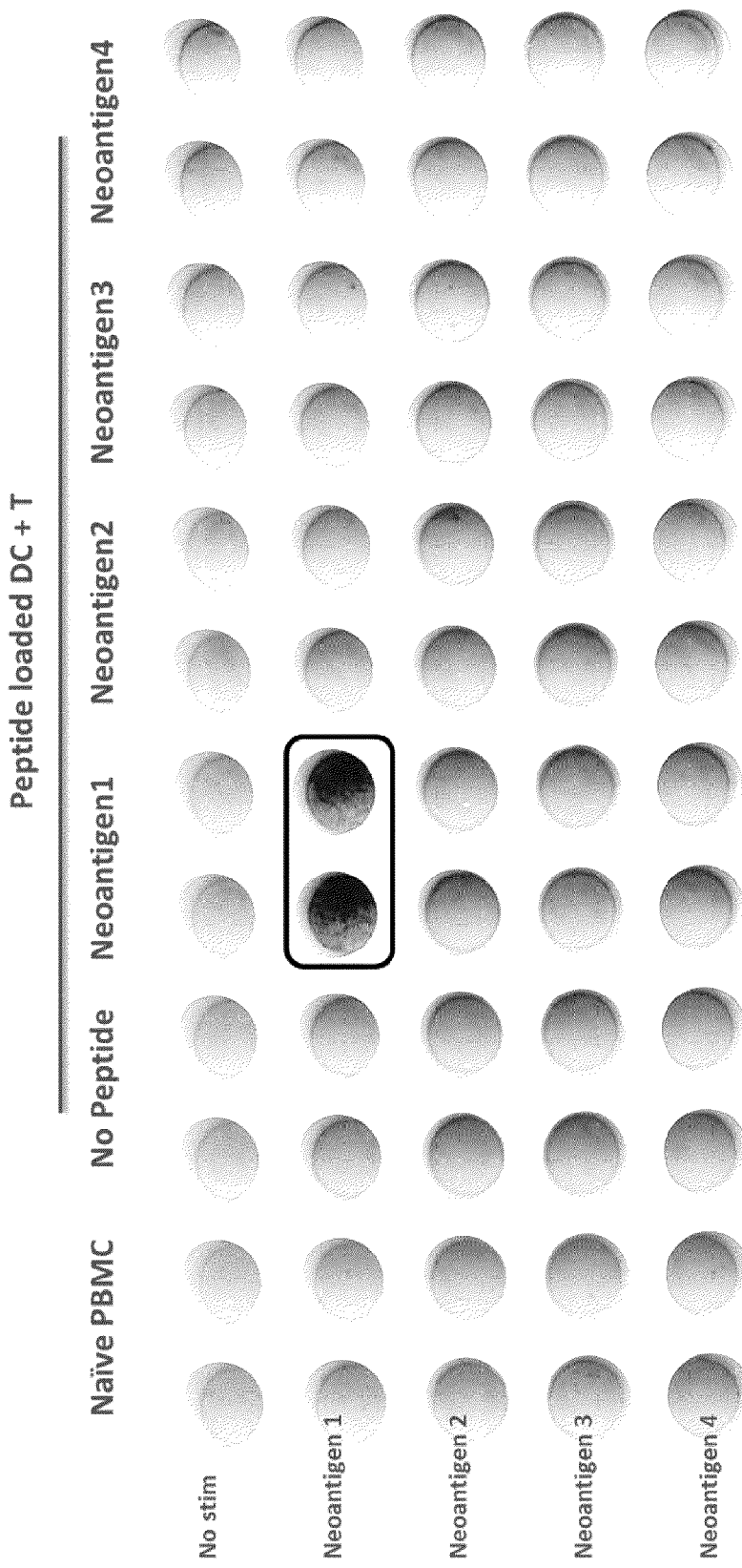
FIG. 17A-D show the results of an ELISpot assay.
Figure 17B:
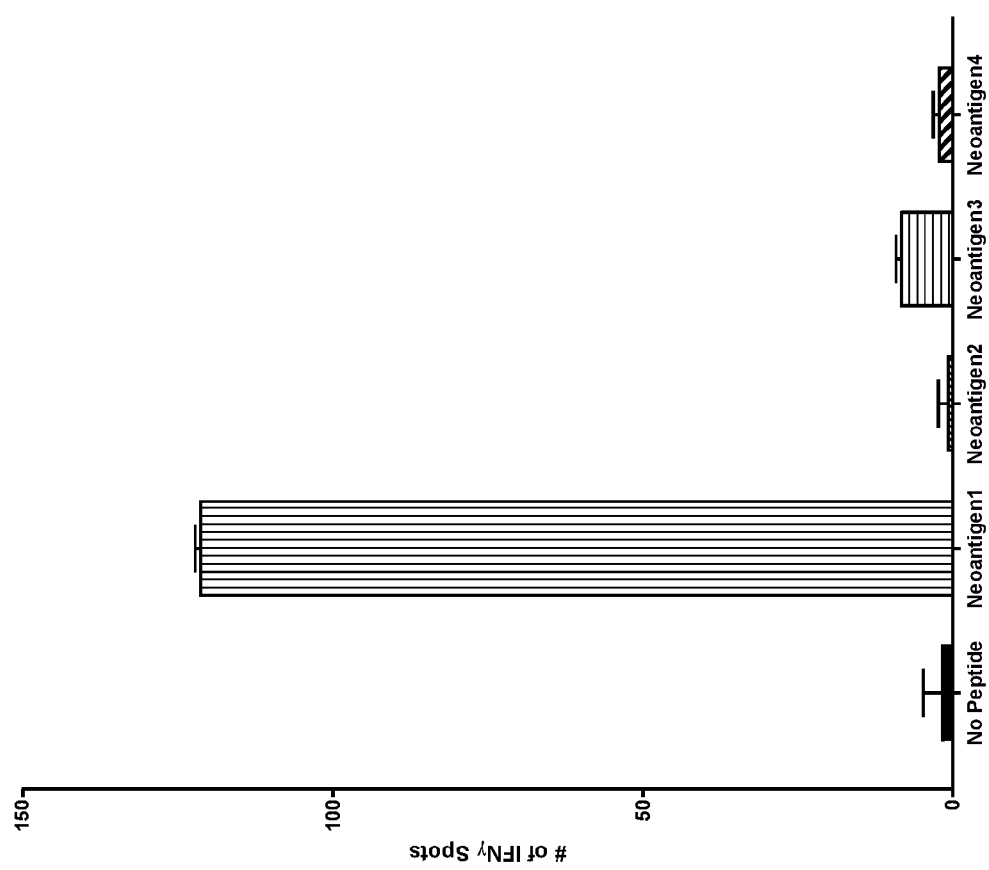
Figure 17C:
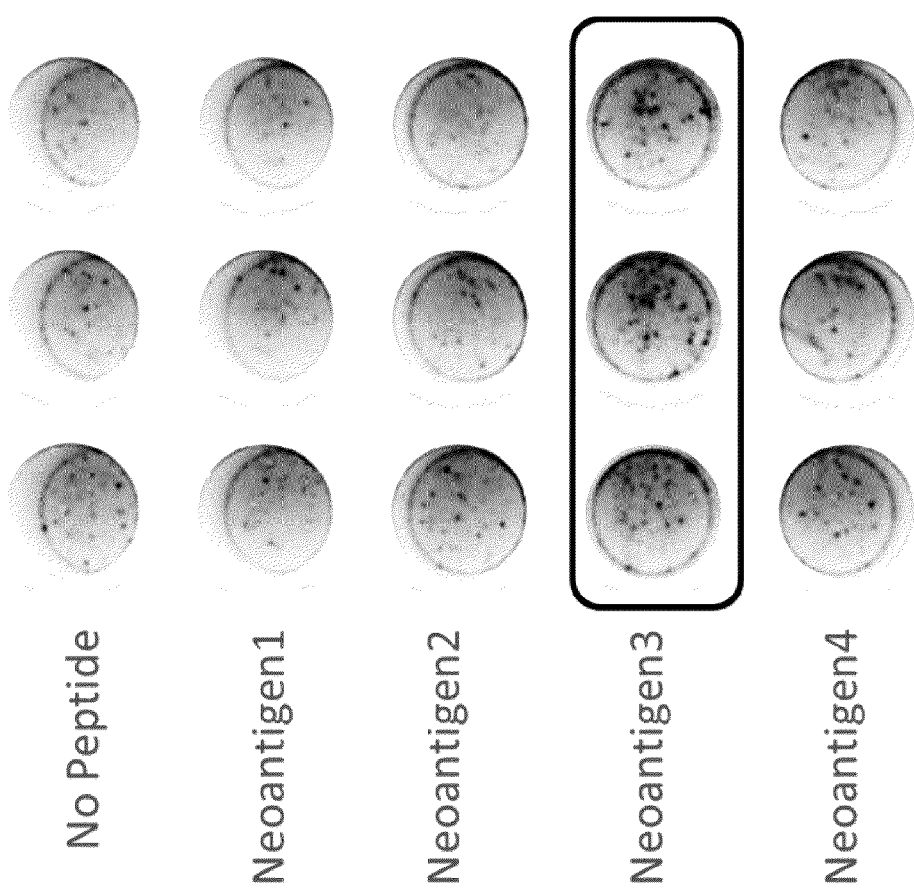
Figure 17D:
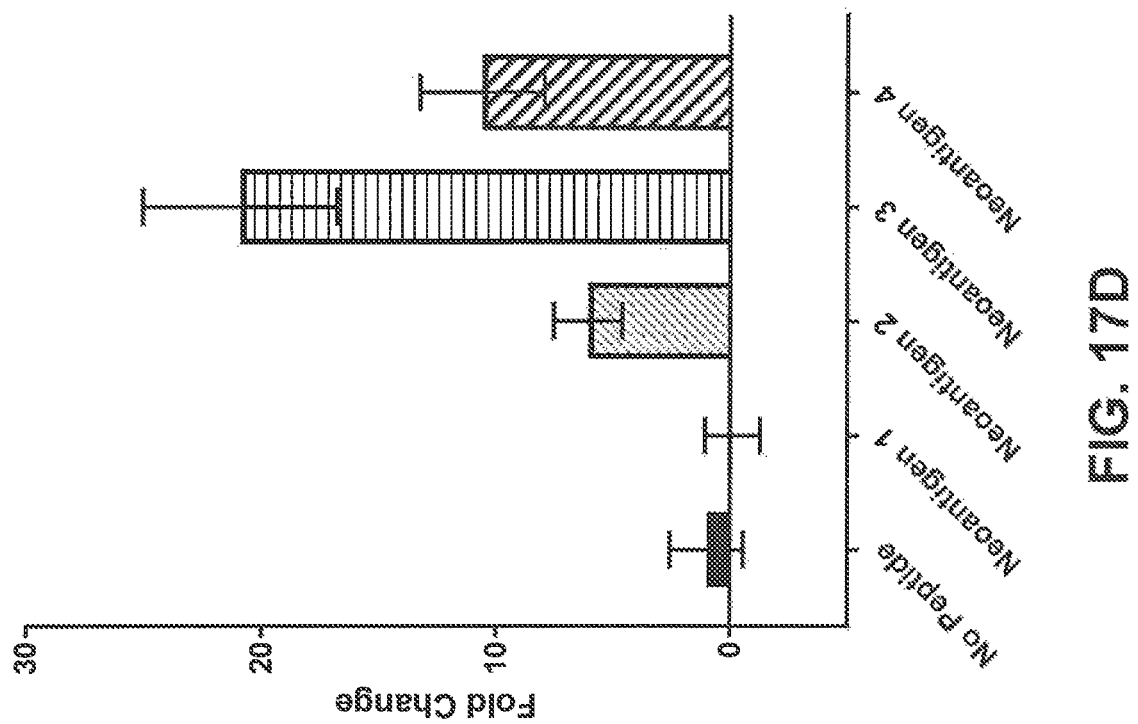

Bulk peripheral blood mononuclear cells (PBMC) were purchased from multiple vendors (StemExpress, HemaCare, Precision Medicine) and were used to generate antigen-reactive CD8+ T-cells as per Wölfl and Greenberg ((2014) Nat Prot. 9(4):950-66; FIG. 15). Briefly, frozen PBMC ($5 \times 10^7$ cells) were thawed and plated on T-75 tissue culture plastic (Corning) in RPM11640, supplemented with 5% human AB serum and 1% penicillin/streptomycin for 2-3 hours. Non-adherent cells were removed and discarded, and adherent cells were cultured in RPM11640/5% human serum, supplemented with 20 ng/mL GM-CSF and 20 ng/mL IL-4 for 5 days. On day 6, media was further supplemented with 20 ng/mL TNF-α. On day 7, mature DC were collected, counted, and loaded with neopeptides that were identified from MHC1-peptidome experiments (FIG. 16). Cells were separated and loaded with each peptide at a final concentration of 10 μg/$10^6$ cells/mL and incubated for 1 day. On day 8, DCs were treated with mitomycin C at 20 μg/mL for 30 min and washed extensively. Concurrent with the treatment of the DC, $10^8$ matched PBMC were thawed and washed with RPM11640. PBMC were then mixed with DC at a ratio of 10:1 in 10 mL RPM11640/5% human AB serum, supplemented with IL-21 at 30 ng/mL in T25 flasks. After 3 days of co-culture (day 11), an additional 10 mL of fresh media was added and supplemented with IL-7 and IL-15 at a final concentration of 5 ng/mL. Following an additional 3 days of co-culture (day 14), an additional 10 mL of fresh media, supplemented with IL-7 and IL-15 at a final concentration of 5 ng/mL, was added and the co-culture was moved to a T-75 flask. On day 17, an additional 20 mL of media, supplemented IL-7 and IL-15 at a final concentration of 10 ng/mL, was added and cells were transferred to a T-175 flask. On day 20, cells were collected, and ELISpot assay was performed as per manufacturer's instructions (R&D Systems). Wells were pre-loaded using peptide at 10 μg/mL final concentration per well, cell density at $2 \times 10^5$ cells per well, duplicate seeding, and overnight incubation. IFNγ spots were developed and read on an AID ELISpot reader as per manufacturer's instructions (FIG. 17A-D).

Exemplary data from antigen priming experiments are shown in FIG. 17A-D. Donor-derived PBMC lots were differentiated into DC and primed with neopeptides as outlined in FIG. 15. Analysis of ELISpot data shows that, in healthy donor PBMC, priming of naïve T-cells by DC presenting neopeptides can result in antigen-specific expansion and maturation of effector (CD8) T-cell populations.

These T-cell populations exhibit antigen-specific re-activation, as evidenced by IFNγ secretion only in the presence of the antigenic peptide and not in the presence of non-priming peptides.

RT-qPCR

RNA was purified from cell lines using RNeasy Mini with DNaseI treatment (Qiagen) and 1-2 μg of RNA reverse transcribed using Superscript VILO reverse transcriptase (ThermoFisher Scientific) in 20 μL according to manufacturer's instructions. RNA lysates were isolated and reverse transcribed using TaqMan Gene Expression Cells-to-CT Kit (ThermoFisher Scientific) according to manufacturer's instructions. Quantitative PCR was performed using TaqMan Gene Expression Master Mix (ThermoFisher Scientific) with transcript probes targeting neoantigen junctions duplexed with GAPDH RNA VIC-PL (ThermoFisher Scientific) and quantified using the ΔΔCt method.

Example 7

7.1 RNA Sequencing and Protein Ligandome Experiment 7.1.1 Methods

RNA sequencing and protein ligandome experiment was performed as described in Example 6 (Section 6.1). For a schematic of an exemplary RNA sequencing and MHC1 ligandome experiment, see FIG. 14.

7.1.2 Results

Twenty nine neopeptides were identified by a high-stringency filtering of the RNAseq and MHC1-bound ligandome data (Table 20). Four neopeptides were selected and extended for the following experiments on triggering immune cell priming. The four selected neopeptides are shown in bold in Table 20.

TABLE 20

| | Neopeptide | SEQ ID NO | Junction (HG19) | Gene | Event type | Observed in |
|---|---|---|---|---|---|---|
| 1 | SPTLPPRSL | 37 | chr12:49663470-49663610:+ | TUBA1C | Intron retention | H1568 |
| 2 | HPSIKRGLSSL | 38 | chr12:42729776-42781257:+ | PPHLN1 | Exon skipping | H1568 |
| 3 | LLLPHHVL | 39 | chr12:49663470-49663610:+ | TUBA1C | Intron retention | H1568 |
| 4 | RTAPGVRPPF | 40 | chr14:35182767-35183743:- | CFL2 | Intron retention | H1568 |
| 5 | RPQKSIQAL | 41 | chr10:28822963-28823162:+ | WAC | Intron retention | H1568 |
| 6 | APAPPPLPA | 42 | chr17:80009840-80011149:+ | GPS1 | Intron retention | H1568 |
| 7 | RPRPSFPVSL | 43 | chr7:55087058-55134942:+ | EGFR | Intron retention | H1568 |
| 8 | RPKHGDGFSL | 44 | chr11:57472287-57472444:- | MED19 | Intron retention | H1568 |
| 9 | GPAPGKTGL | 45 | chr7:75932393-75933118:+ | HSBP1 | Intron retention | H1568 |
| 10 | EAARKGNSL | 46 | chr1:53480715-53504588:+ | SCP2 | Exon skipping | H1568 |
| 11 | RIKEKIEEL | 47 | chr9:72897499-72912881:+ | SMC5 | Exon skipping | H1568 |
| 12 | EIKKRFRQF | 48 | chr1:28531860-28541450:- | DNAJC8 | Exon skipping | H1568 |
| 13 | HESAAMAET | 49 | chr11:102272937-102323254:- | TMEM123 | Exon skipping | HCC1954 |
| 14 | ALKLKQVGV | 50 | chr1:153610924-153617539:+ | CHTOP | Exon skipping | H1568 |
| 15 | DLKKRHITF | 51 | chr13:41323417-41331008:- | MRPS31 | Exon skipping | H1568 |

TABLE 20-continued

Neopeptides

| | Neopeptide | SEQ ID NO | Junction (HG19) | Gene | Event type | Observed in |
|---|---|---|---|---|---|---|
| 16 | DVKRNDIAM | 52 | chr1:41213277-41218822:+ | NFYC | Exon skipping | H1568 |
| 17 | IPSDHILTPA | 53 | chr6:149718900-149720239:+ | TAB2 | Exon skipping | H1568 |
| 18 | TVFSTSSLK | 54 | chr11:61197654-61213412:+ | SDHAF2 | Exon skipping | H1568 |
| 19 | ITSCLLNF | 55 | chr5:137892555-137893090:- | HSPA9 | Intron retention | H1568 |
| 20 | RASPVRGQL | 56 | chr7:75677544-75677893:+ | MDH2 | Intron retention | H1568 |
| 21 | VVRKPVIAL | 57 | chr1:36923582-36929406:- | MRPS15 | Exon skipping | H1568 |
| 22 | LLSEKKKIS | 58 | chr6:31750622-31750872:- | VARS | Intron retention | H1568 |
| 23 | APASKPRPRL | 59 | chr19:3573798-3574380:+ | HMG20B | Intron retention | H1568 |
| 24 | RYGQLSEKF | 60 | chr19:33076813-33078158:+ | PDCD5 | Exon skipping | HCC1954 |
| 25 | VYISNVSKL | 61 | chr3:53920961-53925796:- | SELK | Exon skipping | HCC1954 |
| 26 | LPTKETPSF | 62 | chr2:85133241-85133394:+ | TMSB10 | Alt 3'ss | HCC1954 |
| 27 | GEAPPPPPA | 63 | chr17:80223672-80231181:- | CSNK1D | Intron retention | HCC1954 |
| 28 | LEEISKQEI | 64 | chr17:27804724-27807385:+ | TAOK1 | Exon skipping | HCC1954 |
| 29 | IYNHITVKI | 65 | chr4:2886393-2896308:+ | ADD1 | Exon skipping | HCC1954 |

The protein sequences of the twenty nine neopeptides were extended. The extended protein sequence incorporates both the neopeptide sequence itself in addition to flanking amino acid sequences. The extended protein sequence better facilitates the uptake of protein by dendritic cells and enables antigen presentation and T-cell priming in models with different HLA isotypes. Amino acid sequences of the twenty nine extended neopeptides are set forth in Table 21.

TABLE 21

Amino acid sequences of extended neopeptides

| Gene | SEQ ID NO | Extended neopeptide amino acid sequence* |
|---|---|---|
| TUBA1C | 66 | VDLEPTVIGELTSVTQVRSQGAGTGGLSWGGSAGHSPTLPPRSLSLLLL PHHVLQMKFALALTASSSTLSNSSQARKMLPITMPEGTTPLARRSLTSC WTEFASWLTSAPVERASWESTALVGELVLGSPRCSWNVSQLIMARSPSW SSPFTRRPRFPQL |
| PPHLN1 | 67 | APPRSHPSIKRGLSSL |
| CFL2 | 68 | MVRRARWPGGRGEARKAPRTAPGVRPPF |
| WAC | 69 | WVNCLFVSGRAAAGGGGGGAVPPYLELAGPPELLLTLIRIGLGRRSGRA GGRAGTQCGGERGPGFAAFRPLRPFRRLRVCAVCVRGSALGRSVGLPRG GAAGAPFSSSPAPHPRRVLCRCLLFLFFSCHDRRGDSQPYQVPAEAGVE GLEGAGGGREGLLLERRPQKSIQALRCNTSETSTADPLKIPGLVPLALS SKV |

TABLE 21-continued

Amino acid sequences of extended neopeptides

| Gene | SEQ ID NO | Extended neopeptide amino acid sequence* |
|---|---|---|
| GPS1 | 70 | MPLPVQVFNLQVTSRGRPGPPRPRAPRHWGRAEVEQGRGACARSRSGTL RAGPPRAARVGGCRAEGASPPWLRAAIGGRRAAPAPPPLPAAHGRGSRP PRR |
| EGFR | 71 | QPAQPRTGAPARRPRPRPSFPVSLRSAAPPTGTAGGTGRFVLRPGESGA GGGGDAWDTGLQARRGTAAGTSGAPNRSQLSSLTFPAQLRRIGVSGRKP GAGGRLGPGSRTCAPRCLPRARRGPGAHPRGGRCPPAETALFREAEEGT QKYSLPSDPAGQAAF |
| MED19 | 72 | FRLHTGPVSPVGGRRQMGRPKHGDGFSLQVCSFIMEQNG |
| HSBP1 | 73 | GVVEITGEPPCSCRGEEEASRAGRAGGVRLKRGSRGPGELNVGPAPGKT GLLIPLLRNWECGSLLRALSAL |
| SCP2 | 74 | KMGFPEAARKGNSL |
| SMC5 | 75 | LEARIKEKIEELQQALI |
| DNAJC8 | 76 | EIKKRFRQFKQAVYKQ |
| TMEM123 | 77 | AHESAAMAETLQHVPS |
| CHTOP | 78 | NRPSVQAALKLKQVGV |
| MRPS31 | 79 | KTDDLKKRHITFTLGCGIC |
| NFYC | 80 | MKLDEDVKRNDIAMAI |
| TAB2 | 81 | NSISQIPSDHILTPALFITEMTILDL |
| SDHAF2 | 82 | TVFSTSSLKLNQPQKYLKMKSWPC |
| HSPA9 | 83 | AEEDRRKKVITSCLLNFNLSKAQS |
| MDH2 | 84 | RSFSTSAQVGQTRGGLQAEAPRPGPRASPVRGQL |
| MRPS15 | 85 | RGYVVRKPVIALSVKI |
| VARS | 86 | VDMDFGTGGQGAGPVGRGKDWSCTLAVHLLSEKKKISFSQIDRAWGGSQ GTVLDKWGPGVVSELHPSAKEVSVGRNSVESLMTWAS |
| HMG20B | 87 | EKGSHEEEVRVPALSWGRPRAPAPASKPRPRLDLNCLWLRPQPIFLWKL RPRPVPAATPLTGPLPL |
| PDCD5 | 88 | RYGQLSEKFNRRKVMDS |
| SELK | 89 | MVYISNVSKLCFSKM |
| TMSB10 | 90 | NTLPTKETPSFLLNPHTSWVPRPHREAPRLRVGVAAPLQRPLPALHSH |
| CSNK1D | 91 | FGDIYLGEAPPPPPAARRPGPCGCQDQARSRKEVVAPAGSPRKSRHRRI VARTQRPLG |
| TAOK1 | 92 | GSASDLLEEISKQEISF |
| ADD1 | 93 | QLIYNHITVKINLQGD |

*Underline indicates amino acids derived from the canonical transcript open reading frame (i.e., the canonical peptide sequence).

7.2 T-Cell Priming Experiment 7.2.1 Overview

For a schematic of an exemplary T-cell priming experiment, see FIG. 15.

7.2.2 Materials

Materials used for T-cell priming:
RPMI 1640 Medium (Thermo Fisher Scientific, Cat. No. $A_{10491}$-01)
Penicillin/Streptomycin (100×, Thermo Fisher Scientific, Cat. No. 15140122)
Human Serum Type AB (Sigma, Cat. No. $H_{3667}$-100ML)
Recombinant Human IL-4 (Peprotech, Cat. No. 200-04)
Recombinant Human GM-CSF (Peprotech, Cat. No. 300-03)
Recombinant Human TNF-α (Peprotech, Cat. No. 300-01A)
Human IL-7 (Peprotech, Cat. No. 200-07)
Human IL-15 (Peprotech, Cat. No. 200-15)
Human IL-21 (Peprotech, Cat. No. 200-21)
Peptides (New England Peptide—95% purity, dissolved in DMSO to a 1000×stock at a concentration of 10 μg/μL)
ELISpot kit for Human IFN-γ (R&D Systems, Cat. No. EL285)

7.2.3 Methods

7.2.3.1 Generation and Maturation of Human Monocyte-Derived Dendritic Cells and Loading of Neopeptides Frozen or fresh PBMC were thawed and washed in pre-warmed RPMI media once, and an aliquot of non-adherent cells was reserved for baseline TCR sequencing. PBMC were resuspended in 10 mL of dendritic cells (DC) medium (RPM11640, supplemented with 5% human AB serum and 1% penicillin/streptomycin) at $5 \times 10^6$ cells per mL, for a total of 50 million cells. Cells were transferred to T-75 tissue culture plastic and incubated at 37° C., 5% $CO_2$ for 2-3 hours. After gentle shaking, non-adherent cells were removed and discarded, and adherent (monocyte-enriched) cells were washed three times with pre-warmed DC medium. 10 mL of DC medium supplemented with a final concentration of 20 ng/mL GM-CSF and 20 ng/mL IL-4 was added to adherent cells. Adherent cells were incubated at 37° C., 5% $CO_2$, at 100% humidity for 5 days. On day 6, recombinant TNF-α was added to a final concentration of 20 ng/mL for another 48 hours. On day 7, DC were collected and counted, then loaded with neopeptides (each at 10 µg/$1 \times 10^6$ cells/mL) or no neopeptide control. On day 8, cells were harvested as mature DC. Mature DC were treated with mitomycin C at a final concentration of 20 µg/mL for 30 min at 37° C. followed by extensive washing before co-incubation with T-cells for priming.

7.2.3.2 Start of Co-Culture with Autologous T-Cells

On day 0, frozen or fresh were thawed and washed in pre-warmed media once. PBMC were then resuspended and mixed with DC at a ratio of 10:1 ($10 \times 10^6$:$1 \times 10^6$ cells) in 10 mL RPMI1640/5% human AB serum, supplemented with IL-21 at 30 ng/mL in T25 flasks. After 3 days of co-culture (day 3), an additional 10 mL of fresh media was added and supplemented with IL-7 and IL-15 at a final concentration of 5 ng/mL. Following an additional 3 days of co-culture (day 6), an additional 10 mL of fresh media, supplemented with IL-7 and IL-15 at a final concentration of 5 ng/mL, was added and the co-culture was moved to a T-75 flask. On day 9, an additional 20 mL of media, supplemented IL-7 and IL-15 at a final concentration of 10 ng/mL, was added and cells were transferred to a T-175 flask. On days 11-12, cells were collected, ELISpot assay was performed as per manufacturer's instructions (R&D Systems), and TCR sequencing was performed ($1 \times 10^6$ cells). Wells were pre-loaded using peptide at 10 µg/mL final concentration per well, cell density at $2 \times 10^5$ cells per well, duplicate seeding, and overnight incubation. IFNγ spots were developed and read on an AID ELISpot reader as per manufacturer's instructions.

7.2.4 Results

Exemplary data from antigen priming experiments are provided in Table 22.

TABLE 22

| | T-cell priming data | | | |
|---|---|---|---|---|
| Donor | ELISpot response | Gene | SEQ ID NO | HLA (predicted binding) |
| 1 | +++ | DNAJC8 | 76 | A*31:01/B*40:13 |
| 1 | + | TMEM123 | 77 | A*02:01 |
| 2 | +++ | TMEM123 | 77 | A*02:01 |

TABLE 22-continued

| | T-cell priming data | | | |
|---|---|---|---|---|
| Donor | ELISpot response | Gene | SEQ ID NO | HLA (predicted binding) |
| 2 | + | SCP2 | 74 | B*39:06 |
| 6 | + | DNAJC8 | 76 | C*07:01/B*27 |
| 7 | +++ | DNAJC8 | 76 | C*07:02/C*06:02 |
| 8 | +++ | DNAJC8 | 76 | C*07:01 |
| 8 | + | SMC5 | 75 | C*07:01/B*08:02 |
| 8 | +++ | SCP2 | 74 | C*03:03 |

Donor-derived PBMC lots were differentiated into DC and primed with neopeptides as outlined in FIG. 15. Analysis of ELISpot data shows that, in healthy donor PBMC, priming of naïve T-cells by DC presenting neopeptides can result in antigen-specific expansion and maturation of effector (CD8) T-cell populations. These T-cell populations exhibit antigen-specific re-activation, as evidenced by IFNγ secretion only in the presence of the antigenic peptide and not in the presence of non-priming peptides. The data also suggest that response to neopeptides cannot necessarily be predicted based on HLA.

Example 8

8.1 Identification of Neopeptides

8.1.1 Overview

To identify neopeptides resulting from splicing modulation, peptides 8 to 11 amino acids in length and predicted to bind to MHC class I from the canonical and splicing-modulated proteome were matched separately against tandem mass spectra using a standard target-decoy approach. First, alternatively-spliced mRNA transcripts were translated and compared against a reference proteome. Next, spectra that did not match the reference proteome were searched for matching novel peptides. For a schematic diagram of an exemplary process for identifying novel peptides resulting from splicing modulation, see FIG. 14.

8.1.2 Methods

8.1.2.1 Creating A Database of Potential Neopeptides

To generate a database of potential neopeptides, junction-spanning or intron-containing peptides not found in a reference proteome were identified (see Li et al. (2011) Mol. Cell Proteomics 10(5):M110.006536). Peptides derived from the reference proteome were selected from manually reviewed protein sequences and downloaded. In addition, the proteins were filtered for junctions that are found in normal tissues. As an alternative approach, complete proteins may be translated from splicing events, searched for junction-spanning or intron-containing peptides, and then matched by BLAST against the reference proteome.

To avoid unnecessary statistical tests, only peptides predicted as likely to bind to MHC were used. Protein sequences (both from the reference proteome and from predicted translation of exon-skipped or intron-retained transcripts) were evaluated for high affinity binding to MHC1 alleles using NetMHCPan and/or MHCnuggets software. For both software packages, hits with with strong or weak binding were chosen (i) by raw affinity binding prediction strength (500 nM threshold for weak binding), or (ii) by selecting a large number of random real peptides and identifying the distribution of predicted binding strengths for the peptides. The predicted binding strength for any novel peptides were then matched against this distribution. The thresholds for strong and weak binding measured by the latter method (method (ii)) were predicted binding strengths within the top 0.5% or the top 2.0% of the random real peptides, respectively (see Nielsen and Andreatta (2016) Genome Med. 8(1):33). Currently, MHC prediction is restricted to peptide sequences 8 to 11 amino acids in length and contained in the Immune Epitope Database (IEDB).

8.1.2.2 Identifying Splicing Modulation-Derived Transcripts by RNAseq and RiboSeq Several neopeptides are derived from larger peptide domains (e.g., TUBA1C), while peptide fragments from the remainder of the translated region may risk going undetected. This may be a consequence of either enhanced degradation of the undetected regions, MHC1 binding affinity, or technical challenges associated with detection by mass spectrometry (MS). Generally, RNAseq analysis will overestimate the number of predicted neopeptides (since not all alternatively-spliced transcripts will be translated), while the MHC1-ligandome will underestimate the number of predicted neopeptides.

To establish a list of neopeptides, available splicing modulation-derived variant splice junctions with bound ribosomes were identifed, as a marker of translation to proteins (Andreev et al. (2017) Nucleic Acids Res. 45(2): 513-26). RiboSeq or ribosomal profiling allowed for detection of mRNA sequences (and variant domains) that were undergoing active translation, as evidenced by the presence of ribosomes bound to the transcript, as well as specific exon junction domains.

Example 9

9.1 In Vitro Analysis of Exemplary Anti-HER2 ADCs

9.1.1 Methods

HCC1954, NCI-N87, or MCF7 cells (ATCC) were plated in phenol-red free RPMI+10% FBS (ATCC) or EMEM+ 10% FBS+insulin (0.01 mg/mL) (for MCF7) at $2.5 \times 10^3$ cells per well at 90 μL per well. Cells (n=3 wells per condition) were treated with conjugates in a 3-fold dilution dose-response. After 24 hours, cells were lysed with 50 μL of CL buffer (IgePal CA-630, 5M NaCl, 1M Tris HCl 1M pH 7.4 in water) containing 25 μL/mL of RNAsin (Promega) and incubated for 45 min at RT on a rocker. Resulting mixture (1 μL) was used to assess splicing modulation in a Taqman Fast Virus 1-Step MasterMix (Applied Biosystems) reverse transcription PCR reaction with the following Taqman primers according to the manufacturer's recommendations: SLC25A$_{19}$ (Invitrogen, Hs00222265_m1); FBXW5 (IDT, forward primer: CACACCAGATCGGCATCAA (SEQ ID NO:37), reverse primer: CGATGATGTGTCCGTGTATGT (SEQ ID NO:38), probe: ATCCTGCCACACCAGATGAC-CAC (SEQ ID NO:39), dye: FAM, quencher: ZEN/Iowa Black FQ); TAOK1 (IDT, forward primer: CTGCTTCG-GATTTACTAGAAGAGATA (SEQ ID NO:40), reverse primer: GCGTTCCCACAAAGGAATTG (SEQ ID NO:41), probe: TGCTGACTTTGGCTCTGCTTCCAT (SEQ ID NO:42), dye: FAM, quencher: ZEN/Iowa Black FQ); RPLPO (Invitrogen, Hs99999902_m1).

9.2 In Vivo Efficacy and Pharmacodyamics (PD) of Exemplary Anti-HER2 ADCs

9.2.1 Methods—In Vivo Efficacy in NCI-N87 Xenograft Model

CB17-SCID mice (Charles River Laboratories) were kept in accordance with federal, state, city, & AAALAC-accreditation policies on animal research in the city of Cambridge, Massachusetts. NCI-N87 human gastric carcinoma cell line was purchased from American Type Culture Collection (ATCC No. CRL-5822). Passage 14 cells were used for tumor experiments. Cells were last tested for murine pathogens in September 2016 and *mycoplasma* in December 2018.

Single cell suspension of 5 million cells per 0.1 mL (50% ATCC-modification-RPMI-1640-medium, Cat. No. A$_{10491}$-01 (Thermo-Fisher Scientific); and 50% Corning Matrigel, Cat No. 356254 (VWR Scientific)) was injected subcutaneously on the right lateral flank with a syringe with a 25Ga needle. Mice were randomized on day 0 at a mean tumor volume of 180-183 mm$^3$, n=8 per group for efficacy and n=4 per group for pharmacodynamics (PD). On day 1, test articles were administered (10 mg/kg) at a volume of 5 mL/kg intravenously every 7 days for 2 cycles for efficacy; a single course of treatment was used for PD assessment. Animals in the PD cohorts were euthanized at 24, 48, 72, and/or 96 hours post-dosing of a single dose, depending on the test article. Tumor volume and body weight were measured one or two times weekly until the termination (day 61) of the study. Tumor volume was calculated using the formula length×width$^2$/2. During the study, mice that reached endpoint (tumor size 20 mm$^3$ in any direction or tumor volume starting body weight×100), or had a tumor ulceration or eye infection, were removed.

Compounds were formulated in biological safety cabinets. Test article vehicle was phosphate buffered saline pH 7.4 (Cat No. A$_{10010}$-049 (Thermo-Fisher Scientific)). Groups were as set forth in Table 23.

Anti-tumor activity was calculated as follows:

% T/C formula=treated/control*100

% TGI formula=(vehicle average$_{day\ X}$−treated average$_{day\ X}$)/vehicle average$_{day\ X}$100, wherein day X is day 22.

9.2.2 Methods—In Vivo PD (RT-qPCR)

RNA was purified from tumor samples using MagMAX-96 for Microarrays kit and MagMAX Express-96 Deep Well Magnetic Particle Processor (ThermoFisher Scientific). Tumor samples (size 50-100 mg) were collected in RNAlater buffer and kept at −80° C. until RNA isolation. Tissue homogenization was performed by adding 2-3 ceramic beads and 1 mL of Tri-reagent into a tube containing tumors, followed by disruption on an Omni Bead Ruptor 24 instrument (Omni International). RNA isolation was done according to the manufacturer's instructions.

RNA lysates were isolated and reverse transcribed using TaqMan Fast Virus 1-Step Master Mixt (ThermoFisher Scientific) according to the manufacturer's instructions.

Quantitative PCR from cDNA was performed using TaqMan Gene Expression Master Mix (ThermoFisher Scientific) with transcript probes targeting FBXW5 or TAOK1 junctions duplexed with RPLPO RNA VIC-PL (ThermoFisher Scientific) and quantified using the ΔΔCt method.

TABLE 23

Groups

| Test Articles (efficacy) | Test Articles (PD) |
|---|---|
| Vehicle (PBS) | Vehicle (PBS) |
| TDM1 | TDM1 |
| trastuzumab (AB185) | trastuzumab (AB185) |
| AB185-ADL5-D2 | AB185-ADL5-D2 |
| AB185-ADL1-D4 | AB185-ADL1-D4 |
| AB185-ADL5-D15 | AB185-ADL5-D15 |
| AB185-ADL14-D1 | AB185-ADL14-D1 |

9.3 Results

In Vitro Analysis:

Exemplary anti-HER2 ADCs were measured for antiproliferative activity in two HER2-positive cell lines of different lineage (HCC1954 breast cancer and N87 gastric cancer) and a HER2-negative cell line (MCF7). The efficiency of growth inhibition was measured (GI50 potency), as well as the depth of response (R min compared to control). Alternative splicing in a representative house keeping gene $SLC25A_{19}$ was measured by qPCR after treatment of the ADCs on the specified cell lines. G150 and depth of splicing response were measured. The results of the in vitro analysis are shown in Table 25.

In general, the tested anti-HER2 ADCs showed favorable potency on the antigen positive cell lines and minimal response for viability and splicing in the antigen negative cell line. The ADCs differed in depth of response in cell killing and completeness of alternative junction splicing of $SLC25A_{19}$. The ADCs fell into one of four categories on each of the antigen positive cell lines: 1) high depth of response/lethality and high splicing response; 2) high depth of response/lethality and low splicing response; 3) low depth of response/lethality and high splicing response; or 4) low cell lethality and low splicing response. Several ADCs showed favorable, category 3 behavior on the N87 gastric cancer cell line. AB185-ADL13-D4 was consistently lethal and showed strong depth of splicing response in both HCC1954 and N87 cells. This consistent antigen specific lethality is generally desirable for ADCs and the water soluble linker would allow for even higher drug loading with good conjugate specifications. Switching the linker to ADL23 (EVC tripeptide) surprisingly changed the profile in both cell lines. AB185-ADL1-D12 was also unique in that it is highly lethal on HCC1954, but the cellular potency of the payload is consistently low on a number of solid and heme tumor lines. D12 is also the only payload in this series with a low efflux ratio. Thus, ADCs releasing this payload may be active against multiple drug resistant cancers that express a target antigen.

Figure 18:
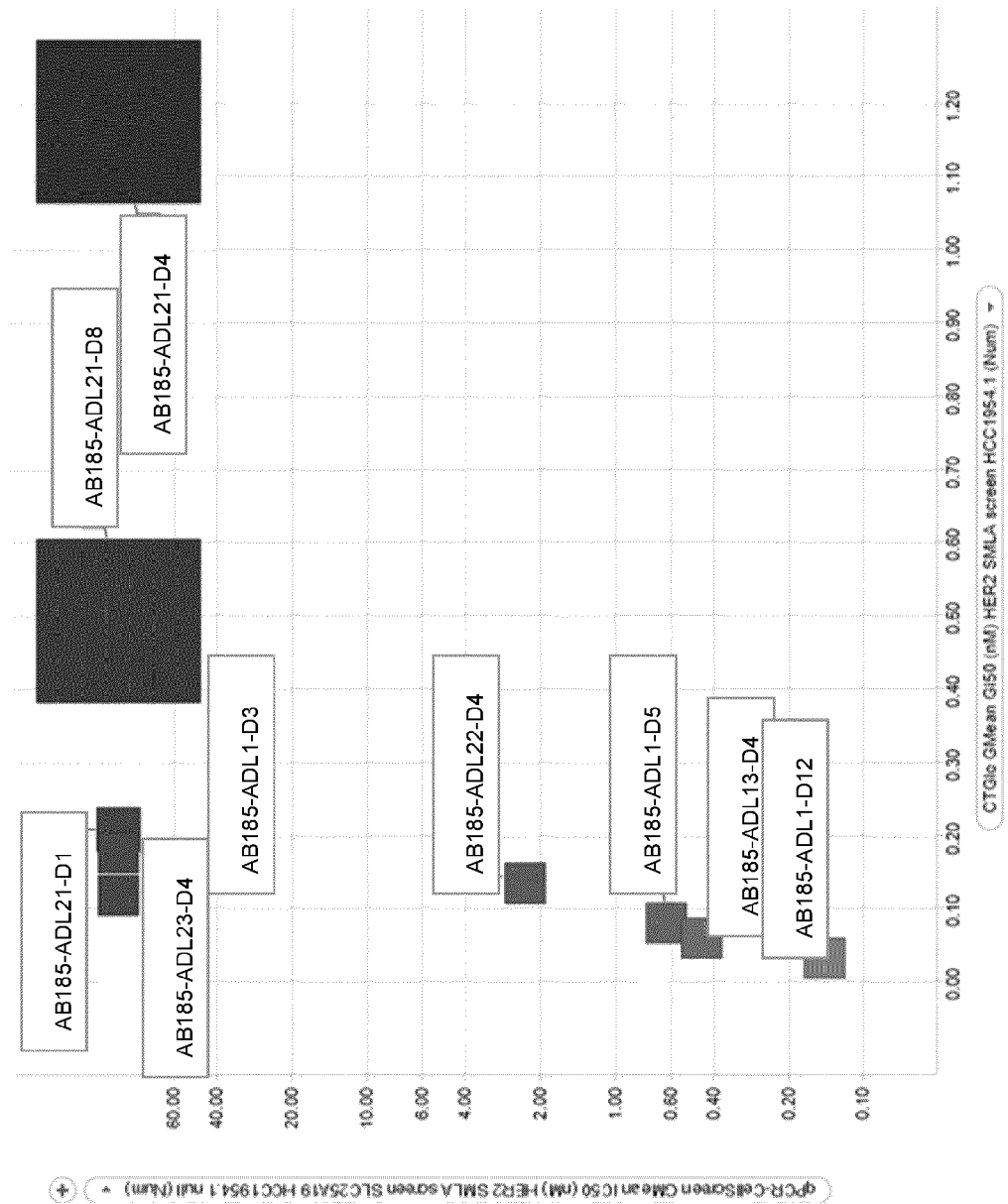
FIG. 18 shows a plot comparing splicing potency (IC50 qPCR) against cellular potency (G150 CTG) for exemplary anti-HER2 ADCs in HCC1954 breast cancer cells. Values shown are sized by cell lethality and shaded by depth of alternative splicing response.

When splicing potency (IC50 qPCR) is compared against cellular potency (G150 CTG) in HCC1954 breast cancer cells, the glucuronide linker and the D12 payload showed favorable properties. The $C_6/C_7$ carbamate switch (D8) payload and the dibasic payload (D5) showed cellular potency but did not demonstrate the most efficient alternative splicing. Switching from a dipeptide to a tripeptide linker with the D4 or the D1 payload reduced alternative splicing efficiency yet cellular activity remained high. See FIG. 18 (sized by cell lethality, shaded by depth of alternative splicing response).

Figure 19:
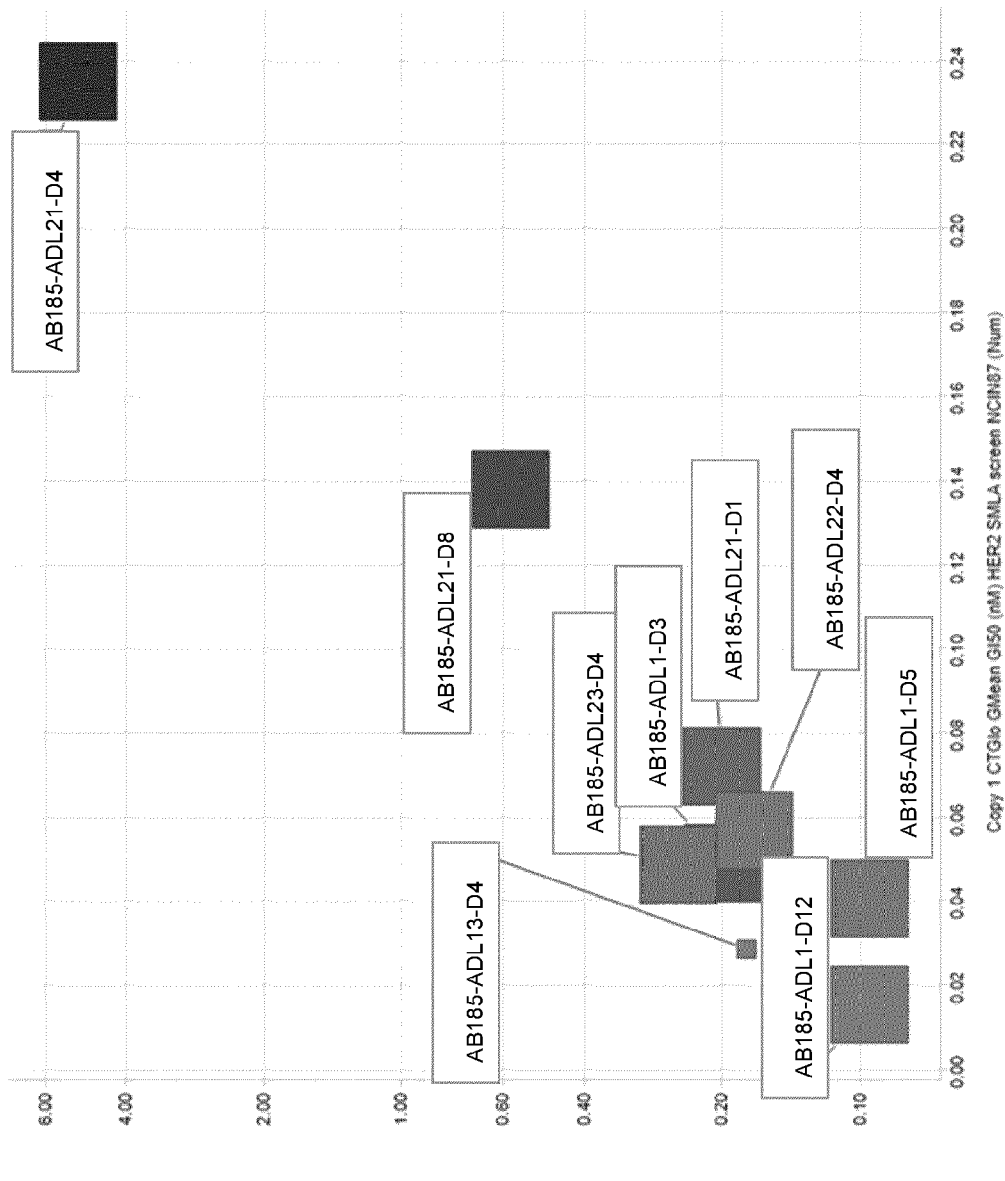
FIG. 19 shows a plot comparing splicing potency (IC50 qPCR) against cellular potency (G150 CTG) for exemplary anti-HER2 ADCs in N87 gastric cancer cells. Values shown are sized by cell lethality and shaded by depth of alternative splicing response.

When splicing potency (IC50 qPCR) is compared against cellular potency (GI50 CTG) in N87 gastric cancer cells, the glucuronide linker (with D4) and the D12 payload showed favorable properties, as in HCC1954. Overall, all ADCs showed minimal splicing and potency on the HER2-negative cell line MCF7. Despite the relatively low cellular potency of the D12 payload, the activity of anti-HER2 ADCs with this payload was high and the payload showed a low efflux ratio. These properties could potentially translate to better efficacy in a multiple drug resistant cancer setting. See FIG. 19 (sized by cell lethality, shaded by depth of alternative splicing response).

Figure 20:
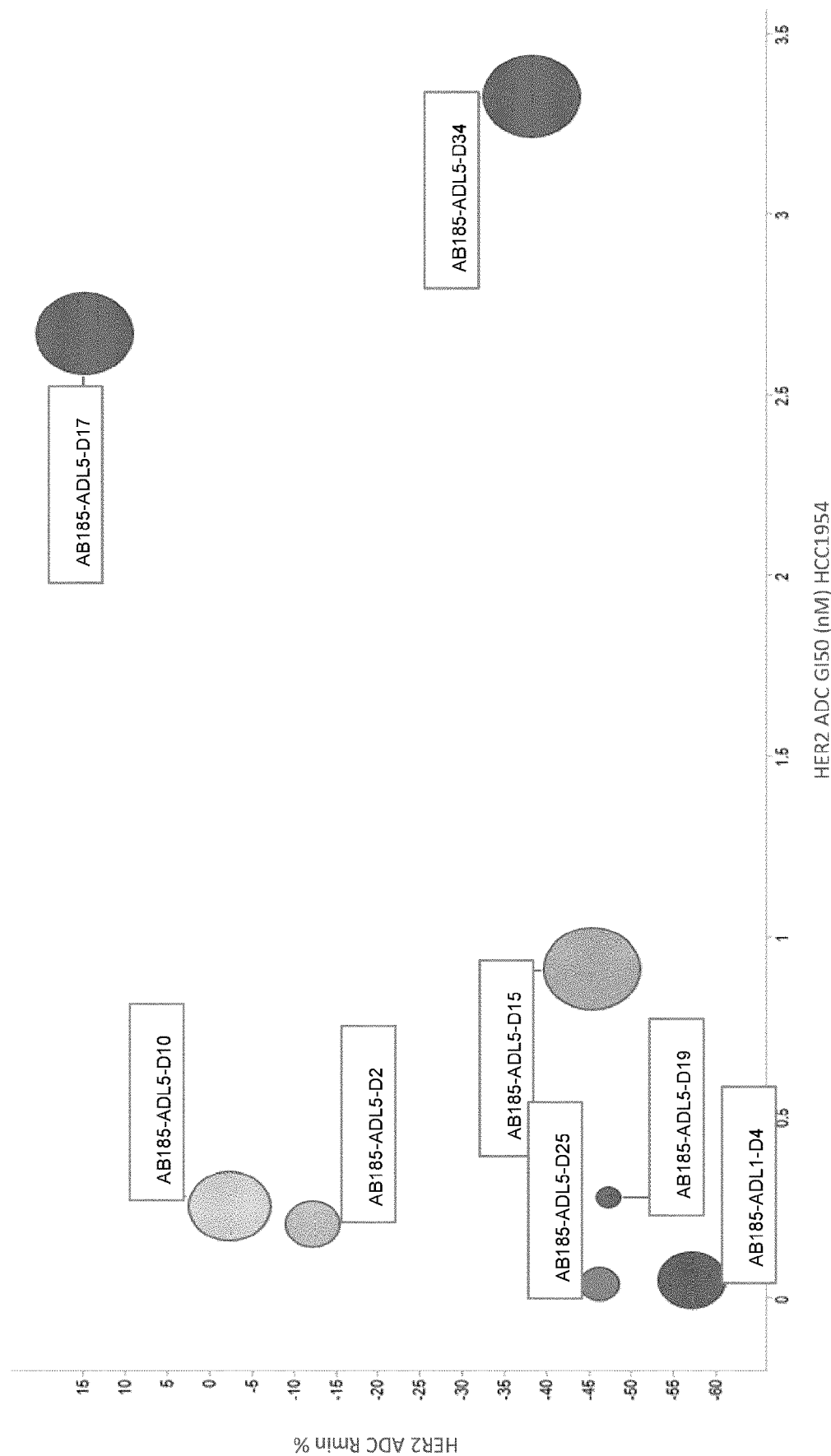
FIG. 20 shows a plot comparing potency and lethality of exemplary anti-HER2 ADCs (in HCC1954 breast cancer cells) against stability and permeability of corresponding payloads. Values shown are sized by payload stability and shaded by payload permeability.

In vitro analysis was performed on additional anti-HER2 ADCs. A comparison between anti-HER2 ADCs and corresponding payloads is shown in Table 26. When potency and lethality of anti-HER2 ADCs is compared against stability and permeability of corresponding payloads (FIG. 20), AB185-ADL5-D15 demonstrated a favorable balance of potency, lethality, chemical stability, and catabolite permeability (e.g., for putative bystander killing). As described below, AB185-ADL5-D15 was also active in vivo and demonstrated potent anti-tumor activity in a NCI-N87 xenograft model.

In Vivo Efficacy:

The human HER2-expressing NCI-N87 gastric cancer cell line and its xenograft model was generated by inoculating NCI-N87 cells into SCID mice to evaluate anti-tumor activity of exemplary anti-HER2 ADCs. Trastuzumab and TDM1 were used as comparators.

Figure 21:
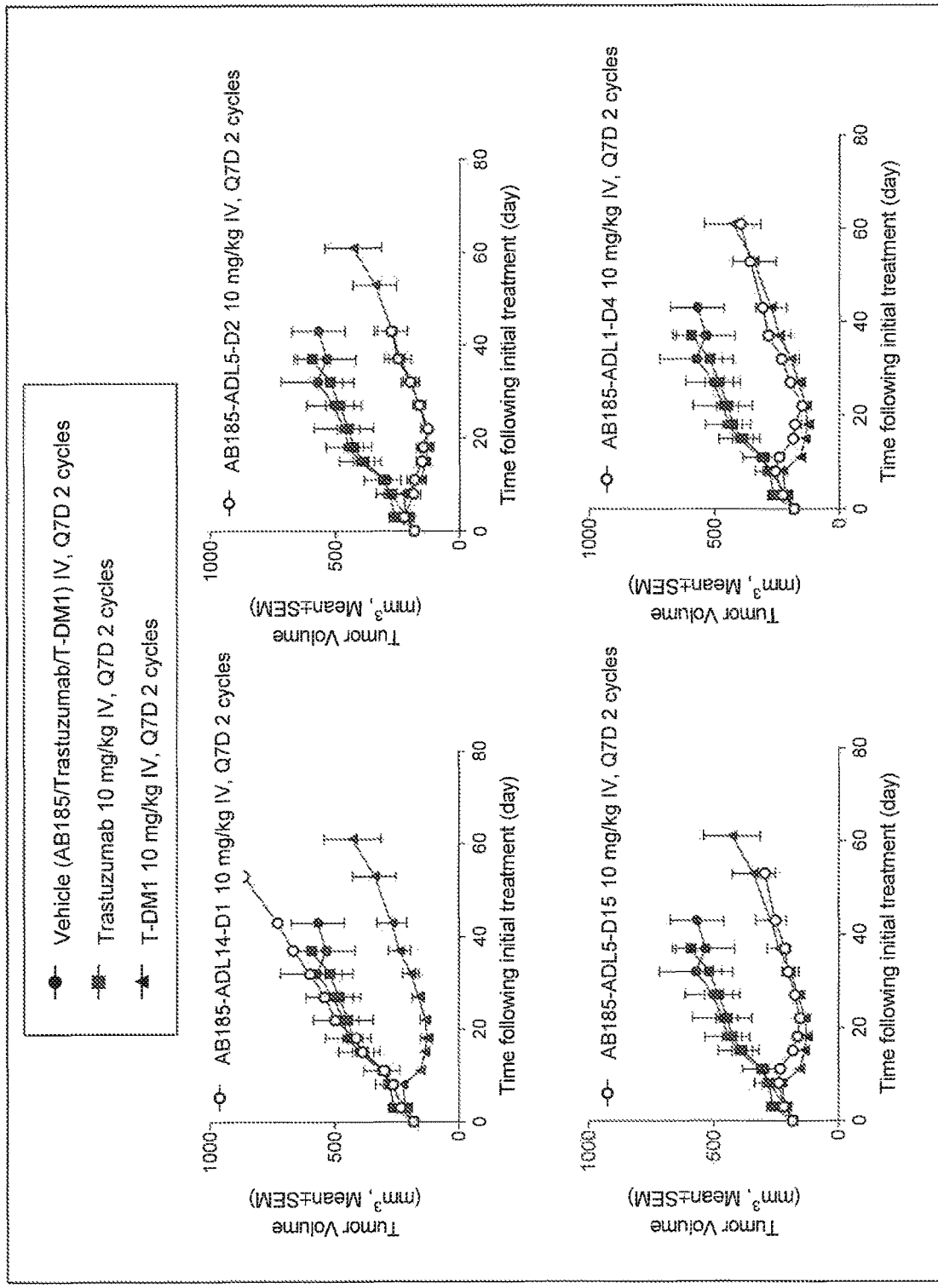
FIG. 21 shows tumor growth kinetics for each group of N87-implanted CB17-SCID mice treated intravenously with vehicle or 10 mg/kg trastuzumab, TDM1, or an exemplary HER2-ADC Q7D for 2 cycles (N=8 per group). Data are represented as mean±standard error of the mean (SEM) (mm$^3$).
Figure 22:
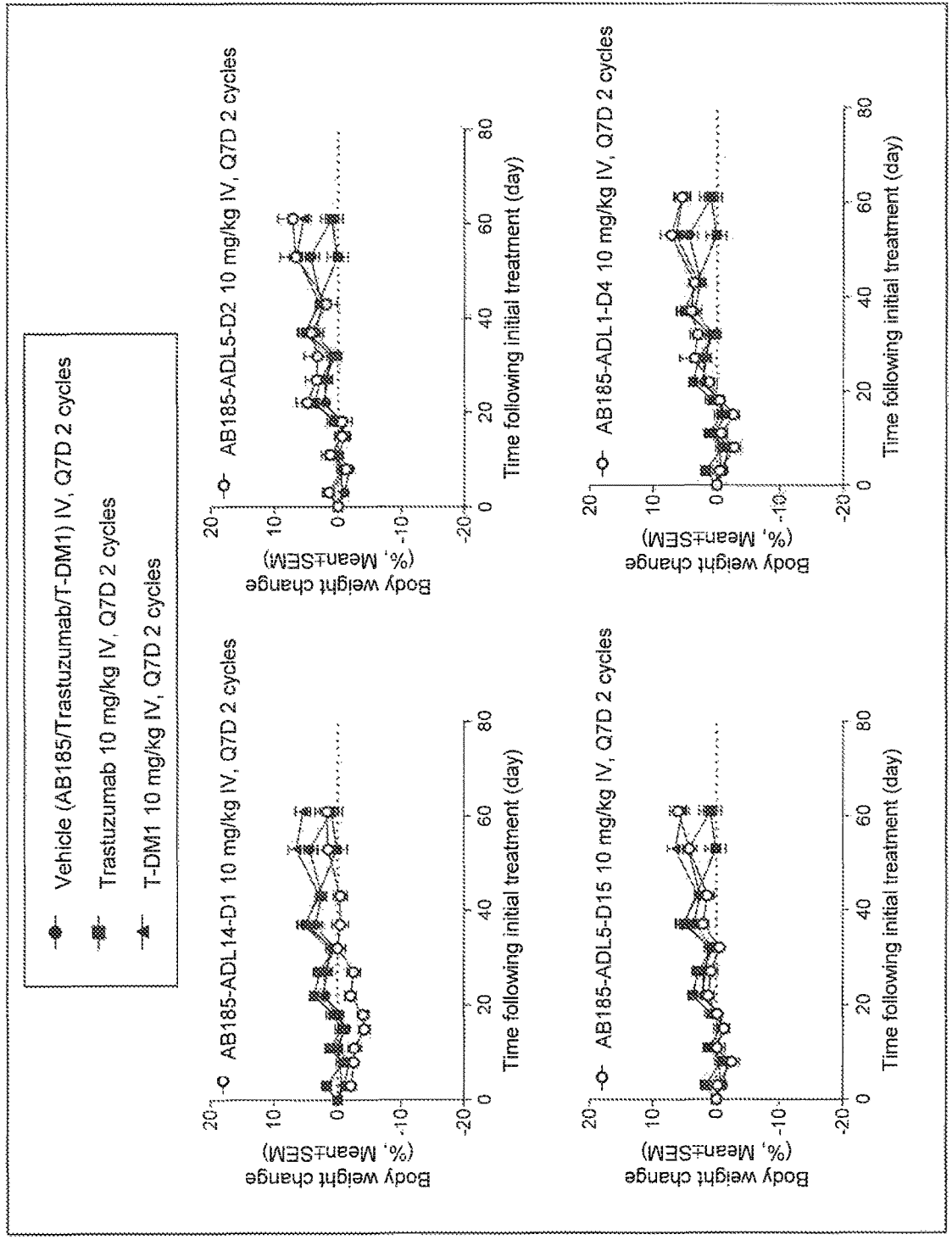
FIG. 22 shows body weight change for each group of N87-implanted CB17-SCID mice treated intravenously with vehicle or 10 mg/kg trastuzumab, TDM1, or an exemplary HER2-ADC Q7D for 2 cycles (N=8 per group). Data are represented as mean±standard error of the mean (SEM) (%).
Figure 23:
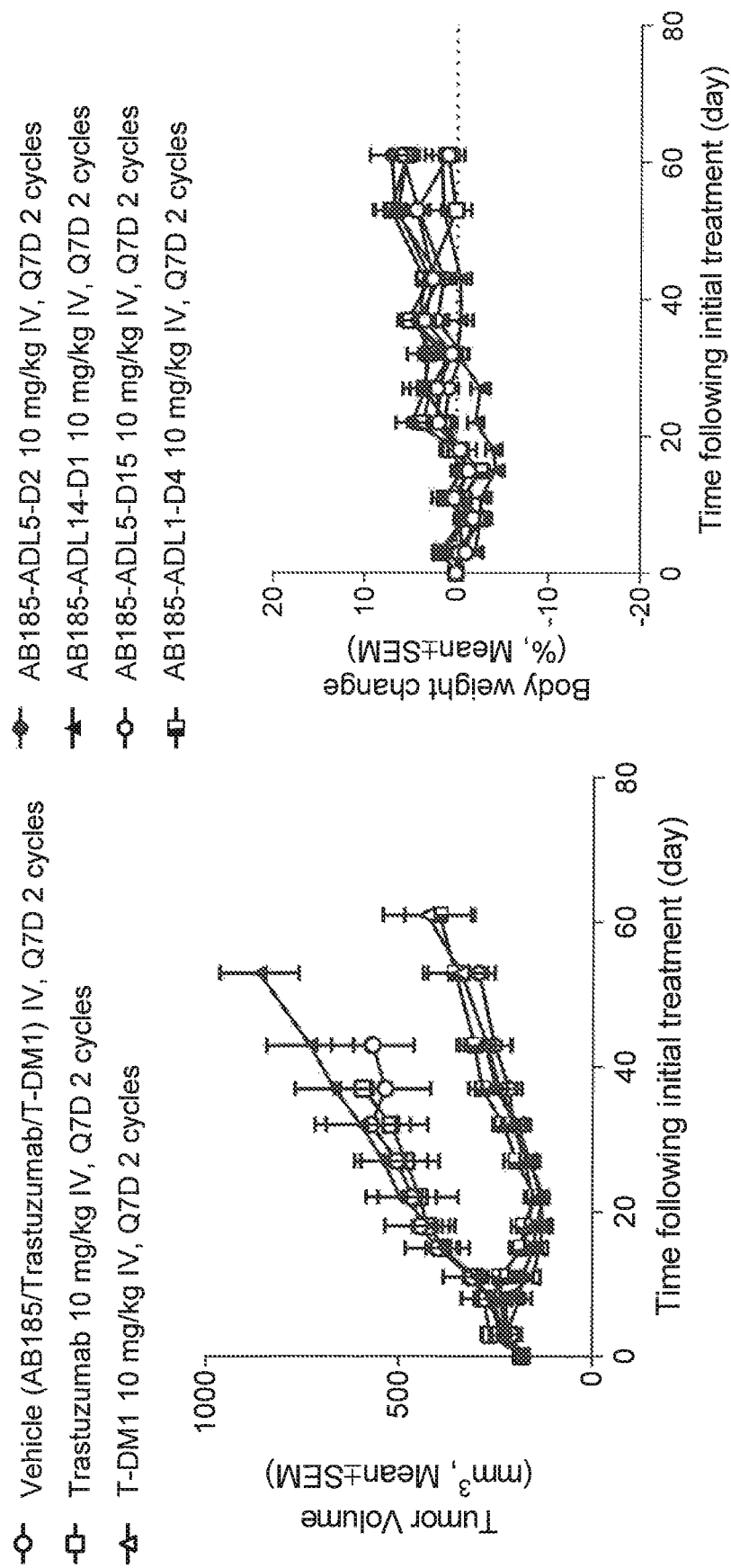
FIG. 23 shows tumor growth kinetics (left) and body weight change (right) for each group of N87-implanted CB17-SCID mice treated intravenously with vehicle or 10 mg/kg trastuzumab, TDM1, or an exemplary HER2-ADC Q7D for 2 cycles (N=8 per group). Data are represented as mean±SEM (tumor volume, mm$^3$) or mean±SEM (body weight, %).

Anti-tumor effects of intravenous trastuzumab, TDM1, and four HER2 ADCs in NCI-N87 xenograft model of gastric carcinoma are shown in FIG. 21 and FIG. 23. Body weight effects are shown in FIG. 22 and FIG. 23. Test article or vehicle was given intravenously (IV) Q7D for 2 cycles. Data represent the mean±SEM (tumor volume, $mm^3$) or ±SEM (body weight, %) (N=8). * $p<0.0001$ versus vehicle group on Day 22 using one-way ANOVA test.

Tabular data for in vitro and in vivo efficacy in NCI-N87 is provided in Table 24. Tabular data represent percent (%) Tumor Growth Inhibition (TGI of Tumor Volume) or % T/C (Tumor Volume) (N=8). AB185-ADL5-D2 was surprisingly active in vivo despite little lethality in vitro, and demonstrated improved in vivo efficacy as compared to, e.g., AB185-ADL14-D1.

TABLE 24

Efficacy of exemplary anti-HER2 ADCs in NCI-N87

| | Day 22 (in vivo) | | NCI-N87 (in vitro) | | |
|---|---|---|---|---|---|
| | TGI (%) | T/C (%) | $GI_{50\ (nM)}$ | $LD_{50\ (nM)}$ | $R_{min}\%$ |
| Vehicle/IV/Q7Dx2 | — | — | — | — | — |
| TDM1/10 mg/kg/ IV/Q7Dx2 | 71 | 29 | 0.1 | 40 | −37 |
| trastuzumab/ 10 mg/kg/IV/Q7Dx2 | 4 | 96 | >200 | >200 | 98 |
| AB185-ADL5-D2/ 10 mg/kg/IV/Q7Dx2 | 73 | 27 | 0.2 | >200 | 0 |
| AB185-ADL1-D4/ 10 mg/kg/IV/Q7Dx2 | 68 | 32 | 0.1 | >200 | −22 |
| AB185-ADL5-D15/ 10 mg/kg/IV/Q7Dx2 | 67 | 33 | 0.1 | >200 | −37 |
| AB185-ADL14-D1/ 10 mg/kg/IV/Q7Dx2 | −7 | 107 | 0.1 | >200 | −40 |

Trastuzumab, an anti-human HER2 antibody and a standard of care therapy for HER2-positive breast cancer, did not demonstrate anti-tumor activity in this model. However, TDM1, a second-line treatment containing trastuzumab plus covalently linked DM1 (a cytotoxic agent) showed significantly better anti-tumor activity (TGI 71%) than trastuzumab alone (TGI 4%). Among the four ADCs tested, ABL185-ADL5-D2, AB185-ADL5-D15, and AB185-ADL1-D4 showed potent anti-tumor activity with Tumor Growth Inhibition (TGI) of 73%, 67%, and 68%, respectively. Tumors of all responding groups eventually started to grow again. No complete response was observed in any group, and one of eight animals in each of the following groups showed a partial response: TDM1, ABL185-ADL5-D2, and AB185-ADL5-D15. All reagents and test articles were well tolerated by mice and minimal body weight loss was observed. Overall, 3 out of the 4 tested anti-HER2 ADCs demonstrated similarly potent anti-tumor activity in comparison with TDM1 in the NCI-N87 tumor model without significant body weight loss.

Figure 24A:
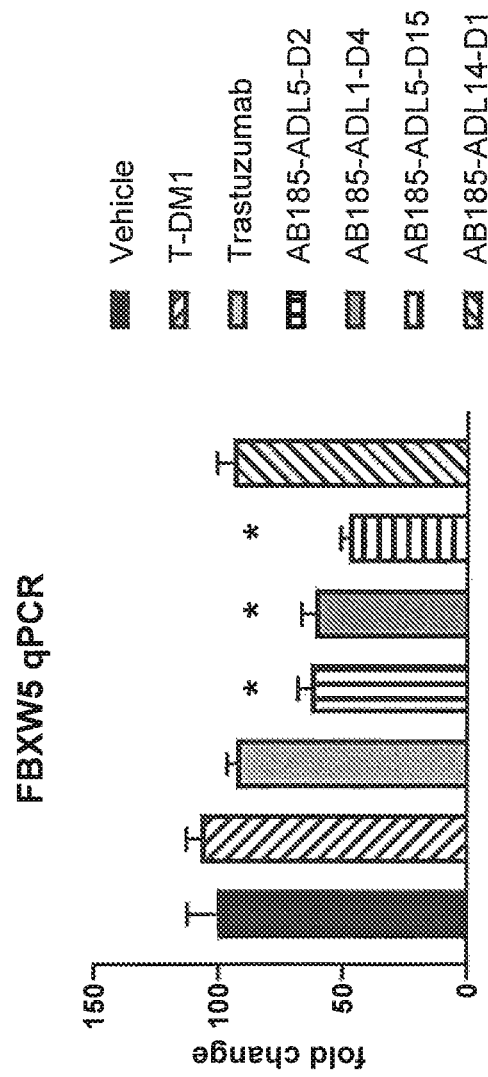
FIG. 24A-24D show pharmacodynamics (PD) modulation of mRNA junctions in N87-implanted CB17-SCID mice treated intravenously with vehicle or 10 mg/kg trastuzumab, TDM1, or an exemplary HER2-ADC Q7D for 2 cycles. RT-qPCR of FBXW5 (mature mRNA transcript) was monitored and is shown in FIG. 24A and FIG. 24C. RT-qPCR of TAOK1 (neojunction transcript) was monitored and is shown in FIG. 24B and FIG. 24D. Animals (N=4 per group) were collected at either 48 hours (FIG. 24A and FIG. 24B) or at the times indicated (FIG. 24C and FIG. 24D). Tumors were isolated for RNA extraction and RT-qPCR.
Figure 24B:
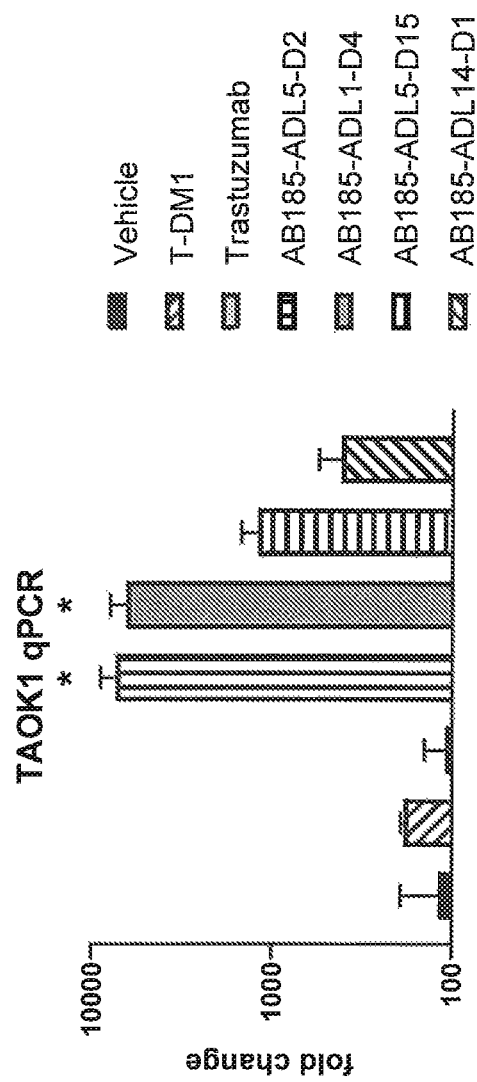
Figure 24C:
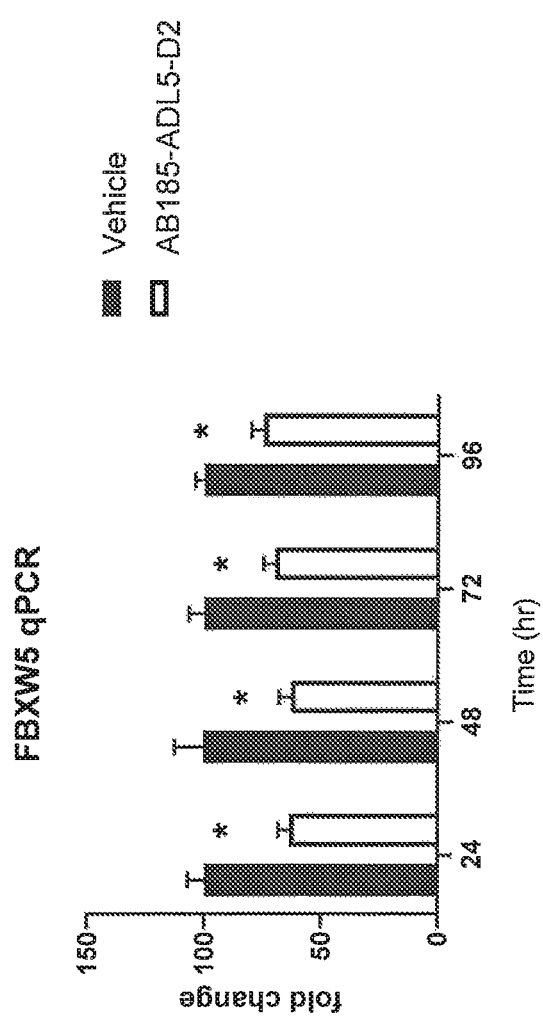
Figure 24D:
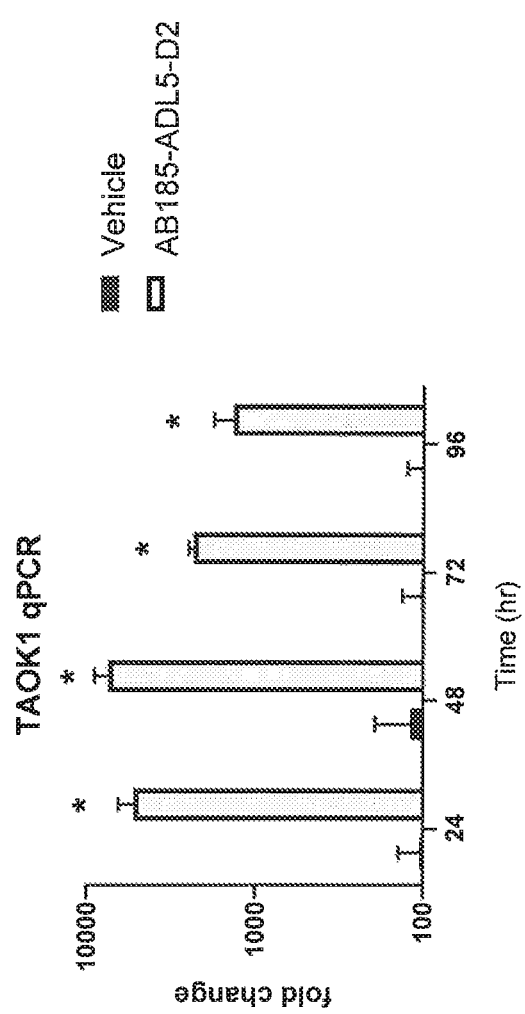

In Vivo PD:

PD modulation of mRNA junctions by intravenous trastuzumab, TDM1, and four anti-HER2 ADCs in NCI-N87 xenograft model of gastric carcinoma is shown in FIG. 24A-24D. RT-qPCR of FBXW5 (mature mRNA transcript) and TAOK1 (neojunction transcript) were monitored. Test article or vehicle was given intravenously (IV) at 10 mg/kg. Animals (N=4 per group) were collected at either 48 hours (FIG. 24A and FIG. 24B) or at the times indicated (FIG. 24C and FIG. 24D). Tumors were isolated for RNA extraction and RT-qPCR. * $p<0.05$ versus vehicle using one-way ANOVA (FIG. 24A and FIG. 24B) or two-way ANOVA (FIG. 24C and FIG. 24D).

Neither trastuzumab nor TDM1 exhibited significant changes in the observed splicing of either FBXW5 or TAOK1. AB185 conjugates ADL5-D2/ADL1-D4/ADL5-D15 all exhibited significant depletion of FBXW5, and AB185 conjugates ADL5-D2/ADL1-D4 exhibited significant increases in TAOK1. ADL5-D15 showed an increase in TAOK1, but did not reach statistical significance. ADL14-D1 did not exhibit statistically significant changes in abundance of either mRNA transcript.

TABLE 25

Characterization of exemplary anti-HER2 ADCs and corresponding payloads

| ADC Batch Id | Linker | Lethality/ Splicing Category (HCC1954, N87) | DAR | Percent Monomer | Free Drug | Conc. | CTGlo GMean GI50 (nM) HER2 SMLA screen HCC1954.1 | CTGlo GMean LD50 (nM) HER2 SMLA screen HCC1954.1 | CTGlo Mean MinResp % HER2 SMLA screen HCC1954.1 |
|---|---|---|---|---|---|---|---|---|---|
| AB185-ADL1-D12 | mc-Val-Cit-PABC | 1.3 | 6.25 | 99% | <1% | 0.82 | 0.032 | 0.09 | −78.471 |
| AB185-ADL13-D4 | b-glucuronide | 1.1 | 4.47 | 99% | <1% | 0.78 | 0.059 | 0.275 | −80.145 |
| AB185-ADL1-D5 | mc-Val-Cit-PABC | 1.3 | 6.14 | 99% | <1% | 1.1 | 0.079 | 0.298 | −81.189 |
| AB185-ADL23-D4 | mc-Glu-Val-Cit-PABC | 2.3 | 5.84 | 99% | <1% | 1.03 | 0.175 | 1.526 | −68.762 |
| AB185-ADL1-D3 | mc-Val-Cit-PABC | 2.3 | 6.75 | 99% | <1% | 1.13 | 0.117 | 0.741 | −77.982 |
| AB185-ADL22-D4 | mc-PEG-Val-Cit-PABC | 1.3 | 3.12 | 99% | <1% | 1.01 | 0.134 | 0.797 | −75.134 |
| AB185-ADL21-D1 | mc-Ala-Ala-Asn-PABC | 2.3 | 5.51 | 99% | <1% | 1.35 | 0.207 | 2.65 | −72.894 |
| AB185-ADL21-D8 | mc-Ala-Ala-Asn-PABC | 4.3 | 6.4 | 99% | <1% | 1.67 | 0.493 | >100.000 | −37.547 |
| AB185-ADL21-D4 | mc-Ala-Ala-Asn-PABC |  | 1.55 | 99% | <1% | 1.11 | 1.174 | >100.000 | 14.652 |
| AB185-ADL15-D2 | mal-CH2CH2-O-CH2CH2-(non-cleavable) | 3, ND | 3.25 | 98.80% | <1% | 1.6 | 0.24 | >200.000 | −13.023 |

TABLE 25-continued

Characterization of exemplary anti-HER2 ADCs and corresponding payloads

| | | | | | | | Properties-HER2 ADCs | | | | | |
|---|---|---|---|---|---|---|---|---|---|---|---|---|
| | | | | | | | antiproliferative activity antigen (+) cell #2 | | | antiproliferative activity antigen (−) cell | | |
| ADC Batch Id | Linker | Lethality/ splicing Category (HCC1954, N87) | DAR | Percent Mono-mer | Free Drug | Conc. | CTGlo GMean GI50 (nM) HER2 SMLA screen NCIN87 | CTGlo GMean LD50 (nM) HER2 SMLA screen NCIN87 | CTGlo Mean MinResp % HER2 SMLA screen NCIN87 | CTGlo GMean GI50 (nM) HER2 SMLA screen MCF7 | CTGlo GMean LD50 (nM) HER2 SMLA screen MCF7 | CTGlo Mean MinResp % HER2 SMLA screen MCF7 |
| AB185-ADL1-D12 | mc-Val-Cit-PABC | 1.3 | 6.25 | 99% | <1% | 0.82 | <0.015 | >100.000 | −35.162 | >100.000 | >100.000 | 53.606 |
| AB185-ADL13-D4 | b-glucuronide | 1.1 | 4.47 | 99% | <1% | 0.78 | 0.029 | 3.436 | −55.322 | >100.000 | >100.000 | 87.451 |
| AB185-ADL1-D5 | mc-Val-Cit-PABC | 1.3 | 6.14 | 99% | <1% | 1.1 | 0.04 | >100.000 | −32.663 | >100.000 | >100.000 | 93.099 |
| AB185-ADL23-D4 | mc-Glu-Val-Cit-PABC | 2.3 | 5.84 | 99% | <1% | 1.03 | 0.049 | >100.000 | −49.316 | >100.000 | >100.000 | 91.248 |
| AB185-ADL1-D3 | mc-Val-Cit-PABC | 2.3 | 6.75 | 99% | <1% | 1.13 | 0.049 | >100.000 | −15.629 | >100.000 | >100.000 | 91.495 |
| AB185-ADL22-D4 | mc-PEG-Val-Cit-PABC | 1.3 | 3.12 | 99% | <1% | 1.01 | 0.057 | >100.000 | −25.808 | >100.000 | >100.000 | 79.996 |
| AB185-ADL21-D1 | mc-Ala-Ala-Asn-PABC | 2.3 | 5.51 | 99% | <1% | 1.35 | 0.072 | >100.000 | −46.965 | >100.000 | >100.000 | 74.018 |
| AB185-ADL21-D8 | mc-Ala-Ala-Asn-PABC | 4.3 | 6.4 | 99% | <1% | 1.67 | 0.138 | >100.000 | −40.873 | >100.000 | >100.000 | 94.772 |
| AB185-ADL21-D4 | mc-Ala-Ala-Asn-PABC | | 1.55 | 99% | <1% | 1.11 | 0.235 | >100.000 | −36.848 | >100.000 | >100.000 | 96.18 |
| AB185-ADL15-D2 | mal-CH2CH2-O-CH2CH2-(non-cleavable) | 3, ND | 3.25 | 98.80% | <1% | 1.6 | 0.115 | >100.000 | −15.056 | | | |

Characterization of exemplary anti-HER2 ADCs and corresponding payloads

| | | | | | | | Properties-HER2 ADCs | | | | | |
|---|---|---|---|---|---|---|---|---|---|---|---|---|
| | | | | | | | splicing PD antigen (+) cell #1 | | splicing PD antigen (+) cell #2 | | splicing PD antigen (−) cell | |
| ADC Batch Id | Linker | Lethality/ splicing Category (HCC1954, N87) | DAR | Percent Mono-mer | Free Drug | Conc. | qPCR-CellScreen GMean IC50 (nM) HER2 SMLA screen SLC25A19 HCC1954.1 null | qPCR-CellScreen Mean MinResp % HER2 SMLA screen SLC25A19 HCC1954.1 null | qPCR-CellScreen GMean IC50 (nM) HER2 SMLA screen SLC25A19 NCIN87 null | qPCR-CellScreen Mean Min Resp % HER2 SMLA screen SLC25A19 NCIN87 null | qPCR-CellScreen GMean IC50 (nM) HER2 SMLA screen SLC25A19 MCF7 null | qPCR-CellScreen Mean MinResp % HER2 SMLA screen SLC25A19 MCF7 null |
| AB185-ADL1-D12 | mc-Val-Cit-PABC | 1.3 | 6.25 | 99% | <1% | 0.82 | 0.144 | −85.744 | 0.095 | −93.185 | >100.000 | −12.254 |
| AB185-ADL13-D4 | b-glucuronide | 1.1 | 4.47 | 99% | <1% | 0.78 | 0.45 | −72.455 | 0.177 | −93.984 | >100.000 | −28.389 |
| AB185-ADL1-D5 | mc-Val-Cit-PABC | 1.3 | 6.14 | 99% | <1% | 1.1 | 0.624 | −65.799 | 0.095 | −91.243 | >100.000 | −10.455 |
| AB185-ADL23-D4 | mc-Glu-Val-Cit-PABC | 2.3 | 5.84 | 99% | <1% | 1.03 | >100.000 | −40.549 | 0.249 | −89.841 | >100.000 | −16.033 |
| AB185-ADL1-D3 | mc-Val-Cit-PABC | 2.3 | 6.75 | 99% | <1% | 1.13 | >100.000 | −38.621 | 0.199 | −78.218 | >100.000 | −24.342 |
| AB185-ADL22-D4 | mc-PEG-Val-Cit-PABC | 1.3 | 3.12 | 99% | <1% | 1.01 | 2.302 | −58.063 | 0.17 | −91.266 | >100.000 | −23.433 |
| AB185-ADL21-D1 | mc-Ala-Ala-Asn-PABC | 2.3 | 5.51 | 99% | <1% | 1.35 | >100.000 | −37.396 | 0.201 | −84.588 | >100.000 | −15.463 |
| AB185-ADL21-D8 | mc-Ala-Ala-Asn-PABC | 4.3 | 6.4 | 99% | <1% | 1.67 | >100.000 | −27.319 | 0.577 | −70.144 | >100.000 | −12.798 |
| AB185-ADL21-D4 | mc-Ala-Ala-Asn-PABC | | 1.55 | 99% | <1% | 1.11 | >100.000 | −16.088 | 5.097 | −54.535 | >100.000 | −12.096 |

TABLE 25-continued

Characterization of exemplary anti-HER2 ADCs and corresponding payloads

| ADC Batch Id | Linker | Lethality/ splicing Category (HCC1954, N87) | DAR | Percent Monomer | Free Drug | Conc. | | | | |
|---|---|---|---|---|---|---|---|---|---|---|
| AB185-ADL15-D2 | mal-CH2CH2-O-CH2CH2- (non-cleavable) | 3, ND | 3.25 | 98.80% | <1% | 1.6 | | | 0.296 | −83.148 |

Characterization of exemplary anti-HER2 ADCs and corresponding payloads

Properties-Corresponding Free Payloads

| | | | | | | | target bidning SPA-ATS | biochemical assay | | |
|---|---|---|---|---|---|---|---|---|---|---|
| ADC Batch Id | Linker | Lethality/ splicing Category (HCC1954, N87) | DAR | Percent Monomer | Free Drug | Conc. | GMean IC50 (nM) SF3B1 (WT) HELA.2 | qPCR-IVS-ATS GMean IC50 (nM) Ad2.1 HELA.2 | qPCR-IVS-ATS GMean IC50 (nM) Ad2.2 HELA.2 | Ratio Ad2.1/2.2 |
| AB185-ADL1-D12 | mc-Val-Cit-PABC | 1.3 | 6.25 | 99% | <1% | 0.82 | | 16.528 | 25.09 | 0.659 |
| AB185-ADL13-D4 | b-glucuronide | 1.1 | 4.47 | 99% | <1% | 0.78 | 8.778 | 20.887 | 17.321 | 1.206 |
| AB185-ADL1-D5 | mc-Val-Cit-PABC | 1.3 | 6.14 | 99% | <1% | 1.1 | | 17.392 | 23.943 | 0.726 |
| AB185-ADL23-D4 | mc-Glu-Val-Cit-PABC | 2.3 | 5.84 | 99% | <1% | 1.03 | 8.778 | 20.887 | 17.321 | 1.206 |
| AB185-ADL1-D3 | mc-Val-Cit-PABC | 2.3 | 6.75 | 99% | <1% | 1.13 | | 9.326 | 10.928 | 0.853 |
| AB185-ADL22-D4 | mc-PEG-Val-Cit-PABC | 1.3 | 3.12 | 99% | <1% | 1.01 | 8.778 | 20.887 | 17.321 | 1.206 |
| AB185-ADL21-D1 | mc-Ala-Ala-Asn-PABC | 2.3 | 5.51 | 99% | <1% | 1.35 | 6.085 | 17.568 | 15.853 | 1.108 |
| AB185-ADL21-D8 | mc-Ala-Ala-Asn-PABC | 4.3 | 6.4 | 99% | <1% | 1.67 | 5.921 | 11.403 | 9.034 | 1.262 |
| AB185-ADL21-D4 | mc-Ala-Ala-Asn-PABC | | 1.55 | 99% | <1% | 1.11 | 8.778 | 20.887 | 17.321 | 1.206 |
| AB185-ADL15-D2 | mal-CH2CH2-O-CH2CH2- (non-cleavable) | 3, ND | 3.25 | 98.80% | <1% | 1.6 | | | | |

Characterization of exemplary anti-HER2 ADCs and corresponding payloads

Properties-Corresponding Free Payloads

| | | | | | | | cellular potency cell line #1 | | cellular potency cell line #2 | |
|---|---|---|---|---|---|---|---|---|---|---|
| ADC Batch Id | Linker | Lethality/ splicing Category (HCC1954, N87) | DAR | Percent Monomer | Free Drug | Conc. | CTGlo-ATS GMean GI50 (nM) 72 h NCIH1650.1 | CTGlo-ATS GMean LD50 (nM) 72 h NCIH1650.1 | CTGlo-ATS GMean GI50 (nM) 72 h NCIH1568.1 | CTGlo-ATS GMean LD50 (nM) 72 h NCIH1568.1 |
| AB185-ADL1-D12 | mc-Val-Cit-PABC | 1.3 | 6.25 | 99% | <1% | 0.82 | 257.925 | >10000.00 | 163.604 | 1193.037 |
| AB185-ADL13-D4 | b-glucuronide | 1.1 | 4.47 | 99% | <1% | 0.78 | 11.941 | 1960.398 | 6.369 | 45.485 |
| AB185-ADL1-D5 | mc-Val-Cit-PABC | 1.3 | 6.14 | 99% | <1% | 1.1 | | | | |
| AB185-ADL23-D4 | mc-Glu-Val-Cit-PABC | 2.3 | 5.84 | 99% | <1% | 1.03 | 11.941 | 1960.398 | 6.369 | 45.485 |
| AB185-ADL1-D3 | mc-Val-Cit-PABC | 2.3 | 6.75 | 99% | <1% | 1.13 | | | | |
| AB185-ADL22-D4 | mc-PEG-Val-Cit-PABC | 1.3 | 3.12 | 99% | <1% | 1.01 | 11.941 | 1960.398 | 6.369 | 45.485 |
| AB185-ADL21-D1 | mc-Ala-Ala-Asn-PABC | 2.3 | 5.51 | 99% | <1% | 1.35 | 12.121 | >10000.00 | 7.363 | 65.737 |
| AB185-ADL21-D8 | mc-Ala-Ala-Asn-PABC | 4.3 | 6.4 | 99% | <1% | 1.67 | 19.15 | >10000.00 | 6.568 | 68.125 |

TABLE 25-continued

| | | | | | | | | | |
|---|---|---|---|---|---|---|---|---|---|
| AB185-ADL21-D4 | mc-Ala-Ala-Asn-PABC | | 1.55 | 99% | <1% | 1.11 | 11.941 | 1960.398 | 6.369 | 45.485 |
| AB185-ADL15-D2 | mal-CH2CH2-O-CH2CH2-(non-cleavable) | 3, ND | 3.25 | 98.80% | <1% | 1.6 | | | | |

Characterization of exemplary anti-HER2 ADCs and corresponding payloads

| | | | | | | Properties-Corresponding Free Payloads | | | | |
|---|---|---|---|---|---|---|---|---|---|---|
| | | | | | | cellular potency cell line #3 | | cellular permeability | | |
| ADC Batch Id | Linker | Lethality/splicing Category (HCC1954, N87) | DAR | Percent Monomer | Free Drug | Conc. | CTGlo-ATS GMean GI50 (nM) 72 h THP1.1 | CTGlo-ATS GMean LD50 (nM) 72 h THP1.1 | Perm. Mean-Caco-2 A-B Perm (10e-6 cm/s) | Perm. Mean Caco-2 B-A Perm (10e-6 cm/s) | ER |
| AB185-ADL1-D12 | mc-Val-Cit-PABC | 1.3 | 6.25 | 99% | <1% | 0.82 | 202.487 | 900.227 | 0.17 | 0.23 | 1.353 |
| AB185-ADL13-D4 | b-glucuronide | 1.1 | 4.47 | 99% | <1% | 0.78 | 10.943 | 33.329 | 0.1 | 1.79 | 17.9 |
| AB185-ADL1-D5 | mc-Val-Cit-PABC | 1.3 | 6.14 | 99% | <1% | 1.1 | | | | | |
| AB185-ADL23-D4 | mc-Glu-Val-Cit-PABC | 2.3 | 5.84 | 99% | <1% | 1.03 | 10.943 | 33.329 | 0.1 | 1.79 | 17.9 |
| AB185-ADL1-D3 | mc-Val-Cit-PABC | 2.3 | 6.75 | 99% | <1% | 1.13 | | | | | |
| AB185-ADL22-D4 | mc-PEG-Val-Cit-PABC | 1.3 | 3.12 | 99% | <1% | 1.01 | 10.943 | 33.329 | 0.1 | 1.79 | 17.9 |
| AB185-ADL21-D1 | mc-Ala-Ala-Asn-PABC | 2.3 | 5.51 | 99% | <1% | 1.35 | 11.085 | 41.408 | 0.14 | 2.05 | 14.64 |
| AB185-ADL21-D8 | mc-Ala-Ala-Asn-PABC | 4.3 | 6.4 | 99% | <1% | 1.67 | 8.745 | 38.969 | 0.128 | 2.027 | 15.88 |
| AB185-ADL21-D4 | mc-Ala-Ala-Asn-PABC | | 1.55 | 99% | <1% | 1.11 | 10.943 | 33.329 | 0.1 | 1.79 | 17.9 |
| AB185-ADL15-D2 | mal-CH2CH2-O-CH2CH2-(non-cleavable) | 3, ND | 3.25 | 98.80% | <1% | 1.6 | | | | | |

TABLE 26

Exemplary anti-HER2 ADCs-HCC1954 cells

| | | | | | Properties-HER2 ADCs antiproliferative activity antigen (+) cell #1 | |
|---|---|---|---|---|---|---|
| ADC Batch Id | Linker | DAR | Permeability Caco-2 A-B (10e-6 cm/s) | pH 5.5 Stability (t1/2, 37C) | CTGlo GMean GI50 (nM) HER2 SMLA screen HCC1954.1 | CTGlo Mean MinResp % HER2 SMLA screen HCC1954.1 |
| AB185-ADL5-D19 | QVal-Ala | 6.600 | 16 | 0.8 | 0.278 | −47.381 |
| AB185-ADL5-D25 | QVal-Ala | 6.000 | 0.14 | 3.4 | 0.038 | −46.265 |
| AB185-ADL5-D2 | QVal-Ala | 4.140 | 0.6 | 4 | 0.206 | −12.239 |
| AB185-ADL1-04 | Val-Cit | 2.800 | 0.1 | 4.5 | 0.050 | −57.212 |
| AB185-ADL5-D10 | QVal-Ala | 4.020 | 1.8 | 5 | 0.254 | −2.273 |
| AB185-ADL1-D16 | Val-Cit | 4.400 | 0.72 | 7 | 2.086 | |
| AB185-ADL5-D17 | QVal-Ala | 3.960 | 20 | 7 | 2.668 | 14.873 |
| AB185-ADL5-D34 | QVal-Ala | | 26 | 7 | 3.325 | −38.285 |
| AB185-ADL5-D15 | QVal-Ala | 4.000 | 3.4 | 7 | 0.912 | −45.388 |

Example 10

10.1 Bioinformatics-Driven Indication/Target Selection

Figure 25:
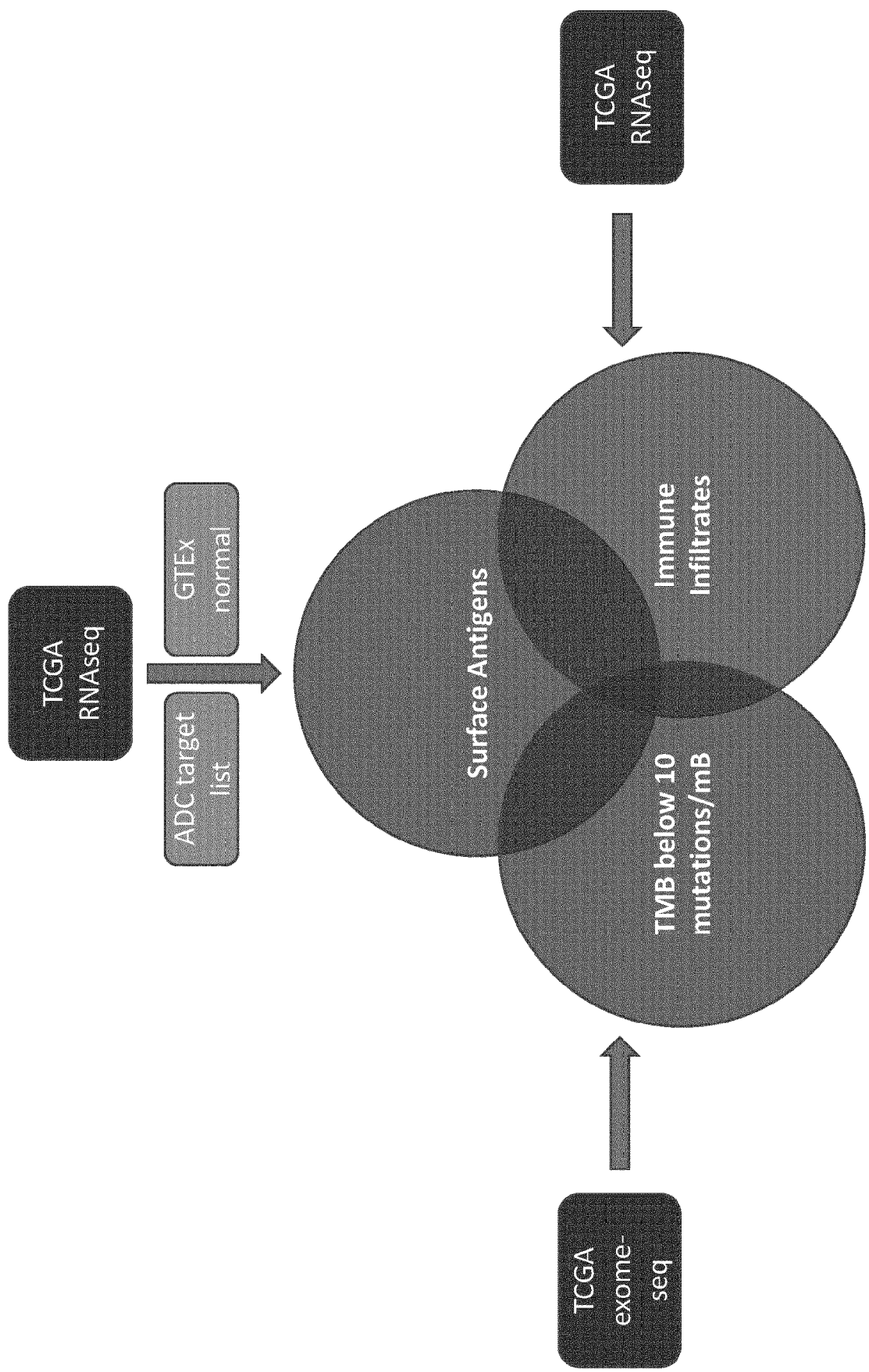
FIG. 25 shows a schematic diagram of an exemplary target indication analysis.

To identify target antigens highly expressed in low tumor mutation burden (TM B) tumors, as compared to normal tissue, a bioinformatics predictive analysis was performed. This example explains 1) how each filter was defined; and 2) how to use the antigen/indication table to identify suitable target/tumor pairs. For a schematic diagram of an exemplary target indication analysis, see FIG. 25.

10.1.1 Overview

Target antigens and indications were identified using a bioinformatics predictive analysis. Data from TCGA was processed for tumor mutation burden (TMB), expression of target antigens for ADC delivery, and tumor immune infiltration. Analyses, using published cutoffs of TMB and infiltration to stratify predicted responders vs. non-responders to immune checkpoint inhibitors (ICI), were performed to identify indications and matching antigens. Surface antigen expression was further filtered to assess a probabilistic population with antigen expression at least 2-fold higher than any normal tissue (as evaluated from the GTEx tissue expression database). Indications (or subsets of a TCGA lineage) with a suitable percentage of patients having one or more target antigens were further analyzed for mutation and immune metrics. Percentages of antigen positive patients having a tumor mutation burden below an aggregate of 10 mutations/megabase and with a T-cell infiltration score above 0.5 were assessed. Indications with an estimate of -50% of patients meeting these criteria are listed in Table 27. Patients in these cohorts (but not limited to these cohorts) may respond to treatment with a splicing modulator ADC (e.g., a splicing modulator ADC described herein).

10.1.2 Methods

Indication Prediction for Annals of Oncology Antigen Table Annotation:
- Antigen: antigen gene name, only 59 genes likely to be good ADC targets from Annals of Oncology literature review (see Moek et al. (2017) Annals of Oncology, 28: 3083-3091) were included in the table (initial full analysis included all in silico surfaceome genes)
- Cohort: TCGA cohort name
- SUBTYPE: TCGA tumor subtype information
- Cases_Total: The total number of cases
- Cases.by.subtype: The number of cases by subtype
- LTPM_median: Expression median value by Log 2(TPM+1)
- LTPM_median_LowTMB: Expression median value by Log 2(TPM+1) for the cases with low TMB (<350)
- LTMB_Median: Median value of Log 10(TMB)
- LTMB_MAD: Robust measurement of standard deviation by MAD value of Log 10(TMB)
- Infil_Median: Median value of infiltration score according to PLoS One T-cell signature
- Infil_MAD: Robust measurement of standard deviation by MAD value of infiltration score according to PLoS One Tcell signature
- Cor.with.Purity: Expression correlation with tumor purity
- GTEX_Tissue: The GTEx tissue name with the highest median value of expression
- GTEX_LTPM_Median: The median expression value of antigen in the GTEx tissue with the highest median value of expression
- Surfaceome.Filter*: Patient population after applying surfaceome filter: expression>2 fold of GTEx normal tissue with the highest median
- LowTMB.Filter: Patient population after applying low TMB filter: <350 per exome-seq (10 per mega bases2)
- LowTMB.Surfaceome.Filter: Patient population after applying both surfaceome and tmb filters
- HiInfil.LowTMB.Surfaceome.Filter: Patient population after applying three filters: surfaceome expression filter, low tmb filter and high infiltration filter
- Surfaceome.Filter.Perc: Percentage of population after applying surfaceome filter: expression >2 fold of GTEx normal tissue with the highest median
- LowTMB.Filter.Perc: Percentage of population after applying low TMB filter: <350
- LowTMB.Surfaceome.Filter.Perc: Percentage of population after applying both surfaceome and tmb filters
- HiInfil.LowTMB.Surfaceome.Filter.Perc: Percentage of population after applying three filters: surfaceome expression filter, low tmb filter, and high infiltration filter Probabilistic Estimation of Patient Population:
Resources compiled:
1. Pan-can immune landscape paper (Ready et al. (2019) Journal of Clinical Oncology, 37:992-1000)
2. TCGA RNA-seq/Exome-seq data bundle from Omicsoft
3. Immune gene signatures (Thorsson et al. (2018) Immunity, 48, 812-830)
4. GTEx data v7

Tumor mutation burden was calculated from the TCGA exome-seq mutation calling using Omicsoft data. PLoS One T-cell signature (CD3D, CD3E, CD2) was used to quantify sample immune infiltration. Z score was generated using log 2(TPM+1) value from TCGA RNA-seq data.

Surfaceome.Filter: Probability of individual patient to have >2 fold expression (log 2(TPM+1)) value comparing to the GTEx normal tissue with the highest median was calculated as follows:
1. Identify the GTEx normal tissue that has the highest median value for this gene among all GTEx normal tissues, assume it is Th
2. Synthesize GTEx data for this gene with 1000 patients for each tissue using Synthetic Minority Over-sampling Technique (SMOTE (Siemers et al. (2017) PLoS One, 12(7):e0179726) maintaining the data distribution by tissue
3. Count the number of times (n times) this patient will be >2 fold of the GTEx synthesized data for the tissue $T_h$, the probability for this patient to be >2 fold of the GTEx normal is n/1000
4. Calculate this probability for every patient
5. The sum of the individual probability is the probabilistic estimation of the cohort population with >2 fold higher than the GTEx normal
6. When applying other filters together, the sum of individual probability will be only for the patients that pass the other filters

10.1.3 EXAMPLES

Target antigens and indications identified using the exemplary bioinformatics predictive analysis described above are set forth in Table 27.

TABLE 27

Exemplary target antigens and indications

| Target Antigen | Indication(s) |
| --- | --- |
| MSLN | ovarian cancer |
| | cervical cancer |
| | pancreatic cancer |
| | lung adenocarcinoma |
| EPHA2 | esophageal cancer |
| FOLH1 | prostate cancer |
| CDH6 | kidney cancer |
| CEACAM5 | colorectal cancer |
| CFC1B | pancreatic cancer |
| ENPP3 | kidney cancer |
| FOLR1 | ovarian cancer |
| HAVCR1 | kidney cancer |
| | esophageal cancer |
| KIT | kidney cancer |
| MET | kidney cancer |
| | esophageal cancer |
| MUC16 | ovarian cancer |
| | cervical cancer |
| | breast cancer |
| SLC39A6 | breast cancer |
| | prostate cancer |
| SLC44A4 | prostate cancer |
| STEAP1 | prostate cancer |

The invention claimed is:

1. An antibody-drug conjugate of Formula (I):

$$Ab-(L-D)_p \qquad (I)$$

wherein
Ab is an antibody or antigen binding fragment which targets a neoplastic cell;
D is a splicing modulator of the formula:

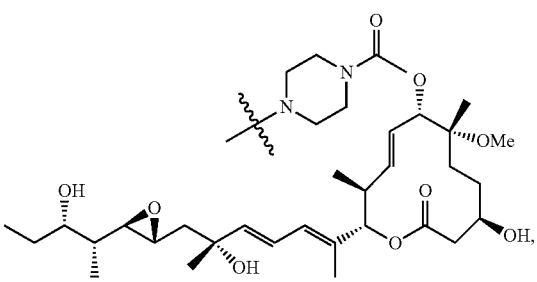

or a pharmaceutically acceptable salt thereof, or of the formula:

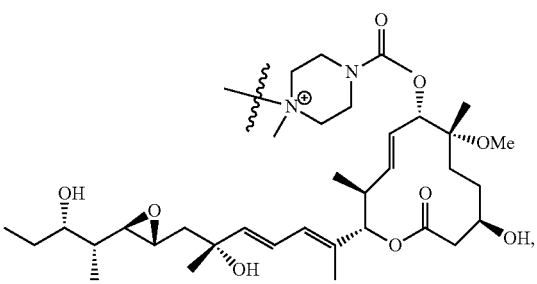 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](O)/C=C/[C@@H]1C ; *[N+]1(C)CCN(C(C)=O)CC1]

or a pharmaceutically acceptable salt thereof;
L is a linker which covalently attaches Ab to D; and
p is an integer from 1 to 15.

2. The antibody-drug conjugate of claim 1, wherein the antibody or antigen binding fragment targets a neoplastic cell derived from a hematological malignancy selected from acute myeloid leukemia and multiple myeloma or a solid tumor selected from a B-cell malignancy, a leukemia, a lymphoma, and a myeloma.

3. The antibody-drug conjugate of claim 2, wherein the solid tumor is selected from breast cancer, gastric cancer, prostate cancer, ovarian cancer, lung cancer, uterine cancer, salivary duct carcinoma, melanoma, colon cancer, cervical cancer, pancreatic cancer, kidney cancer, colorectal cancer, and esophageal cancer.

4. The antibody-drug conjugate of claim 1, wherein the antibody or antigen binding fragment targets a HER2-expressing cell, wherein the antibody or antigen binding fragment comprises three heavy chain complementarity determining regions (HCDR1, HCDR2, and HCDR3) comprising amino acid sequences of SEQ ID NO:1 (HCDR1), SEQ ID NO:2 (HCDR2), and SEQ ID NO:3 (HCDR3); and three light chain complementarity determining regions (LCDR1, LCDR2, and LCDR3) comprising amino acid sequences of SEQ ID NO:4 (LCDR1), SEQ ID NO:5 (LCDR2), and SEQ ID NO:6 (LCDR3); and/or wherein the antibody or antigen binding fragment comprises a heavy chain variable region comprising an amino acid sequence of SEQ ID NO: 19, and a light chain variable region comprising an amino acid sequence of SEQ ID NO:20.

5. The antibody-drug conjugate of claim 1, wherein the antibody or antigen binding fragment targets a CD138-expressing cell; wherein the antibody or antigen binding fragment comprises three heavy chain complementarity determining (HCDR1, HCDR2, and HCDR3) comprising amino acid sequences of SEQ ID NO:7 (HCDR1), SEQ ID NO:8 (HCDR2), and SEQ ID NO:9 (HCDR3); and three light chain complementarity determining regions (LCDR1, LCDR2, and LCDR3) comprising amino acid sequences of SEQ ID NO:10 (LCDR1), SEQ ID NO:11 (LCDR2), and SEQ ID NO:12 (LCDR3); and/or wherein the antibody or antigen binding fragment comprises a heavy chain variable region comprising an amino acid sequence of SEQ ID NO:21, and a light chain variable region comprising an amino acid sequence of SEQ ID NO:22.

6. The antibody-drug conjugate of claim 1, wherein the antibody or antigen binding fragment targets an EPHA2-expressing cell; wherein the antibody or antigen binding fragment comprises three heavy chain complementarity determining (HCDR1, HCDR2, and HCDR3) comprising amino acid sequences of SEQ ID NO: 13 (HCDR1), SEQ ID NO: 14 (HCDR2), and SEQ ID NO:15 (HCDR3); and three light chain complementarity determining regions (LCDR1, LCDR2, and LCDR3) comprising amino acid sequences of SEQ ID NO: 16 (LCDR1), SEQ ID NO: 17 (LCDR2), and SEQ ID NO: 18 (LCDR3); and/or wherein the antibody or antigen binding fragment comprises a heavy chain variable region comprising an amino acid sequence of SEQ ID NO:23, and a light chain variable region comprising an amino acid sequence of SEQ ID NO:24.

7. The antibody-drug conjugate of claim 1, wherein the antibody or antigen binding fragment comprises a human IgG heavy chain constant region and/or wherein the antibody or antigen binding fragment comprises a human Ig kappa light chain constant region.

8. The antibody-drug conjugate of claim 1, wherein the linker L is a cleavable linker comprising a cleavable moiety, wherein the cleavable moiety comprises a cleavable peptide moiety or a cleavable glucuronide moiety.

9. The antibody-drug conjugate of claim 8, wherein cleavable peptide moiety comprises valine-alanine (Val-Ala) or valine-citrulline (Val-Cit).

10. The antibody-drug conjugate of claim 8, wherein the linker attaches to the antibody or antigen binding fragment via a maleimide (Mal) moiety.

11. The antibody-drug conjugate of claim 10, wherein the Mal moiety comprises a maleimidocaproyl (MC).

12. The antibody-drug conjugate of claim 11, wherein the linker comprises MC-Val-Cit or MC-Val-Ala.

13. The antibody-drug conjugate of claim 12, wherein the MC is joined to the antibody or antigen binding fragment via a cysteine residue on the antibody or antigen binding fragment.

14. The antibody-drug conjugate of claim 8, wherein the linker comprises a spacer unit, wherein:
(a) the spacer unit comprises a polyethylene glycol (PEG) moiety, wherein the PEG moiety comprises -(PEG)$_m$- and m is an integer from 1 to 10, or
(b) the spacer unit comprises an alkyl moiety, wherein the alkyl moiety comprises —(CH$_2$)$_n$— and n is an integer from 1 to 10.

15. The antibody-drug conjugate of claim 14, wherein the spacer unit attaches to the antibody or antigen binding fragment via a maleimide (Mal) moiety ("Mal-spacer unit").

16. The antibody-drug conjugate of claim 15, wherein the Mal-spacer unit is joined to the antibody or antigen binding fragment via a cysteine residue on the antibody or antigen binding fragment.

17. The antibody-drug conjugate of claim 15, wherein the Mal-spacer unit comprises an alkyl moiety, and/or a PEG moiety.

18. The antibody-drug conjugate of claim 8, wherein a spacer unit attaches the cleavable moiety in the linker L to the splicing modulator.

19. The antibody-drug conjugate of claim 18, wherein cleavage of the cleavable moiety releases the splicing modulator from the antibody or antigen binding fragment and linker.

20. The antibody-drug conjugate of claim 18, wherein the spacer unit attaching the cleavable moiety in the linker to the splicing modulator is self-immolative.

21. The antibody-drug conjugate of claim 18, wherein the spacer unit attaching the cleavable moiety in the linker to the splicing modulator comprises a p-aminobenzyl (pAB) or p-aminobenzyloxycarbonyl (pABC).

22. The antibody-drug conjugate of claim 21, wherein the pAB or pABC attaches the cleavable moiety in the linker to the splicing modulator.

23. The antibody-drug conjugate of claim 21, wherein the linker comprises Val-Cit-pAB, Val-Ala-pAB, Val-Cit-pABC or Val-Ala-pABC.

24. The antibody-drug conjugate of claim 1, wherein the linker is a non-cleavable linker.

25. The antibody-drug conjugate of claim 1, wherein the linker L comprises:

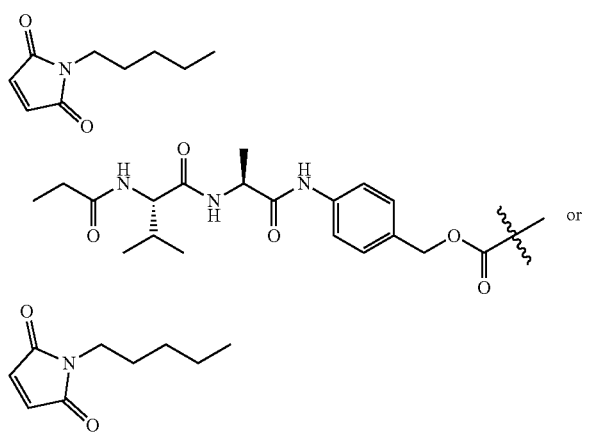

or

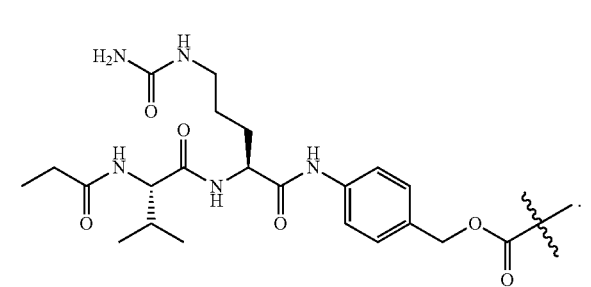

26. The antibody-drug conjugate of claim 1, wherein the splicing modulator D is:

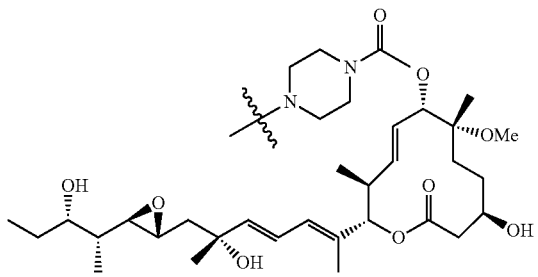

or a pharmaceutically acceptable salt thereof.

27. The antibody-drug conjugate of claim 1, wherein the splicing modulator D is:

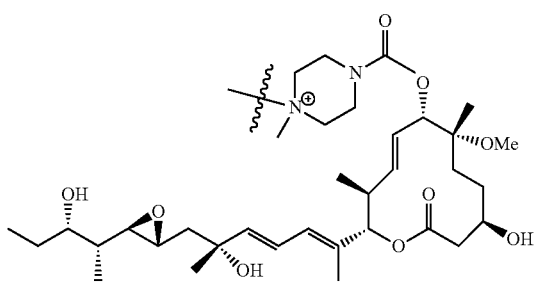 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC)[C@@H](O)/C=C/[C@@H]1C ; *[N+]1(C)CCN(C(C)=O)CC1]

or a pharmaceutically acceptable salt thereof.

28. The antibody-drug conjugate of 1, wherein p is from 1 to 10.

29. A method of treating a subject having, or suspected of having, a neoplastic disorder, comprising administering a therapeutically effective amount of the antibody-drug conjugate of 1.

30. The method of claim 29, wherein the neoplastic disorder is: a hematological malignancy selected from acute myeloid leukemia and multiple myeloma or a solid tumor selected from breast cancer, gastric cancer, prostate cancer, ovarian cancer, lung cancer, uterine cancer, salivary duct carcinoma, melanoma, colon cancer, cervical cancer, pancreatic cancer, kidney cancer, colorectal cancer, and esophageal cancer.

31. A composition comprising a compound of formula:

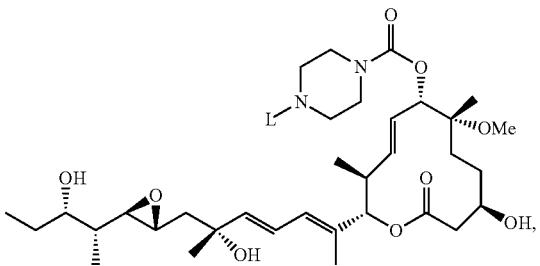

or a pharmaceutically acceptable salt thereof, or comprising a compound of formula:

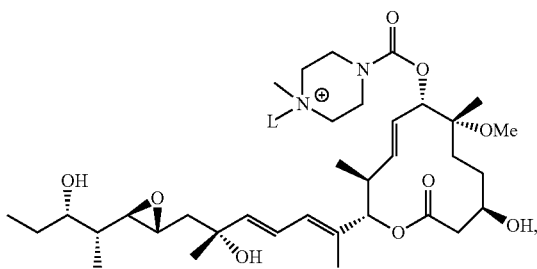

or a pharmaceutically acceptable salt thereof, wherein L is a cleavable linker comprising a cleavable moiety, wherein the cleavable moiety comprises a cleavable peptide moiety or a cleavable glucuronide moiety.

32. The composition of claim 31, wherein the cleavable peptide moiety comprises valine-alanine (Val-Ala) or valine-citrulline (Val-Cit).

33. The composition of claim 31, wherein the linker comprises a maleimide (Mal) moiety.

34. The composition of claim 33, wherein the Mal moiety comprises a maleimidocaproyl (MC).

35. The composition of claim 34, wherein the linker comprises MC-Val-Cit or MC-Val-Ala.

36. The composition of claim 31, wherein the linker comprises a spacer unit, wherein:
(a) the spacer unit comprises a polyethylene glycol (PEG) moiety, wherein the PEG moiety comprises -(PEG)$_m$- and m is an integer from 1 to 10, or
(b) the spacer unit comprises an alkyl moiety, wherein the alkyl moiety comprises —(CH$_2$)$_n$— and n is an integer from 1 to 10.

37. The composition of claim 36, wherein the spacer unit attaches to a maleimide (Mal) moiety ("Mal-spacer unit").

38. The composition of claim 37, wherein the Mal-spacer unit comprises an alkyl moiety, a PEG moiety, or a combination thereof.

39. The composition of claim 31, wherein a spacer unit attaches the cleavable moiety in the linker L to the splicing modulator.

40. The composition of claim 39, wherein the spacer unit attaching the cleavable moiety in the linker to the splicing modulator is self-immolative.

41. The composition of claim 39, wherein the spacer unit attaching the cleavable moiety in the linker to the splicing modulator comprises a p-aminobenzyl (pAB) or p-aminobenzyloxycarbonyl (pABC).

42. The composition of claim 41, wherein the pAB or pABC attaches the cleavable moiety in the linker to the splicing modulator.

43. The composition of claim 41, wherein the linker comprises Val-Cit-pAB, Val-Ala-pAB, Val-Cit-pABC or Val-Ala-pABC.

44. The composition of claim 31, wherein the linker L comprises:

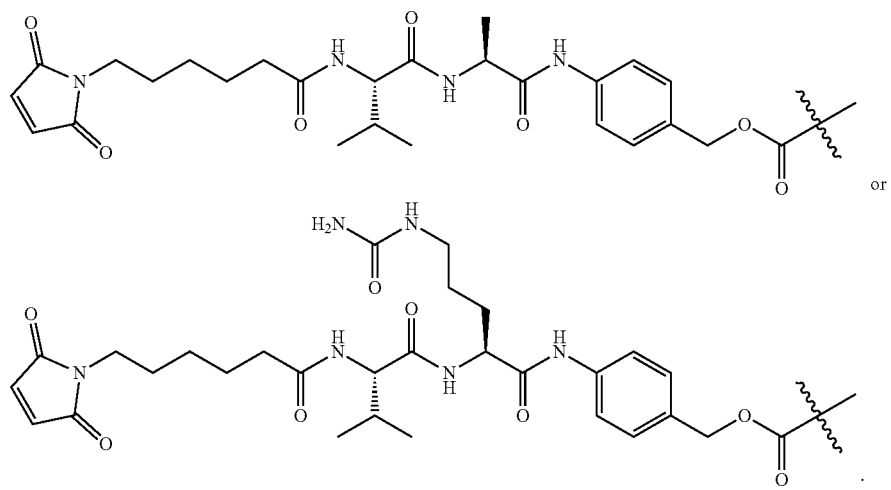

45. The antibody-drug conjugate of claim 1, wherein the antibody or antigen binding fragment targets a CEACAM5-expressing cell.

46. The antibody-drug conjugate of claim 1, wherein the antibody or antigen binding fragment targets a STEAP1-expressing cell.

* * * * *

SEQUENCE LISTING

```
<160> NUMBER OF SEQ ID NOS: 119

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Phe Asn Ile Lys Asp Thr Tyr Ile His
1               5                   10

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Arg Ile Tyr Pro Thr Asn Gly Tyr Thr Arg Tyr Ala Asp Ser Val Lys
1               5                   10                  15

Gly

<210> SEQ ID NO 3
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Trp Gly Gly Asp Gly Phe Tyr Ala Met Asp Val
1               5                   10

<210> SEQ ID NO 4
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 4

Arg Ala Ser Gln Asp Val Asn Thr Ala Val Ala Trp
1               5                   10

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Ser Ala Ser Phe Leu Glu Ser
1               5

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gln Gln His Tyr Thr Thr Pro Pro Thr
1               5

<210> SEQ ID NO 7
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Asn Tyr Trp Ile Glu
1               5

<210> SEQ ID NO 8
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ile Leu Pro Gly Thr Gly Arg Thr Ile Tyr Asn Glu Lys Phe Lys Gly
1               5                   10                  15

Lys Ala

<210> SEQ ID NO 9
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 9

Arg Asp Tyr Tyr Gly Asn Phe Tyr Tyr Ala Met Asp Tyr
1               5                   10

<210> SEQ ID NO 10
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Ala Ser Gln Gly Ile Asn Asn Tyr Leu Asn
1               5                   10

<210> SEQ ID NO 11
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Thr Ser Thr Leu Gln Ser
1               5

<210> SEQ ID NO 12
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gln Gln Tyr Ser Lys Leu Pro Arg Thr
1               5

<210> SEQ ID NO 13
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

His Tyr Met Met Ala
1               5

<210> SEQ ID NO 14
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
-continued

<400> SEQUENCE: 14

Arg Ile Gly Pro Ser Gly Gly Pro Thr His Tyr Ala Asp Ser Val Lys
1               5                   10                  15

Gly

<210> SEQ ID NO 15
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Tyr Asp Ser Gly Tyr Asp Tyr Val Ala Val Ala Gly Pro Ala Glu Tyr
1               5                   10                  15

Phe Gln His

<210> SEQ ID NO 16
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Arg Ala Ser Trp Ser Ile Ser Thr Trp Leu Ala
1               5                   10

<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Lys Ala Ser Asn Leu His Thr
1               5

<210> SEQ ID NO 18
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gln Gln Tyr Asn Ser Tyr Ser Arg Thr
1               5

<210> SEQ ID NO 19
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 20
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr
            100                 105

<210> SEQ ID NO 21
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Gln Val Gln Leu Gln Gln Ser Gly Ser Glu Leu Met Met Pro Gly Ala
1               5                   10                  15

Ser Val Lys Ile Ser Cys Lys Ala Thr Gly Tyr Thr Phe Ser Asn Tyr
            20                  25                  30

Trp Ile Gln Arg Pro Gly His Gly Leu Glu Trp Ile Gly Glu Ile Leu
            35                  40                  45

Pro Gly Thr Gly Arg Thr Ile Tyr Asn Glu Lys Phe Lys Gly Lys Ala
        50                  55                  60

Thr Phe Thr Ala Asp Ile Ser Ser Asn Thr Val Gln Met Gln Leu Ser
65                  70                  75                  80

Ser Leu Thr Ser Glu Asp Ser Ala Val Tyr Tyr Cys Ala Arg Arg Asp
                85                  90                  95

Tyr Tyr Gly Asn Phe Tyr Tyr Ala Met Asp Tyr Trp Gly Gln Gly Thr
            100                 105                 110

Ser Val Thr Val Ser Ser
        115

<210> SEQ ID NO 22
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Glu Leu Leu Ile
        35                  40                  45

Tyr Tyr Thr Ser Thr Leu Gln Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys
            100                 105

<210> SEQ ID NO 23
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Met Met Ala Trp Val Arg Gln Ala Pro Gly Lys Gly Leu Glu Trp Val
        35                  40                  45

Ser Arg Ile Gly Pro Ser Gly Gly Pro Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

-continued

```
Leu Gln Met Asn Ser Leu Arg Ala Glu Asp Thr Ala Val Tyr Tyr Cys
            85                  90                  95

Ala Gly Tyr Asp Ser Gly Tyr Asp Tyr Val Ala Val Ala Gly Pro Ala
        100                 105                 110

Glu Tyr Phe Gln His Trp Gly Gln Gly Thr Leu Val Thr Val Ser Ser
        115                 120                 125

<210> SEQ ID NO 24
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Trp
            20                  25                  30

Leu Ala Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Glu Phe Ser Leu Thr Ile Ser Gly Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105

<210> SEQ ID NO 25
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
    435                 440                 445

Pro Gly Lys
    450

<210> SEQ ID NO 26
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 441
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gln Val Gln Leu Gln Gln Ser Gly Ser Glu Leu Met Met Pro Gly Ala
1               5                   10                  15

Ser Val Lys Ile Ser Cys Lys Ala Thr Gly Tyr Thr Phe Ser Asn Tyr
            20                  25                  30

Trp Ile Gln Arg Pro Gly His Gly Leu Glu Trp Ile Gly Glu Ile Leu
        35                  40                  45

Pro Gly Thr Gly Arg Thr Ile Tyr Asn Glu Lys Phe Lys Gly Lys Ala
    50                  55                  60

Thr Phe Thr Ala Asp Ile Ser Ser Asn Thr Val Gln Met Gln Leu Ser
65                  70                  75                  80

Ser Leu Thr Ser Glu Asp Ser Ala Val Tyr Tyr Cys Ala Arg Arg Asp
                85                  90                  95

Tyr Tyr Gly Asn Phe Tyr Tyr Ala Met Asp Tyr Trp Gly Gln Gly Thr
            100                 105                 110

Ser Val Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140
```

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
            165                 170                 175

Ser Asp Leu Tyr Thr Leu Ser Ser Val Thr Val Pro Ser Ser Thr
        180                 185                 190

Trp Pro Ser Glu Thr Val Thr Cys Asn Val Ala His Pro Ala Ser Ser
            195                 200                 205

Thr Lys Val Asp Lys Lys Ile Val Pro Arg Asp Cys Gly Cys Lys Pro
210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Lys Glu Gln
            340                 345                 350

Met Ala Lys Asp Lys Val Ser Leu Thr Cys Met Ile Thr Asp Phe Phe
            355                 360                 365

Pro Glu Asp Ile Thr Val Glu Trp Gln Trp Asn Gly Gln Pro Ala Glu
        370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly
        435                 440

<210> SEQ ID NO 28
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Glu Leu Leu Ile
        35                  40                  45

-continued

```
Tyr Tyr Thr Ser Thr Leu Gln Ser Gly Val Pro Ser Arg Phe Ser Gly
     50                  55                  60

Ser Gly Ser Gly Thr Asp Tyr Ser Leu Thr Ile Ser Asn Leu Glu Pro
 65                  70                  75                  80

Glu Asp Ile Gly Thr Tyr Tyr Cys Gln Gln Tyr Ser Lys Leu Pro Arg
                 85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
        210

<210> SEQ ID NO 29
<211> LENGTH: 457
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser His Tyr
             20                  25                  30

Met Met Ala Trp Val Arg Gln Ala Pro Gly Lys Gly Leu Glu Trp Val
         35                  40                  45

Ser Arg Ile Gly Pro Ser Gly Gly Pro Thr His Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Tyr Asp Ser Gly Tyr Asp Tyr Val Ala Val Ala Gly Pro Ala
            100                 105                 110

Glu Tyr Phe Gln His Trp Gly Gln Gly Thr Leu Val Thr Val Ser Ser
        115                 120                 125

Ala Ser Thr Lys Gly Pro Ser Val Phe Pro Leu Ala Pro Ser Ser Lys
130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175
```

-continued

```
Gly Val His Thr Phe Pro Ala Val Leu Gln Ser Ser Gly Leu Tyr Ser
            180                 185                 190

Leu Ser Ser Val Val Thr Val Pro Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly
    450                 455

<210> SEQ ID NO 30
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Trp
            20                  25                  30

Leu Ala Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60
```

```
Ser Gly Ser Gly Thr Glu Phe Ser Leu Thr Ile Ser Gly Leu Gln Pro
 65                  70                  75                  80

Asp Asp Phe Ala Thr Tyr Tyr Cys Gln Gln Tyr Asn Ser Tyr Ser Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 1255
<212> TYPE: PRT
<213> ORGANISM: Homo sapiens

<400> SEQUENCE: 31

Met Glu Leu Ala Ala Leu Cys Arg Trp Gly Leu Leu Leu Ala Leu Leu
 1               5                  10                  15

Pro Pro Gly Ala Ala Ser Thr Gln Val Cys Thr Gly Thr Asp Met Lys
                 20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
 50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220
```

```
Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
        260                 265                 270

Thr Tyr Asn Thr Asp Thr Phe Glu Ser Met Pro Asn Pro Glu Gly Arg
    275                 280                 285

Tyr Thr Phe Gly Ala Ser Cys Val Thr Ala Cys Pro Tyr Asn Tyr Leu
290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640
```

-continued

Gly Cys Pro Ala Glu Gln Arg Ala Ser Pro Leu Thr Ser Ile Ile Ser
            645                 650                 655

Ala Val Val Gly Ile Leu Leu Val Val Val Leu Gly Val Phe Gly
        660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
            690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
                740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
            805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
            850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
            965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
        1010                1015                1020

Leu Val Pro Gln Gln Gly Phe Phe Cys Pro Asp Pro Ala Pro Gly
        1025                1030                1035

Ala Gly Gly Met Val His His Arg His Arg Ser Ser Ser Thr Arg
        1040                1045                1050

```
Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 32
<211> LENGTH: 310
<212> TYPE: PRT
<213> ORGANISM: Homo sapiens

<400> SEQUENCE: 32

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
                20                  25                  30

Asp Gln Asp Gly Ser Gly Asp Asp Ser Asp Asn Phe Ser Gly Ser Gly
            35                  40                  45

Ala Gly Ala Leu Gln Asp Ile Thr Leu Ser Gln Gln Thr Pro Ser Thr
    50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Leu Ala Ser Thr Thr Thr Ala Thr Thr
    130                 135                 140
```

```
Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
290                 295                 300

Gln Glu Glu Phe Tyr Ala
305                 310

<210> SEQ ID NO 33
<211> LENGTH: 976
<212> TYPE: PRT
<213> ORGANISM: Homo sapiens

<400> SEQUENCE: 33

Met Glu Leu Gln Ala Ala Arg Ala Cys Phe Ala Leu Leu Trp Gly Cys
1               5                   10                  15

Ala Leu Ala Ala Ala Ala Ala Gln Gly Lys Glu Val Val Leu Leu
            20                  25                  30

Asp Phe Ala Ala Ala Gly Gly Glu Leu Gly Trp Leu Thr His Pro Tyr
        35                  40                  45

Gly Lys Gly Trp Asp Leu Met Gln Asn Ile Met Asn Asp Met Pro Ile
    50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Ile Phe Ile
                85                  90                  95

Glu Leu Lys Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
        115                 120                 125

Asp Tyr Gly Thr Asn Phe Gln Lys Arg Leu Phe Thr Lys Ile Asp Thr
    130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190
```

-continued

```
Ser Val Arg Val Tyr Lys Lys Cys Pro Glu Leu Leu Gln Gly Leu
    195                 200                 205

Ala His Phe Pro Glu Thr Ile Ala Gly Ser Asp Ala Pro Ser Leu Ala
    210                 215                 220

Thr Val Ala Gly Thr Cys Val Asp His Ala Val Val Pro Pro Gly Gly
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
                260                 265                 270

Cys Gln Ala Cys Ser Pro Gly Phe Phe Lys Phe Glu Ala Ser Glu Ser
            275                 280                 285

Pro Cys Leu Glu Cys Pro Glu His Thr Leu Pro Ser Pro Glu Gly Ala
        290                 295                 300

Thr Ser Cys Glu Cys Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
        355                 360                 365

Cys Trp Pro Glu Ser Gly Glu Cys Gly Pro Cys Glu Ala Ser Val Arg
    370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
            420                 425                 430

Ser Ile Asn Gln Thr Glu Pro Pro Lys Val Arg Leu Glu Gly Arg Ser
        435                 440                 445

Thr Thr Ser Leu Ser Val Ser Trp Ser Ile Pro Pro Pro Gln Gln Ser
    450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
            500                 505                 510

Glu Gly Gln Gly Ala Gly Ser Lys Val His Glu Phe Gln Thr Leu Ser
        515                 520                 525

Pro Glu Gly Ser Gly Asn Leu Ala Val Ile Gly Gly Val Ala Val Gly
    530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
                565                 570                 575

Ser Lys Ser Glu Gln Leu Lys Pro Leu Lys Thr Tyr Val Asp Pro His
            580                 585                 590

Thr Tyr Glu Asp Pro Asn Gln Ala Val Leu Lys Phe Thr Thr Glu Ile
        595                 600                 605
```

```
His Pro Ser Cys Val Thr Arg Gln Lys Val Ile Ala Gly Glu Phe
    610             615                 620

Gly Glu Val Tyr Lys Gly Met Leu Lys Thr Ser Ser Gly Lys Glu
625             630                 635                 640

Val Pro Val Ala Ile Lys Thr Leu Lys Ala Gly Tyr Thr Glu Lys Gln
                645                 650                 655

Arg Val Asp Phe Leu Gly Glu Ala Gly Ile Met Gly Gln Phe Ser His
            660                 665                 670

His Asn Ile Ile Arg Leu Glu Gly Val Ile Ser Lys Tyr Lys Pro Met
        675                 680                 685

Met Ile Ile Thr Glu Tyr Met Glu Asn Gly Ala Leu Asp Lys Phe Leu
    690                 695                 700

Arg Glu Lys Asp Gly Glu Phe Ser Val Leu Gln Leu Val Gly Met Leu
705             710                 715                 720

Arg Gly Ile Ala Ala Gly Met Lys Tyr Leu Ala Asn Met Asn Tyr Val
                725                 730                 735

His Arg Asp Leu Ala Ala Arg Asn Ile Leu Val Asn Ser Asn Leu Val
            740                 745                 750

Cys Lys Val Ser Asp Phe Gly Leu Ser Arg Val Leu Glu Asp Asp Pro
        755                 760                 765

Glu Ala Thr Tyr Thr Thr Ser Gly Gly Lys Ile Pro Ile Arg Trp Thr
770             775                 780

Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
                805                 810                 815

Pro Tyr Trp Glu Leu Ser Asn His Glu Val Met Lys Ala Ile Asn Asp
            820                 825                 830

Gly Phe Arg Leu Pro Thr Pro Met Asp Cys Pro Ser Ala Ile Tyr Gln
        835                 840                 845

Leu Met Met Gln Cys Trp Gln Gln Glu Arg Ala Arg Arg Pro Lys Phe
850                 855                 860

Ala Asp Ile Val Ser Ile Leu Asp Lys Leu Ile Arg Ala Pro Asp Ser
865                 870                 875                 880

Leu Lys Thr Leu Ala Asp Phe Asp Pro Arg Val Ser Ile Arg Leu Pro
                885                 890                 895

Ser Thr Ser Gly Ser Glu Gly Val Pro Phe Arg Thr Val Ser Glu Trp
            900                 905                 910

Leu Glu Ser Ile Lys Met Gln Gln Tyr Thr Glu His Phe Met Ala Ala
        915                 920                 925

Gly Tyr Thr Ala Ile Glu Lys Val Val Gln Met Thr Asn Asp Asp Ile
    930                 935                 940

Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
                965                 970                 975

<210> SEQ ID NO 34
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 34

Gly Phe Gly Gly
1

<210> SEQ ID NO 35
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Gly Phe Leu Gly
1

<210> SEQ ID NO 36
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Ala Leu Ala Leu
1

<210> SEQ ID NO 37
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Ser Pro Thr Leu Pro Pro Arg Ser Leu
1               5

<210> SEQ ID NO 38
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

His Pro Ser Ile Lys Arg Gly Leu Ser Ser Leu
1               5                   10

<210> SEQ ID NO 39
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Leu Leu Leu Pro His His Val Leu
1               5
```

```
<210> SEQ ID NO 40
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Arg Thr Ala Pro Gly Val Arg Pro Pro Phe
1               5                   10

<210> SEQ ID NO 41
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Arg Pro Gln Lys Ser Ile Gln Ala Leu
1               5

<210> SEQ ID NO 42
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ala Pro Ala Pro Pro Pro Leu Pro Ala
1               5

<210> SEQ ID NO 43
<211> LENGTH: 630
<212> TYPE: PRT
<213> ORGANISM: Homo sapiens

<400> SEQUENCE: 43

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
                20                  25                  30

Pro Ser Arg Thr Leu Ala Gly Glu Thr Gly Gln Glu Ala Ala Pro Leu
            35                  40                  45

Asp Gly Val Leu Ala Asn Pro Pro Asn Ile Ser Ser Leu Ser Pro Arg
        50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125
```

```
Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
            420                 425                 430

Leu Asp Lys Asp Thr Leu Asp Thr Leu Thr Ala Phe Tyr Pro Gly Tyr
        435                 440                 445

Leu Cys Ser Leu Ser Pro Glu Glu Leu Ser Ser Val Pro Pro Ser Ser
    450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
            500                 505                 510

Thr Glu Asp Leu Lys Ala Leu Ser Gln Gln Asn Val Ser Met Asp Leu
        515                 520                 525

Ala Thr Phe Met Lys Leu Arg Thr Asp Ala Val Leu Pro Leu Thr Val
    530                 535                 540
```

-continued

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
            580                 585                 590

Gly Tyr Leu Val Leu Asp Leu Ser Met Gln Glu Ala Leu Ser Gly Thr
        595                 600                 605

Pro Cys Leu Leu Gly Pro Gly Pro Val Leu Thr Val Leu Ala Leu Leu
610                 615                 620

Leu Ala Ser Thr Leu Ala
625                 630

<210> SEQ ID NO 44
<211> LENGTH: 750
<212> TYPE: PRT
<213> ORGANISM: Homo sapiens

<400> SEQUENCE: 44

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
                20                  25                  30

Phe Leu Leu Gly Phe Leu Phe Gly Trp Phe Ile Lys Ser Ser Asn Glu
            35                  40                  45

Ala Thr Asn Ile Thr Pro Lys His Asn Met Lys Ala Phe Leu Asp Glu
        50                  55                  60

Leu Lys Ala Glu Asn Ile Lys Lys Phe Leu Tyr Asn Phe Thr Gln Ile
65              70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
                100                 105                 110

Tyr Asp Val Leu Leu Ser Tyr Pro Asn Lys Thr His Pro Asn Tyr Ile
            115                 120                 125

Ser Ile Ile Asn Glu Asp Gly Asn Glu Ile Phe Asn Thr Ser Leu Phe
        130                 135                 140

Glu Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

```
Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
                340                 345                 350

Thr Arg Ile Tyr Asn Val Ile Gly Thr Leu Arg Gly Ala Val Glu Pro
                355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
                420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
                500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
            530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
                580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
            610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
                660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
    690                 695                 700
```

```
Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Glu Thr Leu Ser Glu Val Ala
            740                 745                 750

<210> SEQ ID NO 45
<211> LENGTH: 790
<212> TYPE: PRT
<213> ORGANISM: Homo sapiens

<400> SEQUENCE: 45

Met Arg Thr Tyr Arg Tyr Phe Leu Leu Leu Phe Trp Val Gly Gln Pro
1               5                   10                  15

Tyr Pro Thr Leu Ser Thr Pro Leu Ser Lys Arg Thr Ser Gly Phe Pro
            20                  25                  30

Ala Lys Lys Arg Ala Leu Glu Leu Ser Gly Asn Ser Lys Asn Glu Leu
        35                  40                  45

Asn Arg Ser Lys Arg Ser Trp Met Trp Asn Gln Phe Phe Leu Leu Glu
    50                  55                  60

Glu Tyr Thr Gly Ser Asp Tyr Gln Tyr Val Gly Lys Leu His Ser Asp
65                  70                  75                  80

Gln Asp Arg Gly Asp Gly Ser Leu Lys Tyr Ile Leu Ser Gly Asp Gly
                85                  90                  95

Ala Gly Asp Leu Phe Ile Ile Asn Glu Asn Thr Gly Asp Ile Gln Ala
            100                 105                 110

Thr Lys Arg Leu Asp Arg Glu Glu Lys Pro Val Tyr Ile Leu Arg Ala
        115                 120                 125

Gln Ala Ile Asn Arg Arg Thr Gly Arg Pro Val Glu Pro Glu Ser Glu
    130                 135                 140

Phe Ile Ile Lys Ile His Asp Ile Asn Asp Asn Glu Pro Ile Phe Thr
145                 150                 155                 160

Lys Glu Val Tyr Thr Ala Thr Val Pro Glu Met Ser Asp Val Gly Thr
                165                 170                 175

Phe Val Val Gln Val Thr Ala Thr Asp Ala Asp Asp Pro Thr Tyr Gly
            180                 185                 190

Asn Ser Ala Lys Val Val Tyr Ser Ile Leu Gln Gly Gln Pro Tyr Phe
        195                 200                 205

Ser Val Glu Ser Glu Thr Gly Ile Ile Lys Thr Ala Leu Leu Asn Met
    210                 215                 220

Asp Arg Glu Asn Arg Glu Gln Tyr Gln Val Val Ile Gln Ala Lys Asp
225                 230                 235                 240

Met Gly Gly Gln Met Gly Gly Leu Ser Gly Thr Thr Thr Val Asn Ile
                245                 250                 255

Thr Leu Thr Asp Val Asn Asp Asn Pro Pro Arg Phe Pro Gln Ser Thr
            260                 265                 270

Tyr Gln Phe Lys Thr Pro Glu Ser Ser Pro Gly Thr Pro Ile Gly
        275                 280                 285

Arg Ile Lys Ala Ser Asp Ala Asp Val Gly Glu Asn Ala Glu Ile Glu
    290                 295                 300

Tyr Ser Ile Thr Asp Gly Glu Gly Leu Asp Met Phe Asp Val Ile Thr
305                 310                 315                 320

Asp Gln Glu Thr Gln Glu Gly Ile Ile Thr Val Lys Lys Leu Leu Asp
                325                 330                 335
```

```
Phe Glu Lys Lys Lys Val Tyr Thr Leu Lys Val Glu Ala Ser Asn Pro
            340                 345                 350

Tyr Val Glu Pro Arg Phe Leu Tyr Leu Gly Pro Phe Lys Asp Ser Ala
            355                 360                 365

Thr Val Arg Ile Val Val Glu Asp Val Asp Glu Pro Pro Val Phe Ser
370                 375                 380

Lys Leu Ala Tyr Ile Leu Gln Ile Arg Glu Asp Ala Gln Ile Asn Thr
385                 390                 395                 400

Thr Ile Gly Ser Val Thr Ala Gln Asp Pro Asp Ala Ala Arg Asn Pro
                405                 410                 415

Val Lys Tyr Ser Val Asp Arg His Thr Asp Met Asp Arg Ile Phe Asn
            420                 425                 430

Ile Asp Ser Gly Asn Gly Ser Ile Phe Thr Ser Lys Leu Leu Asp Arg
            435                 440                 445

Glu Thr Leu Leu Trp His Asn Ile Thr Val Ile Ala Thr Glu Ile Asn
            450                 455                 460

Asn Pro Lys Gln Ser Ser Arg Val Pro Leu Tyr Ile Lys Val Leu Asp
465                 470                 475                 480

Val Asn Asp Asn Ala Pro Glu Phe Ala Glu Phe Tyr Glu Thr Phe Val
                485                 490                 495

Cys Glu Lys Ala Lys Ala Asp Gln Leu Ile Gln Thr Leu His Ala Val
            500                 505                 510

Asp Lys Asp Asp Pro Tyr Ser Gly His Gln Phe Ser Phe Ser Leu Ala
            515                 520                 525

Pro Glu Ala Ala Ser Gly Ser Asn Phe Thr Ile Gln Asp Asn Lys Asp
            530                 535                 540

Asn Thr Ala Gly Ile Leu Thr Arg Lys Asn Gly Tyr Asn Arg His Glu
545                 550                 555                 560

Met Ser Thr Tyr Leu Leu Pro Val Val Ile Ser Asp Asn Asp Tyr Pro
                565                 570                 575

Val Gln Ser Ser Thr Gly Thr Val Thr Val Arg Val Cys Ala Cys Asp
            580                 585                 590

His His Gly Asn Met Gln Ser Cys His Ala Glu Ala Leu Ile His Pro
            595                 600                 605

Thr Gly Leu Ser Thr Gly Ala Leu Val Ala Ile Leu Leu Cys Ile Val
            610                 615                 620

Ile Leu Leu Val Thr Val Val Leu Phe Ala Ala Leu Arg Arg Gln Arg
625                 630                 635                 640

Lys Lys Glu Pro Leu Ile Ile Ser Lys Glu Asp Ile Arg Asp Asn Ile
                645                 650                 655

Val Ser Tyr Asn Asp Glu Gly Gly Gly Glu Glu Asp Thr Gln Ala Phe
            660                 665                 670

Asp Ile Gly Thr Leu Arg Asn Pro Glu Ala Ile Glu Asp Asn Lys Leu
            675                 680                 685

Arg Arg Asp Ile Val Pro Glu Ala Leu Phe Leu Pro Arg Arg Thr Pro
            690                 695                 700

Thr Ala Arg Asp Asn Thr Asp Val Arg Asp Phe Ile Asn Gln Arg Leu
705                 710                 715                 720

Lys Glu Asn Asp Thr Asp Pro Thr Ala Pro Pro Tyr Asp Ser Leu Ala
                725                 730                 735

Thr Tyr Ala Tyr Glu Gly Thr Gly Ser Val Ala Asp Ser Leu Ser Ser
            740                 745                 750
```

Leu Glu Ser Val Thr Thr Asp Ala Asp Gln Asp Tyr Asp Tyr Leu Ser
            755                 760                 765

Asp Trp Gly Pro Arg Phe Lys Lys Leu Ala Asp Met Tyr Gly Gly Val
770                 775                 780

Asp Ser Asp Lys Asp Ser
785                 790

<210> SEQ ID NO 46
<211> LENGTH: 702
<212> TYPE: PRT
<213> ORGANISM: Homo sapiens

<400> SEQUENCE: 46

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Lys Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Arg Pro Gly Val Asn
                420                 425                 430

Leu Ser Leu Ser Cys His Ala Ala Ser Asn Pro Pro Ala Gln Tyr Ser
            435                 440                 445

Trp Leu Ile Asp Gly Asn Ile Gln Gln His Thr Gln Glu Leu Phe Ile
        450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
        675                 680                 685

Val Gly Ile Met Ile Gly Val Leu Val Gly Val Ala Leu Ile
    690                 695                 700

<210> SEQ ID NO 47
<211> LENGTH: 223
<212> TYPE: PRT
<213> ORGANISM: Homo sapiens

<400> SEQUENCE: 47

```
Met Thr Trp Arg His His Val Arg Leu Leu Phe Thr Val Ser Leu Ala
1               5                   10                  15

Leu Gln Ile Ile Asn Leu Gly Asn Ser Tyr Gln Arg Glu Lys His Asn
            20                  25                  30

Gly Gly Arg Glu Glu Val Thr Lys Val Ala Thr Gln Lys His Arg Gln
        35                  40                  45

Ser Pro Leu Asn Trp Thr Ser Ser His Phe Gly Glu Val Thr Gly Ser
    50                  55                  60

Ala Glu Gly Trp Gly Pro Glu Pro Leu Pro Tyr Ser Trp Ala Phe
65                  70                  75                  80

Gly Glu Gly Ala Ser Ala Arg Pro Arg Cys Cys Arg Asn Gly Gly Thr
                85                  90                  95

Cys Val Leu Gly Ser Phe Cys Val Cys Pro Ala His Phe Thr Gly Arg
                100                 105                 110

Tyr Cys Glu His Asp Gln Arg Arg Ser Glu Cys Gly Ala Leu Glu His
            115                 120                 125

Gly Ala Trp Thr Leu Arg Ala Cys His Leu Cys Arg Cys Ile Phe Gly
        130                 135                 140

Ala Leu His Cys Leu Pro Leu Gln Thr Pro Asp Arg Cys Asp Pro Lys
145                 150                 155                 160

Asp Phe Leu Ala Ser His Ala His Gly Pro Ser Ala Gly Gly Ala Pro
                165                 170                 175

Ser Leu Leu Leu Leu Leu Pro Cys Ala Leu Leu His Arg Leu Leu Arg
                180                 185                 190

Pro Asp Ala Pro Ala His Pro Arg Ser Leu Val Pro Ser Val Leu Gln
            195                 200                 205

Arg Glu Arg Arg Pro Cys Gly Arg Pro Gly Leu Gly His Arg Leu
        210                 215                 220
```

<210> SEQ ID NO 48
<211> LENGTH: 875
<212> TYPE: PRT
<213> ORGANISM: Homo sapiens

<400> SEQUENCE: 48

```
Met Glu Ser Thr Leu Thr Leu Ala Thr Glu Gln Pro Val Lys Lys Asn
1               5                   10                  15

Thr Leu Lys Lys Tyr Lys Ile Ala Cys Ile Val Leu Leu Ala Leu Leu
            20                  25                  30

Val Ile Met Ser Leu Gly Leu Gly Leu Gly Leu Arg Lys Leu
        35                  40                  45

Glu Lys Gln Gly Ser Cys Arg Lys Lys Cys Phe Asp Ala Ser Phe Arg
    50                  55                  60

Gly Leu Glu Asn Cys Arg Cys Asp Val Ala Cys Lys Asp Arg Gly Asp
65                  70                  75                  80

Cys Cys Trp Asp Phe Glu Asp Thr Cys Val Glu Ser Thr Arg Ile Trp
                85                  90                  95

Met Cys Asn Lys Phe Arg Cys Gly Glu Thr Arg Leu Glu Ala Ser Leu
                100                 105                 110

Cys Ser Cys Ser Asp Asp Cys Leu Gln Arg Lys Asp Cys Cys Ala Asp
            115                 120                 125

Tyr Lys Ser Val Cys Gln Gly Glu Thr Ser Trp Leu Glu Glu Asn Cys
        130                 135                 140
```

```
Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
            165                 170                 175

Trp Asp Thr Leu Met Pro Asn Ile Asn Lys Leu Lys Thr Cys Gly Ile
        180                 185                 190

His Ser Lys Tyr Met Arg Ala Met Tyr Pro Thr Lys Thr Phe Pro Asn
        195                 200                 205

His Tyr Thr Ile Val Thr Gly Leu Tyr Pro Glu Ser His Gly Ile Ile
        210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro
            260                 265                 270

Gly Ser Glu Val Ala Ile Asn Gly Ser Phe Pro Ser Ile Tyr Met Pro
        275                 280                 285

Tyr Asn Gly Ser Val Pro Phe Glu Glu Arg Ile Ser Thr Leu Leu Lys
        290                 295                 300

Trp Leu Asp Leu Pro Lys Ala Glu Arg Pro Arg Phe Tyr Thr Met Tyr
305                 310                 315                 320

Phe Glu Glu Pro Asp Ser Ser Gly His Ala Gly Pro Val Ser Ala
                325                 330                 335

Arg Val Ile Lys Ala Leu Gln Val Val Asp His Ala Phe Gly Met Leu
            340                 345                 350

Met Glu Gly Leu Lys Gln Arg Asn Leu His Asn Cys Val Asn Ile Ile
        355                 360                 365

Leu Leu Ala Asp His Gly Met Asp Gln Thr Tyr Cys Asn Lys Met Glu
370                 375                 380

Tyr Met Thr Asp Tyr Phe Pro Arg Ile Asn Phe Phe Tyr Met Tyr Glu
385                 390                 395                 400

Gly Pro Ala Pro Arg Ile Arg Ala His Asn Ile Pro His Asp Phe Phe
            405                 410                 415

Ser Phe Asn Ser Glu Glu Ile Val Arg Asn Leu Ser Cys Arg Lys Pro
        420                 425                 430

Asp Gln His Phe Lys Pro Tyr Leu Thr Pro Asp Leu Pro Lys Arg Leu
        435                 440                 445

His Tyr Ala Lys Asn Val Arg Ile Asp Lys Val His Leu Phe Val Asp
        450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
            485                 490                 495

Leu Ala His Gly Pro Ser Phe Lys Glu Lys Thr Glu Val Glu Pro Phe
        500                 505                 510

Glu Asn Ile Glu Val Tyr Asn Leu Met Cys Asp Leu Leu Arg Ile Gln
        515                 520                 525

Pro Ala Pro Asn Asn Gly Thr His Gly Ser Leu Asn His Leu Leu Lys
        530                 535                 540

Val Pro Phe Tyr Glu Pro Ser His Ala Glu Glu Val Ser Lys Phe Ser
545                 550                 555                 560
```

```
Val Cys Gly Phe Ala Asn Pro Leu Pro Thr Glu Ser Leu Asp Cys Phe
                565                 570                 575

Cys Pro His Leu Gln Asn Ser Thr Gln Leu Glu Gln Val Asn Gln Met
            580                 585                 590

Leu Asn Leu Thr Gln Glu Glu Ile Thr Ala Thr Val Lys Val Asn Leu
        595                 600                 605

Pro Phe Gly Arg Pro Arg Val Leu Gln Lys Asn Val Asp His Cys Leu
    610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
                645                 650                 655

Leu Pro Pro Thr Val Pro Asp Cys Leu Arg Ala Asp Val Arg Val Pro
            660                 665                 670

Pro Ser Glu Ser Gln Lys Cys Ser Phe Tyr Leu Ala Asp Lys Asn Ile
        675                 680                 685

Thr His Gly Phe Leu Tyr Pro Pro Ala Ser Asn Arg Thr Ser Asp Ser
    690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Leu Ile Lys His
                725                 730                 735

Ala Thr Glu Arg Asn Gly Val Asn Val Ser Gly Pro Ile Phe Asp
            740                 745                 750

Tyr Asn Tyr Asp Gly His Phe Asp Ala Pro Asp Glu Ile Thr Lys His
        755                 760                 765

Leu Ala Asn Thr Asp Val Pro Ile Pro Thr His Tyr Phe Val Val Leu
    770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Glu Gly Lys Pro Glu Ala Leu Trp Val Glu Glu Arg Phe
            820                 825                 830

Thr Ala His Ile Ala Arg Val Arg Asp Val Glu Leu Leu Thr Gly Leu
        835                 840                 845

Asp Phe Tyr Gln Asp Lys Val Gln Pro Val Ser Glu Ile Leu Gln Leu
    850                 855                 860

Lys Thr Tyr Leu Pro Thr Phe Glu Thr Thr Ile
865                 870                 875

<210> SEQ ID NO 49
<211> LENGTH: 257
<212> TYPE: PRT
<213> ORGANISM: Homo sapiens

<400> SEQUENCE: 49

Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60
```

```
Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
                 85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
            115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
            195                 200                 205

Cys Ile Gln Met Trp Phe Asp Pro Ala Gln Gly Asn Pro Asn Glu Glu
210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 50
<211> LENGTH: 364
<212> TYPE: PRT
<213> ORGANISM: Homo sapiens

<400> SEQUENCE: 50

Met His Pro Gln Val Val Ile Leu Ser Leu Ile Leu His Leu Ala Asp
 1               5                  10                  15

Ser Val Ala Gly Ser Val Lys Val Gly Gly Glu Ala Gly Pro Ser Val
             20                  25                  30

Thr Leu Pro Cys His Tyr Ser Gly Ala Val Thr Ser Met Cys Trp Asn
             35                  40                  45

Arg Gly Ser Cys Ser Leu Phe Thr Cys Gln Asn Gly Ile Val Trp Thr
         50                  55                  60

Asn Gly Thr His Val Thr Tyr Arg Lys Asp Thr Arg Tyr Lys Leu Leu
 65                  70                  75                  80

Gly Asp Leu Ser Arg Arg Asp Val Ser Leu Thr Ile Glu Asn Thr Ala
                 85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
            115                 120                 125

Val Thr Thr Thr Pro Ile Val Thr Thr Val Pro Thr Val Thr Thr Val
            130                 135                 140

Arg Thr Ser Thr Thr Val Pro Thr Thr Thr Val Pro Met Thr Thr Thr
145                 150                 155                 160

Val Pro Thr Thr Thr Val Pro Thr Thr Met Ser Ile Pro Thr Thr Thr
                165                 170                 175
```

```
Thr Val Leu Thr Thr Met Thr Val Ser Thr Thr Thr Ser Val Pro Thr
            180                 185                 190

Thr Thr Ser Ile Pro Thr Thr Thr Ser Val Pro Val Thr Thr Thr Val
        195                 200                 205

Ser Thr Phe Val Pro Pro Met Pro Leu Pro Arg Gln Asn His Glu Pro
    210                 215                 220

Val Ala Thr Ser Pro Ser Ser Pro Gln Pro Ala Glu Thr His Pro Thr
225                 230                 235                 240

Thr Leu Gln Gly Ala Ile Arg Arg Glu Pro Thr Ser Ser Pro Leu Tyr
                245                 250                 255

Ser Tyr Thr Thr Asp Gly Asn Asp Thr Val Thr Glu Ser Ser Asp Gly
            260                 265                 270

Leu Trp Asn Asn Asn Gln Thr Gln Leu Phe Leu Glu His Ser Leu Leu
        275                 280                 285

Thr Ala Asn Thr Thr Lys Gly Ile Tyr Ala Gly Val Cys Ile Ser Val
    290                 295                 300

Leu Val Leu Leu Ala Leu Leu Gly Val Ile Ile Ala Lys Lys Tyr Phe
305                 310                 315                 320

Phe Lys Lys Glu Val Gln Gln Leu Ser Val Ser Phe Ser Ser Leu Gln
                325                 330                 335

Ile Lys Ala Leu Gln Asn Ala Val Glu Lys Glu Val Gln Ala Glu Asp
            340                 345                 350

Asn Ile Tyr Ile Glu Asn Ser Leu Tyr Ala Thr Asp
            355                 360

<210> SEQ ID NO 51
<211> LENGTH: 976
<212> TYPE: PRT
<213> ORGANISM: Homo sapiens

<400> SEQUENCE: 51

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Pro Ser Pro Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175
```

```
Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
            245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
        290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
            325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
        355                 360                 365

Ser Asn Ile Arg Tyr Val Ser Glu Leu His Leu Thr Arg Leu Lys Gly
        370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
            405                 410                 415

Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
        435                 440                 445

Arg Cys Ser Ala Ser Val Leu Pro Val Asp Val Gln Thr Leu Asn Ser
450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
            485                 490                 495

Val Gly Lys Thr Ser Ala Tyr Phe Asn Phe Ala Phe Lys Gly Asn Asn
        500                 505                 510

Lys Glu Gln Ile His Pro His Thr Leu Phe Thr Pro Leu Leu Ile Gly
        515                 520                 525

Phe Val Ile Val Ala Gly Met Met Cys Ile Ile Val Met Ile Leu Thr
        530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
            565                 570                 575

Pro Tyr Asp His Lys Trp Glu Phe Pro Arg Asn Arg Leu Ser Phe Gly
            580                 585                 590
```

-continued

```
Lys Thr Leu Gly Ala Gly Ala Phe Gly Lys Val Val Glu Ala Thr Ala
            595                 600                 605

Tyr Gly Leu Ile Lys Ser Asp Ala Ala Met Thr Val Ala Val Lys Met
610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
            645                 650                 655

Leu Gly Ala Cys Thr Ile Gly Gly Pro Thr Leu Val Ile Thr Glu Tyr
            660                 665                 670

Cys Cys Tyr Gly Asp Leu Leu Asn Phe Leu Arg Arg Lys Arg Asp Ser
            675                 680                 685

Phe Ile Cys Ser Lys Gln Glu Asp His Ala Glu Ala Ala Leu Tyr Lys
690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
            725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
            755                 760                 765

Leu Leu Ser Phe Ser Tyr Gln Val Ala Lys Gly Met Ala Phe Leu Ala
            770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
            805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
            835                 840                 845

Glu Ser Asp Val Trp Ser Tyr Gly Ile Phe Leu Trp Glu Leu Phe Ser
850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
            885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
            915                 920                 925

Ser Glu Ser Thr Asn His Ile Tyr Ser Asn Leu Ala Asn Cys Ser Pro
            930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
            965                 970                 975

<210> SEQ ID NO 52
<211> LENGTH: 1390
<212> TYPE: PRT
<213> ORGANISM: Homo sapiens
```

<400> SEQUENCE: 52

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His Ile Phe Leu
    50                  55                  60

Gly Ala Thr Asn Tyr Ile Tyr Val Leu Asn Glu Glu Asp Leu Gln Lys
65              70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
                100                 105                 110

Lys Asp Asn Ile Asn Met Ala Leu Val Val Asp Thr Tyr Tyr Asp Asp
            115                 120                 125

Gln Leu Ile Ser Cys Gly Ser Val Asn Arg Gly Thr Cys Gln Arg His
        130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

-continued

```
Thr Leu Leu Arg Asn Ser Ser Gly Cys Glu Ala Arg Arg Asp Glu Tyr
            405                 410                 415

Arg Thr Glu Phe Thr Thr Ala Leu Gln Arg Val Asp Leu Phe Met Gly
        420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
                515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815
```

```
Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Gly Asn Asp
    850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
        915                 920                 925

Gln Asn Phe Thr Gly Leu Ile Ala Gly Val Val Ser Ile Ser Thr Ala
    930                 935                 940

Leu Leu Leu Leu Leu Gly Phe Phe Leu Trp Leu Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
            980                 985                 990

Thr Glu Met Val Ser Asn Glu Ser Val Asp Tyr Arg Ala Thr Phe Pro
        995                 1000                1005

Glu Asp Gln Phe Pro Asn Ser Ser Gln Asn Gly Ser Cys Arg Gln
        1010            1015                1020

Val Gln Tyr Pro Leu Thr Asp Met Ser Pro Ile Leu Thr Ser Gly
        1025            1030                1035

Asp Ser Asp Ile Ser Ser Pro Leu Leu Gln Asn Thr Val His Ile
        1040            1045                1050

Asp Leu Ser Ala Leu Asn Pro Glu Leu Val Gln Ala Val Gln His
        1055            1060                1065

Val Val Ile Gly Pro Ser Ser Leu Ile Val His Phe Asn Glu Val
        1070            1075                1080

Ile Gly Arg Gly His Phe Gly Cys Val Tyr His Gly Thr Leu Leu
        1085            1090                1095

Asp Asn Asp Gly Lys Lys Ile His Cys Ala Val Lys Ser Leu Asn
        1100            1105                1110

Arg Ile Thr Asp Ile Gly Glu Val Ser Gln Phe Leu Thr Glu Gly
        1115            1120                1125

Ile Ile Met Lys Asp Phe Ser His Pro Asn Val Leu Ser Leu Leu
        1130            1135                1140

Gly Ile Cys Leu Arg Ser Glu Gly Ser Pro Leu Val Val Leu Pro
        1145            1150                1155

Tyr Met Lys His Gly Asp Leu Arg Asn Phe Ile Arg Asn Glu Thr
        1160            1165                1170

His Asn Pro Thr Val Lys Asp Leu Ile Gly Phe Gly Leu Gln Val
        1175            1180                1185

Ala Lys Gly Met Lys Tyr Leu Ala Ser Lys Lys Phe Val His Arg
        1190            1195                1200

Asp Leu Ala Ala Arg Asn Cys Met Leu Asp Glu Lys Phe Thr Val
        1205            1210                1215
```

```
Lys Val Ala Asp Phe Gly Leu Ala Arg Asp Met Tyr Asp Lys Glu
1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
1250                1255                1260

Ser Asp Val Trp Ser Phe Gly Val Leu Leu Trp Glu Leu Met Thr
1265                1270                1275

Arg Gly Ala Pro Pro Tyr Pro Asp Val Asn Thr Phe Asp Ile Thr
1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
1310                1315                1320

Ala Glu Met Arg Pro Ser Phe Ser Glu Leu Val Ser Arg Ile Ser
1325                1330                1335

Ala Ile Phe Ser Thr Phe Ile Gly Glu His Tyr Val His Val Asn
1340                1345                1350

Ala Thr Tyr Val Asn Val Lys Cys Val Ala Pro Tyr Pro Ser Leu
1355                1360                1365

Leu Ser Ser Glu Asp Asn Ala Asp Asp Glu Val Asp Thr Arg Pro
1370                1375                1380

Ala Ser Phe Trp Glu Thr Ser
1385                1390

<210> SEQ ID NO 53
<211> LENGTH: 14507
<212> TYPE: PRT
<213> ORGANISM: Homo sapiens

<400> SEQUENCE: 53

Met Leu Lys Pro Ser Gly Leu Pro Gly Ser Ser Pro Thr Arg Ser
1                   5                   10                  15

Leu Met Thr Gly Ser Arg Ser Thr Lys Ala Thr Pro Glu Met Asp Ser
            20                  25                  30

Gly Leu Thr Gly Ala Thr Leu Ser Pro Lys Thr Ser Thr Gly Ala Ile
        35                  40                  45

Val Val Thr Glu His Thr Leu Pro Phe Thr Ser Pro Asp Lys Thr Leu
    50                  55                  60

Ala Ser Pro Thr Ser Ser Val Val Gly Arg Thr Thr Gln Ser Leu Gly
65                  70                  75                  80

Val Met Ser Ser Ala Leu Pro Glu Ser Thr Ser Arg Gly Met Thr His
                85                  90                  95

Ser Glu Gln Arg Thr Ser Pro Ser Leu Ser Pro Gln Val Asn Gly Thr
            100                 105                 110

Pro Ser Arg Asn Tyr Pro Ala Thr Ser Met Val Ser Gly Leu Ser Ser
        115                 120                 125

Pro Arg Thr Arg Thr Ser Ser Thr Glu Gly Asn Phe Thr Lys Glu Ala
        130                 135                 140

Ser Thr Tyr Thr Leu Thr Val Glu Thr Ser Gly Pro Val Thr Glu
145                 150                 155                 160

Lys Tyr Thr Val Pro Thr Glu Ser Thr Thr Glu Gly Asp Ser Thr
                165                 170                 175
```

-continued

```
Glu Thr Pro Trp Asp Thr Arg Tyr Ile Pro Val Lys Ile Thr Ser Pro
            180                 185                 190

Met Lys Thr Phe Ala Asp Ser Thr Ala Ser Lys Glu Asn Ala Pro Val
        195                 200                 205

Ser Met Thr Pro Ala Glu Thr Thr Val Thr Asp Ser His Thr Pro Gly
    210                 215                 220

Arg Thr Asn Pro Ser Phe Gly Thr Leu Tyr Ser Ser Phe Leu Asp Leu
225                 230                 235                 240

Ser Pro Lys Gly Thr Pro Asn Ser Arg Gly Glu Thr Ser Leu Glu Leu
                245                 250                 255

Ile Leu Ser Thr Thr Gly Tyr Pro Phe Ser Ser Pro Glu Pro Gly Ser
            260                 265                 270

Ala Gly His Ser Arg Ile Ser Thr Ser Ala Pro Leu Ser Ser Ser Ala
        275                 280                 285

Ser Val Leu Asp Asn Lys Ile Ser Glu Thr Ser Ile Phe Ser Gly Gln
    290                 295                 300

Ser Leu Thr Ser Pro Leu Ser Pro Gly Val Pro Glu Ala Arg Ala Ser
305                 310                 315                 320

Thr Met Pro Asn Ser Ala Ile Pro Phe Ser Met Thr Leu Ser Asn Ala
                325                 330                 335

Glu Thr Ser Ala Glu Arg Val Arg Ser Thr Ile Ser Ser Leu Gly Thr
            340                 345                 350

Pro Ser Ile Ser Thr Lys Gln Thr Ala Glu Thr Ile Leu Thr Phe His
        355                 360                 365

Ala Phe Ala Glu Thr Met Asp Ile Pro Ser Thr His Ile Ala Lys Thr
    370                 375                 380

Leu Ala Ser Glu Trp Leu Gly Ser Pro Gly Thr Leu Gly Gly Thr Ser
385                 390                 395                 400

Thr Ser Ala Leu Thr Thr Thr Ser Pro Ser Thr Thr Leu Val Ser Glu
                405                 410                 415

Glu Thr Asn Thr His His Ser Thr Ser Gly Lys Glu Thr Glu Gly Thr
            420                 425                 430

Leu Asn Thr Ser Met Thr Pro Leu Glu Thr Ser Ala Pro Gly Glu Glu
        435                 440                 445

Ser Glu Met Thr Ala Thr Leu Val Pro Thr Leu Gly Phe Thr Thr Leu
    450                 455                 460

Asp Ser Lys Ile Arg Ser Pro Ser Gln Val Ser Ser Ser His Pro Thr
465                 470                 475                 480

Arg Glu Leu Arg Thr Thr Gly Ser Thr Ser Gly Arg Gln Ser Ser Ser
                485                 490                 495

Thr Ala Ala His Gly Ser Ser Asp Ile Leu Arg Ala Thr Thr Ser Ser
            500                 505                 510

Thr Ser Lys Ala Ser Ser Trp Thr Ser Glu Ser Thr Ala Gln Gln Phe
        515                 520                 525

Ser Glu Pro Gln His Thr Gln Trp Val Glu Thr Ser Pro Ser Met Lys
    530                 535                 540

Thr Glu Arg Pro Pro Ala Ser Thr Ser Val Ala Ala Pro Ile Thr Thr
545                 550                 555                 560

Ser Val Pro Ser Val Val Ser Gly Phe Thr Thr Leu Lys Thr Ser Ser
                565                 570                 575

Thr Lys Gly Ile Trp Leu Glu Glu Thr Ser Ala Asp Thr Leu Ile Gly
            580                 585                 590
```

-continued

```
Glu Ser Thr Ala Gly Pro Thr Thr His Gln Phe Ala Val Pro Thr Gly
                595                 600                 605

Ile Ser Met Thr Gly Gly Ser Ser Thr Arg Gly Ser Gln Gly Thr Thr
            610                 615                 620

His Leu Leu Thr Arg Ala Thr Ala Ser Ser Glu Thr Ser Ala Asp Leu
625                 630                 635                 640

Thr Leu Ala Thr Asn Gly Val Pro Val Ser Val Ser Pro Ala Val Ser
                645                 650                 655

Lys Thr Ala Ala Gly Ser Ser Pro Gly Gly Thr Lys Pro Ser Tyr
                660                 665                 670

Thr Met Val Ser Ser Val Ile Pro Glu Thr Ser Ser Leu Gln Ser Ser
                675                 680                 685

Ala Phe Arg Glu Gly Thr Ser Leu Gly Leu Thr Pro Leu Asn Thr Arg
            690                 695                 700

His Pro Phe Ser Ser Pro Glu Pro Asp Ser Ala Gly His Thr Lys Ile
705                 710                 715                 720

Ser Thr Ser Ile Pro Leu Leu Ser Ala Ser Val Leu Glu Asp Lys
                725                 730                 735

Val Ser Ala Thr Ser Thr Phe Ser His His Lys Ala Thr Ser Ser Ile
                740                 745                 750

Thr Thr Gly Thr Pro Glu Ile Ser Thr Lys Thr Lys Pro Ser Ser Ala
            755                 760                 765

Val Leu Ser Ser Met Thr Leu Ser Asn Ala Ala Thr Ser Pro Glu Arg
            770                 775                 780

Val Arg Asn Ala Thr Ser Pro Leu Thr His Pro Ser Pro Ser Gly Glu
785                 790                 795                 800

Glu Thr Ala Gly Ser Val Leu Thr Leu Ser Thr Ser Ala Glu Thr Thr
                805                 810                 815

Asp Ser Pro Asn Ile His Pro Thr Gly Thr Leu Thr Ser Glu Ser Ser
            820                 825                 830

Glu Ser Pro Ser Thr Leu Ser Leu Pro Ser Val Ser Gly Val Lys Thr
            835                 840                 845

Thr Phe Ser Ser Ser Thr Pro Ser Thr His Leu Phe Thr Ser Gly Glu
            850                 855                 860

Glu Thr Glu Glu Thr Ser Asn Pro Ser Val Ser Gln Pro Glu Thr Ser
865                 870                 875                 880

Val Ser Arg Val Arg Thr Thr Leu Ala Ser Thr Ser Val Pro Thr Pro
                885                 890                 895

Val Phe Pro Thr Met Asp Thr Trp Pro Thr Arg Ser Ala Gln Phe Ser
                900                 905                 910

Ser Ser His Leu Val Ser Glu Leu Arg Ala Thr Ser Ser Thr Ser Val
            915                 920                 925

Thr Asn Ser Thr Gly Ser Ala Leu Pro Lys Ile Ser His Leu Thr Gly
            930                 935                 940

Thr Ala Thr Met Ser Gln Thr Asn Arg Asp Thr Phe Asn Asp Ser Ala
945                 950                 955                 960

Ala Pro Gln Ser Thr Thr Trp Pro Glu Thr Ser Pro Arg Phe Lys Thr
                965                 970                 975

Gly Leu Pro Ser Ala Thr Thr Thr Val Ser Thr Ser Ala Thr Ser Leu
            980                 985                 990

Ser Ala Thr Val Met Val Ser Lys  Phe Thr Ser Pro Ala  Thr Ser Ser
            995                 1000                1005
```

```
Met Glu Ala Thr Ser Ile Arg Glu Pro Ser Thr Thr Ile Leu Thr
    1010            1015            1020

Thr Glu Thr Thr Asn Gly Pro Gly Ser Met Ala Val Ala Ser Thr
    1025            1030            1035

Asn Ile Pro Ile Gly Lys Gly Tyr Ile Thr Glu Gly Arg Leu Asp
    1040            1045            1050

Thr Ser His Leu Pro Ile Gly Thr Thr Ala Ser Ser Glu Thr Ser
    1055            1060            1065

Met Asp Phe Thr Met Ala Lys Glu Ser Val Ser Met Ser Val Ser
    1070            1075            1080

Pro Ser Gln Ser Met Asp Ala Ala Gly Ser Ser Thr Pro Gly Arg
    1085            1090            1095

Thr Ser Gln Phe Val Asp Thr Phe Ser Asp Asp Val Tyr His Leu
    1100            1105            1110

Thr Ser Arg Glu Ile Thr Ile Pro Arg Asp Gly Thr Ser Ser Ala
    1115            1120            1125

Leu Thr Pro Gln Met Thr Ala Thr His Pro Pro Ser Pro Asp Pro
    1130            1135            1140

Gly Ser Ala Arg Ser Thr Trp Leu Gly Ile Leu Ser Ser Ser Pro
    1145            1150            1155

Ser Ser Pro Thr Pro Lys Val Thr Met Ser Ser Thr Phe Ser Thr
    1160            1165            1170

Gln Arg Val Thr Thr Ser Met Ile Met Asp Thr Val Glu Thr Ser
    1175            1180            1185

Arg Trp Asn Met Pro Asn Leu Pro Ser Thr Thr Ser Leu Thr Pro
    1190            1195            1200

Ser Asn Ile Pro Thr Ser Gly Ala Ile Gly Lys Ser Thr Leu Val
    1205            1210            1215

Pro Leu Asp Thr Pro Ser Pro Ala Thr Ser Leu Glu Ala Ser Glu
    1220            1225            1230

Gly Gly Leu Pro Thr Leu Ser Thr Tyr Pro Glu Ser Thr Asn Thr
    1235            1240            1245

Pro Ser Ile His Leu Gly Ala His Ala Ser Ser Glu Ser Pro Ser
    1250            1255            1260

Thr Ile Lys Leu Thr Met Ala Ser Val Val Lys Pro Gly Ser Tyr
    1265            1270            1275

Thr Pro Leu Thr Phe Pro Ser Ile Glu Thr His Ile His Val Ser
    1280            1285            1290

Thr Ala Arg Met Ala Tyr Ser Ser Gly Ser Ser Pro Glu Met Thr
    1295            1300            1305

Ala Pro Gly Glu Thr Asn Thr Gly Ser Thr Trp Asp Pro Thr Thr
    1310            1315            1320

Tyr Ile Thr Thr Thr Asp Pro Lys Asp Thr Ser Ser Ala Gln Val
    1325            1330            1335

Ser Thr Pro His Ser Val Arg Thr Leu Arg Thr Thr Glu Asn His
    1340            1345            1350

Pro Lys Thr Glu Ser Ala Thr Pro Ala Ala Tyr Ser Gly Ser Pro
    1355            1360            1365

Lys Ile Ser Ser Ser Pro Asn Leu Thr Ser Pro Ala Thr Lys Ala
    1370            1375            1380

Trp Thr Ile Thr Asp Thr Thr Glu His Ser Thr Gln Leu His Tyr
    1385            1390            1395
```

```
Thr Lys Leu Ala Glu Lys Ser Ser Gly Phe Glu Thr Gln Ser Ala
    1400                1405                1410

Pro Gly Pro Val Ser Val Val Ile Pro Thr Ser Pro Thr Ile Gly
    1415                1420                1425

Ser Ser Thr Leu Glu Leu Thr Ser Asp Val Pro Gly Glu Pro Leu
    1430                1435                1440

Val Leu Ala Pro Ser Glu Gln Thr Thr Ile Thr Leu Pro Met Ala
    1445                1450                1455

Thr Trp Leu Ser Thr Ser Leu Thr Glu Glu Met Ala Ser Thr Asp
    1460                1465                1470

Leu Asp Ile Ser Ser Pro Ser Ser Pro Met Ser Thr Phe Ala Ile
    1475                1480                1485

Phe Pro Pro Met Ser Thr Pro Ser His Glu Leu Ser Lys Ser Glu
    1490                1495                1500

Ala Asp Thr Ser Ala Ile Arg Asn Thr Asp Ser Thr Thr Leu Asp
    1505                1510                1515

Gln His Leu Gly Ile Arg Ser Leu Gly Arg Thr Gly Asp Leu Thr
    1520                1525                1530

Thr Val Pro Ile Thr Pro Leu Thr Thr Thr Trp Thr Ser Val Ile
    1535                1540                1545

Glu His Ser Thr Gln Ala Gln Asp Thr Leu Ser Ala Thr Met Ser
    1550                1555                1560

Pro Thr His Val Thr Gln Ser Leu Lys Asp Gln Thr Ser Ile Pro
    1565                1570                1575

Ala Ser Ala Ser Pro Ser His Leu Thr Glu Val Tyr Pro Glu Leu
    1580                1585                1590

Gly Thr Gln Gly Arg Ser Ser Glu Ala Thr Thr Phe Trp Lys
    1595                1600                1605

Pro Ser Thr Asp Thr Leu Ser Arg Glu Ile Glu Thr Gly Pro Thr
    1610                1615                1620

Asn Ile Gln Ser Thr Pro Pro Met Asp Asn Thr Thr Thr Gly Ser
    1625                1630                1635

Ser Ser Ser Gly Val Thr Leu Gly Ile Ala His Leu Pro Ile Gly
    1640                1645                1650

Thr Ser Ser Pro Ala Glu Thr Ser Thr Asn Met Ala Leu Glu Arg
    1655                1660                1665

Arg Ser Ser Thr Ala Thr Val Ser Met Ala Gly Thr Met Gly Leu
    1670                1675                1680

Leu Val Thr Ser Ala Pro Gly Arg Ser Ile Ser Gln Ser Leu Gly
    1685                1690                1695

Arg Val Ser Ser Val Leu Ser Glu Ser Thr Thr Glu Gly Val Thr
    1700                1705                1710

Asp Ser Ser Lys Gly Ser Ser Pro Arg Leu Asn Thr Gln Gly Asn
    1715                1720                1725

Thr Ala Leu Ser Ser Ser Leu Glu Pro Ser Tyr Ala Glu Gly Ser
    1730                1735                1740

Gln Met Ser Thr Ser Ile Pro Leu Thr Ser Ser Pro Thr Thr Pro
    1745                1750                1755

Asp Val Glu Phe Ile Gly Gly Ser Thr Phe Trp Thr Lys Glu Val
    1760                1765                1770

Thr Thr Val Met Thr Ser Asp Ile Ser Lys Ser Ser Ala Arg Thr
    1775                1780                1785
```

```
Glu Ser Ser Ser Ala Thr Leu Met Ser Thr Ala Leu Gly Ser Thr
    1790            1795                1800

Glu Asn Thr Gly Lys Glu Lys Leu Arg Thr Ala Ser Met Asp Leu
    1805            1810                1815

Pro Ser Pro Thr Pro Ser Met Glu Val Thr Pro Trp Ile Ser Leu
    1820            1825                1830

Thr Leu Ser Asn Ala Pro Asn Thr Thr Asp Ser Leu Asp Leu Ser
    1835            1840                1845

His Gly Val His Thr Ser Ser Ala Gly Thr Leu Ala Thr Asp Arg
    1850            1855                1860

Ser Leu Asn Thr Gly Val Thr Arg Ala Ser Arg Leu Glu Asn Gly
    1865            1870                1875

Ser Asp Thr Ser Ser Lys Ser Leu Ser Met Gly Asn Ser Thr His
    1880            1885                1890

Thr Ser Met Thr Tyr Thr Glu Lys Ser Glu Val Ser Ser Ser Ile
    1895            1900                1905

His Pro Arg Pro Glu Thr Ser Ala Pro Gly Ala Glu Thr Thr Leu
    1910            1915                1920

Thr Ser Thr Pro Gly Asn Arg Ala Ile Ser Leu Thr Leu Pro Phe
    1925            1930                1935

Ser Ser Ile Pro Val Glu Glu Val Ile Ser Thr Gly Ile Thr Ser
    1940            1945                1950

Gly Pro Asp Ile Asn Ser Ala Pro Met Thr His Ser Pro Ile Thr
    1955            1960                1965

Pro Pro Thr Ile Val Trp Thr Ser Thr Gly Thr Ile Glu Gln Ser
    1970            1975                1980

Thr Gln Pro Leu His Ala Val Ser Ser Glu Lys Val Ser Val Gln
    1985            1990                1995

Thr Gln Ser Thr Pro Tyr Val Asn Ser Val Ala Val Ser Ala Ser
    2000            2005                2010

Pro Thr His Glu Asn Ser Val Ser Ser Gly Ser Ser Thr Ser Ser
    2015            2020                2025

Pro Tyr Ser Ser Ala Ser Leu Glu Ser Leu Asp Ser Thr Ile Ser
    2030            2035                2040

Arg Arg Asn Ala Ile Thr Ser Trp Leu Trp Asp Leu Thr Thr Ser
    2045            2050                2055

Leu Pro Thr Thr Thr Trp Pro Ser Thr Ser Leu Ser Glu Ala Leu
    2060            2065                2070

Ser Ser Gly His Ser Gly Val Ser Asn Pro Ser Ser Thr Thr Thr
    2075            2080                2085

Glu Phe Pro Leu Phe Ser Ala Ala Ser Thr Ser Ala Ala Lys Gln
    2090            2095                2100

Arg Asn Pro Glu Thr Glu Thr His Gly Pro Gln Asn Thr Ala Ala
    2105            2110                2115

Ser Thr Leu Asn Thr Asp Ala Ser Ser Val Thr Gly Leu Ser Glu
    2120            2125                2130

Thr Pro Val Gly Ala Ser Ile Ser Ser Glu Val Pro Leu Pro Met
    2135            2140                2145

Ala Ile Thr Ser Arg Ser Asp Val Ser Gly Leu Thr Ser Glu Ser
    2150            2155                2160

Thr Ala Asn Pro Ser Leu Gly Thr Ala Ser Ser Ala Gly Thr Lys
    2165            2170                2175
```

```
Leu Thr Arg Thr Ile Ser Leu Pro Thr Ser Glu Ser Leu Val Ser
    2180            2185            2190

Phe Arg Met Asn Lys Asp Pro Trp Thr Val Ser Ile Pro Leu Gly
    2195            2200            2205

Ser His Pro Thr Thr Asn Thr Glu Thr Ser Ile Pro Val Asn Ser
    2210            2215            2220

Ala Gly Pro Pro Gly Leu Ser Thr Val Ala Ser Asp Val Ile Asp
    2225            2230            2235

Thr Pro Ser Asp Gly Ala Glu Ser Ile Pro Thr Val Ser Phe Ser
    2240            2245            2250

Pro Ser Pro Asp Thr Glu Val Thr Thr Ile Ser His Phe Pro Glu
    2255            2260            2265

Lys Thr Thr His Ser Phe Arg Thr Ile Ser Ser Leu Thr His Glu
    2270            2275            2280

Leu Thr Ser Arg Val Thr Pro Ile Pro Gly Asp Trp Met Ser Ser
    2285            2290            2295

Ala Met Ser Thr Lys Pro Thr Gly Ala Ser Pro Ser Ile Thr Leu
    2300            2305            2310

Gly Glu Arg Arg Thr Ile Thr Ser Ala Ala Pro Thr Thr Ser Pro
    2315            2320            2325

Ile Val Leu Thr Ala Ser Phe Thr Glu Thr Ser Thr Val Ser Leu
    2330            2335            2340

Asp Asn Glu Thr Thr Val Lys Thr Ser Asp Ile Leu Asp Ala Arg
    2345            2350            2355

Lys Thr Asn Glu Leu Pro Ser Asp Ser Ser Ser Ser Ser Asp Leu
    2360            2365            2370

Ile Asn Thr Ser Ile Ala Ser Ser Thr Met Asp Val Thr Lys Thr
    2375            2380            2385

Ala Ser Ile Ser Pro Thr Ser Ile Ser Gly Met Thr Ala Ser Ser
    2390            2395            2400

Ser Pro Ser Leu Phe Ser Ser Asp Arg Pro Gln Val Pro Thr Ser
    2405            2410            2415

Thr Thr Glu Thr Asn Thr Ala Thr Ser Pro Ser Val Ser Ser Asn
    2420            2425            2430

Thr Tyr Ser Leu Asp Gly Gly Ser Asn Val Gly Gly Thr Pro Ser
    2435            2440            2445

Thr Leu Pro Pro Phe Thr Ile Thr His Pro Val Glu Thr Ser Ser
    2450            2455            2460

Ala Leu Leu Ala Trp Ser Arg Pro Val Arg Thr Phe Ser Thr Met
    2465            2470            2475

Val Ser Thr Asp Thr Ala Ser Gly Glu Asn Pro Thr Ser Ser Asn
    2480            2485            2490

Ser Val Val Thr Ser Val Pro Ala Pro Gly Thr Trp Thr Ser Val
    2495            2500            2505

Gly Ser Thr Thr Asp Leu Pro Ala Met Gly Phe Leu Lys Thr Ser
    2510            2515            2520

Pro Ala Gly Glu Ala His Ser Leu Leu Ala Ser Thr Ile Glu Pro
    2525            2530            2535

Ala Thr Ala Phe Thr Pro His Leu Ser Ala Ala Val Val Thr Gly
    2540            2545            2550

Ser Ser Ala Thr Ser Glu Ala Ser Leu Leu Thr Thr Ser Glu Ser
    2555            2560            2565
```

```
Lys Ala Ile His Ser Ser Pro Gln Thr Pro Thr Thr Pro Thr Ser
2570                2575                2580

Gly Ala Asn Trp Glu Thr Ser Ala Thr Pro Glu Ser Leu Leu Val
2585                2590                2595

Val Thr Glu Thr Ser Asp Thr Thr Leu Thr Ser Lys Ile Leu Val
2600                2605                2610

Thr Asp Thr Ile Leu Phe Ser Thr Val Ser Thr Pro Pro Ser Lys
2615                2620                2625

Phe Pro Ser Thr Gly Thr Leu Ser Gly Ala Ser Phe Pro Thr Leu
2630                2635                2640

Leu Pro Asp Thr Pro Ala Ile Pro Leu Thr Ala Thr Glu Pro Thr
2645                2650                2655

Ser Ser Leu Ala Thr Ser Phe Asp Ser Thr Pro Leu Val Thr Ile
2660                2665                2670

Ala Ser Asp Ser Leu Gly Thr Val Pro Glu Thr Thr Leu Thr Met
2675                2680                2685

Ser Glu Thr Ser Asn Gly Asp Ala Leu Val Leu Lys Thr Val Ser
2690                2695                2700

Asn Pro Asp Arg Ser Ile Pro Gly Ile Thr Ile Gln Gly Val Thr
2705                2710                2715

Glu Ser Pro Leu His Pro Ser Ser Thr Ser Pro Ser Lys Ile Val
2720                2725                2730

Ala Pro Arg Asn Thr Thr Tyr Glu Gly Ser Ile Thr Val Ala Leu
2735                2740                2745

Ser Thr Leu Pro Ala Gly Thr Thr Gly Ser Leu Val Phe Ser Gln
2750                2755                2760

Ser Ser Glu Asn Ser Glu Thr Thr Ala Leu Val Asp Ser Ser Ala
2765                2770                2775

Gly Leu Glu Arg Ala Ser Val Met Pro Leu Thr Thr Gly Ser Gln
2780                2785                2790

Gly Met Ala Ser Ser Gly Gly Ile Arg Ser Gly Ser Thr His Ser
2795                2800                2805

Thr Gly Thr Lys Thr Phe Ser Ser Leu Pro Leu Thr Met Asn Pro
2810                2815                2820

Gly Glu Val Thr Ala Met Ser Glu Ile Thr Thr Asn Arg Leu Thr
2825                2830                2835

Ala Thr Gln Ser Thr Ala Pro Lys Gly Ile Pro Val Lys Pro Thr
2840                2845                2850

Ser Ala Glu Ser Gly Leu Leu Thr Pro Val Ser Ala Ser Ser Ser
2855                2860                2865

Pro Ser Lys Ala Phe Ala Ser Leu Thr Thr Ala Pro Pro Thr Trp
2870                2875                2880

Gly Ile Pro Gln Ser Thr Leu Thr Phe Glu Phe Ser Glu Val Pro
2885                2890                2895

Ser Leu Asp Thr Lys Ser Ala Ser Leu Pro Thr Pro Gly Gln Ser
2900                2905                2910

Leu Asn Thr Ile Pro Asp Ser Asp Ala Ser Thr Ala Ser Ser Ser
2915                2920                2925

Leu Ser Lys Ser Pro Glu Lys Asn Pro Arg Ala Arg Met Met Thr
2930                2935                2940

Ser Thr Lys Ala Ile Ser Ala Ser Ser Phe Gln Ser Thr Gly Phe
2945                2950                2955
```

-continued

```
Thr Glu Thr Pro Glu Gly Ser Ala Ser Pro Ser Met Ala Gly His
2960                2965                2970

Glu Pro Arg Val Pro Thr Ser Gly Thr Gly Asp Pro Arg Tyr Ala
2975                2980                2985

Ser Glu Ser Met Ser Tyr Pro Asp Pro Ser Lys Ala Ser Ser Ala
2990                2995                3000

Met Thr Ser Thr Ser Leu Ala Ser Lys Leu Thr Thr Leu Phe Ser
3005                3010                3015

Thr Gly Gln Ala Ala Arg Ser Gly Ser Ser Ser Pro Ile Ser
3020                3025                3030

Leu Ser Thr Glu Lys Glu Thr Ser Phe Leu Ser Pro Thr Ala Ser
3035                3040                3045

Thr Ser Arg Lys Thr Ser Leu Phe Leu Gly Pro Ser Met Ala Arg
3050                3055                3060

Gln Pro Asn Ile Leu Val His Leu Gln Thr Ser Ala Leu Thr Leu
3065                3070                3075

Ser Pro Thr Ser Thr Leu Asn Met Ser Gln Glu Glu Pro Pro Glu
3080                3085                3090

Leu Thr Ser Ser Gln Thr Ile Ala Glu Glu Gly Thr Thr Ala
3095                3100                3105

Glu Thr Gln Thr Leu Thr Phe Thr Pro Ser Glu Thr Pro Thr Ser
3110                3115                3120

Leu Leu Pro Val Ser Ser Pro Thr Glu Pro Thr Ala Arg Arg Lys
3125                3130                3135

Ser Ser Pro Glu Thr Trp Ala Ser Ser Ile Ser Val Pro Ala Lys
3140                3145                3150

Thr Ser Leu Val Glu Thr Thr Asp Gly Thr Leu Val Thr Thr Ile
3155                3160                3165

Lys Met Ser Ser Gln Ala Ala Gln Gly Asn Ser Thr Trp Pro Ala
3170                3175                3180

Pro Ala Glu Glu Thr Gly Ser Ser Pro Ala Gly Thr Ser Pro Gly
3185                3190                3195

Ser Pro Glu Met Ser Thr Thr Leu Lys Ile Met Ser Ser Lys Glu
3200                3205                3210

Pro Ser Ile Ser Pro Glu Ile Arg Ser Thr Val Arg Asn Ser Pro
3215                3220                3225

Trp Lys Thr Pro Glu Thr Thr Val Pro Met Glu Thr Thr Val Glu
3230                3235                3240

Pro Val Thr Leu Gln Ser Thr Ala Leu Gly Ser Gly Ser Thr Ser
3245                3250                3255

Ile Ser His Leu Pro Thr Gly Thr Thr Ser Pro Thr Lys Ser Pro
3260                3265                3270

Thr Glu Asn Met Leu Ala Thr Glu Arg Val Ser Leu Ser Pro Ser
3275                3280                3285

Pro Pro Glu Ala Trp Thr Asn Leu Tyr Ser Gly Thr Pro Gly Gly
3290                3295                3300

Thr Arg Gln Ser Leu Ala Thr Met Ser Ser Val Ser Leu Glu Ser
3305                3310                3315

Pro Thr Ala Arg Ser Ile Thr Gly Thr Gly Gln Gln Ser Ser Pro
3320                3325                3330

Glu Leu Val Ser Lys Thr Thr Gly Met Glu Phe Ser Met Trp His
3335                3340                3345
```

```
Gly Ser Thr Gly Gly Thr Gly Asp Thr His Val Ser Leu Ser
    3350            3355            3360

Thr Ser Ser Asn Ile Leu Glu Asp Pro Val Thr Ser Pro Asn Ser
    3365            3370            3375

Val Ser Ser Leu Thr Asp Lys Ser Lys His Lys Thr Glu Thr Trp
    3380            3385            3390

Val Ser Thr Thr Ala Ile Pro Ser Thr Val Leu Asn Asn Lys Ile
    3395            3400            3405

Met Ala Ala Glu Gln Gln Thr Ser Arg Ser Val Asp Glu Ala Tyr
    3410            3415            3420

Ser Ser Thr Ser Ser Trp Ser Asp Gln Thr Ser Gly Ser Asp Ile
    3425            3430            3435

Thr Leu Gly Ala Ser Pro Asp Val Thr Asn Thr Leu Tyr Ile Thr
    3440            3445            3450

Ser Thr Ala Gln Thr Thr Ser Leu Val Ser Leu Pro Ser Gly Asp
    3455            3460            3465

Gln Gly Ile Thr Ser Leu Thr Asn Pro Ser Gly Gly Lys Thr Ser
    3470            3475            3480

Ser Ala Ser Ser Val Thr Ser Pro Ser Ile Gly Leu Glu Thr Leu
    3485            3490            3495

Arg Ala Asn Val Ser Ala Val Lys Ser Asp Ile Ala Pro Thr Ala
    3500            3505            3510

Gly His Leu Ser Gln Thr Ser Ser Pro Ala Glu Val Ser Ile Leu
    3515            3520            3525

Asp Val Thr Thr Ala Pro Thr Pro Gly Ile Ser Thr Thr Ile Thr
    3530            3535            3540

Thr Met Gly Thr Asn Ser Ile Ser Thr Thr Thr Pro Asn Pro Glu
    3545            3550            3555

Val Gly Met Ser Thr Met Asp Ser Thr Pro Ala Thr Glu Arg Arg
    3560            3565            3570

Thr Thr Ser Thr Glu His Pro Ser Thr Trp Ser Ser Thr Ala Ala
    3575            3580            3585

Ser Asp Ser Trp Thr Val Thr Asp Met Thr Ser Asn Leu Lys Val
    3590            3595            3600

Ala Arg Ser Pro Gly Thr Ile Ser Thr Met His Thr Thr Ser Phe
    3605            3610            3615

Leu Ala Ser Ser Thr Glu Leu Asp Ser Met Ser Thr Pro His Gly
    3620            3625            3630

Arg Ile Thr Val Ile Gly Thr Ser Leu Val Thr Pro Ser Ser Asp
    3635            3640            3645

Ala Ser Ala Val Lys Thr Glu Thr Ser Thr Ser Glu Arg Thr Leu
    3650            3655            3660

Ser Pro Ser Asp Thr Thr Ala Ser Thr Pro Ile Ser Thr Phe Ser
    3665            3670            3675

Arg Val Gln Arg Met Ser Ile Ser Val Pro Asp Ile Leu Ser Thr
    3680            3685            3690

Ser Trp Thr Pro Ser Ser Thr Glu Ala Glu Asp Val Pro Val Ser
    3695            3700            3705

Met Val Ser Thr Asp His Ala Ser Thr Lys Thr Asp Pro Asn Thr
    3710            3715            3720

Pro Leu Ser Thr Phe Leu Phe Asp Ser Leu Ser Thr Leu Asp Trp
    3725            3730            3735
```

-continued

```
Asp Thr Gly Arg Ser Leu Ser     Ser Ala Thr Ala     Thr Ser Ala
    3740                3745                3750

Pro Gln Gly Ala Thr Thr Pro     Gln Glu Leu Thr     Leu Glu Thr Met
    3755                3760                3765

Ile Ser Pro Ala Thr Ser Gln     Leu Pro Phe Ser     Ile Gly His Ile
    3770                3775                3780

Thr Ser Ala Val Thr Pro Ala     Ala Met Ala Arg     Ser Ser Gly Val
    3785                3790                3795

Thr Phe Ser Arg Pro Asp Pro     Thr Ser Lys Lys     Ala Glu Gln Thr
    3800                3805                3810

Ser Thr Gln Leu Pro Thr Thr     Thr Ser Ala His     Pro Gly Gln Val
    3815                3820                3825

Pro Arg Ser Ala Ala Thr Thr     Leu Asp Val Ile     Pro His Thr Ala
    3830                3835                3840

Lys Thr Pro Asp Ala Thr Phe     Gln Arg Gln Gly     Gln Thr Ala Leu
    3845                3850                3855

Thr Thr Glu Ala Arg Ala Thr     Ser Asp Ser Trp     Asn Glu Lys Glu
    3860                3865                3870

Lys Ser Thr Pro Ser Ala Pro     Trp Ile Thr Glu     Met Met Asn Ser
    3875                3880                3885

Val Ser Glu Asp Thr Ile Lys     Glu Val Thr Ser     Ser Ser Val
    3890                3895                3900

Leu Arg Thr Leu Asn Thr Leu     Asp Ile Asn Leu     Glu Ser Gly Thr
    3905                3910                3915

Thr Ser Ser Pro Ser Trp Lys     Ser Ser Pro Tyr     Glu Arg Ile Ala
    3920                3925                3930

Pro Ser Glu Ser Thr Thr Asp     Lys Glu Ala Ile     His Pro Ser Thr
    3935                3940                3945

Asn Thr Val Glu Thr Thr Gly     Trp Val Thr Ser     Glu His Ala
    3950                3955                3960

Ser His Ser Thr Ile Pro Ala     His Ser Ala Ser     Ser Lys Leu Thr
    3965                3970                3975

Ser Pro Val Val Thr Thr Ser     Thr Arg Glu Gln     Ala Ile Val Ser
    3980                3985                3990

Met Ser Thr Thr Thr Trp Pro     Glu Ser Thr Arg     Ala Arg Thr Glu
    3995                4000                4005

Pro Asn Ser Phe Leu Thr Ile     Glu Leu Arg Asp     Val Ser Pro Tyr
    4010                4015                4020

Met Asp Thr Ser Ser Thr Thr     Gln Thr Ser Ile     Ile Ser Ser Pro
    4025                4030                4035

Gly Ser Thr Ala Ile Thr Lys     Gly Pro Arg Thr     Glu Ile Thr Ser
    4040                4045                4050

Ser Lys Arg Ile Ser Ser Ser     Phe Leu Ala Gln     Ser Met Arg Ser
    4055                4060                4065

Ser Asp Ser Pro Ser Glu Ala     Ile Thr Arg Leu     Ser Asn Phe Pro
    4070                4075                4080

Ala Met Thr Glu Ser Gly Gly     Met Ile Leu Ala     Met Gln Thr Ser
    4085                4090                4095

Pro Pro Gly Ala Thr Ser Leu     Ser Ala Pro Thr     Leu Asp Thr Ser
    4100                4105                4110

Ala Thr Ala Ser Trp Thr Gly     Thr Pro Leu Ala     Thr Thr Gln Arg
    4115                4120                4125
```

-continued

```
Phe Thr Tyr Ser Glu Lys Thr Leu Phe Ser Lys Gly Pro Glu
    4130            4135            4140

Asp Thr Ser Gln Pro Ser Pro Pro Ser Val Glu Glu Thr Ser Ser
    4145            4150            4155

Ser Ser Ser Leu Val Pro Ile His Ala Thr Thr Ser Pro Ser Asn
    4160            4165            4170

Ile Leu Leu Thr Ser Gln Gly His Ser Pro Ser Thr Pro Pro
    4175            4180            4185

Val Thr Ser Val Phe Leu Ser Glu Thr Ser Gly Leu Gly Lys Thr
    4190            4195            4200

Thr Asp Met Ser Arg Ile Ser Leu Glu Pro Gly Thr Ser Leu Pro
    4205            4210            4215

Pro Asn Leu Ser Ser Thr Ala Gly Glu Ala Leu Ser Thr Tyr Glu
    4220            4225            4230

Ala Ser Arg Asp Thr Lys Ala Ile His His Ser Ala Asp Thr Ala
    4235            4240            4245

Val Thr Asn Met Glu Ala Thr Ser Ser Glu Tyr Ser Pro Ile Pro
    4250            4255            4260

Gly His Thr Lys Pro Ser Lys Ala Thr Ser Pro Leu Val Thr Ser
    4265            4270            4275

His Ile Met Gly Asp Ile Thr Ser Ser Thr Ser Val Phe Gly Ser
    4280            4285            4290

Ser Glu Thr Thr Glu Ile Glu Thr Val Ser Ser Val Asn Gln Gly
    4295            4300            4305

Leu Gln Glu Arg Ser Thr Ser Gln Val Ala Ser Ser Ala Thr Glu
    4310            4315            4320

Thr Ser Thr Val Ile Thr His Val Ser Ser Gly Asp Ala Thr Thr
    4325            4330            4335

His Val Thr Lys Thr Gln Ala Thr Phe Ser Ser Gly Thr Ser Ile
    4340            4345            4350

Ser Ser Pro His Gln Phe Ile Thr Ser Thr Asn Thr Phe Thr Asp
    4355            4360            4365

Val Ser Thr Asn Pro Ser Thr Ser Leu Ile Met Thr Glu Ser Ser
    4370            4375            4380

Gly Val Thr Ile Thr Thr Gln Thr Gly Pro Thr Gly Ala Ala Thr
    4385            4390            4395

Gln Gly Pro Tyr Leu Leu Asp Thr Ser Thr Met Pro Tyr Leu Thr
    4400            4405            4410

Glu Thr Pro Leu Ala Val Thr Pro Asp Phe Met Gln Ser Glu Lys
    4415            4420            4425

Thr Thr Leu Ile Ser Lys Gly Pro Lys Asp Val Ser Trp Thr Ser
    4430            4435            4440

Pro Pro Ser Val Ala Glu Thr Ser Tyr Pro Ser Ser Leu Thr Pro
    4445            4450            4455

Phe Leu Val Thr Thr Ile Pro Pro Ala Thr Ser Thr Leu Gln Gly
    4460            4465            4470

Gln His Thr Ser Ser Pro Val Ser Ala Thr Ser Val Leu Thr Ser
    4475            4480            4485

Gly Leu Val Lys Thr Thr Asp Met Leu Asn Thr Ser Met Glu Pro
    4490            4495            4500

Val Thr Asn Ser Pro Gln Asn Leu Asn Asn Pro Ser Asn Glu Ile
    4505            4510            4515
```

```
Leu Ala Thr Leu Ala Ala Thr Thr Asp Ile Glu Thr Ile His Pro
        4520            4525            4530

Ser Ile Asn Lys Ala Val Thr Asn Met Gly Thr Ala Ser Ser Ala
        4535            4540            4545

His Val Leu His Ser Thr Leu Pro Val Ser Ser Glu Pro Ser Thr
        4550            4555            4560

Ala Thr Ser Pro Met Val Pro Ala Ser Ser Met Gly Asp Ala Leu
        4565            4570            4575

Ala Ser Ile Ser Ile Pro Gly Ser Glu Thr Thr Asp Ile Glu Gly
        4580            4585            4590

Glu Pro Thr Ser Ser Leu Thr Ala Gly Arg Lys Glu Asn Ser Thr
        4595            4600            4605

Leu Gln Glu Met Asn Ser Thr Thr Glu Ser Asn Ile Ile Leu Ser
        4610            4615            4620

Asn Val Ser Val Gly Ala Ile Thr Glu Ala Thr Lys Met Glu Val
        4625            4630            4635

Pro Ser Phe Asp Ala Thr Phe Ile Pro Thr Pro Ala Gln Ser Thr
        4640            4645            4650

Lys Phe Pro Asp Ile Phe Ser Val Ala Ser Ser Arg Leu Ser Asn
        4655            4660            4665

Ser Pro Pro Met Thr Ile Ser Thr His Met Thr Thr Gln Thr
        4670            4675            4680

Gly Ser Ser Gly Ala Thr Ser Lys Ile Pro Leu Ala Leu Asp Thr
        4685            4690            4695

Ser Thr Leu Glu Thr Ser Ala Gly Thr Pro Ser Val Val Thr Glu
        4700            4705            4710

Gly Phe Ala His Ser Lys Ile Thr Thr Ala Met Asn Asn Asp Val
        4715            4720            4725

Lys Asp Val Ser Gln Thr Asn Pro Pro Phe Gln Asp Glu Ala Ser
        4730            4735            4740

Ser Pro Ser Ser Gln Ala Pro Val Leu Val Thr Thr Leu Pro Ser
        4745            4750            4755

Ser Val Ala Phe Thr Pro Gln Trp His Ser Thr Ser Pro Val
        4760            4765            4770

Ser Met Ser Ser Val Leu Thr Ser Ser Leu Val Lys Thr Ala Gly
        4775            4780            4785

Lys Val Asp Thr Ser Leu Glu Thr Val Thr Ser Ser Pro Gln Ser
        4790            4795            4800

Met Ser Asn Thr Leu Asp Asp Ile Ser Val Thr Ser Ala Ala Thr
        4805            4810            4815

Thr Asp Ile Glu Thr Thr His Pro Ser Ile Asn Thr Val Val Thr
        4820            4825            4830

Asn Val Gly Thr Thr Gly Ser Ala Phe Glu Ser His Ser Thr Val
        4835            4840            4845

Ser Ala Tyr Pro Glu Pro Ser Lys Val Thr Ser Pro Asn Val Thr
        4850            4855            4860

Thr Ser Thr Met Glu Asp Thr Thr Ile Ser Arg Ser Ile Pro Lys
        4865            4870            4875

Ser Ser Lys Thr Thr Arg Thr Glu Thr Glu Thr Ser Ser Leu
        4880            4885            4890

Thr Pro Lys Leu Arg Glu Thr Ser Ile Ser Gln Glu Ile Thr Ser
        4895            4900            4905
```

-continued

Ser Thr Glu Thr Ser Thr Val Pro Tyr Lys Glu Leu Thr Gly Ala
4910                4915                4920

Thr Thr Glu Val Ser Arg Thr Asp Val Thr Ser Ser Ser Ser Thr
4925                4930                4935

Ser Phe Pro Gly Pro Asp Gln Ser Thr Val Ser Leu Asp Ile Ser
4940                4945                4950

Thr Glu Thr Asn Thr Arg Leu Ser Thr Ser Pro Ile Met Thr Glu
4955                4960                4965

Ser Ala Glu Ile Thr Ile Thr Gln Thr Gly Pro His Gly Ala
4970                4975                4980

Thr Ser Gln Asp Thr Phe Thr Met Asp Pro Ser Asn Thr Thr Pro
4985                4990                4995

Gln Ala Gly Ile His Ser Ala Met Thr His Gly Phe Ser Gln Leu
5000                5005                5010

Asp Val Thr Thr Leu Met Ser Arg Ile Pro Gln Asp Val Ser Trp
5015                5020                5025

Thr Ser Pro Pro Ser Val Asp Lys Thr Ser Ser Pro Ser Ser Phe
5030                5035                5040

Leu Ser Ser Pro Ala Met Thr Thr Pro Ser Leu Ile Ser Ser Thr
5045                5050                5055

Leu Pro Glu Asp Lys Leu Ser Ser Pro Met Thr Ser Leu Leu Thr
5060                5065                5070

Ser Gly Leu Val Lys Ile Thr Asp Ile Leu Arg Thr Arg Leu Glu
5075                5080                5085

Pro Val Thr Ser Ser Leu Pro Asn Phe Ser Ser Thr Ser Asp Lys
5090                5095                5100

Ile Leu Ala Thr Ser Lys Asp Ser Lys Asp Thr Lys Glu Ile Phe
5105                5110                5115

Pro Ser Ile Asn Thr Glu Glu Thr Asn Val Lys Ala Asn Asn Ser
5120                5125                5130

Gly His Glu Ser His Ser Pro Ala Leu Ala Asp Ser Glu Thr Pro
5135                5140                5145

Lys Ala Thr Thr Gln Met Val Ile Thr Thr Thr Val Gly Asp Pro
5150                5155                5160

Ala Pro Ser Thr Ser Met Pro Val His Gly Ser Ser Glu Thr Thr
5165                5170                5175

Asn Ile Lys Arg Glu Pro Thr Tyr Phe Leu Thr Pro Arg Leu Arg
5180                5185                5190

Glu Thr Ser Thr Ser Gln Glu Ser Ser Phe Pro Thr Asp Thr Ser
5195                5200                5205

Phe Leu Leu Ser Lys Val Pro Thr Gly Thr Ile Thr Glu Val Ser
5210                5215                5220

Ser Thr Gly Val Asn Ser Ser Ser Lys Ile Ser Thr Pro Asp His
5225                5230                5235

Asp Lys Ser Thr Val Pro Pro Asp Thr Phe Thr Gly Glu Ile Pro
5240                5245                5250

Arg Val Phe Thr Ser Ser Ile Lys Thr Lys Ser Ala Glu Met Thr
5255                5260                5265

Ile Thr Thr Gln Ala Ser Pro Pro Glu Ser Ala Ser His Ser Thr
5270                5275                5280

Leu Pro Leu Asp Thr Ser Thr Thr Leu Ser Gln Gly Gly Thr His
5285                5290                5295

```
Ser Thr Val Thr Gln Gly Phe Pro Tyr Ser Glu Val Thr Thr Leu
5300                5305                5310

Met Gly Met Gly Pro Gly Asn Val Ser Trp Met Thr Thr Pro Pro
5315                5320                5325

Val Glu Glu Thr Ser Ser Val Ser Ser Leu Met Ser Ser Pro Ala
5330                5335                5340

Met Thr Ser Pro Ser Pro Val Ser Ser Thr Ser Pro Gln Ser Ile
5345                5350                5355

Pro Ser Ser Pro Leu Pro Val Thr Ala Leu Pro Thr Ser Val Leu
5360                5365                5370

Val Thr Thr Thr Asp Val Leu Gly Thr Thr Ser Pro Glu Ser Val
5375                5380                5385

Thr Ser Ser Pro Pro Asn Leu Ser Ser Ile Thr His Glu Arg Pro
5390                5395                5400

Ala Thr Tyr Lys Asp Thr Ala His Thr Glu Ala Ala Met His His
5405                5410                5415

Ser Thr Asn Thr Ala Val Thr Asn Val Gly Thr Ser Gly Ser Gly
5420                5425                5430

His Lys Ser Gln Ser Ser Val Leu Ala Asp Ser Glu Thr Ser Lys
5435                5440                5445

Ala Thr Pro Leu Met Ser Thr Thr Ser Thr Leu Gly Asp Thr Ser
5450                5455                5460

Val Ser Thr Ser Thr Pro Asn Ile Ser Gln Thr Asn Gln Ile Gln
5465                5470                5475

Thr Glu Pro Thr Ala Ser Leu Ser Pro Arg Leu Arg Glu Ser Ser
5480                5485                5490

Thr Ser Glu Lys Thr Ser Ser Thr Thr Glu Thr Asn Thr Ala Phe
5495                5500                5505

Ser Tyr Val Pro Thr Gly Ala Ile Thr Gln Ala Ser Arg Thr Glu
5510                5515                5520

Ile Ser Ser Ser Arg Thr Ser Ile Ser Asp Leu Asp Arg Pro Thr
5525                5530                5535

Ile Ala Pro Asp Ile Ser Thr Gly Met Ile Thr Arg Leu Phe Thr
5540                5545                5550

Ser Pro Ile Met Thr Lys Ser Ala Glu Met Thr Val Thr Thr Gln
5555                5560                5565

Thr Thr Thr Pro Gly Ala Thr Ser Gln Gly Ile Leu Pro Trp Asp
5570                5575                5580

Thr Ser Thr Thr Leu Phe Gln Gly Gly Thr His Ser Thr Val Ser
5585                5590                5595

Gln Gly Phe Pro His Ser Glu Ile Thr Thr Leu Arg Ser Arg Thr
5600                5605                5610

Pro Gly Asp Val Ser Trp Met Thr Thr Pro Val Glu Glu Thr
5615                5620                5625

Ser Ser Gly Phe Ser Leu Met Ser Pro Ser Met Thr Ser Pro Ser
5630                5635                5640

Pro Val Ser Ser Thr Ser Pro Glu Ser Ile Pro Ser Ser Pro Leu
5645                5650                5655

Pro Val Thr Ala Leu Leu Thr Ser Val Leu Val Thr Thr Thr Asn
5660                5665                5670

Val Leu Gly Thr Thr Ser Pro Glu Pro Val Thr Ser Ser Pro Pro
5675                5680                5685
```

```
Asn Leu Ser Ser Pro Thr Gln Glu Arg Leu Thr Thr Tyr Lys Asp
    5690            5695                5700

Thr Ala His Thr Glu Ala Met His Ala Ser Met His Thr Asn Thr
    5705            5710                5715

Ala Val Ala Asn Val Gly Thr Ser Ile Ser Gly His Glu Ser Gln
    5720            5725                5730

Ser Ser Val Pro Ala Asp Ser His Thr Ser Lys Ala Thr Ser Pro
    5735            5740                5745

Met Gly Ile Thr Phe Ala Met Gly Asp Thr Ser Val Ser Thr Ser
    5750            5755                5760

Thr Pro Ala Phe Phe Glu Thr Arg Ile Gln Thr Glu Ser Thr Ser
    5765            5770                5775

Ser Leu Ile Pro Gly Leu Arg Asp Thr Arg Thr Ser Glu Glu Ile
    5780            5785                5790

Asn Thr Val Thr Glu Thr Ser Thr Val Leu Ser Glu Val Pro Thr
    5795            5800                5805

Thr Thr Thr Thr Glu Val Ser Arg Thr Glu Val Ile Thr Ser Ser
    5810            5815                5820

Arg Thr Thr Ile Ser Gly Pro Asp His Ser Lys Met Ser Pro Tyr
    5825            5830                5835

Ile Ser Thr Glu Thr Ile Thr Arg Leu Ser Thr Phe Pro Phe Val
    5840            5845                5850

Thr Gly Ser Thr Glu Met Ala Ile Thr Asn Gln Thr Gly Pro Ile
    5855            5860                5865

Gly Thr Ile Ser Gln Ala Thr Leu Thr Leu Asp Thr Ser Ser Thr
    5870            5875                5880

Ala Ser Trp Glu Gly Thr His Ser Pro Val Thr Gln Arg Phe Pro
    5885            5890                5895

His Ser Glu Glu Thr Thr Thr Met Ser Arg Ser Thr Lys Gly Val
    5900            5905                5910

Ser Trp Gln Ser Pro Pro Ser Val Glu Glu Thr Ser Ser Pro Ser
    5915            5920                5925

Ser Pro Val Pro Leu Pro Ala Ile Thr Ser His Ser Ser Leu Tyr
    5930            5935                5940

Ser Ala Val Ser Gly Ser Ser Pro Thr Ser Ala Leu Pro Val Thr
    5945            5950                5955

Ser Leu Leu Thr Ser Gly Arg Arg Lys Thr Ile Asp Met Leu Asp
    5960            5965                5970

Thr His Ser Glu Leu Val Thr Ser Ser Leu Pro Ser Ala Ser Ser
    5975            5980                5985

Phe Ser Gly Glu Ile Leu Thr Ser Glu Ala Ser Thr Asn Thr Glu
    5990            5995                6000

Thr Ile His Phe Ser Glu Asn Thr Ala Glu Thr Asn Met Gly Thr
    6005            6010                6015

Thr Asn Ser Met His Lys Leu His Ser Ser Val Ser Ile His Ser
    6020            6025                6030

Gln Pro Ser Gly His Thr Pro Pro Lys Val Thr Gly Ser Met Met
    6035            6040                6045

Glu Asp Ala Ile Val Ser Thr Ser Thr Pro Gly Ser Pro Glu Thr
    6050            6055                6060

Lys Asn Val Asp Arg Asp Ser Thr Ser Pro Leu Thr Pro Glu Leu
    6065            6070                6075
```

-continued

```
Lys Glu Asp Ser Thr Ala Leu Val Met Asn Ser Thr Thr Glu Ser
    6080                6085                6090

Asn Thr Val Phe Ser Ser Val Ser Leu Asp Ala Ala Thr Glu Val
    6095                6100                6105

Ser Arg Ala Glu Val Thr Tyr Tyr Asp Pro Thr Phe Met Pro Ala
    6110                6115                6120

Ser Ala Gln Ser Thr Lys Ser Pro Asp Ile Ser Pro Glu Ala Ser
    6125                6130                6135

Ser Ser His Ser Asn Ser Pro Pro Leu Thr Ile Ser Thr His Lys
    6140                6145                6150

Thr Ile Ala Thr Gln Thr Gly Pro Ser Gly Val Thr Ser Leu Gly
    6155                6160                6165

Gln Leu Thr Leu Asp Thr Ser Thr Ile Ala Thr Ser Ala Gly Thr
    6170                6175                6180

Pro Ser Ala Arg Thr Gln Asp Phe Val Asp Ser Glu Thr Thr Ser
    6185                6190                6195

Val Met Asn Asn Asp Leu Asn Asp Val Leu Lys Thr Ser Pro Phe
    6200                6205                6210

Ser Ala Glu Glu Ala Asn Ser Leu Ser Ser Gln Ala Pro Leu Leu
    6215                6220                6225

Val Thr Thr Ser Pro Ser Pro Val Thr Ser Thr Leu Gln Glu His
    6230                6235                6240

Ser Thr Ser Ser Leu Val Ser Val Thr Ser Val Pro Thr Pro Thr
    6245                6250                6255

Leu Ala Lys Ile Thr Asp Met Asp Thr Asn Leu Glu Pro Val Thr
    6260                6265                6270

Arg Ser Pro Gln Asn Leu Arg Asn Thr Leu Ala Thr Ser Glu Ala
    6275                6280                6285

Thr Thr Asp Thr His Thr Met His Pro Ser Ile Asn Thr Ala Val
    6290                6295                6300

Ala Asn Val Gly Thr Thr Ser Ser Pro Asn Glu Phe Tyr Phe Thr
    6305                6310                6315

Val Ser Pro Asp Ser Asp Pro Tyr Lys Ala Thr Ser Ala Val Val
    6320                6325                6330

Ile Thr Ser Thr Ser Gly Asp Ser Ile Val Ser Thr Ser Met Pro
    6335                6340                6345

Arg Ser Ser Ala Met Lys Lys Ile Glu Ser Glu Thr Thr Phe Ser
    6350                6355                6360

Leu Ile Phe Arg Leu Arg Glu Thr Ser Thr Ser Gln Lys Ile Gly
    6365                6370                6375

Ser Ser Ser Asp Thr Ser Thr Val Phe Asp Lys Ala Phe Thr Ala
    6380                6385                6390

Ala Thr Thr Glu Val Ser Arg Thr Glu Leu Thr Ser Ser Ser Arg
    6395                6400                6405

Thr Ser Ile Gln Gly Thr Glu Lys Pro Thr Met Ser Pro Asp Thr
    6410                6415                6420

Ser Thr Arg Ser Val Thr Met Leu Ser Thr Phe Ala Gly Leu Thr
    6425                6430                6435

Lys Ser Glu Glu Arg Thr Ile Ala Thr Gln Thr Gly Pro His Arg
    6440                6445                6450

Ala Thr Ser Gln Gly Thr Leu Thr Trp Asp Thr Ser Ile Thr Thr
    6455                6460                6465
```

```
Ser Gln Ala Gly Thr His Ser Ala Met Thr His Gly Phe Ser Gln
    6470            6475            6480

Leu Asp Leu Ser Thr Leu Thr Ser Arg Val Pro Glu Tyr Ile Ser
    6485            6490            6495

Gly Thr Ser Pro Pro Ser Val Glu Lys Thr Ser Ser Ser Ser Ser
    6500            6505            6510

Leu Leu Ser Leu Pro Ala Ile Thr Ser Pro Ser Pro Val Pro Thr
    6515            6520            6525

Thr Leu Pro Glu Ser Arg Pro Ser Ser Pro Val His Leu Thr Ser
    6530            6535            6540

Leu Pro Thr Ser Gly Leu Val Lys Thr Thr Asp Met Leu Ala Ser
    6545            6550            6555

Val Ala Ser Leu Pro Pro Asn Leu Gly Ser Thr Ser His Lys Ile
    6560            6565            6570

Pro Thr Thr Ser Glu Asp Ile Lys Asp Thr Glu Lys Met Tyr Pro
    6575            6580            6585

Ser Thr Asn Ile Ala Val Thr Asn Val Gly Thr Thr Thr Ser Glu
    6590            6595            6600

Lys Glu Ser Tyr Ser Ser Val Pro Ala Tyr Ser Glu Pro Pro Lys
    6605            6610            6615

Val Thr Ser Pro Met Val Thr Ser Phe Asn Ile Arg Asp Thr Ile
    6620            6625            6630

Val Ser Thr Ser Met Pro Gly Ser Ser Glu Ile Thr Arg Ile Glu
    6635            6640            6645

Met Glu Ser Thr Phe Ser Leu Ala His Gly Leu Lys Gly Thr Ser
    6650            6655            6660

Thr Ser Gln Asp Pro Ile Val Ser Thr Glu Lys Ser Ala Val Leu
    6665            6670            6675

His Lys Leu Thr Thr Gly Ala Thr Glu Thr Ser Arg Thr Glu Val
    6680            6685            6690

Ala Ser Ser Arg Arg Thr Ser Ile Pro Gly Pro Asp His Ser Thr
    6695            6700            6705

Glu Ser Pro Asp Ile Ser Thr Glu Val Ile Pro Ser Leu Pro Ile
    6710            6715            6720

Ser Leu Gly Ile Thr Glu Ser Ser Asn Met Thr Ile Ile Thr Arg
    6725            6730            6735

Thr Gly Pro Pro Leu Gly Ser Thr Ser Gln Gly Thr Phe Thr Leu
    6740            6745            6750

Asp Thr Pro Thr Thr Ser Ser Arg Ala Gly Thr His Ser Met Ala
    6755            6760            6765

Thr Gln Glu Phe Pro His Ser Glu Met Thr Thr Val Met Asn Lys
    6770            6775            6780

Asp Pro Glu Ile Leu Ser Trp Thr Ile Pro Pro Ser Ile Glu Lys
    6785            6790            6795

Thr Ser Phe Ser Ser Ser Leu Met Pro Ser Pro Ala Met Thr Ser
    6800            6805            6810

Pro Pro Val Ser Ser Thr Leu Pro Lys Thr Ile His Thr Thr Pro
    6815            6820            6825

Ser Pro Met Thr Ser Leu Leu Thr Pro Ser Leu Val Met Thr Thr
    6830            6835            6840

Asp Thr Leu Gly Thr Ser Pro Glu Pro Thr Thr Ser Ser Pro Pro
    6845            6850            6855
```

```
Asn Leu Ser Ser Thr Ser His Glu Ile Leu Thr Thr Asp Glu Asp
    6860            6865            6870

Thr Thr Ala Ile Glu Ala Met His Pro Ser Thr Ser Thr Ala Ala
    6875            6880            6885

Thr Asn Val Glu Thr Ser Ser Gly His Gly Ser Gln Ser Ser
    6890            6895            6900

Val Leu Ala Asp Ser Glu Lys Thr Lys Ala Thr Ala Pro Met Asp
    6905            6910            6915

Thr Thr Ser Thr Met Gly His Thr Thr Val Ser Thr Ser Met Ser
    6920            6925            6930

Val Ser Ser Glu Thr Thr Lys Ile Lys Arg Glu Ser Thr Tyr Ser
    6935            6940            6945

Leu Thr Pro Gly Leu Arg Glu Thr Ser Ile Ser Gln Asn Ala Ser
    6950            6955            6960

Phe Ser Thr Asp Thr Ser Ile Val Leu Ser Glu Val Pro Thr Gly
    6965            6970            6975

Thr Thr Ala Glu Val Ser Arg Thr Glu Val Thr Ser Ser Gly Arg
    6980            6985            6990

Thr Ser Ile Pro Gly Pro Ser Gln Ser Thr Val Leu Pro Glu Ile
    6995            7000            7005

Ser Thr Arg Thr Met Thr Arg Leu Phe Ala Ser Pro Thr Met Thr
    7010            7015            7020

Glu Ser Ala Glu Met Thr Ile Pro Thr Gln Thr Gly Pro Ser Gly
    7025            7030            7035

Ser Thr Ser Gln Asp Thr Leu Thr Leu Asp Thr Ser Thr Thr Lys
    7040            7045            7050

Ser Gln Ala Lys Thr His Ser Thr Leu Thr Gln Arg Phe Pro His
    7055            7060            7065

Ser Glu Met Thr Thr Leu Met Ser Arg Gly Pro Gly Asp Met Ser
    7070            7075            7080

Trp Gln Ser Ser Pro Ser Leu Glu Asn Pro Ser Ser Leu Pro Ser
    7085            7090            7095

Leu Leu Ser Leu Pro Ala Thr Thr Ser Pro Pro Ile Ser Ser
    7100            7105            7110

Thr Leu Pro Val Thr Ile Ser Ser Ser Pro Leu Pro Val Thr Ser
    7115            7120            7125

Leu Leu Thr Ser Ser Pro Val Thr Thr Thr Asp Met Leu His Thr
    7130            7135            7140

Ser Pro Glu Leu Val Thr Ser Ser Pro Pro Lys Leu Ser His Thr
    7145            7150            7155

Ser Asp Glu Arg Leu Thr Thr Gly Lys Asp Thr Thr Asn Thr Glu
    7160            7165            7170

Ala Val His Pro Ser Thr Asn Thr Ala Ala Ser Asn Val Glu Ile
    7175            7180            7185

Pro Ser Ser Gly His Glu Ser Pro Ser Ser Ala Leu Ala Asp Ser
    7190            7195            7200

Glu Thr Ser Lys Ala Thr Ser Pro Met Phe Ile Thr Ser Thr Gln
    7205            7210            7215

Glu Asp Thr Thr Val Ala Ile Ser Thr Pro His Phe Leu Glu Thr
    7220            7225            7230

Ser Arg Ile Gln Lys Glu Ser Ile Ser Ser Leu Ser Pro Lys Leu
    7235            7240            7245
```

```
Arg Glu Thr Gly Ser Ser Val Glu Thr Ser Ser Ala Ile Glu Thr
    7250                7255                    7260

Ser Ala Val Leu Ser Glu Val Ser Ile Gly Ala Thr Thr Glu Ile
    7265                7270                    7275

Ser Arg Thr Glu Val Thr Ser Ser Ser Arg Thr Ser Ile Ser Gly
    7280                7285                    7290

Ser Ala Glu Ser Thr Met Leu Pro Glu Ile Ser Thr Thr Arg Lys
    7295                7300                    7305

Ile Ile Lys Phe Pro Thr Ser Pro Ile Leu Ala Glu Ser Ser Glu
    7310                7315                    7320

Met Thr Ile Lys Thr Gln Thr Ser Pro Pro Gly Ser Thr Ser Glu
    7325                7330                    7335

Ser Thr Phe Thr Leu Asp Thr Ser Thr Thr Pro Ser Leu Val Ile
    7340                7345                    7350

Thr His Ser Thr Met Thr Gln Arg Leu Pro His Ser Glu Ile Thr
    7355                7360                    7365

Thr Leu Val Ser Arg Gly Ala Gly Asp Val Pro Arg Pro Ser Ser
    7370                7375                    7380

Leu Pro Val Glu Glu Thr Ser Pro Pro Ser Ser Gln Leu Ser Leu
    7385                7390                    7395

Ser Ala Met Ile Ser Pro Ser Pro Val Ser Ser Thr Leu Pro Ala
    7400                7405                    7410

Ser Ser His Ser Ser Ser Ala Ser Val Thr Ser Leu Leu Thr Pro
    7415                7420                    7425

Gly Gln Val Lys Thr Thr Glu Val Leu Asp Ala Ser Ala Glu Pro
    7430                7435                    7440

Glu Thr Ser Ser Pro Pro Ser Leu Ser Ser Thr Ser Val Glu Ile
    7445                7450                    7455

Leu Ala Thr Ser Glu Val Thr Thr Asp Thr Glu Lys Ile His Pro
    7460                7465                    7470

Phe Ser Asn Thr Ala Val Thr Lys Val Gly Thr Ser Ser Ser Gly
    7475                7480                    7485

His Glu Ser Pro Ser Ser Val Leu Pro Asp Ser Glu Thr Thr Lys
    7490                7495                    7500

Ala Thr Ser Ala Met Gly Thr Ile Ser Ile Met Gly Asp Thr Ser
    7505                7510                    7515

Val Ser Thr Leu Thr Pro Ala Leu Ser Asn Thr Arg Lys Ile Gln
    7520                7525                    7530

Ser Glu Pro Ala Ser Ser Leu Thr Thr Arg Leu Arg Glu Thr Ser
    7535                7540                    7545

Thr Ser Glu Glu Thr Ser Leu Ala Thr Glu Ala Asn Thr Val Leu
    7550                7555                    7560

Ser Lys Val Ser Thr Gly Ala Thr Thr Glu Val Ser Arg Thr Glu
    7565                7570                    7575

Ala Ile Ser Phe Ser Arg Thr Ser Met Ser Gly Pro Glu Gln Ser
    7580                7585                    7590

Thr Met Ser Gln Asp Ile Ser Ile Gly Thr Ile Pro Arg Ile Ser
    7595                7600                    7605

Ala Ser Ser Val Leu Thr Glu Ser Ala Lys Met Thr Ile Thr Thr
    7610                7615                    7620

Gln Thr Gly Pro Ser Glu Ser Thr Leu Glu Ser Thr Leu Asn Leu
    7625                7630                    7635
```

```
Asn Thr Ala Thr Thr Pro Ser Trp Val Glu Thr His Ser Ile Val
7640                 7645                 7650

Ile Gln Gly Phe Pro His Pro Glu Met Thr Thr Ser Met Gly Arg
7655                 7660                 7665

Gly Pro Gly Gly Val Ser Trp Pro Ser Pro Pro Phe Val Lys Glu
7670                 7675                 7680

Thr Ser Pro Pro Ser Ser Pro Leu Ser Leu Pro Ala Val Thr Ser
7685                 7690                 7695

Pro His Pro Val Ser Thr Thr Phe Leu Ala His Ile Pro Pro Ser
7700                 7705                 7710

Pro Leu Pro Val Thr Ser Leu Leu Thr Ser Gly Pro Ala Thr Thr
7715                 7720                 7725

Thr Asp Ile Leu Gly Thr Ser Thr Glu Pro Gly Thr Ser Ser Ser
7730                 7735                 7740

Ser Ser Leu Ser Thr Thr Ser His Glu Arg Leu Thr Thr Tyr Lys
7745                 7750                 7755

Asp Thr Ala His Thr Glu Ala Val His Pro Ser Thr Asn Thr Gly
7760                 7765                 7770

Gly Thr Asn Val Ala Thr Thr Ser Ser Gly Tyr Lys Ser Gln Ser
7775                 7780                 7785

Ser Val Leu Ala Asp Ser Ser Pro Met Cys Thr Thr Ser Thr Met
7790                 7795                 7800

Gly Asp Thr Ser Val Leu Thr Ser Thr Pro Ala Phe Leu Glu Thr
7805                 7810                 7815

Arg Arg Ile Gln Thr Glu Leu Ala Ser Ser Leu Thr Pro Gly Leu
7820                 7825                 7830

Arg Glu Ser Ser Gly Ser Glu Gly Thr Ser Ser Gly Thr Lys Met
7835                 7840                 7845

Ser Thr Val Leu Ser Lys Val Pro Thr Gly Ala Thr Thr Glu Ile
7850                 7855                 7860

Ser Lys Glu Asp Val Thr Ser Ile Pro Gly Pro Ala Gln Ser Thr
7865                 7870                 7875

Ile Ser Pro Asp Ile Ser Thr Arg Thr Val Ser Trp Phe Ser Thr
7880                 7885                 7890

Ser Pro Val Met Thr Glu Ser Ala Glu Ile Thr Met Asn Thr His
7895                 7900                 7905

Thr Ser Pro Leu Gly Ala Thr Thr Gln Gly Thr Ser Thr Leu Asp
7910                 7915                 7920

Thr Ser Ser Thr Thr Ser Leu Thr Met Thr His Ser Thr Ile Ser
7925                 7930                 7935

Gln Gly Phe Ser His Ser Gln Met Ser Thr Leu Met Arg Arg Gly
7940                 7945                 7950

Pro Glu Asp Val Ser Trp Met Ser Pro Pro Leu Leu Glu Lys Thr
7955                 7960                 7965

Arg Pro Ser Phe Ser Leu Met Ser Ser Pro Ala Thr Thr Ser Pro
7970                 7975                 7980

Ser Pro Val Ser Ser Thr Leu Pro Glu Ser Ile Ser Ser Ser Pro
7985                 7990                 7995

Leu Pro Val Thr Ser Leu Leu Thr Ser Gly Leu Ala Lys Thr Thr
8000                 8005                 8010

Asp Met Leu His Lys Ser Ser Glu Pro Val Thr Asn Ser Pro Ala
8015                 8020                 8025
```

```
Asn Leu Ser Ser Thr Ser Val Glu Ile Leu Ala Thr Ser Glu Val
        8030            8035            8040

Thr Thr Asp Thr Glu Lys Thr His Pro Ser Ser Asn Arg Thr Val
        8045            8050            8055

Thr Asp Val Gly Thr Ser Ser Gly His Glu Ser Thr Ser Phe
        8060            8065            8070

Val Leu Ala Asp Ser Gln Thr Ser Lys Val Thr Ser Pro Met Val
        8075            8080            8085

Ile Thr Ser Thr Met Glu Asp Thr Ser Val Ser Thr Ser Thr Pro
        8090            8095            8100

Gly Phe Phe Glu Thr Ser Arg Ile Gln Thr Glu Pro Thr Ser Ser
        8105            8110            8115

Leu Thr Leu Gly Leu Arg Lys Thr Ser Ser Ser Glu Gly Thr Ser
        8120            8125            8130

Leu Ala Thr Glu Met Ser Thr Val Leu Ser Gly Val Pro Thr Gly
        8135            8140            8145

Ala Thr Ala Glu Val Ser Arg Thr Glu Val Thr Ser Ser Ser Arg
        8150            8155            8160

Thr Ser Ile Ser Gly Phe Ala Gln Leu Thr Val Ser Pro Glu Thr
        8165            8170            8175

Ser Thr Glu Thr Ile Thr Arg Leu Pro Thr Ser Ser Ile Met Thr
        8180            8185            8190

Glu Ser Ala Glu Met Met Ile Lys Thr Gln Thr Asp Pro Pro Gly
        8195            8200            8205

Ser Thr Pro Glu Ser Thr His Thr Val Asp Ile Ser Thr Thr Pro
        8210            8215            8220

Asn Trp Val Glu Thr His Ser Thr Val Thr Gln Arg Phe Ser His
        8225            8230            8235

Ser Glu Met Thr Thr Leu Val Ser Arg Ser Pro Gly Asp Met Leu
        8240            8245            8250

Trp Pro Ser Gln Ser Ser Val Glu Glu Thr Ser Ser Ala Ser Ser
        8255            8260            8265

Leu Leu Ser Leu Pro Ala Thr Thr Ser Pro Ser Pro Val Ser Ser
        8270            8275            8280

Thr Leu Val Glu Asp Phe Pro Ser Ala Ser Leu Pro Val Thr Ser
        8285            8290            8295

Leu Leu Asn Pro Gly Leu Val Ile Thr Thr Asp Arg Met Gly Ile
        8300            8305            8310

Ser Arg Glu Pro Gly Thr Ser Ser Thr Ser Asn Leu Ser Ser Thr
        8315            8320            8325

Ser His Glu Arg Leu Thr Thr Leu Glu Asp Thr Val Asp Thr Glu
        8330            8335            8340

Asp Met Gln Pro Ser Thr His Thr Ala Val Thr Asn Val Arg Thr
        8345            8350            8355

Ser Ile Ser Gly His Glu Ser Gln Ser Ser Val Leu Ser Asp Ser
        8360            8365            8370

Glu Thr Pro Lys Ala Thr Ser Pro Met Gly Thr Thr Tyr Thr Met
        8375            8380            8385

Gly Glu Thr Ser Val Ser Ile Ser Thr Ser Asp Phe Phe Glu Thr
        8390            8395            8400

Ser Arg Ile Gln Ile Glu Pro Thr Ser Ser Leu Thr Ser Gly Leu
        8405            8410            8415
```

```
Arg Glu Thr Ser Ser Ser Glu Arg Ile Ser Ser Ala Thr Glu Gly
    8420            8425                8430

Ser Thr Val Leu Ser Glu Val Pro Ser Gly Ala Thr Thr Glu Val
    8435            8440                8445

Ser Arg Thr Glu Val Ile Ser Ser Arg Gly Thr Ser Met Ser Gly
    8450            8455                8460

Pro Asp Gln Phe Thr Ile Ser Pro Asp Ile Ser Thr Glu Ala Ile
    8465            8470                8475

Thr Arg Leu Ser Thr Ser Pro Ile Met Thr Glu Ser Ala Glu Ser
    8480            8485                8490

Ala Ile Thr Ile Glu Thr Gly Ser Pro Gly Ala Thr Ser Glu Gly
    8495            8500                8505

Thr Leu Thr Leu Asp Thr Ser Thr Thr Thr Phe Trp Ser Gly Thr
    8510            8515                8520

His Ser Thr Ala Ser Pro Gly Phe Ser His Ser Glu Met Thr Thr
    8525            8530                8535

Leu Met Ser Arg Thr Pro Gly Asp Val Pro Trp Pro Ser Leu Pro
    8540            8545                8550

Ser Val Glu Glu Ala Ser Ser Val Ser Ser Ser Leu Ser Ser Pro
    8555            8560                8565

Ala Met Thr Ser Thr Ser Phe Phe Ser Thr Leu Pro Glu Ser Ile
    8570            8575                8580

Ser Ser Ser Pro His Pro Val Thr Ala Leu Leu Thr Leu Gly Pro
    8585            8590                8595

Val Lys Thr Thr Asp Met Leu Arg Thr Ser Ser Glu Pro Glu Thr
    8600            8605                8610

Ser Ser Pro Pro Asn Leu Ser Ser Thr Ser Ala Glu Ile Leu Ala
    8615            8620                8625

Thr Ser Glu Val Thr Lys Asp Arg Glu Lys Ile His Pro Ser Ser
    8630            8635                8640

Asn Thr Pro Val Val Asn Val Gly Thr Val Ile Tyr Lys His Leu
    8645            8650                8655

Ser Pro Ser Ser Val Leu Ala Asp Leu Val Thr Thr Lys Pro Thr
    8660            8665                8670

Ser Pro Met Ala Thr Thr Ser Thr Leu Gly Asn Thr Ser Val Ser
    8675            8680                8685

Thr Ser Thr Pro Ala Phe Pro Glu Thr Met Met Thr Gln Pro Thr
    8690            8695                8700

Ser Ser Leu Thr Ser Gly Leu Arg Glu Ile Ser Thr Ser Gln Glu
    8705            8710                8715

Thr Ser Ser Ala Thr Glu Arg Ser Ala Ser Leu Ser Gly Met Pro
    8720            8725                8730

Thr Gly Ala Thr Thr Lys Val Ser Arg Thr Glu Ala Leu Ser Leu
    8735            8740                8745

Gly Arg Thr Ser Thr Pro Gly Pro Ala Gln Ser Thr Ile Ser Pro
    8750            8755                8760

Glu Ile Ser Thr Glu Thr Ile Thr Arg Ile Ser Thr Pro Leu Thr
    8765            8770                8775

Thr Thr Gly Ser Ala Glu Met Thr Ile Thr Pro Lys Thr Gly His
    8780            8785                8790

Ser Gly Ala Ser Ser Gln Gly Thr Phe Thr Leu Asp Thr Ser Ser
    8795            8800                8805
```

```
Arg Ala Ser Trp Pro Gly Thr His Ser Ala Ala Thr His Arg Ser
8810            8815            8820

Pro His Ser Gly Met Thr Thr Pro Met Ser Arg Gly Pro Glu Asp
8825            8830            8835

Val Ser Trp Pro Ser Arg Pro Ser Val Glu Lys Thr Ser Pro Pro
8840            8845            8850

Ser Ser Leu Val Ser Leu Ser Ala Val Thr Ser Pro Ser Pro Leu
8855            8860            8865

Tyr Ser Thr Pro Ser Glu Ser Ser His Ser Ser Pro Leu Arg Val
8870            8875            8880

Thr Ser Leu Phe Thr Pro Val Met Met Lys Thr Thr Asp Met Leu
8885            8890            8895

Asp Thr Ser Leu Glu Pro Val Thr Thr Ser Pro Pro Ser Met Asn
8900            8905            8910

Ile Thr Ser Asp Glu Ser Leu Ala Thr Ser Lys Ala Thr Met Glu
8915            8920            8925

Thr Glu Ala Ile Gln Leu Ser Glu Asn Thr Ala Val Thr Gln Met
8930            8935            8940

Gly Thr Ile Ser Ala Arg Gln Glu Phe Tyr Ser Ser Tyr Pro Gly
8945            8950            8955

Leu Pro Glu Pro Ser Lys Val Thr Ser Pro Val Val Thr Ser Ser
8960            8965            8970

Thr Ile Lys Asp Ile Val Ser Thr Thr Ile Pro Ala Ser Ser Glu
8975            8980            8985

Ile Thr Arg Ile Glu Met Glu Ser Thr Ser Thr Leu Thr Pro Thr
8990            8995            9000

Pro Arg Glu Thr Ser Thr Ser Gln Glu Ile His Ser Ala Thr Lys
9005            9010            9015

Pro Ser Thr Val Pro Tyr Lys Ala Leu Thr Ser Ala Thr Ile Glu
9020            9025            9030

Asp Ser Met Thr Gln Val Met Ser Ser Ser Arg Gly Pro Ser Pro
9035            9040            9045

Asp Gln Ser Thr Met Ser Gln Asp Ile Ser Thr Glu Val Ile Thr
9050            9055            9060

Arg Leu Ser Thr Ser Pro Ile Lys Thr Glu Ser Thr Glu Met Thr
9065            9070            9075

Ile Thr Thr Gln Thr Gly Ser Pro Gly Ala Thr Ser Arg Gly Thr
9080            9085            9090

Leu Thr Leu Asp Thr Ser Thr Thr Phe Met Ser Gly Thr His Ser
9095            9100            9105

Thr Ala Ser Gln Gly Phe Ser His Ser Gln Met Thr Ala Leu Met
9110            9115            9120

Ser Arg Thr Pro Gly Asp Val Pro Trp Leu Ser His Pro Ser Val
9125            9130            9135

Glu Glu Ala Ser Ser Ala Ser Phe Ser Leu Ser Ser Pro Val Met
9140            9145            9150

Thr Ser Ser Ser Pro Val Ser Ser Thr Leu Pro Asp Ser Ile His
9155            9160            9165

Ser Ser Ser Leu Pro Val Thr Ser Leu Leu Thr Ser Gly Leu Val
9170            9175            9180

Lys Thr Thr Glu Leu Leu Gly Thr Ser Ser Glu Pro Glu Thr Ser
9185            9190            9195
```

```
Ser Pro Pro Asn Leu Ser Ser Thr Ser Ala Glu Ile Leu Ala Ile
    9200            9205                9210

Thr Glu Val Thr Thr Asp Thr Glu Lys Leu Glu Met Thr Asn Val
    9215            9220                9225

Val Thr Ser Gly Tyr Thr His Glu Ser Pro Ser Ser Val Leu Ala
    9230            9235                9240

Asp Ser Val Thr Thr Lys Ala Thr Ser Ser Met Gly Ile Thr Tyr
    9245            9250                9255

Pro Thr Gly Asp Thr Asn Val Leu Thr Ser Thr Pro Ala Phe Ser
    9260            9265                9270

Asp Thr Ser Arg Ile Gln Thr Lys Ser Lys Leu Ser Leu Thr Pro
    9275            9280                9285

Gly Leu Met Glu Thr Ser Ile Ser Glu Glu Thr Ser Ser Ala Thr
    9290            9295                9300

Glu Lys Ser Thr Val Leu Ser Ser Val Pro Thr Gly Ala Thr Thr
    9305            9310                9315

Glu Val Ser Arg Thr Glu Ala Ile Ser Ser Ser Arg Thr Ser Ile
    9320            9325                9330

Pro Gly Pro Ala Gln Ser Thr Met Ser Ser Asp Thr Ser Met Glu
    9335            9340                9345

Thr Ile Thr Arg Ile Ser Thr Pro Leu Thr Arg Lys Glu Ser Thr
    9350            9355                9360

Asp Met Ala Ile Thr Pro Lys Thr Gly Pro Ser Gly Ala Thr Ser
    9365            9370                9375

Gln Gly Thr Phe Thr Leu Asp Ser Ser Thr Ala Ser Trp Pro
    9380            9385                9390

Gly Thr His Ser Ala Thr Thr Gln Arg Phe Pro Gln Ser Val Val
    9395            9400                9405

Thr Thr Pro Met Ser Arg Gly Pro Glu Asp Val Ser Trp Pro Ser
    9410            9415                9420

Pro Leu Ser Val Glu Lys Asn Ser Pro Pro Ser Ser Leu Val Ser
    9425            9430                9435

Ser Ser Ser Val Thr Ser Pro Ser Pro Leu Tyr Ser Thr Pro Ser
    9440            9445                9450

Gly Ser Ser His Ser Ser Pro Val Pro Val Thr Ser Leu Phe Thr
    9455            9460                9465

Ser Ile Met Met Lys Ala Thr Asp Met Leu Asp Ala Ser Leu Glu
    9470            9475                9480

Pro Glu Thr Thr Ser Ala Pro Asn Met Asn Ile Thr Ser Asp Glu
    9485            9490                9495

Ser Leu Ala Ala Ser Lys Ala Thr Thr Glu Thr Glu Ala Ile His
    9500            9505                9510

Val Phe Glu Asn Thr Ala Ala Ser His Val Glu Thr Thr Ser Ala
    9515            9520                9525

Thr Glu Glu Leu Tyr Ser Ser Pro Gly Phe Ser Glu Pro Thr
    9530            9535                9540

Lys Val Ile Ser Pro Val Val Thr Ser Ser Ser Ile Arg Asp Asn
    9545            9550                9555

Met Val Ser Thr Thr Met Pro Gly Ser Ser Gly Ile Thr Arg Ile
    9560            9565                9570

Glu Ile Glu Ser Met Ser Ser Leu Thr Pro Gly Leu Arg Glu Thr
    9575            9580                9585
```

-continued

Arg Thr Ser Gln Asp Ile Thr Ser Ser Thr Glu Thr Ser Thr Val
9590                9595                9600

Leu Tyr Lys Met Pro Ser Gly Ala Thr Pro Glu Val Ser Arg Thr
9605                9610                9615

Glu Val Met Pro Ser Ser Arg Thr Ser Ile Pro Gly Pro Ala Gln
9620                9625                9630

Ser Thr Met Ser Leu Asp Ile Ser Asp Glu Val Val Thr Arg Leu
9635                9640                9645

Ser Thr Ser Pro Ile Met Thr Glu Ser Ala Glu Ile Thr Ile Thr
9650                9655                9660

Thr Gln Thr Gly Tyr Ser Leu Ala Thr Ser Gln Val Thr Leu Pro
9665                9670                9675

Leu Gly Thr Ser Met Thr Phe Leu Ser Gly Thr His Ser Thr Met
9680                9685                9690

Ser Gln Gly Leu Ser His Ser Glu Met Thr Asn Leu Met Ser Arg
9695                9700                9705

Gly Pro Glu Ser Leu Ser Trp Thr Ser Pro Arg Phe Val Glu Thr
9710                9715                9720

Thr Arg Ser Ser Ser Ser Leu Thr Ser Leu Pro Leu Thr Thr Ser
9725                9730                9735

Leu Ser Pro Val Ser Ser Thr Leu Leu Asp Ser Ser Pro Ser Ser
9740                9745                9750

Pro Leu Pro Val Thr Ser Leu Ile Leu Pro Gly Leu Val Lys Thr
9755                9760                9765

Thr Glu Val Leu Asp Thr Ser Ser Glu Pro Lys Thr Ser Ser Ser
9770                9775                9780

Pro Asn Leu Ser Ser Thr Ser Val Glu Ile Pro Ala Thr Ser Glu
9785                9790                9795

Ile Met Thr Asp Thr Glu Lys Ile His Pro Ser Ser Asn Thr Ala
9800                9805                9810

Val Ala Lys Val Arg Thr Ser Ser Ser Val His Glu Ser His Ser
9815                9820                9825

Ser Val Leu Ala Asp Ser Glu Thr Thr Ile Thr Ile Pro Ser Met
9830                9835                9840

Gly Ile Thr Ser Ala Val Asp Asp Thr Thr Val Phe Thr Ser Asn
9845                9850                9855

Pro Ala Phe Ser Glu Thr Arg Arg Ile Pro Thr Glu Pro Thr Phe
9860                9865                9870

Ser Leu Thr Pro Gly Phe Arg Glu Thr Ser Thr Glu Glu Thr
9875                9880                9885

Thr Ser Ile Thr Glu Thr Ser Ala Val Leu Tyr Gly Val Pro Thr
9890                9895                9900

Ser Ala Thr Thr Glu Val Ser Met Thr Glu Ile Met Ser Ser Asn
9905                9910                9915

Arg Ile His Ile Pro Asp Ser Asp Gln Ser Thr Met Ser Pro Asp
9920                9925                9930

Ile Ile Thr Glu Val Ile Thr Arg Leu Ser Ser Ser Ser Met Met
9935                9940                9945

Ser Glu Ser Thr Gln Met Thr Ile Thr Thr Gln Lys Ser Ser Pro
9950                9955                9960

Gly Ala Thr Ala Gln Ser Thr Leu Thr Leu Ala Thr Thr Thr Ala
9965                9970                9975

```
Pro Leu Ala Arg Thr His Ser   Thr Val Pro Pro Arg   Phe Leu His
    9980                9985                9990

Ser Glu Met Thr Thr Leu Met   Ser Arg Ser Pro Glu   Asn Pro Ser
    9995               10000                10005

Trp Lys Ser Ser Leu Phe Val   Glu Lys Thr Ser Ser   Ser Ser Ser
   10010               10015               10020

Leu Leu Ser Leu Pro Val Thr   Thr Ser Pro Ser Val   Ser Ser Thr
   10025               10030               10035

Leu Pro Gln Ser Ile Pro Ser   Ser Ser Phe Ser Val   Thr Ser Leu
   10040               10045               10050

Leu Thr Pro Gly Met Val Lys   Thr Thr Asp Thr Ser   Thr Glu Pro
   10055               10060               10065

Gly Thr Ser Leu Ser Pro Asn   Leu Ser Gly Thr Ser   Val Glu Ile
   10070               10075               10080

Leu Ala Ala Ser Glu Val Thr   Thr Asp Thr Glu Lys   Ile His Pro
   10085               10090               10095

Ser Ser Ser Met Ala Val Thr   Asn Val Gly Thr Thr   Ser Ser Gly
   10100               10105               10110

His Glu Leu Tyr Ser Ser Val   Ser Ile His Ser Glu   Pro Ser Lys
   10115               10120               10125

Ala Thr Tyr Pro Val Gly Thr   Pro Ser Ser Met Ala   Glu Thr Ser
   10130               10135               10140

Ile Ser Thr Ser Met Pro Ala   Asn Phe Glu Thr Thr   Gly Phe Glu
   10145               10150               10155

Ala Glu Pro Phe Ser His Leu   Thr Ser Gly Phe Arg   Lys Thr Asn
   10160               10165               10170

Met Ser Leu Asp Thr Ser Ser   Val Thr Pro Thr Asn   Thr Pro Ser
   10175               10180               10185

Ser Pro Gly Ser Thr His Leu   Leu Gln Ser Ser Lys   Thr Asp Phe
   10190               10195               10200

Thr Ser Ser Ala Lys Thr Ser   Ser Pro Asp Trp Pro   Pro Ala Ser
   10205               10210               10215

Gln Tyr Thr Glu Ile Pro Val   Asp Ile Ile Thr Pro   Phe Asn Ala
   10220               10225               10230

Ser Pro Ser Ile Thr Glu Ser   Thr Gly Ile Thr Ser   Phe Pro Glu
   10235               10240               10245

Ser Arg Phe Thr Met Ser Val   Thr Glu Ser Thr His   His Leu Ser
   10250               10255               10260

Thr Asp Leu Leu Pro Ser Ala   Glu Thr Ile Ser Thr   Gly Thr Val
   10265               10270               10275

Met Pro Ser Leu Ser Glu Ala   Met Thr Ser Phe Ala   Thr Thr Gly
   10280               10285               10290

Val Pro Arg Ala Ile Ser Gly   Ser Gly Ser Pro Phe   Ser Arg Thr
   10295               10300               10305

Glu Ser Gly Pro Gly Asp Ala   Thr Leu Ser Thr Ile   Ala Glu Ser
   10310               10315               10320

Leu Pro Ser Ser Thr Pro Val   Pro Phe Ser Ser Ser   Thr Phe Thr
   10325               10330               10335

Thr Thr Asp Ser Ser Thr Ile   Pro Ala Leu His Glu   Ile Thr Ser
   10340               10345               10350

Ser Ser Ala Thr Pro Tyr Arg   Val Asp Thr Ser Leu   Gly Thr Glu
   10355               10360               10365
```

-continued

| | | | | | | | | | | | |
|---|---|---|---|---|---|---|---|---|---|---|---|
| Ser | Ser | Thr | Thr | Glu | Gly | Arg | Leu | Val | Met | Val | Ser | Thr | Leu | Asp |
| | 10370 | | | | 10375 | | | | 10380 | | |
| Thr | Ser | Ser | Gln | Pro | Gly | Arg | Thr | Ser | Ser | Ser | Pro | Ile | Leu | Asp |
| | 10385 | | | | 10390 | | | | 10395 | | |
| Thr | Arg | Met | Thr | Glu | Ser | Val | Glu | Leu | Gly | Thr | Val | Thr | Ser | Ala |
| | 10400 | | | | 10405 | | | | 10410 | | |
| Tyr | Gln | Val | Pro | Ser | Leu | Ser | Thr | Arg | Leu | Thr | Arg | Thr | Asp | Gly |
| | 10415 | | | | 10420 | | | | 10425 | | |
| Ile | Met | Glu | His | Ile | Thr | Lys | Ile | Pro | Asn | Glu | Ala | Ala | His | Arg |
| | 10430 | | | | 10435 | | | | 10440 | | |
| Gly | Thr | Ile | Arg | Pro | Val | Lys | Gly | Pro | Gln | Thr | Ser | Thr | Ser | Pro |
| | 10445 | | | | 10450 | | | | 10455 | | |
| Ala | Ser | Pro | Lys | Gly | Leu | His | Thr | Gly | Gly | Thr | Lys | Arg | Met | Glu |
| | 10460 | | | | 10465 | | | | 10470 | | |
| Thr | Thr | Thr | Thr | Ala | Leu | Lys | Thr | Thr | Thr | Ala | Leu | Lys | Thr |
| | 10475 | | | | 10480 | | | | 10485 | | |
| Thr | Ser | Arg | Ala | Thr | Leu | Thr | Thr | Ser | Val | Tyr | Thr | Pro | Thr | Leu |
| | 10490 | | | | 10495 | | | | 10500 | | |
| Gly | Thr | Leu | Thr | Pro | Leu | Asn | Ala | Ser | Met | Gln | Met | Ala | Ser | Thr |
| | 10505 | | | | 10510 | | | | 10515 | | |
| Ile | Pro | Thr | Glu | Met | Met | Ile | Thr | Thr | Pro | Tyr | Val | Phe | Pro | Asp |
| | 10520 | | | | 10525 | | | | 10530 | | |
| Val | Pro | Glu | Thr | Thr | Ser | Ser | Leu | Ala | Thr | Ser | Leu | Gly | Ala | Glu |
| | 10535 | | | | 10540 | | | | 10545 | | |
| Thr | Ser | Thr | Ala | Leu | Pro | Arg | Thr | Thr | Pro | Ser | Val | Phe | Asn | Arg |
| | 10550 | | | | 10555 | | | | 10560 | | |
| Glu | Ser | Glu | Thr | Thr | Ala | Ser | Leu | Val | Ser | Arg | Ser | Gly | Ala | Glu |
| | 10565 | | | | 10570 | | | | 10575 | | |
| Arg | Ser | Pro | Val | Ile | Gln | Thr | Leu | Asp | Val | Ser | Ser | Ser | Glu | Pro |
| | 10580 | | | | 10585 | | | | 10590 | | |
| Asp | Thr | Thr | Ala | Ser | Trp | Val | Ile | His | Pro | Ala | Glu | Thr | Ile | Pro |
| | 10595 | | | | 10600 | | | | 10605 | | |
| Thr | Val | Ser | Lys | Thr | Thr | Pro | Asn | Phe | Phe | His | Ser | Glu | Leu | Asp |
| | 10610 | | | | 10615 | | | | 10620 | | |
| Thr | Val | Ser | Ser | Thr | Ala | Thr | Ser | His | Gly | Ala | Asp | Val | Ser | Ser |
| | 10625 | | | | 10630 | | | | 10635 | | |
| Ala | Ile | Pro | Thr | Asn | Ile | Ser | Pro | Ser | Glu | Leu | Asp | Ala | Leu | Thr |
| | 10640 | | | | 10645 | | | | 10650 | | |
| Pro | Leu | Val | Thr | Ile | Ser | Gly | Thr | Asp | Thr | Ser | Thr | Thr | Phe | Pro |
| | 10655 | | | | 10660 | | | | 10665 | | |
| Thr | Leu | Thr | Lys | Ser | Pro | His | Glu | Thr | Glu | Thr | Arg | Thr | Thr | Trp |
| | 10670 | | | | 10675 | | | | 10680 | | |
| Leu | Thr | His | Pro | Ala | Glu | Thr | Ser | Ser | Thr | Ile | Pro | Arg | Thr | Ile |
| | 10685 | | | | 10690 | | | | 10695 | | |
| Pro | Asn | Phe | Ser | His | His | Glu | Ser | Asp | Ala | Thr | Pro | Ser | Ile | Ala |
| | 10700 | | | | 10705 | | | | 10710 | | |
| Thr | Ser | Pro | Gly | Ala | Glu | Thr | Ser | Ser | Ala | Ile | Pro | Ile | Met | Thr |
| | 10715 | | | | 10720 | | | | 10725 | | |
| Val | Ser | Pro | Gly | Ala | Glu | Asp | Leu | Val | Thr | Ser | Gln | Val | Thr | Ser |
| | 10730 | | | | 10735 | | | | 10740 | | |
| Ser | Gly | Thr | Asp | Arg | Asn | Met | Thr | Ile | Pro | Thr | Leu | Thr | Leu | Ser |
| | 10745 | | | | 10750 | | | | 10755 | | |

```
Pro Gly Glu Pro Lys Thr Ile  Ala Ser Leu Val Thr  His Pro Glu
    10760            10765              10770

Ala Gln Thr Ser Ser Ala Ile  Pro Thr Ser Thr Ile  Ser Pro Ala
    10775            10780              10785

Val Ser Arg Leu Val Thr Ser  Met Val Thr Ser Leu  Ala Ala Lys
    10790            10795              10800

Thr Ser Thr Thr Asn Arg Ala  Leu Thr Asn Ser Pro  Gly Glu Pro
    10805            10810              10815

Ala Thr Thr Val Ser Leu Val  Thr His Pro Ala Gln  Thr Ser Pro
    10820            10825              10830

Thr Val Pro Trp Thr Thr Ser  Ile Phe Phe His Ser  Lys Ser Asp
    10835            10840              10845

Thr Thr Pro Ser Met Thr Thr  Ser His Gly Ala Glu  Ser Ser Ser
    10850            10855              10860

Ala Val Pro Thr Pro Thr Val  Ser Thr Glu Val Pro  Gly Val Val
    10865            10870              10875

Thr Pro Leu Val Thr Ser Ser  Arg Ala Val Ile Ser  Thr Thr Ile
    10880            10885              10890

Pro Ile Leu Thr Leu Ser Pro  Gly Glu Pro Glu Thr  Thr Pro Ser
    10895            10900              10905

Met Ala Thr Ser His Gly Glu  Glu Ala Ser Ser Ala  Ile Pro Thr
    10910            10915              10920

Pro Thr Val Ser Pro Gly Val  Pro Gly Val Val Thr  Ser Leu Val
    10925            10930              10935

Thr Ser Ser Arg Ala Val Thr  Ser Thr Thr Ile Pro  Ile Leu Thr
    10940            10945              10950

Phe Ser Leu Gly Glu Pro Glu  Thr Thr Pro Ser Met  Ala Thr Ser
    10955            10960              10965

His Gly Thr Glu Ala Gly Ser  Ala Val Pro Thr Val  Leu Pro Glu
    10970            10975              10980

Val Pro Gly Met Val Thr Ser  Leu Val Ala Ser Ser  Arg Ala Val
    10985            10990              10995

Thr Ser Thr Thr Leu Pro Thr  Leu Thr Leu Ser Pro  Gly Glu Pro
    11000            11005              11010

Glu Thr Thr Pro Ser Met Ala  Thr Ser His Gly Ala  Glu Ala Ser
    11015            11020              11025

Ser Thr Val Pro Thr Val Ser  Pro Glu Val Pro Gly  Val Val Thr
    11030            11035              11040

Ser Leu Val Thr Ser Ser Ser  Gly Val Asn Ser Thr  Ser Ile Pro
    11045            11050              11055

Thr Leu Ile Leu Ser Pro Gly  Glu Leu Glu Thr Thr  Pro Ser Met
    11060            11065              11070

Ala Thr Ser His Gly Ala Glu  Ala Ser Ser Ala Val  Pro Thr Pro
    11075            11080              11085

Thr Val Ser Pro Gly Val Ser  Gly Val Val Thr Pro  Leu Val Thr
    11090            11095              11100

Ser Ser Arg Ala Val Thr Ser  Thr Thr Ile Pro Ile  Leu Thr Leu
    11105            11110              11115

Ser Ser Ser Glu Pro Glu Thr  Thr Pro Ser Met Ala  Thr Ser His
    11120            11125              11130

Gly Val Glu Ala Ser Ser Ala  Val Leu Thr Val Ser  Pro Glu Val
    11135            11140              11145
```

| | | | | | | | | | | | |
|---|---|---|---|---|---|---|---|---|---|---|---|
|Pro|Gly 11150|Met|Val|Thr|Ser 11155|Leu|Val|Thr|Ser|Ser 11160|Arg|Ala|Val|Thr|
|Ser|Thr 11165|Thr|Ile|Pro|Thr 11170|Leu|Thr|Ile|Ser|Ser 11175|Asp|Glu|Pro|Glu|
|Thr|Thr 11180|Thr|Ser|Leu|Val 11185|Thr|His|Ser|Glu|Ala 11190|Lys|Met|Ile|Ser|
|Ala|Ile 11195|Pro|Thr|Leu|Ala 11200|Val|Ser|Pro|Thr|Val 11205|Gln|Gly|Leu|Val|
|Thr|Ser 11210|Leu|Val|Thr|Ser 11215|Ser|Gly|Ser|Glu|Thr 11220|Ser|Ala|Phe|Ser|
|Asn|Leu 11225|Thr|Val|Ala|Ser 11230|Ser|Gln|Pro|Glu|Thr 11235|Ile|Asp|Ser|Trp|
|Val|Ala 11240|His|Pro|Gly|Thr 11245|Glu|Ala|Ser|Ser|Val 11250|Val|Pro|Thr|Leu|
|Thr|Val 11255|Ser|Thr|Gly|Glu 11260|Pro|Phe|Thr|Asn|Ile 11265|Ser|Leu|Val|Thr|
|His|Pro 11270|Ala|Glu|Ser|Ser 11275|Ser|Thr|Leu|Pro|Arg 11280|Thr|Thr|Ser|Arg|
|Phe|Ser 11285|His|Ser|Glu|Leu 11290|Asp|Thr|Met|Pro|Ser 11295|Thr|Val|Thr|Ser|
|Pro|Glu 11300|Ala|Glu|Ser|Ser 11305|Ser|Ala|Ile|Ser|Thr 11310|Thr|Ile|Ser|Pro|
|Gly|Ile 11315|Pro|Gly|Val|Leu 11320|Thr|Ser|Leu|Val|Thr 11325|Ser|Ser|Gly|Arg|
|Asp|Ile 11330|Ser|Ala|Thr|Phe 11335|Pro|Thr|Val|Pro|Glu 11340|Ser|Pro|His|Glu|
|Ser|Glu 11345|Ala|Thr|Ala|Ser 11350|Trp|Val|Thr|His|Pro 11355|Ala|Val|Thr|Ser|
|Thr|Thr 11360|Val|Pro|Arg|Thr 11365|Thr|Pro|Asn|Tyr|Ser 11370|His|Ser|Glu|Pro|
|Asp|Thr 11375|Thr|Pro|Ser|Ile 11380|Ala|Thr|Ser|Pro|Gly 11385|Ala|Glu|Ala|Thr|
|Ser|Asp 11390|Phe|Pro|Thr|Ile 11395|Thr|Val|Ser|Pro|Asp 11400|Val|Pro|Asp|Met|
|Val|Thr 11405|Ser|Gln|Val|Thr 11410|Ser|Ser|Gly|Thr|Asp 11415|Thr|Ser|Ile|Thr|
|Ile|Pro 11420|Thr|Leu|Thr|Leu 11425|Ser|Ser|Gly|Glu|Pro 11430|Glu|Thr|Thr|Thr|
|Ser|Phe 11435|Ile|Thr|Tyr|Ser 11440|Glu|Thr|His|Thr|Ser 11445|Ser|Ala|Ile|Pro|
|Thr|Leu 11450|Pro|Val|Ser|Pro 11455|Gly|Ala|Ser|Lys|Met 11460|Leu|Thr|Ser|Leu|
|Val|Ile 11465|Ser|Ser|Gly|Thr 11470|Asp|Ser|Thr|Thr|Thr 11475|Phe|Pro|Thr|Leu|
|Thr|Glu 11480|Thr|Pro|Tyr|Glu 11485|Pro|Glu|Thr|Thr|Ala 11490|Ile|Gln|Leu|Ile|
|His|Pro 11495|Ala|Glu|Thr|Asn 11500|Thr|Met|Val|Pro|Arg 11505|Thr|Thr|Pro|Lys|
|Phe|Ser 11510|His|Ser|Lys|Ser 11515|Asp|Thr|Thr|Leu|Pro 11520|Val|Ala|Ile|Thr|
|Ser|Pro 11525|Gly|Pro|Glu|Ala 11530|Ser|Ser|Ala|Val|Ser 11535|Thr|Thr|Thr|Ile|

```
Ser Pro Asp Met Ser Asp Leu Val Thr Ser Leu Val Pro Ser Ser
    11540              11545              11550

Gly Thr Asp Thr Ser Thr Thr Phe Pro Thr Leu Ser Glu Thr Pro
    11555              11560              11565

Tyr Glu Pro Glu Thr Thr Ala Thr Trp Leu Thr His Pro Ala Glu
    11570              11575              11580

Thr Ser Thr Thr Val Ser Gly Thr Ile Pro Asn Phe Ser His Arg
    11585              11590              11595

Gly Ser Asp Thr Ala Pro Ser Met Val Thr Ser Pro Gly Val Asp
    11600              11605              11610

Thr Arg Ser Gly Val Pro Thr Thr Thr Ile Pro Pro Ser Ile Pro
    11615              11620              11625

Gly Val Val Thr Ser Gln Val Thr Ser Ser Ala Thr Asp Thr Ser
    11630              11635              11640

Thr Ala Ile Pro Thr Leu Thr Pro Ser Pro Gly Glu Pro Glu Thr
    11645              11650              11655

Thr Ala Ser Ser Ala Thr His Pro Gly Thr Gln Thr Gly Phe Thr
    11660              11665              11670

Val Pro Ile Arg Thr Val Pro Ser Ser Glu Pro Asp Thr Met Ala
    11675              11680              11685

Ser Trp Val Thr His Pro Pro Gln Thr Ser Thr Pro Val Ser Arg
    11690              11695              11700

Thr Thr Ser Ser Phe Ser His Ser Ser Pro Asp Ala Thr Pro Val
    11705              11710              11715

Met Ala Thr Ser Pro Arg Thr Glu Ala Ser Ser Ala Val Leu Thr
    11720              11725              11730

Thr Ile Ser Pro Gly Ala Pro Glu Met Val Thr Ser Gln Ile Thr
    11735              11740              11745

Ser Ser Gly Ala Ala Thr Ser Thr Thr Val Pro Thr Leu Thr His
    11750              11755              11760

Ser Pro Gly Met Pro Glu Thr Thr Ala Leu Leu Ser Thr His Pro
    11765              11770              11775

Arg Thr Glu Thr Ser Lys Thr Phe Pro Ala Ser Thr Val Phe Pro
    11780              11785              11790

Gln Val Ser Glu Thr Thr Ala Ser Leu Thr Ile Arg Pro Gly Ala
    11795              11800              11805

Glu Thr Ser Thr Ala Leu Pro Thr Gln Thr Thr Ser Ser Leu Phe
    11810              11815              11820

Thr Leu Leu Val Thr Gly Thr Ser Arg Val Asp Leu Ser Pro Thr
    11825              11830              11835

Ala Ser Pro Gly Val Ser Ala Lys Thr Ala Pro Leu Ser Thr His
    11840              11845              11850

Pro Gly Thr Glu Thr Ser Thr Met Ile Pro Thr Ser Thr Leu Ser
    11855              11860              11865

Leu Gly Leu Leu Glu Thr Thr Gly Leu Leu Ala Thr Ser Ser Ser
    11870              11875              11880

Ala Glu Thr Ser Thr Ser Thr Leu Thr Leu Thr Val Ser Pro Ala
    11885              11890              11895

Val Ser Gly Leu Ser Ser Ala Ser Ile Thr Thr Asp Lys Pro Gln
    11900              11905              11910

Thr Val Thr Ser Trp Asn Thr Glu Thr Ser Pro Ser Val Thr Ser
    11915              11920              11925
```

```
Val Gly Pro Pro Glu Phe Ser Arg Thr Val Thr Gly Thr Thr Met
    11930               11935               11940

Thr Leu Ile Pro Ser Glu Met Pro Thr Pro Pro Lys Thr Ser His
    11945               11950               11955

Gly Glu Gly Val Ser Pro Thr Thr Ile Leu Arg Thr Thr Met Val
    11960               11965               11970

Glu Ala Thr Asn Leu Ala Thr Thr Gly Ser Ser Pro Thr Val Ala
    11975               11980               11985

Lys Thr Thr Thr Thr Phe Asn Thr Leu Ala Gly Ser Leu Phe Thr
    11990               11995               12000

Pro Leu Thr Thr Pro Gly Met Ser Thr Leu Ala Ser Glu Ser Val
    12005               12010               12015

Thr Ser Arg Thr Ser Tyr Asn His Arg Ser Trp Ile Ser Thr Thr
    12020               12025               12030

Ser Ser Tyr Asn Arg Arg Tyr Trp Thr Pro Ala Thr Ser Thr Pro
    12035               12040               12045

Val Thr Ser Thr Phe Ser Pro Gly Ile Ser Thr Ser Ser Ile Pro
    12050               12055               12060

Ser Ser Thr Ala Ala Thr Val Pro Phe Met Val Pro Phe Thr Leu
    12065               12070               12075

Asn Phe Thr Ile Thr Asn Leu Gln Tyr Glu Glu Asp Met Arg His
    12080               12085               12090

Pro Gly Ser Arg Lys Phe Asn Ala Thr Glu Arg Glu Leu Gln Gly
    12095               12100               12105

Leu Leu Lys Pro Leu Phe Arg Asn Ser Ser Leu Glu Tyr Leu Tyr
    12110               12115               12120

Ser Gly Cys Arg Leu Ala Ser Leu Arg Pro Glu Lys Asp Ser Ser
    12125               12130               12135

Ala Thr Ala Val Asp Ala Ile Cys Thr His Arg Pro Asp Pro Glu
    12140               12145               12150

Asp Leu Gly Leu Asp Arg Glu Arg Leu Tyr Trp Glu Leu Ser Asn
    12155               12160               12165

Leu Thr Asn Gly Ile Gln Glu Leu Gly Pro Tyr Thr Leu Asp Arg
    12170               12175               12180

Asn Ser Leu Tyr Val Asn Gly Phe Thr His Arg Ser Ser Met Pro
    12185               12190               12195

Thr Thr Ser Thr Pro Gly Thr Ser Thr Val Asp Val Gly Thr Ser
    12200               12205               12210

Gly Thr Pro Ser Ser Ser Pro Ser Pro Thr Thr Ala Gly Pro Leu
    12215               12220               12225

Leu Met Pro Phe Thr Leu Asn Phe Thr Ile Thr Asn Leu Gln Tyr
    12230               12235               12240

Glu Glu Asp Met Arg Arg Thr Gly Ser Arg Lys Phe Asn Thr Met
    12245               12250               12255

Glu Ser Val Leu Gln Gly Leu Leu Lys Pro Leu Phe Lys Asn Thr
    12260               12265               12270

Ser Val Gly Pro Leu Tyr Ser Gly Cys Arg Leu Thr Leu Leu Arg
    12275               12280               12285

Pro Glu Lys Asp Gly Ala Ala Thr Gly Val Asp Ala Ile Cys Thr
    12290               12295               12300

His Arg Leu Asp Pro Lys Ser Pro Gly Leu Asn Arg Glu Gln Leu
    12305               12310               12315
```

```
Tyr Trp Glu Leu Ser Lys Leu     Thr Asn Asp Ile     Glu Leu Gly
    12320               12325               12330

Pro Tyr Thr Leu Asp Arg Asn     Ser Leu Tyr Val     Asn Gly Phe Thr
    12335               12340               12345

His Gln Ser Ser Val Ser Thr     Thr Ser Thr Pro     Gly Thr Ser Thr
    12350               12355               12360

Val Asp Leu Arg Thr Ser Gly     Thr Pro Ser Ser Leu     Ser Ser Pro
    12365               12370               12375

Thr Ile Met Ala Ala Gly Pro     Leu Leu Val Pro Phe     Thr Leu Asn
    12380               12385               12390

Phe Thr Ile Thr Asn Leu Gln     Tyr Gly Glu Asp Met     Gly His Pro
    12395               12400               12405

Gly Ser Arg Lys Phe Asn Thr     Thr Glu Arg Val Leu     Gln Gly Leu
    12410               12415               12420

Leu Gly Pro Ile Phe Lys Asn     Thr Ser Val Gly Pro     Leu Tyr Ser
    12425               12430               12435

Gly Cys Arg Leu Thr Ser Leu     Arg Ser Glu Lys Asp     Gly Ala Ala
    12440               12445               12450

Thr Gly Val Asp Ala Ile Cys     Ile His His Leu Asp     Pro Lys Ser
    12455               12460               12465

Pro Gly Leu Asn Arg Glu Arg     Leu Tyr Trp Glu Leu     Ser Gln Leu
    12470               12475               12480

Thr Asn Gly Ile Lys Glu Leu     Gly Pro Tyr Thr Leu     Asp Arg Asn
    12485               12490               12495

Ser Leu Tyr Val Asn Gly Phe     Thr His Arg Thr Ser     Val Pro Thr
    12500               12505               12510

Ser Ser Thr Pro Gly Thr Ser     Thr Val Asp Leu Gly     Thr Ser Gly
    12515               12520               12525

Thr Pro Phe Ser Leu Pro Ser     Pro Ala Thr Ala Gly     Pro Leu Leu
    12530               12535               12540

Val Leu Phe Thr Leu Asn Phe     Thr Ile Thr Asn Leu     Lys Tyr Glu
    12545               12550               12555

Glu Asp Met His Arg Pro Gly     Ser Arg Lys Phe Asn     Thr Thr Glu
    12560               12565               12570

Arg Val Leu Gln Thr Leu Leu     Gly Pro Met Phe Lys     Asn Thr Ser
    12575               12580               12585

Val Gly Leu Leu Tyr Ser Gly     Cys Arg Leu Thr Leu     Leu Arg Ser
    12590               12595               12600

Glu Lys Asp Gly Ala Ala Thr     Gly Val Asp Ala Ile     Cys Thr His
    12605               12610               12615

Arg Leu Asp Pro Lys Ser Pro     Gly Val Asp Arg Glu     Gln Leu Tyr
    12620               12625               12630

Trp Glu Leu Ser Gln Leu Thr     Asn Gly Ile Lys Glu     Leu Gly Pro
    12635               12640               12645

Tyr Thr Leu Asp Arg Asn Ser     Leu Tyr Val Asn Gly     Phe Thr His
    12650               12655               12660

Trp Ile Pro Val Pro Thr Ser     Ser Thr Pro Gly Thr     Ser Thr Val
    12665               12670               12675

Asp Leu Gly Ser Gly Thr Pro     Ser Ser Leu Pro Ser     Pro Thr Thr
    12680               12685               12690

Ala Gly Pro Leu Leu Val Pro     Phe Thr Leu Asn Phe     Thr Ile Thr
    12695               12700               12705
```

```
Asn Leu Lys Tyr Glu Glu Asp Met His Cys Pro Gly Ser Arg Lys
    12710               12715               12720

Phe Asn Thr Thr Glu Arg Val Leu Gln Ser Leu Leu Gly Pro Met
    12725               12730               12735

Phe Lys Asn Thr Ser Val Gly Pro Leu Tyr Ser Gly Cys Arg Leu
    12740               12745               12750

Thr Leu Leu Arg Ser Glu Lys Asp Gly Ala Ala Thr Gly Val Asp
    12755               12760               12765

Ala Ile Cys Thr His Arg Leu Asp Pro Lys Ser Pro Gly Val Asp
    12770               12775               12780

Arg Glu Gln Leu Tyr Trp Glu Leu Ser Gln Leu Thr Asn Gly Ile
    12785               12790               12795

Lys Glu Leu Gly Pro Tyr Thr Leu Asp Arg Asn Ser Leu Tyr Val
    12800               12805               12810

Asn Gly Phe Thr His Gln Thr Ser Ala Pro Asn Thr Ser Thr Pro
    12815               12820               12825

Gly Thr Ser Thr Val Asp Leu Gly Thr Ser Gly Thr Pro Ser Ser
    12830               12835               12840

Leu Pro Ser Pro Thr Ser Ala Gly Pro Leu Leu Val Pro Phe Thr
    12845               12850               12855

Leu Asn Phe Thr Ile Thr Asn Leu Gln Tyr Glu Glu Asp Met His
    12860               12865               12870

His Pro Gly Ser Arg Lys Phe Asn Thr Thr Glu Arg Val Leu Gln
    12875               12880               12885

Gly Leu Leu Gly Pro Met Phe Lys Asn Thr Ser Val Gly Leu Leu
    12890               12895               12900

Tyr Ser Gly Cys Arg Leu Thr Leu Leu Arg Pro Glu Lys Asn Gly
    12905               12910               12915

Ala Ala Thr Gly Met Asp Ala Ile Cys Ser His Arg Leu Asp Pro
    12920               12925               12930

Lys Ser Pro Gly Leu Asn Arg Glu Gln Leu Tyr Trp Glu Leu Ser
    12935               12940               12945

Gln Leu Thr His Gly Ile Lys Glu Leu Gly Pro Tyr Thr Leu Asp
    12950               12955               12960

Arg Asn Ser Leu Tyr Val Asn Gly Phe Thr His Arg Ser Ser Val
    12965               12970               12975

Ala Pro Thr Ser Thr Pro Gly Thr Ser Thr Val Asp Leu Gly Thr
    12980               12985               12990

Ser Gly Thr Pro Ser Ser Leu Pro Ser Pro Thr Thr Ala Val Pro
    12995               13000               13005

Leu Leu Val Pro Phe Thr Leu Asn Phe Thr Ile Thr Asn Leu Gln
    13010               13015               13020

Tyr Gly Glu Asp Met Arg His Pro Gly Ser Arg Lys Phe Asn Thr
    13025               13030               13035

Thr Glu Arg Val Leu Gln Gly Leu Leu Gly Pro Leu Phe Lys Asn
    13040               13045               13050

Ser Ser Val Gly Pro Leu Tyr Ser Gly Cys Arg Leu Ile Ser Leu
    13055               13060               13065

Arg Ser Glu Lys Asp Gly Ala Ala Thr Gly Val Asp Ala Ile Cys
    13070               13075               13080

Thr His His Leu Asn Pro Gln Ser Pro Gly Leu Asp Arg Glu Gln
    13085               13090               13095
```

```
Leu Tyr Trp Gln Leu Ser Gln Met Thr Asn Gly Ile Lys Glu Leu
13100               13105               13110
Gly Pro Tyr Thr Leu Asp Arg Asn Ser Leu Tyr Val Asn Gly Phe
13115               13120               13125
Thr His Arg Ser Ser Gly Leu Thr Thr Ser Thr Pro Trp Thr Ser
13130               13135               13140
Thr Val Asp Leu Gly Thr Ser Gly Thr Pro Ser Pro Val Pro Ser
13145               13150               13155
Pro Thr Thr Thr Gly Pro Leu Leu Val Pro Phe Thr Leu Asn Phe
13160               13165               13170
Thr Ile Thr Asn Leu Gln Tyr Glu Glu Asn Met Gly His Pro Gly
13175               13180               13185
Ser Arg Lys Phe Asn Ile Thr Glu Ser Val Leu Gln Gly Leu Leu
13190               13195               13200
Lys Pro Leu Phe Lys Ser Thr Ser Val Gly Pro Leu Tyr Ser Gly
13205               13210               13215
Cys Arg Leu Thr Leu Leu Arg Pro Glu Lys Asp Gly Val Ala Thr
13220               13225               13230
Arg Val Asp Ala Ile Cys Thr His Arg Pro Asp Pro Lys Ile Pro
13235               13240               13245
Gly Leu Asp Arg Gln Gln Leu Tyr Trp Glu Leu Ser Gln Leu Thr
13250               13255               13260
His Ser Ile Thr Glu Leu Gly Pro Tyr Thr Leu Asp Arg Asp Ser
13265               13270               13275
Leu Tyr Val Asn Gly Phe Thr Gln Arg Ser Ser Val Pro Thr Thr
13280               13285               13290
Ser Thr Pro Gly Thr Phe Thr Val Gln Pro Glu Thr Ser Glu Thr
13295               13300               13305
Pro Ser Ser Leu Pro Gly Pro Thr Ala Thr Gly Pro Val Leu Leu
13310               13315               13320
Pro Phe Thr Leu Asn Phe Thr Ile Thr Asn Leu Gln Tyr Glu Glu
13325               13330               13335
Asp Met Arg Arg Pro Gly Ser Arg Lys Phe Asn Thr Thr Glu Arg
13340               13345               13350
Val Leu Gln Gly Leu Leu Met Pro Leu Phe Lys Asn Thr Ser Val
13355               13360               13365
Ser Ser Leu Tyr Ser Gly Cys Arg Leu Thr Leu Leu Arg Pro Glu
13370               13375               13380
Lys Asp Gly Ala Ala Thr Arg Val Asp Ala Val Cys Thr His Arg
13385               13390               13395
Pro Asp Pro Lys Ser Pro Gly Leu Asp Arg Glu Arg Leu Tyr Trp
13400               13405               13410
Lys Leu Ser Gln Leu Thr His Gly Ile Thr Glu Leu Gly Pro Tyr
13415               13420               13425
Thr Leu Asp Arg His Ser Leu Tyr Val Asn Gly Phe Thr His His Gln
13430               13435               13440
Ser Ser Met Thr Thr Thr Arg Thr Pro Asp Thr Ser Thr Met His
13445               13450               13455
Leu Ala Thr Ser Arg Thr Pro Ala Ser Leu Ser Gly Pro Met Thr
13460               13465               13470
Ala Ser Pro Leu Leu Val Leu Phe Thr Ile Asn Phe Thr Ile Thr
13475               13480               13485
```

```
Asn Leu Arg Tyr Glu Glu Asn    Met His His Pro Gly    Ser Arg Lys
    13490               13495                13500

Phe Asn Thr Thr Glu Arg Val    Leu Gln Gly Leu Leu    Arg Pro Val
    13505               13510                13515

Phe Lys Asn Thr Ser Val Gly    Pro Leu Tyr Ser Gly    Cys Arg Leu
    13520               13525                13530

Thr Leu Leu Arg Pro Lys Lys    Asp Gly Ala Ala Thr    Lys Val Asp
    13535               13540                13545

Ala Ile Cys Thr Tyr Arg Pro    Asp Pro Lys Ser Pro    Gly Leu Asp
    13550               13555                13560

Arg Glu Gln Leu Tyr Trp Glu    Leu Ser Gln Leu Thr    His Ser Ile
    13565               13570                13575

Thr Glu Leu Gly Pro Tyr Thr    Leu Asp Arg Asp Ser    Leu Tyr Val
    13580               13585                13590

Asn Gly Phe Thr Gln Arg Ser    Ser Val Pro Thr Thr    Ser Ile Pro
    13595               13600                13605

Gly Thr Pro Thr Val Asp Leu    Gly Thr Ser Gly Thr    Pro Val Ser
    13610               13615                13620

Lys Pro Gly Pro Ser Ala Ala    Ser Pro Leu Leu Val    Leu Phe Thr
    13625               13630                13635

Leu Asn Phe Thr Ile Thr Asn    Leu Arg Tyr Glu Glu    Asn Met Gln
    13640               13645                13650

His Pro Gly Ser Arg Lys Phe    Asn Thr Thr Glu Arg    Val Leu Gln
    13655               13660                13665

Gly Leu Leu Arg Ser Leu Phe    Lys Ser Thr Ser Val    Gly Pro Leu
    13670               13675                13680

Tyr Ser Gly Cys Arg Leu Thr    Leu Leu Arg Pro Glu    Lys Asp Gly
    13685               13690                13695

Thr Ala Thr Gly Val Asp Ala    Ile Cys Thr His His    Pro Asp Pro
    13700               13705                13710

Lys Ser Pro Arg Leu Asp Arg    Glu Gln Leu Tyr Trp    Glu Leu Ser
    13715               13720                13725

Gln Leu Thr His Asn Ile Thr    Glu Leu Gly Pro Tyr    Ala Leu Asp
    13730               13735                13740

Asn Asp Ser Leu Phe Val Asn    Gly Phe Thr His Arg    Ser Ser Val
    13745               13750                13755

Ser Thr Thr Ser Thr Pro Gly    Thr Pro Thr Val Tyr    Leu Gly Ala
    13760               13765                13770

Ser Lys Thr Pro Ala Ser Ile    Phe Gly Pro Ser Ala    Ala Ser His
    13775               13780                13785

Leu Leu Ile Leu Phe Thr Leu    Asn Phe Thr Ile Thr    Asn Leu Arg
    13790               13795                13800

Tyr Glu Glu Asn Met Trp Pro    Gly Ser Arg Lys Phe    Asn Thr Thr
    13805               13810                13815

Glu Arg Val Leu Gln Gly Leu    Leu Arg Pro Leu Phe    Lys Asn Thr
    13820               13825                13830

Ser Val Gly Pro Leu Tyr Ser    Gly Cys Arg Leu Thr    Leu Leu Arg
    13835               13840                13845

Pro Glu Lys Asp Gly Glu Ala    Thr Gly Val Asp Ala    Ile Cys Thr
    13850               13855                13860

His Arg Pro Asp Pro Thr Gly    Pro Gly Leu Asp Arg    Glu Gln Leu
    13865               13870                13875
```

-continued

| | | | | | | | | | | | |
|---|---|---|---|---|---|---|---|---|---|---|---|
|Tyr|Leu|Glu|Leu|Ser|Gln|Leu|Thr|His|Ser|Ile|Thr|Glu|Leu|Gly|
| | | | |13880| | | |13885| | | |13890| | |

| Tyr | Leu | Glu | Leu | Ser | Gln | Leu | Thr | His | Ser | Ile | Thr | Glu | Leu | Gly |
|---|---|---|---|---|---|---|---|---|---|---|---|---|---|---|
| | | | | 13880 | | | | 13885 | | | | 13890 | | |
| Pro | Tyr | Thr | Leu | Asp | Arg | Asp | Ser | Leu | Tyr | Val | Asn | Gly | Phe | Thr |
| | | | | 13895 | | | | 13900 | | | | 13905 | | |
| His | Arg | Ser | Ser | Val | Pro | Thr | Thr | Ser | Thr | Gly | Val | Val | Ser | Glu |
| | | | | 13910 | | | | 13915 | | | | 13920 | | |
| Glu | Pro | Phe | Thr | Leu | Asn | Phe | Thr | Ile | Asn | Asn | Leu | Arg | Tyr | Met |
| | | | | 13925 | | | | 13930 | | | | 13935 | | |
| Ala | Asp | Met | Gly | Gln | Pro | Gly | Ser | Leu | Lys | Phe | Asn | Ile | Thr | Asp |
| | | | | 13940 | | | | 13945 | | | | 13950 | | |
| Asn | Val | Met | Gln | His | Leu | Leu | Ser | Pro | Leu | Phe | Gln | Arg | Ser | Ser |
| | | | | 13955 | | | | 13960 | | | | 13965 | | |
| Leu | Gly | Ala | Arg | Tyr | Thr | Gly | Cys | Arg | Val | Ile | Ala | Leu | Arg | Ser |
| | | | | 13970 | | | | 13975 | | | | 13980 | | |
| Val | Lys | Asn | Gly | Ala | Glu | Thr | Arg | Val | Asp | Leu | Leu | Cys | Thr | Tyr |
| | | | | 13985 | | | | 13990 | | | | 13995 | | |
| Leu | Gln | Pro | Leu | Ser | Gly | Pro | Gly | Leu | Pro | Ile | Lys | Gln | Val | Phe |
| | | | | 14000 | | | | 14005 | | | | 14010 | | |
| His | Glu | Leu | Ser | Gln | Gln | Thr | His | Gly | Ile | Thr | Arg | Leu | Gly | Pro |
| | | | | 14015 | | | | 14020 | | | | 14025 | | |
| Tyr | Ser | Leu | Asp | Lys | Asp | Ser | Leu | Tyr | Leu | Asn | Gly | Tyr | Asn | Glu |
| | | | | 14030 | | | | 14035 | | | | 14040 | | |
| Pro | Gly | Pro | Asp | Glu | Pro | Pro | Thr | Thr | Pro | Lys | Pro | Ala | Thr | Thr |
| | | | | 14045 | | | | 14050 | | | | 14055 | | |
| Phe | Leu | Pro | Pro | Leu | Ser | Glu | Ala | Thr | Thr | Ala | Met | Gly | Tyr | His |
| | | | | 14060 | | | | 14065 | | | | 14070 | | |
| Leu | Lys | Thr | Leu | Thr | Leu | Asn | Phe | Thr | Ile | Ser | Asn | Leu | Gln | Tyr |
| | | | | 14075 | | | | 14080 | | | | 14085 | | |
| Ser | Pro | Asp | Met | Gly | Lys | Gly | Ser | Ala | Thr | Phe | Asn | Ser | Thr | Glu |
| | | | | 14090 | | | | 14095 | | | | 14100 | | |
| Gly | Val | Leu | Gln | His | Leu | Leu | Arg | Pro | Leu | Phe | Gln | Lys | Ser | Ser |
| | | | | 14105 | | | | 14110 | | | | 14115 | | |
| Met | Gly | Pro | Phe | Tyr | Leu | Gly | Cys | Gln | Leu | Ile | Ser | Leu | Arg | Pro |
| | | | | 14120 | | | | 14125 | | | | 14130 | | |
| Glu | Lys | Asp | Gly | Ala | Ala | Thr | Gly | Val | Asp | Thr | Thr | Cys | Thr | Tyr |
| | | | | 14135 | | | | 14140 | | | | 14145 | | |
| His | Pro | Asp | Pro | Val | Gly | Pro | Gly | Leu | Asp | Ile | Gln | Gln | Leu | Tyr |
| | | | | 14150 | | | | 14155 | | | | 14160 | | |
| Trp | Glu | Leu | Ser | Gln | Leu | Thr | His | Gly | Val | Thr | Gln | Leu | Gly | Phe |
| | | | | 14165 | | | | 14170 | | | | 14175 | | |
| Tyr | Val | Leu | Asp | Arg | Asp | Ser | Leu | Phe | Ile | Asn | Gly | Tyr | Ala | Pro |
| | | | | 14180 | | | | 14185 | | | | 14190 | | |
| Gln | Asn | Leu | Ser | Ile | Arg | Gly | Glu | Tyr | Gln | Ile | Asn | Phe | His | Ile |
| | | | | 14195 | | | | 14200 | | | | 14205 | | |
| Val | Asn | Trp | Asn | Leu | Ser | Asn | Pro | Asp | Pro | Thr | Ser | Ser | Glu | Tyr |
| | | | | 14210 | | | | 14215 | | | | 14220 | | |
| Ile | Thr | Leu | Leu | Arg | Asp | Ile | Gln | Asp | Lys | Val | Thr | Thr | Leu | Tyr |
| | | | | 14225 | | | | 14230 | | | | 14235 | | |
| Lys | Gly | Ser | Gln | Leu | His | Asp | Thr | Phe | Arg | Phe | Cys | Leu | Val | Thr |
| | | | | 14240 | | | | 14245 | | | | 14250 | | |
| Asn | Leu | Thr | Met | Asp | Ser | Val | Leu | Val | Thr | Val | Lys | Ala | Leu | Phe |
| | | | | 14255 | | | | 14260 | | | | 14265 | | |

```
Ser  Ser  Asn  Leu  Asp  Pro  Ser  Leu  Val  Glu  Gln  Val  Phe  Leu  Asp
     14270              14275                   14280

Lys  Thr  Leu  Asn  Ala  Ser  Phe  His  Trp  Leu  Gly  Ser  Thr  Tyr  Gln
     14285              14290                   14295

Leu  Val  Asp  Ile  His  Val  Thr  Glu  Met  Glu  Ser  Ser  Val  Tyr  Gln
     14300              14305                   14310

Pro  Thr  Ser  Ser  Ser  Ser  Thr  Gln  His  Phe  Tyr  Leu  Asn  Phe  Thr
     14315              14320                   14325

Ile  Thr  Asn  Leu  Pro  Tyr  Ser  Gln  Asp  Lys  Ala  Gln  Pro  Gly  Thr
     14330              14335                   14340

Thr  Asn  Tyr  Gln  Arg  Asn  Lys  Arg  Asn  Ile  Glu  Asp  Ala  Leu  Asn
     14345              14350                   14355

Gln  Leu  Phe  Arg  Asn  Ser  Ser  Ile  Lys  Ser  Tyr  Phe  Ser  Asp  Cys
     14360              14365                   14370

Gln  Val  Ser  Thr  Phe  Arg  Ser  Val  Pro  Asn  Arg  His  His  Thr  Gly
     14375              14380                   14385

Val  Asp  Ser  Leu  Cys  Asn  Phe  Ser  Pro  Leu  Ala  Arg  Arg  Val  Asp
     14390              14395                   14400

Arg  Val  Ala  Ile  Tyr  Glu  Glu  Phe  Leu  Arg  Met  Thr  Arg  Asn  Gly
     14405              14410                   14415

Thr  Gln  Leu  Gln  Asn  Phe  Thr  Leu  Asp  Arg  Ser  Ser  Val  Leu  Val
     14420              14425                   14430

Asp  Gly  Tyr  Ser  Pro  Asn  Arg  Asn  Glu  Pro  Leu  Thr  Gly  Asn  Ser
     14435              14440                   14445

Asp  Leu  Pro  Phe  Trp  Ala  Val  Ile  Leu  Ile  Gly  Leu  Ala  Gly  Leu
     14450              14455                   14460

Leu  Gly  Val  Ile  Thr  Cys  Leu  Ile  Cys  Gly  Val  Leu  Val  Thr  Thr
     14465              14470                   14475

Arg  Arg  Arg  Lys  Lys  Glu  Gly  Glu  Tyr  Asn  Val  Gln  Gln  Gln  Cys
     14480              14485                   14490

Pro  Gly  Tyr  Tyr  Gln  Ser  His  Leu  Asp  Leu  Glu  Asp  Leu  Gln
     14495              14500                   14505
```

<210> SEQ ID NO 54
<211> LENGTH: 755
<212> TYPE: PRT
<213> ORGANISM: Homo sapiens

<400> SEQUENCE: 54

```
Met  Ala  Arg  Lys  Leu  Ser  Val  Ile  Leu  Ile  Leu  Thr  Phe  Ala  Leu  Ser
1                   5                   10                  15

Val  Thr  Asn  Pro  Leu  His  Glu  Leu  Lys  Ala  Ala  Phe  Pro  Gln  Thr
                    20                  25                  30

Thr  Glu  Lys  Ile  Ser  Pro  Asn  Trp  Glu  Ser  Gly  Ile  Asn  Val  Asp  Leu
            35                  40                  45

Ala  Ile  Ser  Thr  Arg  Gln  Tyr  His  Leu  Gln  Gln  Leu  Phe  Tyr  Arg  Tyr
    50                  55                  60

Gly  Glu  Asn  Asn  Ser  Leu  Ser  Val  Glu  Gly  Phe  Arg  Lys  Leu  Leu  Gln
65                  70                  75                  80

Asn  Ile  Gly  Ile  Asp  Lys  Ile  Lys  Arg  Ile  His  Ile  His  His  Asp  His
                85                  90                  95

Asp  His  His  Ser  Asp  His  Glu  His  Ser  Asp  His  Glu  Arg  His  Ser
                100                 105                 110
```

```
Asp His Glu His His Ser Glu His Glu His His Ser Asp His Asp His
            115                 120                 125
His Ser His His Asn His Ala Ala Ser Gly Lys Asn Lys Arg Lys Ala
        130                 135                 140
Leu Cys Pro Asp His Asp Ser Asp Ser Ser Gly Lys Asp Pro Arg Asn
145                 150                 155                 160
Ser Gln Gly Lys Gly Ala His Arg Pro Glu His Ala Ser Gly Arg Arg
                165                 170                 175
Asn Val Lys Asp Ser Val Ser Ala Ser Glu Val Thr Ser Thr Val Tyr
            180                 185                 190
Asn Thr Val Ser Glu Gly Thr His Phe Leu Glu Thr Ile Glu Thr Pro
        195                 200                 205
Arg Pro Gly Lys Leu Phe Pro Lys Asp Val Ser Ser Thr Pro Pro
210                 215                 220
Ser Val Thr Ser Lys Ser Arg Val Ser Arg Leu Ala Gly Arg Lys Thr
225                 230                 235                 240
Asn Glu Ser Val Ser Glu Pro Arg Lys Gly Phe Met Tyr Ser Arg Asn
                245                 250                 255
Thr Asn Glu Asn Pro Gln Glu Cys Phe Asn Ala Ser Lys Leu Leu Thr
            260                 265                 270
Ser His Gly Met Gly Ile Gln Val Pro Leu Asn Ala Thr Glu Phe Asn
        275                 280                 285
Tyr Leu Cys Pro Ala Ile Ile Asn Gln Ile Asp Ala Arg Ser Cys Leu
        290                 295                 300
Ile His Thr Ser Glu Lys Lys Ala Glu Ile Pro Pro Lys Thr Tyr Ser
305                 310                 315                 320
Leu Gln Ile Ala Trp Val Gly Gly Phe Ile Ala Ile Ser Ile Ile Ser
                325                 330                 335
Phe Leu Ser Leu Leu Gly Val Ile Leu Val Pro Leu Met Asn Arg Val
            340                 345                 350
Phe Phe Lys Phe Leu Leu Ser Phe Leu Val Ala Leu Ala Val Gly Thr
        355                 360                 365
Leu Ser Gly Asp Ala Phe Leu His Leu Leu Pro His Ser His Ala Ser
        370                 375                 380
His His His Ser His Ser His Glu Glu Pro Ala Met Glu Met Lys Arg
385                 390                 395                 400
Gly Pro Leu Phe Ser His Leu Ser Ser Gln Asn Ile Glu Glu Ser Ala
                405                 410                 415
Tyr Phe Asp Ser Thr Trp Lys Gly Leu Thr Ala Leu Gly Gly Leu Tyr
            420                 425                 430
Phe Met Phe Leu Val Glu His Val Leu Thr Leu Ile Lys Gln Phe Lys
        435                 440                 445
Asp Lys Lys Lys Lys Asn Gln Lys Lys Pro Glu Asn Asp Asp Asp Val
        450                 455                 460
Glu Ile Lys Lys Gln Leu Ser Lys Tyr Glu Ser Gln Leu Ser Thr Asn
465                 470                 475                 480
Glu Glu Lys Val Asp Thr Asp Asp Arg Thr Glu Gly Tyr Leu Arg Ala
                485                 490                 495
Asp Ser Gln Glu Pro Ser His Phe Asp Ser Gln Gln Pro Ala Val Leu
            500                 505                 510
Glu Glu Glu Glu Val Met Ile Ala His Ala His Pro Gln Glu Val Tyr
        515                 520                 525
```

```
Asn Glu Tyr Val Pro Arg Gly Cys Lys Asn Lys Cys His Ser His Phe
            530                 535                 540

His Asp Thr Leu Gly Gln Ser Asp Leu Ile His His His His Asp
545                 550                 555                 560

Tyr His His Ile Leu His His His His Gln Asn His His Pro His
                565                 570                 575

Ser His Ser Gln Arg Tyr Ser Arg Glu Glu Leu Lys Asp Ala Gly Val
            580                 585                 590

Ala Thr Leu Ala Trp Met Val Ile Met Gly Asp Gly Leu His Asn Phe
            595                 600                 605

Ser Asp Gly Leu Ala Ile Gly Ala Ala Phe Thr Glu Gly Leu Ser Ser
610                 615                 620

Gly Leu Ser Thr Ser Val Ala Val Phe Cys His Glu Leu Pro His Glu
625                 630                 635                 640

Leu Gly Asp Phe Ala Val Leu Leu Lys Ala Gly Met Thr Val Lys Gln
                645                 650                 655

Ala Val Leu Tyr Asn Ala Leu Ser Ala Met Leu Ala Tyr Leu Gly Met
            660                 665                 670

Ala Thr Gly Ile Phe Ile Gly His Tyr Ala Glu Asn Val Ser Met Trp
            675                 680                 685

Ile Phe Ala Leu Thr Ala Gly Leu Phe Met Tyr Val Ala Leu Val Asp
690                 695                 700

Met Val Pro Glu Met Leu His Asn Asp Ala Ser Asp His Gly Cys Ser
705                 710                 715                 720

Arg Trp Gly Tyr Phe Phe Leu Gln Asn Ala Gly Met Leu Leu Gly Phe
                725                 730                 735

Gly Ile Met Leu Leu Ile Ser Ile Phe Glu His Lys Ile Val Phe Arg
            740                 745                 750

Ile Asn Phe
755

<210> SEQ ID NO 55
<211> LENGTH: 710
<212> TYPE: PRT
<213> ORGANISM: Homo sapiens

<400> SEQUENCE: 55

Met Gly Gly Lys Gln Arg Asp Glu Asp Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
        35                  40                  45

Ile Val Val Gly Ile Val Ala Trp Leu Tyr Gly Asp Pro Arg Gln Val
    50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
    130                 135                 140
```

-continued

```
Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Pro Ser Ala Pro
            165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
            195                 200                 205

Ile Asp Ser Leu Asn Ala Arg Asp Ile Ser Val Lys Ile Phe Glu Asp
210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Arg Leu Val Ala Gly Pro
            245                 250                 255

Leu Val Leu Val Leu Ile Leu Gly Val Leu Gly Val Leu Ala Tyr Gly
            260                 265                 270

Ile Tyr Tyr Cys Trp Glu Glu Tyr Arg Val Leu Arg Asp Lys Gly Ala
            275                 280                 285

Ser Ile Ser Gln Leu Gly Phe Thr Thr Asn Leu Ser Ala Tyr Gln Ser
            290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
            325                 330                 335

Ala Ile Ala Leu Leu Lys Glu Ala Ser Lys Ala Val Gly Gln Met Met
            340                 345                 350

Ser Thr Met Phe Tyr Pro Leu Val Thr Phe Val Leu Leu Leu Ile Cys
            355                 360                 365

Ile Ala Tyr Trp Ala Met Thr Ala Leu Tyr Leu Ala Thr Ser Gly Gln
            370                 375                 380

Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
            405                 410                 415

Ser Ser Cys Pro Gly Leu Met Cys Val Phe Gln Gly Tyr Ser Ser Lys
            420                 425                 430

Gly Leu Ile Gln Arg Ser Val Phe Asn Leu Gln Ile Tyr Gly Val Leu
            435                 440                 445

Gly Leu Phe Trp Thr Leu Asn Trp Val Leu Ala Leu Gly Gln Cys Val
            450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
            485                 490                 495

Tyr His Thr Gly Ser Leu Ala Phe Gly Ala Leu Ile Leu Thr Leu Val
            500                 505                 510

Gln Ile Ala Arg Val Ile Leu Glu Tyr Ile Asp His Lys Leu Arg Gly
            515                 520                 525

Val Gln Asn Pro Val Ala Arg Cys Ile Met Cys Cys Phe Lys Cys Cys
            530                 535                 540

Leu Trp Cys Leu Glu Lys Phe Ile Lys Phe Leu Asn Arg Asn Ala Tyr
545                 550                 555                 560
```

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Leu Asp
            580                 585                 590

Lys Val Thr Asp Leu Leu Leu Phe Phe Gly Lys Leu Leu Val Val Gly
            595                 600                 605

Gly Val Gly Val Leu Ser Phe Phe Phe Ser Gly Arg Ile Pro Gly
            610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
                645                 650                 655

Ser Val Phe Gly Met Cys Val Asp Thr Leu Phe Leu Cys Phe Leu Glu
            660                 665                 670

Asp Leu Glu Arg Asn Asn Gly Ser Leu Asp Arg Pro Tyr Tyr Met Ser
            675                 680                 685

Lys Ser Leu Leu Lys Ile Leu Gly Lys Lys Asn Glu Ala Pro Pro Asp
690                 695                 700

Asn Lys Lys Arg Lys Lys
705                 710

<210> SEQ ID NO 56
<211> LENGTH: 339
<212> TYPE: PRT
<213> ORGANISM: Homo sapiens

<400> SEQUENCE: 56

Met Glu Ser Arg Lys Asp Ile Thr Asn Gln Glu Leu Trp Lys Met
1               5                   10                  15

Lys Pro Arg Arg Asn Leu Glu Glu Asp Asp Tyr Leu His Lys Asp Thr
            20                  25                  30

Gly Glu Thr Ser Met Leu Lys Arg Pro Val Leu Leu His Leu His Gln
        35                  40                  45

Thr Ala His Ala Asp Glu Phe Asp Cys Pro Ser Glu Leu Gln His Thr
    50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Arg Glu Val Ile His
                85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
        115                 120                 125

Val Tyr Leu Pro Gly Val Ile Ala Ala Ile Val Gln Leu His Asn Gly
    130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
    210                 215                 220

```
Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ser Lys
            245                 250                 255

Leu Gly Ile Val Ser Leu Leu Gly Thr Ile His Ala Leu Ile Phe
        260                 265                 270

Ala Trp Asn Lys Trp Ile Asp Ile Lys Gln Phe Val Trp Tyr Thr Pro
        275                 280                 285

Pro Thr Phe Met Ile Ala Val Phe Leu Pro Ile Val Val Leu Ile Phe
        290                 295                 300

Lys Ser Ile Leu Phe Leu Pro Cys Leu Arg Lys Lys Ile Leu Lys Ile
305                 310                 315                 320

Arg His Gly Trp Glu Asp Val Thr Lys Ile Asn Lys Thr Glu Ile Cys
                325                 330                 335

Ser Gln Leu

<210> SEQ ID NO 57
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Val Val Arg Lys Pro Val Ile Ala Leu
1               5

<210> SEQ ID NO 58
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Leu Leu Ser Glu Lys Lys Lys Ile Ser
1               5

<210> SEQ ID NO 59
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Ala Pro Ala Ser Lys Pro Arg Pro Arg Leu
1               5                   10

<210> SEQ ID NO 60
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 60

Arg Tyr Gly Gln Leu Ser Glu Lys Phe
1               5

<210> SEQ ID NO 61
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Val Tyr Ile Ser Asn Val Ser Lys Leu
1               5

<210> SEQ ID NO 62
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Leu Pro Thr Lys Glu Thr Pro Ser Phe
1               5

<210> SEQ ID NO 63
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gly Glu Ala Pro Pro Pro Pro Pro Ala
1               5

<210> SEQ ID NO 64
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Leu Glu Glu Ile Ser Lys Gln Glu Ile
1               5

<210> SEQ ID NO 65
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Ile Tyr Asn His Ile Thr Val Lys Ile
1               5
```

<210> SEQ ID NO 66
<211> LENGTH: 160
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Val Asp Leu Glu Pro Thr Val Ile Gly Glu Leu Thr Ser Val Thr Gln
1               5                   10                  15

Val Arg Ser Gln Gly Ala Gly Thr Gly Gly Leu Ser Trp Gly Gly Ser
            20                  25                  30

Ala Gly His Ser Pro Thr Leu Pro Pro Arg Ser Leu Ser Leu Leu Leu
        35                  40                  45

Leu Pro His His Val Leu Gln Met Lys Phe Ala Leu Ala Leu Thr Ala
    50                  55                  60

Ser Ser Ser Thr Leu Ser Asn Ser Ser Gln Ala Arg Lys Met Leu Pro
65                  70                  75                  80

Ile Thr Met Pro Glu Gly Thr Thr Pro Leu Ala Arg Arg Ser Leu Thr
                85                  90                  95

Ser Cys Trp Thr Glu Phe Ala Ser Trp Leu Thr Ser Ala Pro Val Phe
            100                 105                 110

Arg Ala Ser Trp Phe Ser Thr Ala Leu Val Gly Glu Leu Val Leu Gly
        115                 120                 125

Ser Pro Arg Cys Ser Trp Asn Val Ser Gln Leu Ile Met Ala Arg Ser
    130                 135                 140

Pro Ser Trp Ser Ser Pro Phe Thr Arg Arg Pro Arg Phe Pro Gln Leu
145                 150                 155                 160

<210> SEQ ID NO 67
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Ala Pro Pro Arg Ser His Pro Ser Ile Lys Arg Gly Leu Ser Ser Leu
1               5                   10                  15

<210> SEQ ID NO 68
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Met Val Arg Arg Ala Arg Trp Pro Gly Gly Arg Gly Glu Ala Arg Lys
1               5                   10                  15

Ala Pro Arg Thr Ala Pro Gly Val Arg Pro Pro Phe
            20                  25

<210> SEQ ID NO 69
<211> LENGTH: 199

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Trp Val Asn Cys Leu Phe Val Ser Gly Arg Ala Ala Gly Gly Gly
1               5                   10                  15

Gly Gly Gly Ala Val Pro Pro Tyr Leu Glu Leu Ala Gly Pro Pro Phe
            20                  25                  30

Leu Leu Leu Thr Leu Ile Arg Ile Gly Leu Gly Arg Arg Ser Gly Arg
            35                  40                  45

Ala Gly Gly Arg Ala Gly Thr Gln Cys Gly Gly Glu Arg Gly Pro Gly
        50                  55                  60

Phe Ala Ala Phe Arg Pro Leu Arg Pro Phe Arg Arg Leu Arg Val Cys
65                  70                  75                  80

Ala Val Cys Val Arg Gly Ser Ala Leu Gly Arg Ser Val Gly Leu Pro
                85                  90                  95

Arg Gly Gly Ala Ala Gly Ala Pro Phe Ser Ser Pro Ala Pro His
            100                 105                 110

Pro Arg Arg Val Leu Cys Arg Cys Leu Leu Phe Leu Phe Phe Ser Cys
            115                 120                 125

His Asp Arg Arg Gly Asp Ser Gln Pro Tyr Gln Val Pro Ala Glu Ala
        130                 135                 140

Gly Val Glu Gly Leu Glu Gly Ala Gly Gly Arg Glu Gly Leu Leu
145                 150                 155                 160

Leu Glu Arg Arg Pro Gln Lys Ser Ile Gln Ala Leu Arg Cys Asn Thr
                165                 170                 175

Ser Glu Thr Ser Thr Ala Asp Pro Leu Lys Ile Pro Gly Leu Val Pro
            180                 185                 190

Leu Ala Leu Ser Ser Lys Val
            195

<210> SEQ ID NO 70
<211> LENGTH: 101
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Met Pro Leu Pro Val Gln Val Phe Asn Leu Gln Val Thr Ser Arg Gly
1               5                   10                  15

Arg Pro Gly Pro Pro Arg Pro Arg Ala Pro Arg His Trp Gly Arg Ala
            20                  25                  30

Glu Val Glu Gln Gly Arg Gly Ala Cys Ala Arg Ser Arg Ser Gly Thr
            35                  40                  45

Leu Arg Ala Gly Pro Pro Arg Ala Ala Arg Val Gly Gly Cys Arg Ala
        50                  55                  60

Glu Gly Ala Ser Pro Pro Trp Leu Arg Ala Ala Ile Gly Gly Arg Arg
65                  70                  75                  80
```

Ala Ala Pro Ala Pro Pro Leu Pro Ala Ala His Gly Arg Gly Ser
            85                  90                  95

Arg Pro Pro Arg Arg
            100

<210> SEQ ID NO 71
<211> LENGTH: 162
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Gln Pro Ala Gln Pro Arg Thr Gly Ala Pro Ala Arg Arg Pro Arg Pro
1               5                   10                  15

Arg Pro Ser Phe Pro Val Ser Leu Arg Ser Ala Ala Pro Pro Thr Gly
                20                  25                  30

Thr Ala Gly Gly Thr Gly Arg Phe Val Leu Arg Pro Gly Glu Ser Gly
                35                  40                  45

Ala Gly Gly Gly Asp Ala Trp Asp Thr Gly Leu Gln Ala Arg Arg
50                  55                  60

Gly Thr Ala Ala Gly Thr Ser Gly Ala Pro Asn Arg Ser Gln Leu Ser
65                  70                  75                  80

Ser Leu Thr Phe Pro Ala Gln Leu Arg Arg Ile Gly Val Ser Gly Arg
                85                  90                  95

Lys Pro Gly Ala Gly Gly Arg Leu Gly Pro Gly Ser Arg Thr Cys Ala
                100                 105                 110

Pro Arg Cys Leu Pro Arg Ala Arg Arg Gly Pro Gly Ala His Pro Arg
                115                 120                 125

Gly Gly Arg Cys Pro Pro Ala Glu Thr Ala Leu Phe Arg Glu Ala Glu
130                 135                 140

Glu Gly Thr Gln Lys Tyr Ser Leu Pro Ser Asp Pro Ala Gly Gln Ala
145                 150                 155                 160

Ala Phe

<210> SEQ ID NO 72
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Phe Arg Leu His Thr Gly Pro Val Ser Pro Val Gly Gly Arg Arg Gln
1               5                   10                  15

Met Gly Arg Pro Lys His Gly Asp Gly Phe Ser Leu Gln Val Cys Ser
                20                  25                  30

Phe Ile Met Glu Gln Asn Gly
        35

<210> SEQ ID NO 73
<211> LENGTH: 71
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 73

Gly Val Val Glu Ile Thr Gly Glu Pro Pro Cys Ser Cys Arg Gly Glu
1               5                   10                  15

Glu Glu Ala Ser Arg Ala Gly Arg Ala Gly Gly Val Arg Leu Lys Arg
            20                  25                  30

Gly Ser Arg Gly Pro Gly Glu Leu Asn Val Gly Pro Ala Pro Gly Lys
        35                  40                  45

Thr Gly Leu Leu Ile Pro Leu Leu Arg Asn Trp Glu Cys Gly Ser Leu
    50                  55                  60

Leu Arg Ala Leu Ser Ala Leu
65                  70

<210> SEQ ID NO 74
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 74

Lys Met Gly Phe Pro Glu Ala Ala Arg Lys Gly Asn Ser Leu
1               5                   10

<210> SEQ ID NO 75
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 75

Leu Glu Ala Arg Ile Lys Glu Lys Ile Glu Glu Leu Gln Gln Ala Leu
1               5                   10                  15

Ile

<210> SEQ ID NO 76
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 76

Glu Ile Lys Lys Arg Phe Arg Gln Phe Lys Gln Ala Val Tyr Lys Gln
1               5                   10                  15

<210> SEQ ID NO 77
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 77

Ala His Glu Ser Ala Ala Met Ala Glu Thr Leu Gln His Val Pro Ser
1               5                   10                  15

<210> SEQ ID NO 78
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Asn Arg Pro Ser Val Gln Ala Ala Leu Lys Leu Lys Gln Val Gly Val
1               5                   10                  15

<210> SEQ ID NO 79
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Lys Thr Asp Asp Leu Lys Lys Arg His Ile Thr Phe Thr Leu Gly Cys
1               5                   10                  15

Gly Ile Cys

<210> SEQ ID NO 80
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Met Lys Leu Asp Glu Asp Val Lys Arg Asn Asp Ile Ala Met Ala Ile
1               5                   10                  15

<210> SEQ ID NO 81
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Asn Ser Ile Ser Gln Ile Pro Ser Asp His Ile Leu Thr Pro Ala Leu
1               5                   10                  15

Phe Ile Thr Phe Met Thr Ile Leu Asp Leu
            20                  25

<210> SEQ ID NO 82
<211> LENGTH: 24
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 82

Thr Val Phe Ser Thr Ser Ser Leu Lys Leu Asn Gln Pro Gln Lys Tyr
1               5                   10                  15

Leu Lys Met Lys Ser Trp Pro Cys
            20

<210> SEQ ID NO 83
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Ala Glu Glu Asp Arg Arg Lys Lys Val Ile Thr Ser Cys Leu Leu Asn
1               5                   10                  15

Phe Asn Leu Ser Lys Ala Gln Ser
            20

<210> SEQ ID NO 84
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Arg Ser Phe Ser Thr Ser Ala Gln Val Gly Gln Thr Arg Gly Gly Leu
1               5                   10                  15

Gln Ala Glu Ala Pro Arg Pro Gly Pro Arg Ala Ser Pro Val Arg Gly
            20                  25                  30

Gln Leu

<210> SEQ ID NO 85
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Arg Gly Tyr Val Val Arg Lys Pro Val Ile Ala Leu Ser Val Lys Ile
1               5                   10                  15

<210> SEQ ID NO 86
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Val Asp Met Asp Phe Gly Thr Gly Gly Gln Gly Ala Gly Pro Val Gly
1               5                   10                  15
```

-continued

Arg Gly Lys Asp Trp Ser Cys Thr Leu Ala Val His Leu Leu Ser Glu
            20                  25                  30

Lys Lys Lys Ile Ser Phe Ser Gln Ile Asp Arg Ala Trp Gly Gly Ser
        35                  40                  45

Gln Gly Thr Val Leu Asp Lys Trp Gly Pro Gly Val Val Ser Glu Leu
    50                  55                  60

His Pro Ser Ala Lys Glu Val Ser Val Gly Arg Asn Ser Val Glu Ser
65                  70                  75                  80

Leu Met Thr Trp Ala Ser
                85

<210> SEQ ID NO 87
<211> LENGTH: 66
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Glu Lys Gly Ser His Glu Glu Val Arg Val Pro Ala Leu Ser Trp
1               5                   10                  15

Gly Arg Pro Arg Ala Pro Ala Pro Ala Ser Lys Pro Arg Pro Arg Leu
            20                  25                  30

Asp Leu Asn Cys Leu Trp Leu Arg Pro Gln Pro Ile Phe Leu Trp Lys
        35                  40                  45

Leu Arg Pro Arg Pro Val Pro Ala Ala Thr Pro Leu Thr Gly Pro Leu
    50                  55                  60

Pro Leu
65

<210> SEQ ID NO 88
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Arg Tyr Gly Gln Leu Ser Glu Lys Phe Asn Arg Arg Lys Val Met Asp
1               5                   10                  15

Ser

<210> SEQ ID NO 89
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Met Val Tyr Ile Ser Asn Val Ser Lys Leu Cys Phe Ser Lys Met
1               5                   10                  15

<210> SEQ ID NO 90
<211> LENGTH: 48
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 90

Asn Thr Leu Pro Thr Lys Glu Thr Pro Ser Phe Leu Leu Asn Pro His
1               5                   10                  15

Thr Ser Trp Val Pro Arg Pro His Arg Glu Ala Pro Arg Leu Arg Val
                20                  25                  30

Gly Val Ala Ala Pro Leu Gln Arg Pro Leu Pro Ala Leu His Ser His
            35                  40                  45

<210> SEQ ID NO 91
<211> LENGTH: 58
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

Phe Gly Asp Ile Tyr Leu Gly Glu Ala Pro Pro Pro Pro Ala Ala
1               5                   10                  15

Arg Arg Pro Gly Pro Cys Gly Cys Gln Asp Gln Ala Arg Ser Arg Lys
                20                  25                  30

Glu Val Val Ala Pro Ala Gly Ser Pro Arg Lys Ser Arg His Arg Arg
            35                  40                  45

Ile Val Ala Arg Thr Gln Arg Pro Leu Gly
        50                  55

<210> SEQ ID NO 92
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Gly Ser Ala Ser Asp Leu Leu Glu Glu Ile Ser Lys Gln Glu Ile Ser
1               5                   10                  15

Phe

<210> SEQ ID NO 93
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Gln Leu Ile Tyr Asn His Ile Thr Val Lys Ile Asn Leu Gln Gly Asp
1               5                   10                  15

<210> SEQ ID NO 94
<211> LENGTH: 10
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 94

Arg Pro Arg Pro Ser Phe Pro Val Ser Leu
1               5                   10

<210> SEQ ID NO 95
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Arg Pro Lys His Gly Asp Gly Phe Ser Leu
1               5                   10

<210> SEQ ID NO 96
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Gly Pro Ala Pro Gly Lys Thr Gly Leu
1               5

<210> SEQ ID NO 97
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Glu Ala Ala Arg Lys Gly Asn Ser Leu
1               5

<210> SEQ ID NO 98
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Arg Ile Lys Glu Lys Ile Glu Glu Leu
1               5

<210> SEQ ID NO 99
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Glu Ile Lys Lys Arg Phe Arg Gln Phe
1               5

<210> SEQ ID NO 100
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

His Glu Ser Ala Ala Met Ala Glu Thr
1               5

<210> SEQ ID NO 101
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Ala Leu Lys Leu Lys Gln Val Gly Val
1               5

<210> SEQ ID NO 102
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Asp Leu Lys Lys Arg His Ile Thr Phe
1               5

<210> SEQ ID NO 103
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Asp Val Lys Arg Asn Asp Ile Ala Met
1               5

<210> SEQ ID NO 104
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Ile Pro Ser Asp His Ile Leu Thr Pro Ala
1               5                   10

<210> SEQ ID NO 105
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Thr Val Phe Ser Thr Ser Ser Leu Lys
1               5

<210> SEQ ID NO 106
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Ile Thr Ser Cys Leu Leu Asn Phe
1               5

<210> SEQ ID NO 107
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Arg Ala Ser Pro Val Arg Gly Gln Leu
1               5

<210> SEQ ID NO 108
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 108
cacaccagat cggcatcaa                                                19

<210> SEQ ID NO 109
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 109
cgatgatgtg tccgtgtatg t                                         21

<210> SEQ ID NO 110
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 110
atcctgccac accagatgac cac                                       23

<210> SEQ ID NO 111
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 111
ctgcttcgga tttactagaa gagata                                    26

<210> SEQ ID NO 112
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 112
gcgttcccac aaaggaattg                                           20

<210> SEQ ID NO 113
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 113
tgctgacttt ggctctgctt ccat                                      24

<210> SEQ ID NO 114
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 114
actctcttcc gcatcgctgt                                                  20

<210> SEQ ID NO 115
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 115
ccgacgggtt tccgatccaa                                                  20

<210> SEQ ID NO 116
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 116
ctgttgggct cgcggttg                                                    18

<210> SEQ ID NO 117
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 117
tggcatcaga ttgcaaagac                                                  20

<210> SEQ ID NO 118
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 118
acgccgggtg atgtatctat                                                  20

<210> SEQ ID NO 119
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 119
cgaaacgcac ccgtcagacg                                                  20
```